United States Patent
Zink

(10) Patent No.: US 10,919,880 B2
(45) Date of Patent: *Feb. 16, 2021

(54) ORGANIC MOLECULES, IN PARTICULAR FOR USE IN OPTOELECTRONIC DEVICES

(71) Applicant: CYNORA GMBH, Bruchsal (DE)

(72) Inventor: Daniel Zink, Bruchsal (DE)

(73) Assignee: CYNORA GMBH, Bruchsal (DE)

( * ) Notice: Subject to any disclaimer, the term of this patent is extended or adjusted under 35 U.S.C. 154(b) by 147 days.

This patent is subject to a terminal disclaimer.

(21) Appl. No.: 16/110,098

(22) Filed: Aug. 23, 2018

(65) Prior Publication Data

US 2019/0062312 A1    Feb. 28, 2019

(30) Foreign Application Priority Data

Aug. 25, 2017   (DE) ............. 10 2017 119 592.0
Sep. 25, 2017   (DE) ............. 10 2017 122 199.9

(51) Int. Cl.
| | |
|---|---|
| C07D 403/00 | (2006.01) |
| H01B 1/12 | (2006.01) |
| C07D 403/10 | (2006.01) |
| H01L 51/00 | (2006.01) |
| H01L 51/50 | (2006.01) |
| C07D 519/00 | (2006.01) |
| C07D 403/14 | (2006.01) |

(52) U.S. Cl.
CPC ......... *C07D 403/10* (2013.01); *C07D 403/14* (2013.01); *C07D 519/00* (2013.01); *H01B 1/12* (2013.01); *H01L 51/0071* (2013.01); *H01L 51/0072* (2013.01); *H01L 51/5024* (2013.01); *H01L 51/001* (2013.01); *H01L 51/5012* (2013.01); *H01L 51/5056* (2013.01); *H01L 51/5072* (2013.01); *H01L 51/5088* (2013.01); *H01L 51/5096* (2013.01)

(58) Field of Classification Search
CPC . H01B 1/00; H01B 1/12; H01B 1/121; C07D 487/00; C07D 487/02; C07D 403/00; C07D 403/10; H01L 51/0032; H01L 51/0035

See application file for complete search history.

(56) References Cited

U.S. PATENT DOCUMENTS

| | | | |
|---|---|---|---|
| 2005/0236976 A1 | 10/2005 | Leung et al. | |
| 2019/0198778 A1* | 6/2019 | Bergmann | .......... H01L 51/0061 |
| 2019/0198779 A1* | 6/2019 | Bergmann | ........... C07D 209/86 |

FOREIGN PATENT DOCUMENTS

| | | |
|---|---|---|
| WO | WO-2011/025066 A1 | 3/2011 |
| WO | WO-2016/108596 A2 | 7/2016 |

* cited by examiner

*Primary Examiner* — Mark Kopec
(74) *Attorney, Agent, or Firm* — Laura W. Smalley

(57) ABSTRACT

Organic molecules are provided that exhibit emission maxima in the blue, sky-blue or green spectral range. The organic molecules exhibit emission maxima between 420 nm and 520 nm, preferably between 440 nm and 495 nm, more preferably between 450 nm and 470 nm. The photoluminescence quantum yields of the organic molecules are 20% or more. The molecules exhibit thermally activated delayed fluorescence (TADF). The molecules can be used in an optoelectronic device, for example an organic light-emitting diode (OLED), leading to higher efficiencies of the device. Corresponding OLEDs have a higher stability than OLEDs with known emitter materials and comparable color.

16 Claims, 4 Drawing Sheets

ORGANIC MOLECULES, IN PARTICULAR FOR USE IN OPTOELECTRONIC DEVICES

TECHNICAL FIELD

Figure 1:
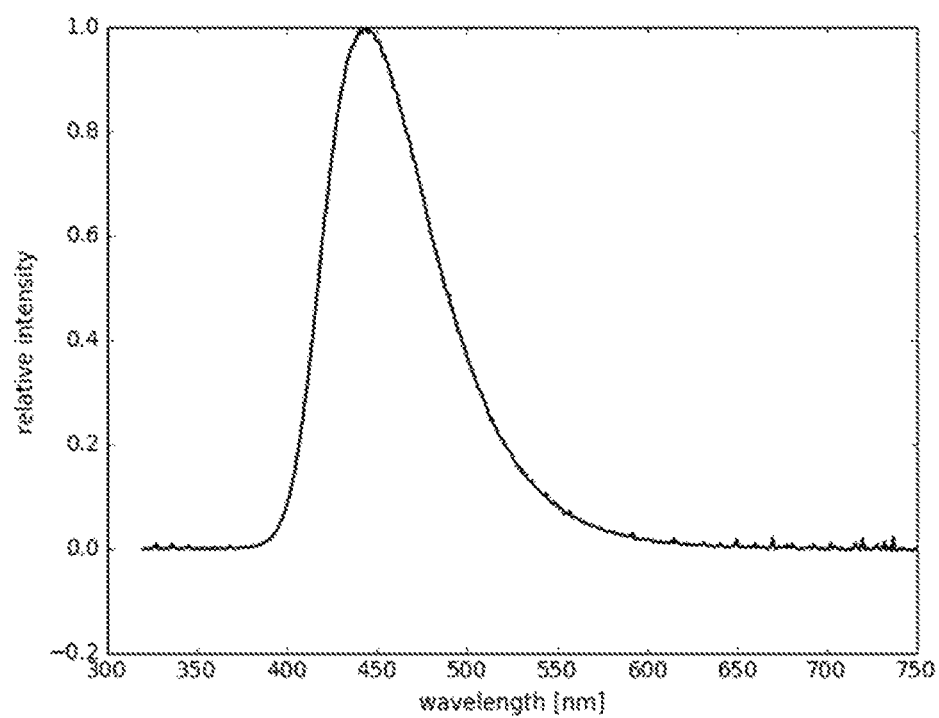

The invention relates to organic molecules and their use in organic light-emitting diodes (OLEDs) and in other optoelectronic devices.

DESCRIPTION

The object of the present invention is to provide molecules which are suitable for use in organic optoelectronic devices.

This object is achieved by the invention which provides a new class of organic molecules.

According to the invention the organic molecules are purely organic molecules, i.e. they do not contain any metal ions in contrast to metal complexes known for use in organic optoelectronic devices.

According to the present invention, the organic molecules exhibit emission maxima in the blue, sky-blue or green spectral range. The organic molecules exhibit in particular emission maxima between 420 nm and 520 nm, preferably between 440 nm and 495 nm, more preferably between 450 nm and 470 nm. The photoluminescence quantum yields of the organic molecules according to the invention are, in particular, 20% or more. The molecules according to the invention exhibit in particular thermally activated delayed fluorescence (TADF). The use of the molecules according to the invention in an optoelectronic device, for example an organic light-emitting diode (OLED), leads to higher efficiencies of the device. Corresponding OLEDs have a higher stability than OLEDs with known emitter materials and comparable color.

The organic light-emitting molecules of the invention comprise or consist of a first chemical moiety comprising or consisting of a structure of Formula I,

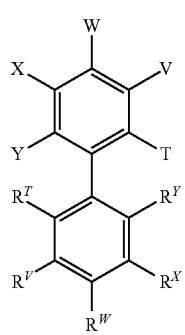

Formula I and two second chemical moieties, each independently from another comprising or consisting of a structure of Formula II,

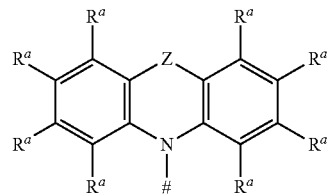

Formula II wherein the first chemical moiety is linked to each of the two second chemical moieties via a single bond.

T is selected from the group consisting of $R^A$ and $R^1$.

V is selected from the group consisting of $R^A$ and $R^1$.

W is the binding site of a single bond linking the first chemical moiety to one of the two second chemical moieties or is selected from the group consisting of $R^A$ and $R^2$.

X is the binding site of a single bond linking the first chemical moiety to one of the two second chemical moieties or is $R^2$.

Y is the binding site of a single bond linking the first chemical moiety to one of the two second chemical moieties or is $R^2$.

$R^A$ is selected from the group consisting of a structure of Formula A1 and a structure of Formula A2,

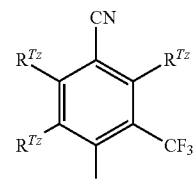

Formula A1

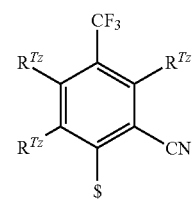

Formula A2 wherein $ represents the binding site of the single bond connecting $R^A$ and the first chemical moiety.

$R^T$ is selected from the group consisting of CN and $R^I$.

$R^V$ is selected from the group consisting of CN and $R^I$.

$R^W$ is the binding site of a single bond linking the first chemical moiety to one of the two second chemical moieties or is selected from the group consisting of CN and $R^I$.

$R^X$ is the binding site of a single bond linking the first chemical moiety to one of the two second chemical moieties or is $R^I$.

$R^Y$ is the binding site of a single bond linking the first chemical moiety to one of the two second chemical moieties or is $R^I$.

# represents the binding site of a single bond linking the second chemical moieties to the first chemical moiety;

Z is at each occurrence independently from another selected from the group consisting of a direct bond, $CR^3R^4$, $C=CR^3R^4$, $C=O$, $C=NR^3$, $NR^3$, O, $SiR^3R^4$, S, S(O) and $S(O)_2$;

$R^1$ is at each occurrence independently from another selected from the group consisting of hydrogen,
deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium; and
$C_6$-$C_{18}$-aryl,
which is optionally substituted with one or more substituents $R^6$.

$R^2$ is at each occurrence independently from another selected from the group consisting of
hydrogen,
deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium; and
$C_6$-$C_{18}$-aryl,
which is optionally substituted with one or more substituents $R^6$.

$R^I$ is at each occurrence independently from another selected from the group consisting of
hydrogen,
deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium; and
$C_6$-$C_{18}$-aryl,
which is optionally substituted with one or more substituents $R^6$.

$R^{Tz}$ is at each occurrence independently from another selected from the group consisting of
hydrogen,
deuterium,
$C_1$-$C_5$-alkyl,
wherein one or more hydrogen atoms are optionally substituted by deuterium; and
$C_6$-$C_{18}$-aryl,
which is optionally substituted with one or more substituents $R^6$.

$R^a$, $R^3$ and $R^4$ is at each occurrence independently from another selected from the group consisting of hydrogen, deuterium, $N(R^5)_2$, $OR^5$, $Si(R^5)_3$, $B(OR^5)_2$, $OSO_2R^5$, $CF_3$, CN, F, Br, I, $C_1$-$C_{40}$-alkyl,
which is optionally substituted with one or more substituents $R^5$ and
wherein one or more non-adjacent $CH_2$-groups are optionally substituted by $R^5C$=$CR^5$, C=O, $Si(R^5)_2$, $Ge(R^5)_2$, $Sn(R^5)_2$, C=O, C=S, C=Se, C=$NR^5$, P(=O)($R^5$), SO, $OC_2$, $NR^5$, O, S or $CONR^5$;
$C_1$-$C_{40}$-alkoxy,
which is optionally substituted with one or more substituents $R^5$ and
wherein one or more non-adjacent $CH_2$-groups are optionally substituted by $R^5C$=$CR^5$, C≡C, $Si(R^5)_2$, $Ge(R^5)_2$, $Sn(R^5)_2$, C=O, C=S, C=Se, C=$NR^5$, P(=O)($R^5$), SO, $OC_2$, $NR^5$, O, S or $CONR^5$;
$C_1$-$C_{40}$-thioalkoxy,
which is optionally substituted with one or more substituents $R^5$ and
wherein one or more non-adjacent $CH_2$-groups are optionally substituted by $R^5C$=$CR^5$, C=C, $Si(R^5)_2$, $Ge(R^5)_2$, $Sn(R^5)_2$, C=O, C=S, C=Se, C=$NR^5$, P(=O)($R^5$), SO, $OC_2$, $NR^5$, O, S or $CONR^5$;
$C_2$-$C_{40}$-alkenyl,
which is optionally substituted with one or more substituents $R^5$ and
wherein one or more non-adjacent $CH_2$-groups are optionally substituted by $R^5C$=$CR^5$, C=C, $Si(R^5)_2$, $Ge(R^5)_2$, $Sn(R^5)_2$, C=O, C=S, C=Se, C=$NR^5$, P(=O)($R^5$), SO, $OC_2$, $NR^5$, O, S or $CONR^5$;
$C_2$-$C_{40}$-alkynyl,
which is optionally substituted with one or more substituents $R^5$ and
wherein one or more non-adjacent $CH_2$-groups are optionally substituted by $R^5C$=$CR^5$, C=C, $Si(R^5)_2$, $Ge(R^5)_2$, $Sn(R^5)_2$, C=O, C=S, C=Se, C=$NR^5$, P(=O)($R^5$), SO, $OC_2$, $NR^5$, O, S or $CONR^5$; $C_6$-$C_{60}$-aryl,
which is optionally substituted with one or more substituents $R^5$; and
$C_3$-$C_{57}$-heteroaryl,
which is optionally substituted with one or more substituents $R^5$.

$R^5$ is at each occurrence independently from another selected from the group consisting of hydrogen, deuterium, $N(R^6)_2$, $OR^6$, $Si(R^6)_3$, $B(OR^6)_2$, $OSO_2R^6$, $CF_3$, CN, F, Br, I,
$C_1$-$C_{40}$-alkyl,
which is optionally substituted with one or more substituents $R^6$ and
wherein one or more non-adjacent $CH_2$-groups are optionally substituted by $R^6C$=$CR^6$, C=C, $Si(R^6)_2$, $Ge(R^6)_2$, $Sn(R^6)_2$, C=O, C=S, C=Se, C=$NR^6$, P(=O)($R^6$), SO, $OC_2$, $NR^6$, O, S or $CONR^6$;
$C_1$-$C_{40}$-alkoxy,
which is optionally substituted with one or more substituents $R^6$ and
wherein one or more non-adjacent $CH_2$-groups are optionally substituted by $R^6C$=$CR^6$, C=C, $Si(R^6)_2$, $Ge(R^6)_2$, $Sn(R^6)_2$, C=O, C=S, C=Se, C=$NR^6$, P(=O)($R^6$), SO, $OC_2$, $NR^6$, O, S or $CONR^6$;
$C_1$-$C_{40}$-thioalkoxy,
which is optionally substituted with one or more substituents $R^6$ and
wherein one or more non-adjacent $CH_2$-groups are optionally substituted by $R^6C$=$CR^6$, C=C, $Si(R^6)_2$, $Ge(R^6)_2$, $Sn(R^6)_2$, C=O, C=S, C=Se, C=$NR^6$, P(=O)($R^6$), SO, $OC_2$, $NR^6$, O, S or $CONR^6$;
$C_2$-$C_{40}$-alkenyl,
which is optionally substituted with one or more substituents $R^6$ and
wherein one or more non-adjacent $CH_2$-groups are optionally substituted by $R^6C$=$CR^6$, C=C, $Si(R^6)_2$, $Ge(R^6)_2$, $Sn(R^6)_2$, C=O, C=S, C=Se, C=$NR^6$, P(=O)($R^6$), SO, $OC_2$, $NR^6$, O, S or $CONR^6$;
$C_2$-$C_{40}$-alkynyl, which is optionally substituted with one or more substituents R⁶ and wherein one or more non-adjacent CH₂-groups are optionally substituted by R⁶C=CR⁶, C=C, Si(R⁶)₂, Ge(R⁶)₂, Sn(R⁶)₂, C=O, C=S, C=Se, C=NR⁶, P(=O)(R⁶), SO, OC₂, NR⁶, O, S or CONR⁶; C₆-C₆₀-aryl, which is optionally substituted with one or more substituents R⁶; and C₃-C₅₇-heteroaryl, which is optionally substituted with one or more substituents R⁶.

R⁶ is at each occurrence independently from another selected from the group consisting of hydrogen, deuterium, OPh, CF₃, CN, F, C₁-C₅-alkyl, wherein optionally one or more hydrogen atoms are independently from each other substituted by deuterium, CN, CF₃, or F;

C₁-C₅-alkoxy, wherein optionally one or more hydrogen atoms are independently from each other substituted by deuterium, CN, CF₃, or F;

C₁-C₅-thioalkoxy, wherein optionally one or more hydrogen atoms are independently from each other substituted by deuterium, CN, CF₃, or F;

C₂-C₅-alkenyl, wherein optionally one or more hydrogen atoms are independently from each other substituted by deuterium, CN, CF₃, or F;

C₂-C₅-alkynyl, wherein optionally one or more hydrogen atoms are independently from each other substituted by deuterium, CN, CF₃, or F;

C₆-C₁₈-aryl, which is optionally substituted with one or more C₁-C₅-alkyl substituents;

C₃-C₁₇-heteroaryl, which is optionally substituted with one or more C₁-C₅-alkyl substituents;

N(C₆-C₁₈-aryl)₂,

N(C₃-C₁₇-heteroaryl)₂; and

N(C₃-C₁₇-heteroaryl)(C₆-C₁₈-aryl).

Optionally, the substituents $R^a$, $R^3$, $R^4$ or $R^5$, independently from each other, form a mono- or polycyclic, aliphatic, aromatic and/or benzo-fused ring system with one or more substituents $R^a$, $R^3$, $R^4$, or $R^5$.

According to the invention, exactly one substituent selected from the group consisting of T, V and W is $R^A$; exactly one substituent selected from the group consisting of $R^T$, $R^V$ and $R^W$ is CN; exactly one substituent selected from the group consisting of W, Y and X represents the binding site of a single bond linking the first chemical moiety and one of the two second chemical moieties and exactly one substituent selected from the group consisting of $R^W$, $R^Y$ and $R^X$ represents the binding site of a single bond linking the first chemical moiety and one of the two second chemical moieties.

In one embodiment of the invention, the first chemical moiety comprises or consists of a structure of Formula Ia-1 or comprises or consists of a structure of Formula Ia-2:

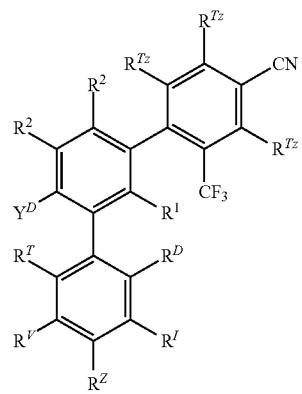

Formula Ia-1

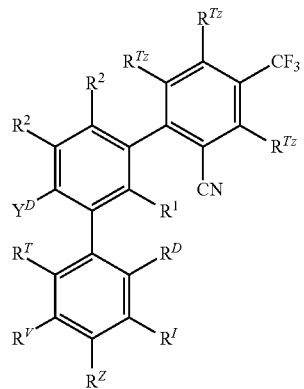

Formula Ia-2 wherein $R^Z$ is selected from the group consisting of $R^I$ and CN, $Y^D$ is the binding site of a single bond linking the first chemical moiety to one of the two second chemical moieties, $R^D$ is the binding site of a single bond linking the first chemical moiety to one of the two second chemical moieties, and wherein exactly one substituent selected from the group consisting of $R^V$, $R^T$ and $R^Z$ is CN, and apart from that the aforementioned definitions apply.

In one embodiment, $R^1$, $R^2$, and $R^I$ is at each occurrence independently from another selected from the group consisting of hydrogen (H), methyl, mesityl, tolyl and phenyl. The term tolyl comprises 2-tolyl, 3-tolyl and 4-tolyl.

In one embodiment, $R^1$, $R^2$, and $R^I$ is at each occurrence independently from another selected from the group consisting of hydrogen (H), methyl, and phenyl.

In one embodiment, $R^V$ is CN.
In one embodiment, $R^T$ is CN.
In one embodiment, $R^W$ is CN.
In one embodiment, V is $R^A$.
In one embodiment, T is $R^A$.
In one embodiment, W is $R^A$.
In one embodiment, $R^V$ is CN and W is $R^A$.
In one embodiment, $R^V$ is CN and V is $R^A$.
In one embodiment, $R^V$ is CN and T is $R^A$.
In one embodiment, $R^T$ is CN and W is $R^A$.
In one embodiment, $R^T$ is CN and V is $R^A$.
In one embodiment, $R^T$ is CN and T is $R^A$.
In one embodiment, $R^W$ is CN and W is $R^A$.
In one embodiment, $R^W$ is CN and V is $R^A$.
In one embodiment, $R^W$ is CN and T is $R^A$.
In one embodiment, $R^A$ comprises or consists of a structure of Formula A1.

In one embodiment, $R^A$ comprises or consists of a structure of Formula A2.

In a further embodiment of the invention, $R^{Tz}$ is independently from each other selected from the group consisting of H, methyl, and phenyl, wherein phenyl is optionally substituted with one or more substituents $R^6$.

In a further embodiment of the invention, $R^{Tz}$ is independently from each other selected from the group consisting of H, methyl and phenyl.

In a further embodiment of the invention, $R^{Tz}$ is H at each occurrence.

In a further embodiment of the invention, each of the two second chemical moieties at each occurrence, independently from another, comprise or consist of a structure of Formula IIa:

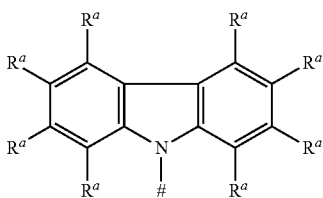

Formula IIa wherein # and $R^a$ are as defined above.

In a further embodiment of the invention, $R^a$ is at each occurrence independently from another selected from the group consisting of:
H,
Me,
$^iPr$,
$^tBu$,
CN,
$CF_3$,
Ph, which is optionally substituted with one or more substituents independently from each other selected from the group consisting of Me, $^iPr$, $^tBu$, CN, $CF_3$, and Ph,
pyridinyl, which is optionally substituted with one or more substituents independently from each other selected from the group consisting of Me, $^iPr$, $^tBu$, CN, $CF_3$, and Ph,
pyrimidinyl, which is optionally substituted with one or more substituents independently from each other selected from the group consisting of Me, $^iPr$, $^tBu$, CN, $CF_3$, and Ph,
carbazolyl, which is optionally substituted with one or more substituents independently from each other selected from the group consisting of Me, $^iPr$, $^tBu$, CN, $CF_3$, and Ph,
triazinyl, which is optionally substituted with one or more substituents independently from each other selected from the group consisting of Me, $^iPr$, $^tBu$, CN, $CF_3$, and Ph, and $N(Ph)_2$.

In a further embodiment of the invention, $R^a$ is at each occurrence independently from another selected from the group consisting of:
H,
Me,
$^iPr$,
$^tBu$,
CN,
$CF_3$,
Ph, which is optionally substituted with one or more substituents independently from each other selected from the group consisting of Me, $^iPr$, $^tBu$, CN, $CF_3$, and Ph,
pyridinyl, which is optionally substituted with one or more substituents independently from each other selected from the group consisting of Me, $^iPr$, $^tBu$, CN, $CF_3$, and Ph,
pyrimidinyl, which is optionally substituted with one or more substituents independently from each other selected from the group consisting of Me, $^iPr$, $^tBu$, CN, $CF_3$, and Ph, and
triazinyl, which is optionally substituted with one or more substituents independently from each other selected from the group consisting of Me, $^iPr$, $^tBu$, CN, $CF_3$, and Ph.

In a further embodiment of the invention, $R^a$ is at each occurrence independently from another selected from the group consisting of:
H,
Me,
$^tBu$,
Ph, which is optionally substituted with one or more substituents independently from each other selected from the group consisting of Me, $^iPr$, $^tBu$, CN, $CF_3$, and Ph,
triazinyl, which is optionally substituted with one or more substituents independently from each other selected from the group consisting of Me, $^iPr$, $^tBu$, CN, $CF_3$, and Ph.

In a further embodiment of the invention, $R^a$ is H at each occurrence.

In a further embodiment of the invention, each of the two second chemical moieties independently from another comprise or consist of a structure of Formula IIb, a structure of Formula IIb-2, a structure of Formula IIb-3 or a structure of Formula IIb-4:

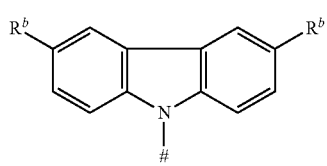

Formula IIb

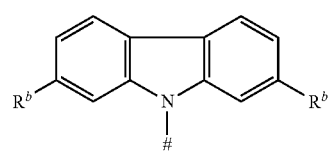

Formula IIb-2

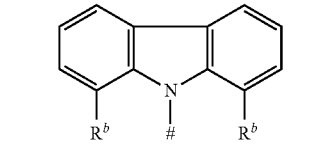

Formula IIb-3

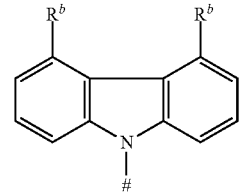

Formula IIb-4 wherein
$R^b$ is at each occurrence independently from another selected from the group consisting of:
deuterium,
$N(R^5)_2$,
$OR^5$,
$Si(R^5)_3$, B(OR⁵)₂,
OSO₂R⁵,
CF₃,
CN,
F,
Br,
I,
C₁-C₄₀-alkyl,
which is optionally substituted with one or more substituents R⁵ and
wherein one or more non-adjacent CH₂-groups are optionally substituted by R⁵C=CR⁵, C=O, Si(R⁵)₂, Ge(R⁵)₂, Sn(R⁵)₂, C=O, C=S, C=Se, C=NR⁵, P(=O)(R⁵), SO, OC₂, NR⁵, O, S or CONR⁵;
C₁-C₄₀-alkoxy,
which is optionally substituted with one or more substituents R⁵ and
wherein one or more non-adjacent CH₂-groups are optionally substituted by R⁵C=CR⁵, C=O, Si(R⁵)₂, Ge(R⁵)₂, Sn(R⁵)₂, C=O, C=S, C=Se, C=NR⁵, P(=O)(R⁵), SO, OC₂, NR⁵, O, S or CONR⁵;
C₁-C₄₀-thioalkoxy,
which is optionally substituted with one or more substituents R⁵ and
wherein one or more non-adjacent CH₂-groups are optionally substituted by R⁵C=CR⁵, C=O, Si(R⁵)₂, Ge(R⁵)₂, Sn(R⁵)₂, C=O, C=S, C=Se, C=NR⁵, P(=O)(R⁵), SO, OC₂, NR⁵, O, S or CONR⁵;
C₂-C₄₀-alkenyl,
which is optionally substituted with one or more substituents R⁵ and
wherein one or more non-adjacent CH₂-groups are optionally substituted by R⁵C=CR⁵, C=C, Si(R⁵)₂, Ge(R⁵)₂, Sn(R⁵)₂, C=O, C=S, C=Se, C=NR⁵, P(=O)(R⁵), SO, OC₂, NR⁵, O, S or CONR⁵;
C₂-C₄₀-alkynyl,
which is optionally substituted with one or more substituents R⁵ and
wherein one or more non-adjacent CH₂-groups are optionally substituted by R⁵C=CR⁵, C=C, Si(R⁵)₂, Ge(R⁵)₂, Sn(R⁵)₂, C=O, C=S, C=Se, C=NR⁵, P(=O)(R⁵), SO, OC₂, NR⁵, O, S or CONR⁵;
C₆-C₆₀-aryl,
which is optionally substituted with one or more substituents R⁵; and
C₃-C₅₇-heteroaryl,
which is optionally substituted with one or more substituents R⁵.

Apart from that, the aforementioned definitions apply.

In another embodiment of the invention, each of the two second chemical moieties at each occurrence, independently from another, comprise or consist of a structure of Formula IIc, a structure of Formula IIc-2, a structure of Formula IIc-3 or a structure of Formula IIc-4:

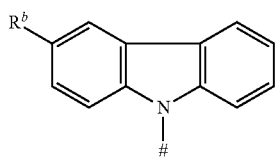

Formula IIc

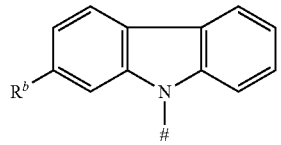

Formula IIc-2

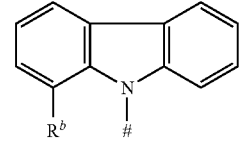

Formula IIc-3

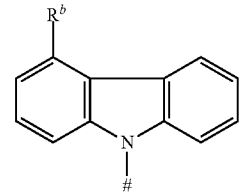

Formula IIc-4 wherein the aforementioned definitions apply.

In a further embodiment of the invention, R^b is at each occurrence independently from another selected from the group consisting of:
Me,
^iPr,
^tBu,
CN,
CF₃,
Ph, which is optionally substituted with one or more substituents independently from each other selected from the group consisting of Me, ^iPr, ^tBu, CN, CF₃, and Ph,
pyridinyl, which is optionally substituted with one or more substituents independently from each other selected from the group consisting of Me, ^iPr, ^tBu, CN, CF₃, and Ph,
carbazolyl, which is optionally substituted with one or more substituents independently from each other selected from the group consisting of Me, ^iPr, ^tBu, CN, CF₃, and Ph,
triazinyl, which is optionally substituted with one or more substituents independently from each other selected from the group consisting of Me, ^iPr, ^tBu, CN, CF₃, and Ph; and
N(Ph)₂.

In a further embodiment of the invention, R^b is at each occurrence independently from another selected from the group consisting of:
Me,
^iPr,
^tBu,
CN,
CF₃,
Ph, which is optionally substituted with one or more substituents independently from each other selected from the group consisting of Me, ^iPr, ^tBu, CN, CF₃, and Ph,
pyridinyl, which is optionally substituted with one or more substituents independently from each other selected from the group consisting of Me, ^iPr, ^tBu, CN, CF₃, and Ph,
pyrimidinyl, which is optionally substituted with one or more substituents independently from each other selected from the group consisting of Me, ^iPr, ^tBu, CN, CF₃, and Ph, and
triazinyl, which is optionally substituted with one or more substituents independently from each other selected from the group consisting of Me, ^iPr, ^tBu, CN, CF₃, and Ph.

In a further embodiment of the invention, $R^b$ is at each occurrence independently from another selected from the group consisting of:

Me, $^t$Bu,

Ph, which is optionally substituted with one or more substituents independently from each other selected from the group consisting of Me, $^i$Pr, $^t$Bu, CN, CF$_3$, and Ph, triazinyl, which is optionally substituted with one or more substituents independently from each other selected from the group consisting of Me, $^i$Pr, $^t$Bu, CN, CF$_3$, and Ph.

In the following, exemplary embodiments of the second chemical moiety are shown:

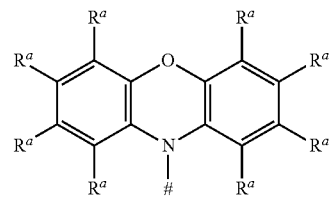

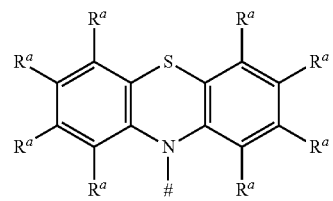

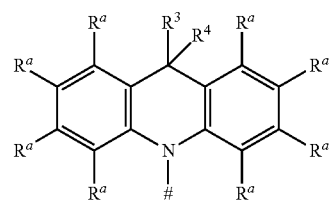

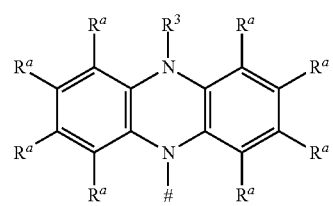

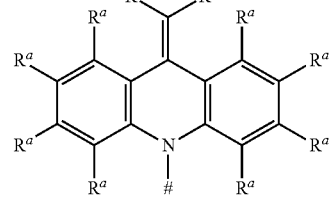

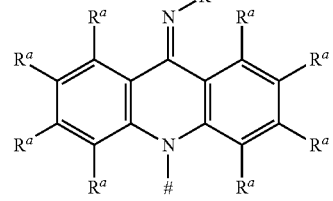

-continued

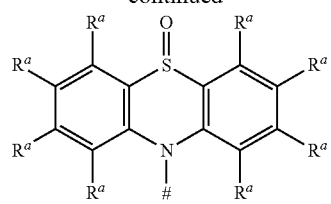

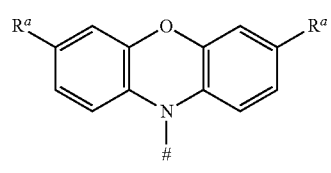

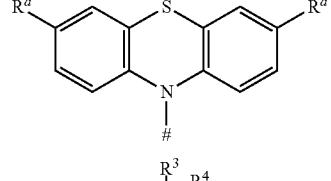

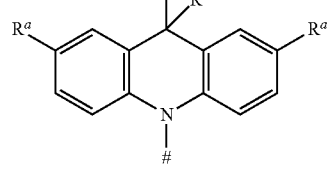

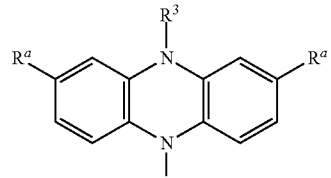

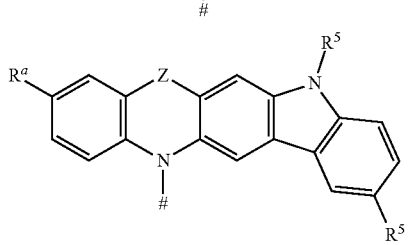

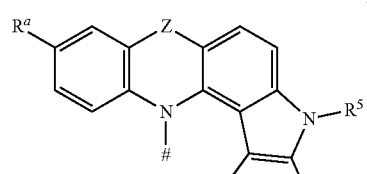

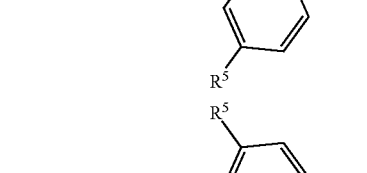

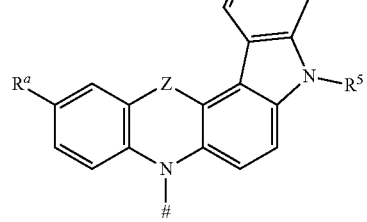

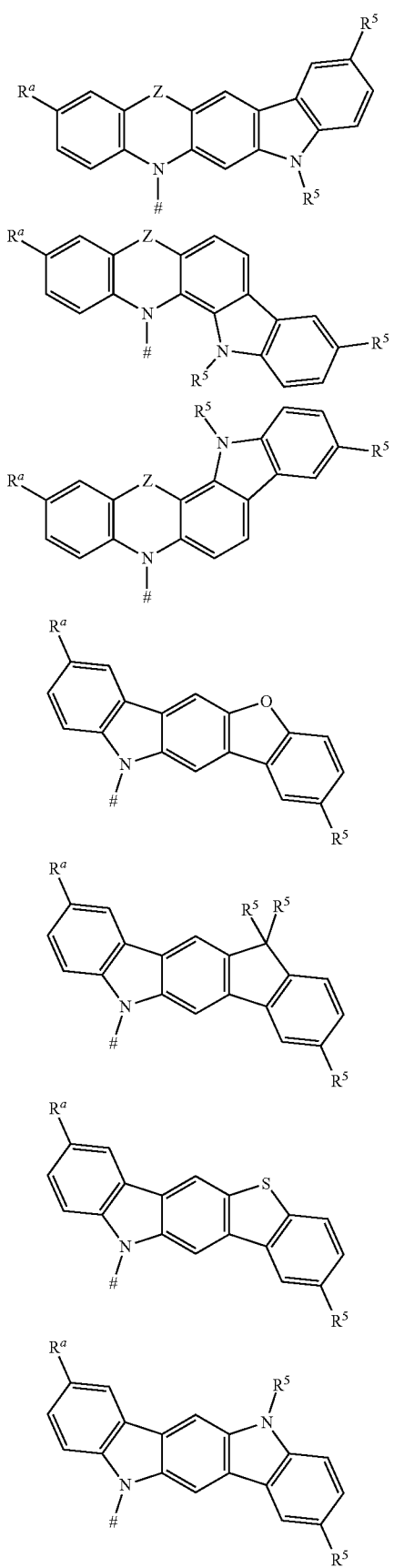
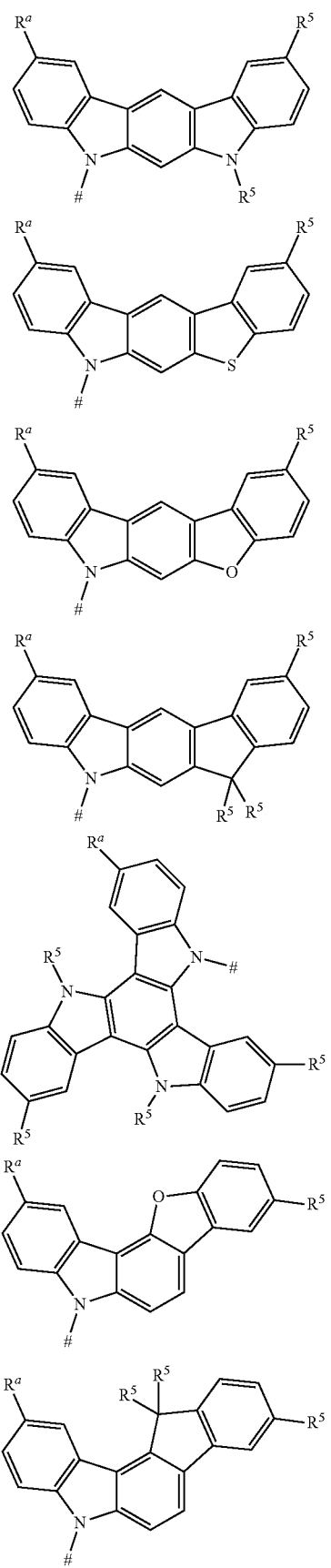

-continued
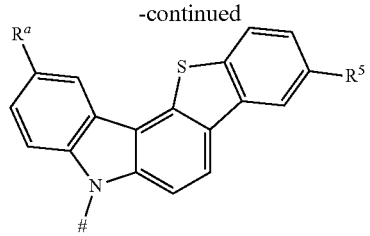
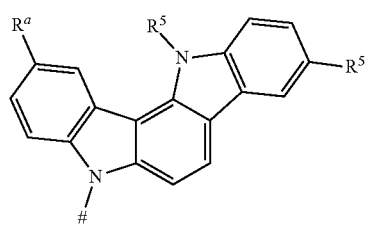
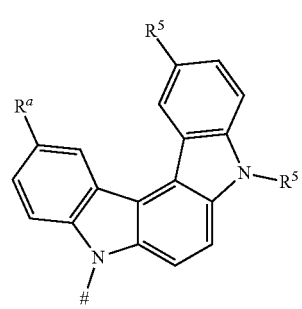
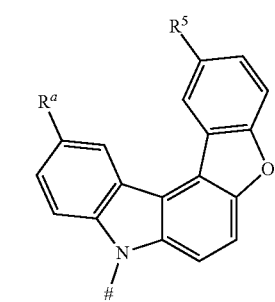
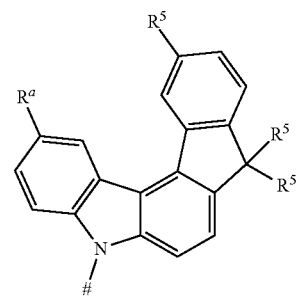
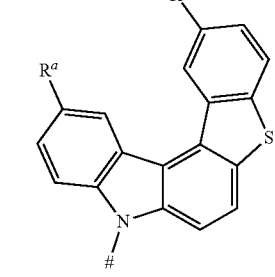
-continued
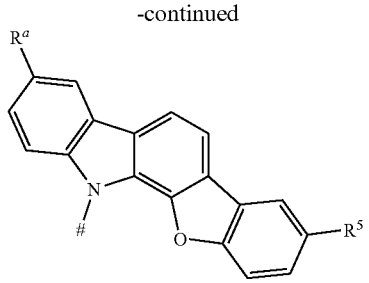
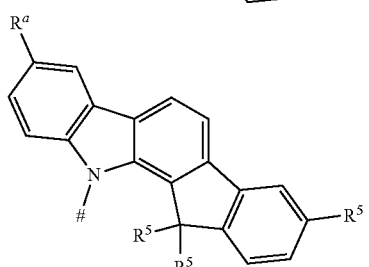
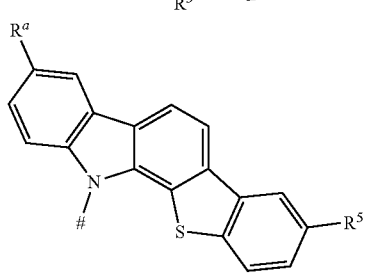
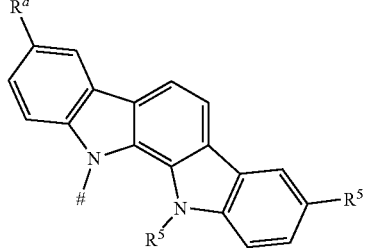
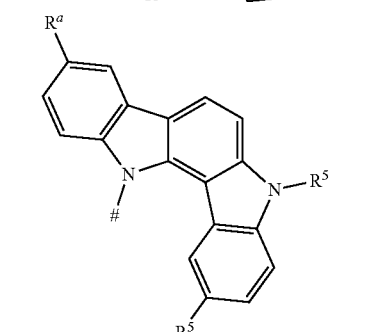
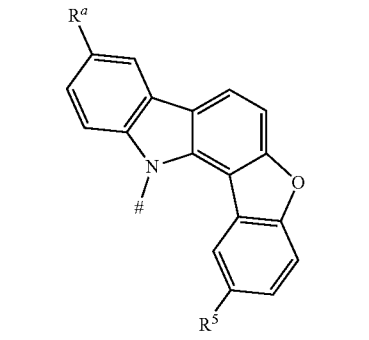

-continued

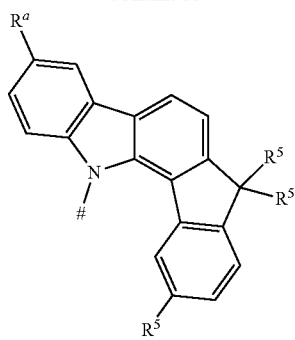

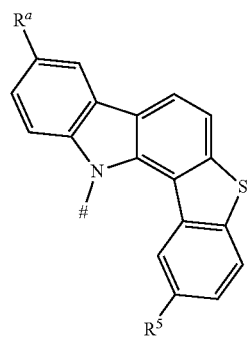

wherein for #, Z, $R^a$, $R^3$, $R^4$ and $R^5$, the aforementioned definitions apply.

In one embodiment, $R^a$ and $R^5$ is at each occurrence independently from another selected from the group consisting of hydrogen (H), methyl (Me), i-propyl ($CH(CH_3)_2$) ($^i$Pr), t-butyl ($^t$Bu), phenyl (Ph), CN, $CF_3$, and diphenylamine ($NPh_2$).

In one embodiment of the invention, the organic molecules comprise or consist of a structure of Formula IIIA or Formula IIIB:

Formula IIIA

Formula IIIB

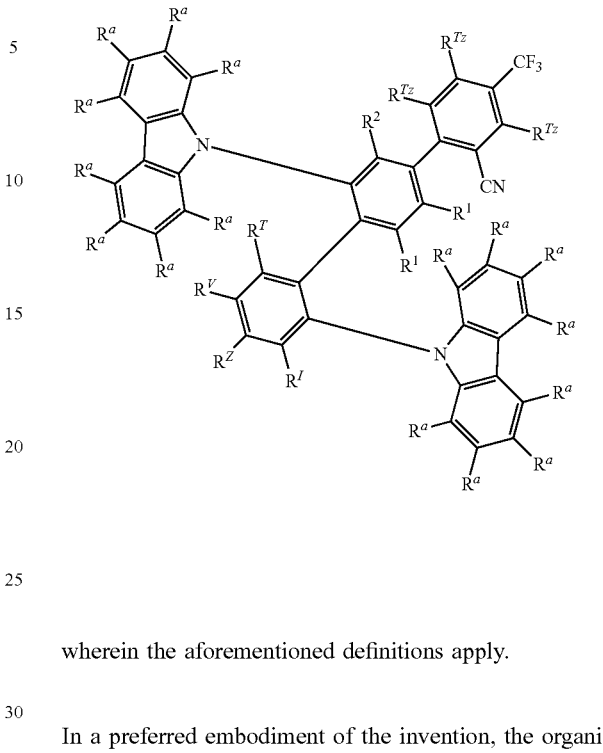

wherein the aforementioned definitions apply.

In a preferred embodiment of the invention, the organic molecules comprise or consist of a structure of Formula IIIA and $R^V$ is CN.

In a further embodiment of the invention, the organic molecules comprise or consist of a structure selected from the group of Formula III-1 and Formula III-2:

Formula III-1

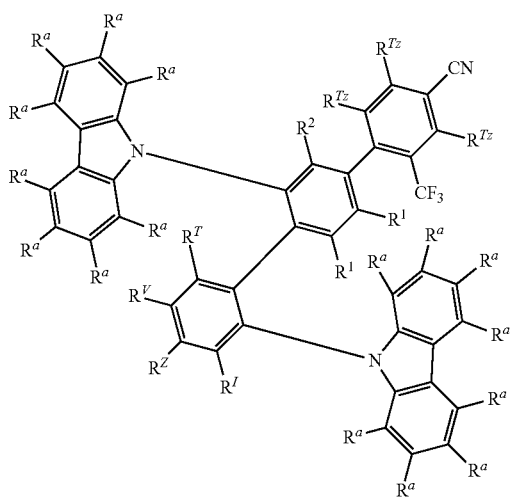

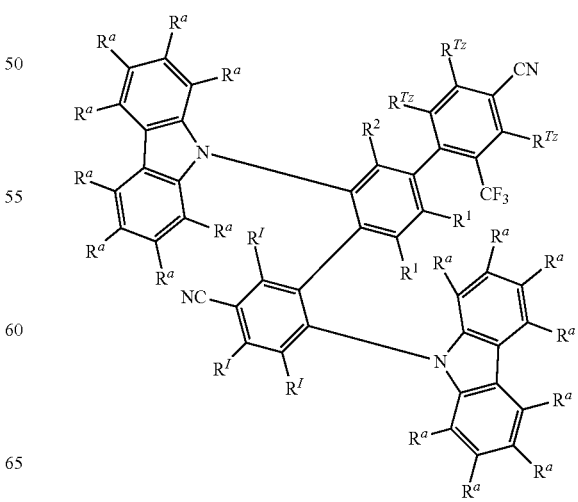

-continued

Formula III-2

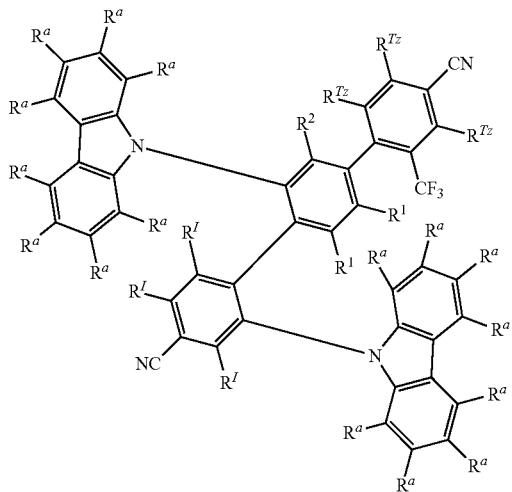

wherein the aforementioned definitions apply.

In a further embodiment of the invention, the organic molecules comprise or consist of a structure selected from the group of Formula IIIa-1 and Formula IIIa-2:

Formula IIIa-1

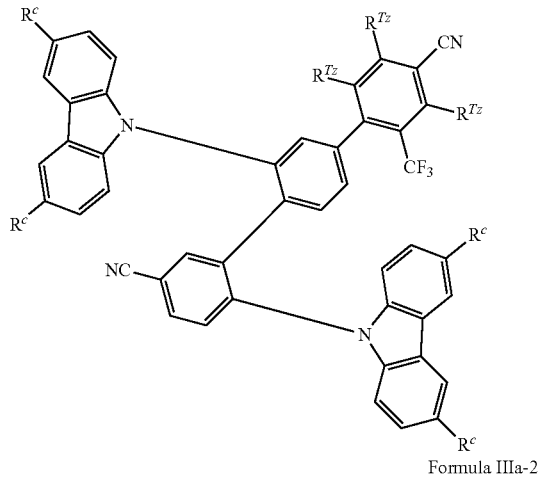

Formula IIIa-2

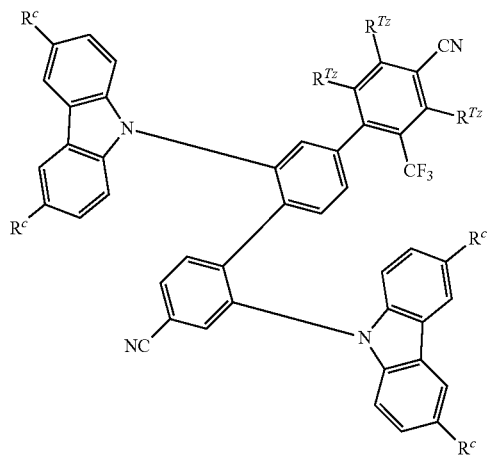

wherein $R^c$ is at each occurrence independently from another selected from the group consisting of:

Me,
$^i$Pr,
$^t$Bu,
Ph, which is optionally substituted with one or more substituents independently from each other selected from the group consisting of Me, $^i$Pr, $^t$Bu, CN, $CF_3$, and Ph,
pyridinyl, which is optionally substituted with one or more substituents independently from each other selected from the group consisting of Me, $^i$Pr, $^t$Bu, CN, $CF_3$, and Ph,
pyrimidinyl, which is optionally substituted with one or more substituents independently from each other selected from the group consisting of Me, $^i$Pr, $^t$Bu, CN, $CF_3$, and Ph,
carbazolyl, which is optionally substituted with one or more substituents independently from each other selected from the group consisting of Me, $^i$Pr, $^t$Bu, CN, $CF_3$, and Ph,
triazinyl, which is optionally substituted with one or more substituents independently from each other selected from the group consisting of Me, $^i$Pr, $^t$Bu, CN, $CF_3$, and Ph;
and $N(Ph)_2$.

In a preferred embodiment of the invention, the organic molecules comprise or consist of a structure of Formula IIIa-1.

In a further embodiment of the invention, the organic molecules comprise or consist of a structure selected from the group of Formula IIIb-1 and Formula IIIb-2:

Formula IIIb-1

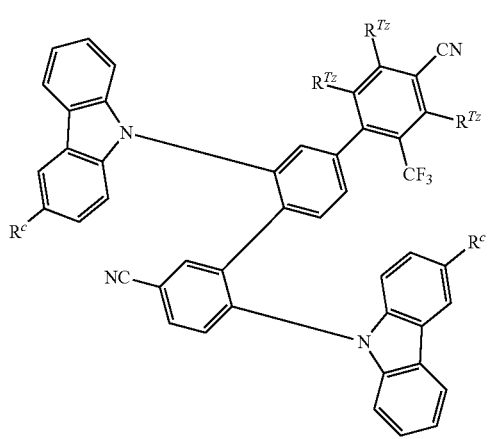

Formula IIIb-2

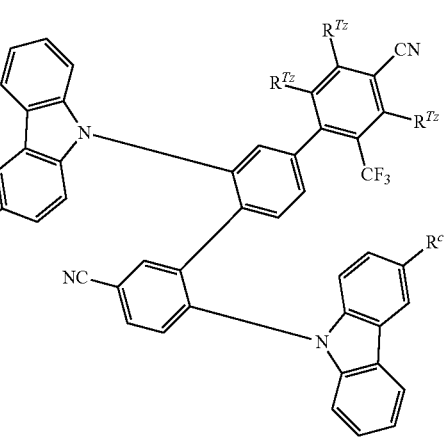

wherein the aforementioned definitions apply.

In a preferred embodiment of the invention, the organic molecules comprise or consist of a structure of Formula IIIb-1.

In a further embodiment of the invention, the organic molecules comprise or consist of a structure selected from the group of Formula IIIc-1 and Formula IIIc-2:

Formula IIIc-1

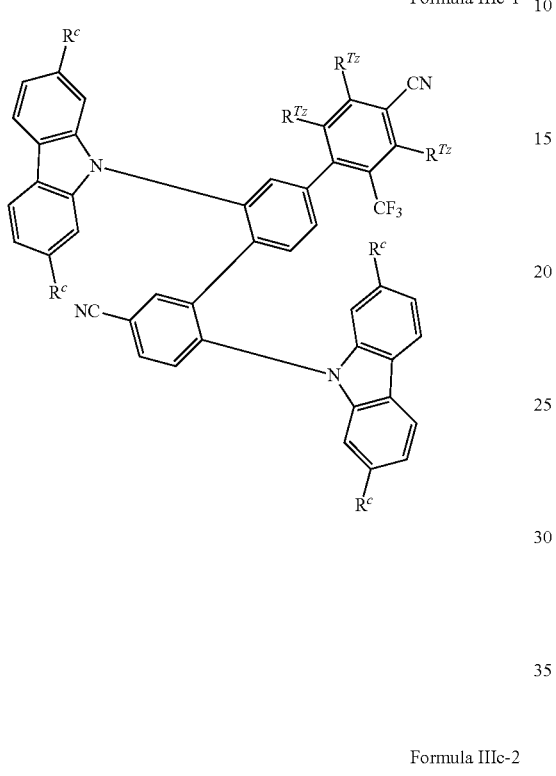

Formula IIIc-2

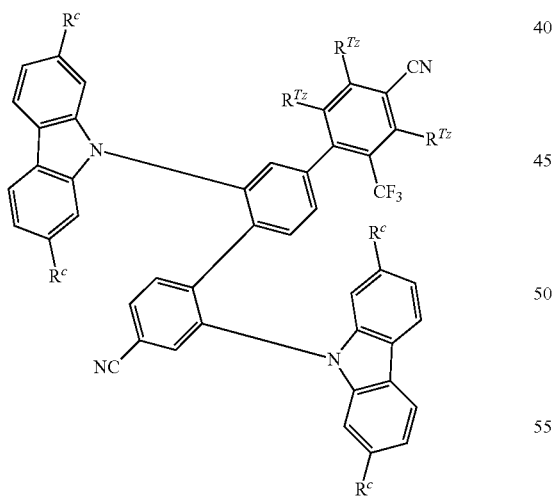

wherein the aforementioned definitions apply.

In a preferred embodiment of the invention, the organic molecules comprise or consist of a structure of Formula IIIc-1.

In a further embodiment of the invention, the organic molecules comprise or consist of a structure selected from the group of Formula IIId-1 and Formula IIId-2:

Formula IIId-1

Formula IIId-2

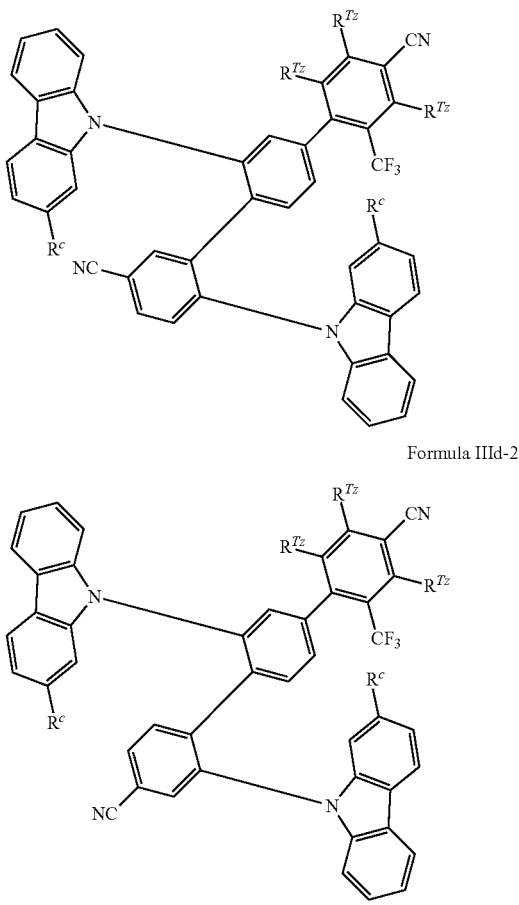

wherein the aforementioned definitions apply.

In a preferred embodiment of the invention, the organic molecules comprise or consist of a structure of Formula IIId-1.

In one embodiment of the invention, the organic molecules comprise or consist of a structure of Formula IVA or Formula IVB:

Formula IVA

-continued

Formula IVB

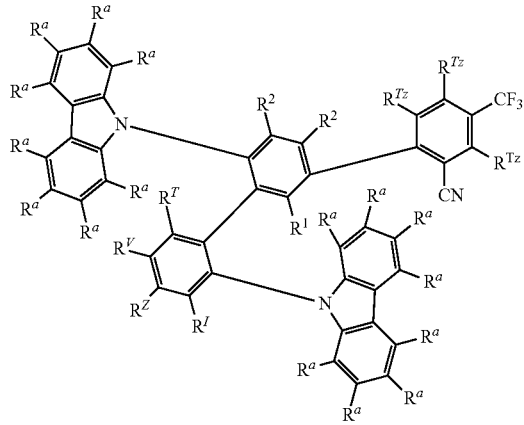

wherein the aforementioned definitions apply.

In a preferred embodiment of the invention, the organic molecules comprise or consist of a structure of Formula IVA and $R^V$ is CN.

In a further embodiment of the invention, the organic molecules comprise or consist of a structure selected from the group of Formula IV-1 and Formula IV-2:

Formula IV-1

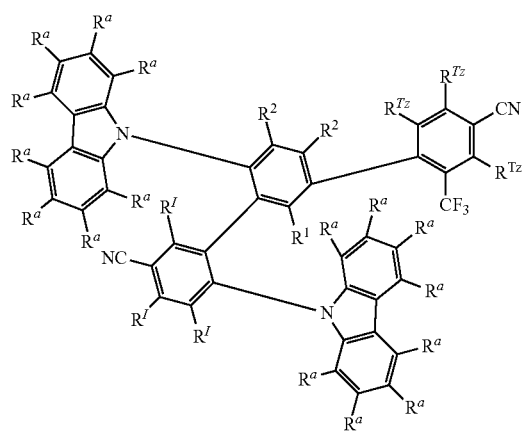

Formula IV-2

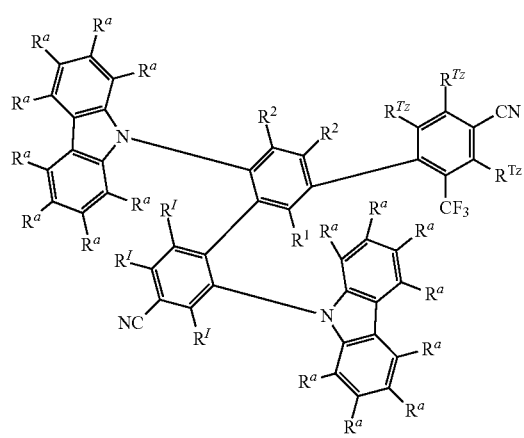

wherein the aforementioned definitions apply.

In a further embodiment of the invention, the organic molecules comprise or consist of a structure selected from the group of Formula IVa-1 and Formula IVa-2:

Formula IVa-1

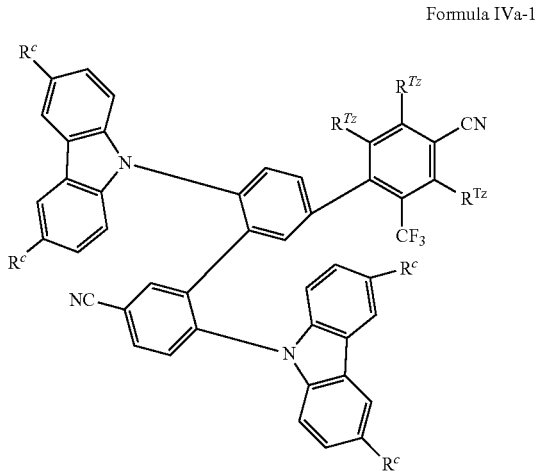

Formula IVa-2

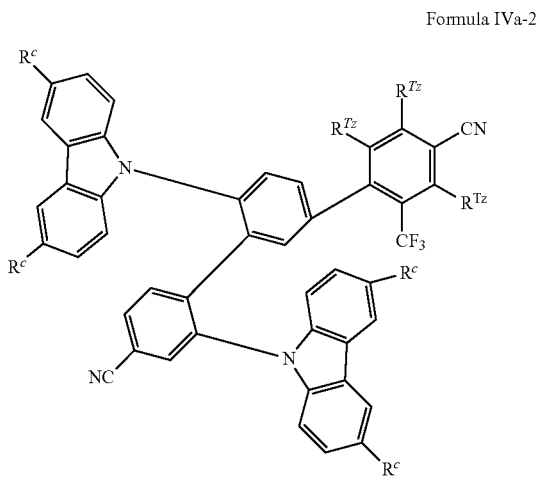

wherein the aforementioned definitions apply.

In a preferred embodiment of the invention, the organic molecules comprise or consist of a structure of Formula IVa-1.

In a further embodiment of the invention, the organic molecules comprise or consist of a structure selected from the group of Formula IVb-1 and Formula IVb-2:

Formula IVb-1

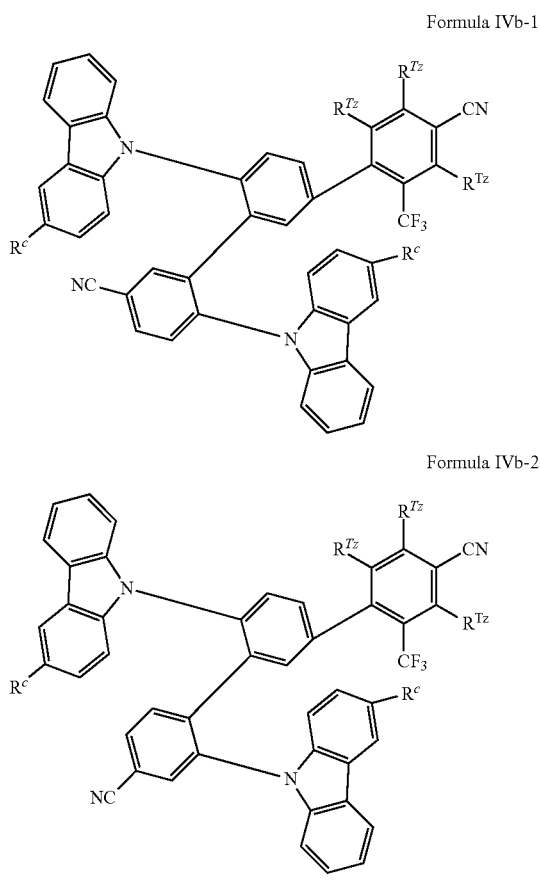

Formula IVb-2

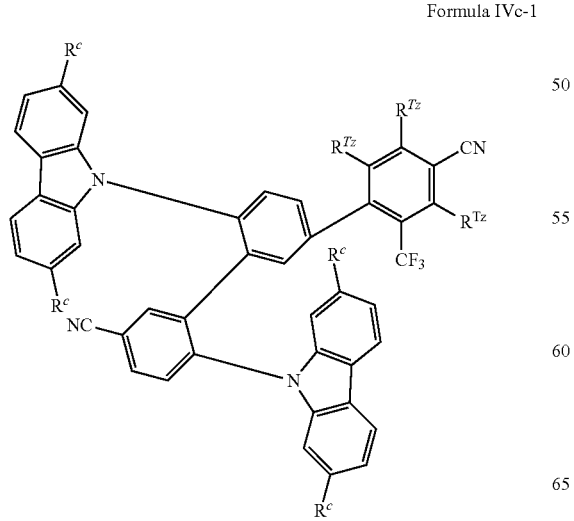

wherein the aforementioned definitions apply.

In a preferred embodiment of the invention, the organic molecules comprise or consist of a structure of Formula IVb-1.

In a further embodiment of the invention, the organic molecules comprise or consist of a structure selected from the group of Formula IVc-1 and Formula IVc-2:

Formula IVc-1

Formula IVc-2

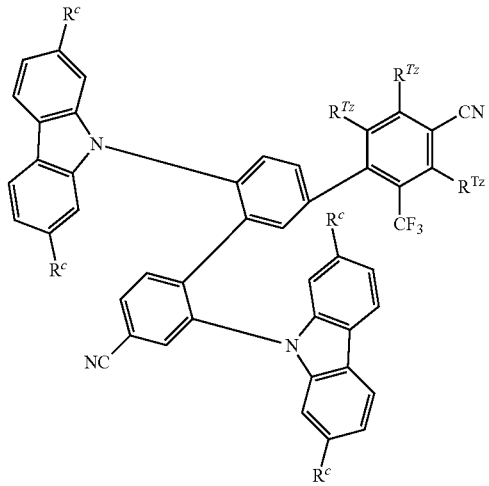

wherein the aforementioned definitions apply.

In a preferred embodiment of the invention, the organic molecules comprise or consist of a structure of Formula IVc-1.

In a further embodiment of the invention, the organic molecules comprise or consist of a structure selected from the group of Formula IVd-1 and Formula IVd-2:

Formula IVd-1

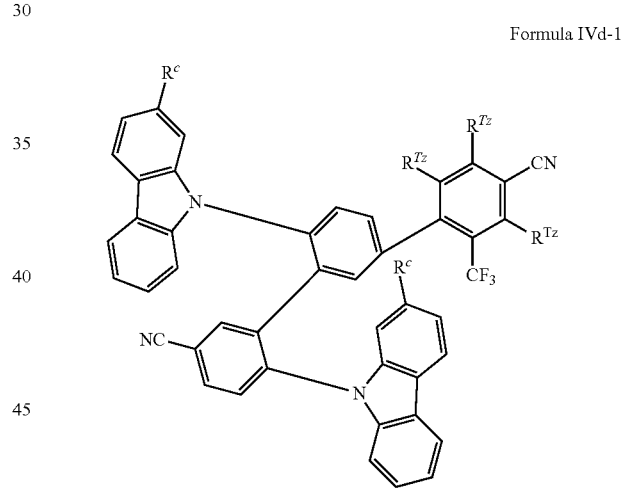

Formula IVd-2

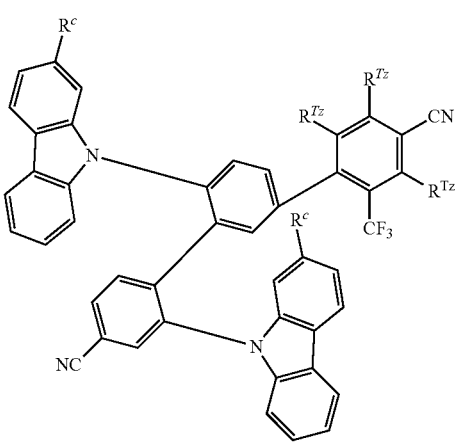

wherein the aforementioned definitions apply.

In a preferred embodiment of the invention, the organic molecules comprise or consist of a structure of Formula IVd-1.

In one embodiment of the invention, the organic molecules comprise or consist of a structure of Formula VA or Formula VB:

Formula VA

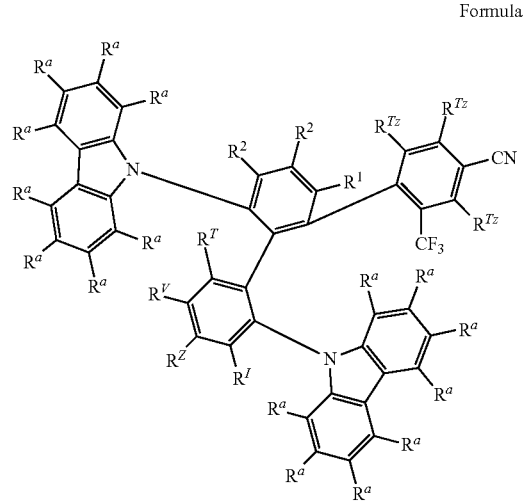

Formula VB

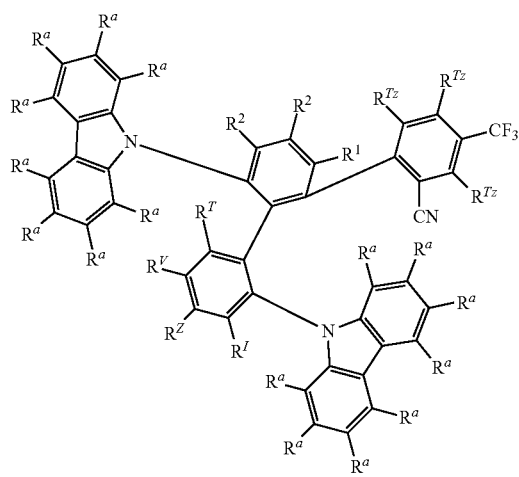

wherein the aforementioned definitions apply and wherein exactly one substituent selected from the group consisting of $R^T$, $R^V$ and $R^Z$ is CN.

In a preferred embodiment of the invention, the organic molecules comprise or consist of a structure of Formula VA and $R^V$ is CN.

In a further embodiment of the invention, the organic molecules comprise or consist of a structure selected from the group of Formula V-1 and Formula V-2:

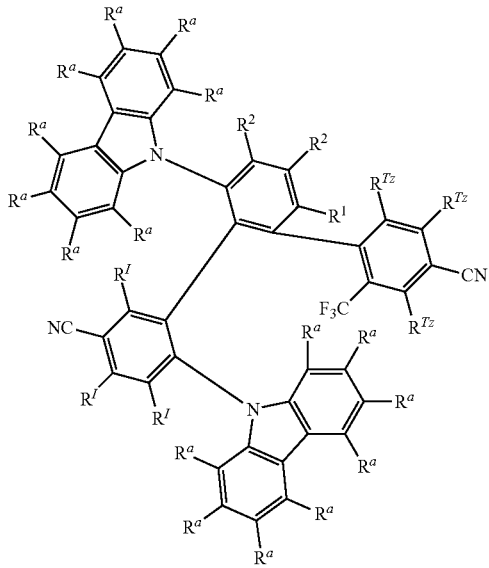

wherein the aforementioned definitions apply.

In one embodiment of the invention, the organic molecules comprise or consist of a structure of Formula VIA or Formula VIB:

Formula VIA

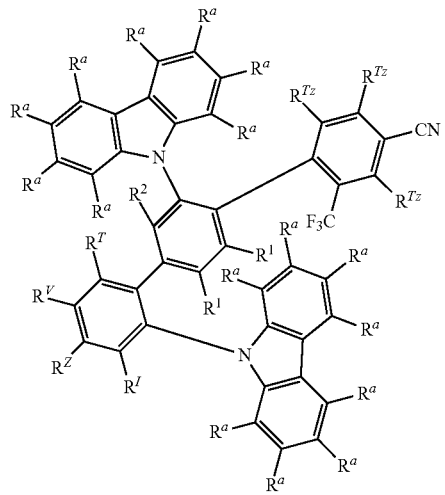

In one embodiment of the invention, the organic molecules comprise or consist of a structure of Formula VIIA or Formula VIIB:

Formula VIIA

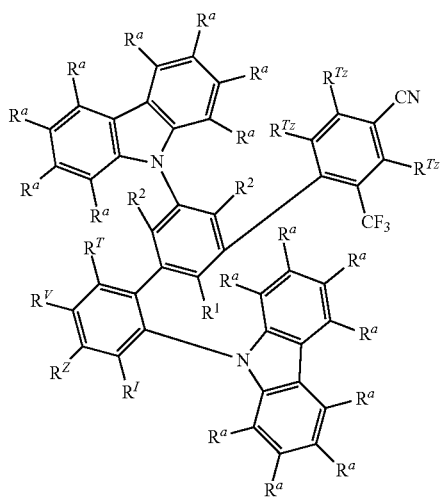

Formula VIB

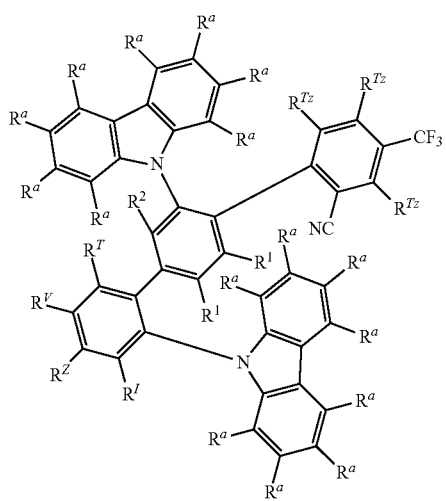

Formula VIIB

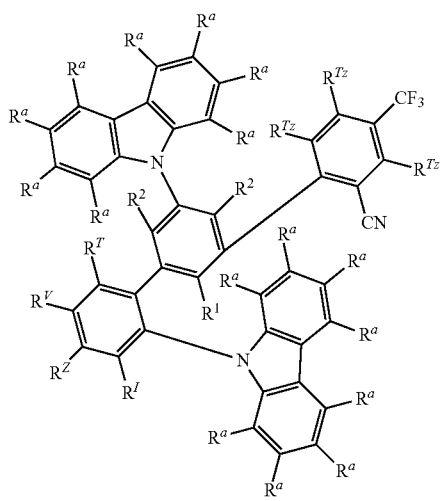

wherein the aforementioned definitions apply.

In another embodiment of the invention, the organic molecules comprise or consist of a structure of Formula VIA and $R^V$ is CN.

wherein the aforementioned definitions apply and wherein exactly one substituent selected from the group consisting of $R^T$, $R^V$ and $R^Z$ is CN.

In another embodiment of the invention, the organic molecules comprise or consist of a structure of Formula VIIA and $R^V$ is CN.

In one embodiment of the invention, the organic molecules comprise or consist of a structure of Formula VIIIA or Formula VIIIB:

Formula VIIIA

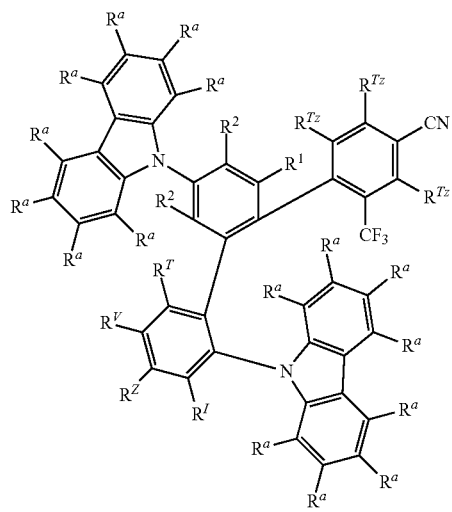

In one embodiment of the invention, the organic molecules comprise or consist of a structure of Formula IXA or Formula IXB:

Formula IXA

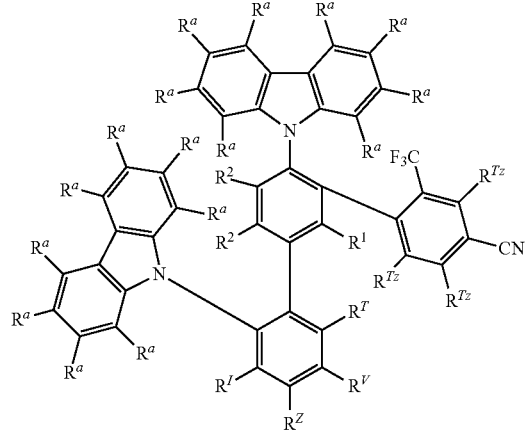

Formula VIIIB

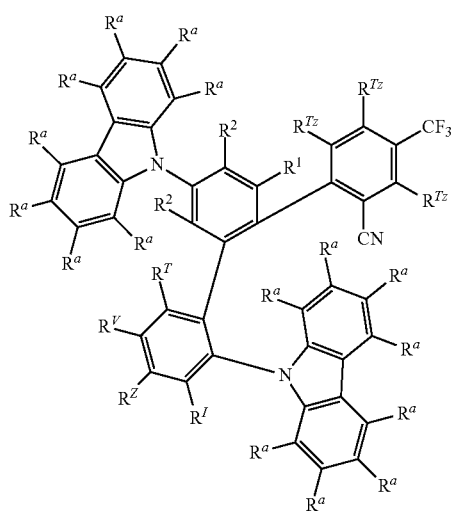

Formula IXB

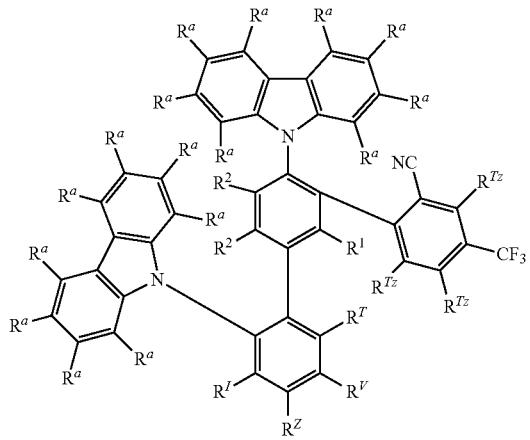

wherein the aforementioned definitions apply and wherein exactly one substituent selected from the group consisting of $R^T$, $R^V$ and $R^Z$ is CN.

In another embodiment of the invention, the organic molecules comprise or consist of a structure of Formula VIIIA and $R^V$ is CN.

wherein the aforementioned definitions apply and wherein exactly one substituent selected from the group consisting of $R^T$, $R^V$ and $R^Z$ is CN.

In another embodiment of the invention, the organic molecules comprise or consist of a structure of Formula IXA and $R^V$ is CN.

In one embodiment of the invention, the organic molecules comprise or consist of a structure of Formula XA or Formula XB:

Formula XA

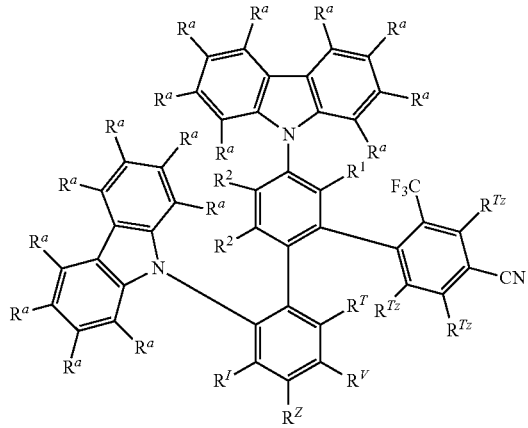

In one embodiment of the invention, the organic molecules comprise or consist of a structure of Formula XIA or Formula XIB:

Formula XIA

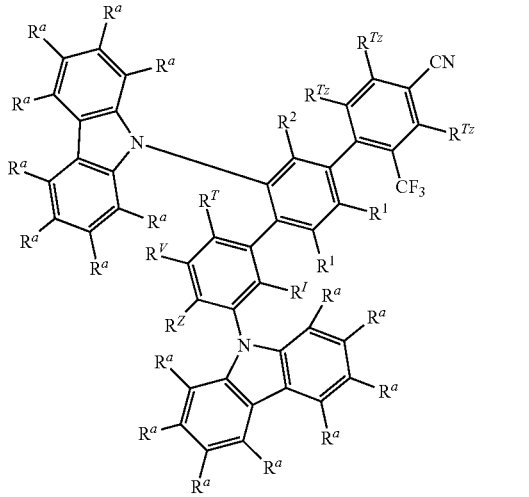

Formula XB

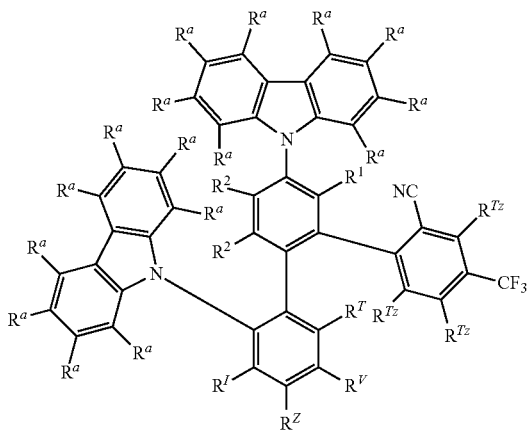

Formula XIB

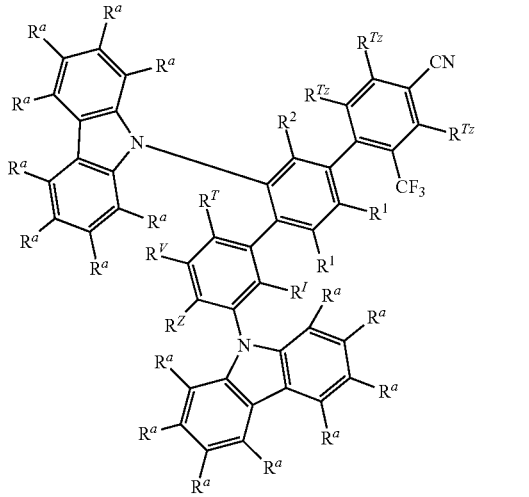

wherein the aforementioned definitions apply and wherein exactly one substituent selected from the group consisting of $R^T$, $R^V$ and $R^Z$ is CN.

In another embodiment of the invention, the organic molecules comprise or consist of a structure of Formula XA and $R^V$ is CN.

wherein the aforementioned definitions apply, and wherein exactly one substituent selected from the group consisting of $R^V$, $R^T$ and $R^Z$ is CN.

In another embodiment of the invention, the organic molecules comprise or consist of a structure of Formula XIA and $R^T$ is CN.

In one embodiment of the invention, the organic molecules comprise or consist of a structure of Formula XIIA or Formula XIIB:

Formula XIIA

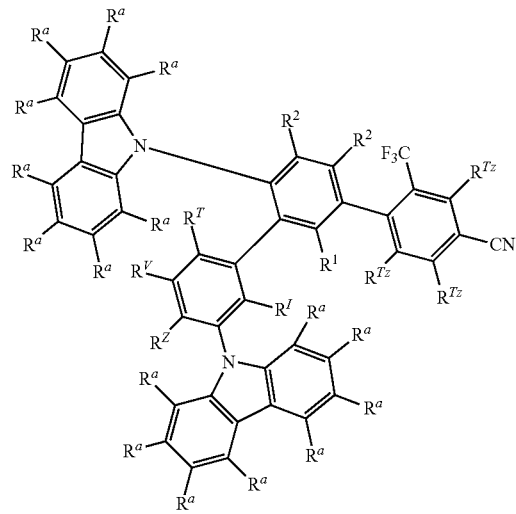

In one embodiment of the invention, the organic molecules comprise or consist of a structure of Formula XIIIA or Formula XIIIB:

Formula XXIIIA

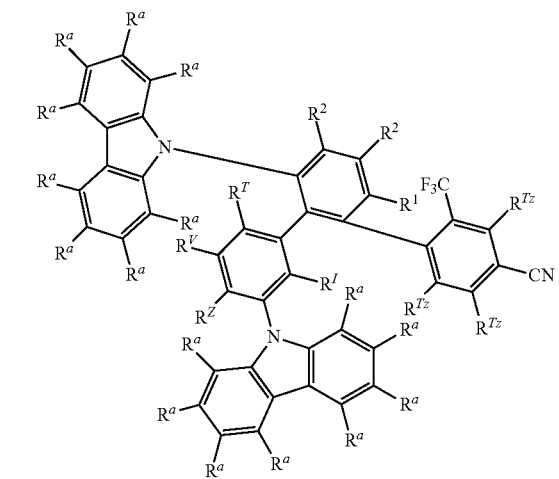

Formula XIIB

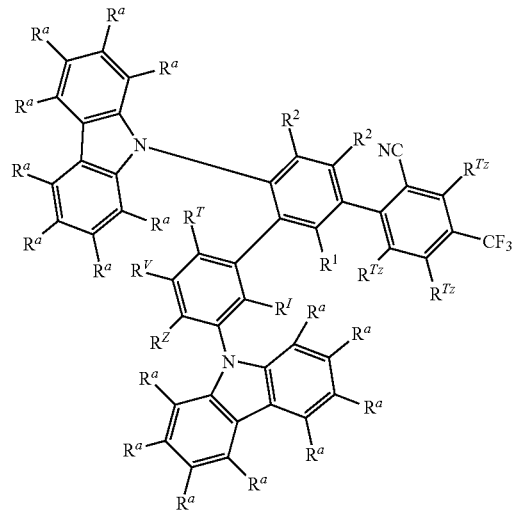

Formula XIIIB wherein the aforementioned definitions apply, and wherein exactly one substituent selected from the group consisting of $R^V$, $R^T$ and $R^Z$ is CN.

In another embodiment of the invention, the organic molecules comprise or consist of a structure of Formula XIIA and $R^T$ is CN.

wherein the aforementioned definitions apply, and wherein exactly one substituent selected from the group consisting of $R^V$, $R^T$ and $R^Z$ is CN.

In another embodiment of the invention, the organic molecules comprise or consist of a structure of Formula XIIIA and $R^T$ is CN.

In one embodiment of the invention, the organic molecules comprise or consist of a structure of Formula XIVA or Formula XIVB:

Formula XIVA

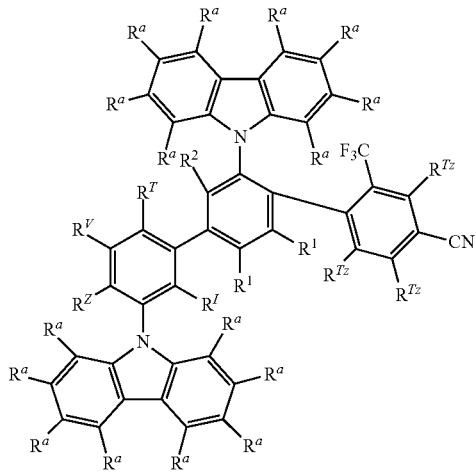

In one embodiment of the invention, the organic molecules comprise or consist of a structure of Formula XVA or Formula XVB:

Formula XVA

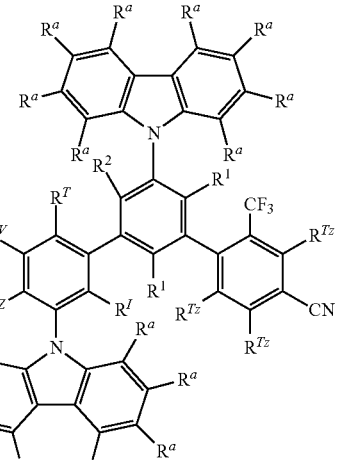

Formula XIVB

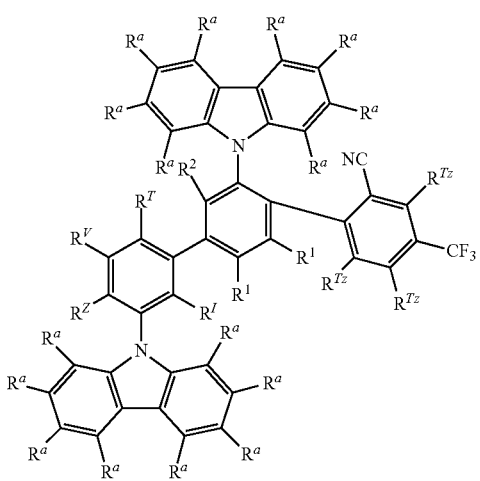

Formula XVB

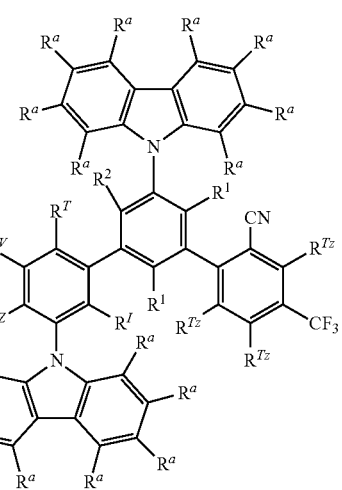

wherein the aforementioned definitions apply, and wherein exactly one substituent selected from the group consisting of $R^V$, $R^T$ and $R^Z$ is CN.

In another embodiment of the invention, the organic molecules comprise or consist of a structure of Formula XIVA and $R^T$ is CN.

wherein the aforementioned definitions apply, and wherein exactly one substituent selected from the group consisting of $R^V$, $R^T$ and $R^Z$ is CN.

In another embodiment of the invention, the organic molecules comprise or consist of a structure of Formula XVA and $R^T$ is CN.

In one embodiment of the invention, the organic molecules comprise or consist of a structure of Formula XVIA or Formula XVIB:

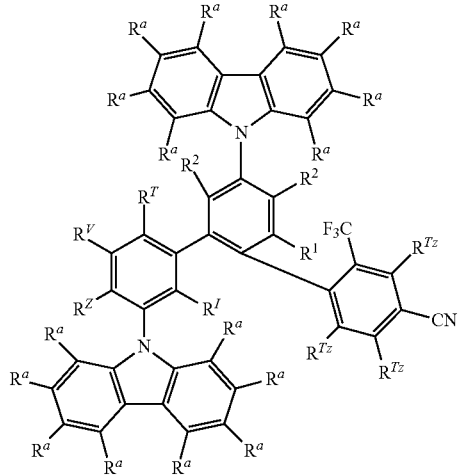

Formula XVIA

In one embodiment of the invention, the organic molecules comprise or consist of a structure of Formula XVIIA or Formula XVIIB:

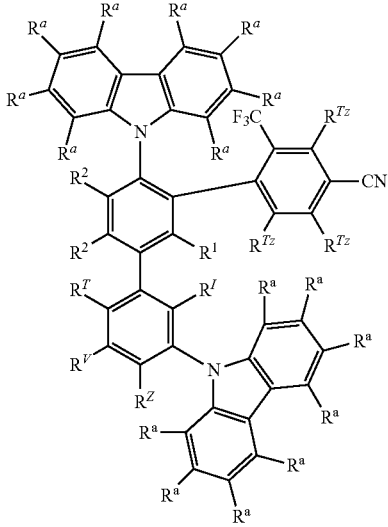

Formula XVIIA

Formula XVIIB

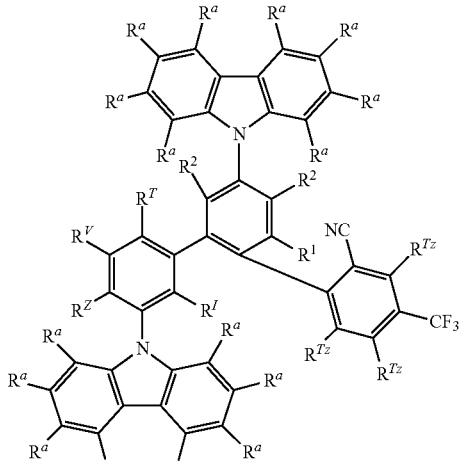

Formula XVIB wherein the aforementioned definitions apply, and wherein exactly one substituent selected from the group consisting of $R^V$, $R^T$ and $R^Z$ is CN.

In another embodiment of the invention, the organic molecules comprise or consist of a structure of Formula XVIA and $R^T$ is CN.

wherein the aforementioned definitions apply, and wherein exactly one substituent selected from the group consisting of $R^V$, $R^T$ and $R^Z$ is CN.

In another embodiment of the invention, the organic molecules comprise or consist of a structure of Formula XVIIA and $R^T$ is CN.

In one embodiment of the invention, the organic molecules comprise or consist of a structure of Formula XVIIIA or Formula XVIIIB:

Formula XVIIIA

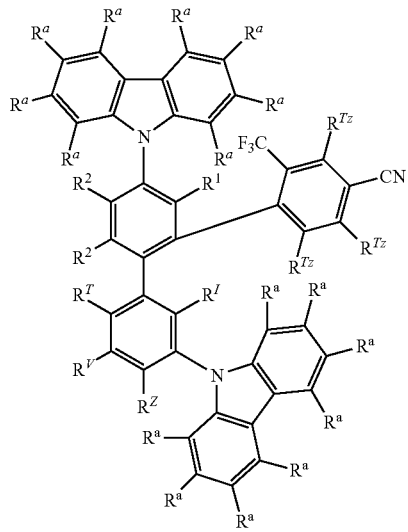

Formula XVIIIB

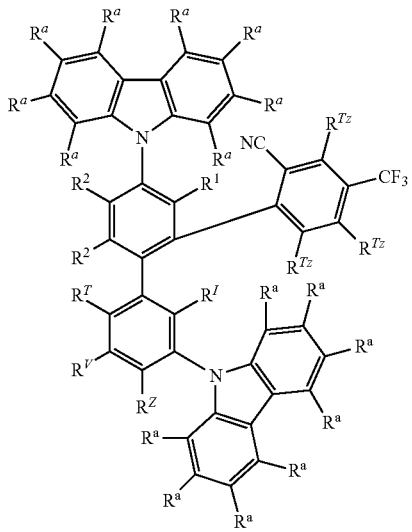

wherein the aforementioned definitions apply, and wherein exactly one substituent selected from the group consisting of $R^V$, $R^T$ and $R^Z$ is CN.

In another embodiment of the invention, the organic molecules comprise or consist of a structure of Formula XVIIIA and $R^T$ is CN.

In one embodiment of the invention, the organic molecules comprise or consist of a structure of Formula XIXA or Formula XIXB:

Formula XIXA

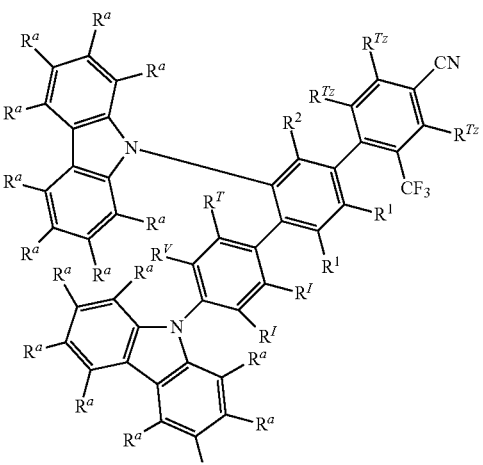

Formula XIXB

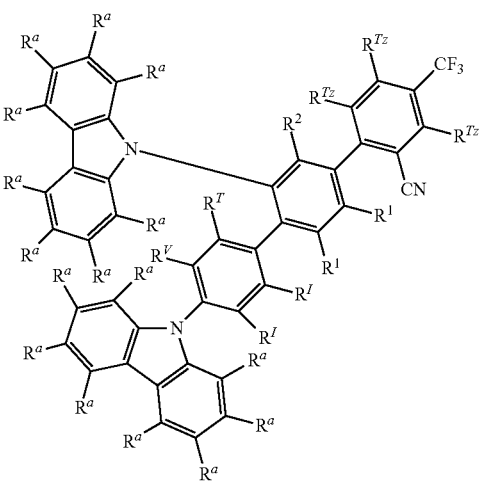

wherein the aforementioned definitions apply, and wherein exactly one substituent selected from the group consisting of $R^V$ and $R^T$ is CN.

In another embodiment of the invention, the organic molecules comprise or consist of a structure of Formula XIXA and $R^T$ is CN.

In one embodiment of the invention, the organic molecules comprise or consist of a structure of Formula XXA or Formula XXB:

Formula XXA

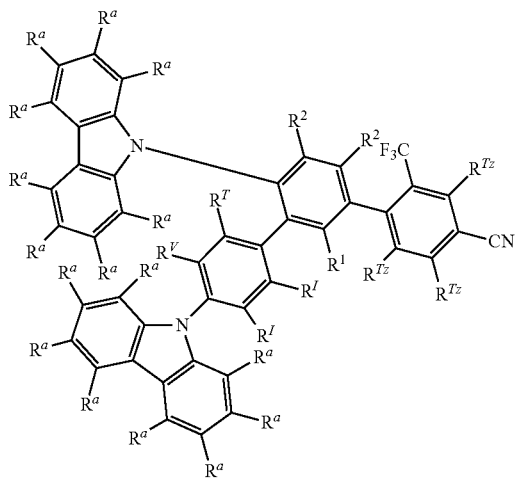

In one embodiment of the invention, the organic molecules comprise or consist of a structure of Formula XXIA or Formula XXIB:

Formula XXIA

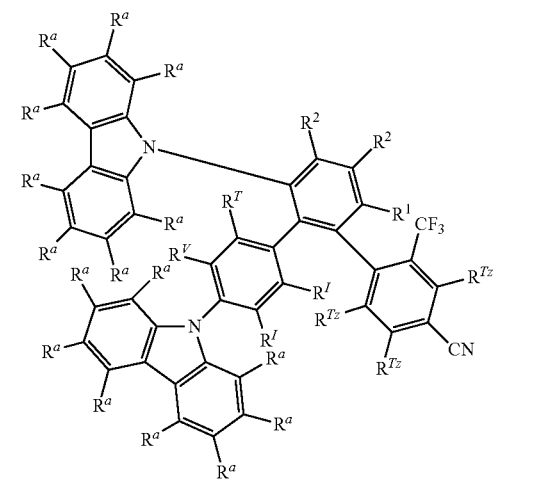

Formula XXB

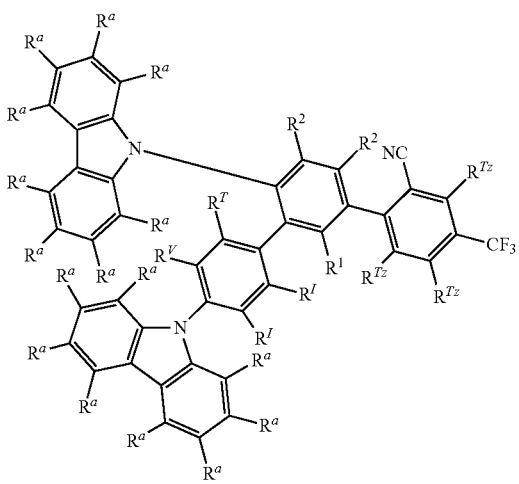

Formula XXIB

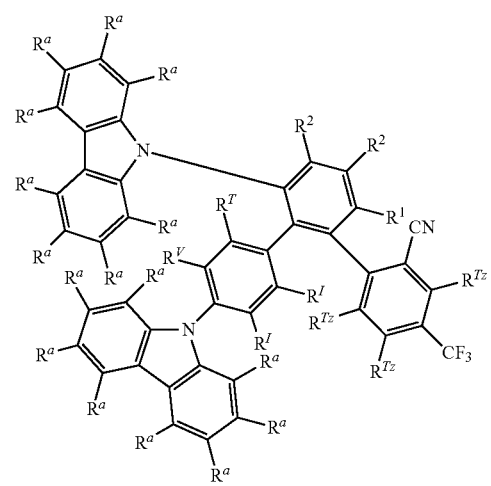

wherein the aforementioned definitions apply,
and wherein exactly one substituent selected from the group consisting of $R^V$ and $R^T$ is CN.

In another embodiment of the invention, the organic molecules comprise or consist of a structure of Formula XXA and $R^T$ is CN.

wherein the aforementioned definitions apply,
and wherein exactly one substituent selected from the group consisting of $R^V$ and $R^T$ is CN.

In another embodiment of the invention, the organic molecules comprise or consist of a structure of Formula XXIA and $R^T$ is CN.

In one embodiment of the invention, the organic molecules comprise or consist of a structure of Formula XXIIA or Formula XXIIB:

Formula XXIIA

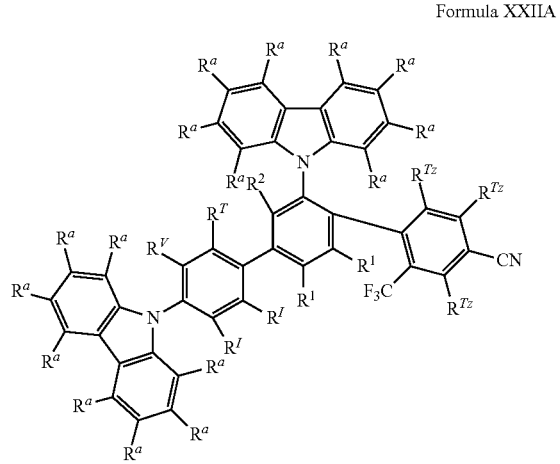

In one embodiment of the invention, the organic molecules comprise or consist of a structure of Formula XXIIIA or of Formula XXIIIB:

Formula XXIIIA

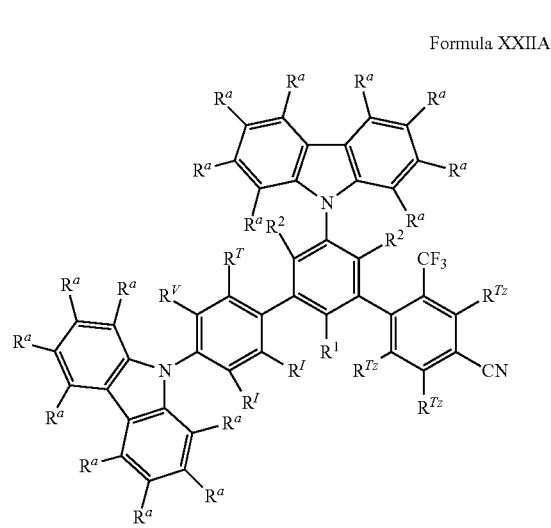

Formula XXIIB

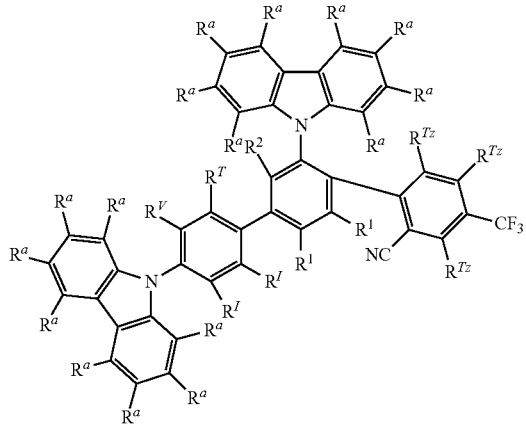

Formula XXIIIB

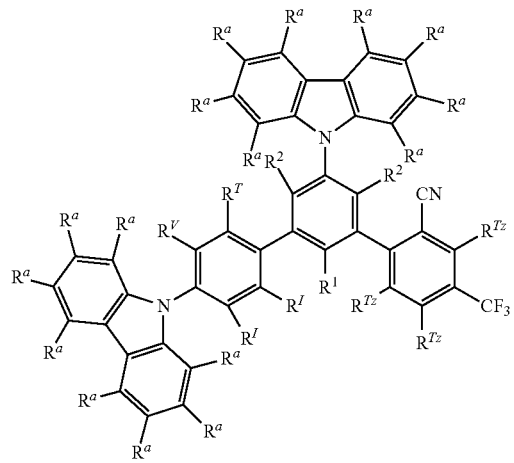

wherein the aforementioned definitions apply, and wherein exactly one substituent selected from the group consisting of $R^V$ and $R^T$ is CN.

In another embodiment of the invention, the organic molecules comprise or consist of a structure of Formula XXIIA and $R^T$ is CN.

wherein the aforementioned definitions apply, and wherein exactly one substituent selected from the group consisting of $R^V$ and $R^T$ is CN.

In another embodiment of the invention, the organic molecules comprise or consist of a structure of Formula XXIIIA and $R^T$ is CN.

In one embodiment of the invention, the organic molecules comprise or consist of a structure of Formula XXIVA or Formula XXIVB:

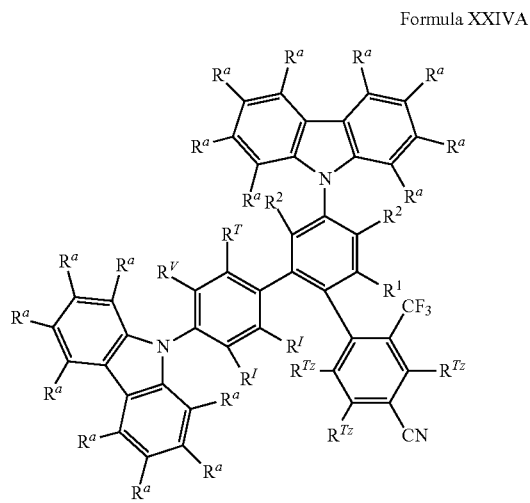

Formula XXIVA

In one embodiment of the invention, the organic molecules comprise or consist of a structure of Formula XXVIIIA or Formula XXVIIIB:

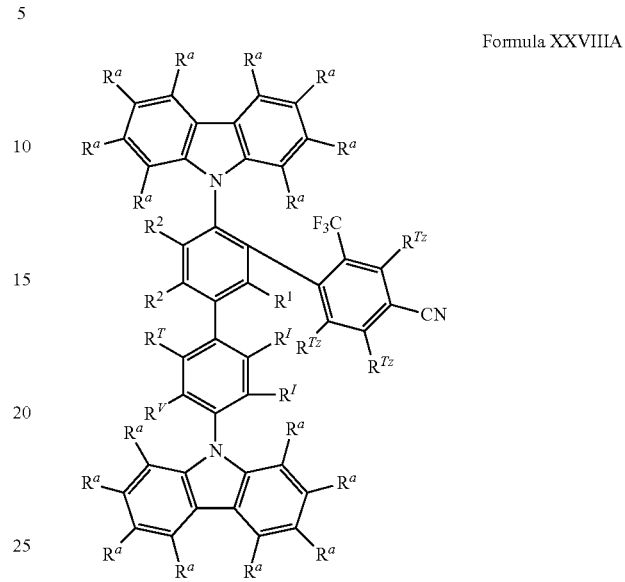

Formula XXVIIIA

Formula XXXVIIIB

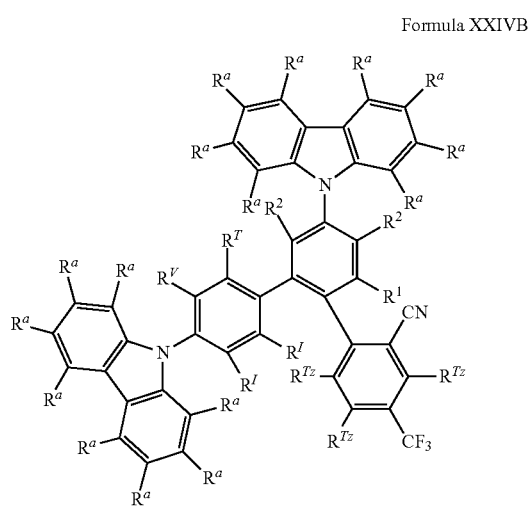

Formula XXIVB wherein the aforementioned definitions apply, and wherein exactly one substituent selected from the group consisting of $R^V$ and $R^T$ is CN.

In another embodiment of the invention, the organic molecules comprise or consist of a structure of Formula XXVIIA and $R^T$ is CN.

wherein the aforementioned definitions apply, and wherein exactly one substituent selected from the group consisting of $R^V$ and $R^T$ is CN.

In another embodiment of the invention, the organic molecules comprise or consist of a structure of Formula XXVIIIA and $R^T$ is CN.

In one embodiment of the invention, the organic molecules comprise or consist of a structure of Formula XXIXA or Formula XXIXB:

Formula XXIXA

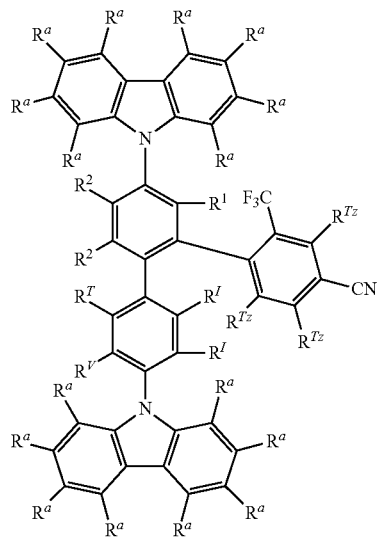

Formula XXIXB

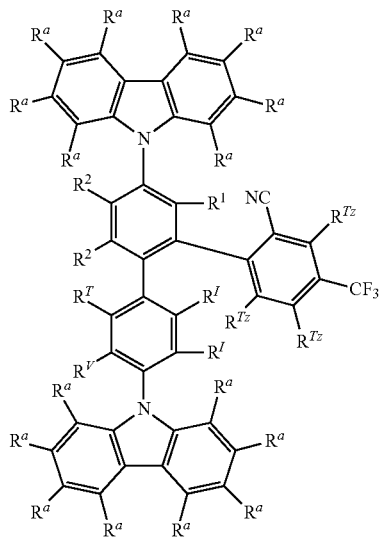

wherein the aforementioned definitions apply,
and wherein exactly one substituent selected from the group consisting of $R^V$ and $R^T$ is CN.

In another embodiment of the invention, the organic molecules comprise or consist of a structure of Formula XXIXA and $R^T$ is CN.

In one embodiment of the invention $R^c$ is at each occurrence independently from another selected from the group consisting of:
Me,
$^iPr$,
$^tBu$,
Ph, which is optionally substituted with one or more substituents independently from each other selected from the group consisting of Me, $^iPr$, $^tBu$, CN, $CF_3$ and Ph; and
triazinyl, which is optionally substituted with one or more substituents independently from each other selected from the group consisting of Me, $^iPr$, $^tBu$, CN, $CF_3$ and Ph.

As used throughout the present application, the terms "aryl" and "aromatic" may be understood in the broadest sense as any mono-, bi- or polycyclic aromatic moieties. Accordingly, an aryl group contains 6 to 60 aromatic ring atoms, and a heteroaryl group contains 5 to 60 aromatic ring atoms, of which at least one is a heteroatom. Notwithstanding, throughout the application the number of aromatic ring atoms may be given as subscripted number in the definition of certain substituents. In particular, the heteroaromatic ring includes one to three heteroatoms. Again, the terms "heteroaryl" and "heteroaromatic" may be understood in the broadest sense as any mono-, bi- or polycyclic heteroaromatic moieties that include at least one heteroatom. The heteroatoms may at each occurrence be the same or different and be individually selected from the group consisting of N, O and S. Accordingly, the term "arylene" refers to a divalent substituent that bears two binding sites to other molecular structures and thereby serving as a linker structure. In case, a group in the exemplary embodiments is defined differently from the definitions given here, for example, the number of aromatic ring atoms or number of heteroatoms differs from the given definition, the definition in the exemplary embodiments is to be applied. According to the invention, a condensed (annulated) aromatic or heteroaromatic polycycle is built of two or more single aromatic or heteroaromatic cycles, which formed the polycycle via a condensation reaction.

In particular, as used throughout the present application the term aryl group or heteroaryl group comprises groups which can be bound via any position of the aromatic or heteroaromatic group, derived from benzene, naphthaline, anthracene, phenanthrene, pyrene, dihydropyrene, chrysene, perylene, fluoranthene, benzanthracene, benzphenanthrene, tetracene, pentacene, benzpyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthoimidazole, phenanthroimidazole, pyridoimidazole, pyrazinoimidazole, quinoxalinoimidazole, oxazole, benzoxazole, napthooxazole, anthroxazol, phenanthroxazol, isoxazole, 1,2-thiazole, 1,3-thiazole, benzothiazole, pyridazine, benzopyridazine, pyrimidine, benzopyrimidine, 1,3,5-triazine, quinoxaline, pyrazine, phenazine, naphthyridine, carboline, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the abovementioned groups.

As used throughout the present application the term cyclic group may be understood in the broadest sense as any mono-, bi- or polycyclic moieties.

As used throughout the present application, the term biphenyl as a substituent may be understood in the broadest sense as ortho-biphenyl, meta-biphenyl, or para-biphenyl, wherein ortho, meta and para is defined in regard to the binding site to another chemical moiety.

As used throughout the present application, the term alkyl group may be understood in the broadest sense as any linear, branched, or cyclic alkyl substituent. In particular, the term alkyl comprises the substituents methyl (Me), ethyl (Et), n-propyl ($^nPr$), i-propyl ($^iPr$), cyclopropyl, n-butyl ($^nBu$), i-butyl ($^iBu$), s-butyl ($^sBu$), t-butyl ($^tBu$), cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, 2,2,2-trifluorethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyln-n-hexadec-1-yl, 1,1-diethyl-n-octadec-1-yl, 1-(n-propyl)-cyclohex-1-yl, 1-(n-butyl)-cyclohex-1-yl, 1-(n-hexyl)-cyclohex-1-yl, 1-(n-octyl)-cyclohex-1-yl and 1-(n-decyl)-cyclohex-1-yl.

As used throughout the present application, the term alkenyl comprises linear, branched, and cyclic alkenyl substituents. The term alkenyl group exemplarily comprises the substituents ethenyl, propenyl, butenyl, pentenyl, cyclopentenyl, hexenyl, cyclohexenyl, heptenyl, cycloheptenyl, octenyl, cyclooctenyl or cyclooctadienyl.

As used throughout the present application, the term alkynyl comprises linear, branched, and cyclic alkynyl substituents. The term alkynyl group exemplarily comprises ethynyl, propynyl, butynyl, pentynyl, hexynyl, heptynyl or octynyl.

As used throughout the present application, the term alkoxy comprises linear, branched, and cyclic alkoxy substituents. The term alkoxy group exemplarily comprises methoxy, ethoxy, n-propoxy, i-propoxy, n-butoxy, i-butoxy, s-butoxy, t-butoxy and 2-methylbutoxy.

As used throughout the present application, the term thioalkoxy comprises linear, branched, and cyclic thioalkoxy substituents, in which the O of the exemplarily alkoxy groups is replaced by S.

As used throughout the present application, the terms "halogen" and "halo" may be understood in the broadest sense as being preferably fluorine, chlorine, bromine or iodine.

Whenever hydrogen (H) is mentioned herein, it could also be replaced by deuterium at each occurrence.

It is understood that when a molecular fragment is described as being a substituent or otherwise attached to another moiety, its name may be written as if it were a fragment (e.g. naphtyl, dibenzofuryl) or as if it were the whole molecule (e.g. naphthalene, dibenzofuran). As used herein, these different ways of designating a substituent or attached fragment are considered to be equivalent.

In one embodiment, the organic molecules according to the invention have an excited state lifetime of not more than 150 μs, of not more than 100 μs, in particular of not more than 50 μs, more preferably of not more than 10 μs or not more than 7 μs in a film of poly(methyl methacrylate) (PMMA) with 10% by weight of organic molecule at room temperature.

In one embodiment of the invention, the organic molecules according to the invention represent thermally-activated delayed fluorescence (TADF) emitters, which exhibit a $\Delta E_{ST}$ value, which corresponds to the energy difference between the first excited singlet state (S1) and the first excited triplet state (T1), of less than 5000 cm$^{-1}$, preferably less than 3000 cm$^{-1}$, more preferably less than 1500 cm$^{-1}$, even more preferably less than 1000 cm$^{-1}$ or even less than 500 cm$^{-1}$.

In a further embodiment of the invention, the organic molecules according to the invention have an emission peak in the visible or nearest ultraviolet range, i.e., in the range of a wavelength of from 380 to 800 nm, with a full width at half maximum of less than 0.50 eV, preferably less than 0.48 eV, more preferably less than 0.45 eV, even more preferably less than 0.43 eV or even less than 0.40 eV in a film of poly(methyl methacrylate) (PMMA) with 10% by weight of organic molecule at room temperature.

In a further embodiment of the invention, the organic molecules according to the invention have a "blue material index" (BMI), calculated by dividing the photoluminescence quantum yield (PLQY) in % by the CIEy color coordinate of the emitted light, of more than 150, in particular more than 200, preferably more than 250, more preferably of more than 300 or even more than 500.

Orbital and excited state energies can be determined either by means of experimental methods or by calculations employing quantum-chemical methods, in particular density functional theory calculations. The energy of the highest occupied molecular orbital $E^{HOMO}$ is determined by methods known to the person skilled in the art from cyclic voltammetry measurements with an accuracy of 0.1 eV. The energy of the lowest unoccupied molecular orbital $E^{LUMO}$ is calculated as $E^{HOMO}+E^{gap}$, wherein $E^{gap}$ is determined as follows: For host compounds, the onset of the emission spectrum of a film with 10% by weight of host in poly(methyl methacrylate) (PMMA) is used as $E^{gap}$, unless stated otherwise. For emitter molecules, $E^{gap}$ is determined as the energy at which the excitation and emission spectra of a film with 10% by weight of emitter in PMMA cross.

The energy of the first excited triplet state T1 is determined from the onset of the emission spectrum at low temperature, typically at 77 K. For host compounds, where the first excited singlet state and the lowest triplet state are energetically separated by >0.4 eV, the phosphorescence is usually visible in a steady-state spectrum in 2-Me-THF. The triplet energy can thus be determined as the onset of the phosphorescence spectrum. For TADF emitter molecules, the energy of the first excited triplet state T1 is determined from the onset of the delayed emission spectrum at 77 K, if not otherwise stated measured in a film of PMMA with 10% by weight of emitter. Both for host and emitter compounds, the energy of the first excited singlet state S1 is determined from the onset of the emission spectrum, if not otherwise stated measured in a film of PMMA with 10% by weight of host or emitter compound.

The onset of an emission spectrum is determined by computing the intersection of the tangent to the emission spectrum with the x-axis. The tangent to the emission spectrum is set at the high-energy side of the emission band and at the point at half maximum of the maximum intensity of the emission spectrum.

A further aspect of the invention relates to a process for preparing organic molecules of the invention(with an optional subsequent reaction), wherein a bromo-fluorobenzonitrile, which is substituted with three $R^I$, is used as a reactant:

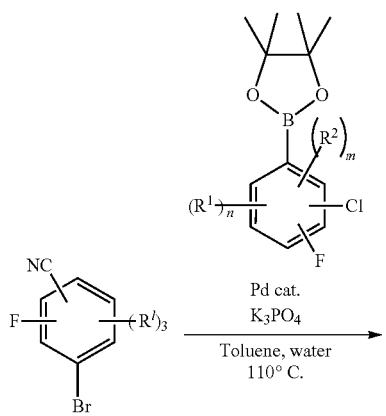

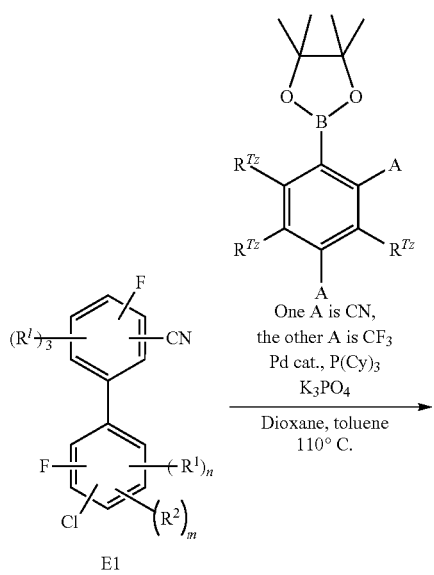

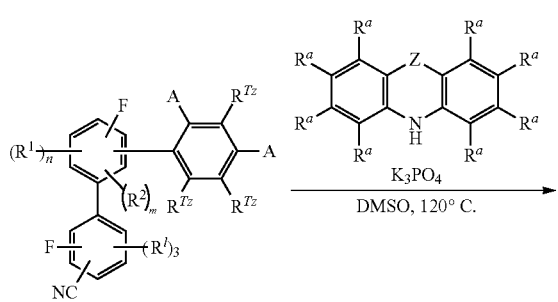

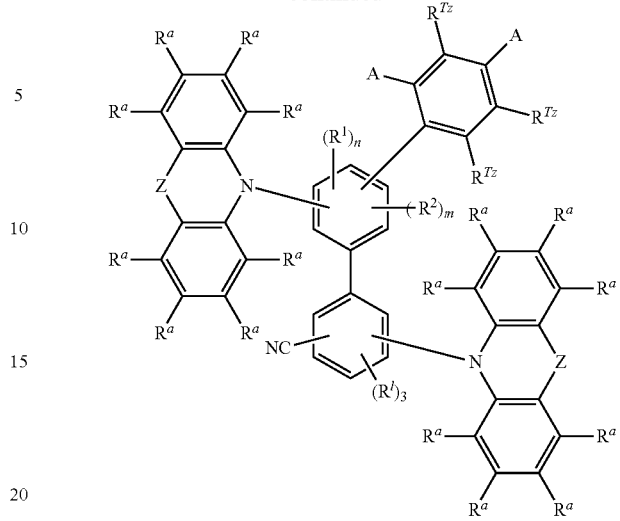

n = 1 or 2
m = 1 or 2
n + m = 3

According to the invention, in the reaction for the synthesis of E1, a boronic acid or an equivalent boronic acid ester can be used instead of a boronic pinacol ester. Exemplary boronic acid esters or boronic acids are 2-chloro-6-fluorophenylboronic ester or acid, 2-chloro-5-fluorophenylboronic ester or acid, 2-chloro-4-fluorophenylboronic ester or acid, 3-chloro-6-fluorophenylboronic ester or acid, 3-chloro-5-fluorophenylboronic ester or acid, 3-chloro-4-fluorophenylboronic ester or acid, 4-chloro-6-fluorophenylboronic ester or acid and 4-chloro-5-fluorophenylboronic ester or acid.

For the reaction of a nitrogen heterocycle in a nucleophilic aromatic substitution with an aryl halide, preferably an aryl fluoride, typical conditions include the use of a base, such as tribasic potassium phosphate or sodium hydride, for example, in an aprotic polar solvent, such as dimethyl sulfoxide (DMSO) or N,N-dimethylformamide (DMF), for example.

An alternative synthesis route comprises the introduction of a nitrogen heterocycle via copper- or palladium-catalyzed coupling to an aryl halide or aryl pseudohalide, preferably an aryl bromide, an aryl iodide, aryl triflate or an aryl tosylate.

A further aspect of the invention relates to the use of an organic molecule according to the invention as a luminescent emitter or as an absorber, and/or as a host material and/or as an electron transport material, and/or as a hole injection material, and/or as a hole blocking material in an optoelectronic device.

The organic optoelectronic device, also referred to as optoelectronic device, may be understood in the broadest sense as any device based on organic materials that is suitable for emitting light in the visible or nearest ultraviolet (UV) range, i.e., in the range of a wavelength of from 380 to 800 nm. More preferably, the organic optoelectronic device may be able to emit light in the visible range, i.e., of from 400 nm to 800 nm.

In the context of such use, the organic optoelectronic device is more particularly selected from the group consisting of:
organic light-emitting diodes (OLEDs),
light-emitting electrochemical cells, OLED sensors, especially in gas and vapour sensors not hermetically externally shielded,
organic diodes,
organic solar cells,
organic transistors,
organic field-effect transistors,
organic lasers and
down-conversion elements.

In a preferred embodiment in the context of such use, the organic optoelectronic device is a device selected from the group consisting of an organic light emitting diode (OLED), a light emitting electrochemical cell (LEC), and a light-emitting transistor.

In the case of the use, the fraction of the organic molecule according to the invention in the emission layer in an organic optoelectronic device, more particularly in an OLED, is 1% to 99% by weight, more particularly 5% to 80% by weight. In an alternative embodiment, the proportion of the organic molecule in the emission layer is 100% by weight.

In one embodiment, the light-emitting layer comprises not only the organic molecules according to the invention, but also a host material whose triplet (T1) and singlet (S1) energy levels are energetically higher than the triplet (T1) and singlet (S1) energy levels of the organic molecule.

A further aspect of the invention relates to a composition comprising or consisting of:
(a) at least one organic molecule according to the invention, in particular in the form of an emitter and/or a host, and
(b) one or more emitter and/or host materials, which differ from the organic molecule according to the invention and
(c) optional one or more dyes and/or one or more solvents.

In one embodiment, the light-emitting layer comprises (or essentially consists of) a composition comprising or consisting of:
(a) at least one organic molecule according to the invention, in particular in the form of an emitter and/or a host, and
(b) one or more emitter and/or host materials, which differ from the organic molecule according to the invention and
(c) optional one or more dyes and/or one or more solvents.

In a particular embodiment, the light-emitting layer EML comprises (or essentially consists of) a composition comprising or consisting of:
(i) 1-50% by weight, preferably 5-40% by weight, in particular 10-30% by weight, of one or more organic molecules according to the invention;
(ii) 5-99% by weight, preferably 30-94.9% by weight, in particular 40-89% by weight, of at least one host compound H; and
(iii) optionally 0-94% by weight, preferably 0.1-65% by weight, in particular 1-50% by weight, of at least one further host compound D with a structure differing from the structure of the molecules according to the invention; and
(iv) optionally 0-94% by weight, preferably 0-65% by weight, in particular 0-50% by weight, of a solvent; and
(v) optionally 0-30% by weight, in particular 0-20% by weight, preferably 0-5% by weight, of at least one further emitter molecule F with a structure differing from the structure of the molecules according to the invention.

Preferably, energy can be transferred from the host compound H to the one or more organic molecules according to the invention, in particular transferred from the first excited triplet state T1(H) of the host compound H to the first excited triplet state T1(E) of the one or more organic molecules according to the invention E and/or from the first excited singlet state S1(H) of the host compound H to the first excited singlet state S1(E) of the one or more organic molecules according to the invention E.

In a further embodiment, the light-emitting layer EML comprises (or essentially consists of) a composition comprising or consisting of:
(i) 1-50% by weight, preferably 5-40% by weight, in particular 10-30% by weight, of one organic molecule according to the invention;
(ii) 5-99% by weight, preferably 30-94.9% by weight, in particular 40-89% by weight, of one host compound H; and
(iii) optionally 0-94% by weight, preferably 0.1-65% by weight, in particular 1-50% by weight, of at least one further host compound D with a structure differing from the structure of the molecules according to the invention; and
(iv) optionally 0-94% by weight, preferably 0-65% by weight, in particular 0-50% by weight, of a solvent; and
(v) optionally 0-30% by weight, in particular 0-20% by weight, preferably 0-5% by weight, of at least one further emitter molecule F with a structure differing from the structure of the molecules according to the invention.

In one embodiment, the host compound H has a highest occupied molecular orbital HOMO(H) having an energy $E^{HOMO}(H)$ in the range of from −5 to −6.5 eV and the at least one further host compound D has a highest occupied molecular orbital HOMO(D) having an energy $E^{HOMO}(D)$, wherein $E^{HOMO}(H) > E^{HOMO}(D)$.

In a further embodiment, the host compound H has a lowest unoccupied molecular orbital LUMO(H) having an energy $E^{LUMO}(H)$ and the at least one further host compound D has a lowest unoccupied molecular orbital LUMO(D) having an energy $E^{LUMO}(D)$, wherein $E^{LUMO}(H) > E^{LUMO}(D)$.

In one embodiment, the host compound H has a highest occupied molecular orbital HOMO(H) having an energy $E^{HOMO}(H)$ and a lowest unoccupied molecular orbital LUMO(H) having an energy $E^{LUMO}(H)$, and
the at least one further host compound D has a highest occupied molecular orbital HOMO(D) having an energy $E^{HOMO}(D)$ and a lowest unoccupied molecular orbital LUMO(D) having an energy $E^{LUMO}(D)$,
the organic molecule according to the invention E has a highest occupied molecular orbital HOMO(E) having an energy $E^{HOMO}(E)$ and a lowest unoccupied molecular orbital LUMO(E) having an energy $E^{LUMO}(E)$,
wherein
$E^{HOMO}(H) > E^{HOMO}(D)$ and the difference between the energy level of the highest occupied molecular orbital HOMO(E) of the organic molecule according to the invention E ($E^{HOMO}(E)$) and the energy level of the highest occupied molecular orbital HOMO(H) of the host compound H ($E^{HOMO}(H)$) is between −0.5 eV and 0.5 eV, more preferably between −0.3 eV and 0.3 eV, even more preferably between −0.2 eV and 0.2 eV or even between −0.1 eV and 0.1 eV; and
$E^{LUMO}(H) > E^{LUMO}(D)$ and the difference between the energy level of the lowest unoccupied molecular orbital LUMO(E) of the organic molecule according to the invention E ($E^{LUMO}(E)$) and the lowest unoccupied molecular orbital LUMO(D) of the at least one further host compound D ($E^{LUMO}(D)$) is between −0.5 eV and 0.5 eV, more preferably between −0.3 eV and 0.3 eV, even more preferably between −0.2 eV and 0.2 eV or even between −0.1 eV and 0.1 eV.

In a further aspect, the invention relates to an organic optoelectronic device comprising an organic molecule or a composition of the type described here, more particularly in the form of a device selected from the group consisting of organic light-emitting diode (OLED), light-emitting electrochemical cell, OLED sensor, more particularly gas and vapour sensors not hermetically externally shielded, organic diode, organic solar cell, organic transistor, organic field-effect transistor, organic laser and down-conversion element.

In a preferred embodiment, the organic optoelectronic device is a device selected from the group consisting of an organic light emitting diode (OLED), a light emitting electrochemical cell (LEC), and a light-emitting transistor.

In one embodiment of the organic optoelectronic device of the invention, the organic molecule according to the invention E is used as emission material in a light-emitting layer EML.

In one embodiment of the organic optoelectronic device of the invention, the light-emitting layer EML consists of the composition according to the invention described here.

Exemplarily, when the organic optoelectronic device is an OLED, it may have the following layer structure:
1. substrate
2. anode layer A
3. hole injection layer, HIL
4. hole transport layer, HTL
5. electron blocking layer, EBL
6. emitting layer, EML
7. hole blocking layer, HBL
8. electron transport layer, ETL
9. electron injection layer, EIL
10. cathode layer, wherein the OLED comprises each layer selected from the group of HIL, HTL, EBL, HBL, ETL, and EIL only in an optional fashion, different layers may be merged and the OLED may comprise more than one layer of each layer type defined above.

Furthermore, the organic optoelectronic device may optionally comprise one or more protective layers protecting the device from damaging exposure to harmful species in the environment including, for example, moisture, vapor and/or gases.

In one embodiment of the invention, the organic optoelectronic device is an OLED, which has the following inverted layer structure:
1. substrate
2. cathode layer
3. electron injection layer, EIL
4. electron transport layer, ETL
5. hole blocking layer, HBL
6. emitting layer, B
7. electron blocking layer, EBL
8. hole transport layer, HTL
9. hole injection layer, HIL
10. anode layer A wherein the OLED only optionally comprises each layer selected from the group of HIL, HTL, EBL, HBL, ETL, and EIL. Moreover, different layers may be merged and the OLED may comprise more than one layer of each layer types defined above.

In one embodiment of the invention, the organic optoelectronic device is an OLED, which may exhibit stacked architecture. In this architecture, contrary to the typical arrangement, where the OLEDs are placed side by side, the individual units are stacked on top of each other. Blended light may be generated with OLEDs exhibiting a stacked architecture, in particular white light may be generated by stacking blue, green and red OLEDs. Furthermore, the OLED exhibiting a stacked architecture may optionally comprise a charge generation layer (CGL), which is typically located between two OLED subunits and typically consists of a n-doped and p-doped layer with the n-doped layer of one CGL being typically located closer to the anode layer.

In one embodiment of the invention, the organic optoelectronic device is an OLED, which comprises two or more emission layers between anode and cathode. In particular, this so-called tandem OLED comprises three emission layers, wherein one emission layer emits red light, one emission layer emits green light and one emission layer emits blue light, and optionally may comprise further layers such as charge generation layers, blocking or transporting layers between the individual emission layers. In a further embodiment, the emission layers are adjacently stacked. In a further embodiment, the tandem OLED comprises a charge generation layer between each two emission layers. In addition, adjacent emission layers or emission layers separated by a charge generation layer may be merged.

The substrate may be formed by any material or composition of materials. Most frequently, glass slides are used as substrates. Alternatively, thin metal layers (e.g., copper, gold, silver or aluminum films) or plastic films or slides may be used. This may allow a higher degree of flexibility. The anode layer A is mostly composed of materials allowing to obtain an (essentially) transparent film. As at least one of both electrodes should be (essentially) transparent in order to allow light emission from the OLED, either the anode layer A or the cathode layer C is transparent. Preferably, the anode layer A comprises a large content or even consists of transparent conductive oxides (TCOs). Such anode layer A may, for example, comprise indium tin oxide, aluminum zinc oxide, fluorine doped tin oxide, indium zinc oxide, PbO, SnO, zirconium oxide, molybdenum oxide, vanadium oxide, wolfram oxide, graphite, doped Si, doped Ge, doped GaAs, doped polyaniline, doped polypyrrol and/or doped polythiophene.

The anode layer A (essentially) may consist of indium tin oxide (ITO) (e.g., $(InO_3)_{0.9}(SnO_2)_{0.1}$). The roughness of the anode layer A caused by the transparent conductive oxides (TCOs) may be compensated by using a hole injection layer (HIL). Further, the HIL may facilitate the injection of quasi charge carriers (i.e., holes) in that the transport of the quasi charge carriers from the TCO to the hole transport layer (HTL) is facilitated. The hole injection layer (HIL) may comprise poly-3,4-ethylendioxy thiophene (PEDOT), polystyrene sulfonate (PSS), $MoO_2$, $V_2O_5$, CuPC or CuI, in particular a mixture of PEDOT and PSS. The hole injection layer (HIL) may also prevent the diffusion of metals from the anode layer A into the hole transport layer (HTL). The HIL may exemplarily comprise PEDOT:PSS (poly-3,4-ethylendioxy thiophene:polystyrene sulfonate), PEDOT (poly-3,4-ethylendioxy thiophene), mMTDATA (4,4',4''-tris[phenyl(m-tolyl)amino]triphenylamine), Spiro-TAD (2,2',7,7'-tetrakis(n,n-diphenylamino)-9,9'-spirobifluorene), DNTPD (N1,N1'-(biphenyl-4,4'-diyl)bis(N1-phenyl-N4,N4-di-m-tolylbenzene-1,4-diamine), NPB (N,N'-nis-(1-naphthalenyl)-N,N'-bis-phenyl-(1,1'-biphenyl)-4,4'-diamine), NPNPB (N,N'-diphenyl-N,N'-di-[4-(N,N-diphenyl-amino)phenyl]benzidine), MeO-TPD (N,N,N',N'-tetrakis(4-methoxyphenyl)benzidine), HAT-CN (1,4,5,8,9,11-hexaazatriphenylen-hexacarbonitrile) and/or Spiro-NPD (N,N'-diphenyl-N,N'-bis-(1-naphthyl)-9,9'-spirobifluorene-2,7-diamine).

Adjacent to the anode layer A or hole injection layer (HIL), a hole transport layer (HTL) is typically located. Herein, any hole transport compound may be used. Exemplarily, electron-rich heteroaromatic compounds such as triarylamines and/or carbazoles may be used as hole transport compound. The HTL may decrease the energy barrier between the anode layer A and the light-emitting layer EML. The hole transport layer (HTL) may also be an electron blocking layer (EBL). Preferably, hole transport compounds bear comparably high energy levels of their triplet states T1. For example, the hole transport layer (HTL) may comprise a star-shaped heterocycle such as tris(4-carbazoyl-9-ylphenyl)amine (TCTA), poly-TPD (poly(4-butylphenyl-diphenyl-amine)), [alpha]-NPD (poly(4-butylphenyl-diphenyl-amine)), TAPC (4,4'-cyclohexyliden-bis[N,N-bis(4-methylphenyl)benzenamine]), 2-TNATA (4,4',4''-tris[2-naphthyl(phenyl)amino]triphenylamine), Spiro-TAD, DNTPD, NPB, NPNPB, MeO-TPD, HAT-CN and/or TrisPcz (9,9'-diphenyl-6-(9-phenyl-9H-carbazol-3-yl)-9H,9'H-3,3'-bicarbazole). In addition, the HTL may comprise a p-doped layer, which may be composed of an inorganic or organic dopant in an organic hole-transporting matrix. Transition metal oxides such as vanadium oxide, molybdenum oxide or tungsten oxide may exemplarily be used as inorganic dopant. Tetrafluorotetracyanoquinodimethane ($F_4$-TCNQ), copper-pentafluorobenzoate (Cu(I)pFBz) or transition metal complexes may exemplarily be used as organic dopant.

The EBL may exemplarily comprise mCP (1,3-bis(carbazol-9-yl)benzene), TCTA, 2-TNATA, mCBP (3,3-di(9H-carbazol-9-yl)biphenyl), tris-Pcz, CzSi (9-(4-tert-Butylphenyl)-3,6-bis(triphenylsilyl)-9H-carbazole), and/or DCB (N,N'-dicarbazolyl-1,4-dimethylbenzene).

Adjacent to the hole transport layer (HTL), typically, the light-emitting layer EML is located. The light-emitting layer EML comprises at least one light emitting molecule. Particularly, the EML comprises at least one light emitting molecule according to the invention E. In one embodiment, the light-emitting layer comprises only the organic molecules according to the invention. Typically, the EML additionally comprises one or more host materials H. Exemplarily, the host material H is selected from CBP (4,4'-Bis-(N-carbazolyl)-biphenyl), mCP, mCBP Sif87 (dibenzo[b,d]thiophen-2-yltriphenylsilane), CzSi, Sif88 (dibenzo[b,d]thiophen-2-yl)diphenylsilane), DPEPO (bis[2-(diphenylphosphino)phenyl] ether oxide), 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine) and/or TST (2,4,6-tris(9,9'-spirobifluorene-2-yl)-1,3,5-triazine). The host material H typically should be selected to exhibit first triplet (T1) and first singlet (S1) energy levels, which are energetically higher than the first triplet (T1) and first singlet (S1) energy levels of the organic molecule.

In one embodiment of the invention, the EML comprises a so-called mixed-host system with at least one hole-dominant host and one electron-dominant host. In a particular embodiment, the EML comprises exactly one light emitting organic molecule according to the invention and a mixed-host system comprising T2T as electron-dominant host and a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole as hole-dominant host. In a further embodiment the EML comprises 50-80% by weight, preferably 60-75% by weight of a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole; 10-45% by weight, preferably 15-30% by weight of T2T and 5-40% by weight, preferably 10-30% by weight of light emitting molecule according to the invention.

Adjacent to the light-emitting layer EML, an electron transport layer (ETL) may be located. Herein, any electron transporter may be used. Exemplarily, electron-poor compounds such as, e.g., benzimidazoles, pyridines, triazoles, oxadiazoles (e.g., 1,3,4-oxadiazole), phosphinoxides and sulfone, may be used. An electron transporter may also be a star-shaped heterocycle such as 1,3,5-tri(1-phenyl-1H-benzo[d]imidazol-2-yl)phenyl (TPBi). The ETL may comprise NBphen (2,9-bis(naphthalen-2-yl)-4,7-diphenyl-1,10-phenanthroline), $Alq_3$ (Aluminum-tris(8-hydroxyquinoline)), TSPO1 (diphenyl-4-triphenylsilylphenyl-phosphinoxide), BPyTP2 (2,7-di(2,2'-bipyridin-5-yl)triphenyle), Sif87 (dibenzo[b,d]thiophen-2-yltriphenylsilane), Sif88 (dibenzo[b,d]thiophen-2-yl)diphenylsilane), BmPyPhB (1,3-bis[3,5-di(pyridin-3-yl)phenyl]benzene) and/or BTB (4,4'-bis-[2-(4,6-diphenyl-1,3,5-triazinyl)]-1,1'-biphenyl). Optionally, the ETL may be doped with materials such as Liq. The electron transport layer (ETL) may also block holes or a holeblocking layer (HBL) is introduced. The HBL may exemplarily comprise BCP (2,9-dimethyl-4,7-diphenyl-1,10-phenanthroline=Bathocuproine), BAlq (bis(8-hydroxy-2-methylquinoline)-(4-phenylphenoxy)aluminum), NBphen (2,9-bis(naphthalen-2-yl)-4,7-diphenyl-1,10-phenanthroline), $Alq_3$ (Aluminum-tris(8-hydroxyquinoline)), TSPO1 (diphenyl-4-triphenylsilylphenyl-phosphinoxide), T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluorene-2-yl)-1,3,5-triazine), and/or TCB/TCP (1,3,5-tris(N-carbazolyl)benzol/1,3,5-tris(carbazol)-9-yl) benzene).

Adjacent to the electron transport layer (ETL), a cathode layer C may be located. Exemplarily, the cathode layer C may comprise or may consist of a metal (e.g., Al, Au, Ag, Pt, Cu, Zn, Ni, Fe, Pb, LiF, Ca, Ba, Mg, In, W, or Pd) or a metal alloy. For practical reasons, the cathode layer may also consist of (essentially) intransparent metals such as Mg, Ca or Al. Alternatively or additionally, the cathode layer C may also comprise graphite and or carbon nanotubes (CNTs). Alternatively, the cathode layer C may also consist of nanoscalic silver wires.

An OLED may further, optionally, comprise a protection layer between the electron transport layer (ETL) and the cathode layer C (which may be designated as electron injection layer (EIL)). This layer may comprise lithium fluoride, cesium fluoride, silver, Liq (8-hydroxyquinolinolatolithium), $Li_2O$, $BaF_2$, MgO and/or NaF.

Optionally, also the electron transport layer (ETL) and/or a hole blocking layer (HBL) may comprise one or more host compounds H.

In order to modify the emission spectrum and/or the absorption spectrum of the light-emitting layer EML further, the light-emitting layer EML may further comprise one or more further emitter molecules F. Such an emitter molecule F may be any emitter molecule known in the art. Preferably such an emitter molecule F is a molecule with a structure differing from the structure of the molecules according to the invention E. The emitter molecule F may optionally be a TADF emitter. Alternatively, the emitter molecule F may optionally be a fluorescent and/or phosphorescent emitter molecule which is able to shift the emission spectrum and/or the absorption spectrum of the light-emitting layer EML. Exemplarily, the triplet and/or singlet excitons may be transferred from the organic emitter molecule according to the invention to the emitter molecule F before relaxing to the ground state S0 by emitting light typically red-shifted in comparison to the light emitted by an organic molecule. Optionally, the emitter molecule F may also provoke two-photon effects (i.e., the absorption of two photons of half the energy of the absorption maximum).

Optionally, an organic optoelectronic device (e.g., an OLED) may exemplarily be an essentially white organic optoelectronic device. Exemplarily, such white organic optoelectronic device may comprise at least one (deep) blue emitter molecule and one or more emitter molecules emitting green and/or red light. Then, there may also optionally be energy transmittance between two or more molecules as described above.

As used herein, if not defined more specifically in the particular context, the designation of the colors of emitted and/or absorbed light is as follows:

violet: wavelength range of >380-420 nm;

deep blue: wavelength range of >420-480 nm;

sky blue: wavelength range of >480-500 nm;

green: wavelength range of >500-560 nm;

yellow: wavelength range of >560-580 nm;

orange: wavelength range of >580-620 nm;

red: wavelength range of >620-800 nm.

With respect to emitter molecules, such colors refer to the emission maximum. Therefore, exemplarily, a deep blue emitter has an emission maximum in the range of from >420 to 480 nm, a sky blue emitter has an emission maximum in the range of from >480 to 500 nm, a green emitter has an emission maximum in a range of from >500 to 560 nm, a red emitter has an emission maximum in a range of from >620 to 800 nm.

A deep blue emitter may preferably have an emission maximum of below 480 nm, more preferably below 470 nm, even more preferably below 465 nm or even below 460 nm. It will typically be above 420 nm, preferably above 430 nm, more preferably above 440 nm or even above 450 nm.

Accordingly, a further aspect of the present invention relates to an OLED, which exhibits an external quantum efficiency at 1000 cd/m$^2$ of more than 8%, more preferably of more than 10%, more preferably of more than 13%, even more preferably of more than 15% or even more than 20% and/or exhibits an emission maximum between 420 nm and 500 nm, preferably between 430 nm and 490 nm, more preferably between 440 nm and 480 nm, even more preferably between 450 nm and 470 nm and/or exhibits a LT80 value at 500 cd/m$^2$ of more than 100 h, preferably more than 200 h, more preferably more than 400 h, even more preferably more than 750 h or even more than 1000 h. Accordingly, a further aspect of the present invention relates to an OLED, whose emission exhibits a CIEy color coordinate of less than 0.45, preferably less than 0.30, more preferably less than 0.20 or even more preferably less than 0.15 or even less than 0.10.

A further aspect of the present invention relates to an OLED, which emits light at a distinct color point. According to the present invention, the OLED emits light with a narrow emission band (small full width at half maximum (FWHM)). In one aspect, the OLED according to the invention emits light with a FWHM of the main emission peak of less than 0.50 eV, preferably less than 0.48 eV, more preferably less than 0.45 eV, even more preferably less than 0.43 eV or even less than 0.40 eV.

A further aspect of the present invention relates to an OLED, which emits light with CIEx and CIEy color coordinates close to the CIEx (=0.131) and CIEy (=0.046) color coordinates of the primary color blue (CIEx=0.131 and CIEy=0.046) as defined by ITU-R Recommendation BT.2020 (Rec. 2020) and thus is suited for the use in Ultra High Definition (UHD) displays, e.g. UHD-TVs. Accordingly, a further aspect of the present invention relates to an OLED, whose emission exhibits a CIEx color coordinate of between 0.02 and 0.30, preferably between 0.03 and 0.25, more preferably between 0.05 and 0.20 or even more preferably between 0.08 and 0.18 or even between 0.10 and 0.15 and/or a CIEy color coordinate of between 0.00 and 0.45, preferably between 0.01 and 0.30, more preferably between 0.02 and 0.20 or even more preferably between 0.03 and 0.15 or even between 0.04 and 0.10.

In a further aspect, the invention relates to a method for producing an optoelectronic component. In this case an organic molecule of the invention is used.

The organic optoelectronic device, in particular the OLED according to the present invention can be fabricated by any means of vapor deposition and/or liquid processing. Accordingly, at least one layer is prepared by means of a sublimation process, prepared by means of an organic vapor phase deposition process, prepared by means of a carrier gas sublimation process, solution processed or printed.

The methods used to fabricate the organic optoelectronic device, in particular the OLED according to the present invention are known in the art. The different layers are individually and successively deposited on a suitable substrate by means of subsequent deposition processes. The individual layers may be deposited using the same or differing deposition methods.

Vapor deposition processes exemplarily comprise thermal (co)evaporation, chemical vapor deposition and physical vapor deposition. For active matrix OLED display, an AMO-LED backplane is used as substrate. The individual layer may be processed from solutions or dispersions employing adequate solvents. Solution deposition process exemplarily comprise spin coating, dip coating and jet printing. Liquid processing may optionally be carried out in an inert atmosphere (e.g., in a nitrogen atmosphere) and the solvent may optionally be completely or partially removed by means known in the state of the art.

EXAMPLES

General synthesis scheme I

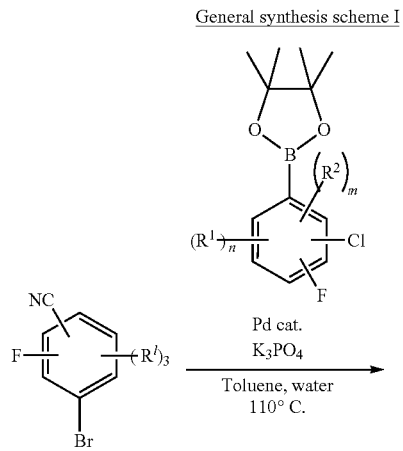

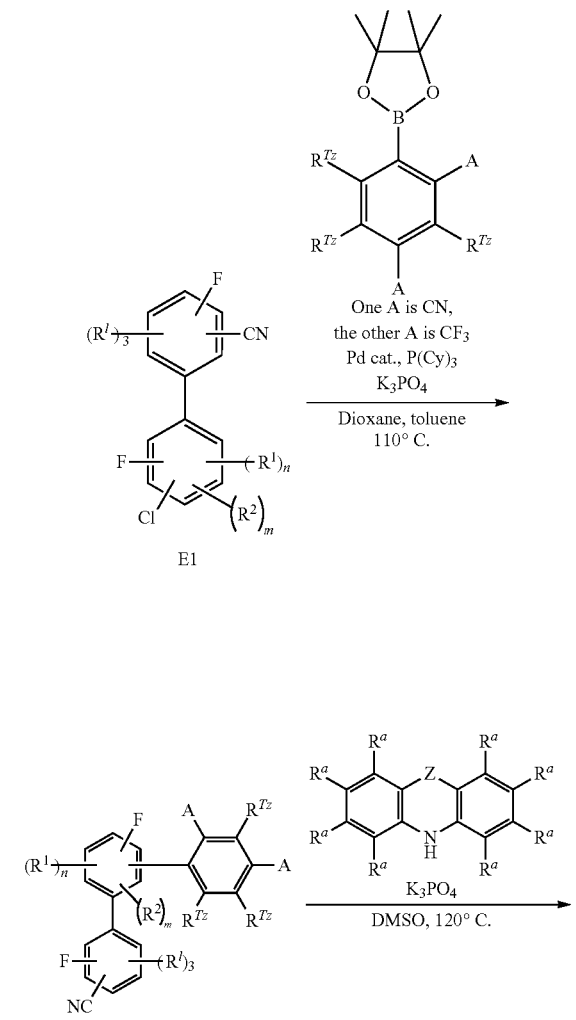

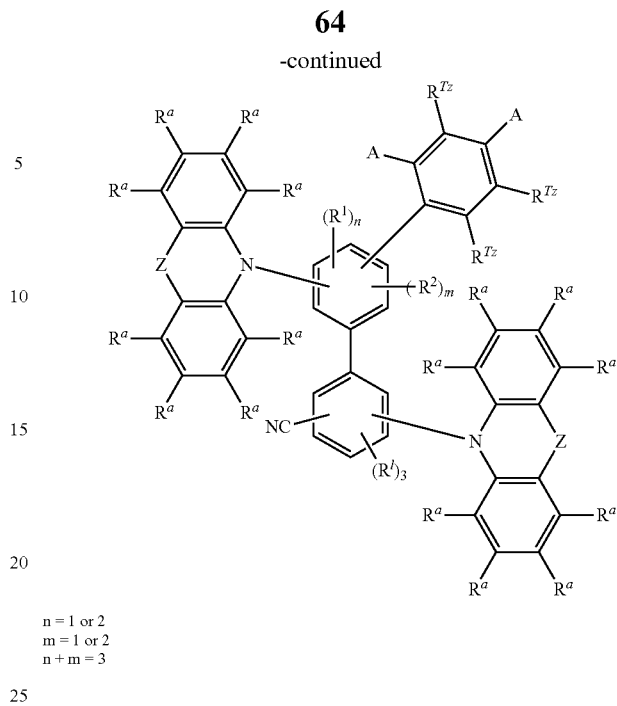

n = 1 or 2
m = 1 or 2
n + m = 3

General Procedure for Synthesis AAV0:

4-bromo-3-(trifluoromethyl)benzonitrile or 2-bromo-5-(trifluoromethyl)benzonitrile (1.00 equivalents), bis(pinacolato)diboron (1.5 equivalents), $Pd_2(dbbf)Cl_2$ ([1,1'-bis(diphenylphosphino)ferrocene]dichloropalladium(II); 0.03 equivalent) and potassium acetate (3.00 equivalents) are stirred under nitrogen atmosphere in dioxane at 110° C. for 5 h. To the reaction mixture Celite® and active carbon are added and stirred at 110° C. for 15 min. Subsequently the reaction mixture is hot filtered and the residue was washed with hot dioxane. The filtrate was washed with brine. The combined organic phases are washed with saturated sodium chloride solution, dried over $MgSO_4$ and the solvent is evaporated under reduced pressure. The residue is purified by recrystallization or alternatively is stirred in hot ethanol and filtered and I0 is obtained as solid.

General Procedure for Synthesis AAV1:

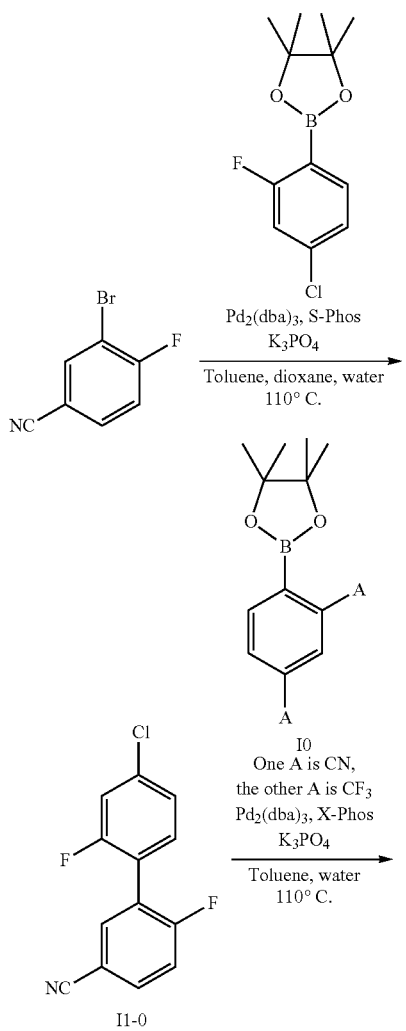

3-bromo-4-fluorobenzonitrile (1.00 equivalents), 4-chloro-2-fluorophenylboronic ester (1.2 equivalents), $Pd_2(dba)_3$ ([Tris(dibenzylideneacetone)dipalladium(O)]; 0.02 equivalents), S-Phos ([2-Dicyclohexylphoshino-2',6'-dimethoxy-1,1'-biphenyl]; 0.08 equivalents) and tribasic potassium phosphate (3.00 equivalents) are stirred under nitrogen atmosphere in a toluene/water mixture (ratio of 4:1) at 110° C. for 15 h. To the reaction mixture Celite® and active carbon are added and stirred at 110° C. for 15 min.

Subsequently the reaction mixture is hot filtered and the residue washed with toluene. The reaction mixture is poured into 300 mL of a saturated sodium chloride solution and extracted with ethyl acetate. The combined organic phases are washed with saturated sodium chloride solution, dried over $MgSO_4$ and the solvent is evaporated under reduced pressure. The residue is purified by chromatography (or by recrystallization or alternatively is stirred in hot ethanol and filtered) and I1-0 is obtained as solid.

In a subsequent reaction, I1-0 (1.00 equivalents), I0 (1.30 equivalents), $Pd_2(dba)_3$ ([Tris(dibenzylideneacetone)dipalladium(O)]; 0.04 equivalents), X-Phos (2-(dicyclohexylphosphino)-2",4",6"-triisopropylbiphenyl, 0.16 equivalents) and tribasic potassium phosphate (2.50 equivalents) are stirred under nitrogen atmosphere in a toluene/water mixture (ratio of 4:1) at 110° C. for 15 h. To the reaction mixture Celite® and active carbon are added and stirred at 110° C. for 15 min.

Subsequently the reaction mixture is hot filtered and the residue washed with toluene. The reaction mixture is poured into 300 mL of a saturated sodium chloride solution and extracted with ethyl acetate. The combined organic phases are washed with saturated sodium chloride solution, dried over $MgSO_4$ and the solvent is evaporated under reduced pressure. The residue is purified by chromatography (or by recrystallization or alternatively is stirred in hot ethanol and filtered) and Z1 is obtained as solid.

General Procedure for Synthesis AAV2:

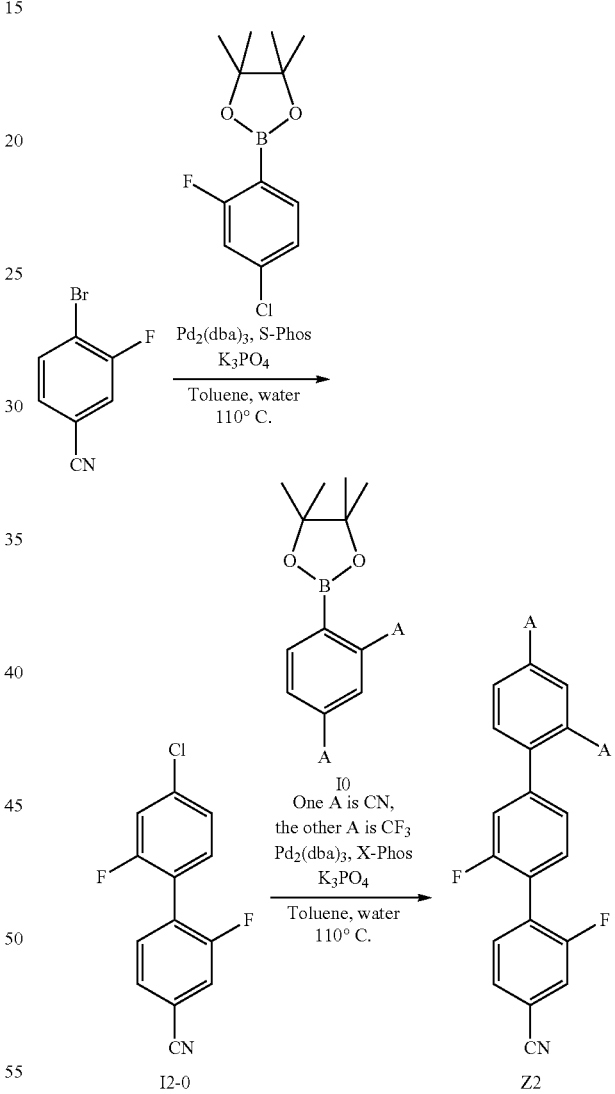

The synthesis of Z2 is carried out according to AAV1, wherein 4-bromo-3-fluorobenzonitrile reacts with 4-chloro-2-fluorophenylboronic ester.

4-bromo-3-fluorobenzonitrile (1.00 equivalents), 4-chloro-2-fluorophenylboronic ester (1.2 equivalents), $Pd_2(dba)_3$ ([Tris(dibenzylideneacetone)dipalladium(O)]; 0.02 equivalents), S-Phos ([2-Dicyclohexylphoshino-2',6'-dimethoxy-1,1'-biphenyl]; 0.08 equivalents) and tribasic potassium phosphate (3.00 equivalents) are stirred under nitrogen atmosphere in a toluene/water mixture (ratio of 4:1) at 110°

C. for 15 h. To the reaction mixture Celite® and active carbon are added and stirred at 110° C. for 15 min.

Subsequently the reaction mixture is hot filtered and the residue washed with toluene. The reaction mixture is poured into 300 mL of a saturated sodium chloride solution and extracted with ethyl acetate. The combined organic phases are washed with saturated sodium chloride solution, dried over MgSO$_4$ and the solvent is evaporated under reduced pressure.

The residue is purified by chromatography (or by recrystallization or alternatively is stirred in hot ethanol and filtered) and I2-0 is obtained as solid.

In a subsequent reaction, I2-0 (1.00 equivalents), I0 (1.30 equivalents), Pd$_2$(dba)$_3$ ([Tris(dibenzylideneacetone)dipalladium(O)]; 0.04 equivalents), X-Phos (2-(dicyclohexylphosphino)-2'',4'',6''-triisopropylbiphenyl, 0.16 equivalents) and tribasic potassium phosphate (2.50 equivalents) are stirred under nitrogen atmosphere in a toluene/water mixture (ratio of 4:1) at 110° C. for 15 h. To the reaction mixture Celite® and active carbon are added and stirred at 110° C. for 15 min.

Subsequently the reaction mixture is hot filtered and the residue washed with toluene. The reaction mixture is poured into 300 mL of a saturated sodium chloride solution and extracted with ethyl acetate. The combined organic phases are washed with saturated sodium chloride solution, dried over MgSO$_4$ and the solvent is evaporated under reduced pressure. The residue is purified by chromatography (or by recrystallization or alternatively is stirred in hot ethanol and filtered) and Z2 is obtained as solid.

General Procedure for Synthesis AAV3:

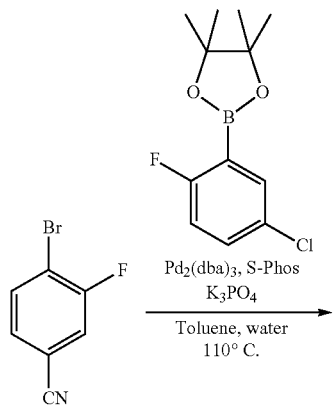

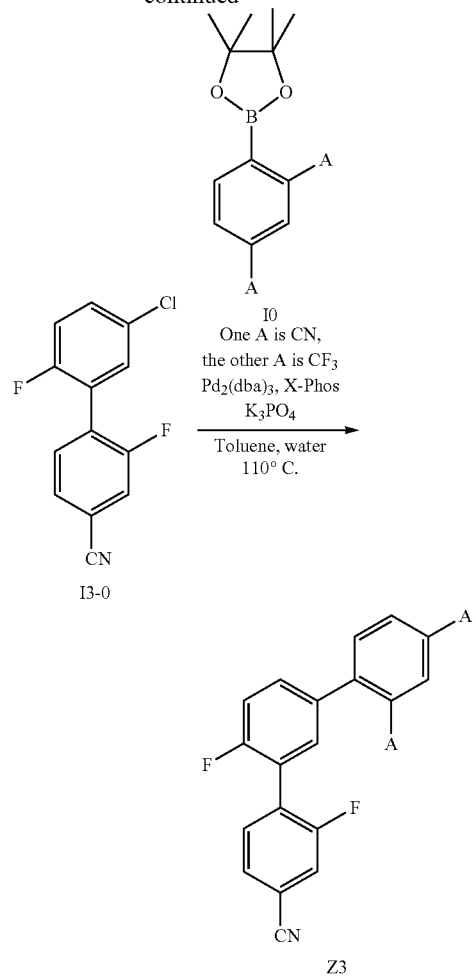

The synthesis of Z3 is carried out according to AAV1, wherein 4-bromo-3-fluorobenzonitrile reacts with 5-chloro-2-fluorophenylboronic ester. 4-bromo-3-fluorobenzonitrile (1.00 equivalents), 5-chloro-2-fluorophenylboronic ester (1.2 equivalents), Pd$_2$(dba)$_3$ ([Tris(dibenzylideneacetone)dipalladium(O)]; 0.02 equivalents), S-Phos ([2-Dicyclohexylphoshino-2',6'-dimethoxy-1,1'-biphenyl]; 0.08 equivalents) and tribasic potassium phosphate (3.00 equivalents) are stirred under nitrogen atmosphere in a toluene/water mixture (ratio of 4:1) at 110° C. for 15 h. To the reaction mixture Celite® and active carbon are added and stirred at 110° C. for 15 min.

Subsequently the reaction mixture is hot filtered and the residue washed with toluene. The reaction mixture is poured into 300 mL of a saturated sodium chloride solution and extracted with ethyl acetate. The combined organic phases are washed with saturated sodium chloride solution, dried over MgSO$_4$ and the solvent is evaporated under reduced pressure. The residue is purified by chromatography (or by recrystallization or alternatively is stirred in hot ethanol and filtered) and I3-0 is obtained as solid.

In a subsequent reaction, I3-0 (1.00 equivalents), I0 (1.30 equivalents), Pd$_2$(dba)$_3$ ([Tris(dibenzylideneacetone)dipalladium(O)]; 0.04 equivalents), X-Phos (2-(dicyclohexylphosphino)-2'',4'',6''-triisopropylbiphenyl, 0.16 equivalents) and tribasic potassium phosphate (2.50 equivalents) are stirred under nitrogen atmosphere in a toluene/water mixture (ratio of 4:1) at 110° C. for 15 h. To the reaction mixture Celite® and active carbon are added and stirred at 110° C. for 15 min.

Subsequently the reaction mixture is hot filtered and the residue washed with toluene. The reaction mixture is poured into 300 mL of a saturated sodium chloride solution and extracted with ethyl acetate. The combined organic phases are washed with saturated sodium chloride solution, dried over $MgSO_4$ and the solvent is evaporated under reduced pressure. The residue is purified by chromatography (or by recrystallization or alternatively is stirred in hot ethanol and filtered) and Z3 is obtained as solid.

General Procedure for Synthesis AAV4:

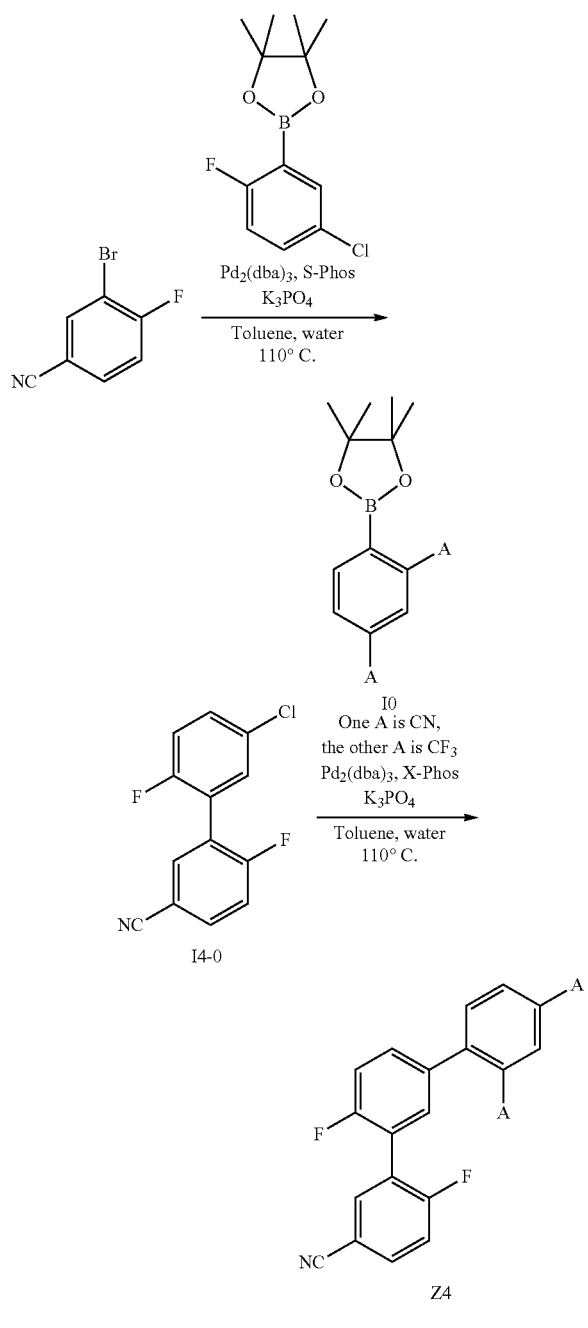

The synthesis of Z4 is carried out according to AAV1, wherein 3-bromo-4-fluorobenzonitrile reacts with 5-chloro-2-fluorophenylboronic ester.

3-bromo-4-fluorobenzonitrile (1.00 equivalents), 5-chloro-2-fluorophenylboronic ester (1.2 equivalents), $Pd_2(dba)_3$ ([Tris(dibenzylideneacetone)dipalladium(O)]; 0.02 equivalents), S-Phos ([2-Dicyclohexylphoshino-2',6'-dimethoxy-1,1'-biphenyl]; 0.08 equivalents) and tribasic potassium phosphate (3.00 equivalents) are stirred under nitrogen atmosphere in a toluene/water mixture (ratio of 4:1) at 110° C. for 15 h. To the reaction mixture Celite® and active carbon are added and stirred at 110° C. for 15 min.

Subsequently the reaction mixture is hot filtered and the residue washed with toluene. The reaction mixture is poured into 300 mL of a saturated sodium chloride solution and extracted with ethyl acetate. The combined organic phases are washed with saturated sodium chloride solution, dried over $MgSO_4$ and the solvent is evaporated under reduced pressure.

The residue is purified by chromatography (or by recrystallization or alternatively is stirred in hot ethanol and filtered) and I4-0 is obtained as solid.

In a subsequent reaction, I4-0 (1.00 equivalents), I0 (1.30 equivalents), $Pd_2(dba)_3$ ([Tris(dibenzylideneacetone)dipalladium(O)]; 0.04 equivalents), X-Phos (2-(dicyclohexylphosphino)-2",4",6"-triisopropylbiphenyl, 0.16 equivalents) and tribasic potassium phosphate (2.50 equivalents) are stirred under nitrogen atmosphere in a toluene/water mixture (ratio of 4:1) at 110° C. for 15 h. To the reaction mixture Celite® and active carbon are added and stirred at 110° C. for 15 min.

Subsequently the reaction mixture is hot filtered and the residue washed with toluene. The reaction mixture is poured into 300 mL of a saturated sodium chloride solution and extracted with ethyl acetate. The combined organic phases are washed with saturated sodium chloride solution, dried over $MgSO_4$ and the solvent is evaporated under reduced pressure.

The residue is purified by chromatography (or by recrystallization or alternatively is stirred in hot ethanol and filtered) and Z4 is obtained as solid.

General Procedure for Synthesis AAV5:

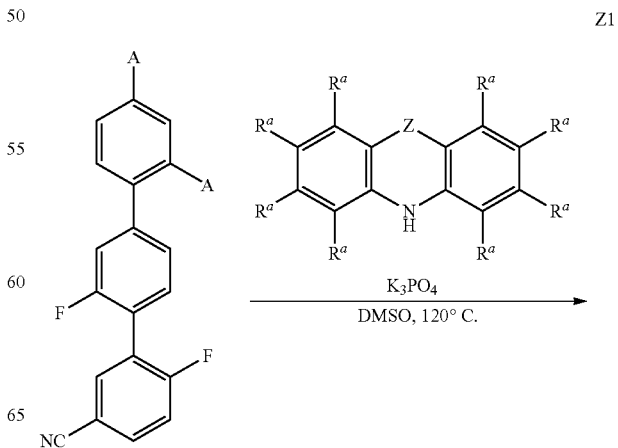

-continued
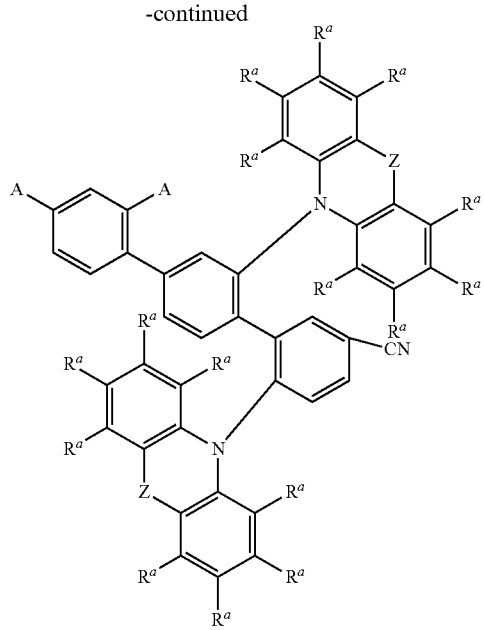
One A is CN, the other A is CF₃
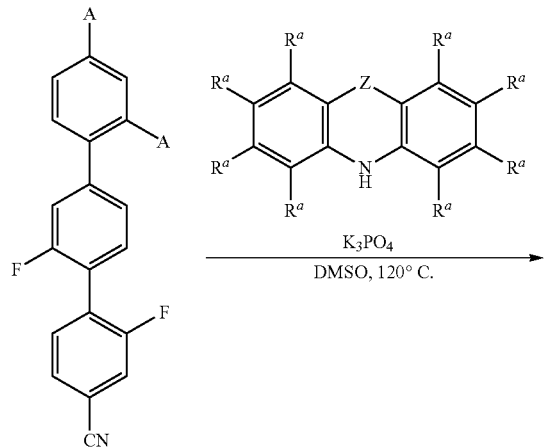
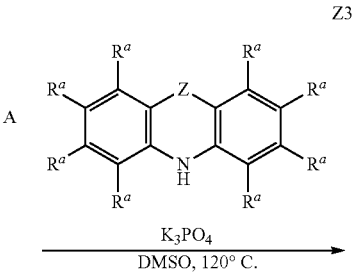
One A is CN, the other A is CF₃
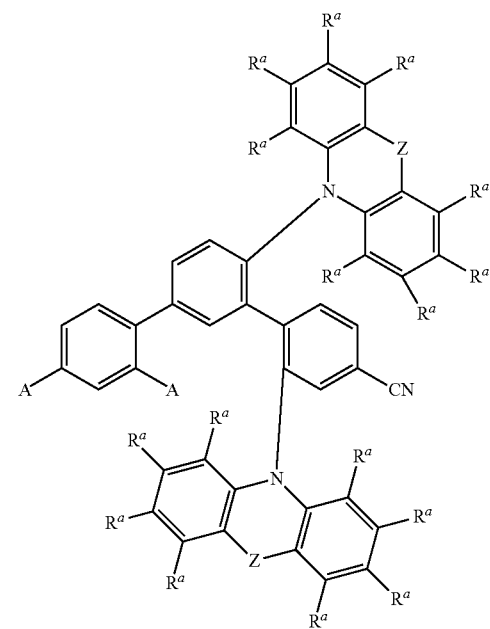
One A is CN, the other A is CF₃
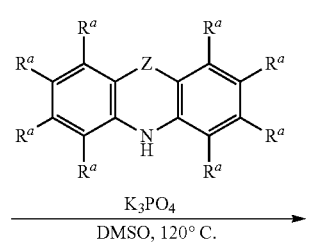

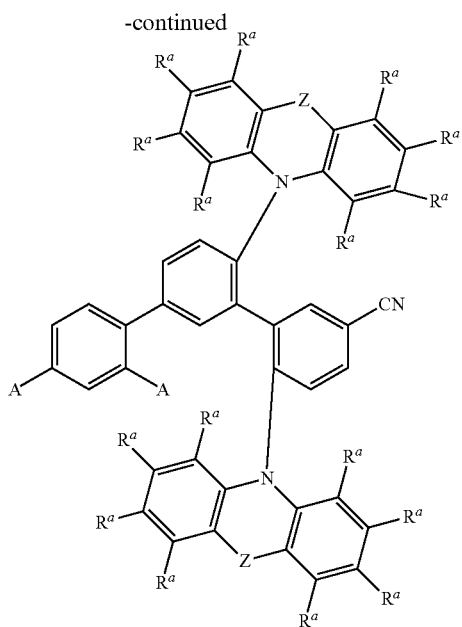

One A is CN, the other A is CF₃

Z1, Z2, Z3 or Z4 (1 equivalent each), the corresponding donor molecule D-H (2.20 equivalents) and tribasic potassium phosphate (4.40 equivalents) are suspended under nitrogen atmosphere in DMSO and stirred at 120° C. (20 h). Subsequently the reaction mixture is poured into a saturated sodium chloride solution and the precipitate is filtered and washed with water. The solid is then dissolved in dichloromethane, dried over MgSO₄ and the solvent is evaporated under reduced pressure. The crude product is purified by recrystallization out of ethanol or by flash chromatography. The product is obtained as a solid.

In particular, the donor molecule D-H is a 3,6-substituted carbazole (e.g., 3,6-dimethylcarbazole, 3,6-diphenylcarbazole, 3,6-di-tert-butylcarbazole), a 2,7-substituted carbazole (e.g., 2,7-dimethylcarbazole, 2,7-diphenylcarbazole, 2,7-di-tert-butylcarbazole), a 1,8-substituted carbazole (e.g., 1,8-dimethylcarbazole, 1,8-diphenylcarbazole, 1,8-di-tert-butylcarbazole), a 1-substituted carbazole (e.g., 1-methylcarbazole, 1-phenylcarbazole, 1-tert-butylcarbazole), a 2-substituted carbazole (e.g., 2-methylcarbazole, 2-phenylcarbazole, 2-tert-butylcarbazole), or a 3-substituted carbazole (e.g., 3-methylcarbazole, 3-phenylcarbazole, 3-tert-butylcarbazole).

For example, a halogen-substituted carbazole, particularly 3-bromocarbazole, can be used as D-H.

In a subsequent reaction a boronic acid ester functional group or boronic acid functional group may be exemplarily introduced at the position of the one or more halogen substituents, which was introduced via D-H, to yield the corresponding carbazol-3-ylboronic acid ester or carbazol-3-ylboronic acid, e.g., via the reaction with bis(pinacolato) diboron (CAS No. 73183-34-3). Subsequently, one or more substituents $R^a$ may be introduced in place of the boronic acid ester group or the boronic acid group via a coupling reaction with the corresponding halogenated reactant $R^a$-Hal, preferably $R^a$—Cl and $R^a$—Br.

Alternatively, one or more substituents $R^a$ may be introduced at the position of the one or more halogen substituents, which was introduced via D-H, via the reaction with a boronic acid of the substituent $R^a$ [$R^a$—B(OH)₂] or a corresponding boronic acid ester.

Cyclic Voltammetry

Cyclic voltammograms are measured from solutions having concentration of $10^{-3}$ mol/L of the organic molecules in dichloromethane or a suitable solvent and a suitable supporting electrolyte (e.g. 0.1 mol/L of tetrabutylammonium hexafluorophosphate). The measurements are conducted at room temperature under nitrogen atmosphere with a three-electrode assembly (Working and counter electrodes: Pt wire, reference electrode: Pt wire) and calibrated using FeCp₂/FeCp₂⁺ as internal standard. The HOMO data was corrected using ferrocene as internal standard against SCE.

Density functional theory calculation Molecular structures are optimized employing the BP86 functional and the resolution of identity approach (RI). Excitation energies are calculated using the (BP86) optimized structures employing Time-Dependent DFT (TD-DFT) methods. Orbital and excited state energies are calculated with the B3LYP functional. Def2-SVP basis sets (and a m4-grid for numerical integration are used. The Turbomole program package is used for all calculations.

Photophysical Measurements

Sample pretreatment: Spin-coating

Apparatus: Spin150, SPS euro.

The sample concentration is 10 mg/ml, dissolved in a suitable solvent.

Program: 1) 3 s at 400 U/min; 20 s at 1000 U/min at 1000 Upm/s. 3) 10 s at 4000 U/min at 1000 Upm/s. After coating, the films are tried at 70° C. for 1 min.

Photoluminescence spectroscopy and TCSPC (Time-correlated single-photon counting) Steady-state emission spectroscopy is measured by a Horiba Scientific, Modell FluoroMax-4 equipped with a 150 W Xenon-Arc lamp, excitation- and emissions monochromators and a Hamamatsu R928 photomultiplier and a time-correlated single-photon counting option. Emissions and excitation spectra are corrected using standard correction fits.

Excited state lifetimes are determined employing the same system using the TCSPC method with FM-2013 equipment and a Horiba Yvon TCSPC hub.

Excitation Sources:

NanoLED 370 (wavelength: 371 nm, pulse duration: 1.1 ns)

NanoLED 290 (wavelength: 294 nm, pulse duration: <1 ns)

SpectraLED 310 (wavelength: 314 nm)

SpectraLED 355 (wavelength: 355 nm).

Data analysis (exponential fit) is done using the software suite DataStation and DAS6 analysis software. The fit is specified using the chi-squared-test.

Photoluminescence Quantum Yield Measurements

For photoluminescence quantum yield (PLQY) measurements an Absolute PL Quantum Yield Measurement C9920-03G system (Hamamatsu Photonics) is used. Quantum yields and CIE coordinates are determined using the software U6039-05 version 3.6.0. Emission maxima are given in nm, quantum yields D in % and CIE coordinates as x,y values. PLQY is determined using the following protocol:

1) Quality assurance: Anthracene in ethanol (known concentration) is used as reference
2) Excitation wavelength: the absorption maximum of the organic molecule is determined and the molecule is excited using this wavelength
3) Measurement Quantum yields are measured, for sample, of solutions or films under nitrogen atmosphere. The yield is calculated using the equation:

$$\Phi_{PL} = \frac{n_{photon}, \text{emited}}{n_{photon}, \text{absorbed}} = \frac{\int \frac{\lambda}{hc}[Int_{emitted}^{sample}(\lambda) - Int_{absorbed}^{sample}(\lambda)]d\lambda}{\int \frac{\lambda}{hc}[Int_{emitted}^{reference}(\lambda) - Int_{absorbed}^{reference}(\lambda)]d\lambda}$$

wherein $n_{photon}$ denotes the photon count and Int. the intensity.

Production and Characterization of Organic Optoelectronic Devices

OLED devices comprising organic molecules according to the invention can be produced via vacuum-deposition methods. If a layer contains more than one compound, the weight-percentage of one or more compounds is given in %. The total weight-percentage values amount to 100%, thus if a value is not given, the fraction of this compound equals to the difference between the given values and 100%.

The not fully optimized OLEDs are characterized using standard methods and measuring electroluminescence spectra, the external quantum efficiency (in %) in dependency on the intensity, calculated using the light detected by the photodiode, and the current. The OLED device lifetime is extracted from the change of the luminance during operation at constant current density. The LT50 value corresponds to the time, where the measured luminance decreased to 50% of the initial luminance, analogously LT80 corresponds to the time point, at which the measured luminance decreased to 80% of the initial luminance, LT 95 to the time point, at which the measured luminance decreased to 95% of the initial luminance etc.

Accelerated lifetime measurements are performed (e.g. applying increased current densities). Exemplarily LT80 values at 500 cd/m² are determined using the following equation:

$$LT80\left(500\frac{cd^2}{m^2}\right) = LT80(L_0)\left(\frac{L_0}{500\frac{cd^2}{m^2}}\right)^{1.6}$$

wherein $L_0$ denotes the initial luminance at the applied current density.

The values correspond to the average of several pixels (typically two to eight), the standard deviation between these pixels is given.

HPLC-MS:

HPLC-MS spectroscopy is performed on a HPLC by Agilent (1100 series) with MS-detector (Thermo LTQ XL). A reverse phase column 4.6 mm×150 mm, particle size 5.0 μm from Waters (without pre-column) is used in the HPLC. The HPLC-MS measurements are performed at room temperature (rt) with the solvents acetonitrile, water and THF in the following concentrations:

| solvent A: | H₂O (90%) | MeCN (10%) |
| solvent B: | H₂O (10%) | MeCN (90%) |
| solvent C: | THF (100%) | |

From a solution with a concentration of 0.5 mg/ml an injection volume of 15 μL is taken for the measurements. The following gradient is used:

| Flow rate [ml/min] | time [min] | A [%] | B [%] | D [%] |
|---|---|---|---|---|
| 3 | 0 | 40 | 50 | 10 |
| 3 | 10 | 10 | 15 | 75 |
| 3 | 16 | 10 | 15 | 75 |
| 3 | 16.01 | 40 | 50 | 10 |
| 3 | 20 | 40 | 50 | 10 |

Ionisation of the probe is performed by APCI (atmospheric pressure chemical ionization).

Example 1

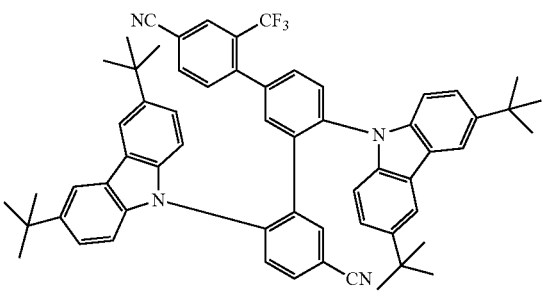 [SMILES: CC(C)(C)c1ccc2c(c1)c1cc(C(C)(C)C)ccc1n2-c1ccc(C#N)cc1-c1cc(-c2ccc(C#N)cc2C(F)(F)F)ccc1-n1c2ccc(C(C)(C)C)cc2c2cc(C(C)(C)C)ccc21]

Example 1 was synthesized according to AAV4 and AAV5, wherein the synthesis AAV5 had a yield of 9%.
MS (HPLC-MS):

| Molecular Formula | Retention Time | m/z calculated | m/z found |
|---|---|---|---|
| C₆₁H₅₇F₃N₄ | 12.66 min | 902.45 | 902.72 |

FIG. 1 depicts the emission spectrum of example 1 (10% by weight in PMMA). The emission maximum ($\lambda_{max}$) is at 444 nm. The photoluminescence quantum yield (PLQY) is 85%, the full width at half maximum (FWHM) is 0.43 eV and the emission lifetime is 173 μs. The resulting CIE, coordinate is determined at 0.16 and the CIE coordinate at 0.11.

Example 2

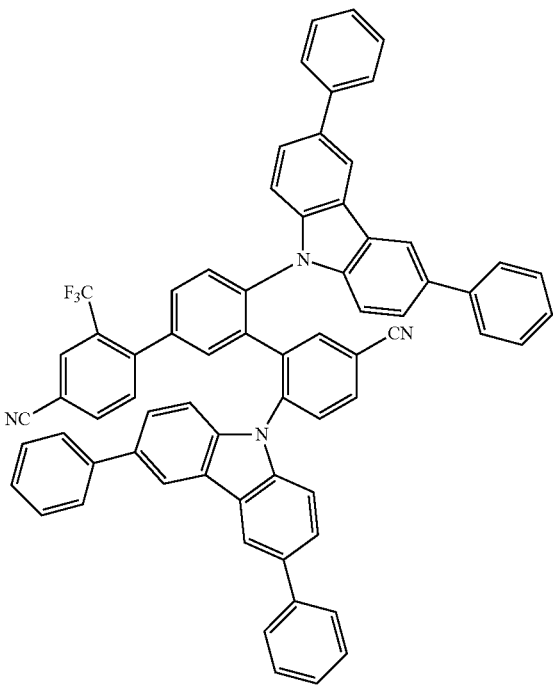 [SMILES: N#Cc1ccc(-n2c3ccc(-c4ccccc4)cc3c3cc(-c4ccccc4)ccc32)c(-c2cc(-c3ccc(C#N)cc3C(F)(F)F)ccc2-n2c3ccc(-c4ccccc4)cc3c3cc(-c4ccccc4)ccc32)c1]

Example 2 was synthesized according to AAV4 and AAV5, wherein the synthesis AAV5 had a yield of 21%.

MS (HPLC-MS):

| Molecular Formula | Retention Time | m/z calculated | m/z found |
|---|---|---|---|
| $C_{69}H_{41}F_3N_4$ | 10.18 min | 982.33 | 982.70 |

Figure 2:
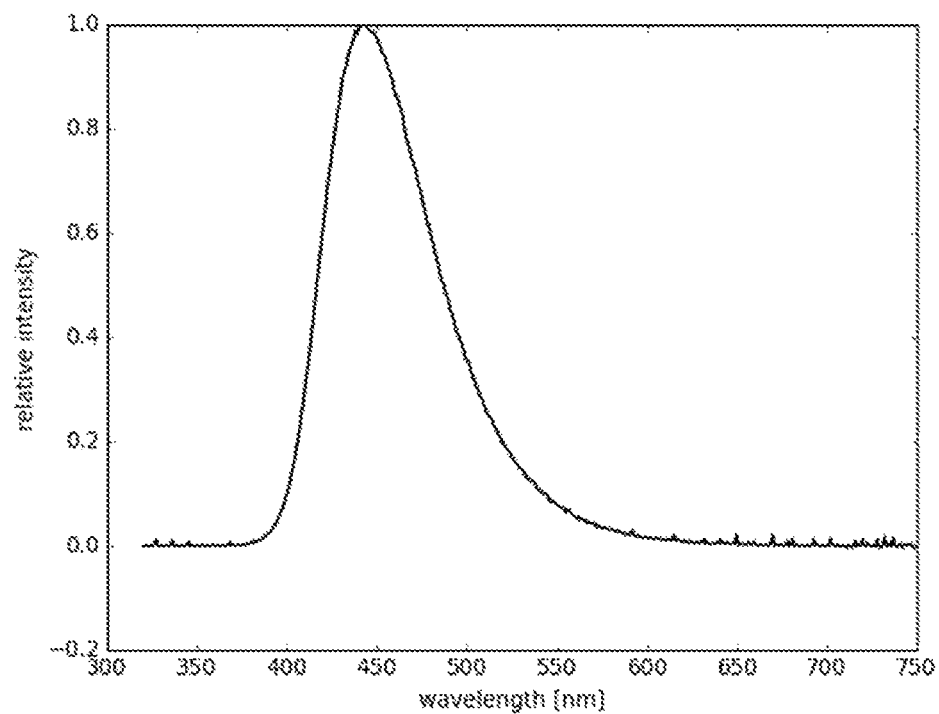

FIG. 2 depicts the emission spectrum of example 2 (10% by weight in PMMA). The emission maximum ($\lambda_{max}$) is at 444 nm. The photoluminescence quantum yield (PLQY) is 69%, the full width at half maximum (FWHM) is 0.43 eV and the emission lifetime is 254 µs. The resulting $CIE_x$ coordinate is determined at 0.16 and the CIE coordinate at 0.11.

Example 3

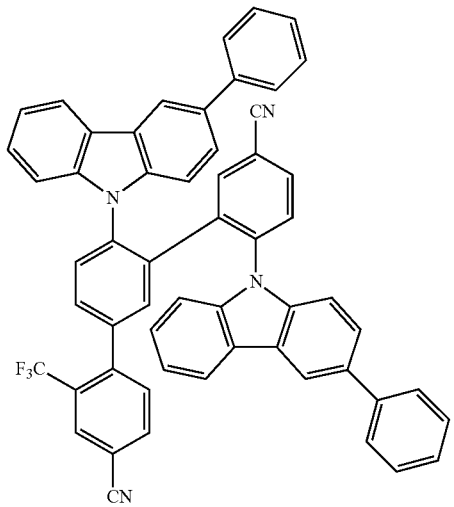 [SMILES: N#Cc1ccc(-n2c3ccccc3c3cc(-c4ccccc4)ccc32)c(-c2cc(-c3ccc(C#N)cc3C(F)(F)F)ccc2-n2c3ccccc3c3cc(-c4ccccc4)ccc32)c1]

Example 3 was synthesized according to AAV4 and AAV5, wherein the synthesis AAV5 had a yield of 5%.

MS (HPLC-MS):

| Molecular Formula | Retention Time | m/z calculated | m/z found |
|---|---|---|---|
| $C_{57}H_{33}F_3N_4$ | 9.05 min | 830.27 | 830.61 |

Figure 3:
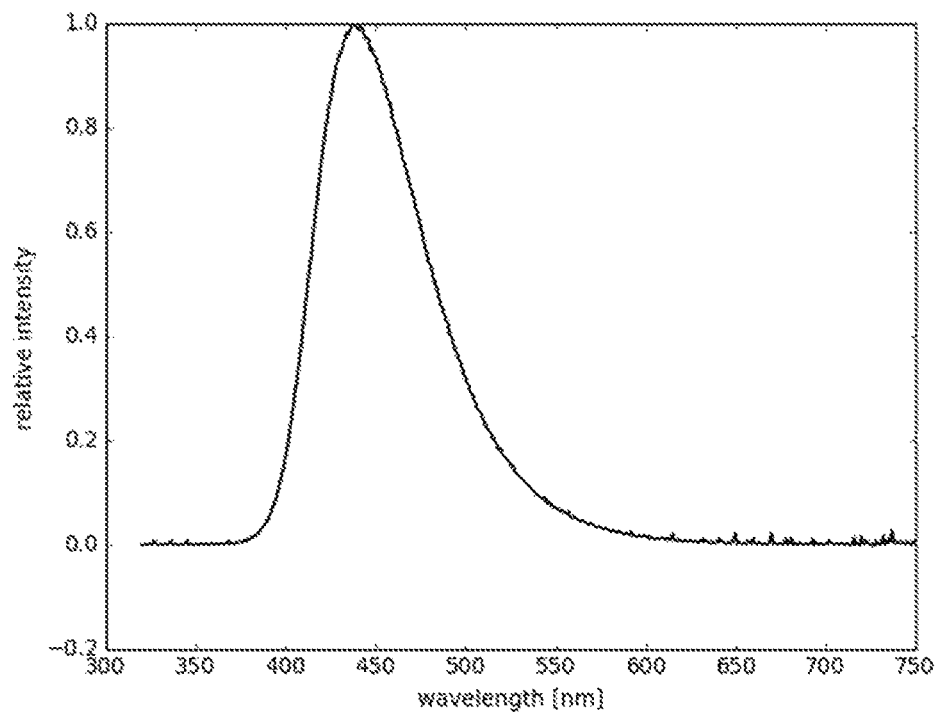

FIG. 3 depicts the emission spectrum of example 3 (10% by weight in PMMA). The emission maximum ($\lambda_{max}$) is at 438 nm. The photoluminescence quantum yield (PLQY) is 70%, the full width at half maximum (FWHM) is 0.44 eV and the emission lifetime is 556 µs. The resulting $CIE_x$ coordinate is determined at 0.16 and the CIE coordinate at 0.10.

Example 4

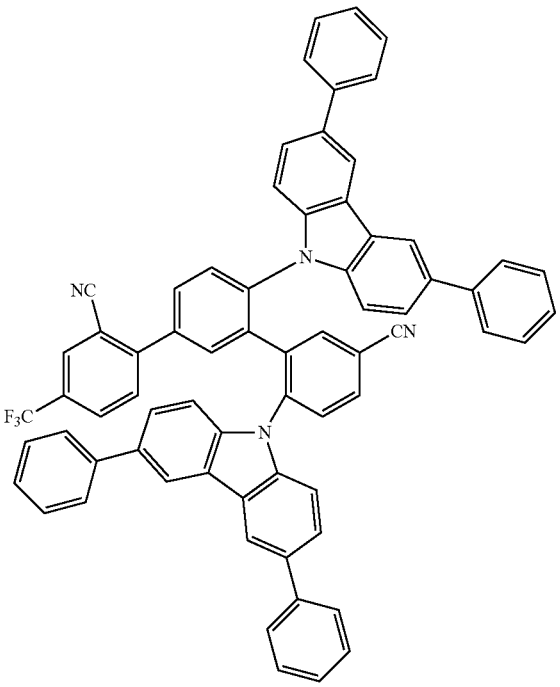 [SMILES: N#Cc1ccc(-n2c3ccc(-c4ccccc4)cc3c3cc(-c4ccccc4)ccc32)c(-c2cc(-c3ccc(C(F)(F)F)cc3C#N)ccc2-n2c3ccc(-c4ccccc4)cc3c3cc(-c4ccccc4)ccc32)c1]

Example 4 was synthesized according to AAV4 and AAV5, wherein the synthesis AAV5 had a yield of 29%.

MS (HPLC-MS):

| Molecular Formula | Retention Time | m/z calculated | m/z found |
|---|---|---|---|
| $C_{69}H_{41}F_3N_4$ | 10.57 min | 982.33 | 982.34 |

Figure 4:
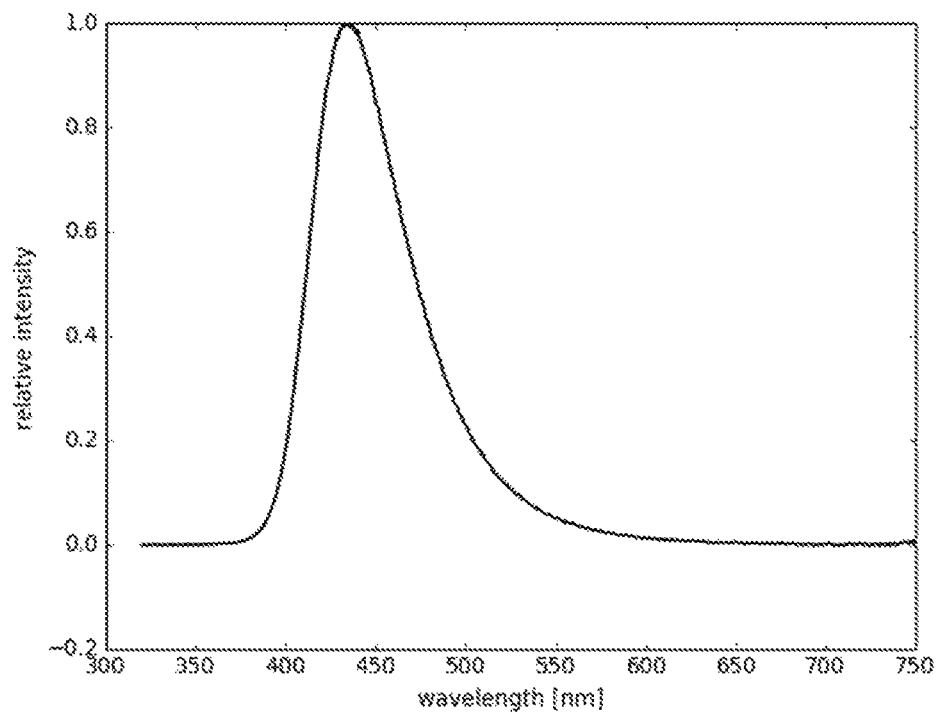

FIG. 4 depicts the emission spectrum of example 4 (10% by weight in PMMA). The emission maximum is at 435 nm. The photoluminescence quantum yield (PLQY) is 54%, the full width at half maximum is 0.40 eV and the emission lifetime is 425 µs. The resulting $CIE_x$ coordinate is determined at 0.16 and the CIE coordinate at 0.08.

Example 5

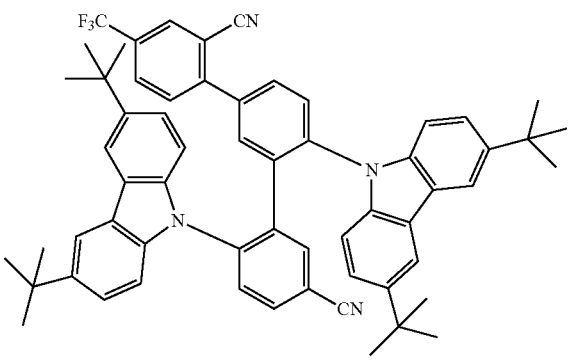 [SMILES: CC(C)(C)c1ccc2c(c1)c1cc(C(C)(C)C)ccc1n2-c1ccc(C#N)cc1-c1cc(-c2ccc(C(F)(F)F)cc2C#N)ccc1-n1c2ccc(C(C)(C)C)cc2c2cc(C(C)(C)C)ccc21]

Example 5 was synthesized according to AAV4 and AAV5, wherein the synthesis AAV5 had a yield of 22%.

Figure 5:
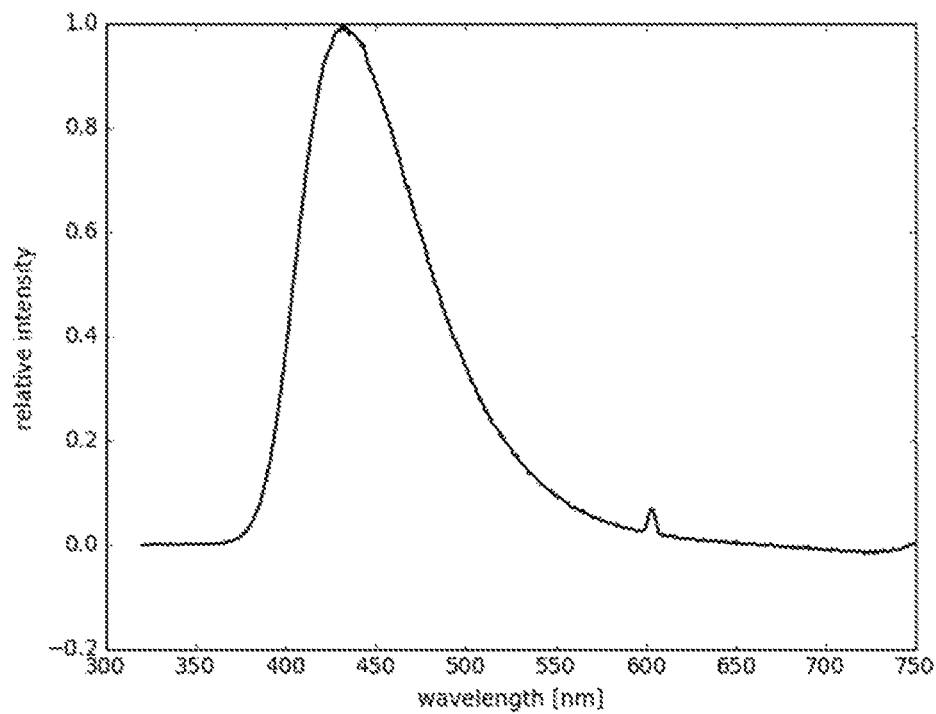

FIG. 5 depicts the emission spectrum of example 5 (10% by weight in PMMA). The emission maximum is at 431 nm. The photoluminescence quantum yield (PLQY) is 61%, the full width at half maximum is 0.49 eV and the emission lifetime is 577 µs. The resulting $CIE_x$ coordinate is determined at 0.16 and the CIE coordinate at 0.11.

Example 6

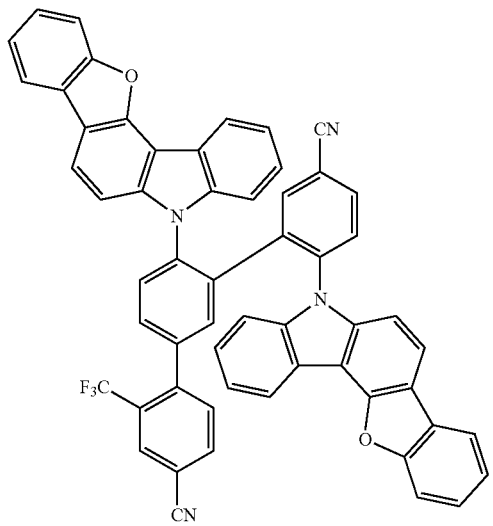 [SMILES: N#Cc1ccc(-n2c3ccccc3c3c4oc5ccccc5c4ccc32)c(-c2cc(-c3ccc(C#N)cc3C(F)(F)F)ccc2-n2c3ccccc3c3c4oc5ccccc5c4ccc32)c1]

Example 6 was synthesized according to AAV4 and AAV5, wherein the synthesis AAV5 had a yield of 7%.

Figure 6:
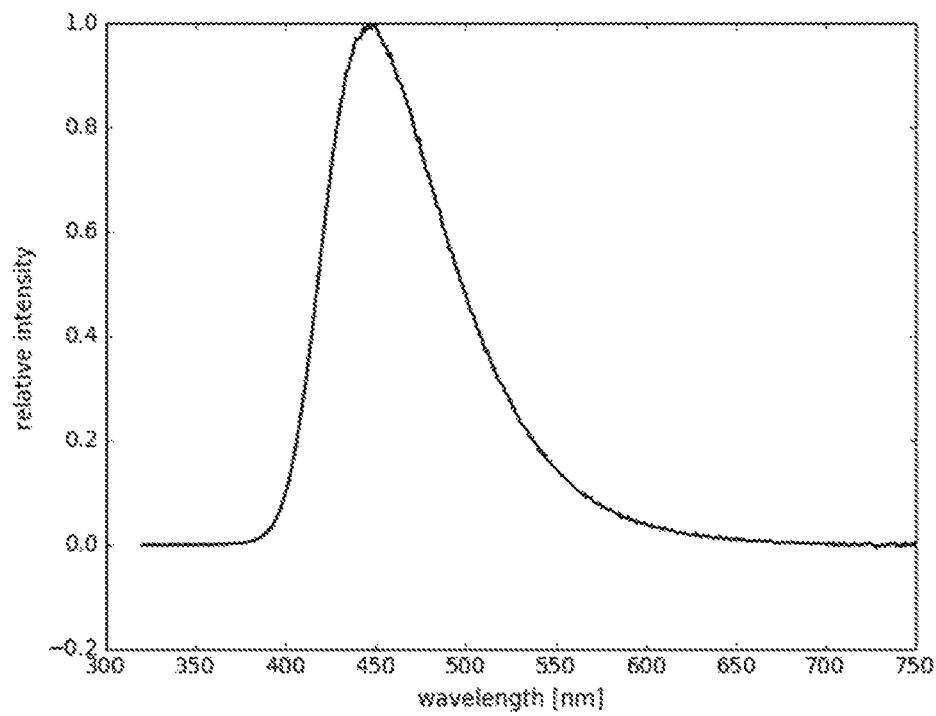

FIG. 6 depicts the emission spectrum of example 6 (10% by weight in PMMA). The emission maximum ($\lambda_{max}$) is at 446 nm. The photoluminescence quantum yield (PLQY) is 66%, the full width at half maximum (FWHM) is 0.48 eV and the emission lifetime is 125 µs. The resulting $CIE_x$ coordinate is determined at 0.15 and the CIE coordinate at 0.15.

Example 7

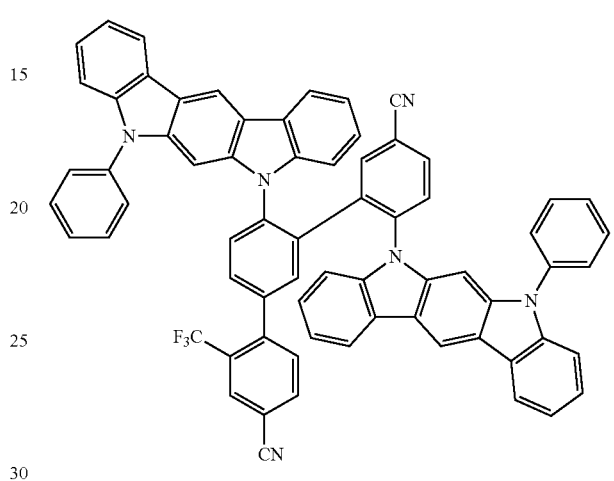

Example 7 was synthesized according to AAV4 and AAV5, wherein the synthesis AAV5 had a yield of 10%.

Figure 7:
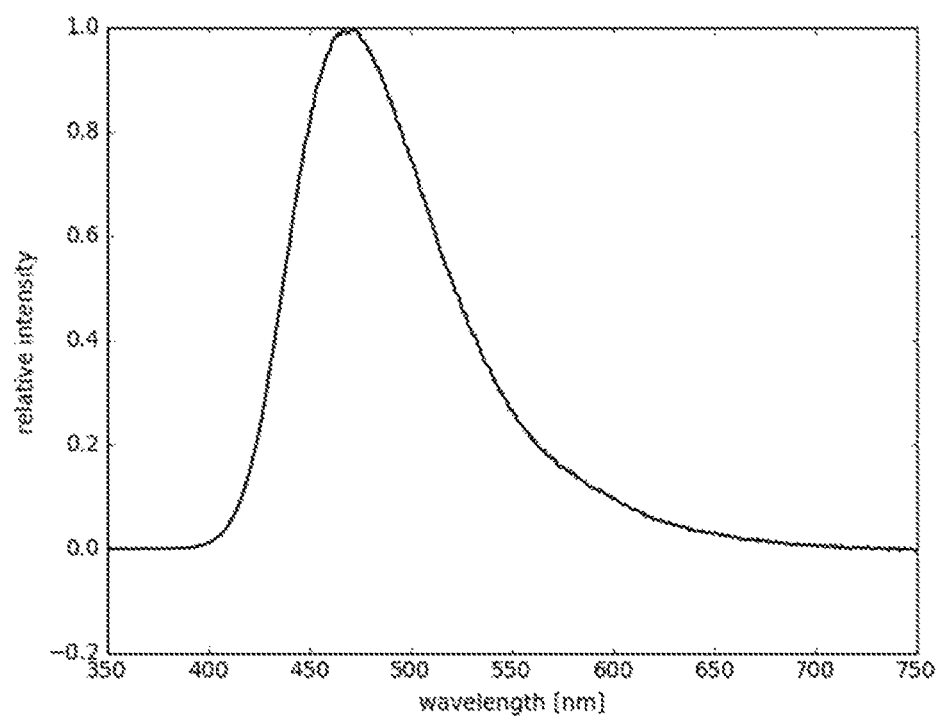

FIG. 7 depicts the emission spectrum of example 7 (10% by weight in PMMA). The emission maximum ($\lambda_{max}$) is at 471 nm. The photoluminescence quantum yield (PLQY) is 68%, the full width at half maximum (FWHM) is 0.46 eV and the emission lifetime is 189 µs. The resulting CIE, coordinate is determined at 0.18 and the CIE coordinate at 0.24.

Additional Examples of Organic Molecules of the Invention

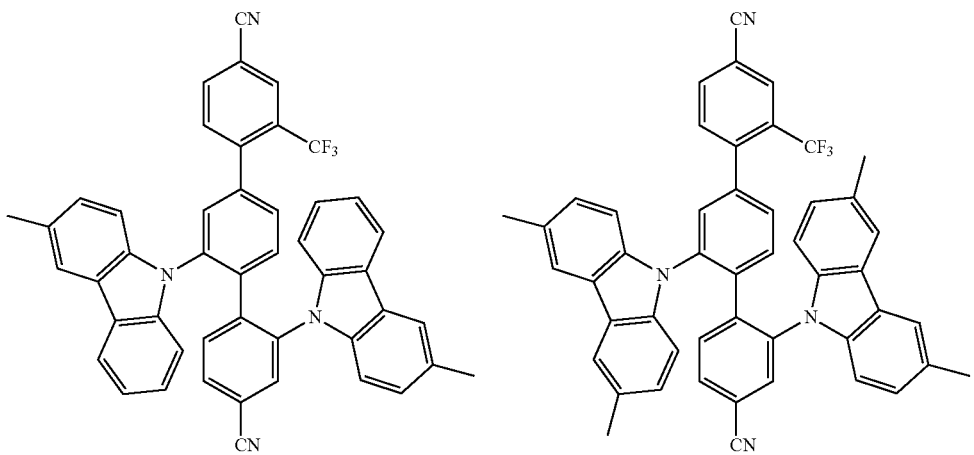

-continued
81
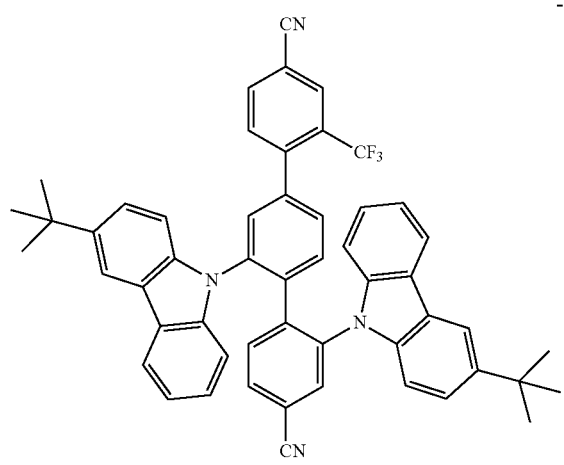
82
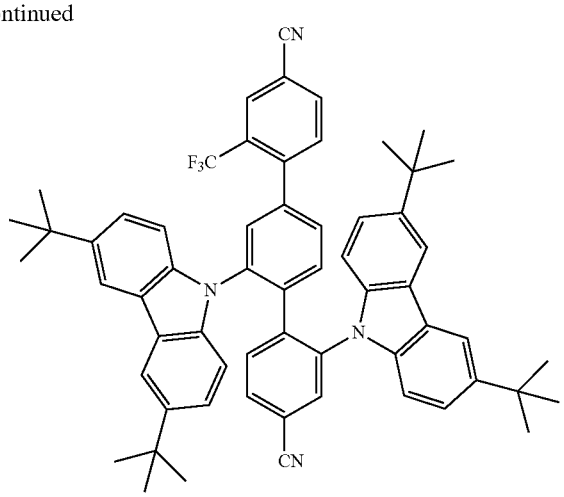
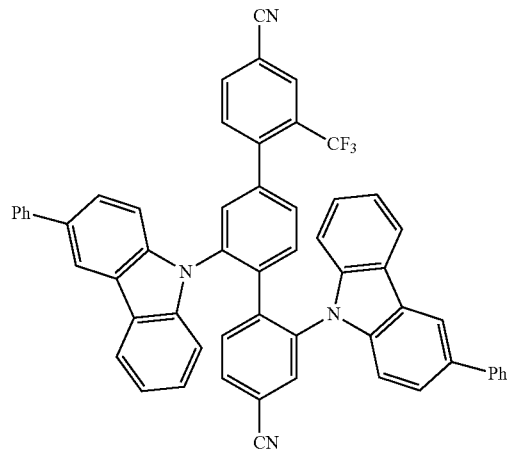
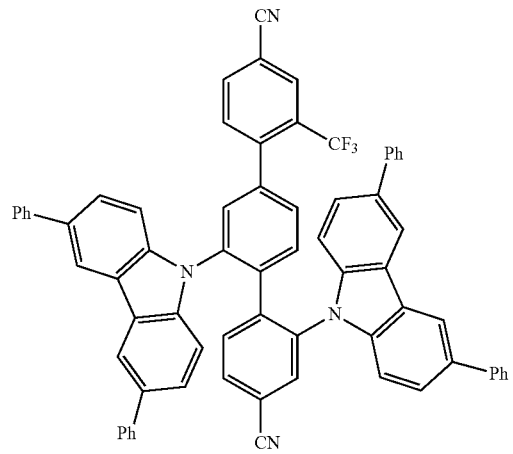
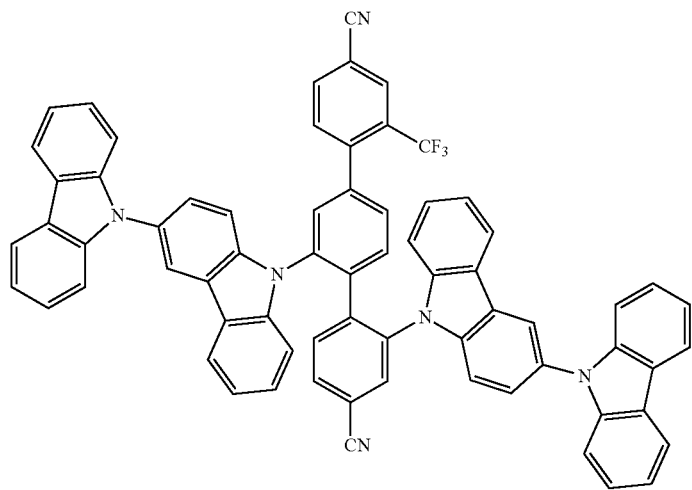

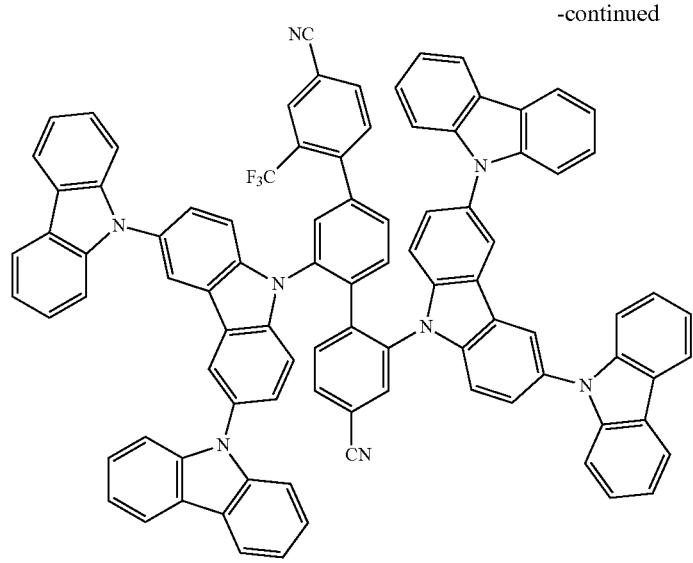
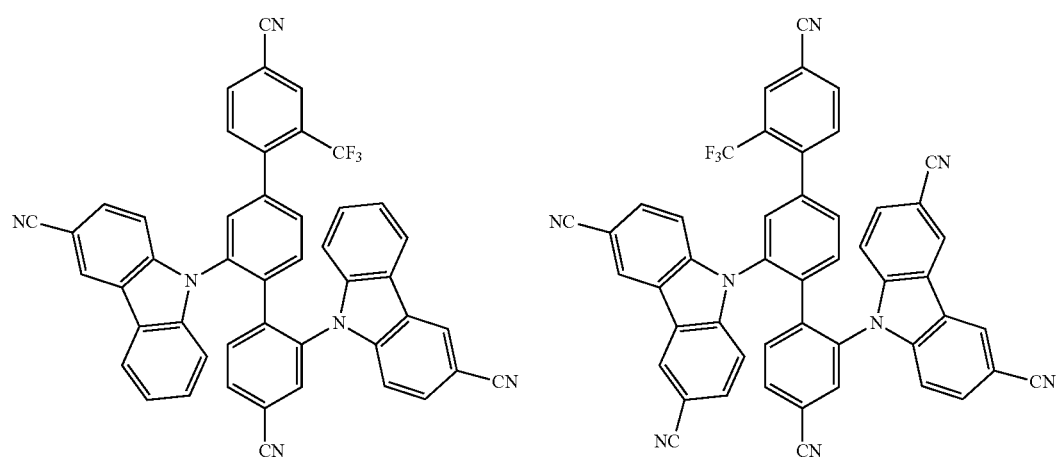
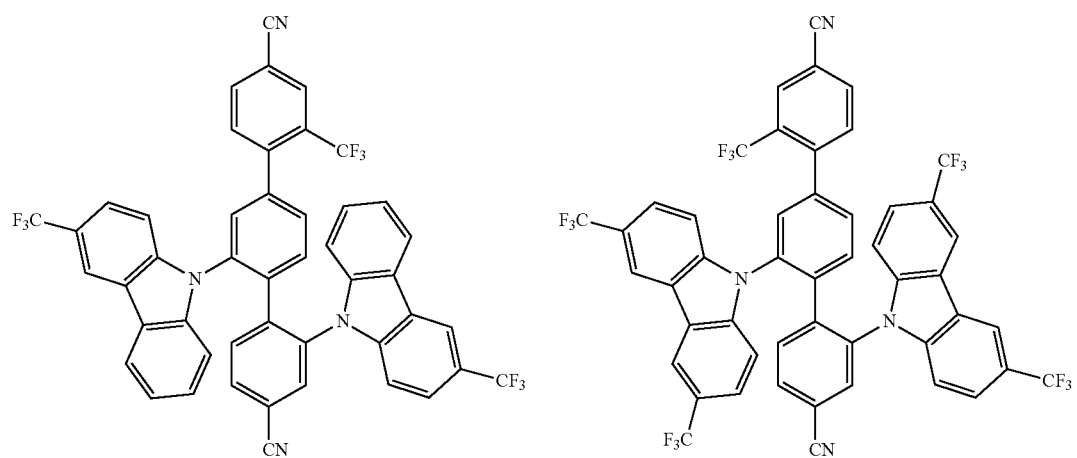

-continued
| 85 | 86 |
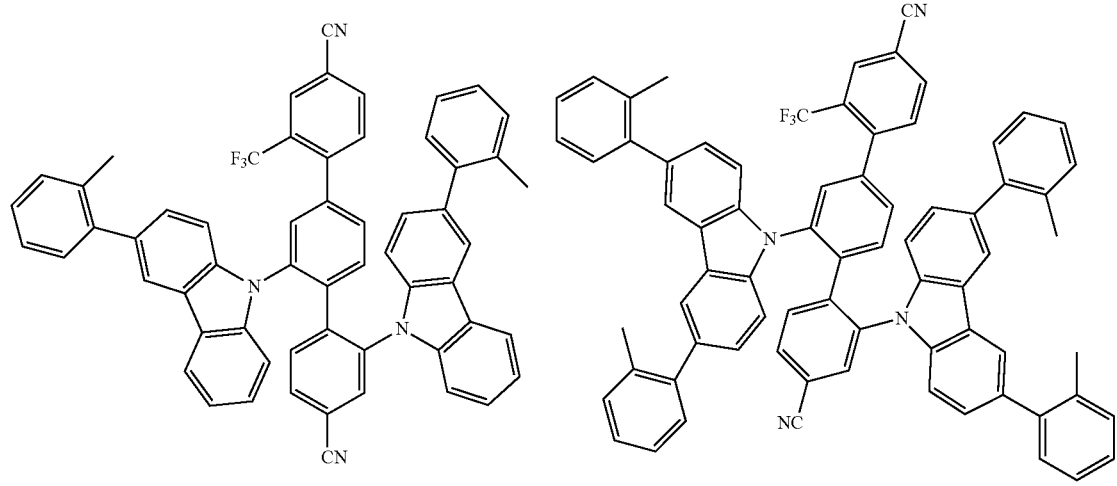
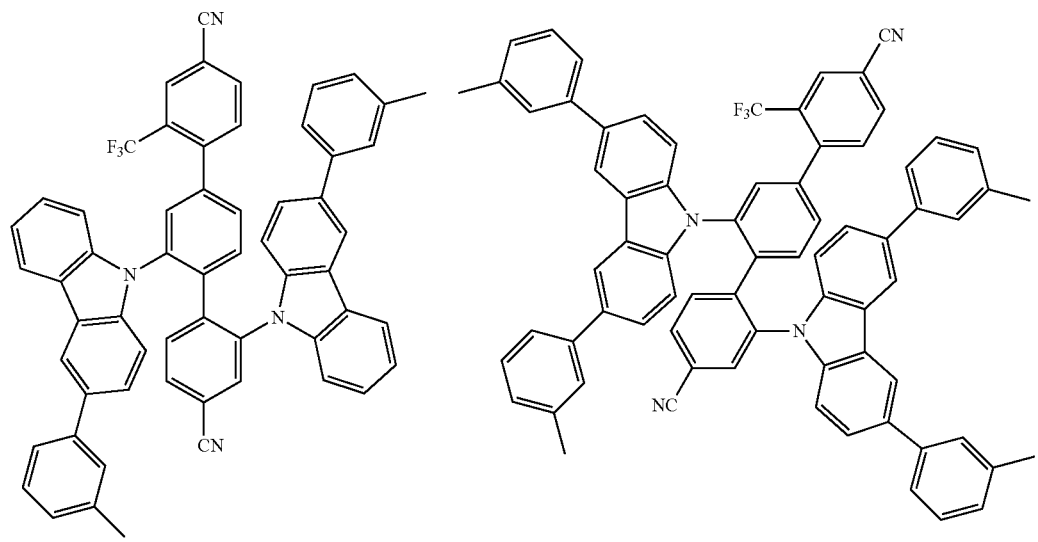
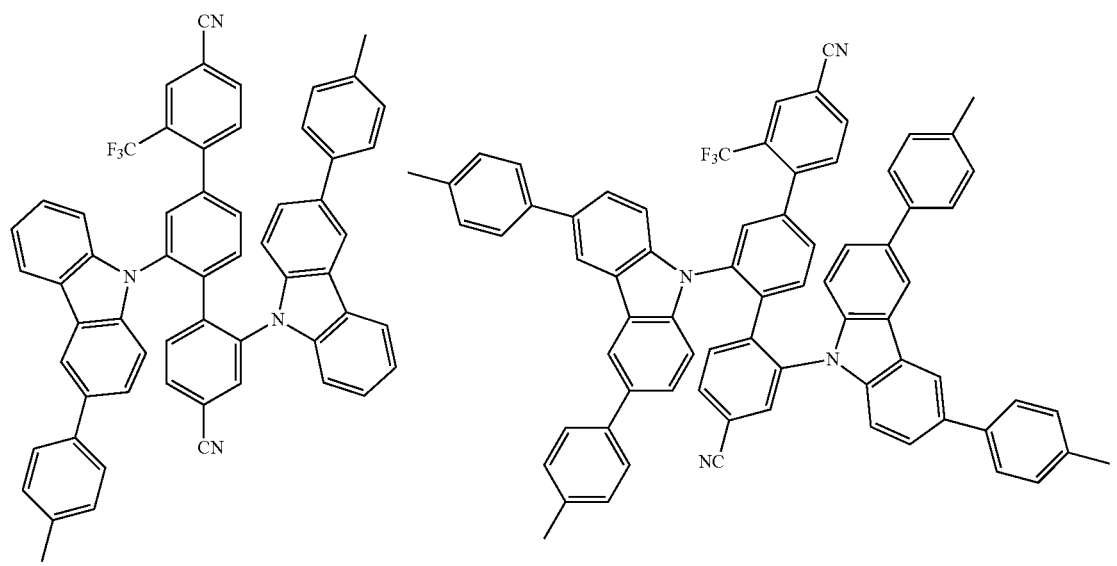

-continued
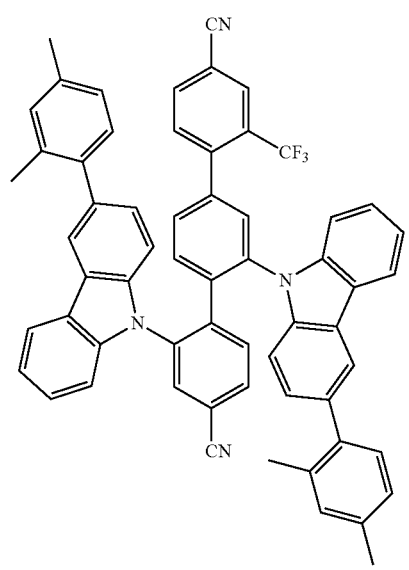
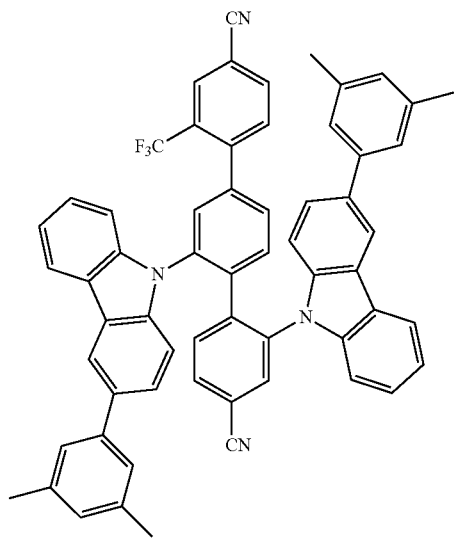
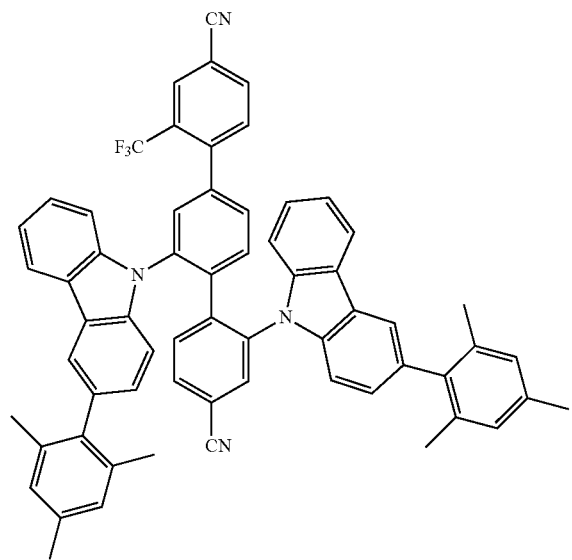
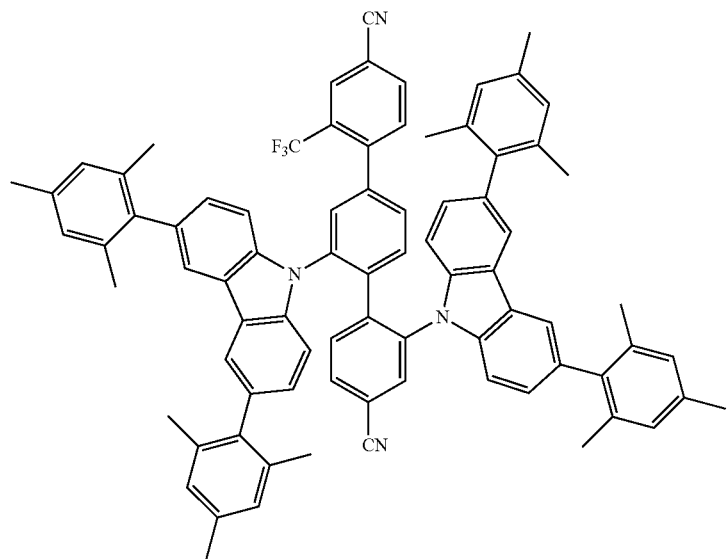

-continued
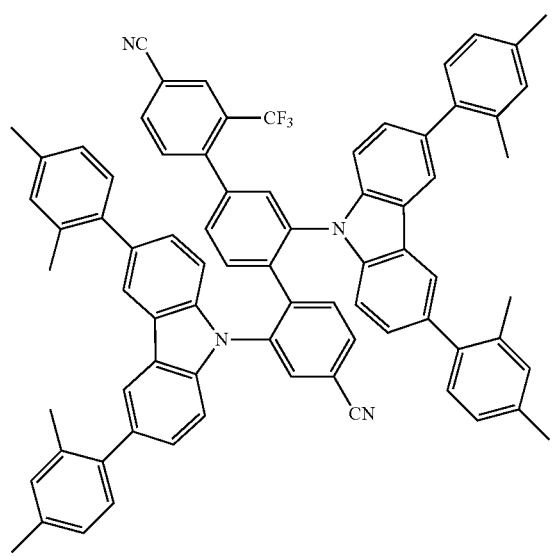
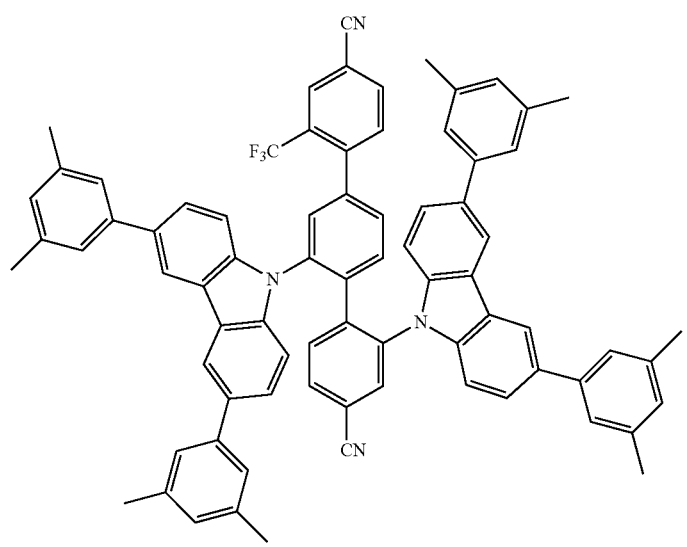
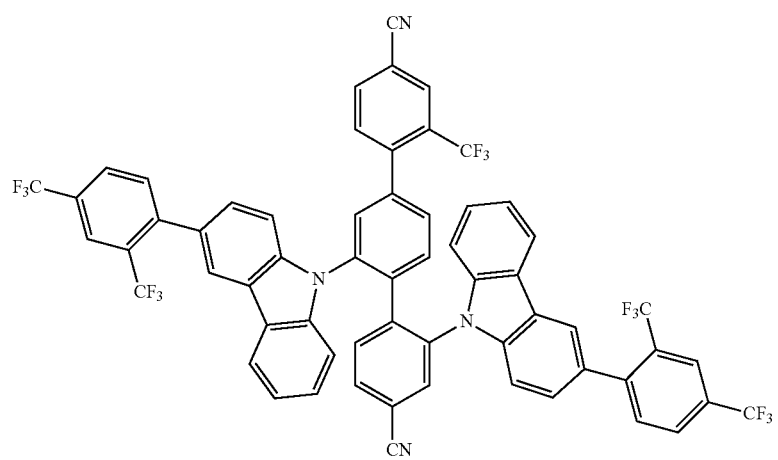

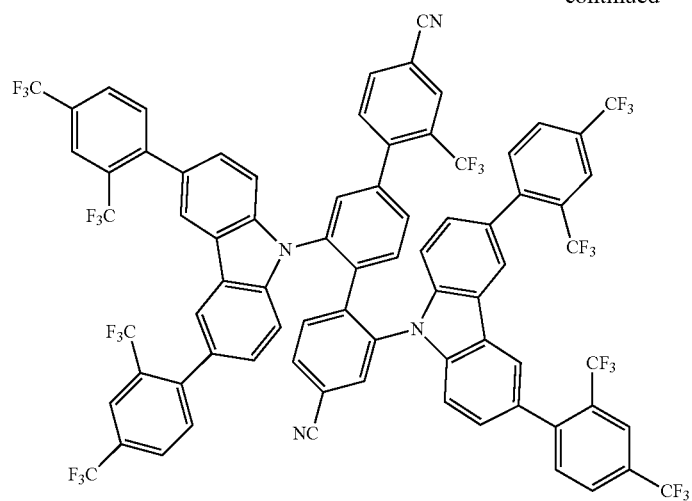
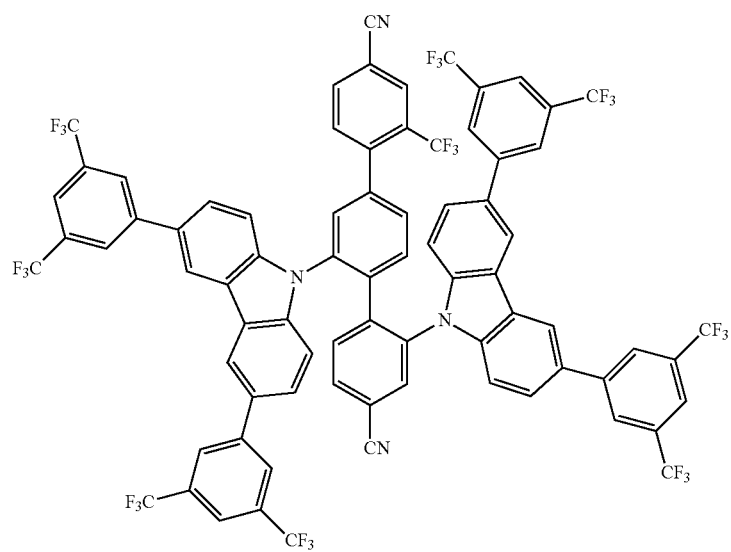
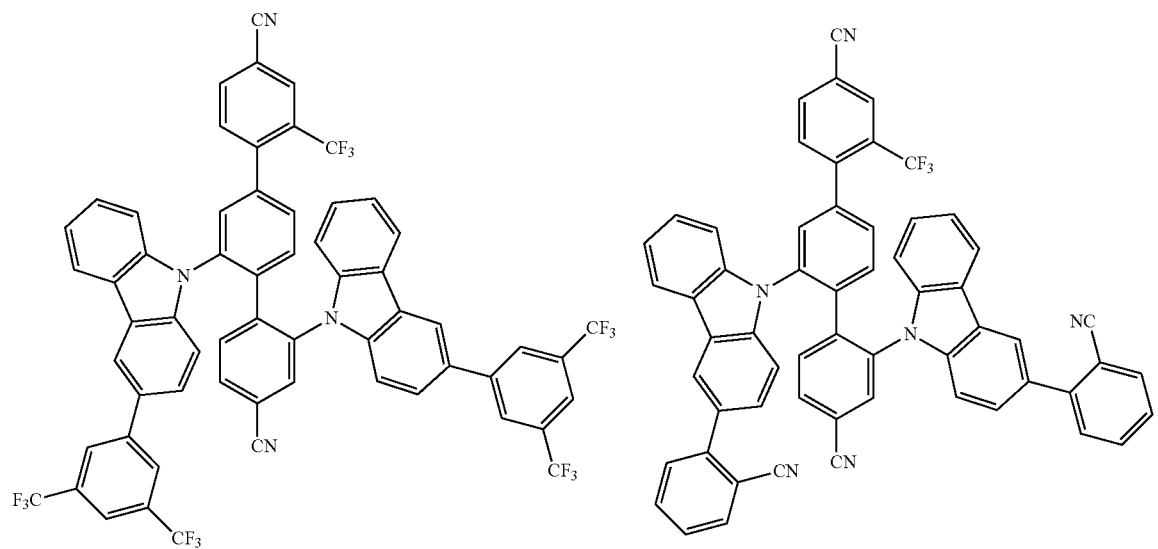

93 94
-continued
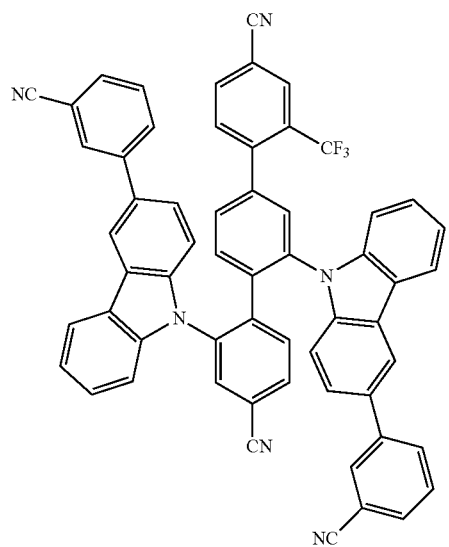
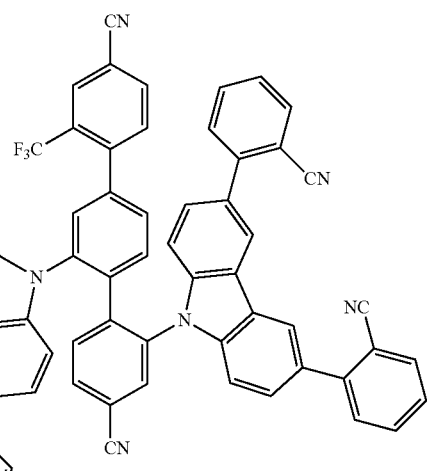
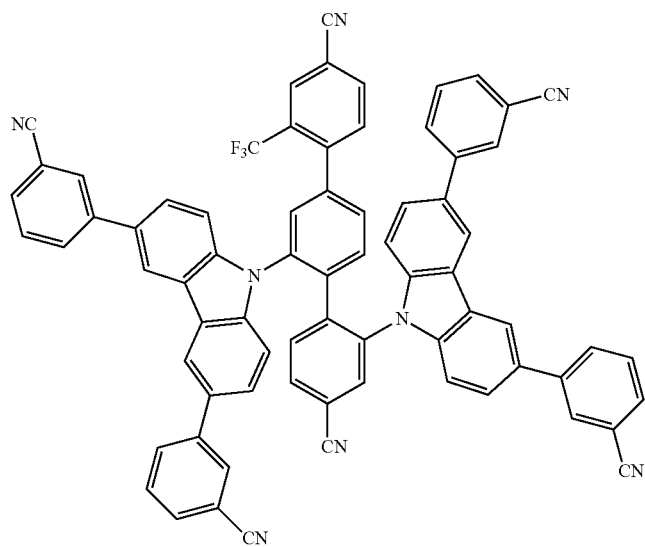
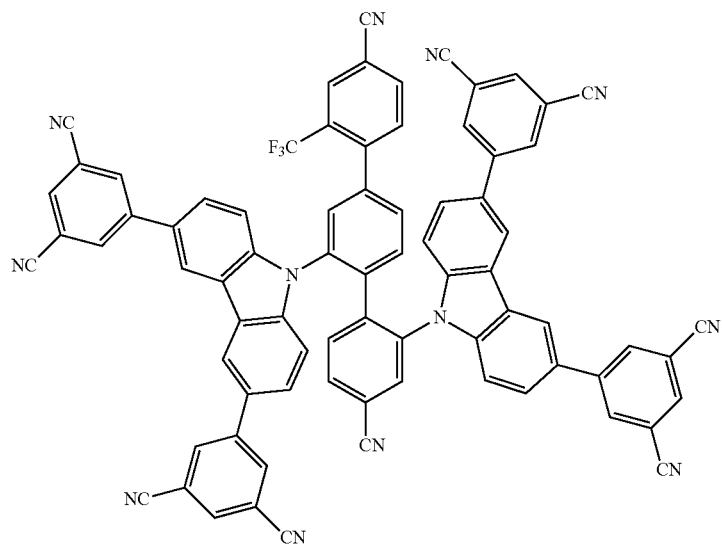

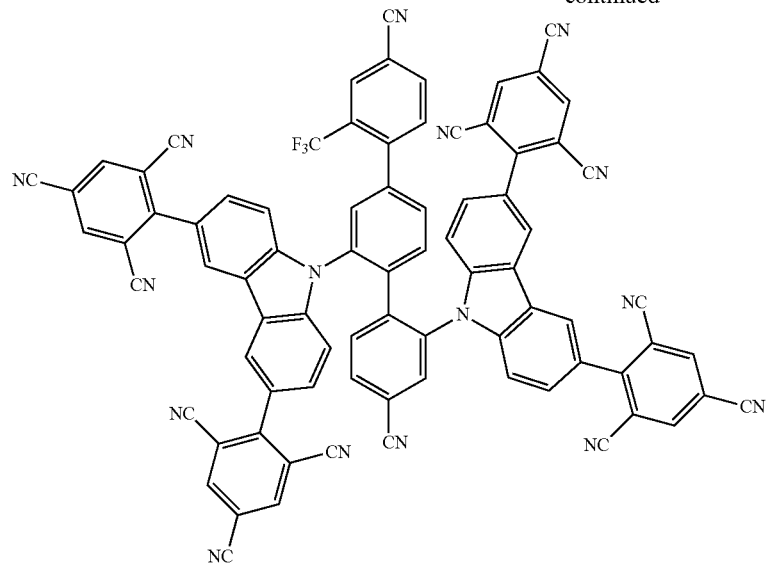
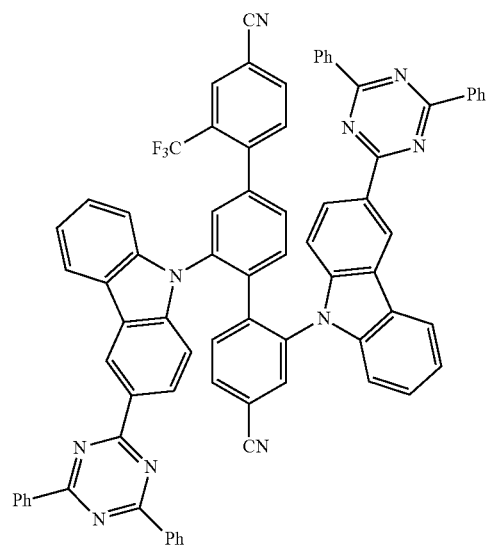
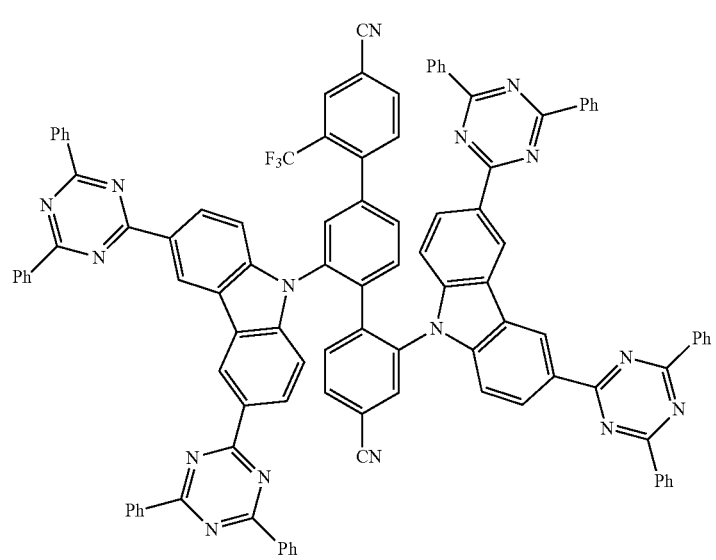
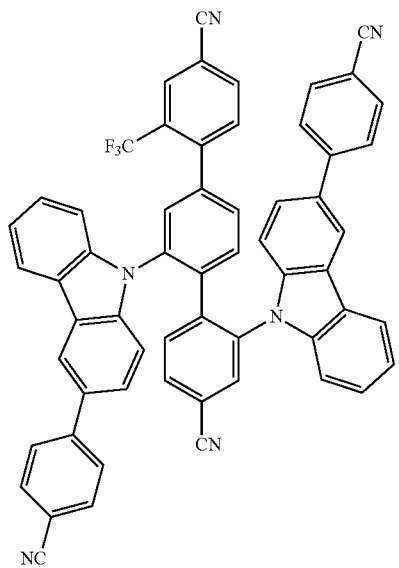

-continued
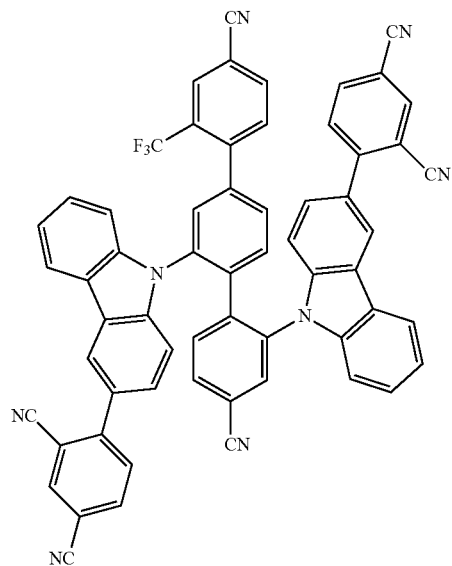
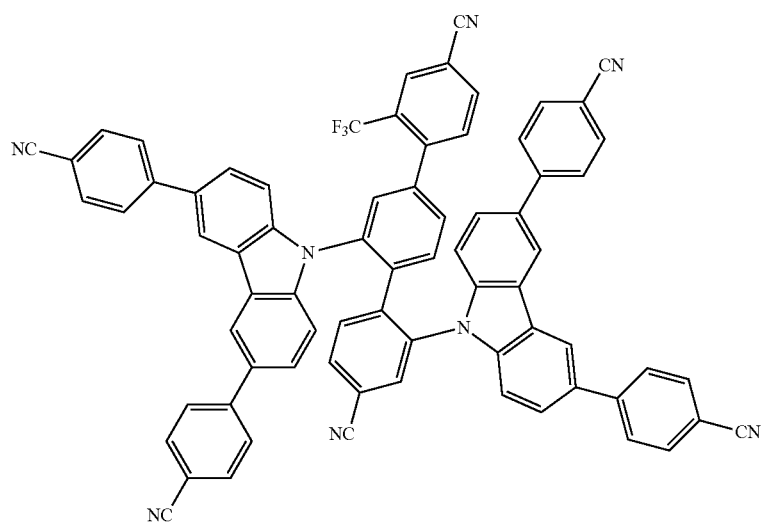
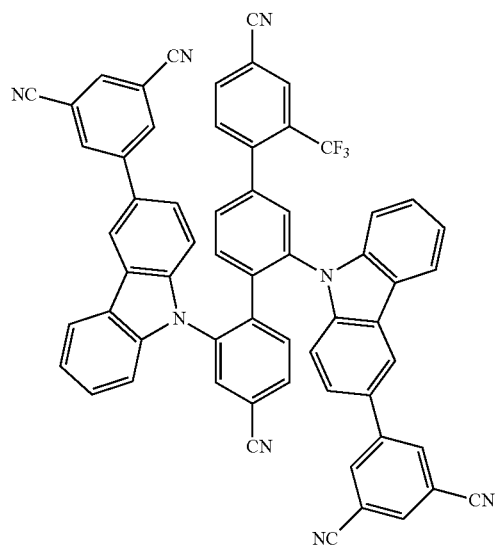

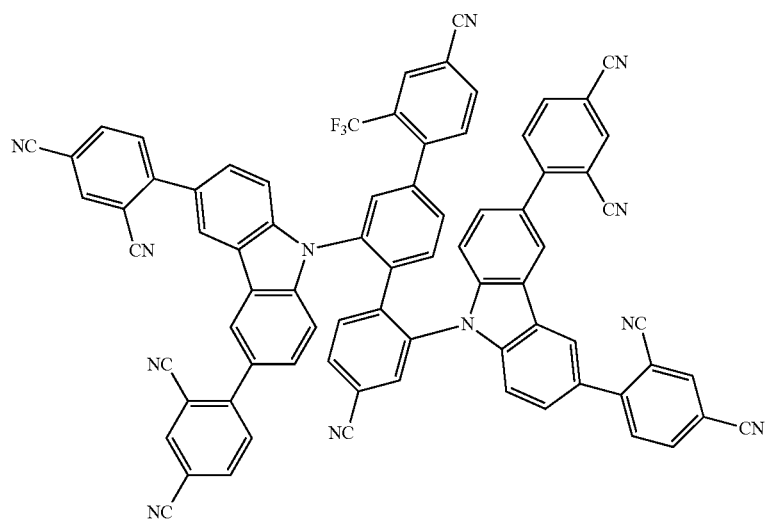
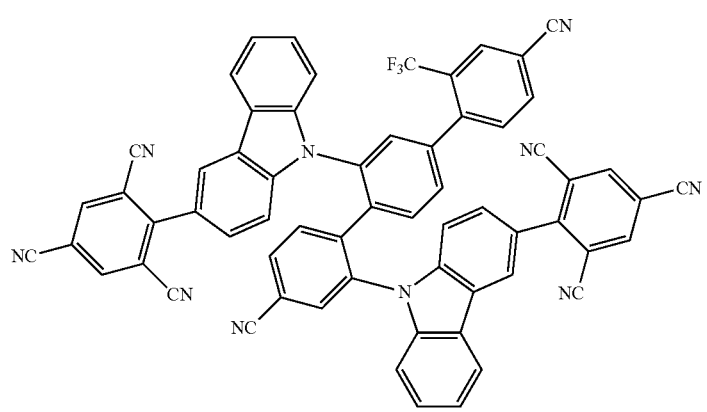
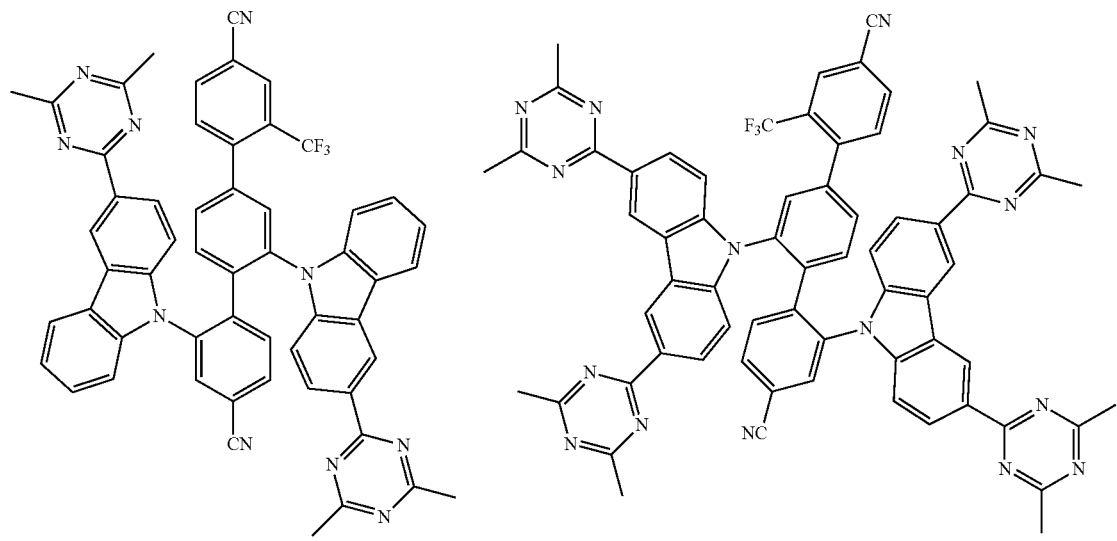

101 102
-continued
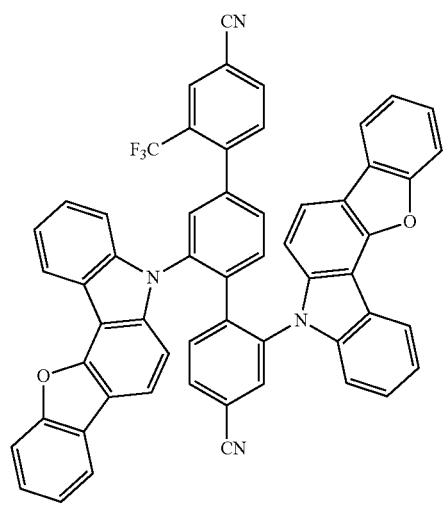
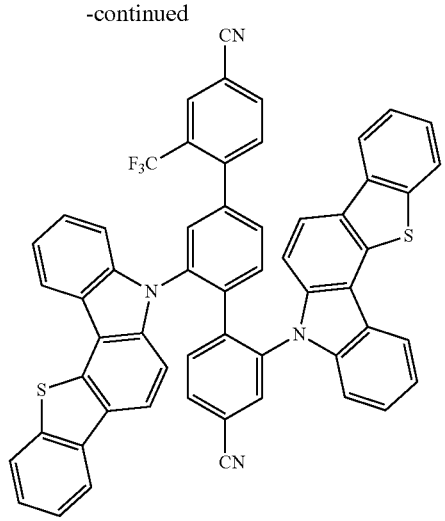
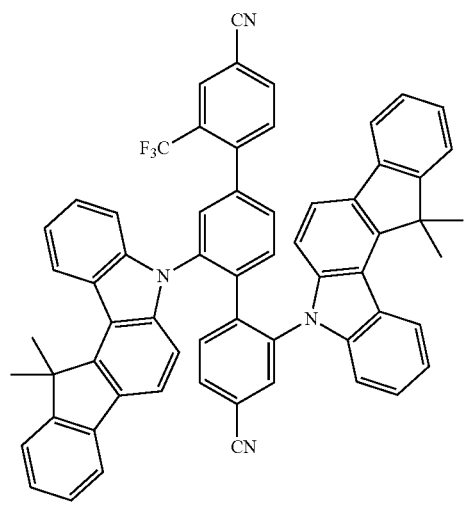
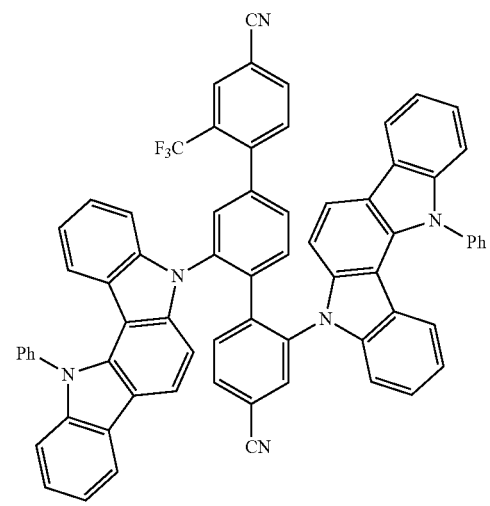
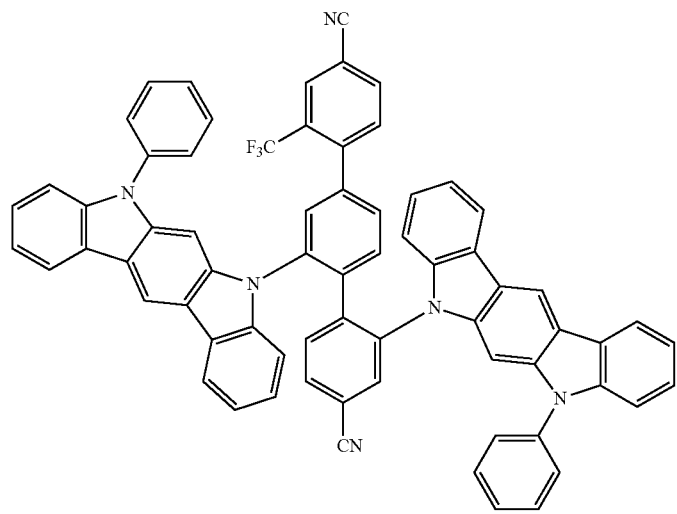
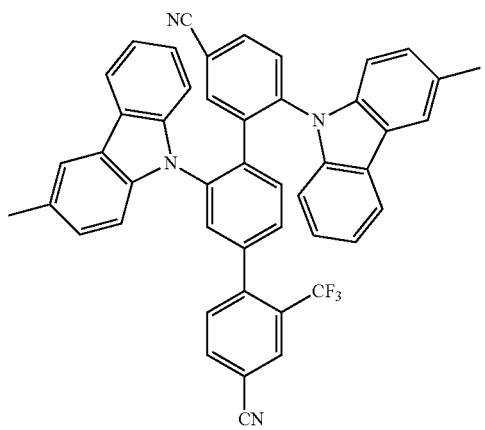

103
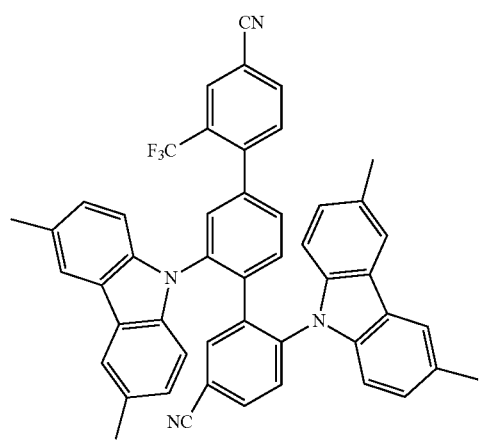
104
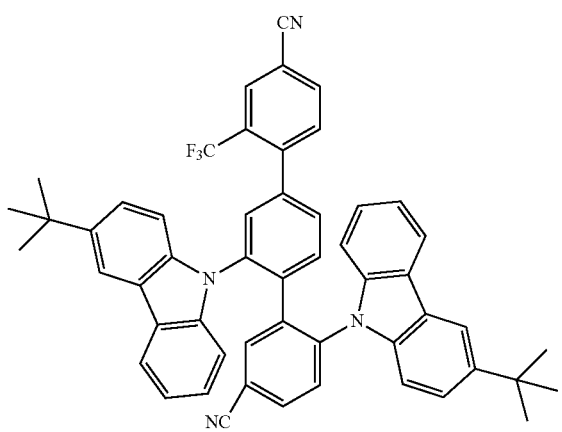
-continued
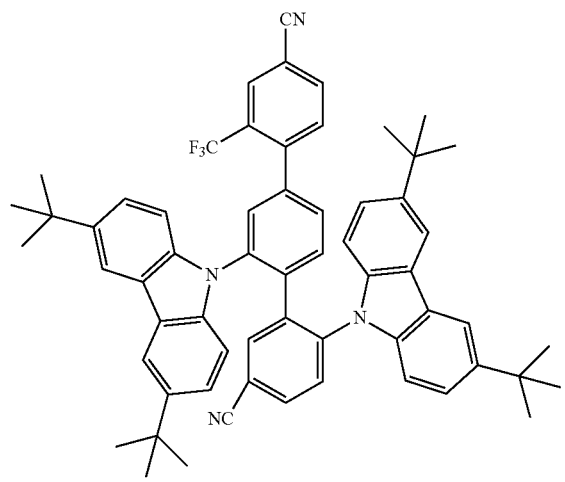
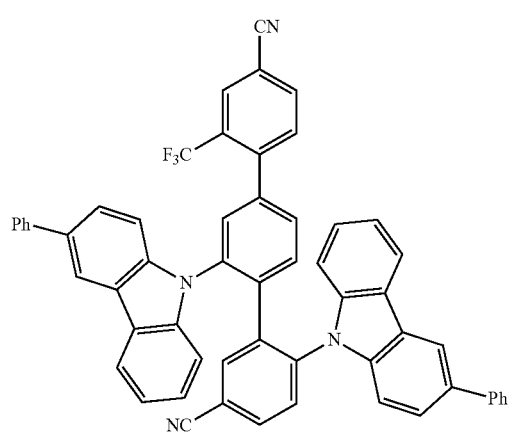
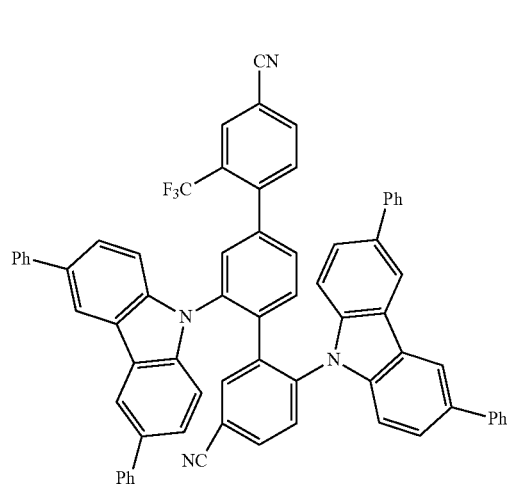
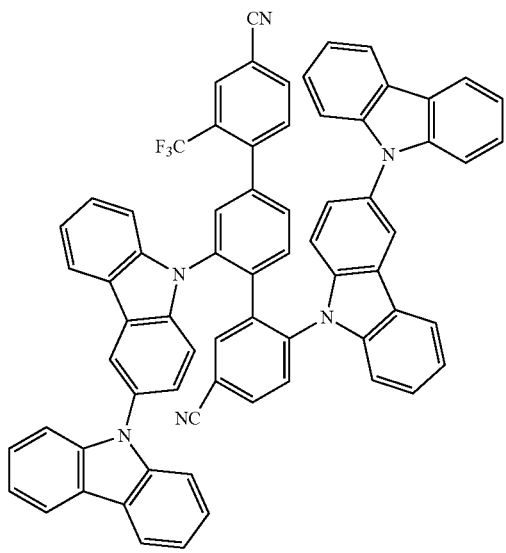

105
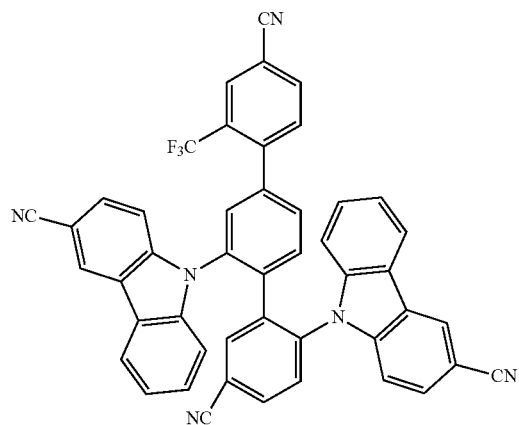
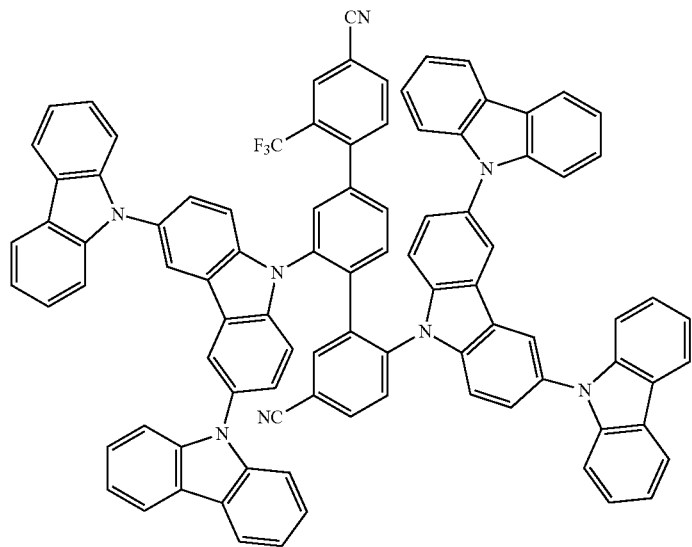
106
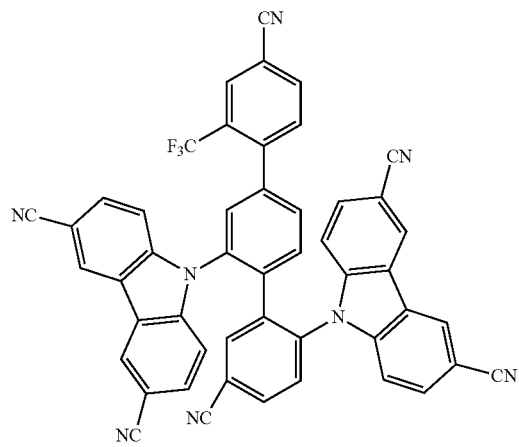
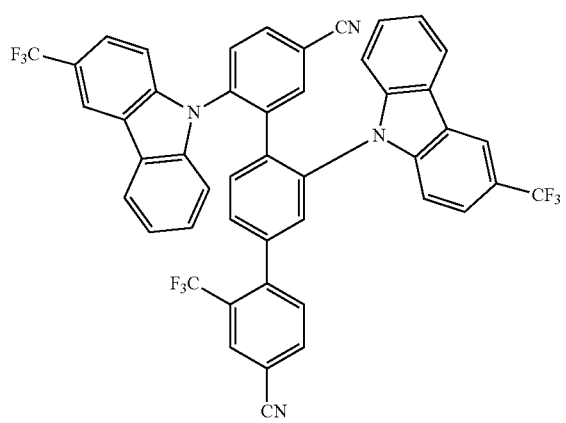

-continued
107
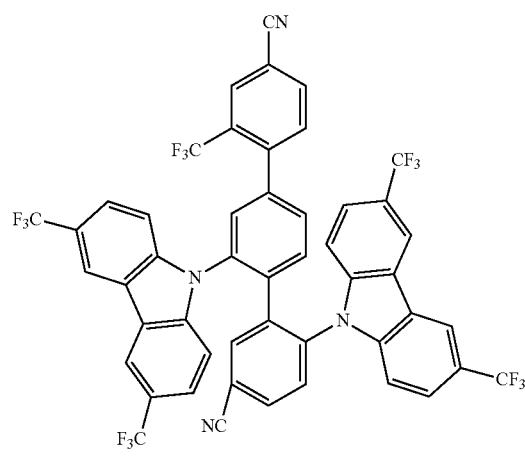
108
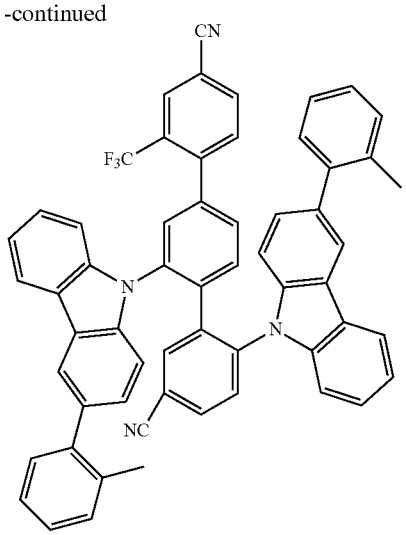
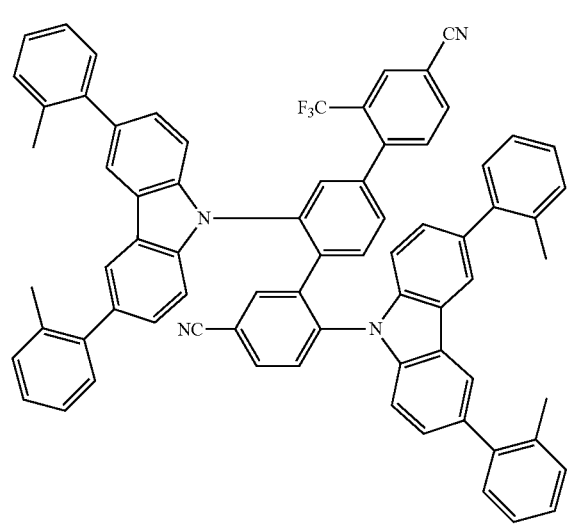
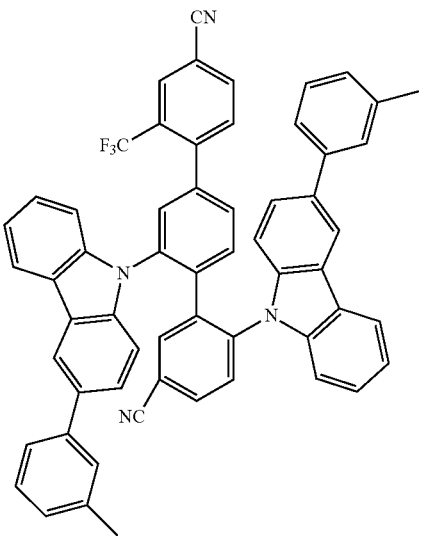
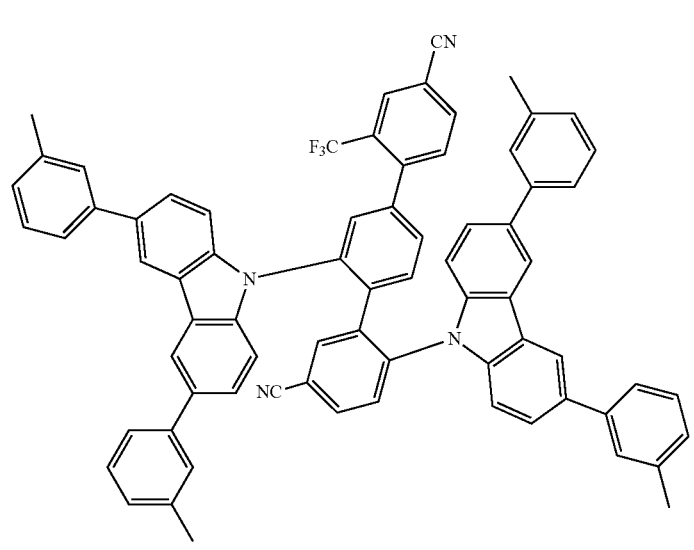
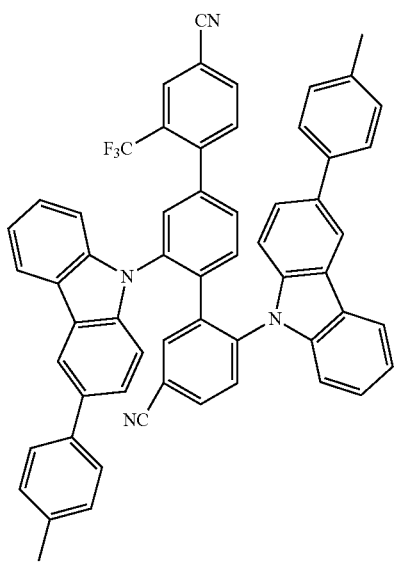

-continued
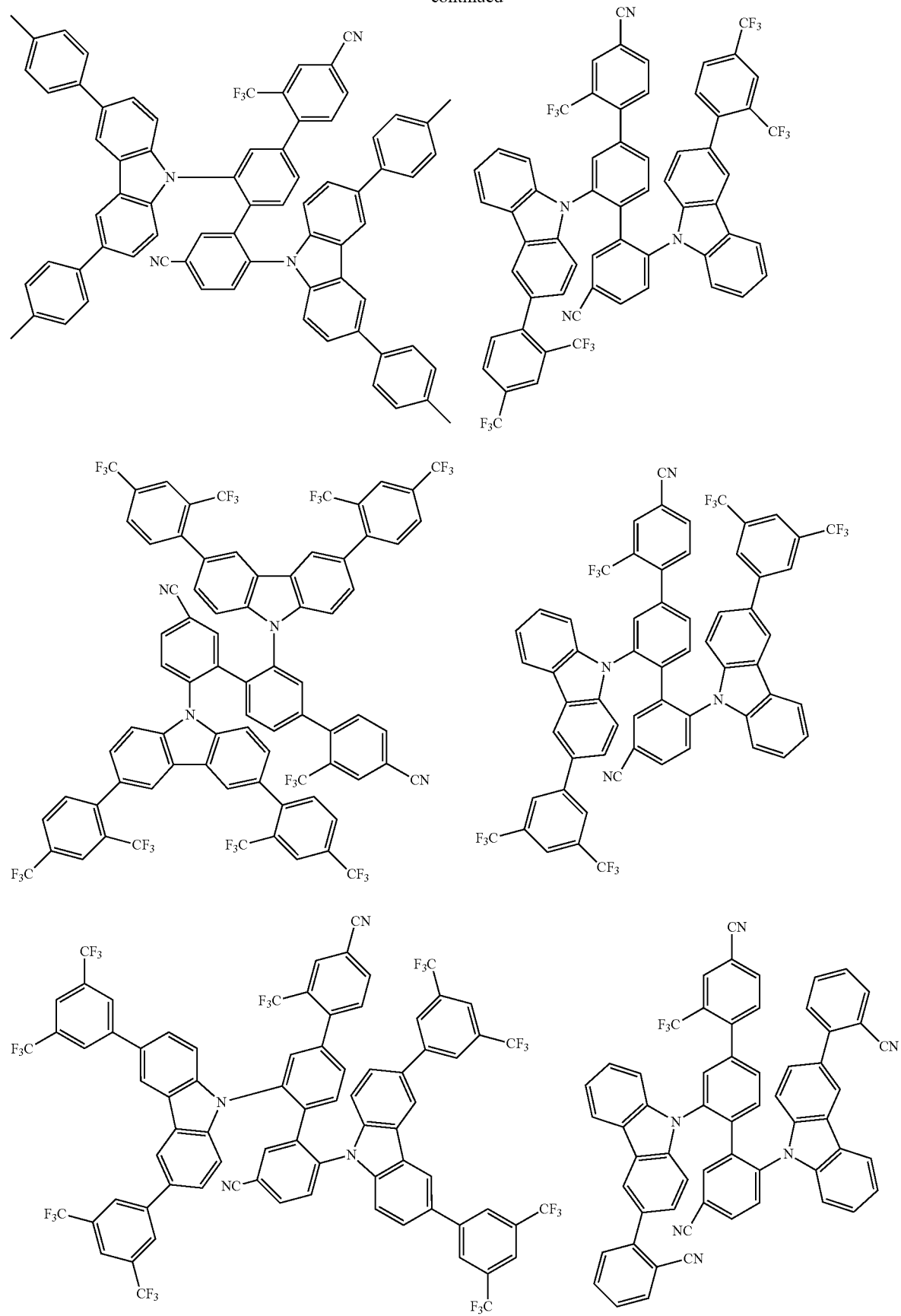

-continued
111
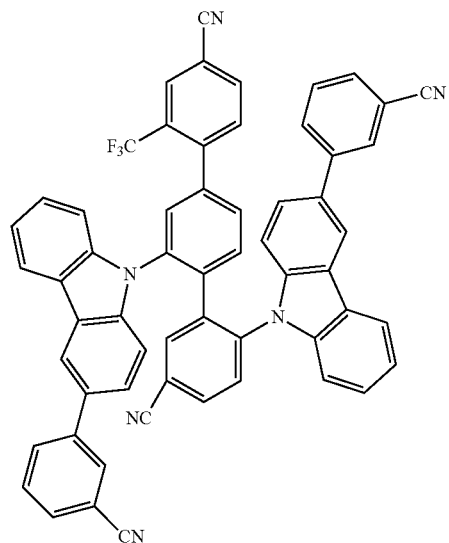
112
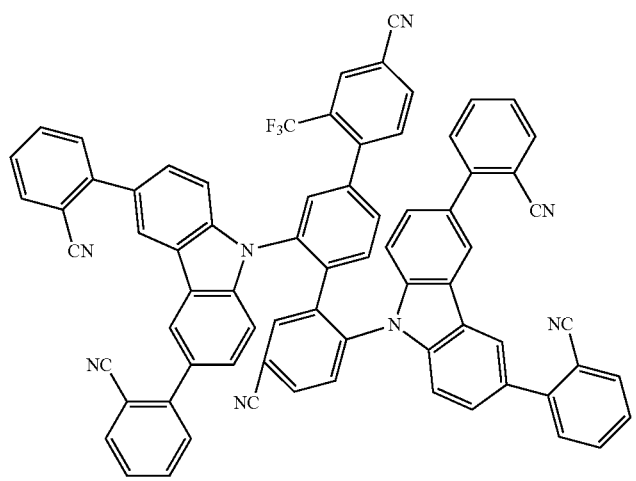
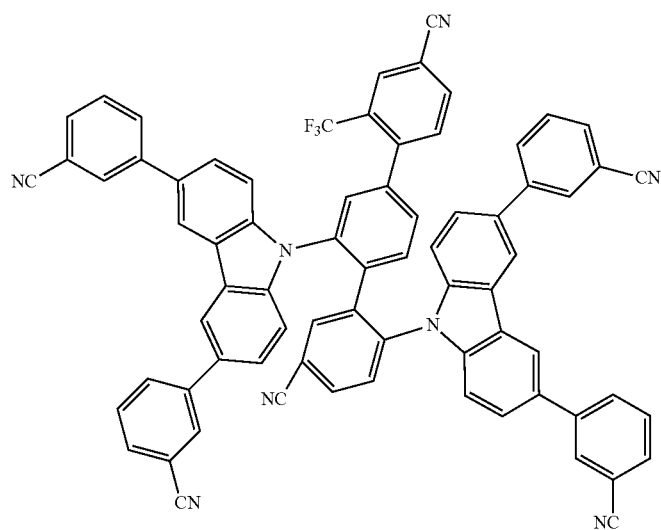
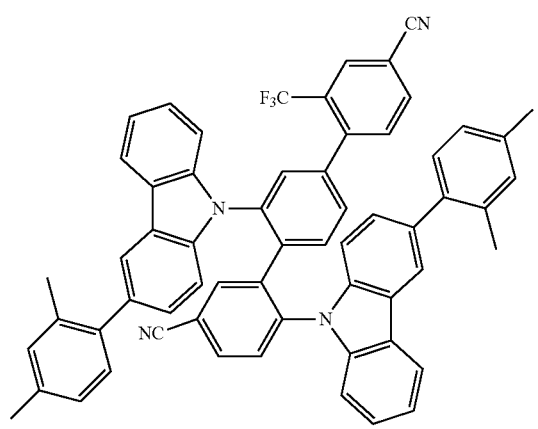
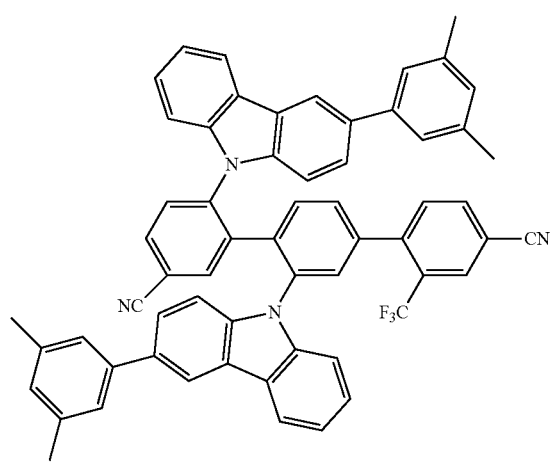
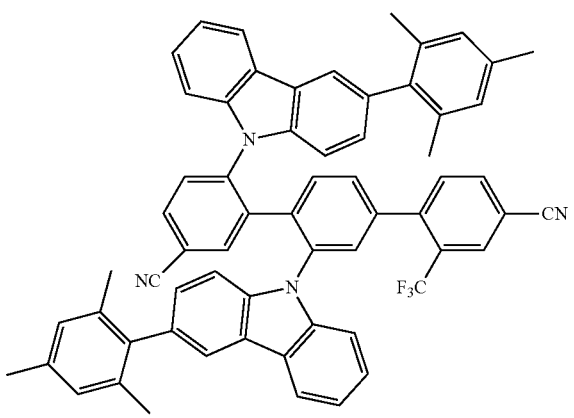

-continued
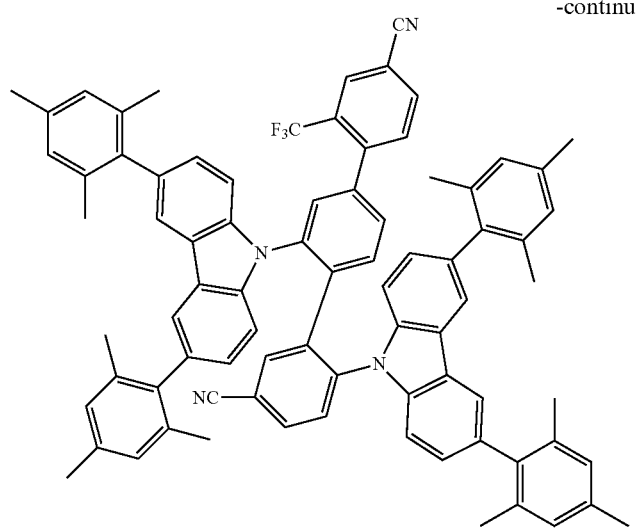
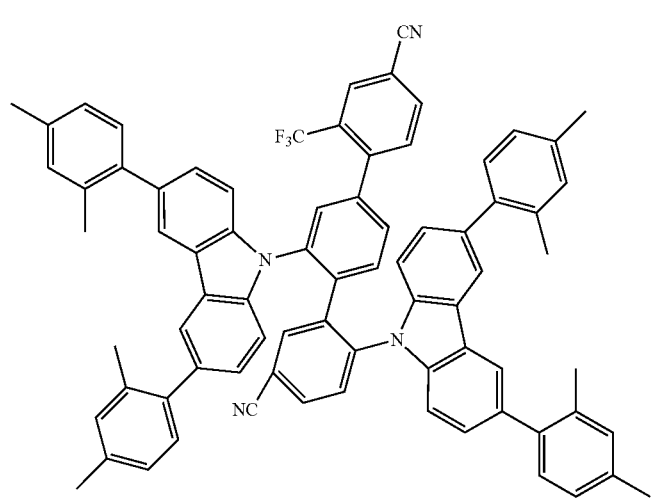
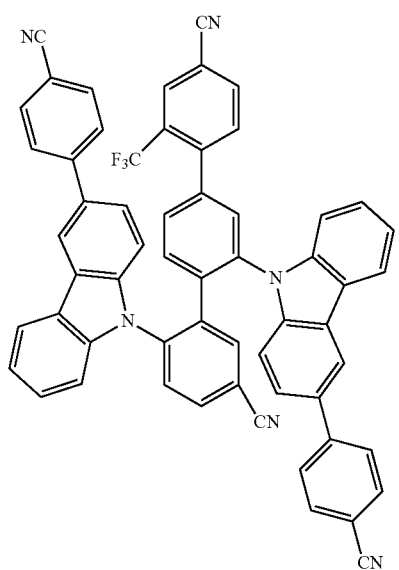
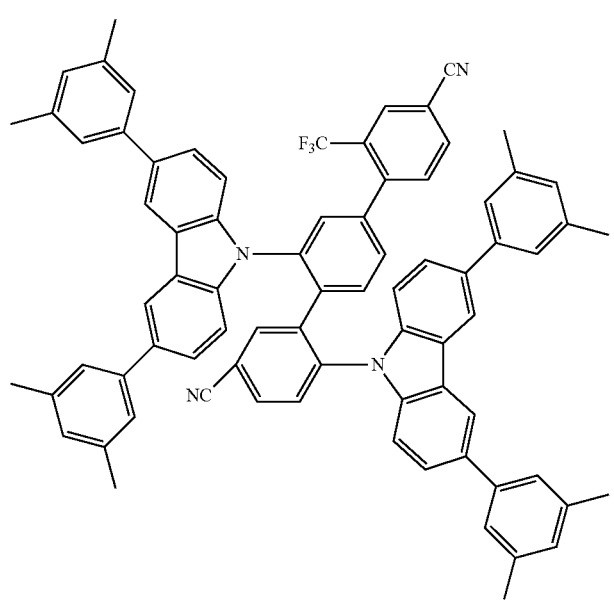
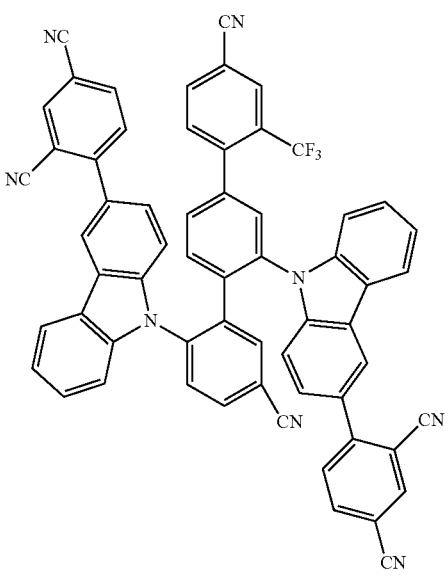

-continued
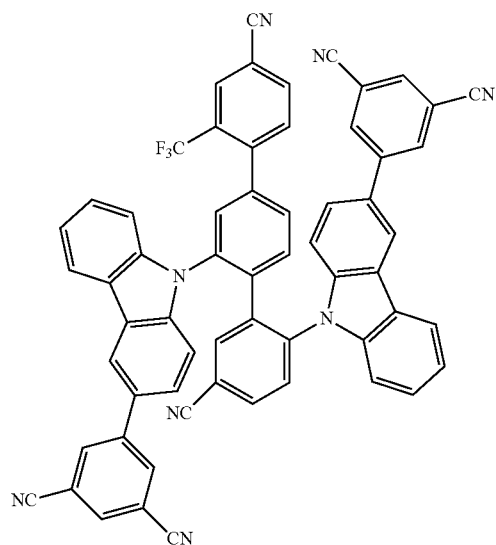
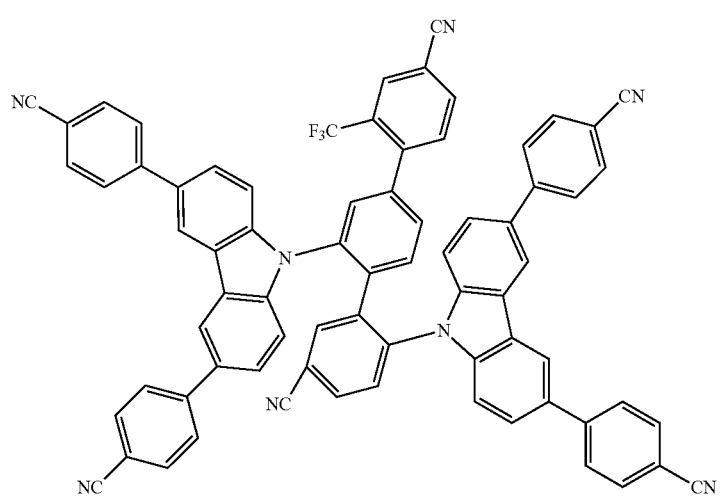
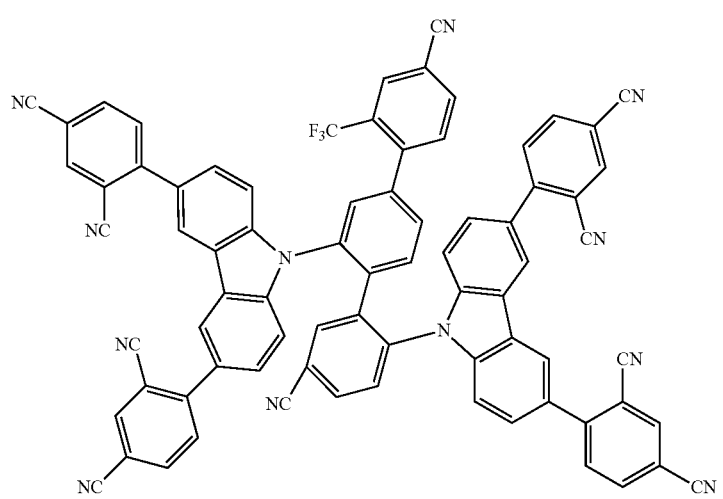

-continued
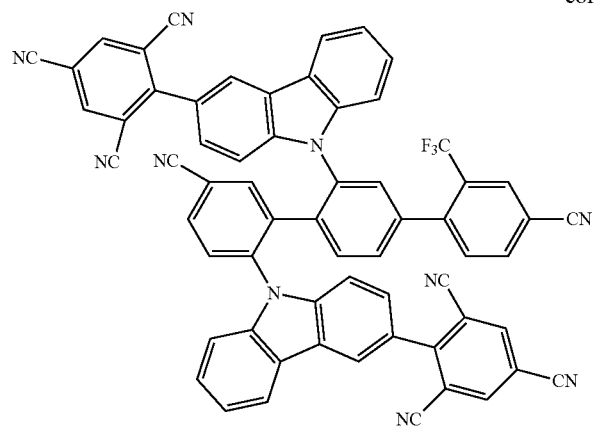
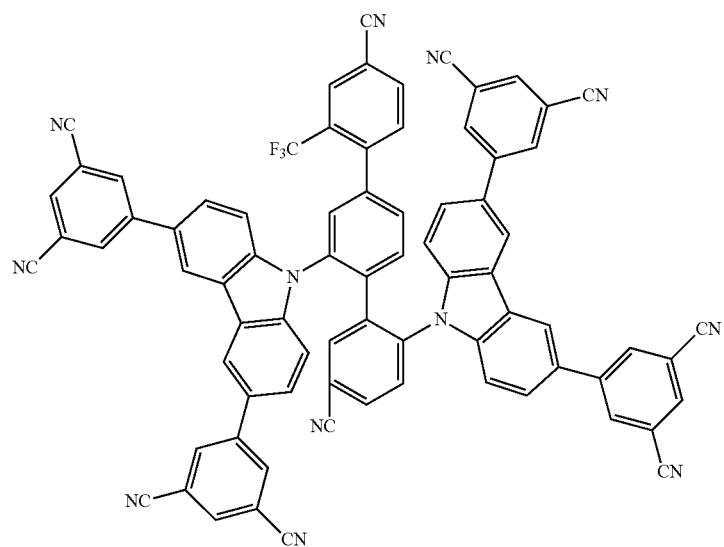
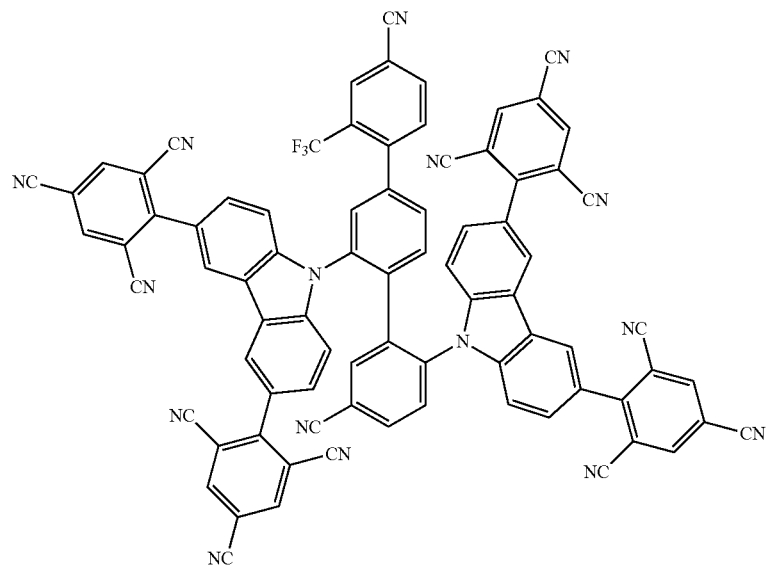

-continued
119
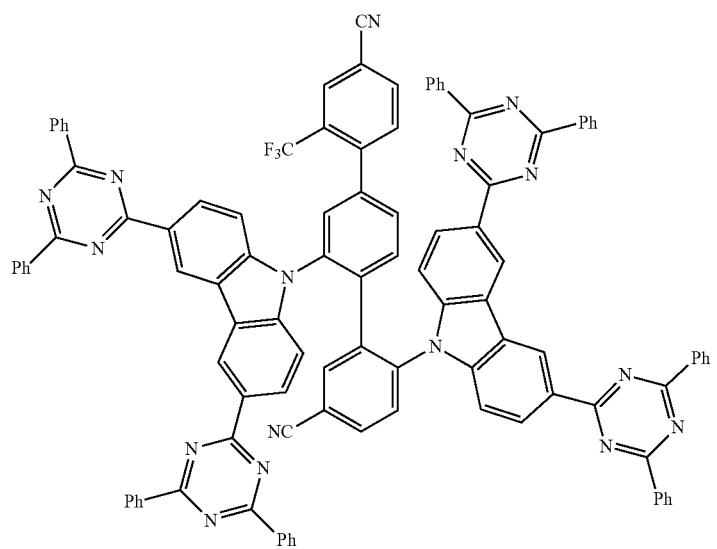
120
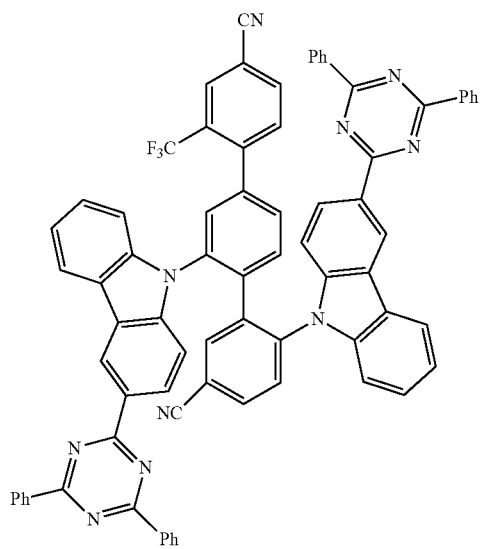
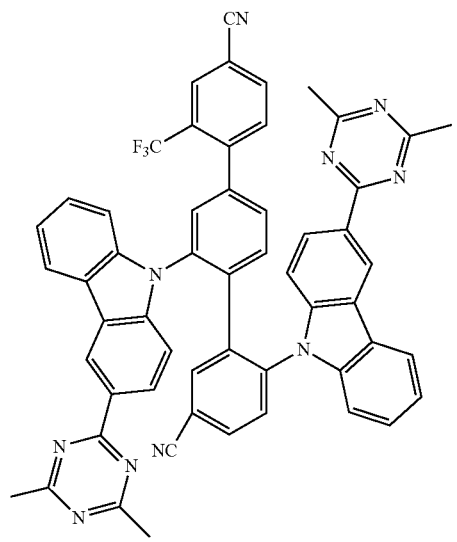
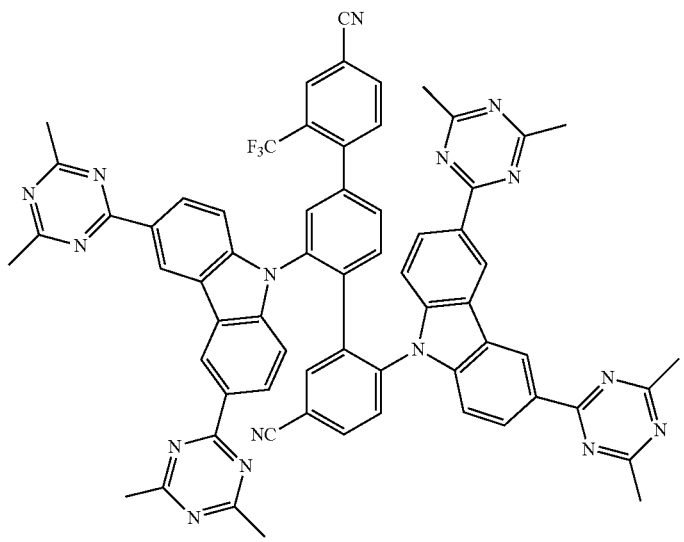
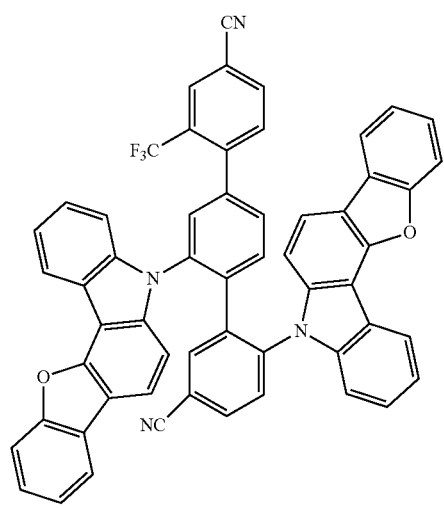
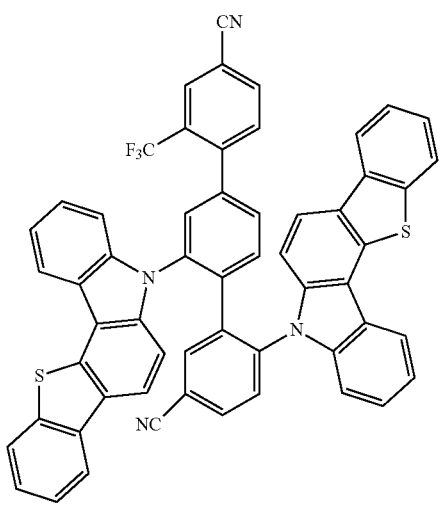

-continued
121
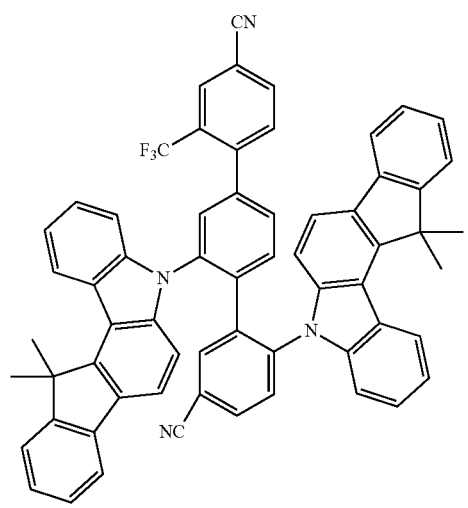
122
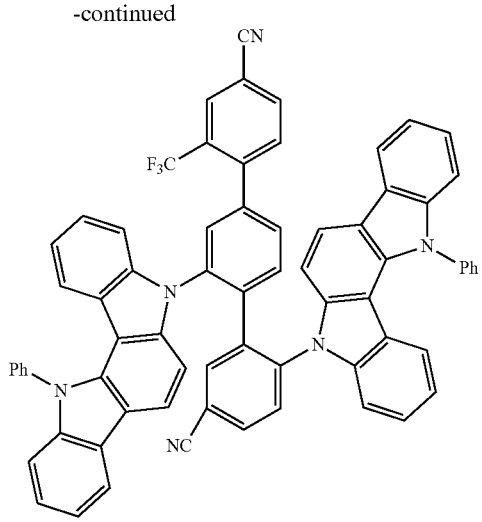
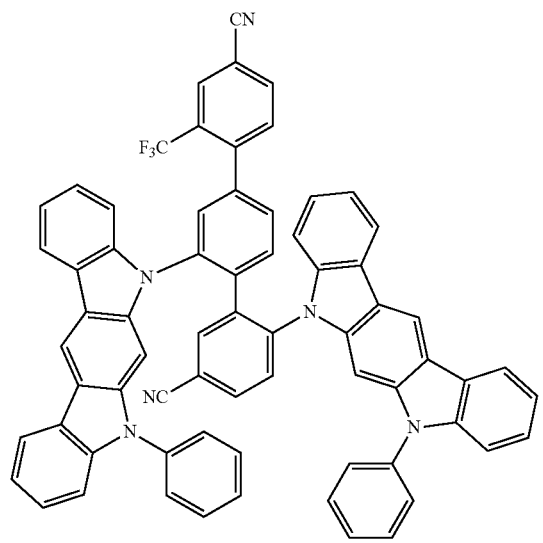
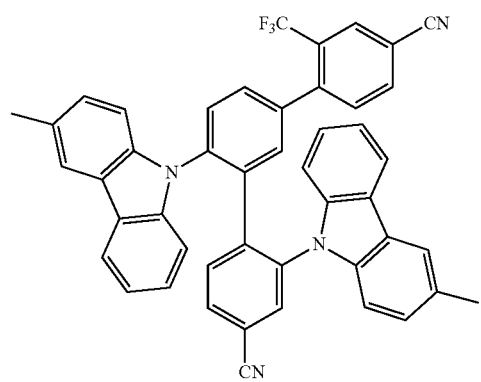
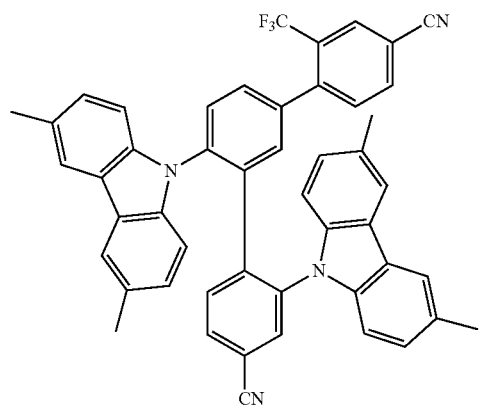
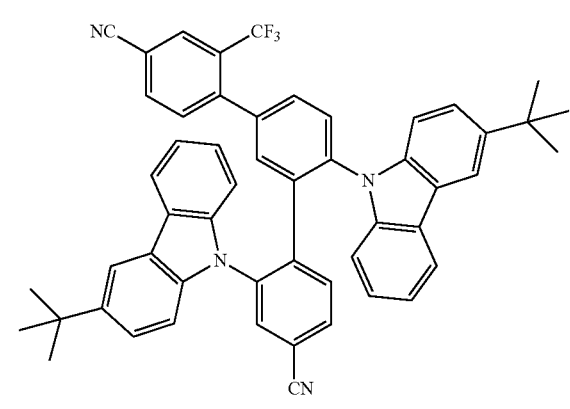

123
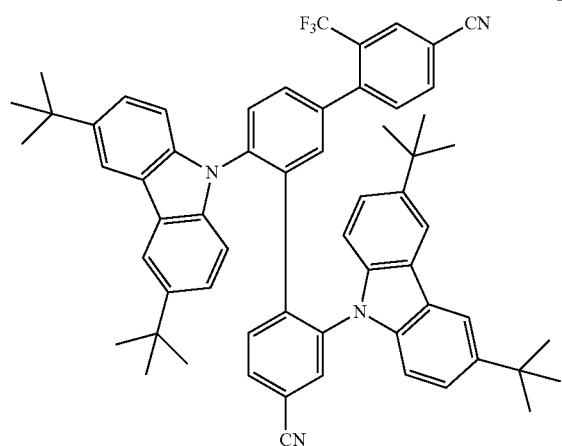
124
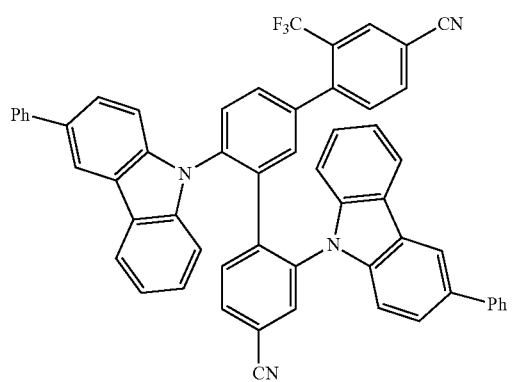
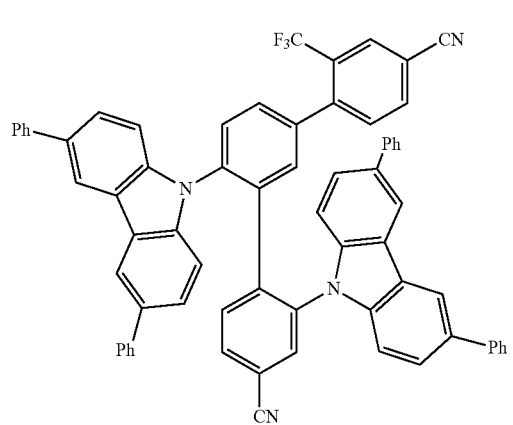
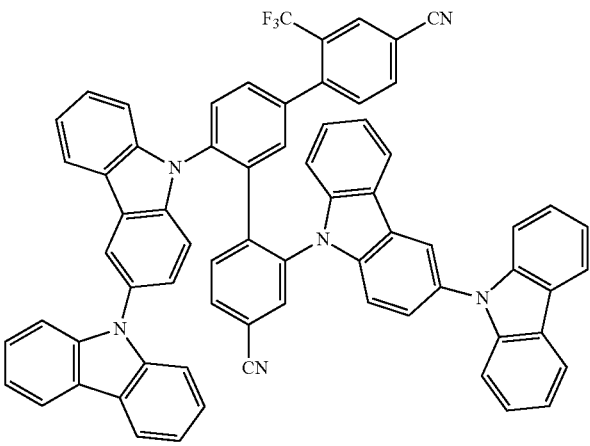
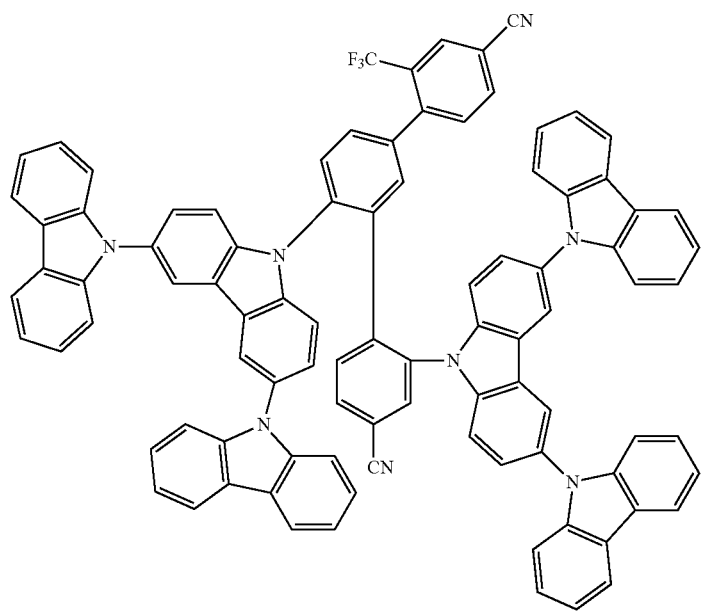

-continued
125
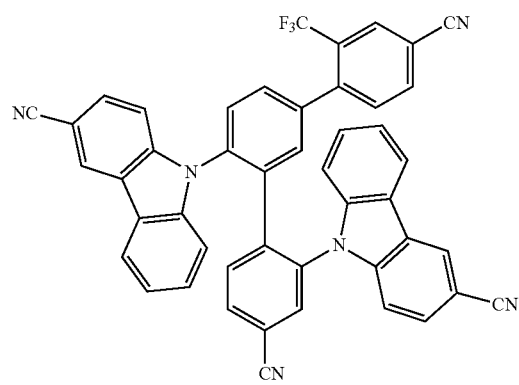
126
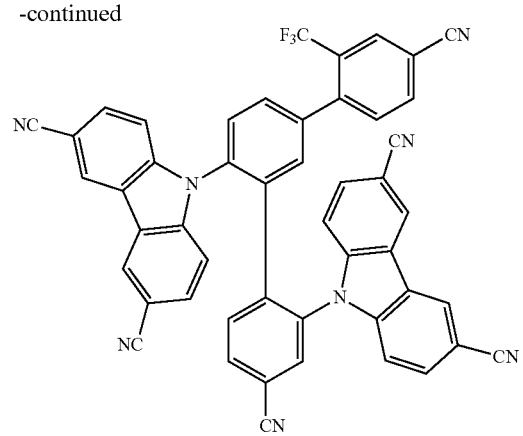
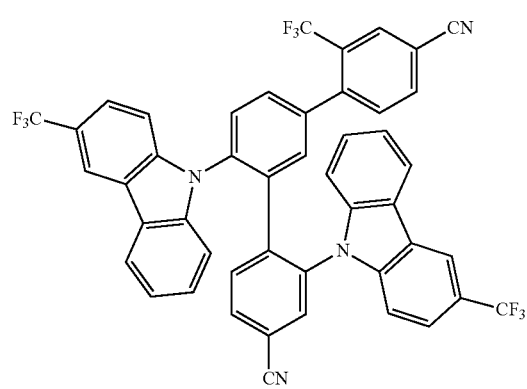
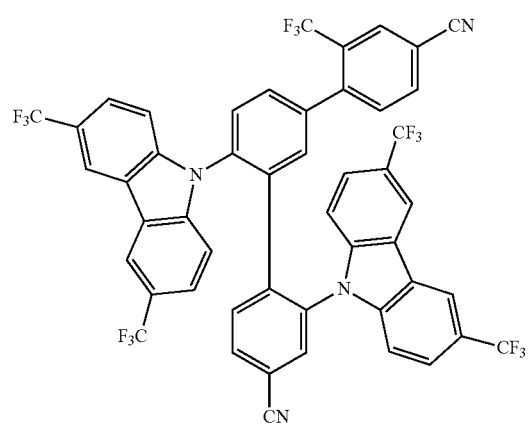
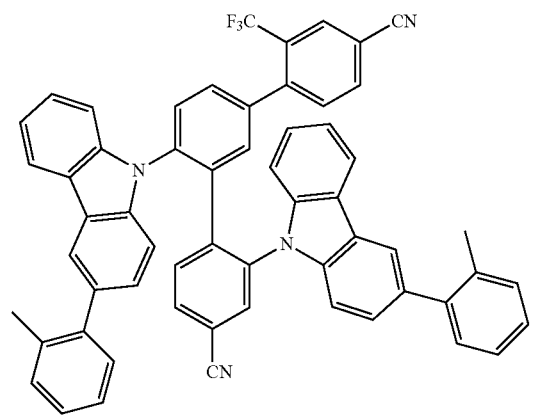
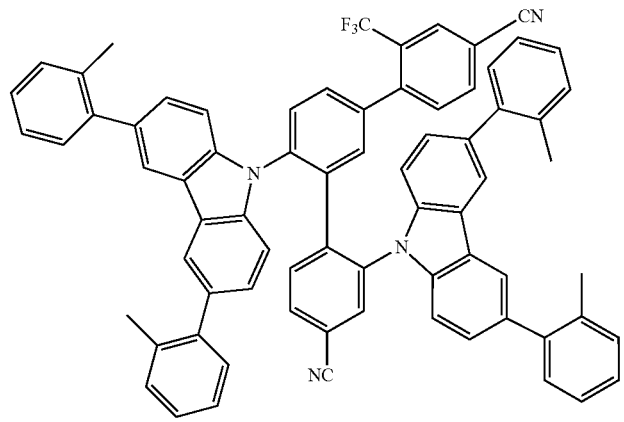

127
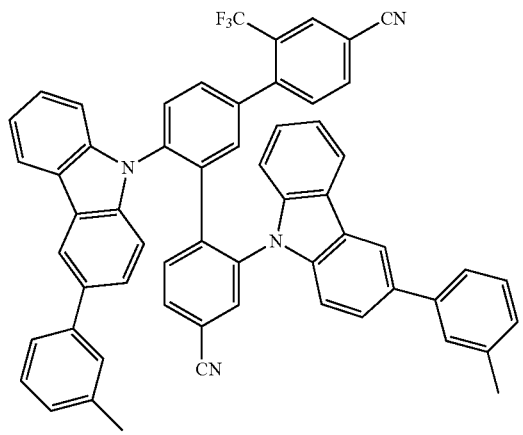
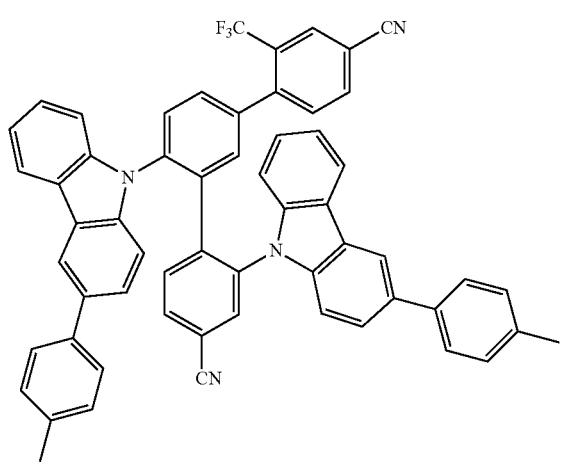
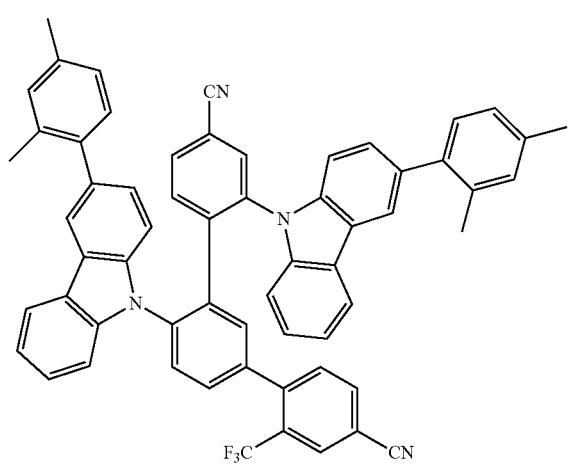
128
-continued
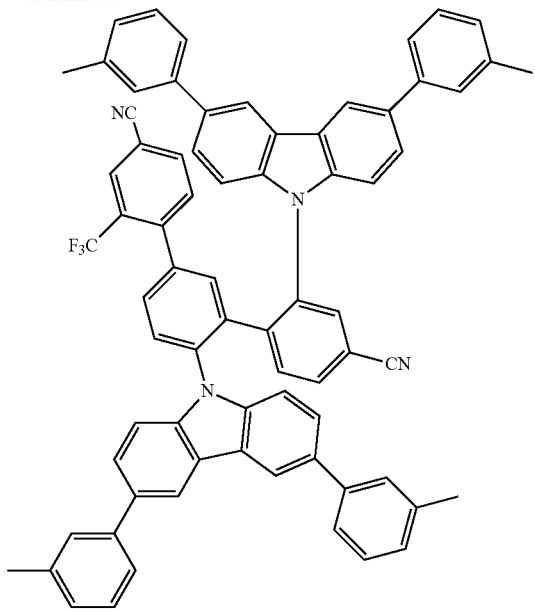
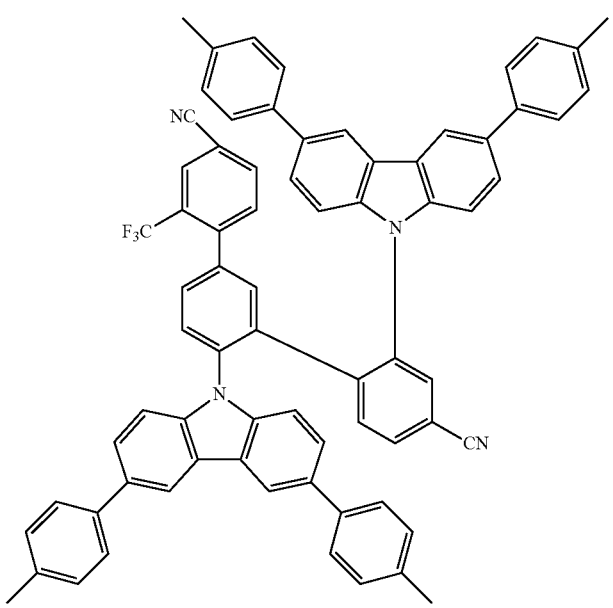
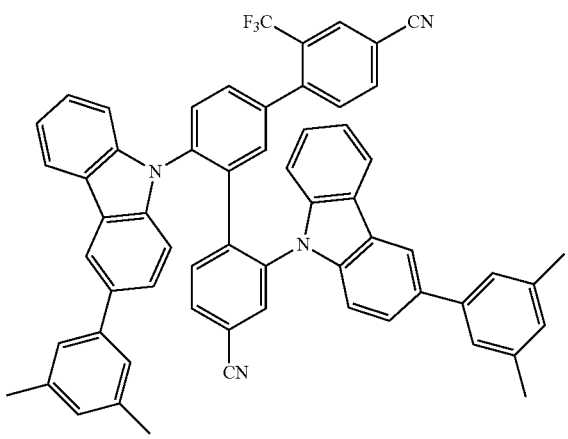

-continued
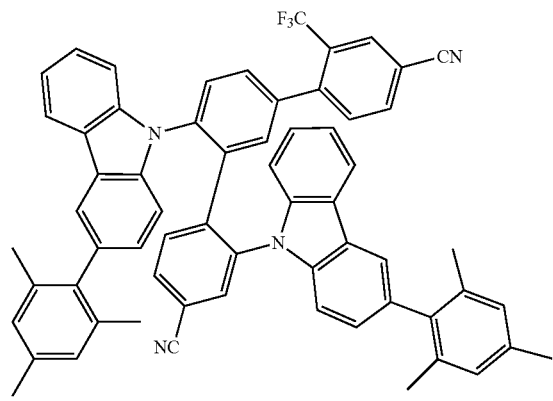
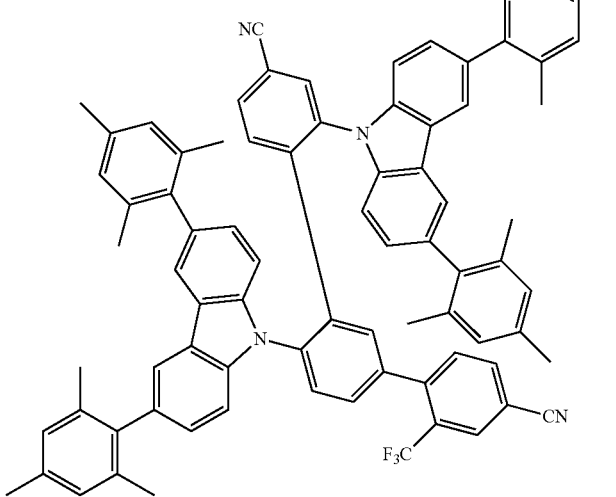
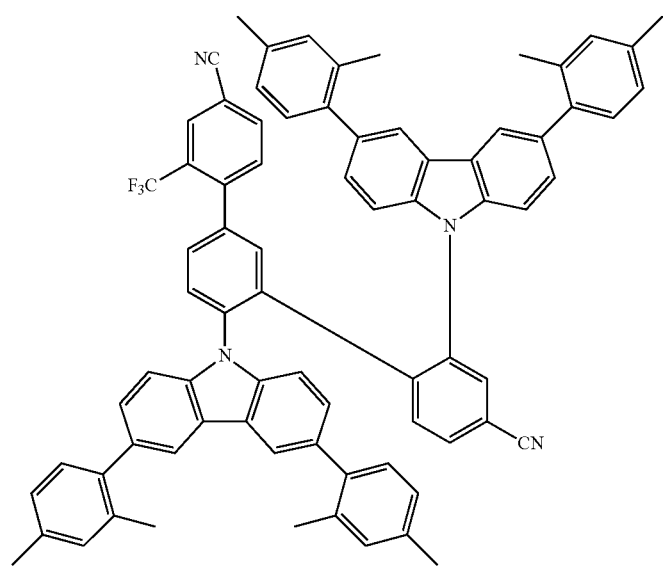
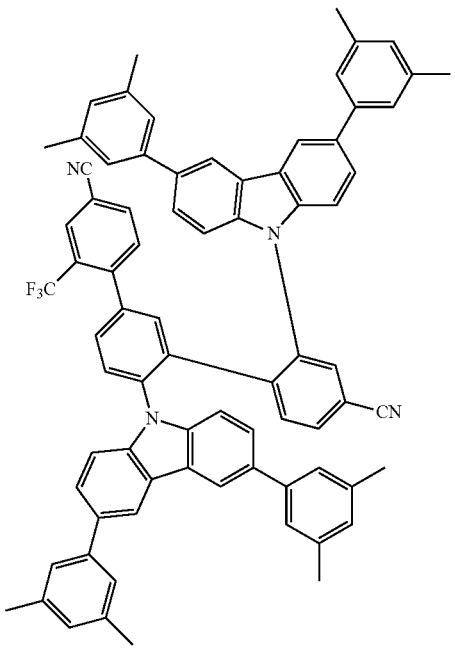
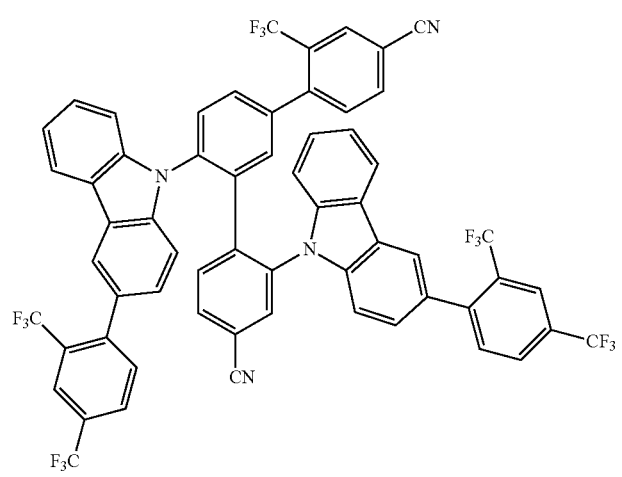

-continued
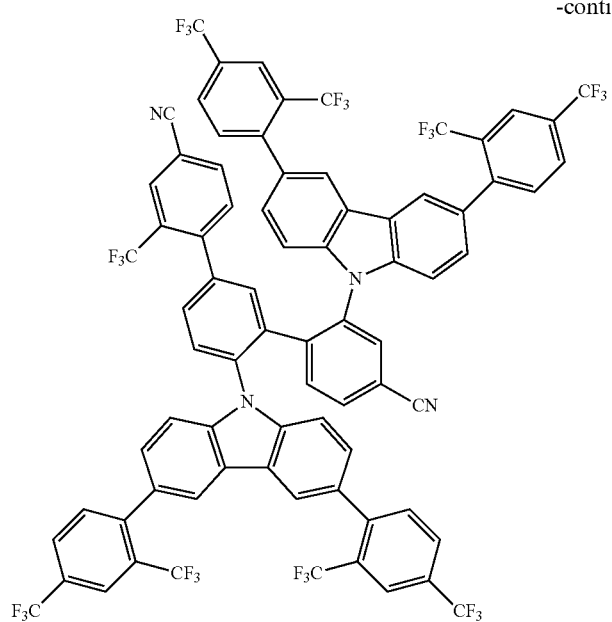
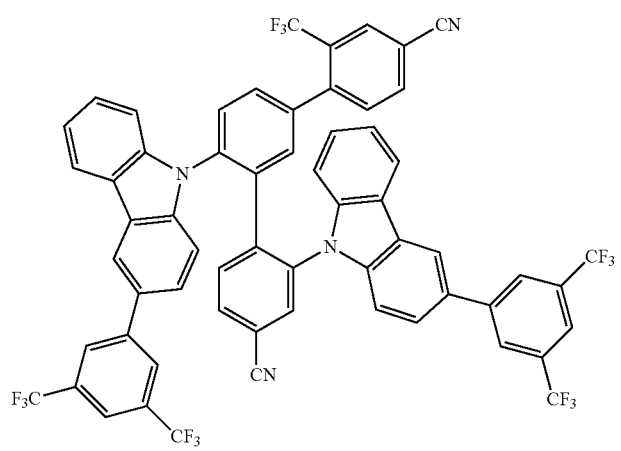
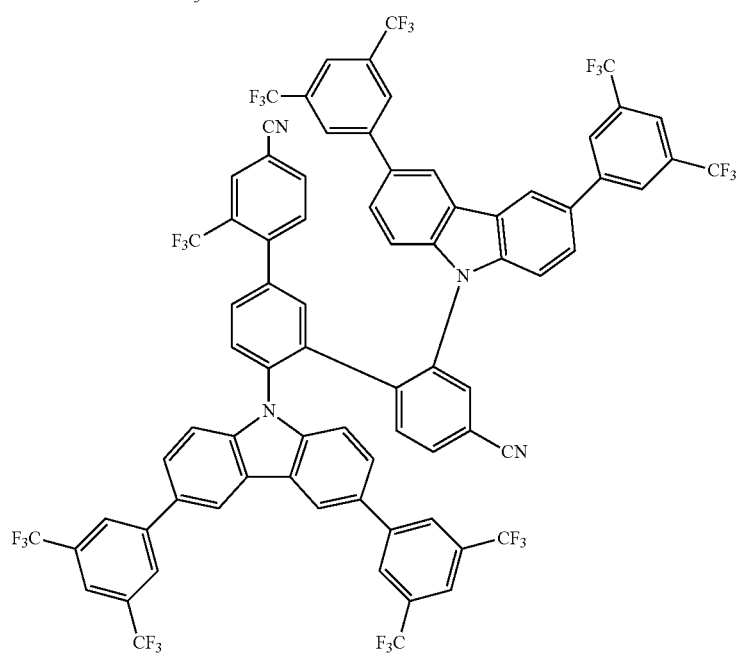

-continued
133
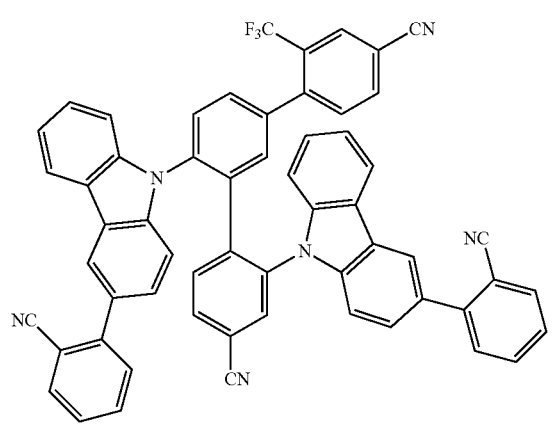
134
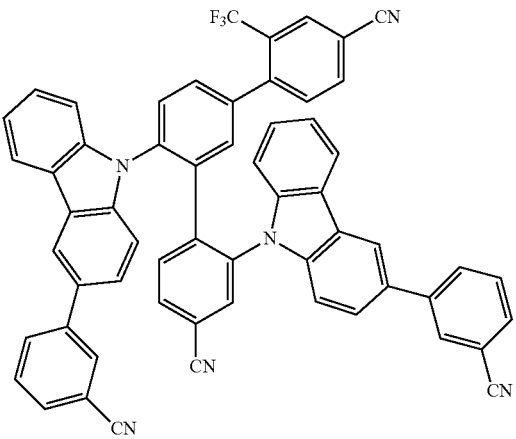
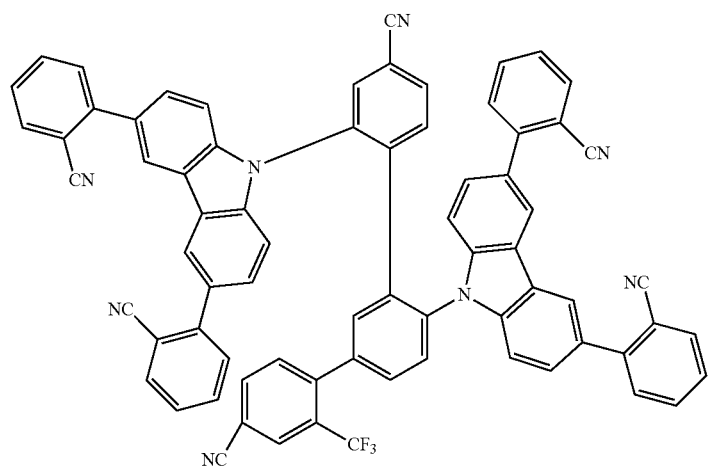
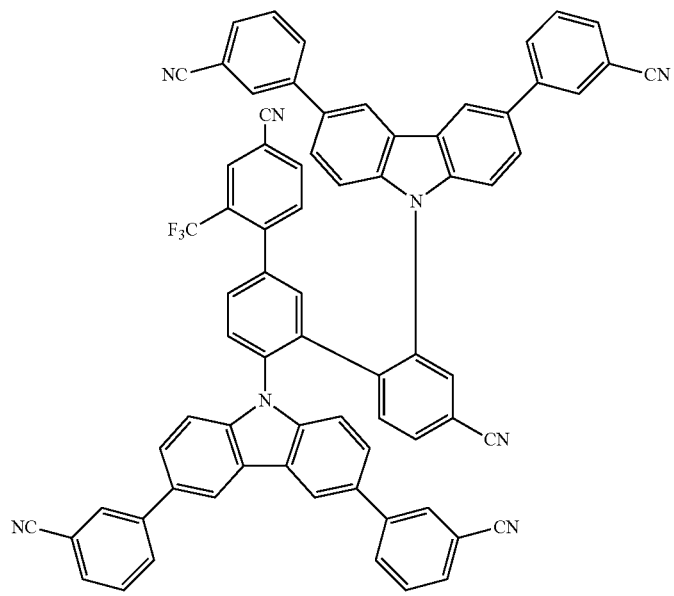

-continued
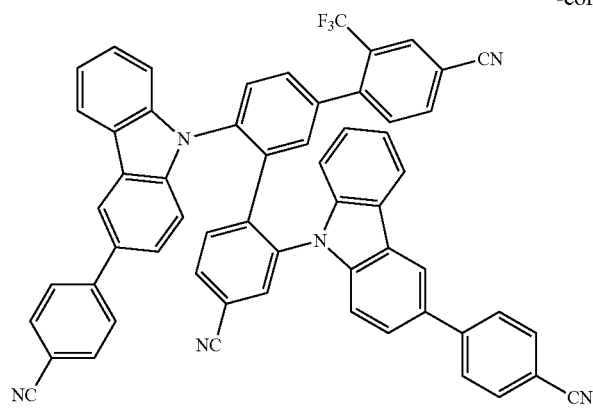
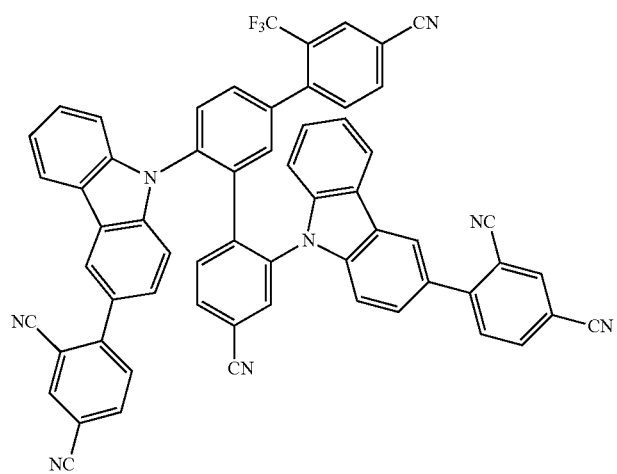
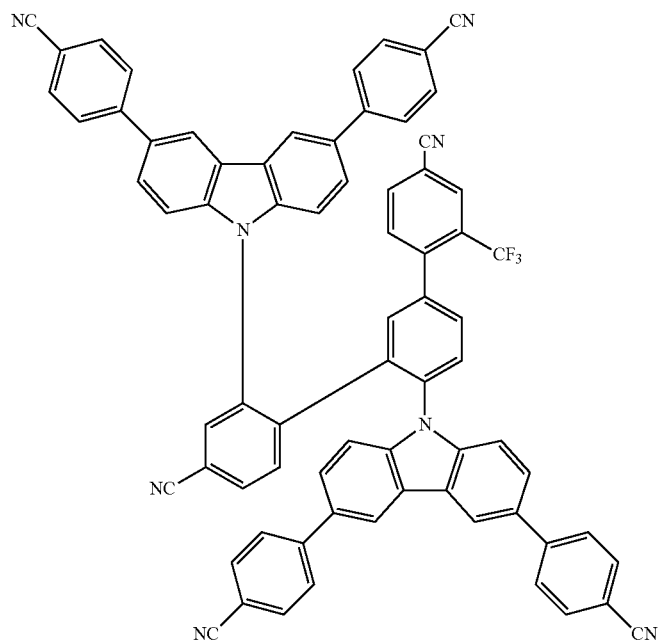

-continued
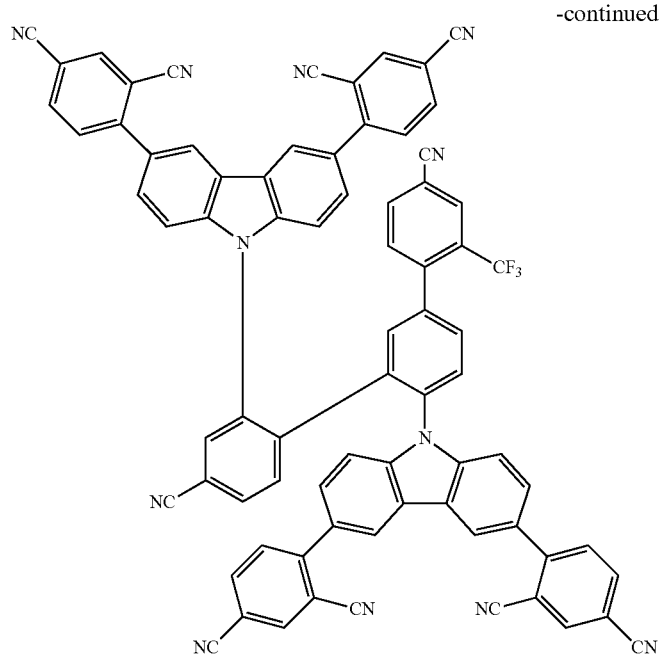
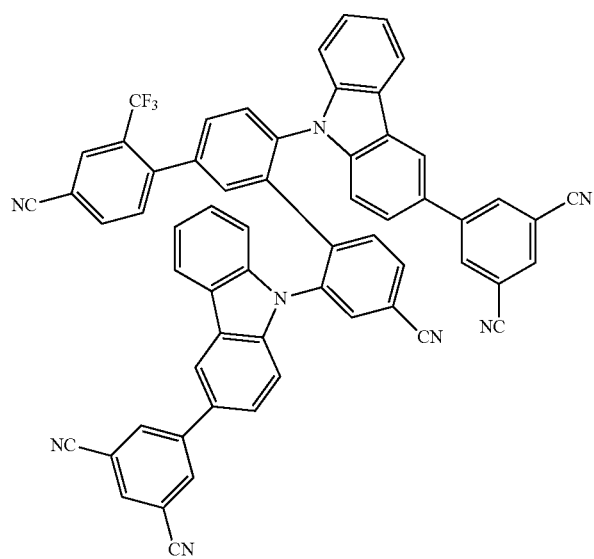

-continued
| 139 | 140 |
|---|---|
| 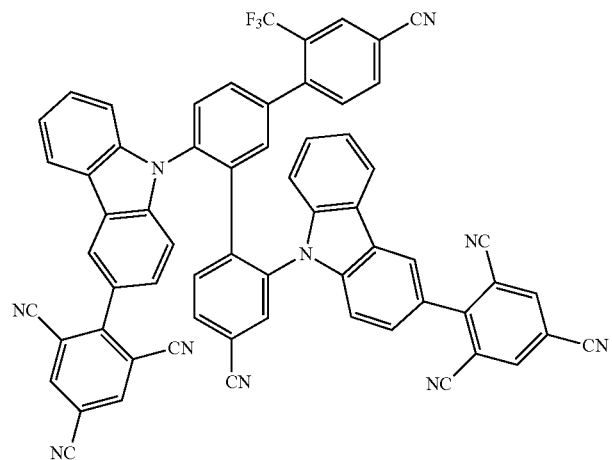 | 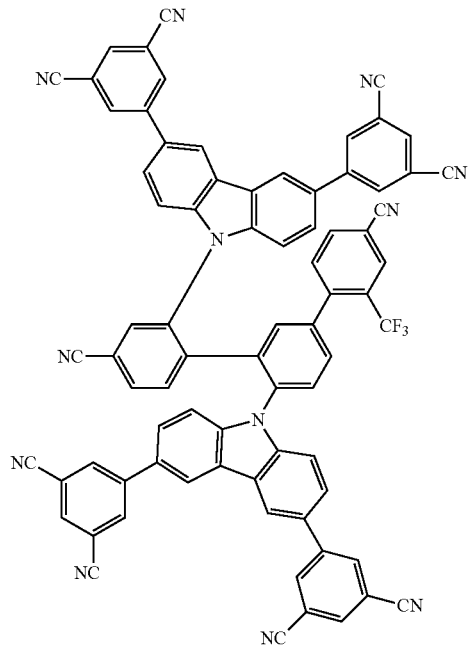 |
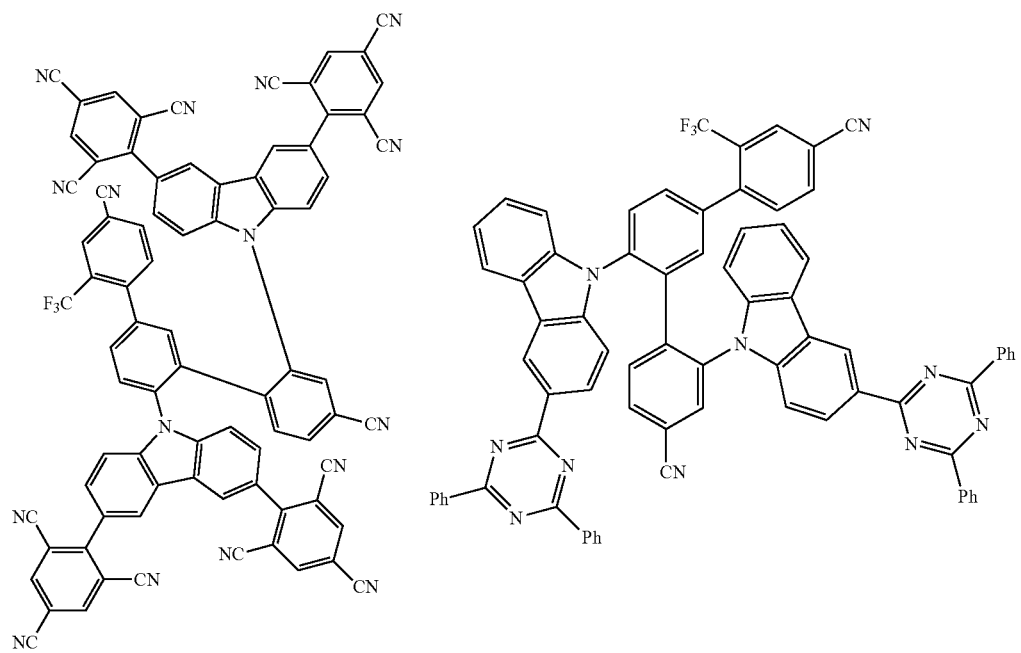

-continued
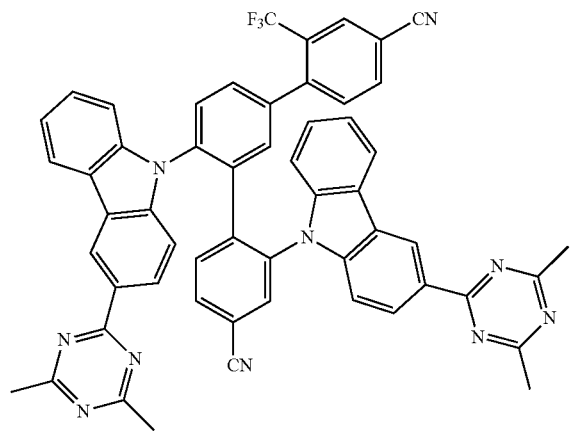
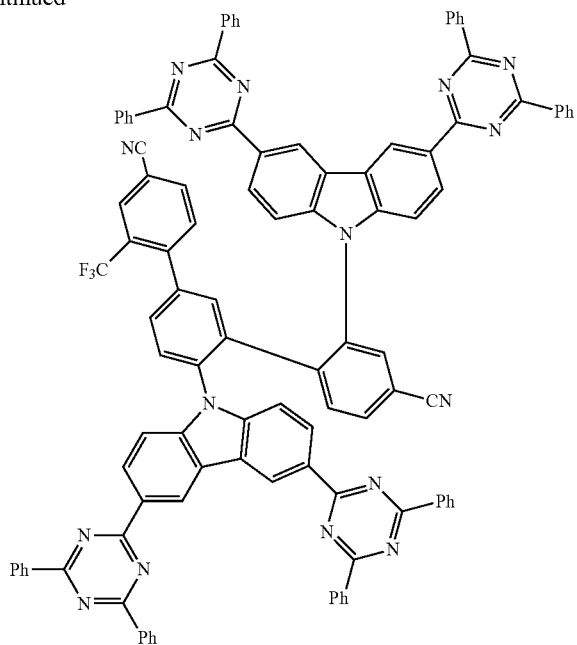
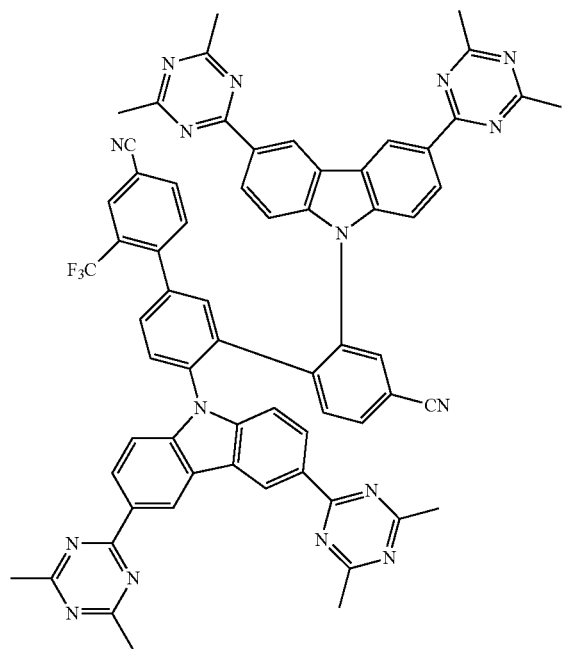
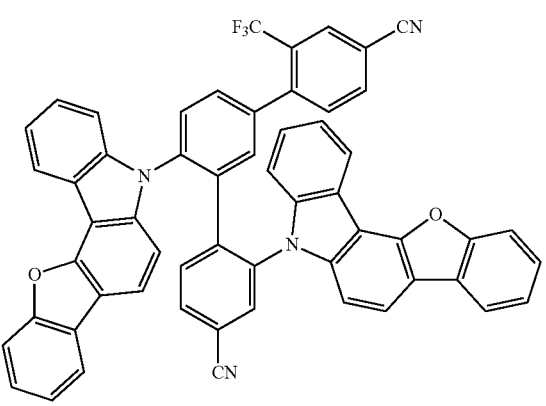
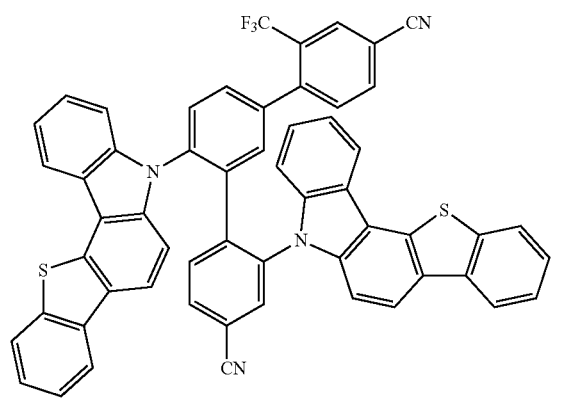
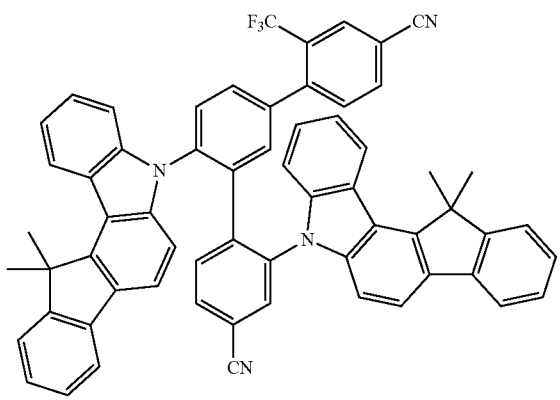

-continued
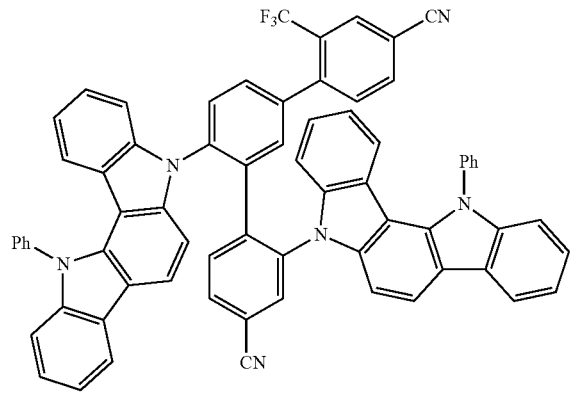
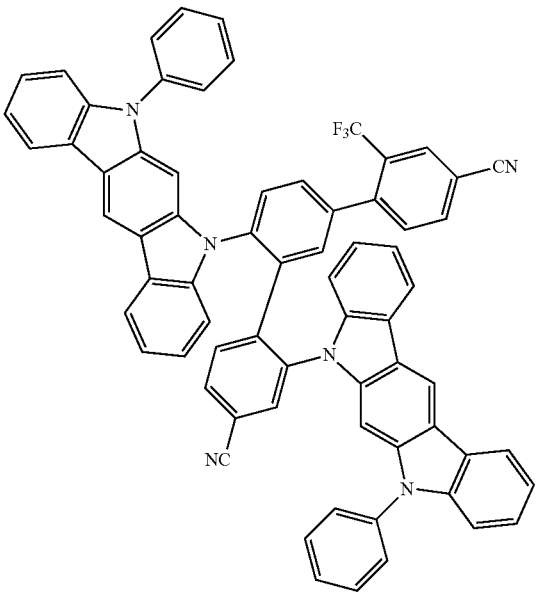
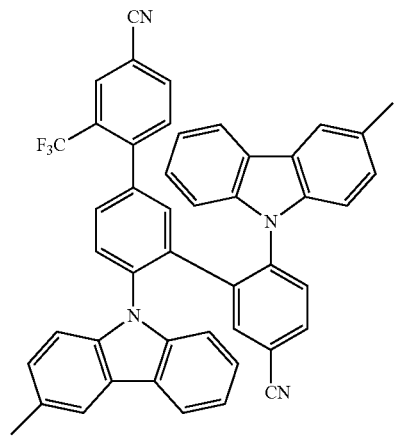
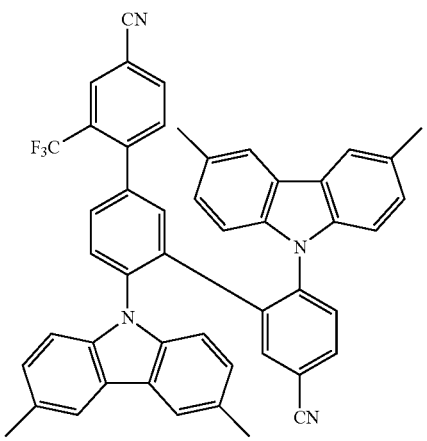
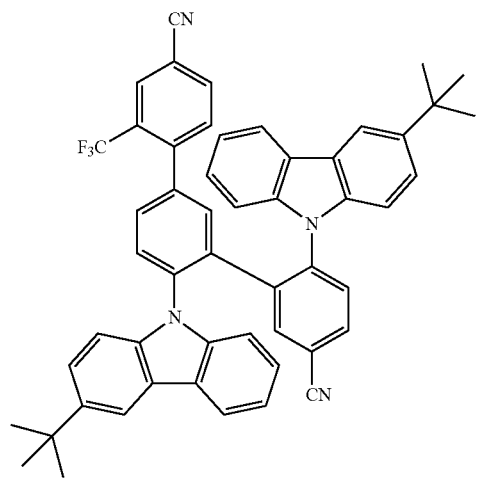
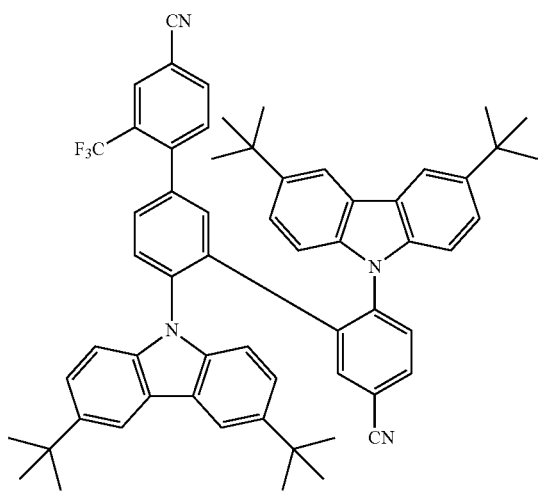

-continued
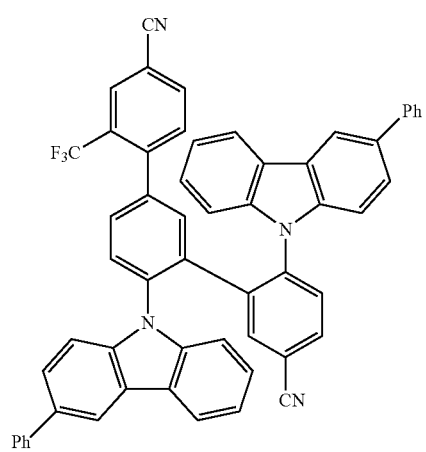
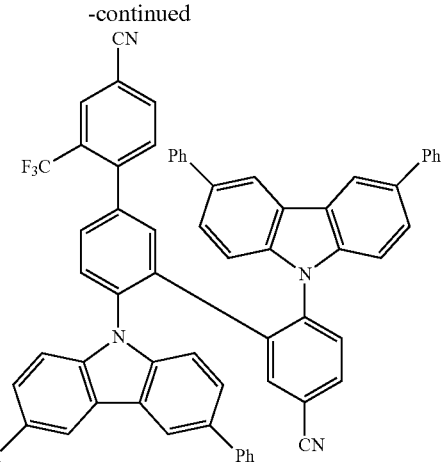
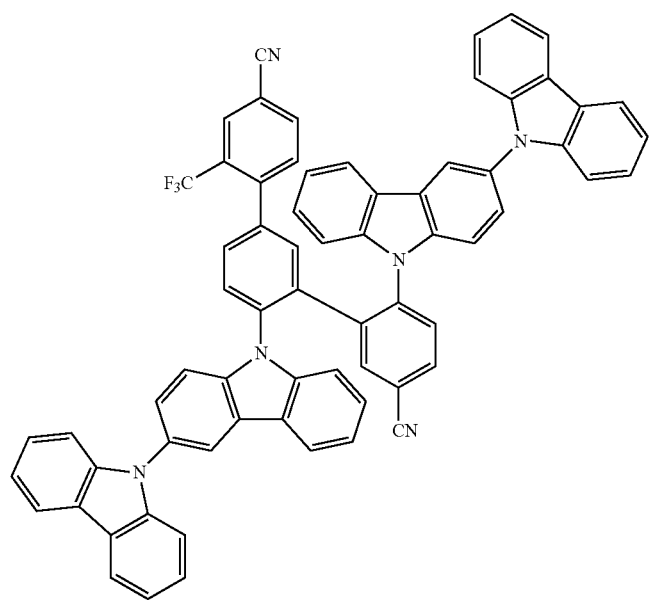
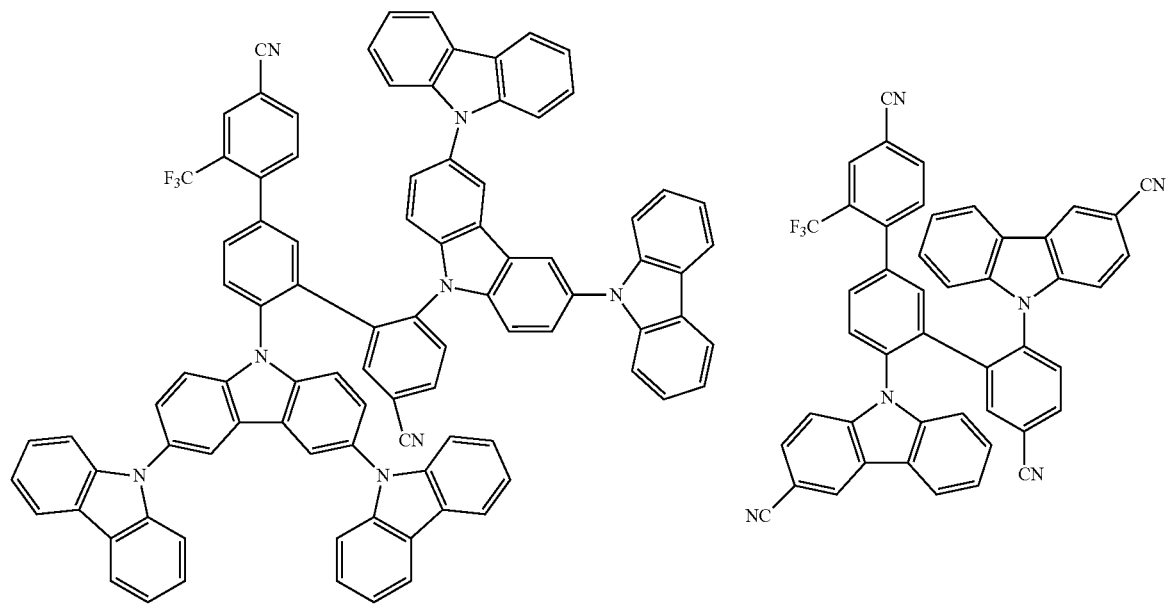

-continued
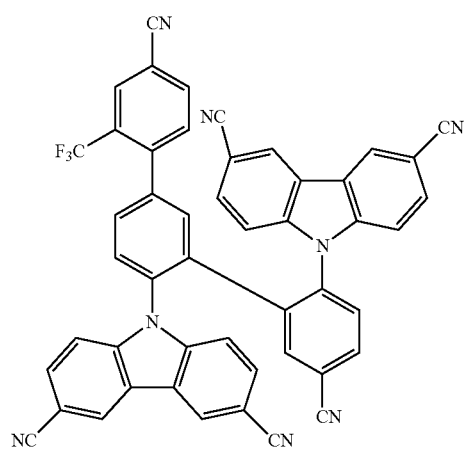
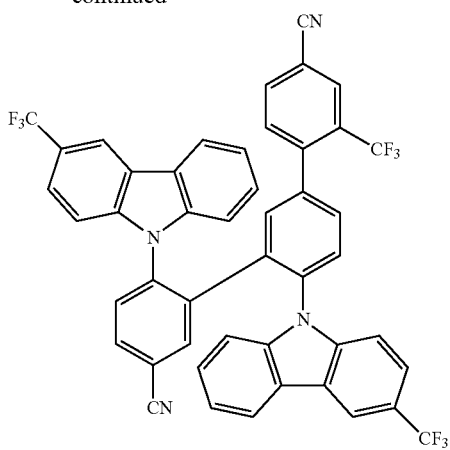
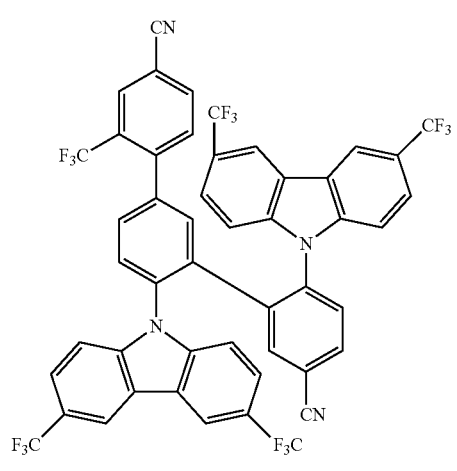
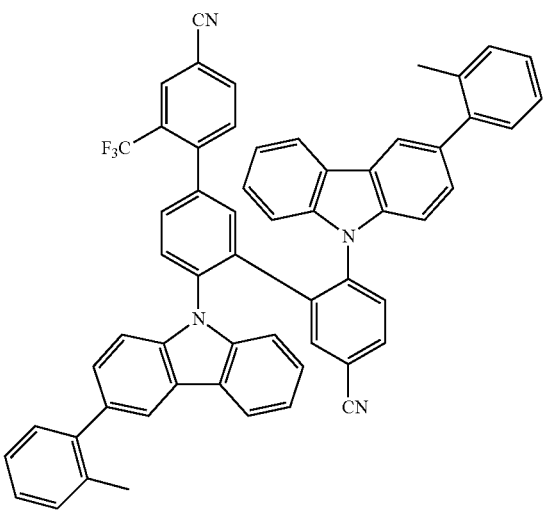
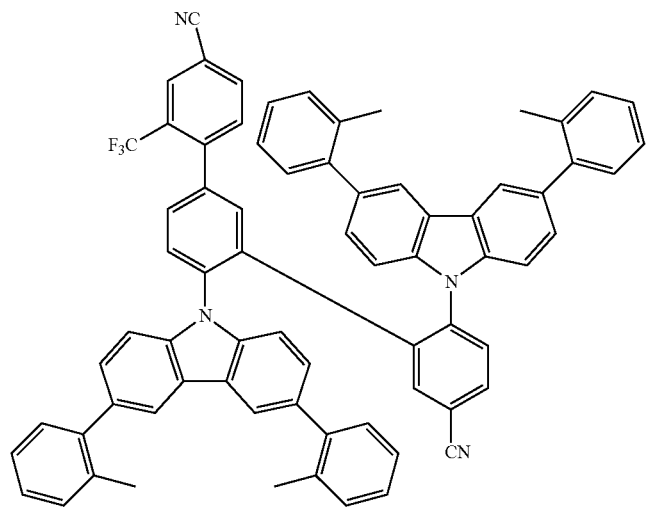

149 150
-continued
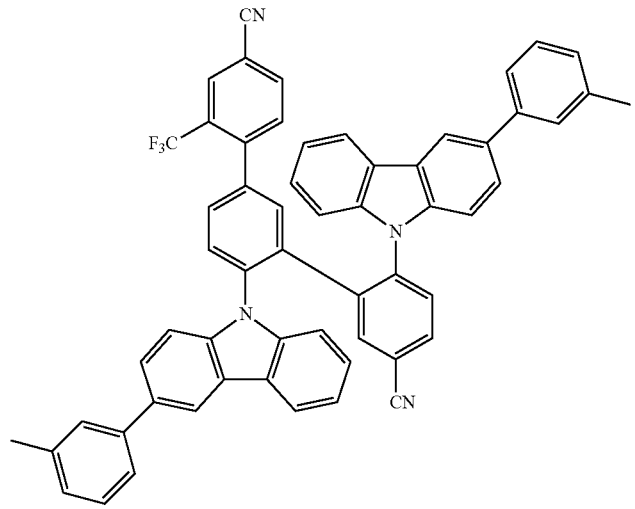
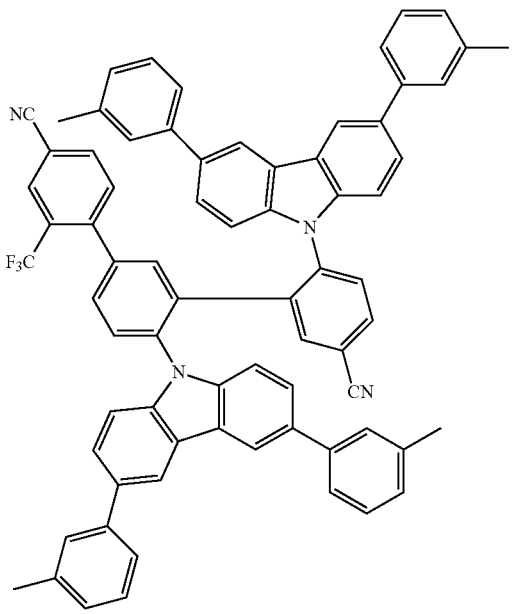
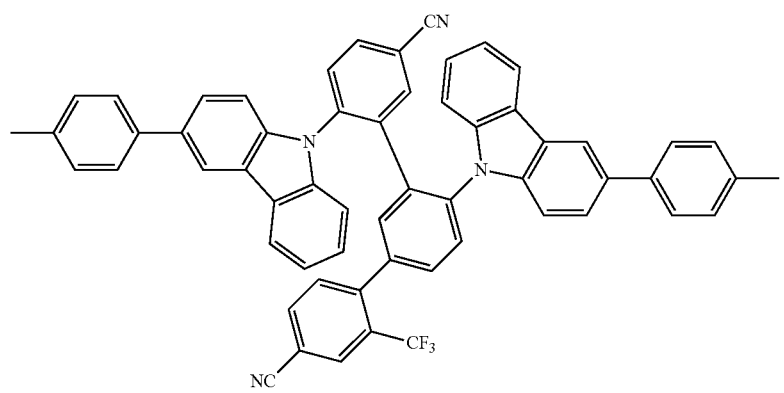
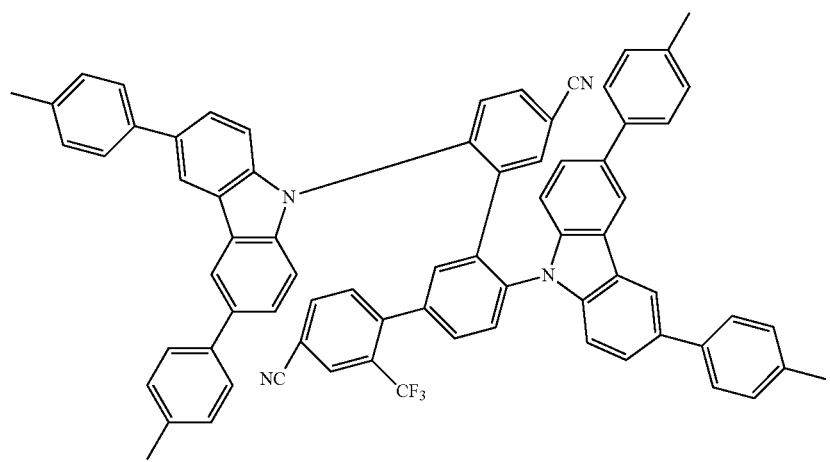

-continued
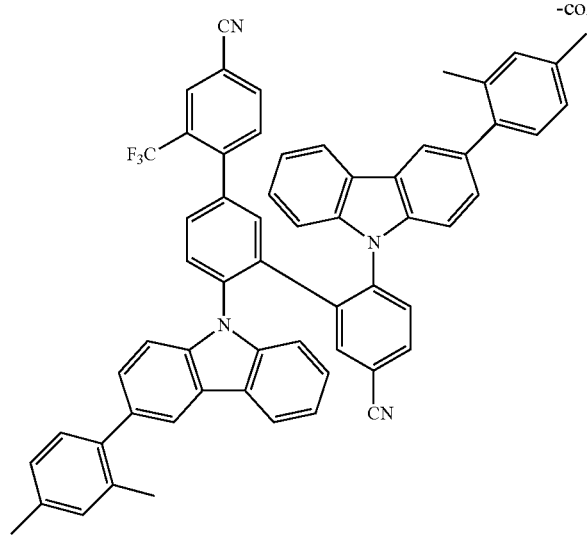
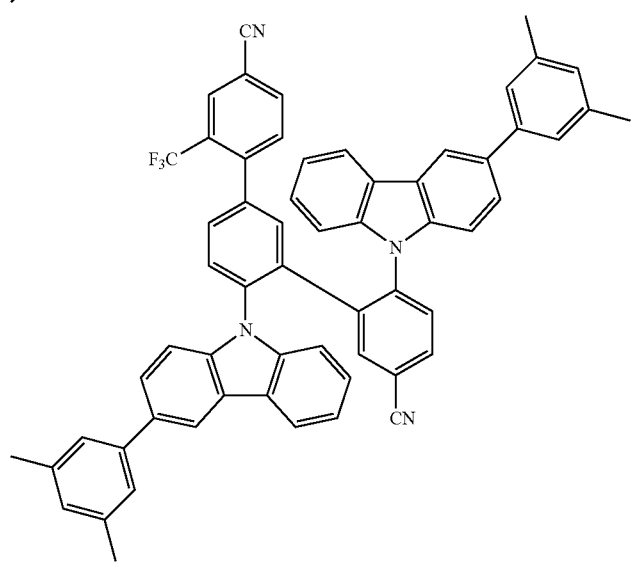
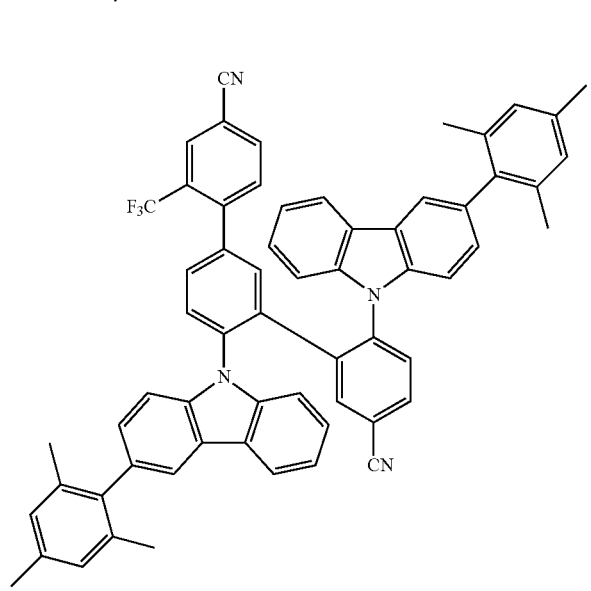
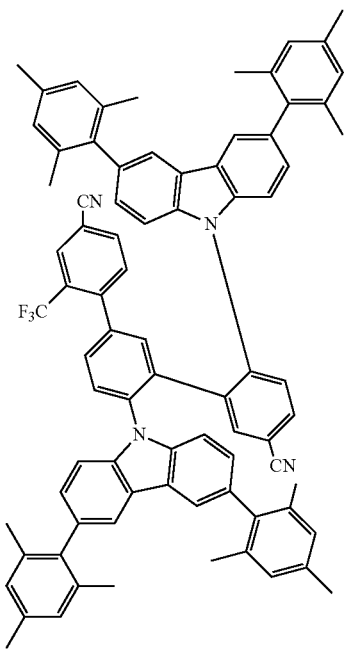

153
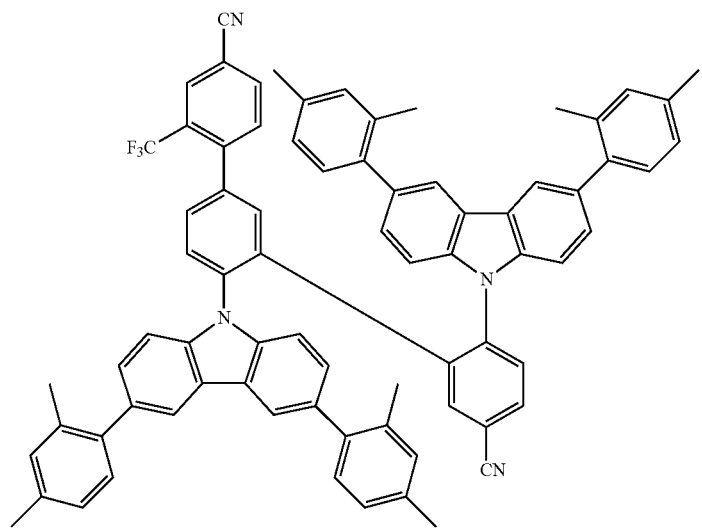
154
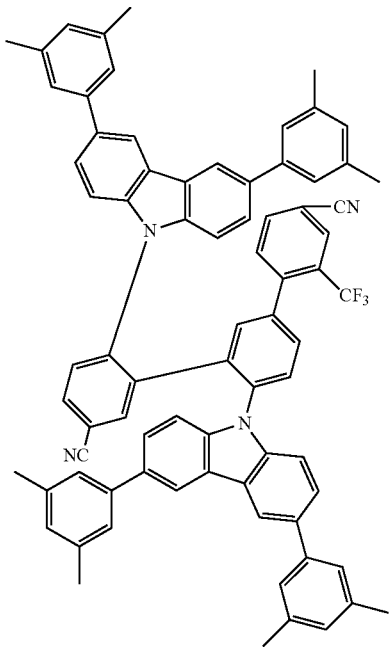
-continued
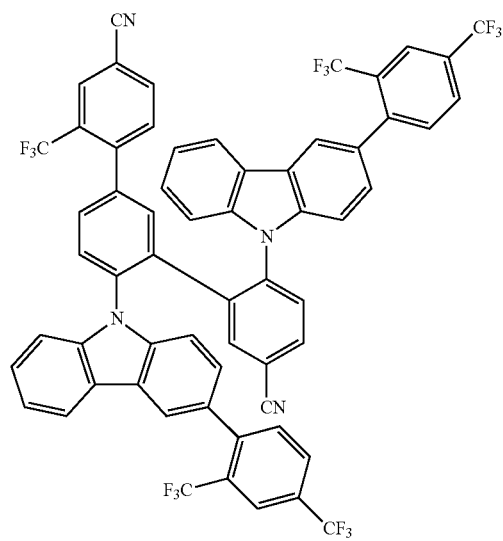

-continued
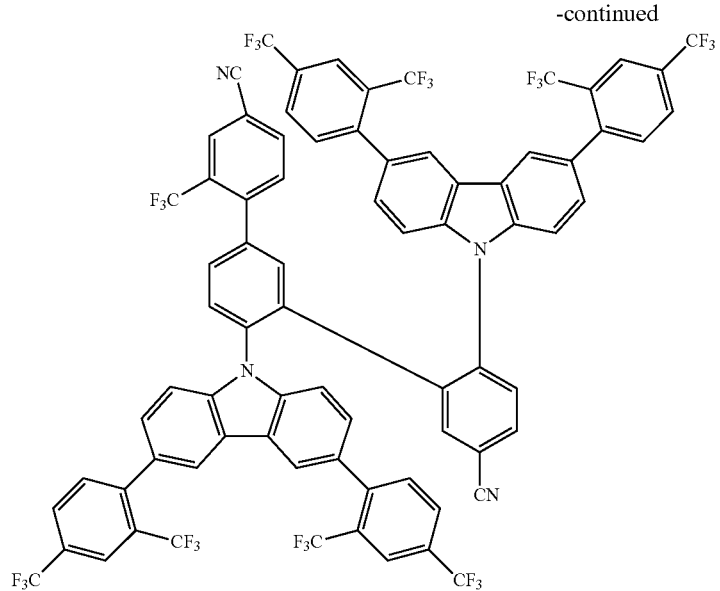
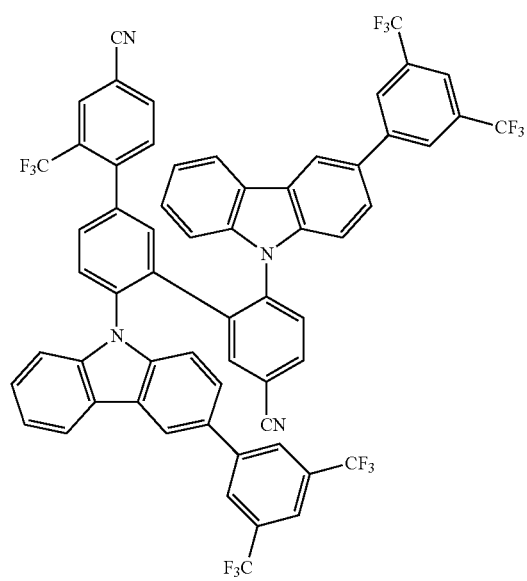

-continued
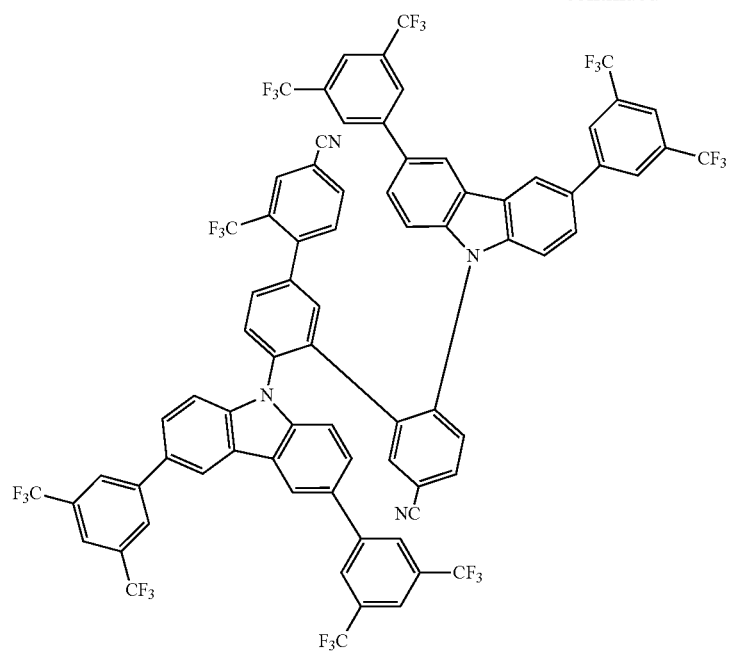
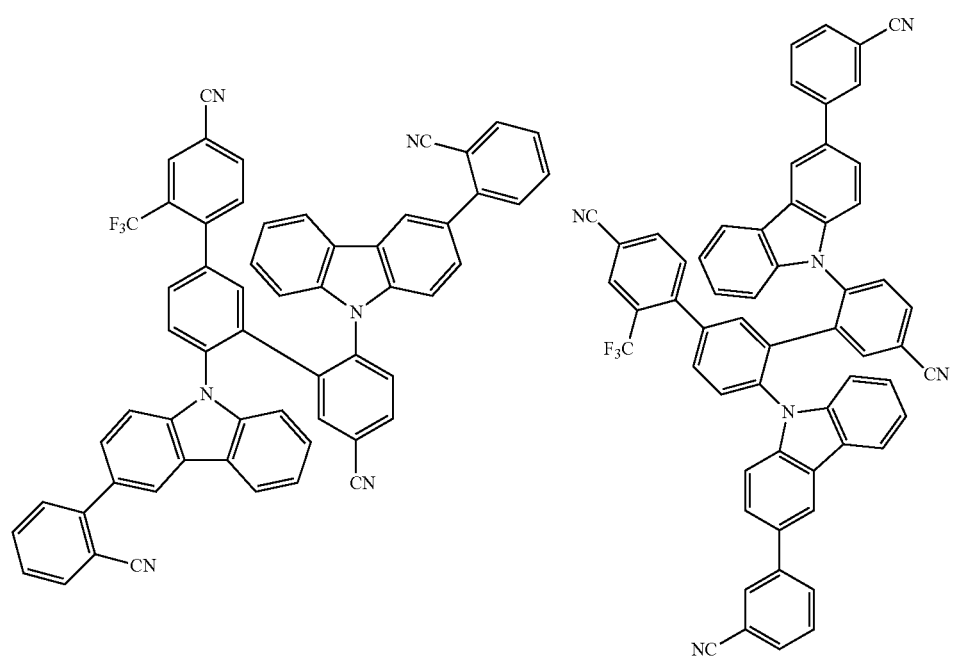

-continued
159
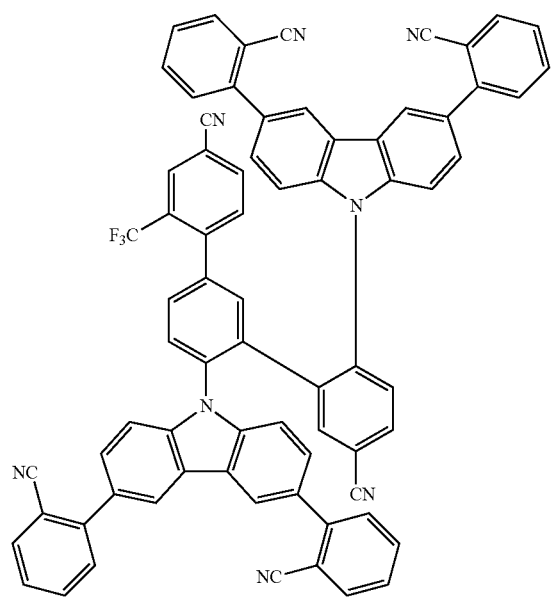
160
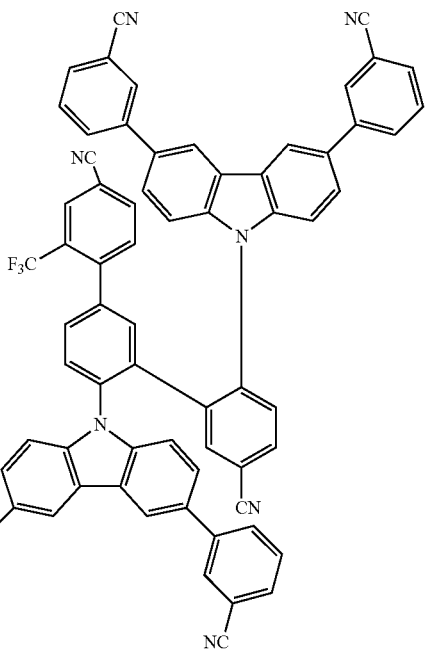
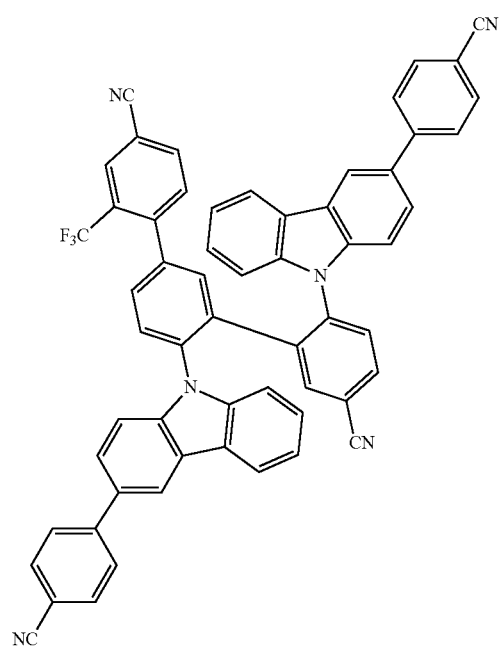 [SMILES: N#Cc1ccc(-c2ccc3c(c2)c2ccccc2n3-c2ccc(C#N)cc2-c2cc(-c3ccc(C#N)cc3C(F)(F)F)ccc2-n2c3ccccc3c3cc(-c4ccc(C#N)cc4)ccc32)cc1]
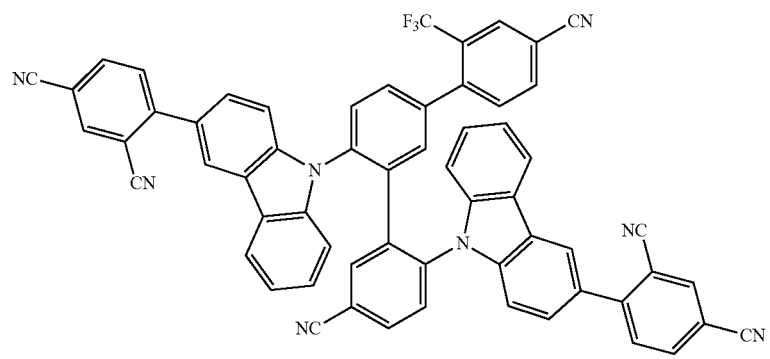

-continued
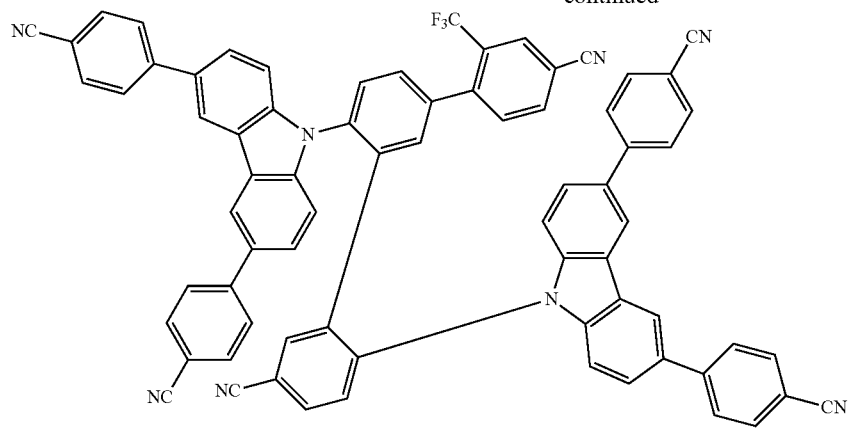
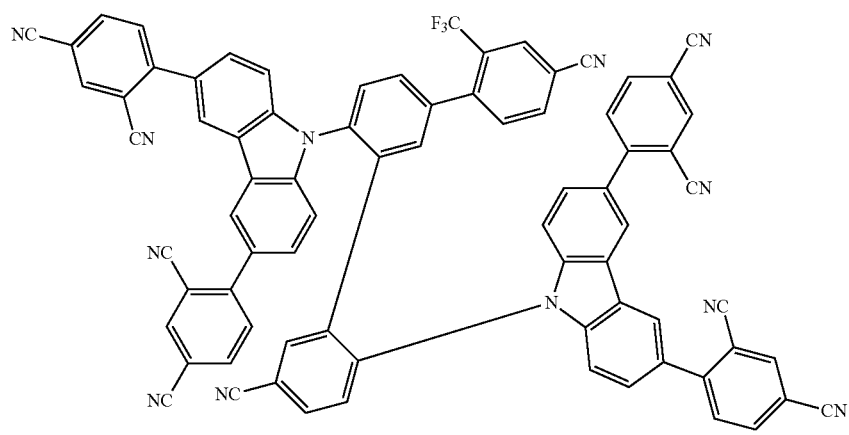
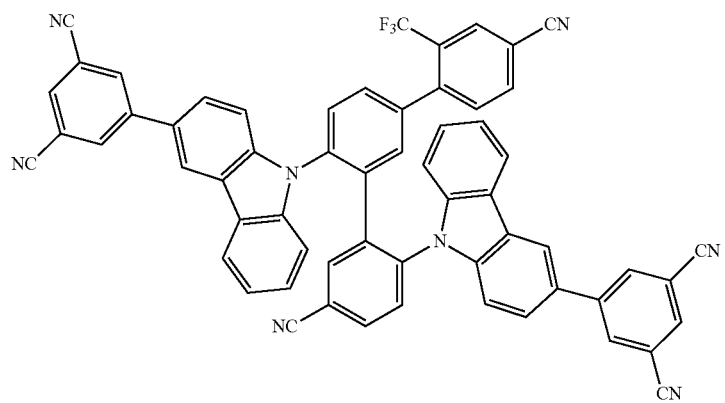

-continued
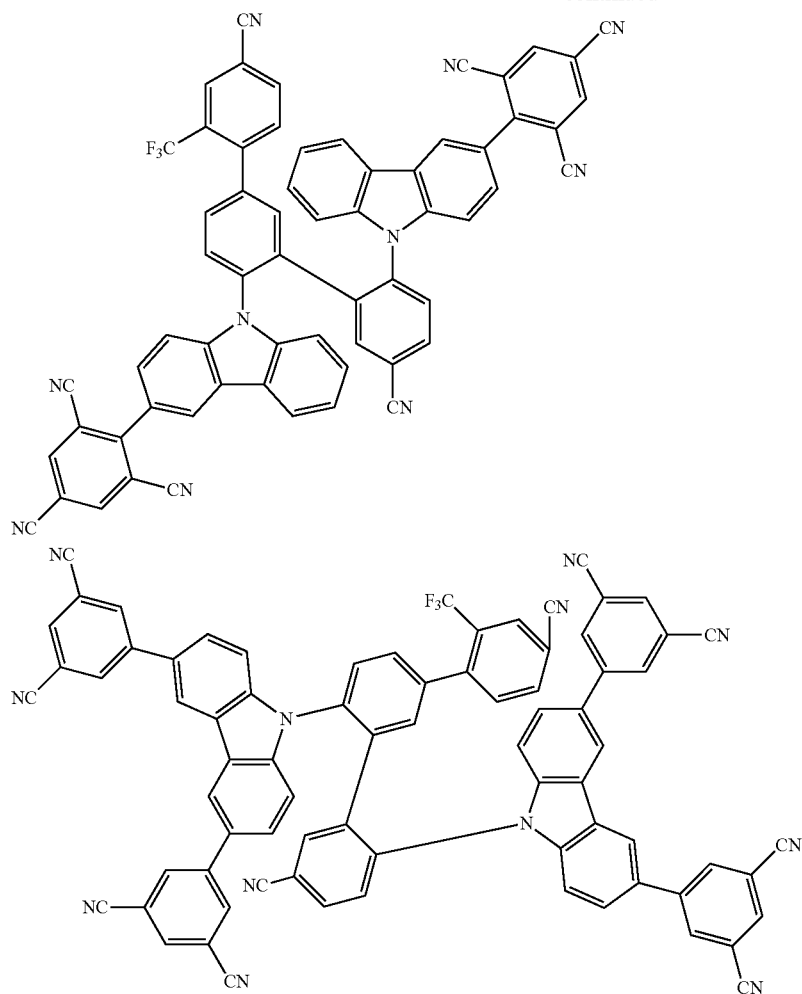
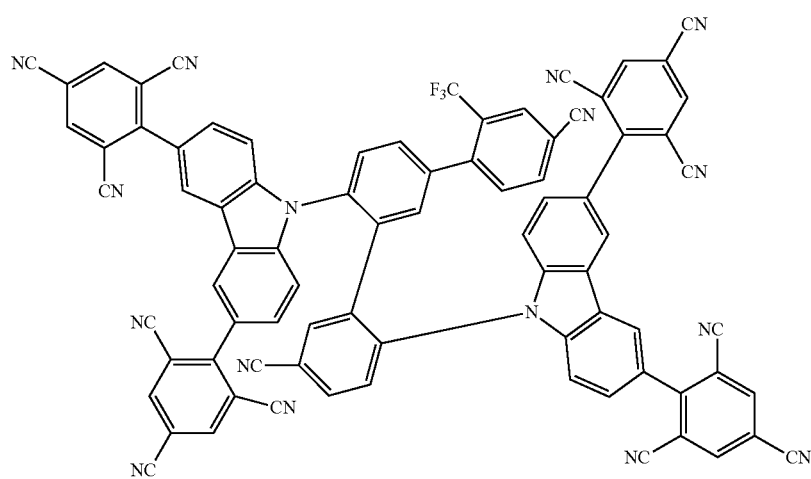

-continued
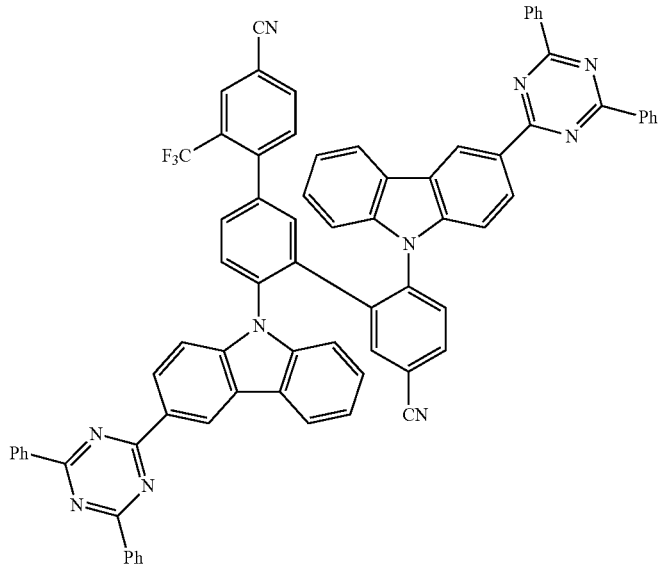
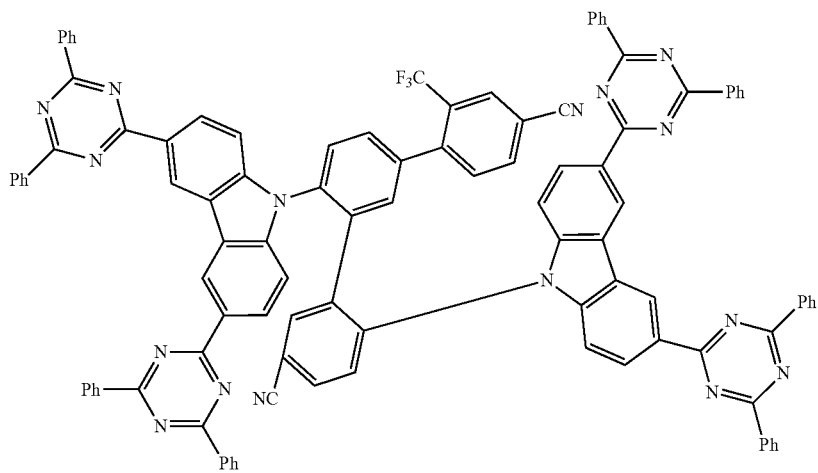
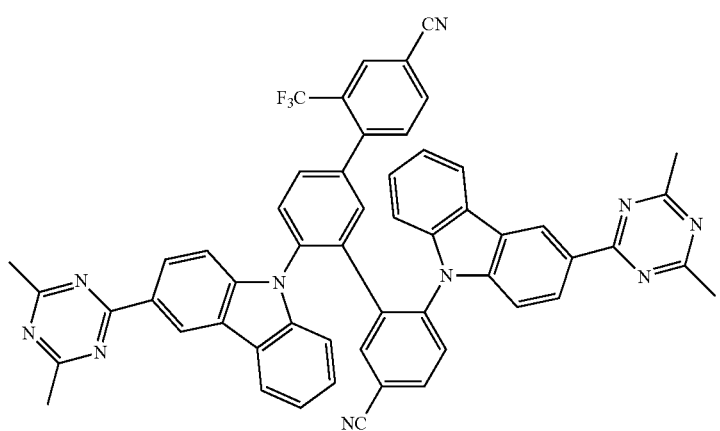

167                                    -continued                                    168
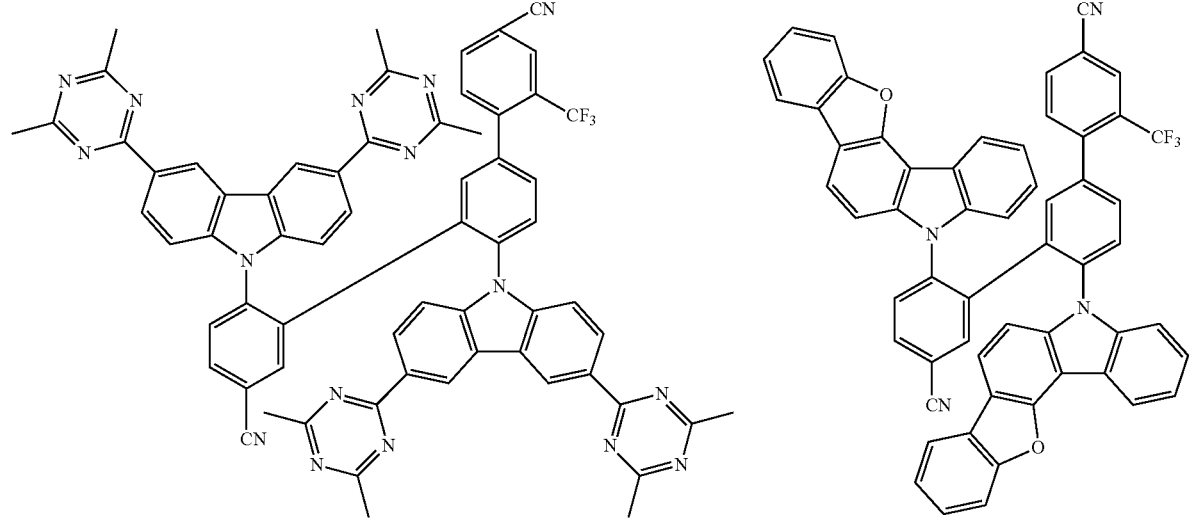
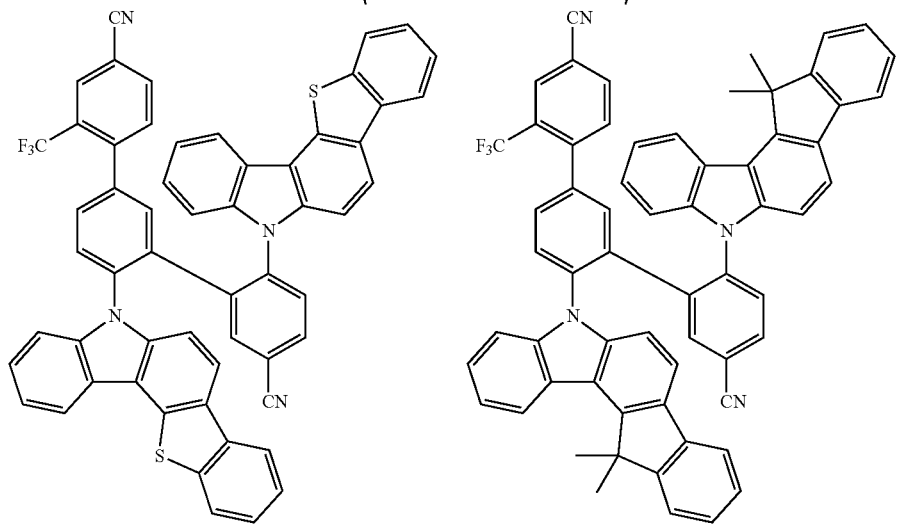
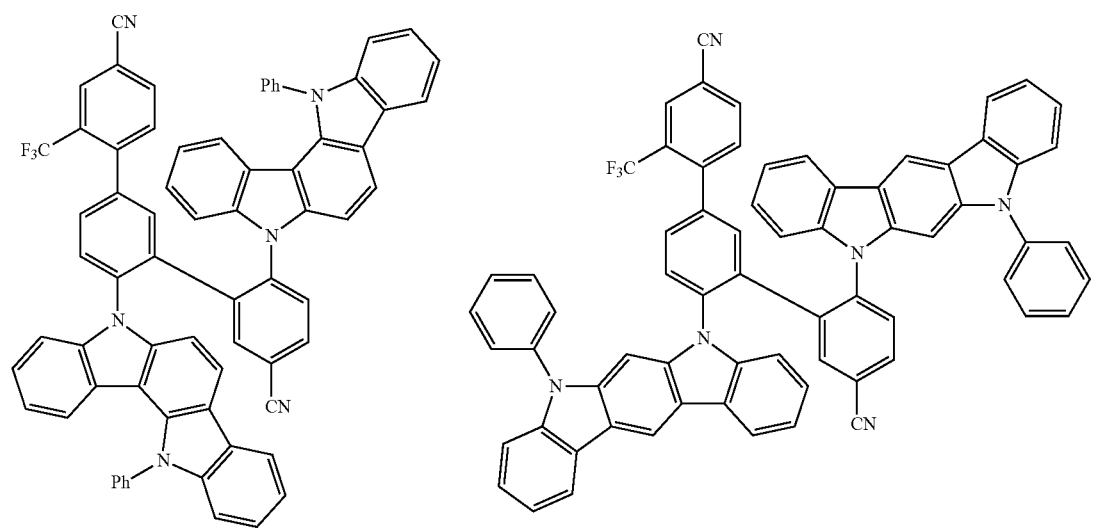

-continued
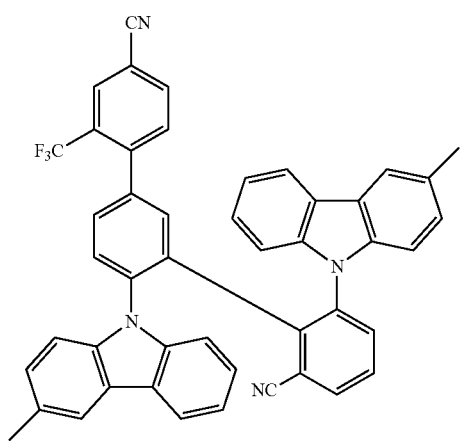
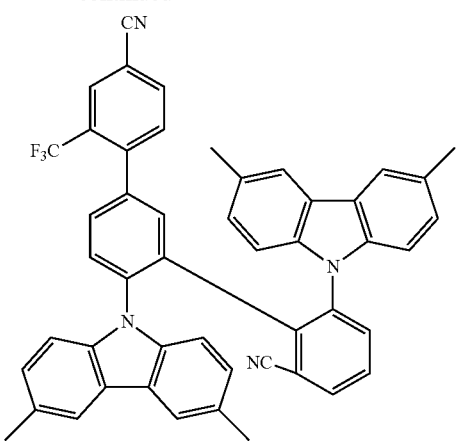
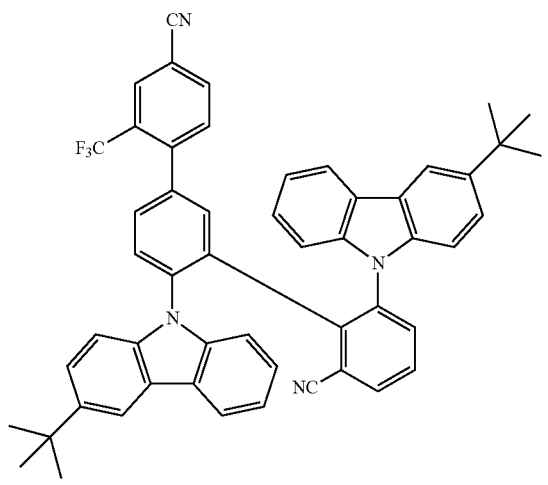
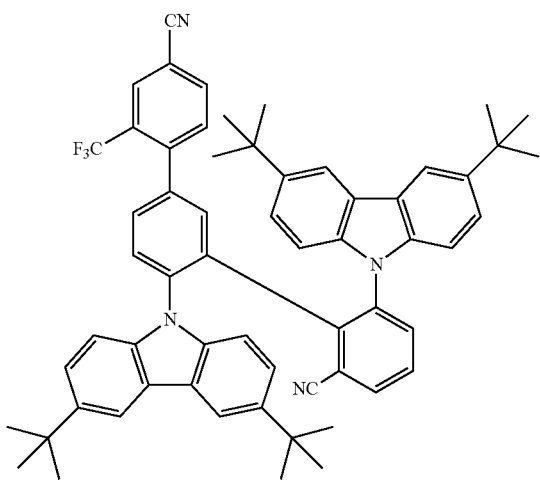
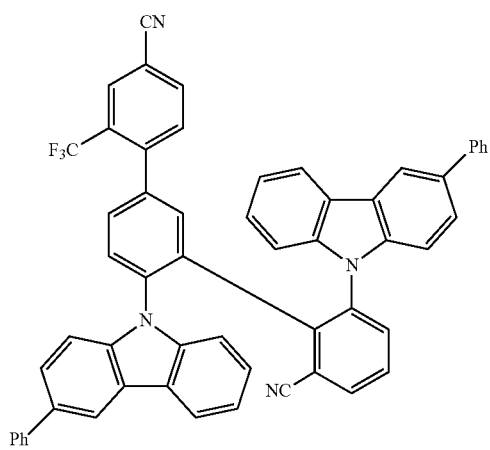
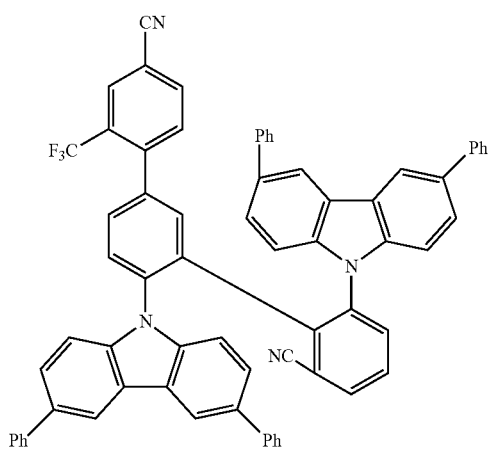

-continued
171
172
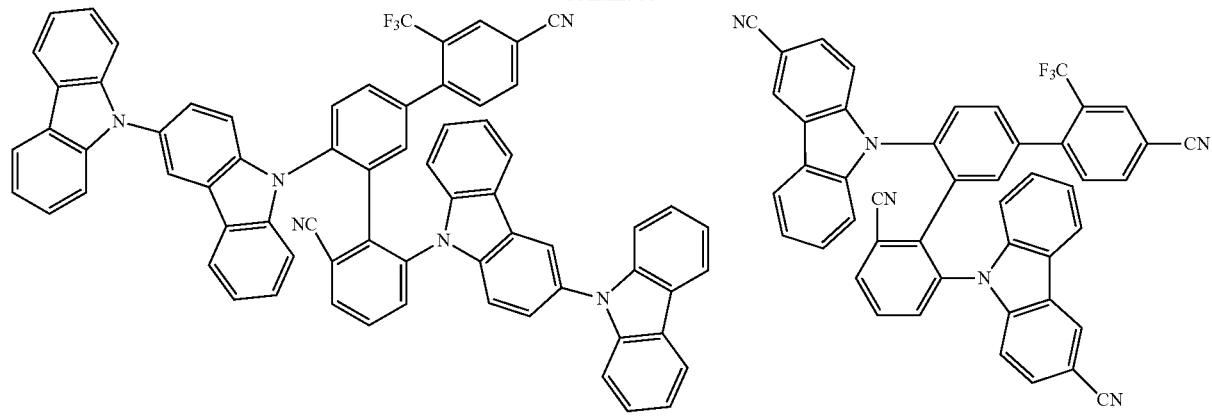
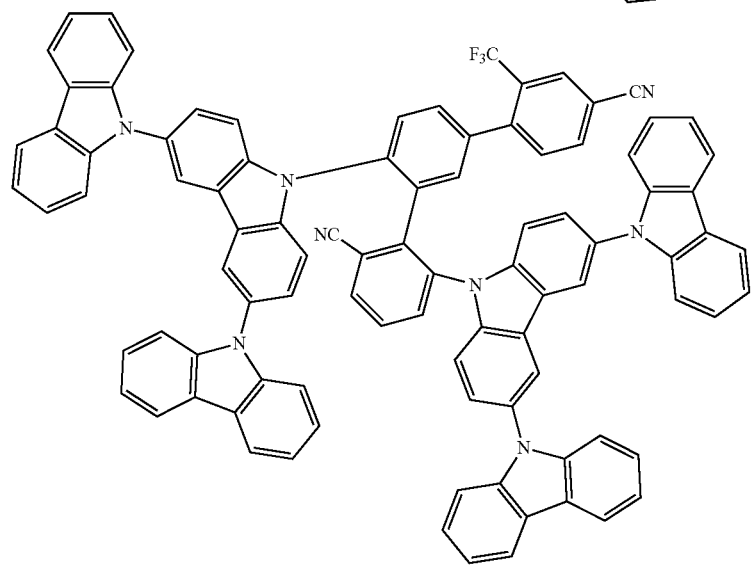
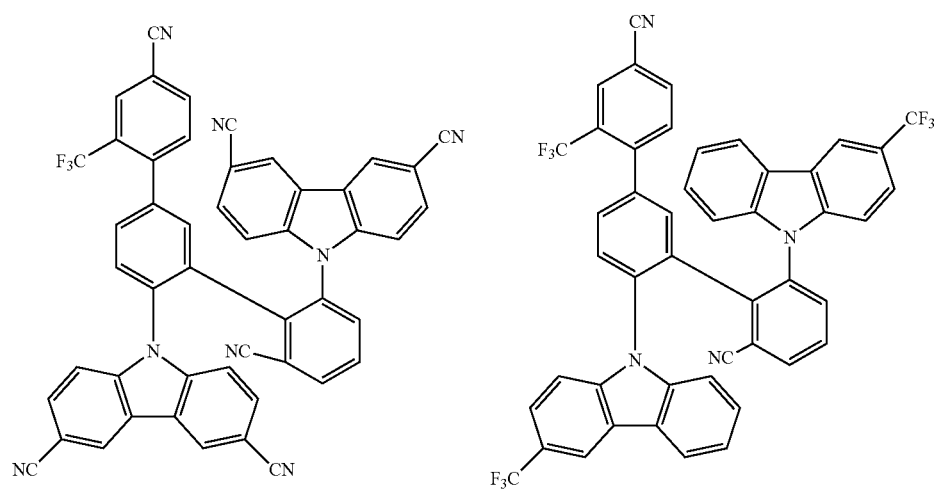

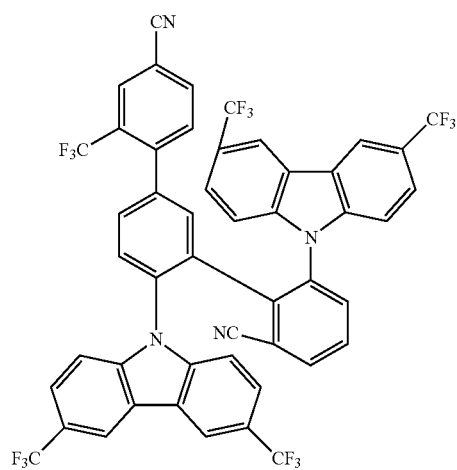
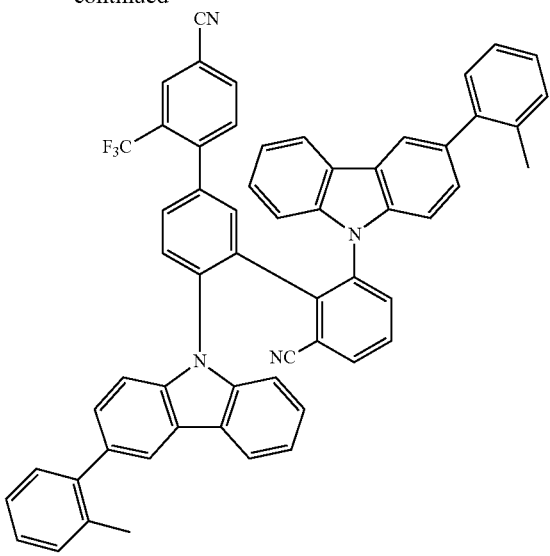
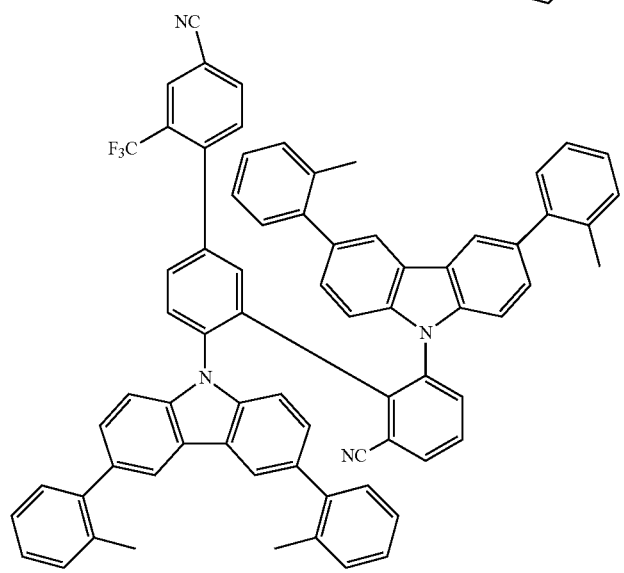
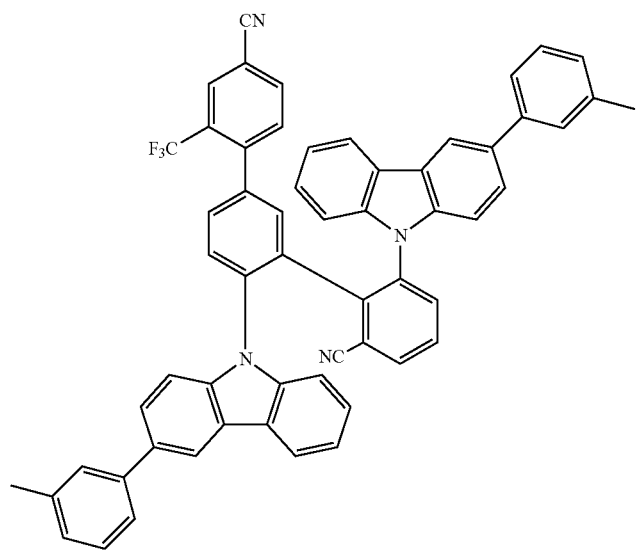

175 176
-continued
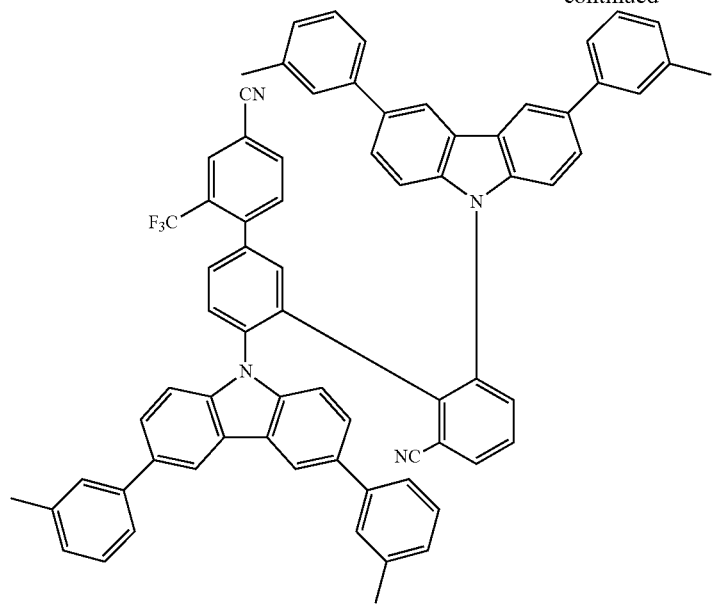
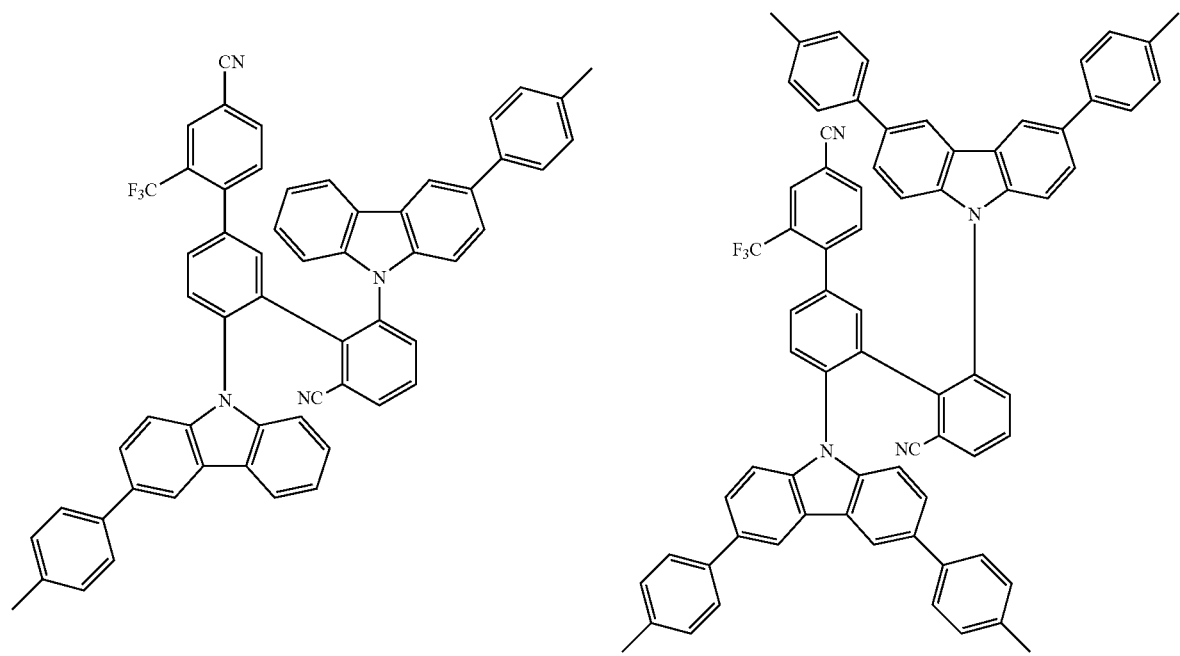

-continued
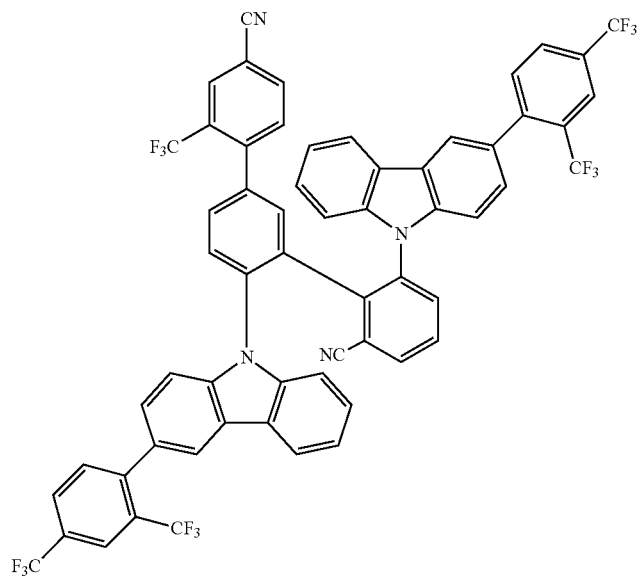
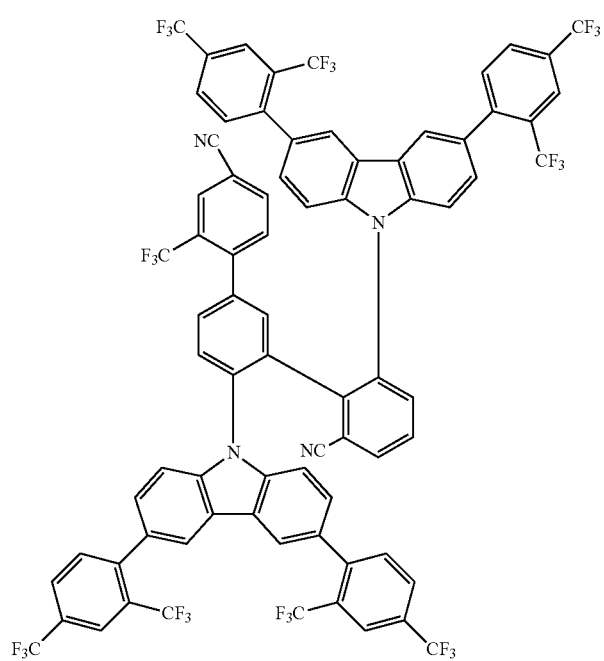

-continued
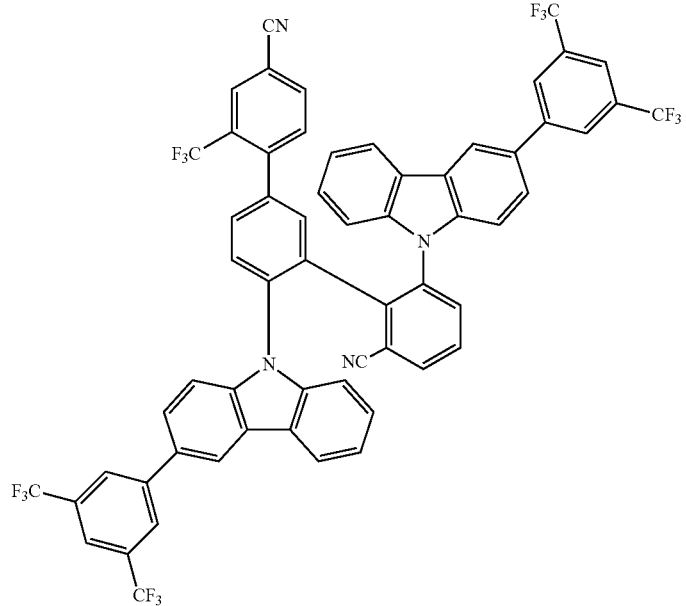
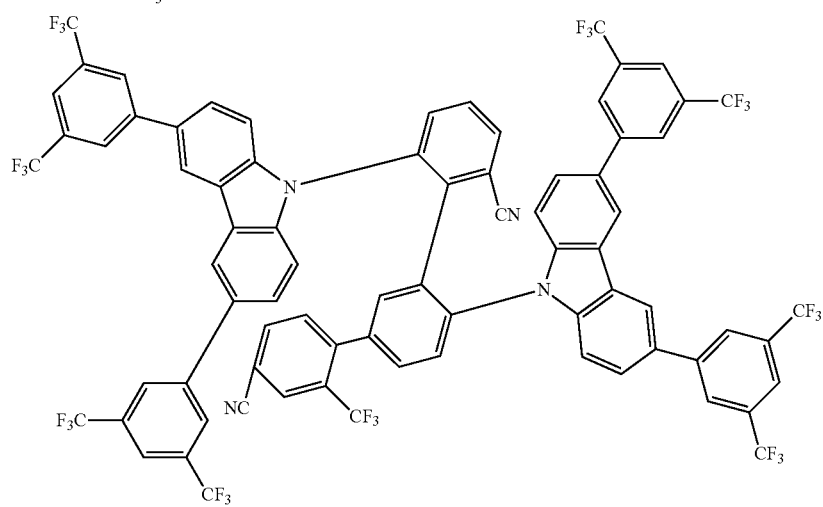
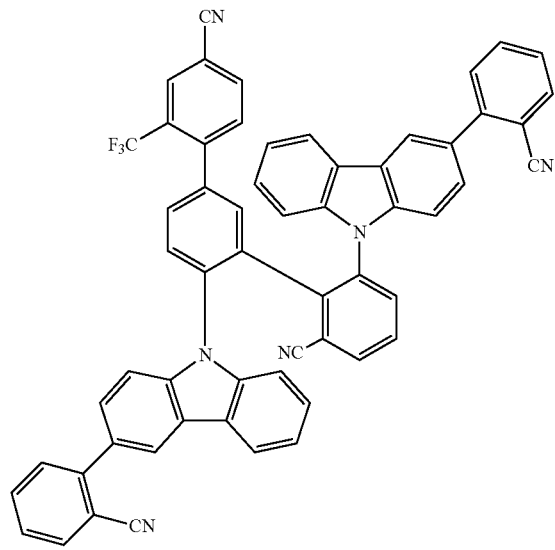

181 182
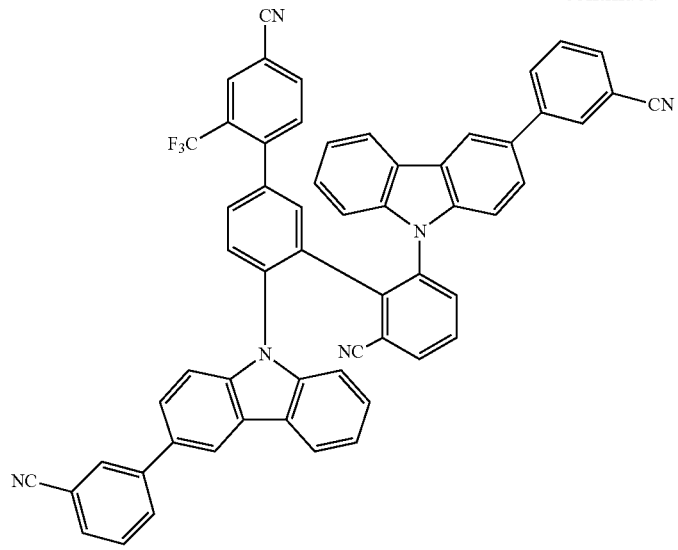
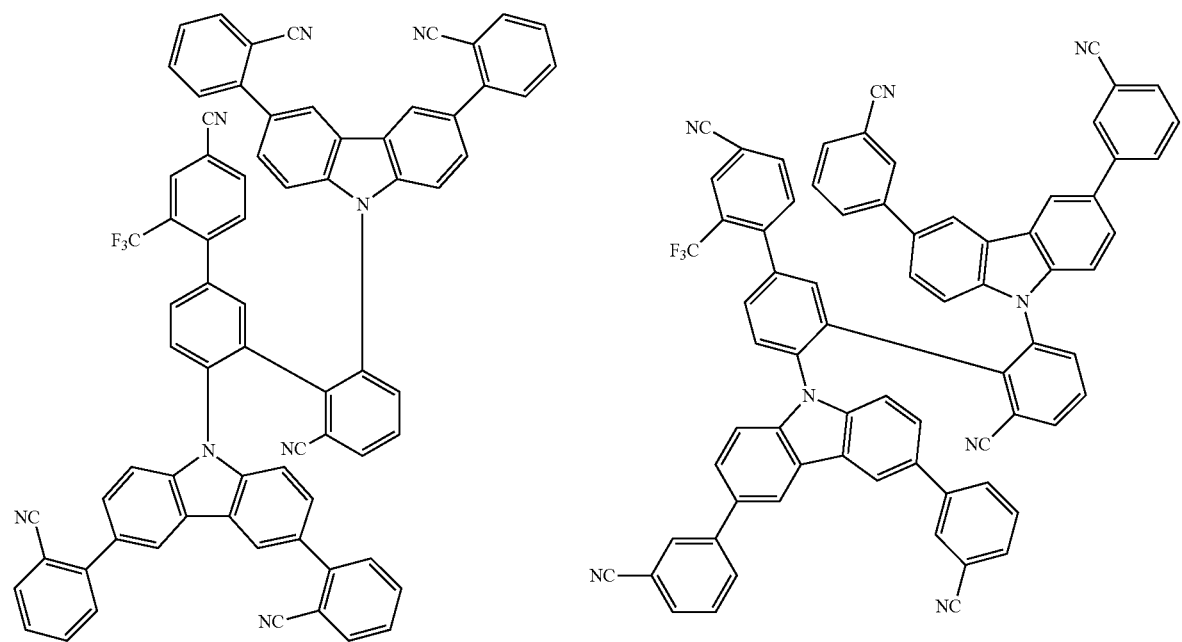

-continued
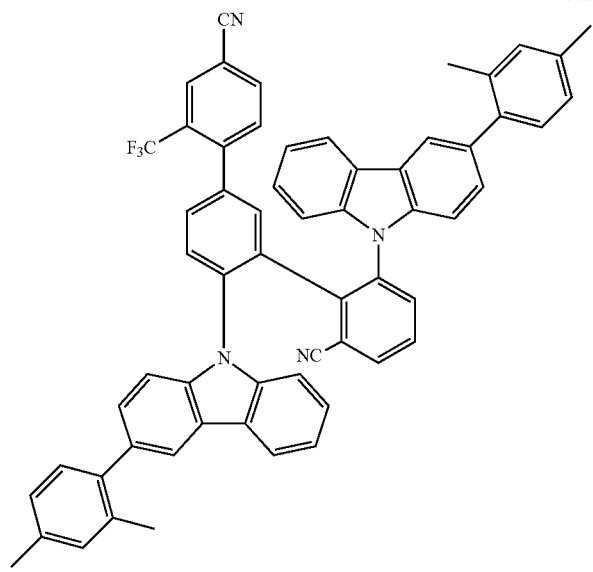
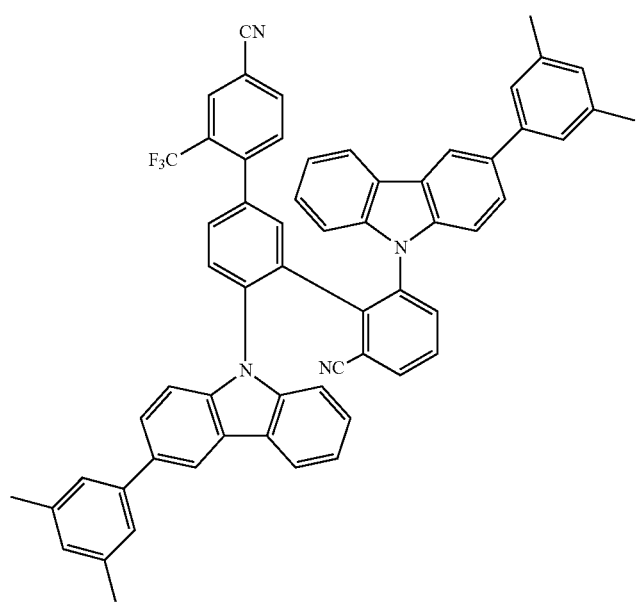

-continued
185
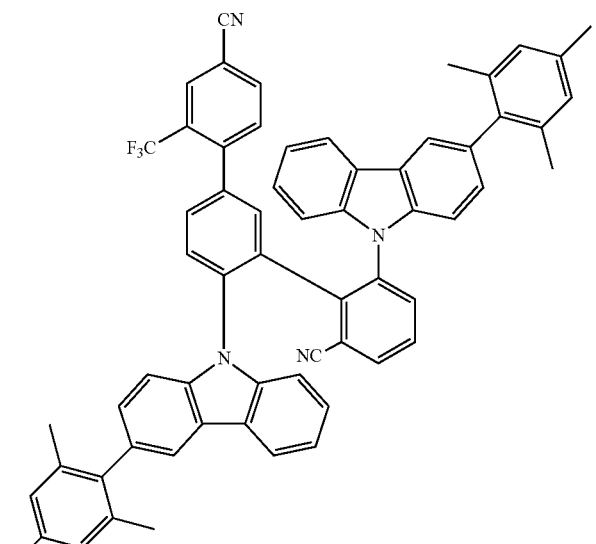
186
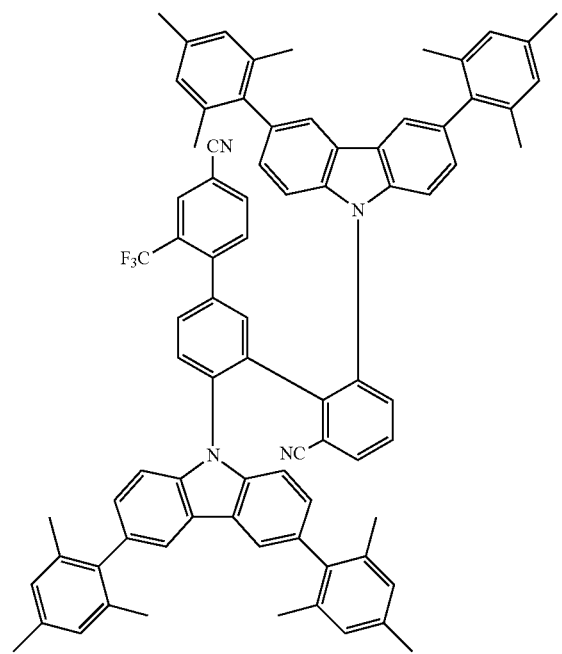
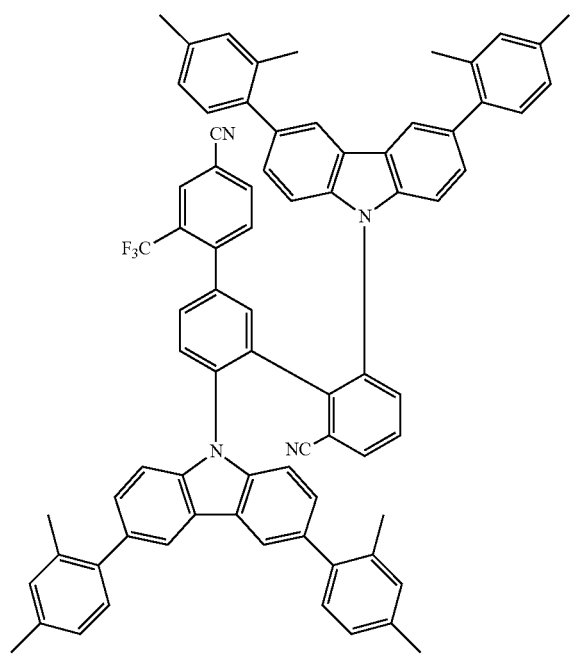
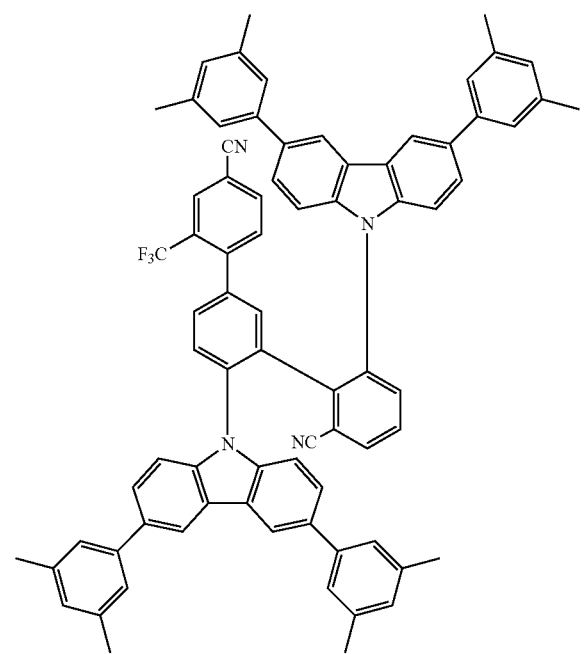

-continued
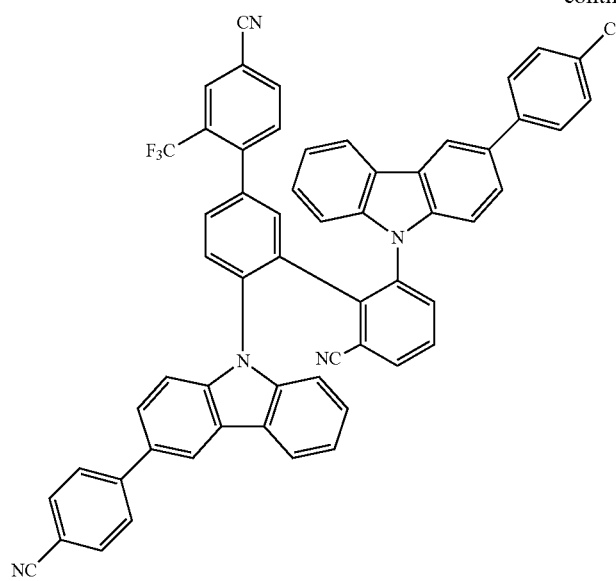
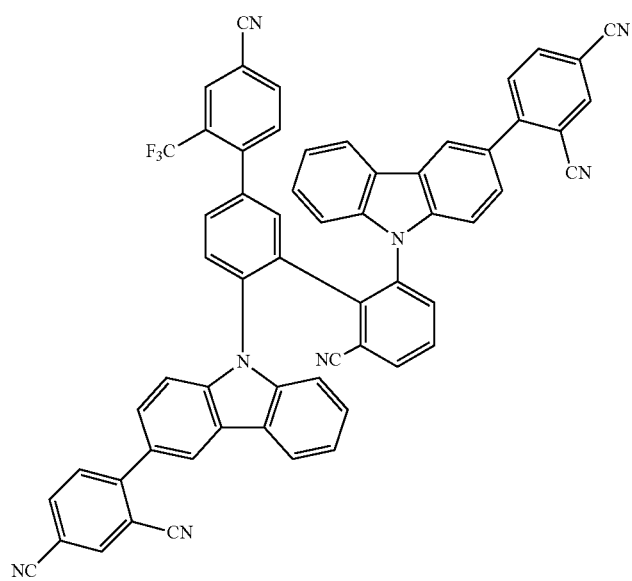

-continued
189
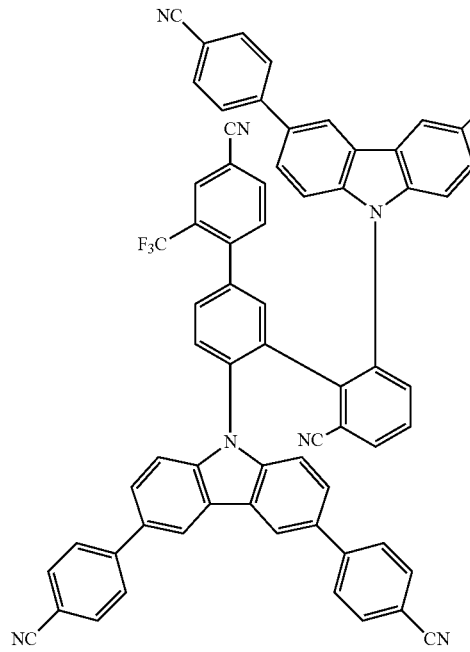
190
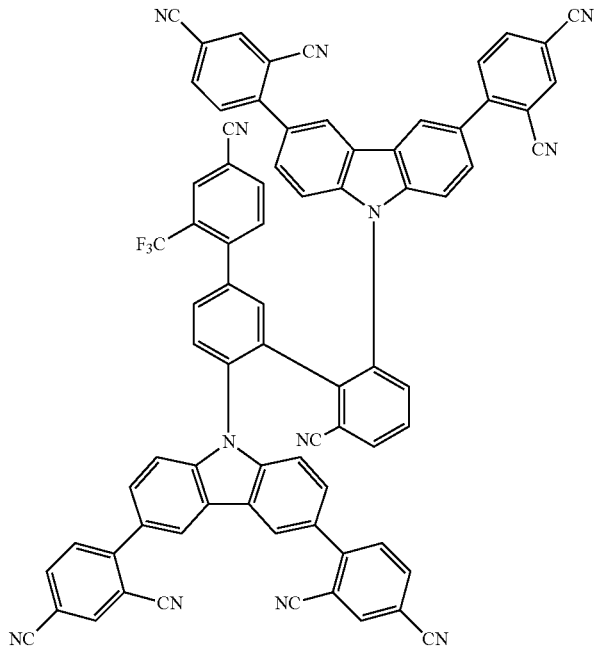
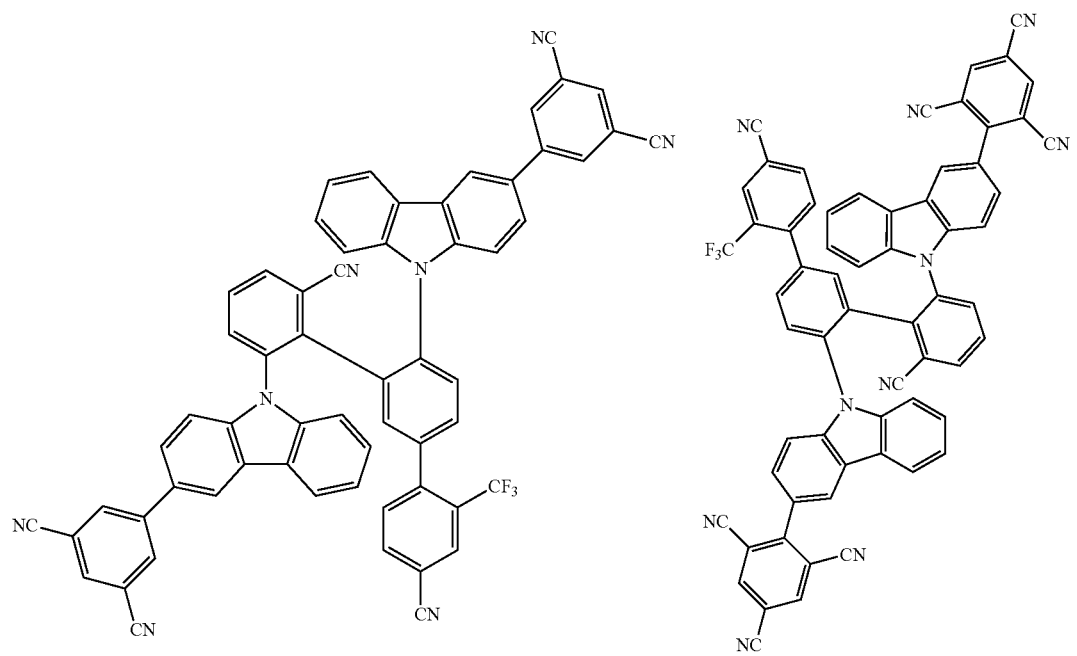

191
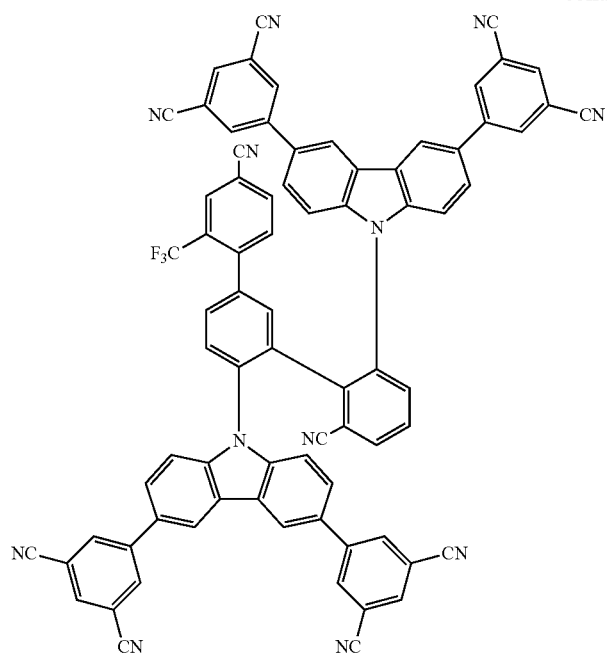
192
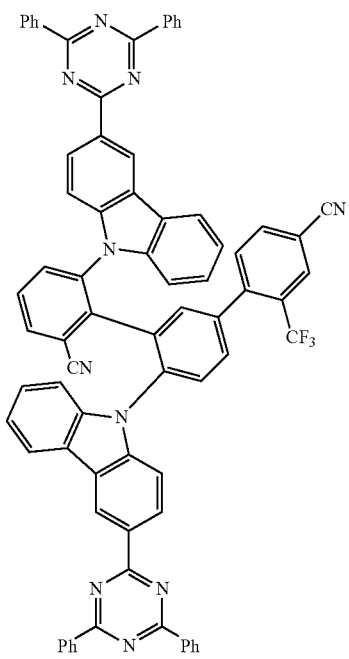

-continued
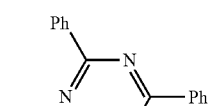
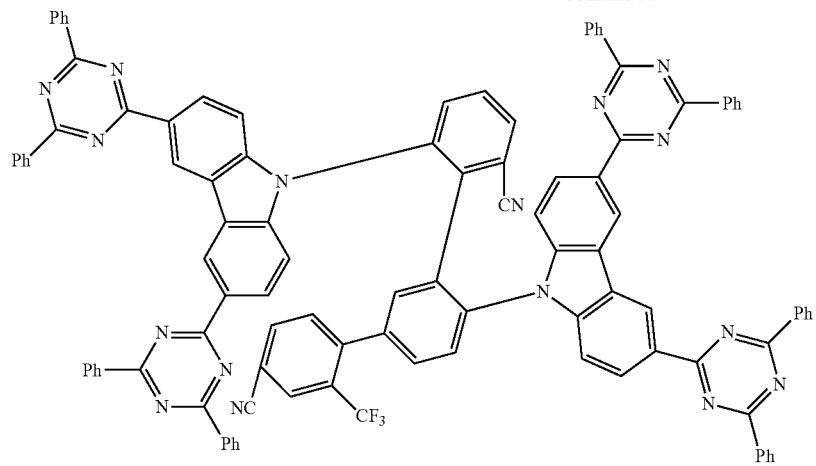
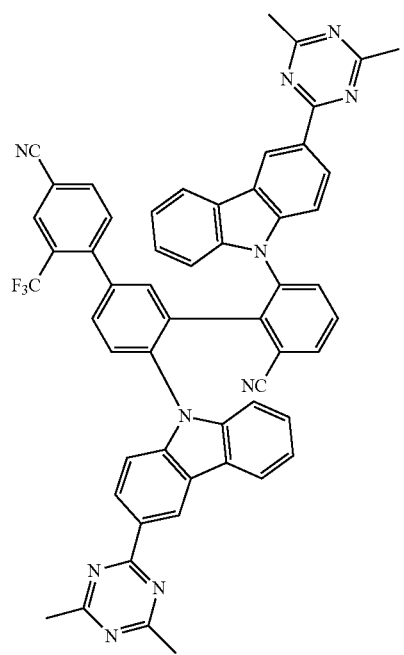
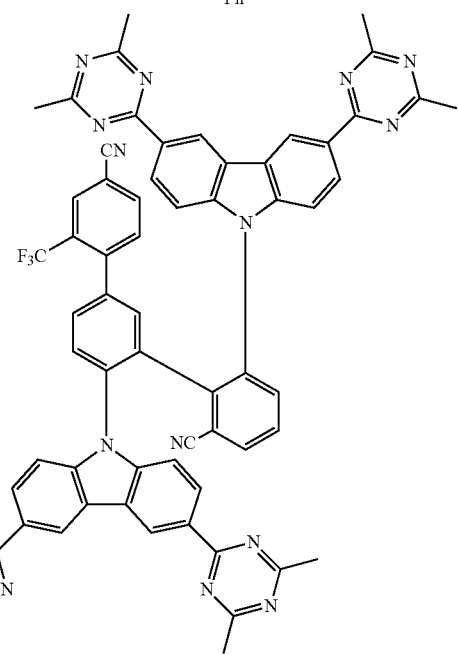
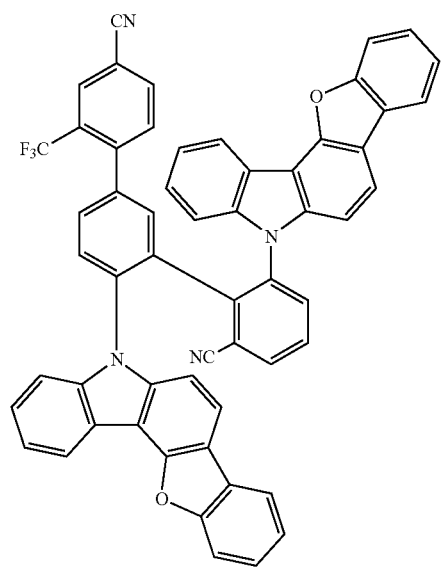
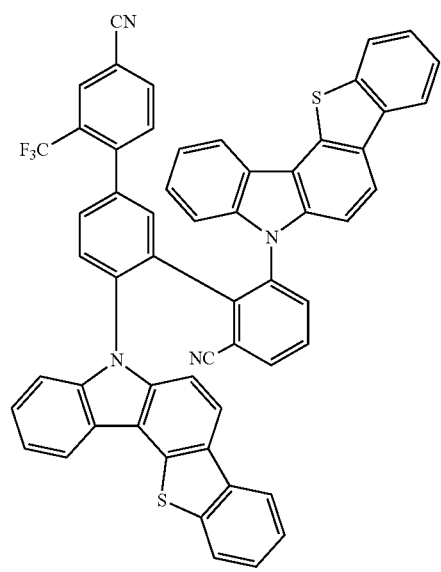

195
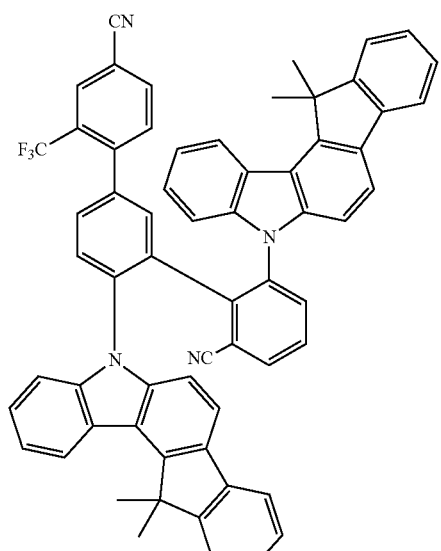
196
-continued
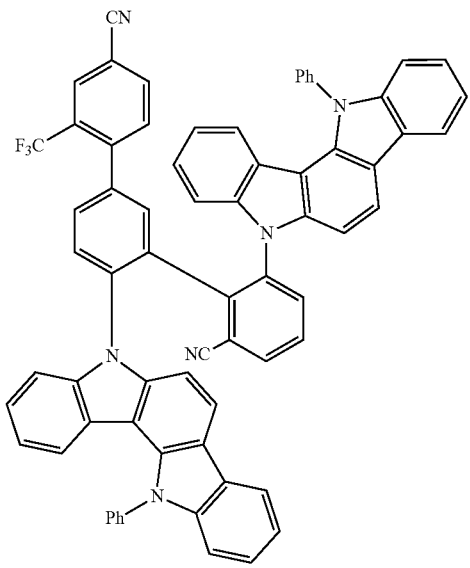
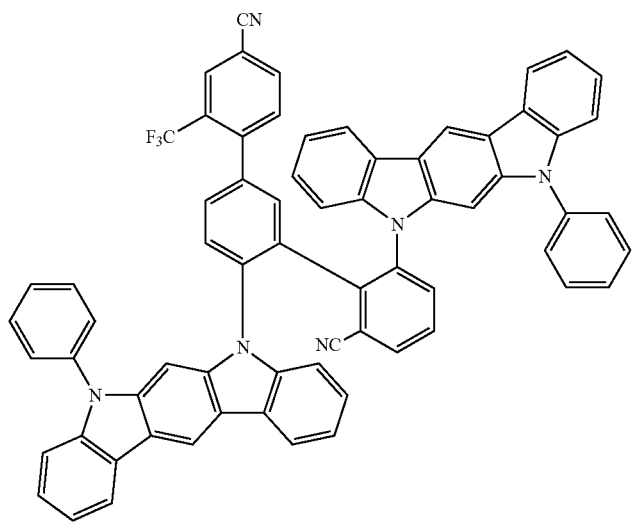
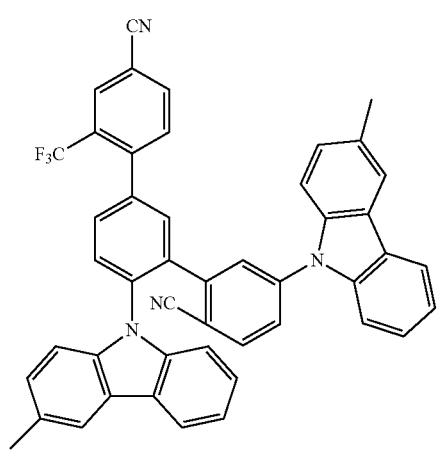
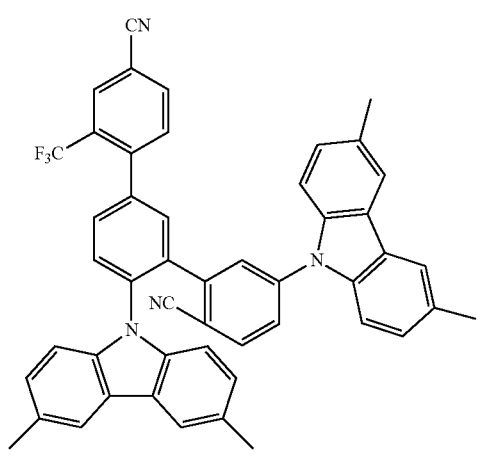
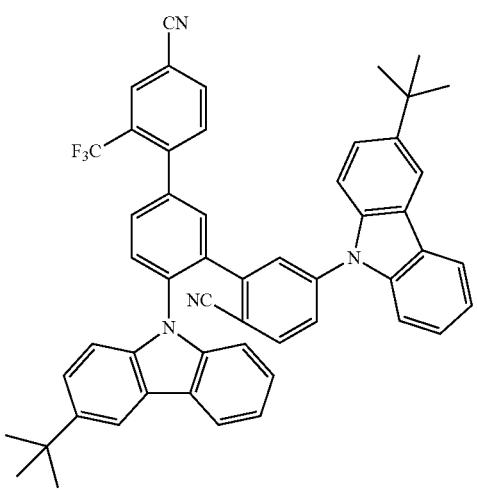

-continued
197
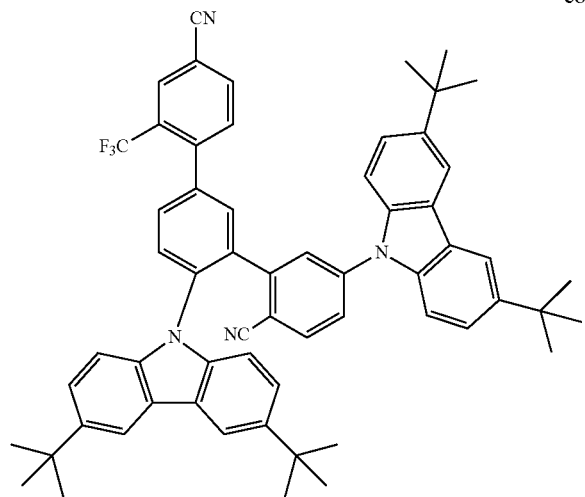
198
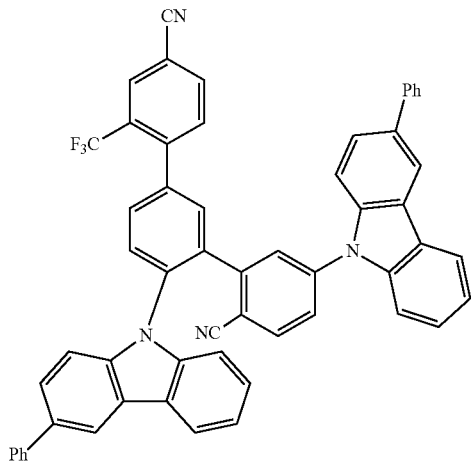
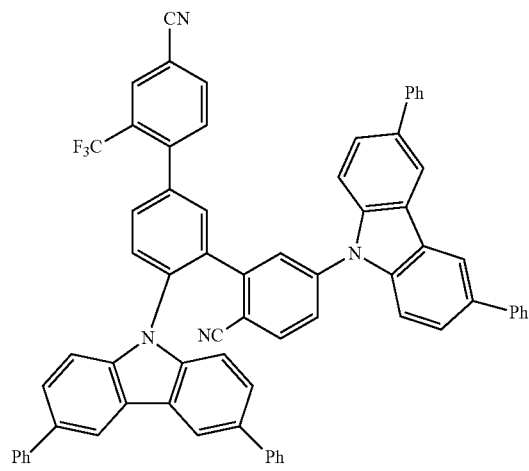
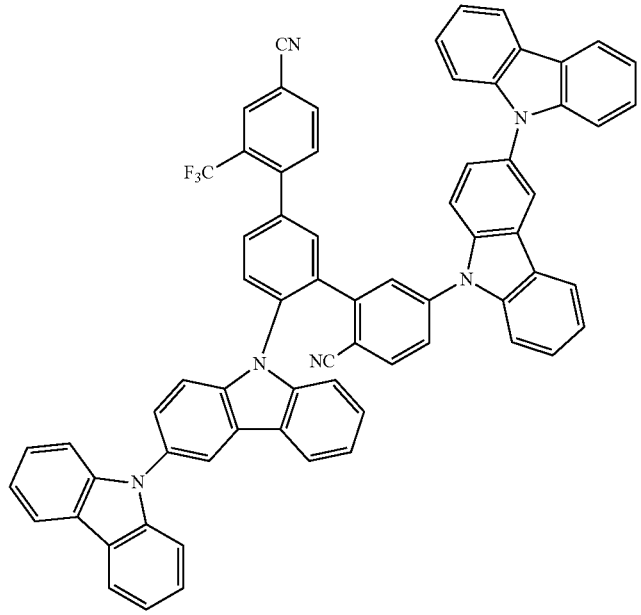
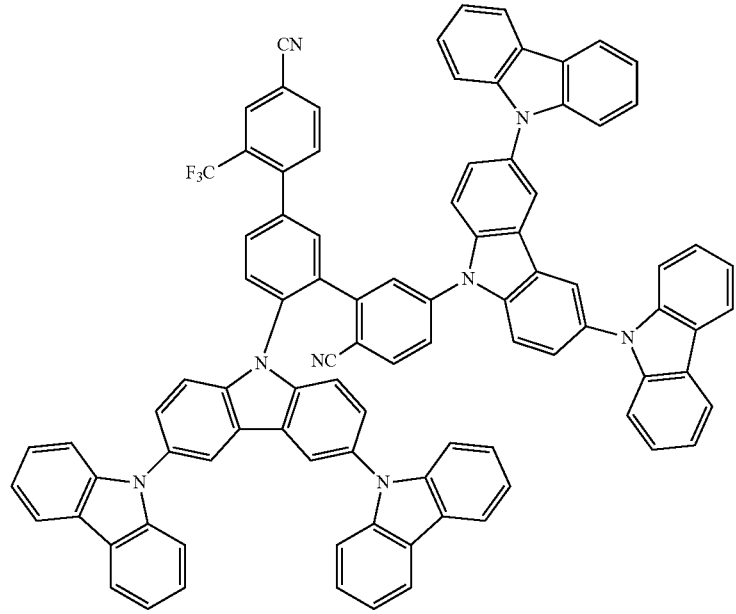

199
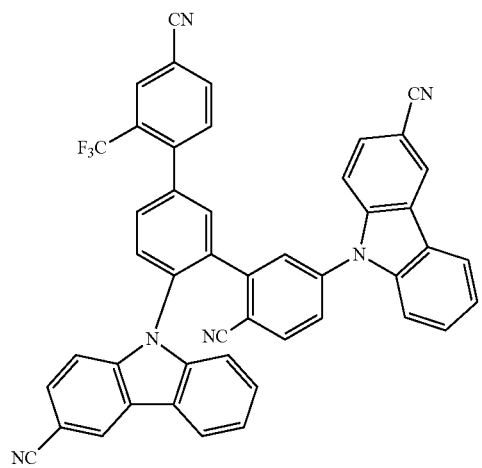
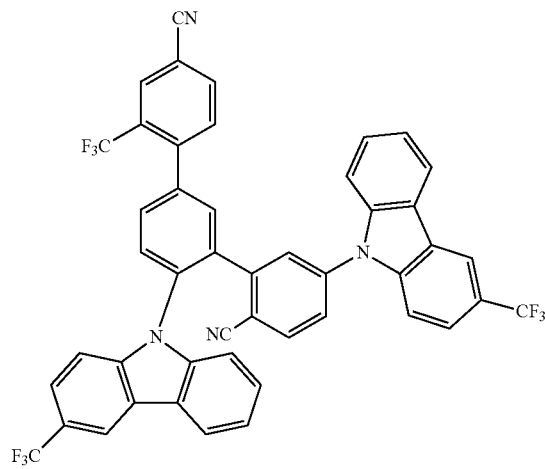
200
-continued
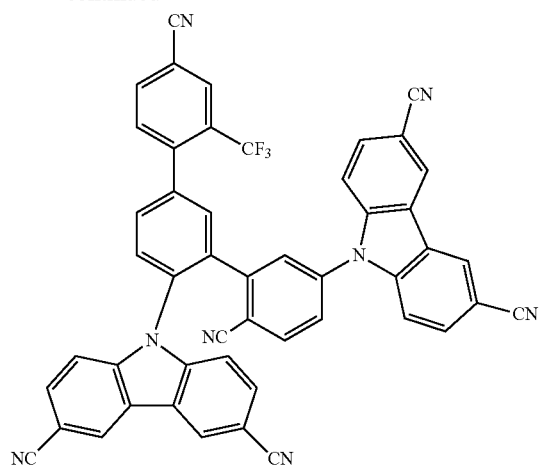
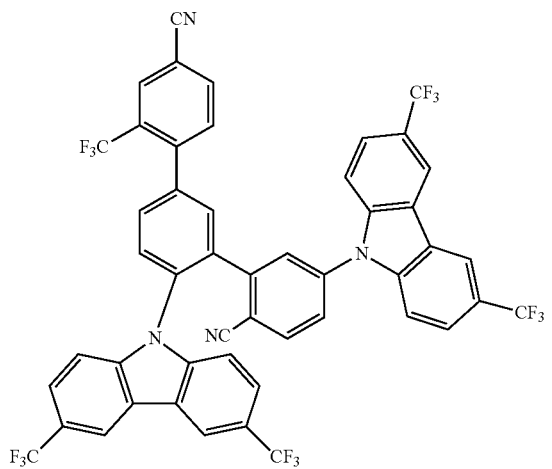
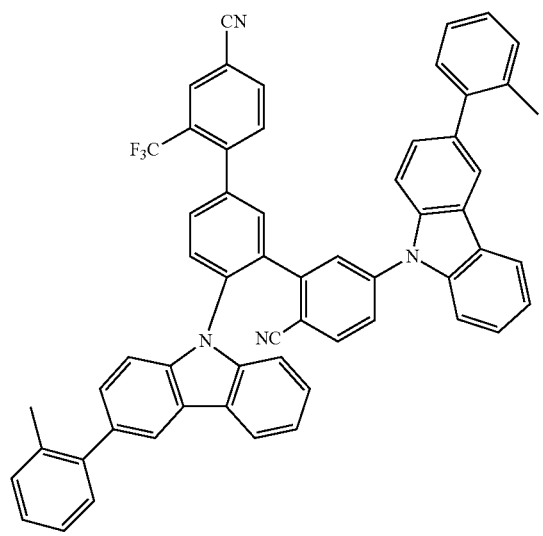
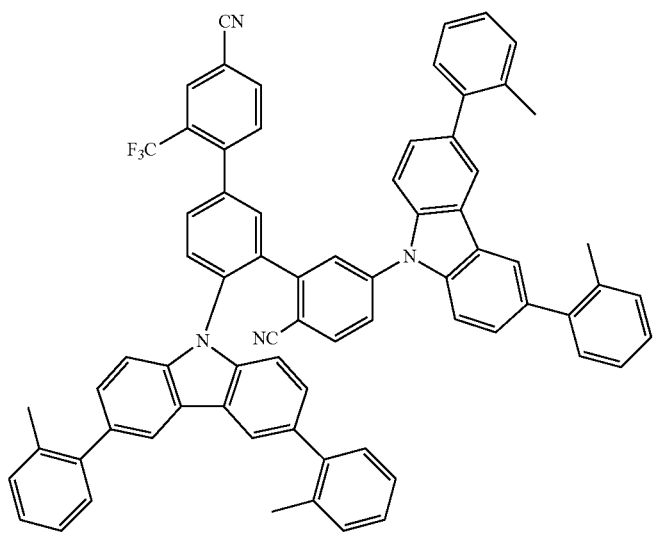

201
-continued
202
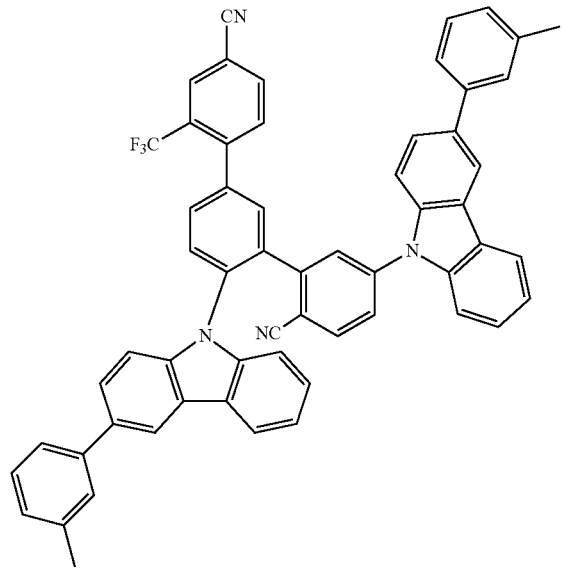
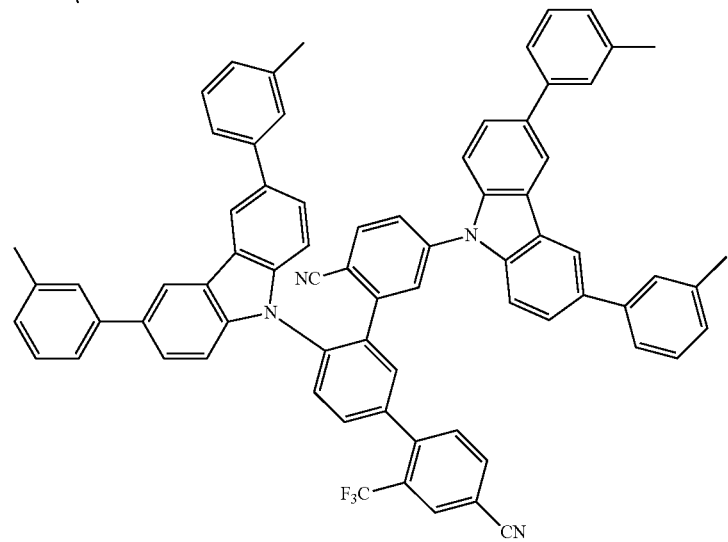
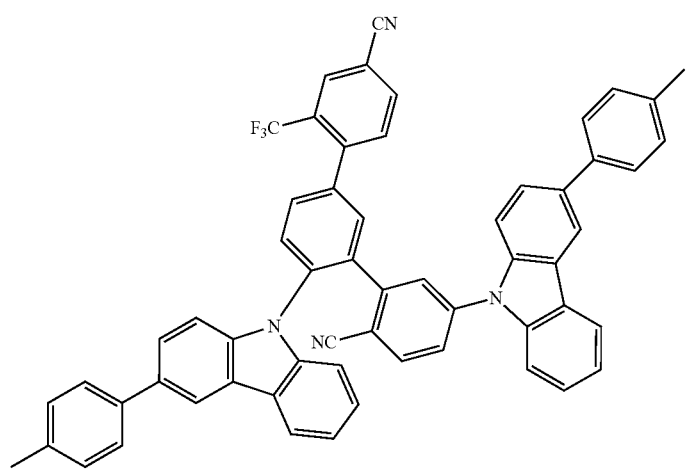

203 204
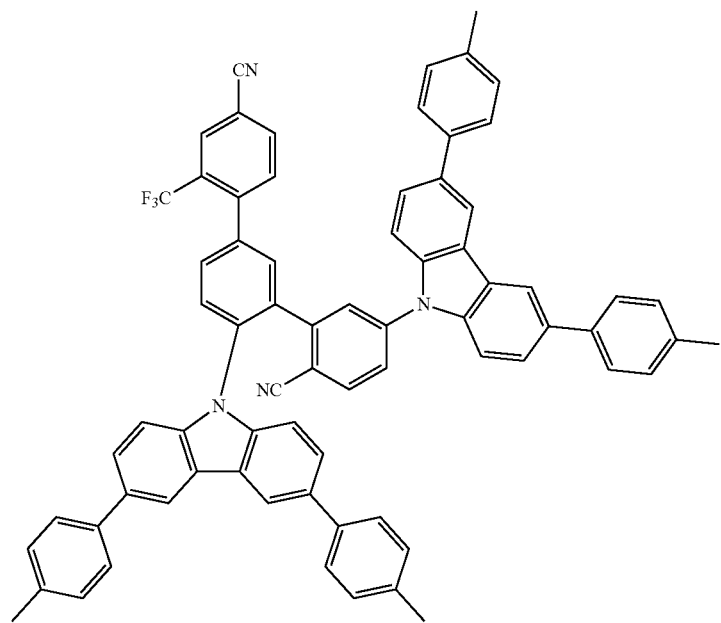
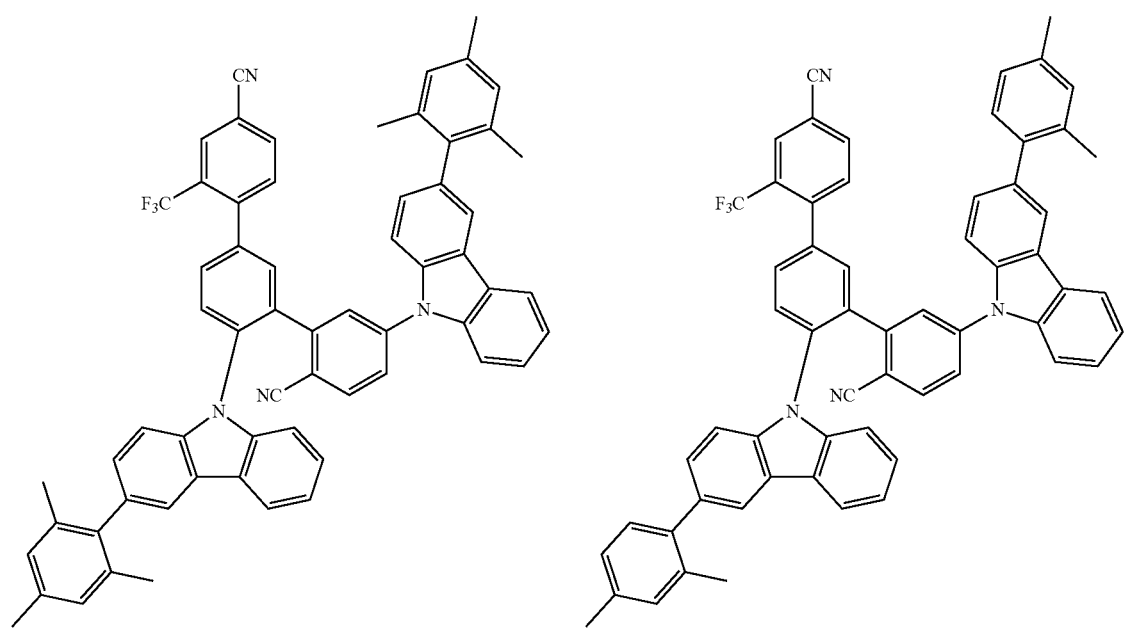

-continued
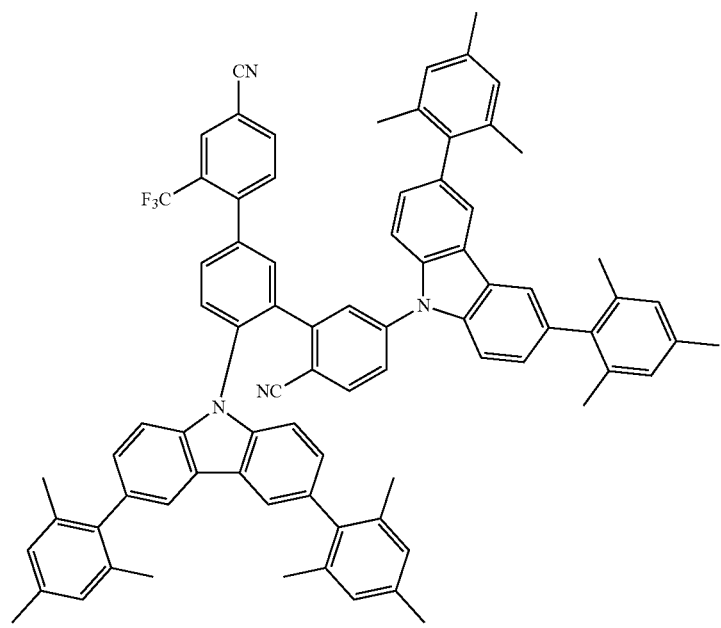
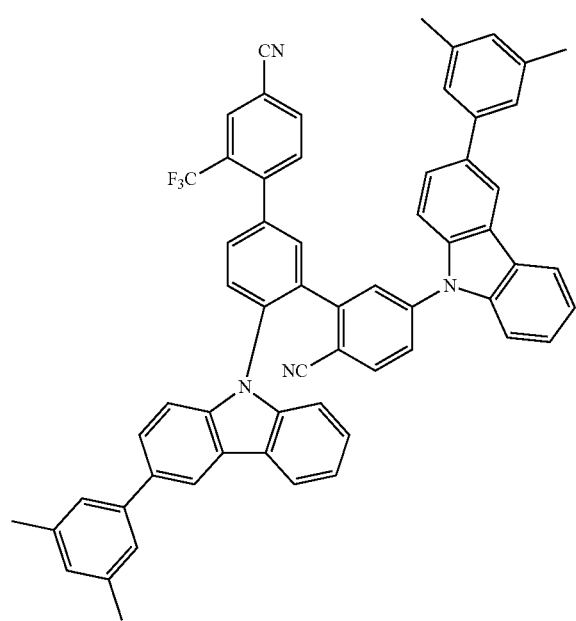

-continued
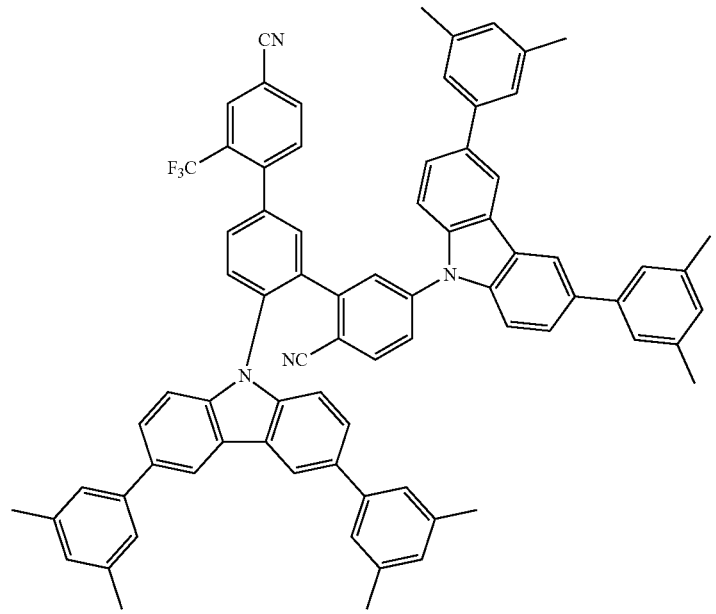
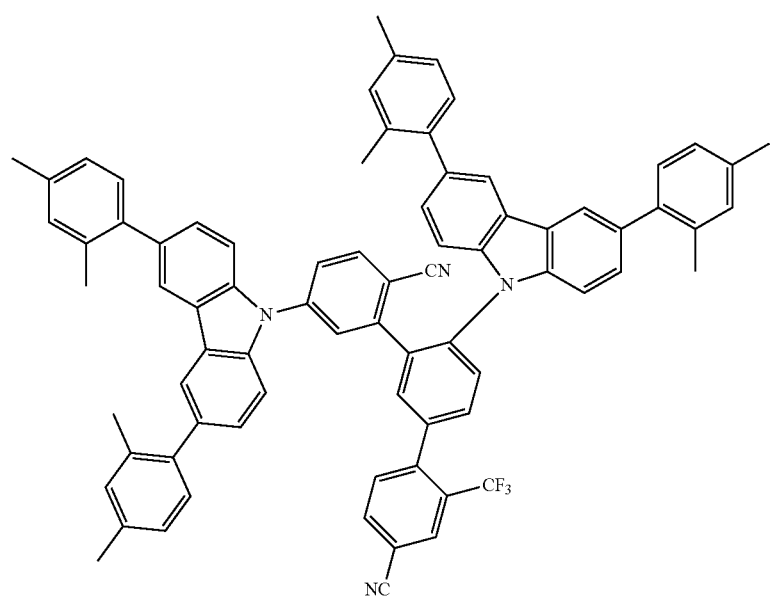
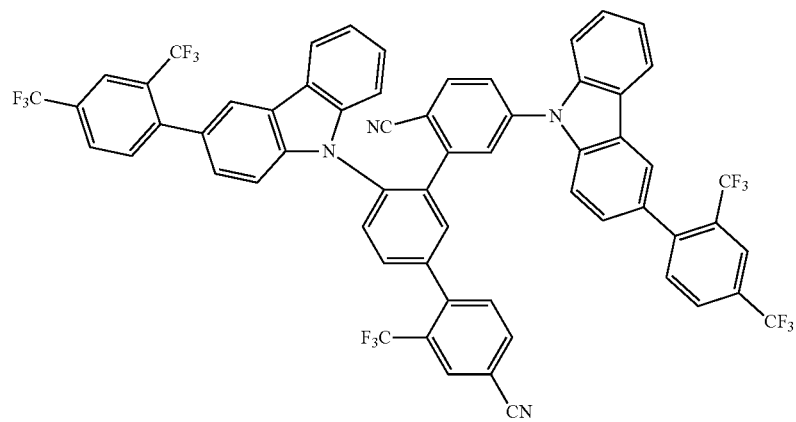

-continued
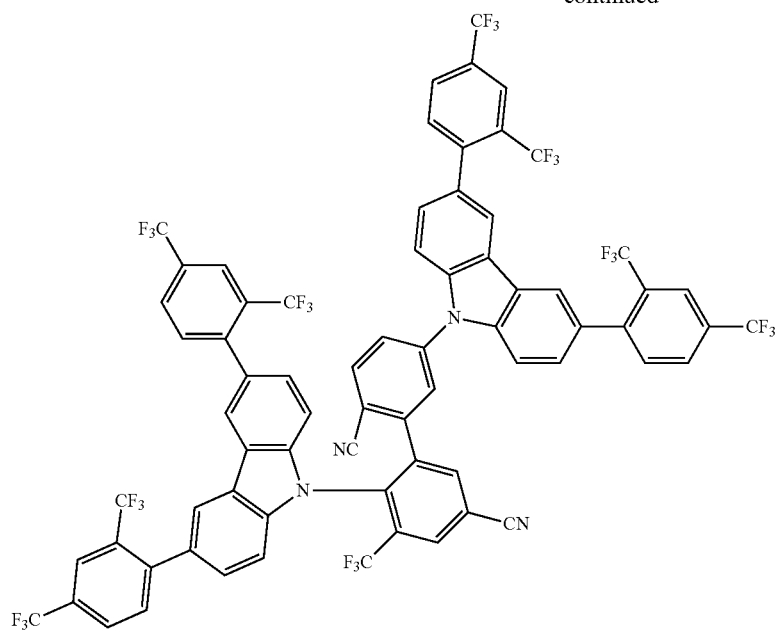
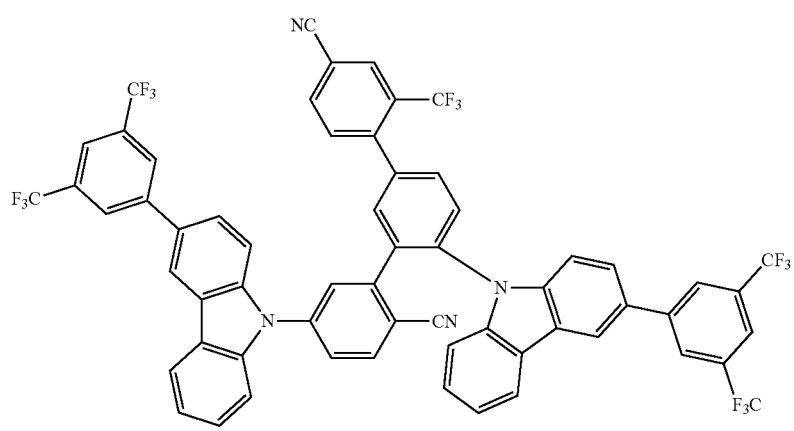

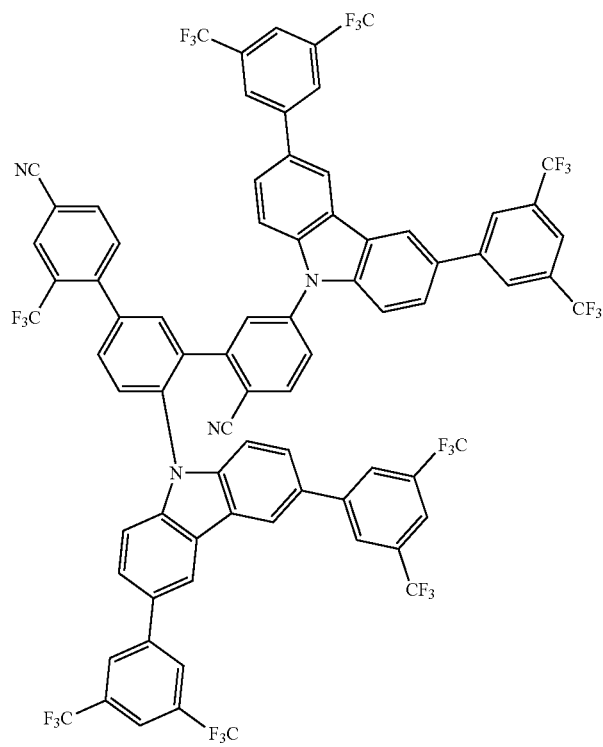
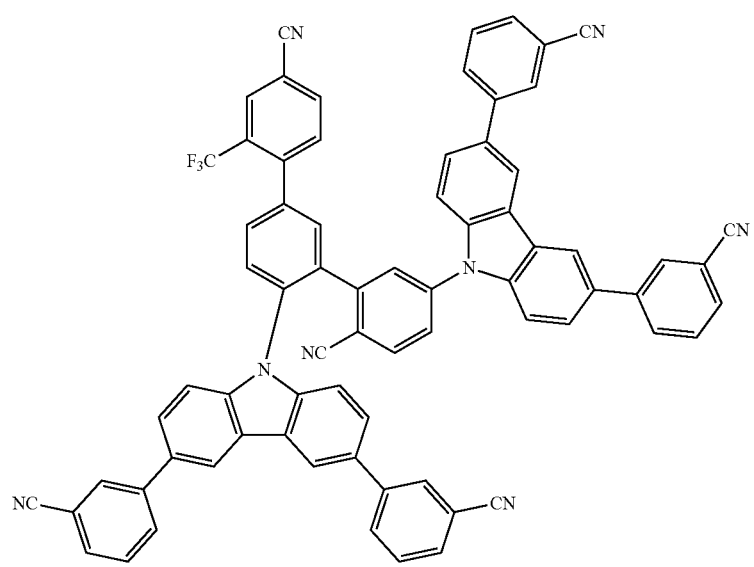

-continued
213
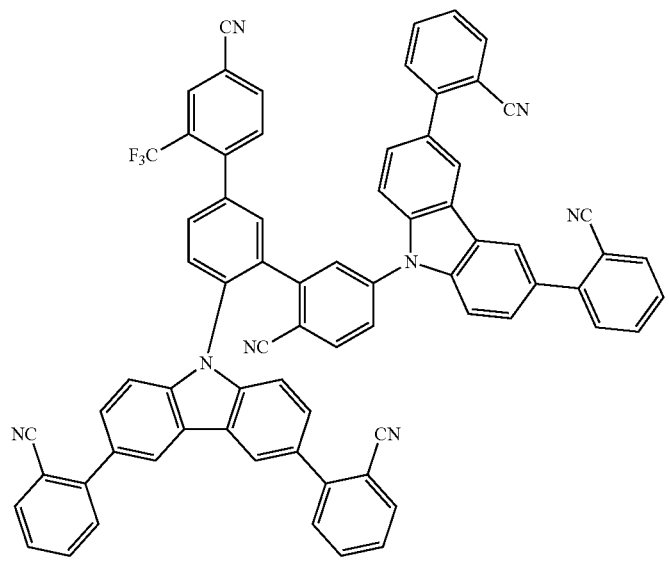
214
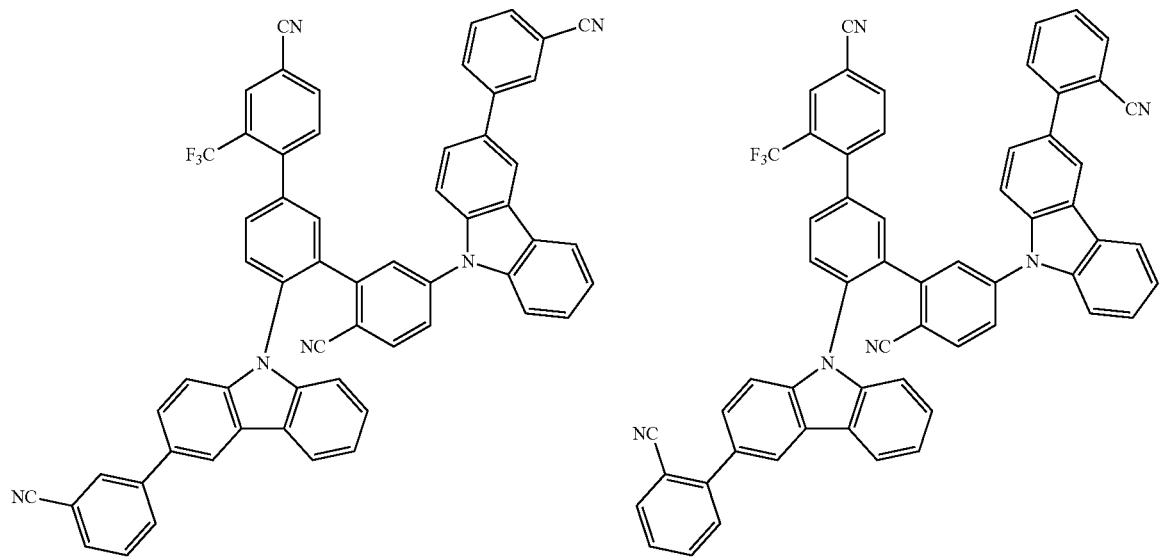

-continued
215
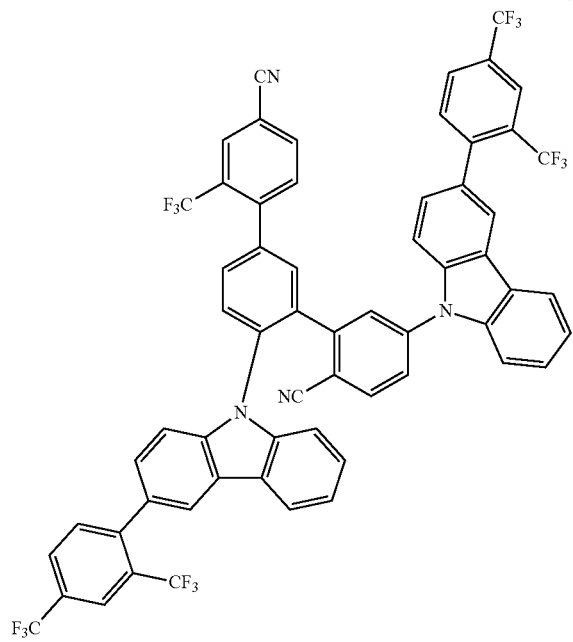
216
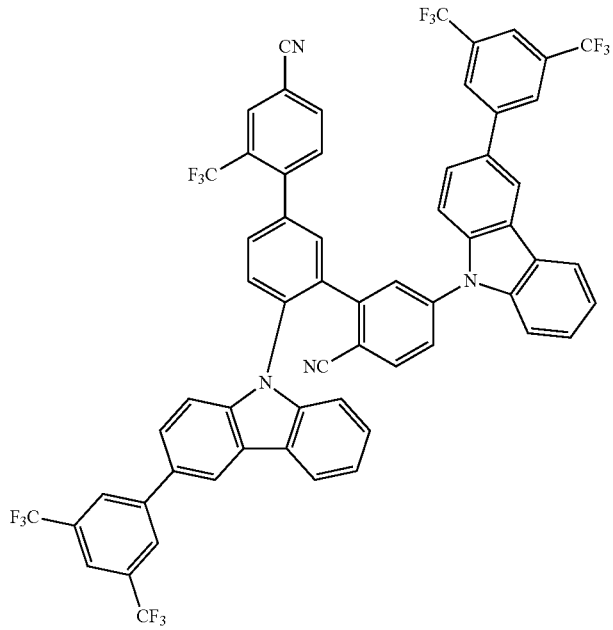
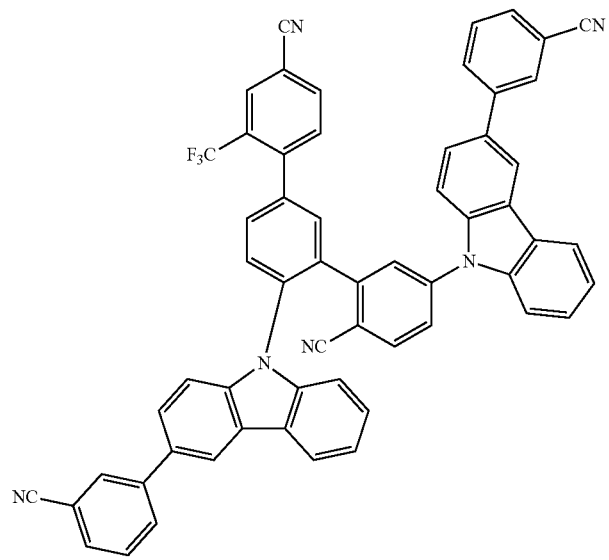

-continued
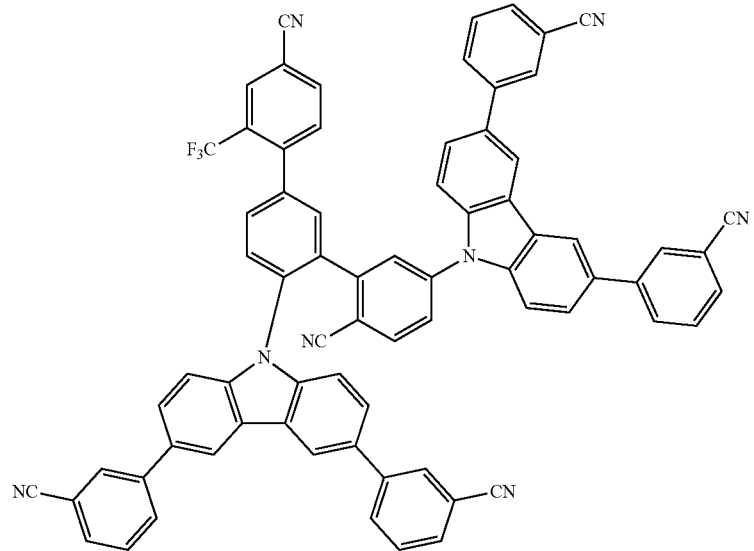
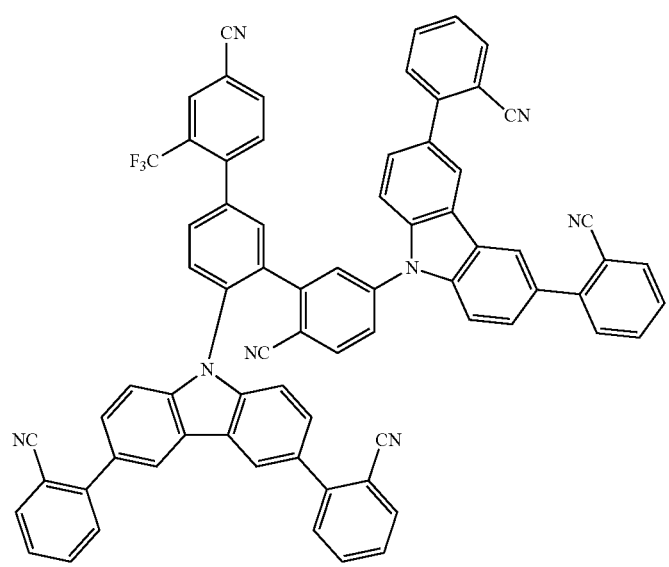

-continued
| 219 | 220 |
|---|---|
| 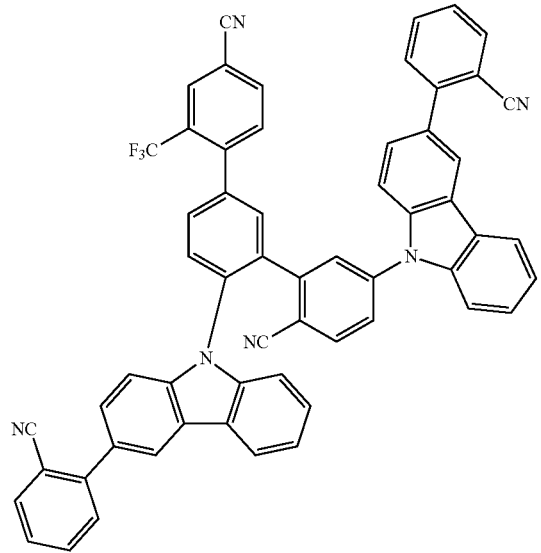 | 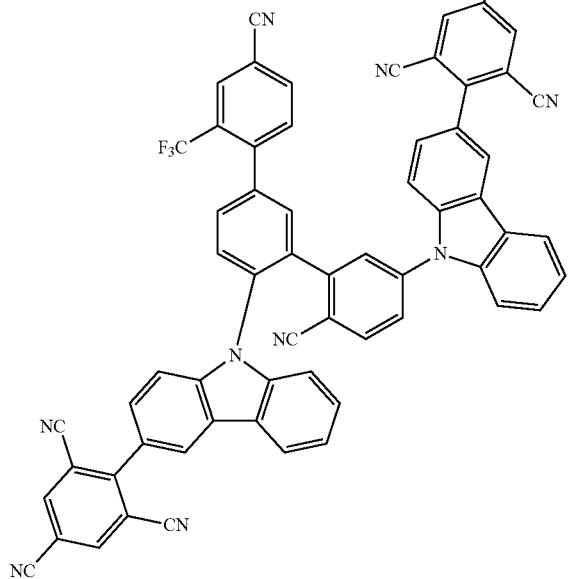 |
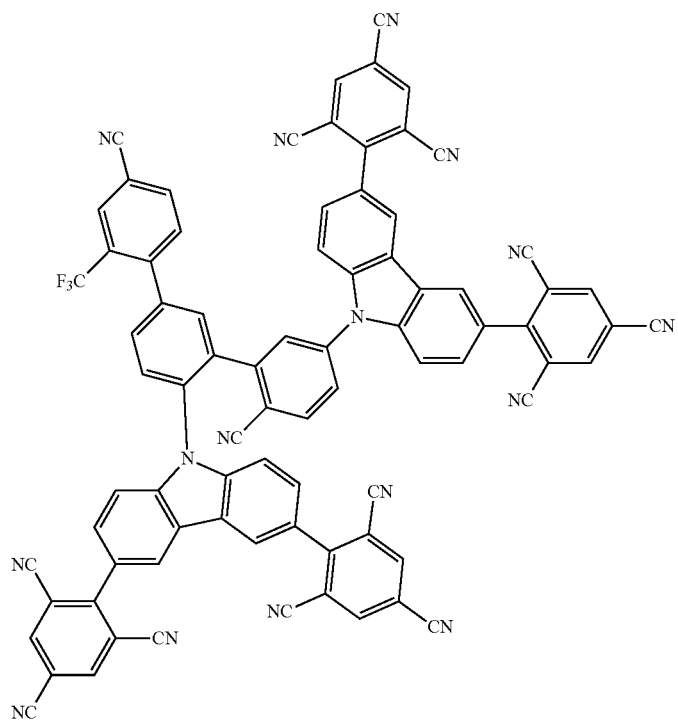

-continued
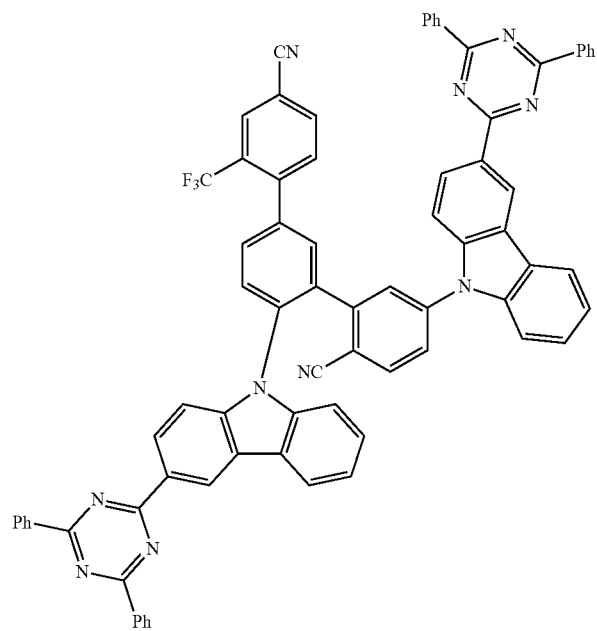
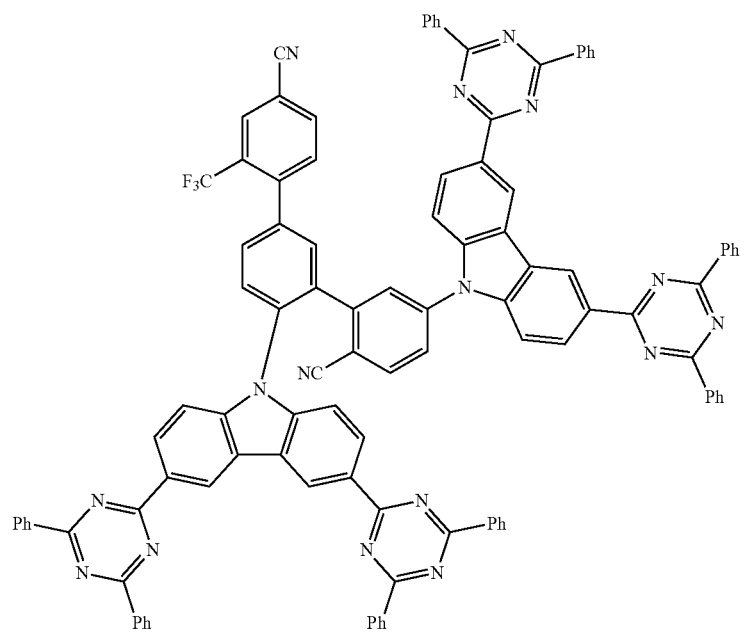

-continued
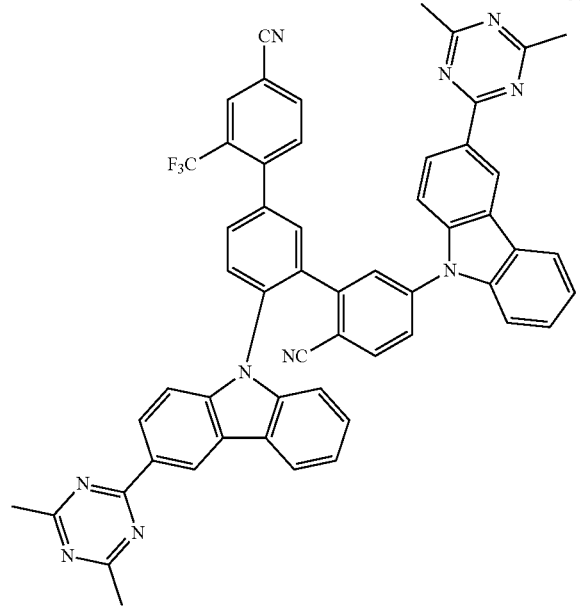
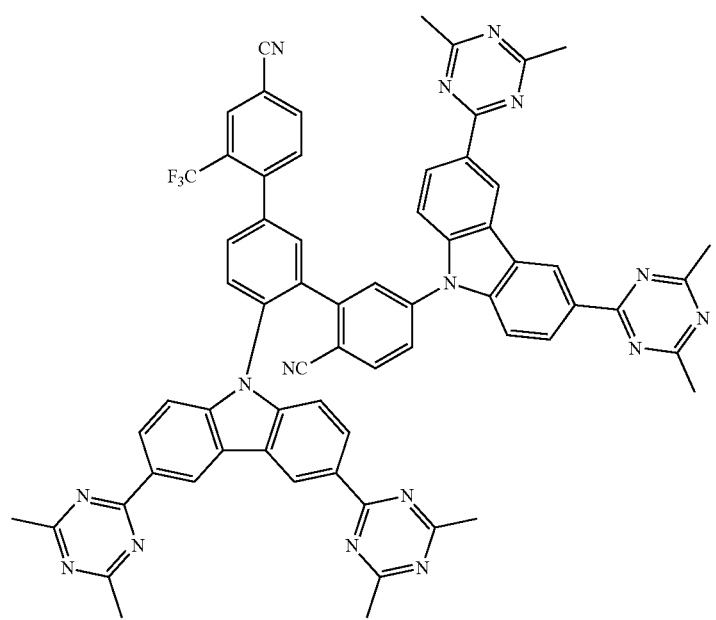

225 226
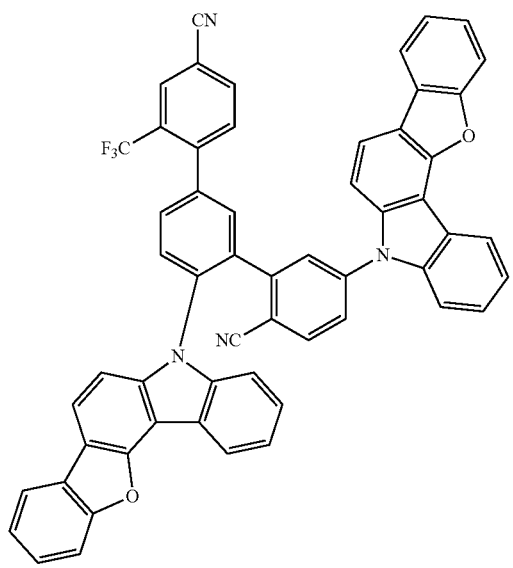
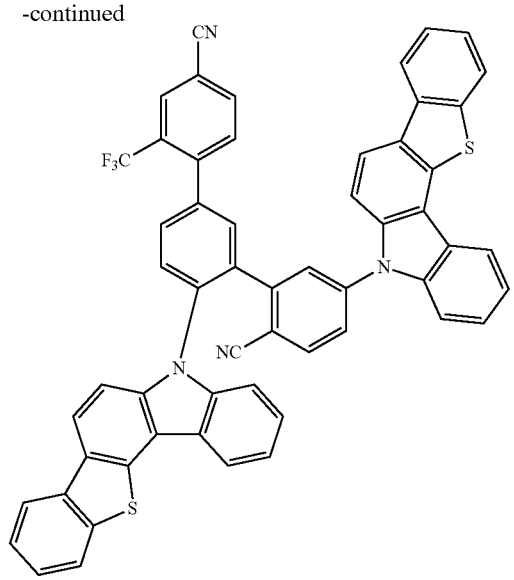
-continued
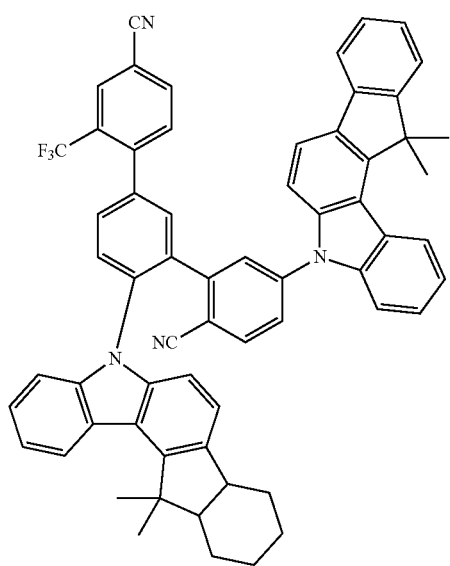
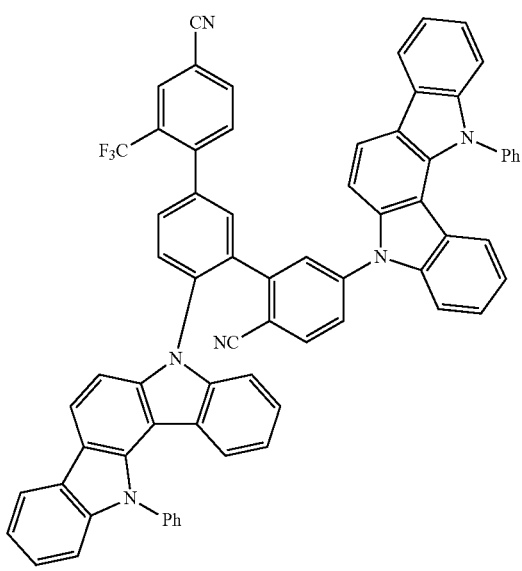
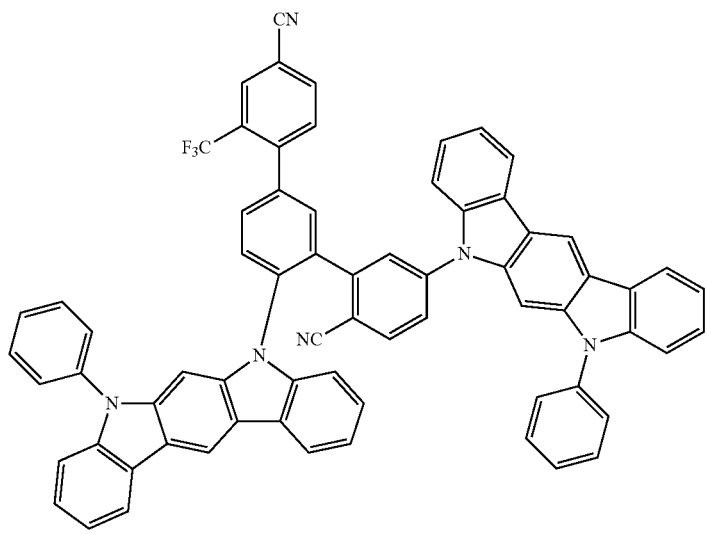

-continued
227
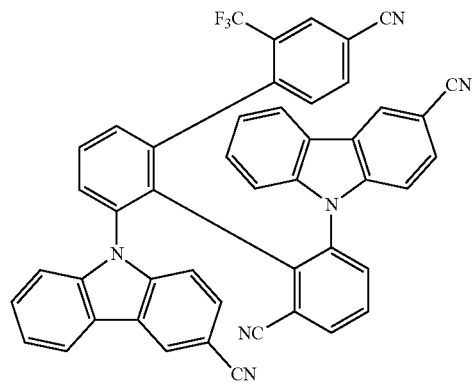
228
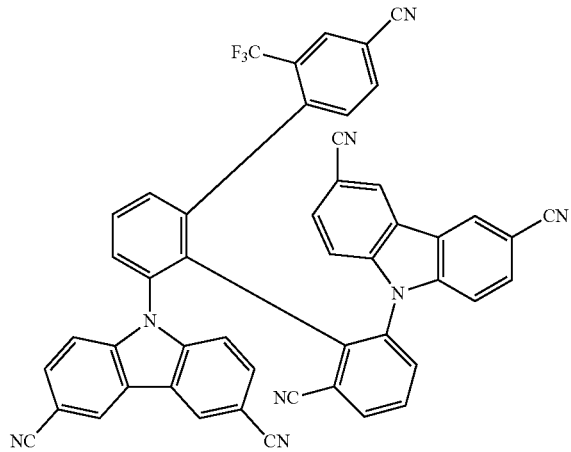
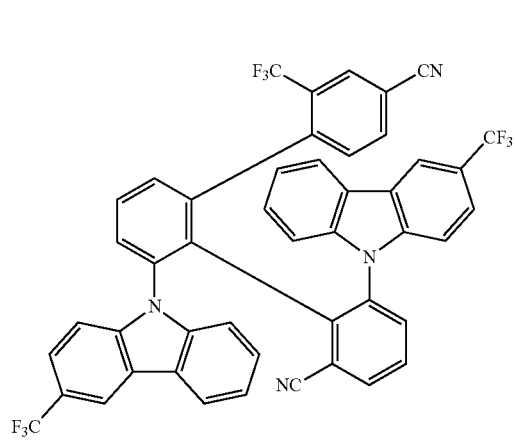
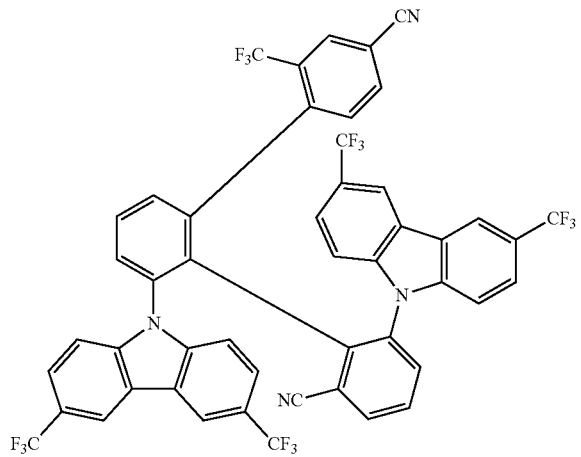
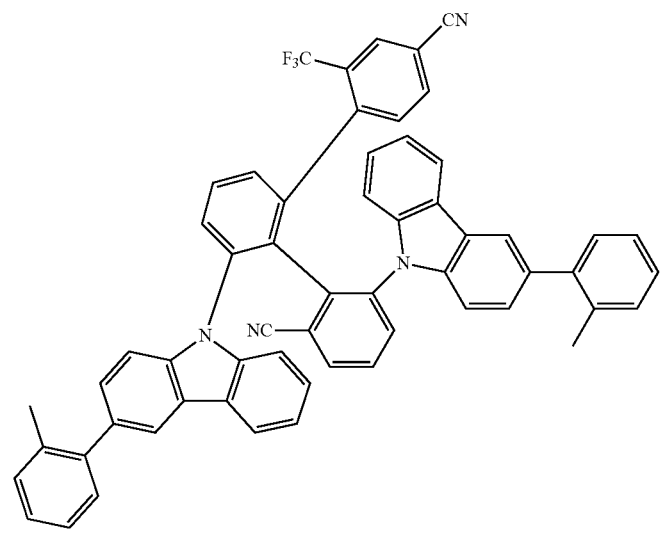

-continued
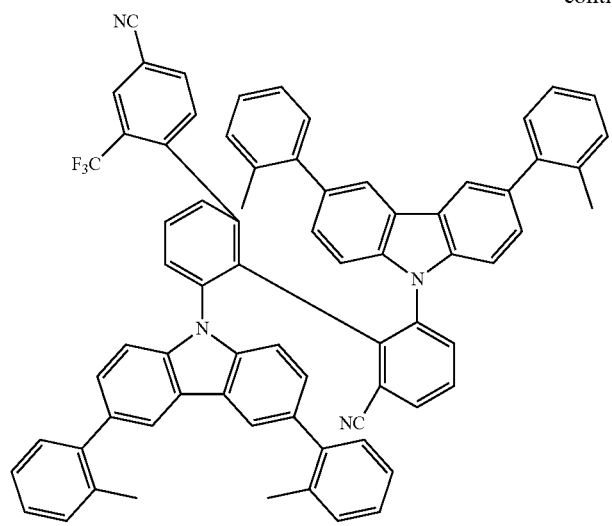
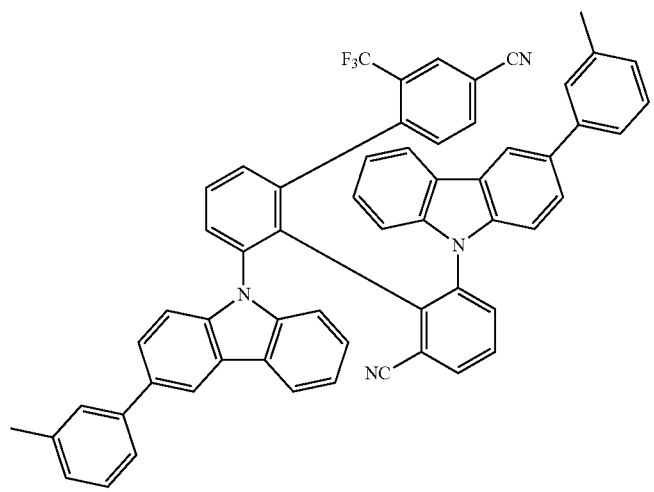
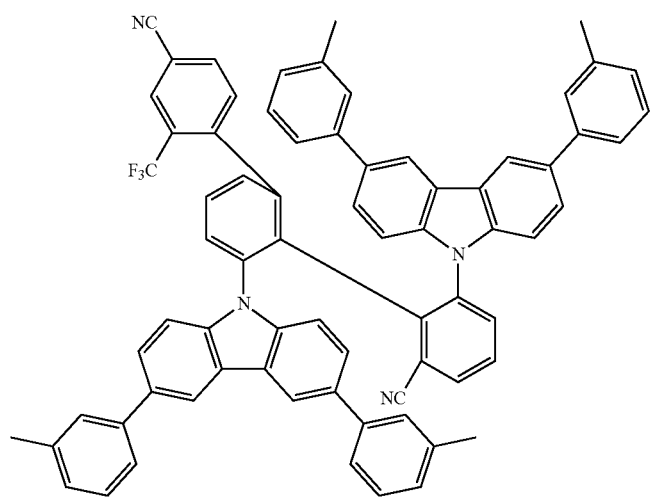

231
-continued
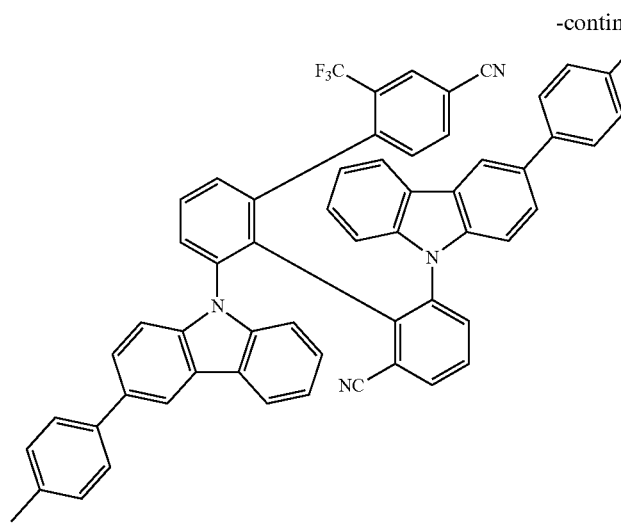
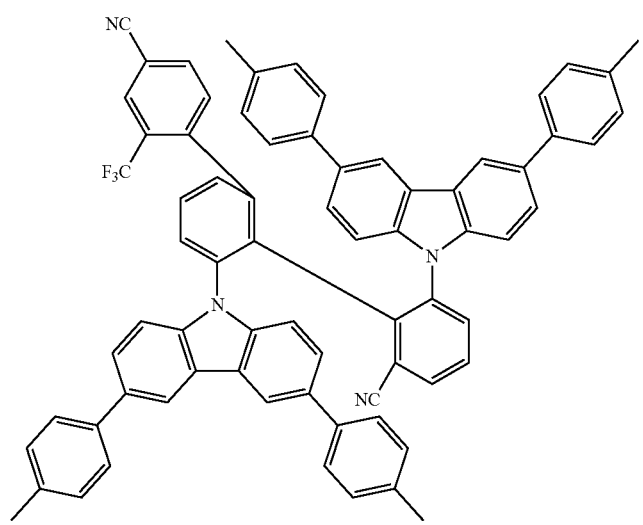
232
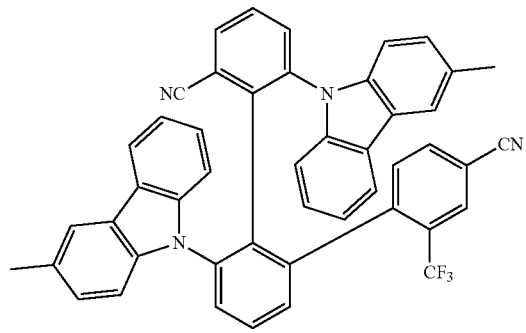
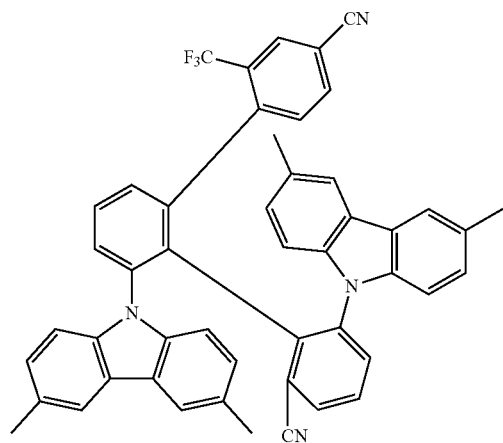
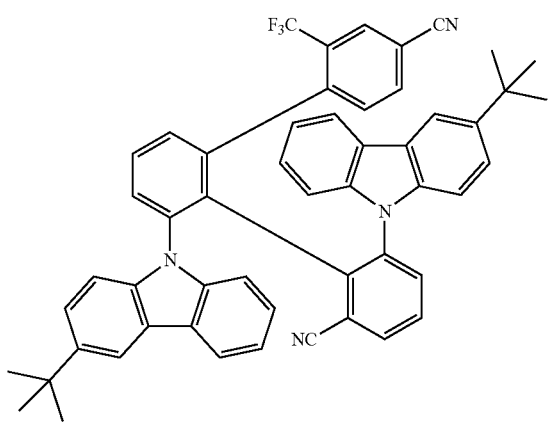

233 234
-continued
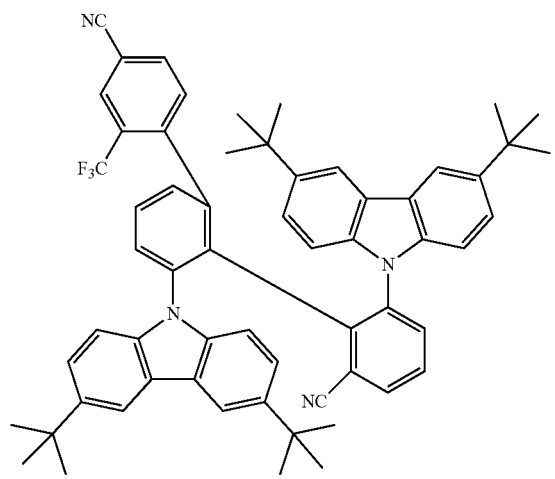
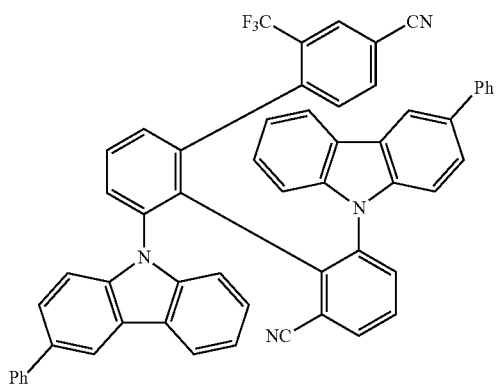
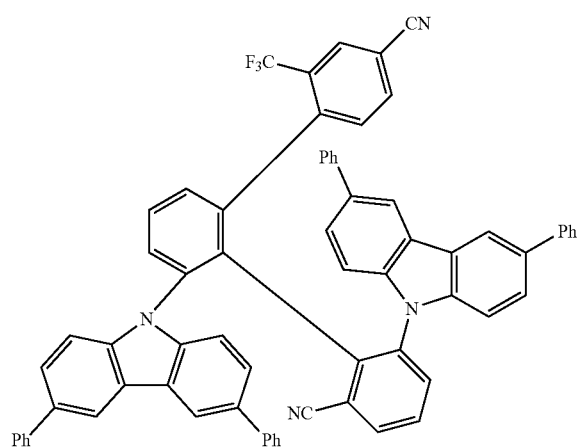
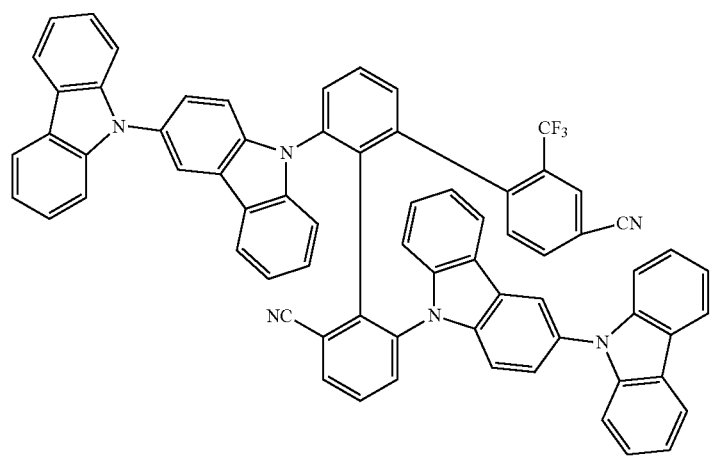

235
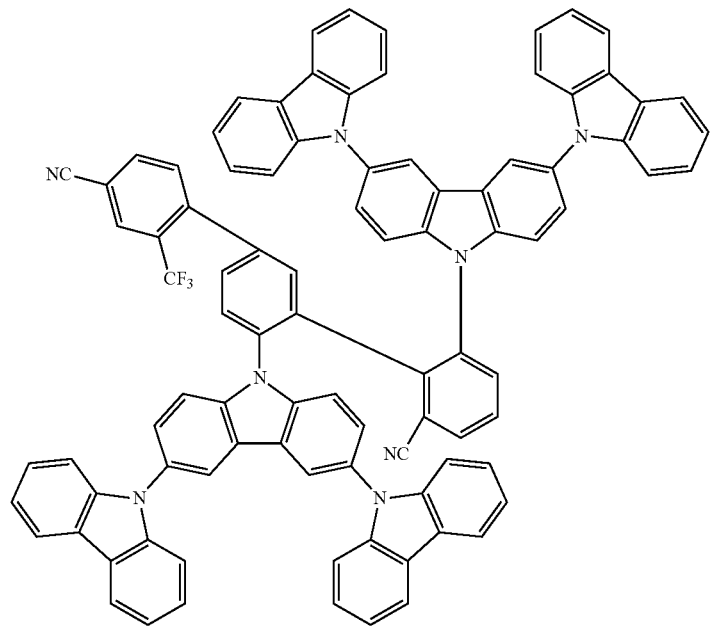
236
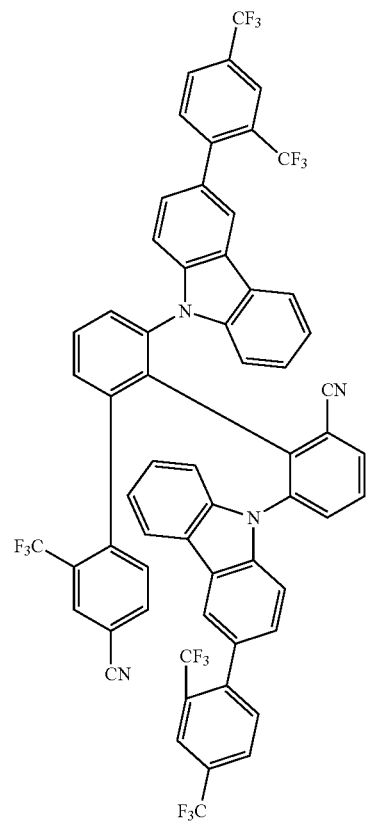
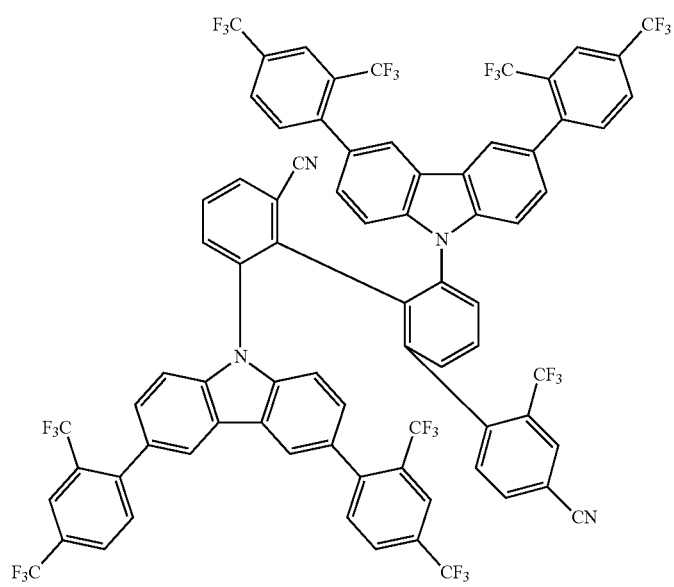
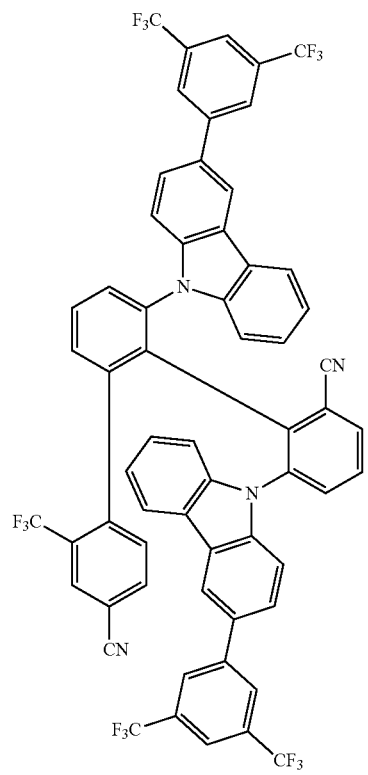

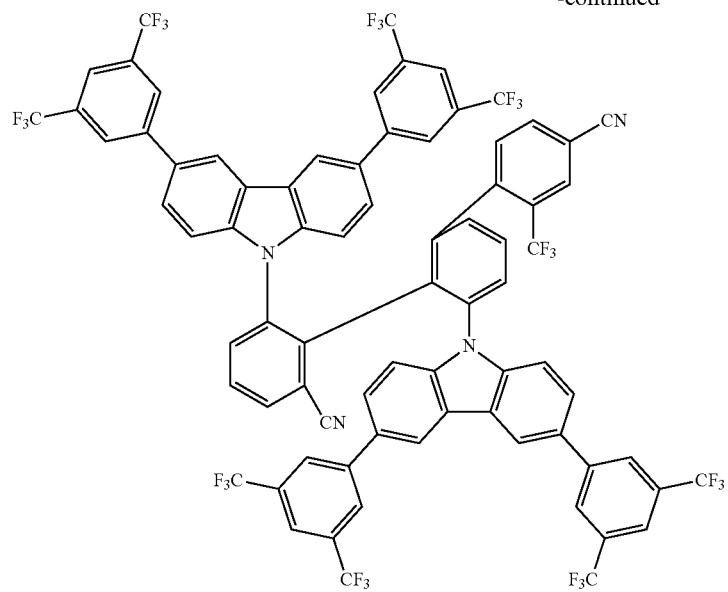
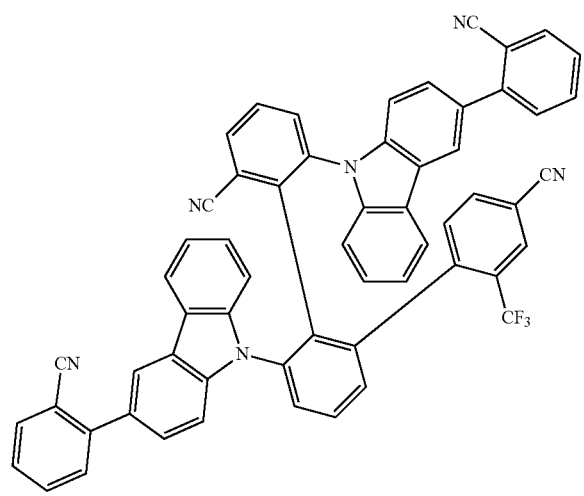
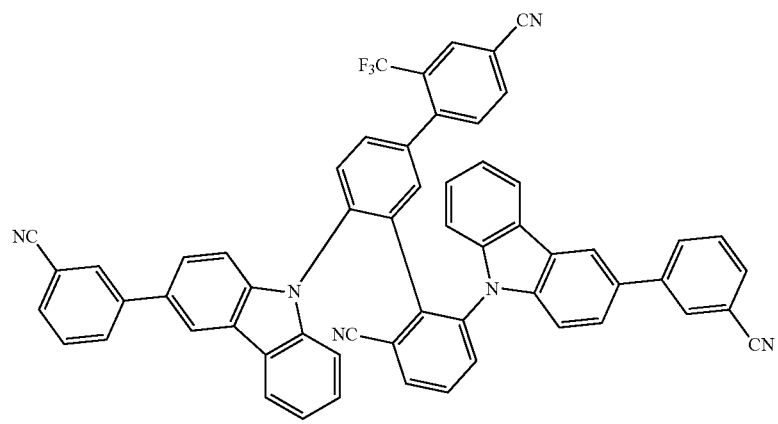

239 240
-continued
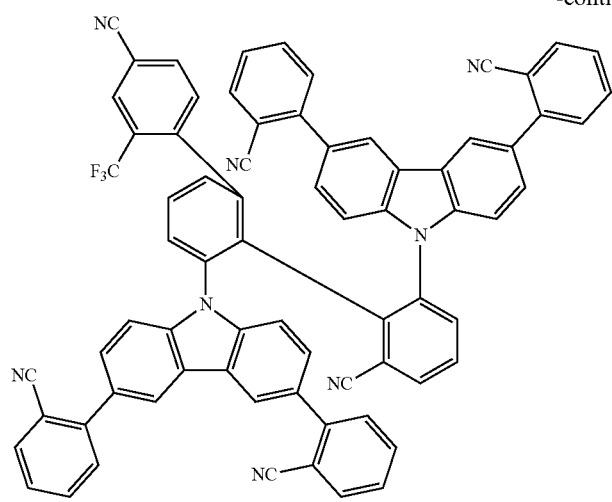
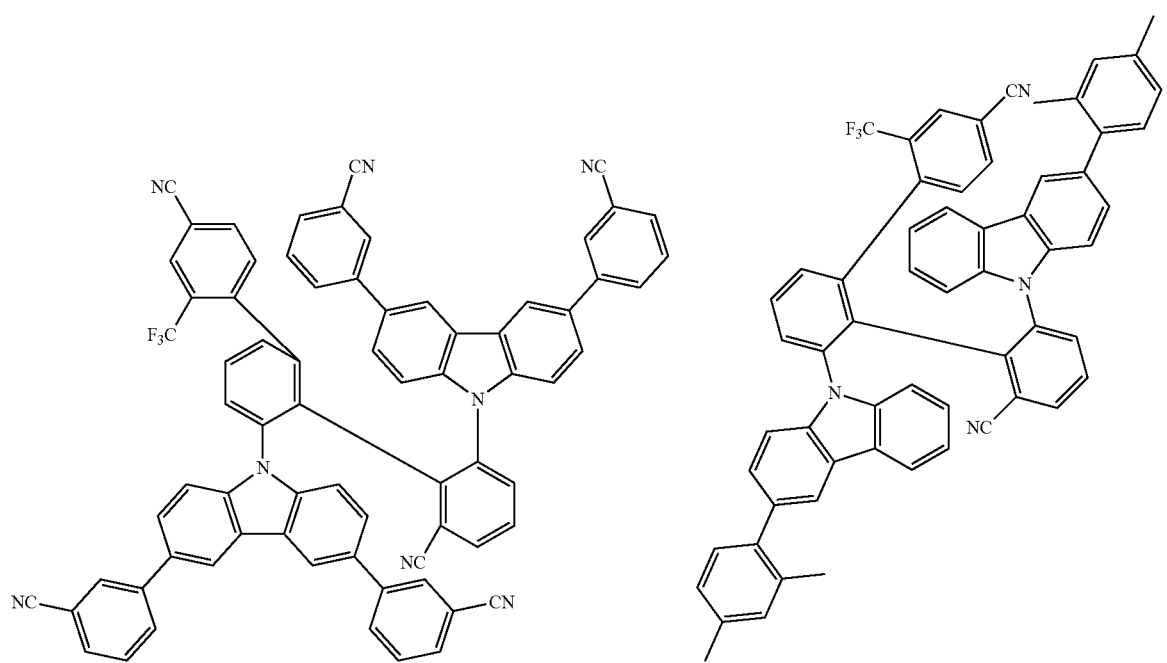

-continued
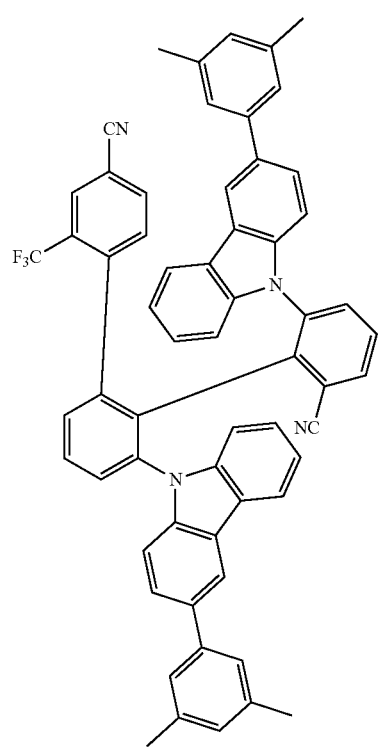
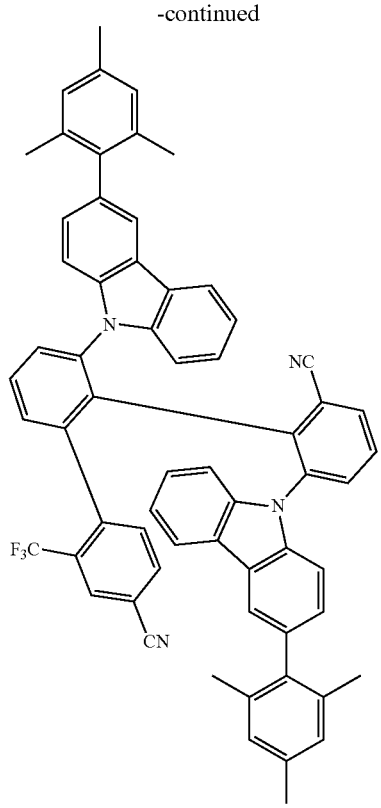
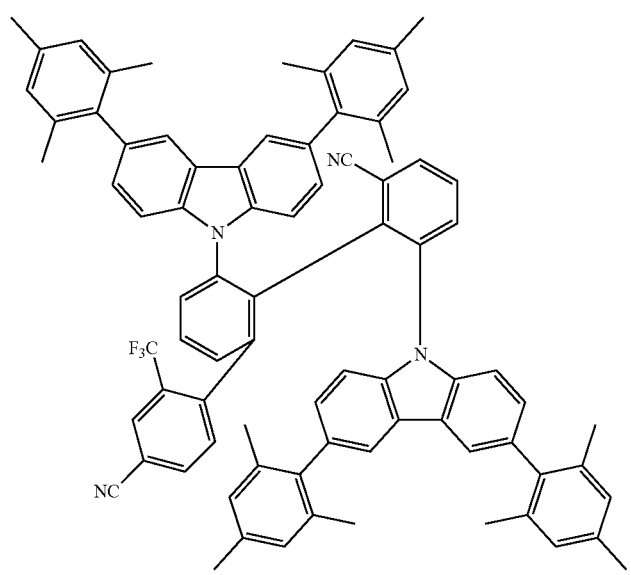

243
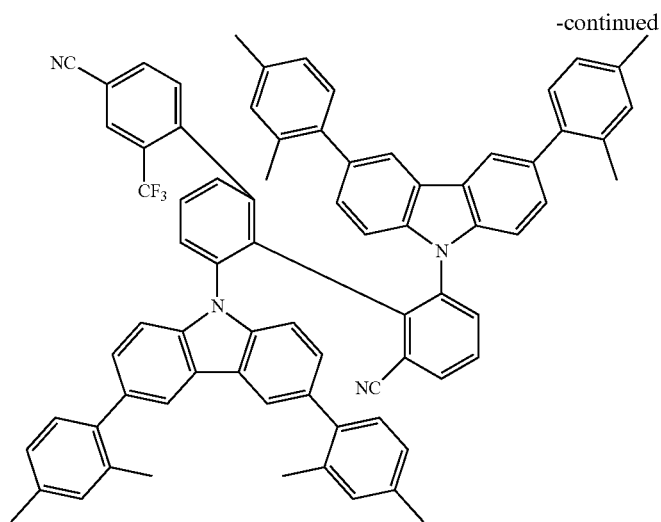
-continued
244
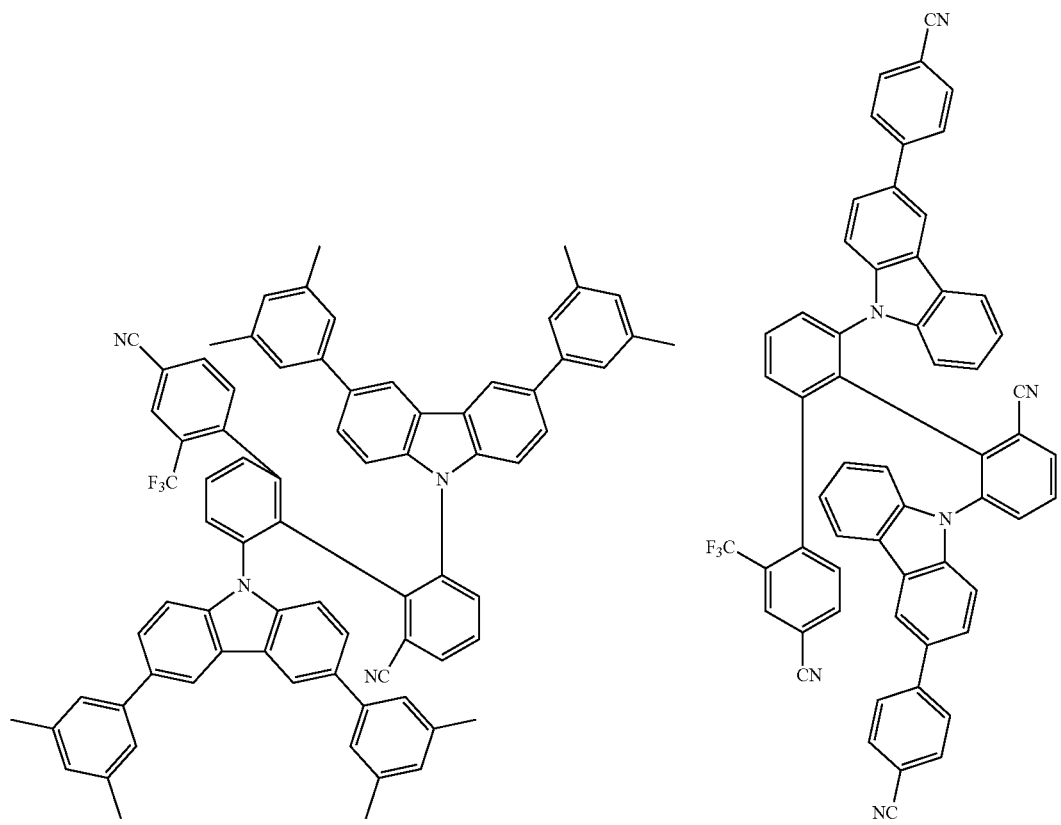

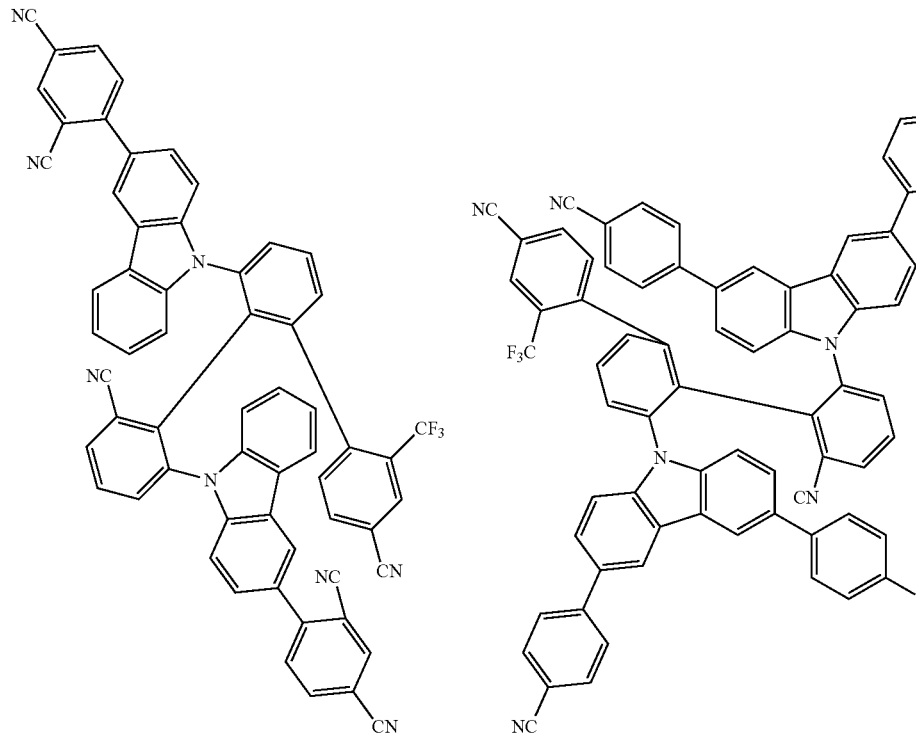
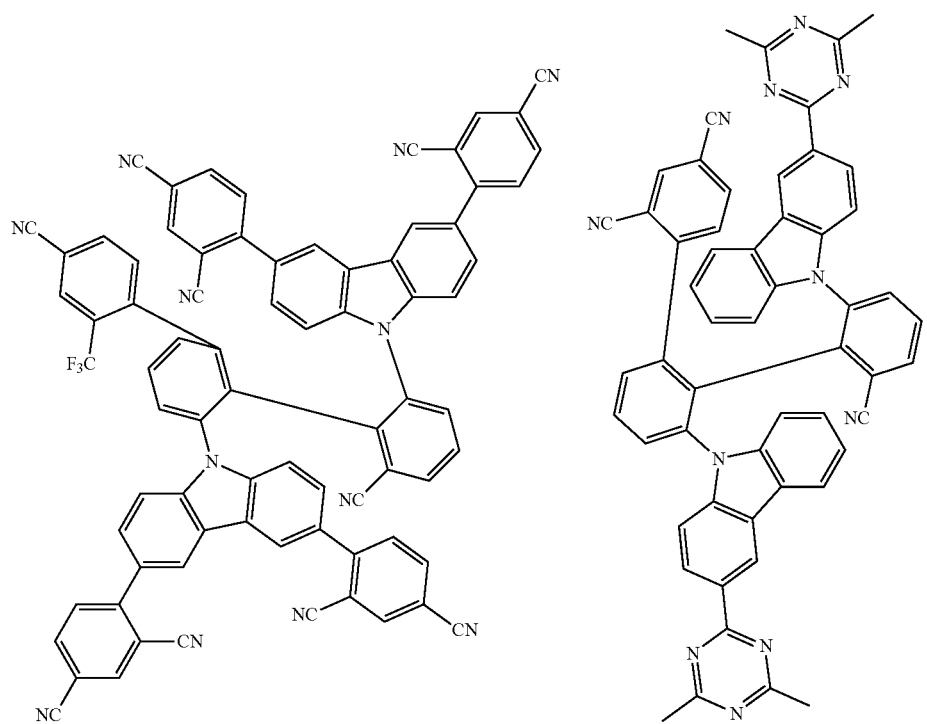

-continued
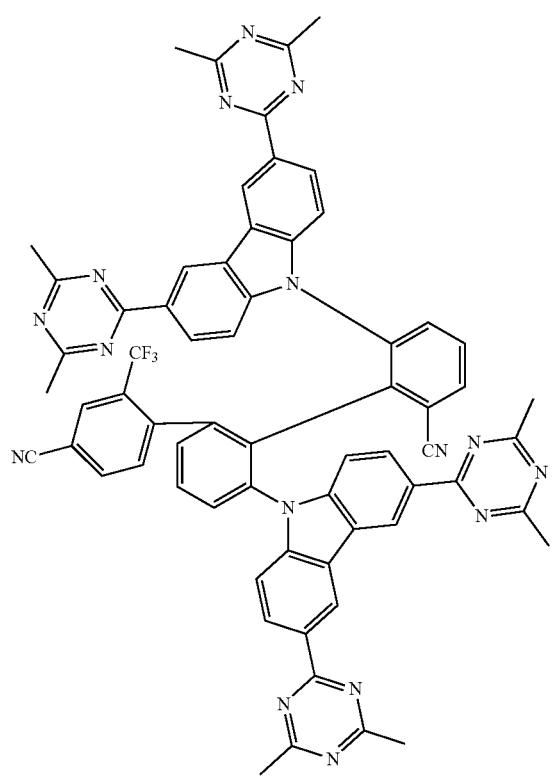
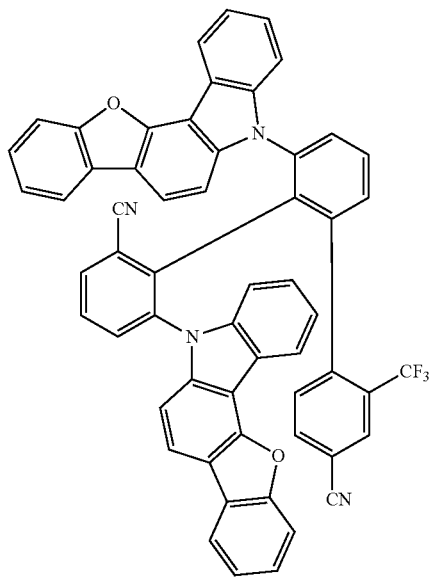
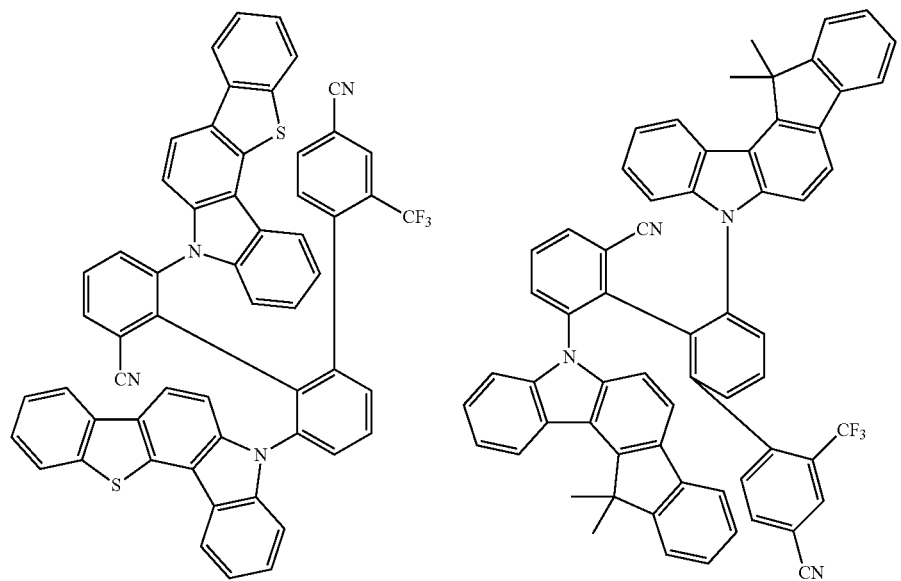

-continued
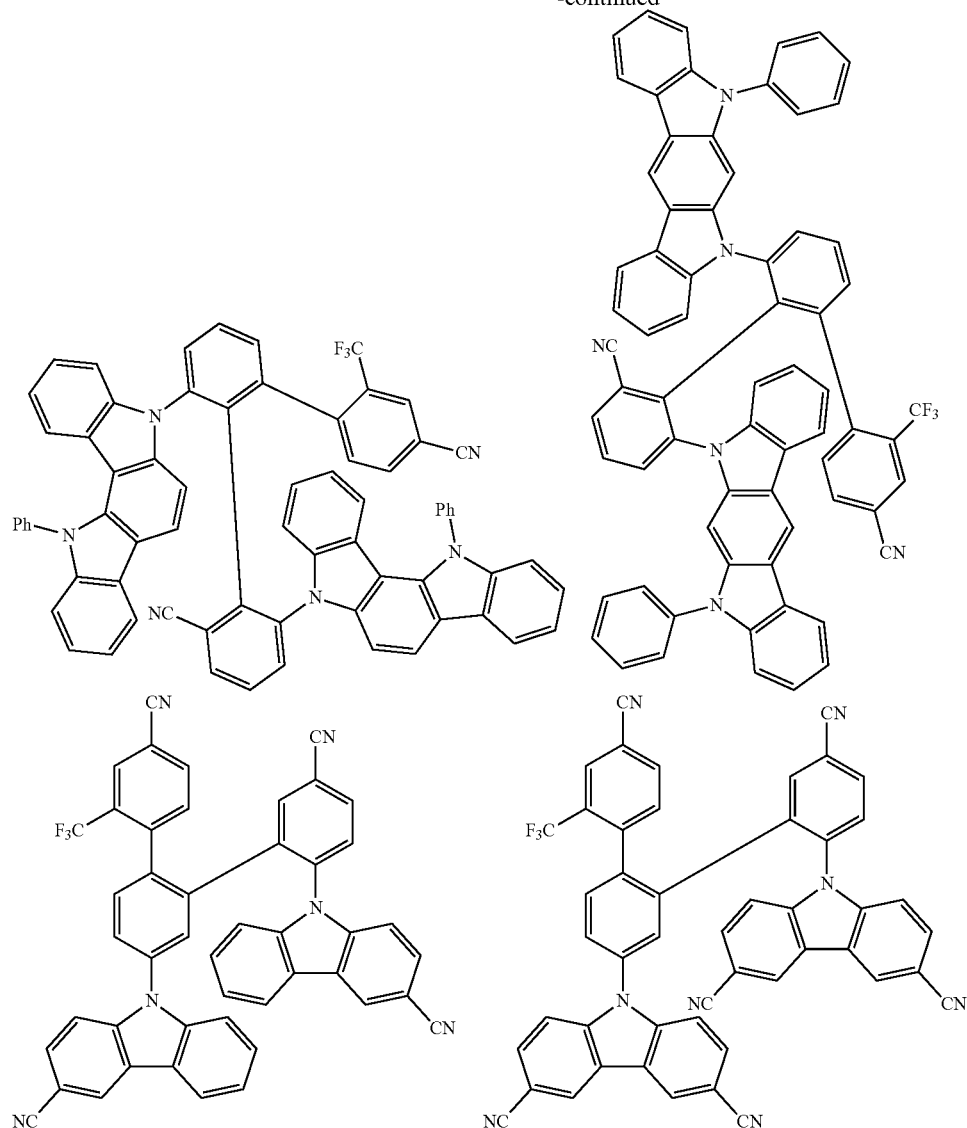
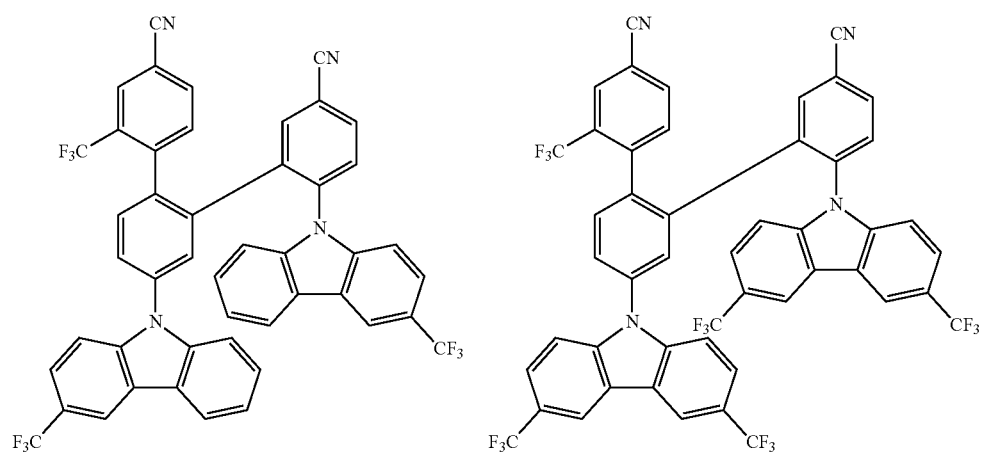

251
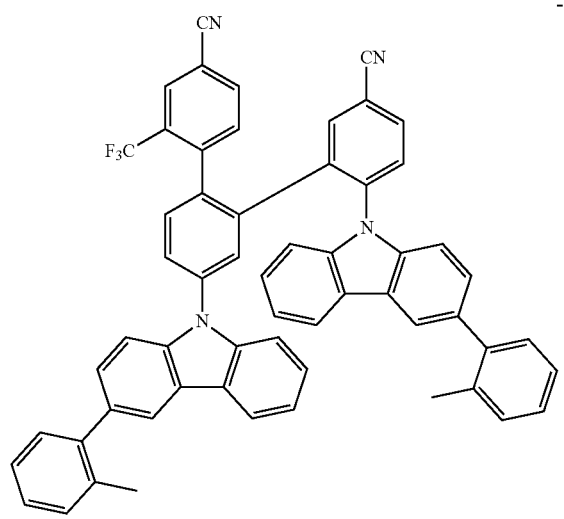
252 -continued
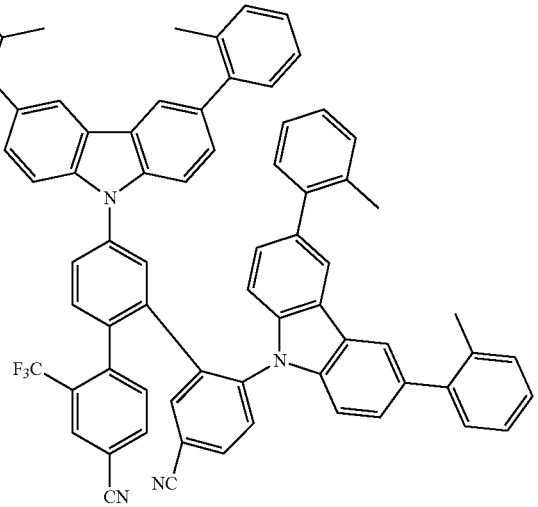
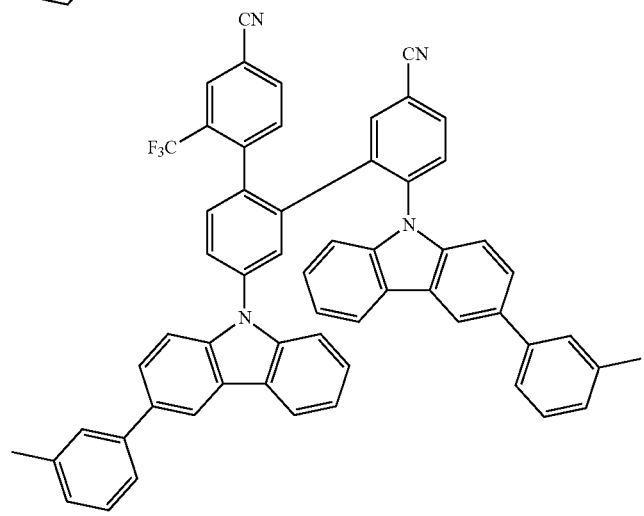
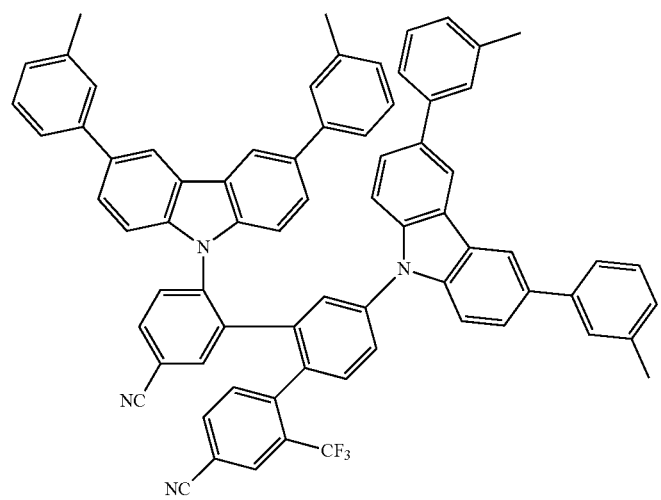

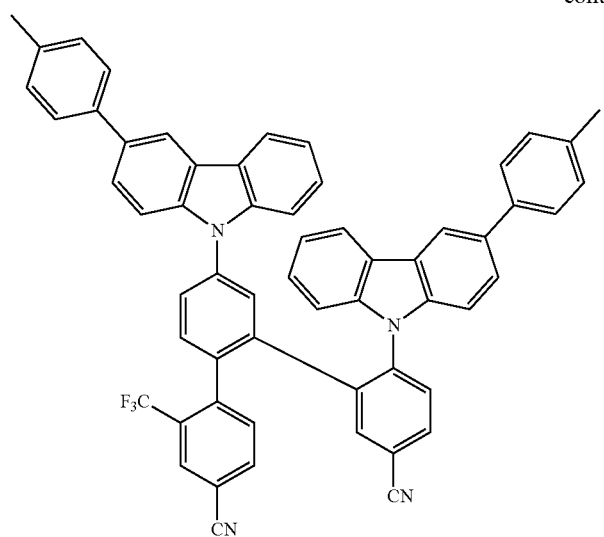
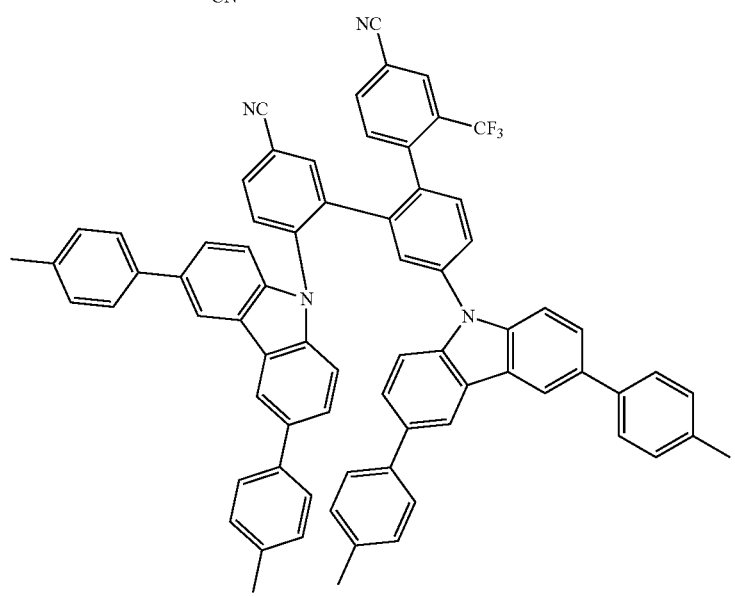
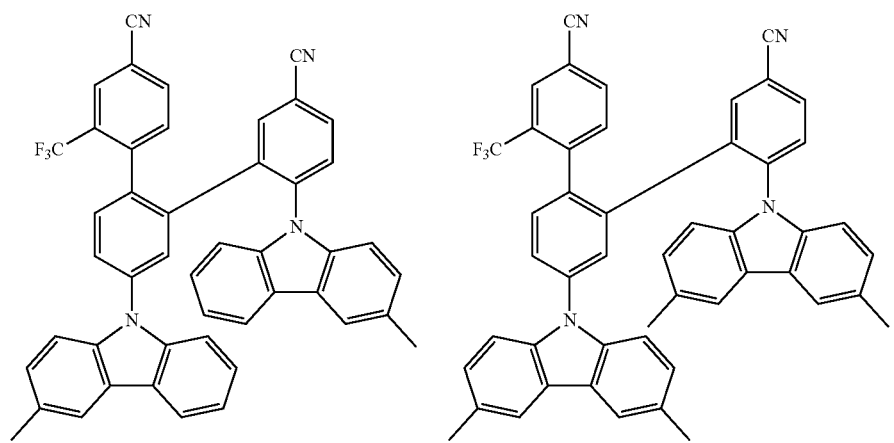

255 256
-continued
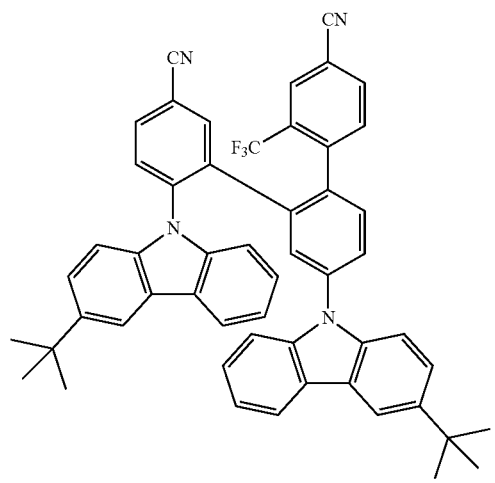
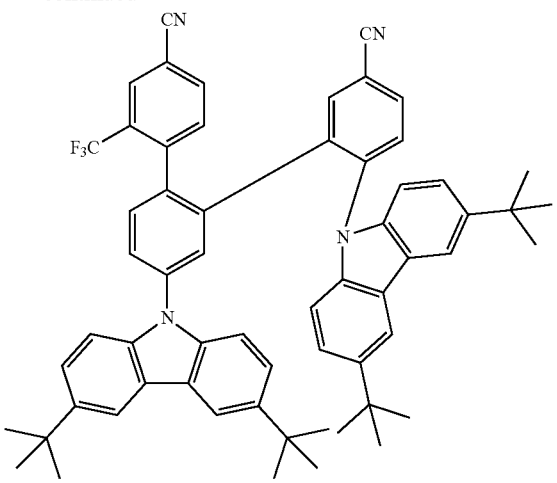
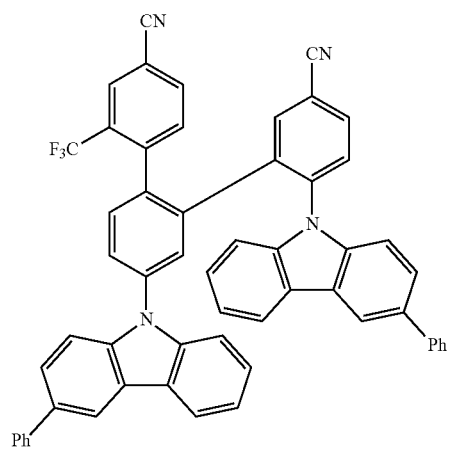
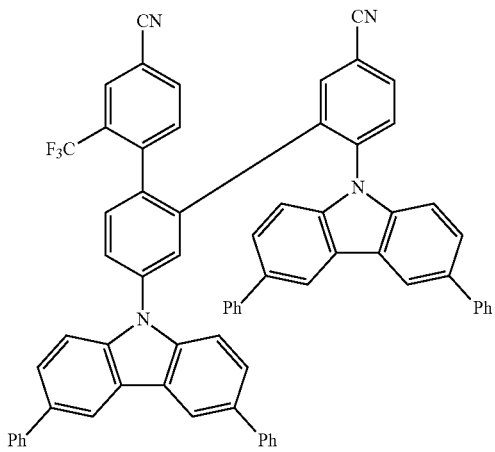
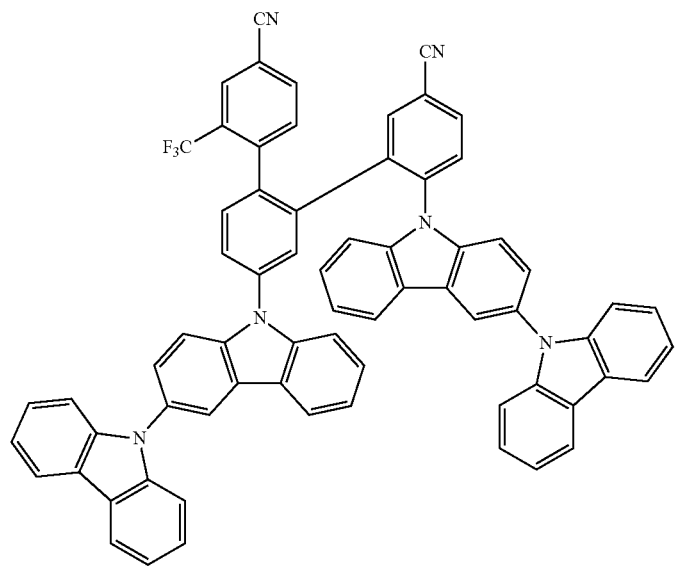

257 258
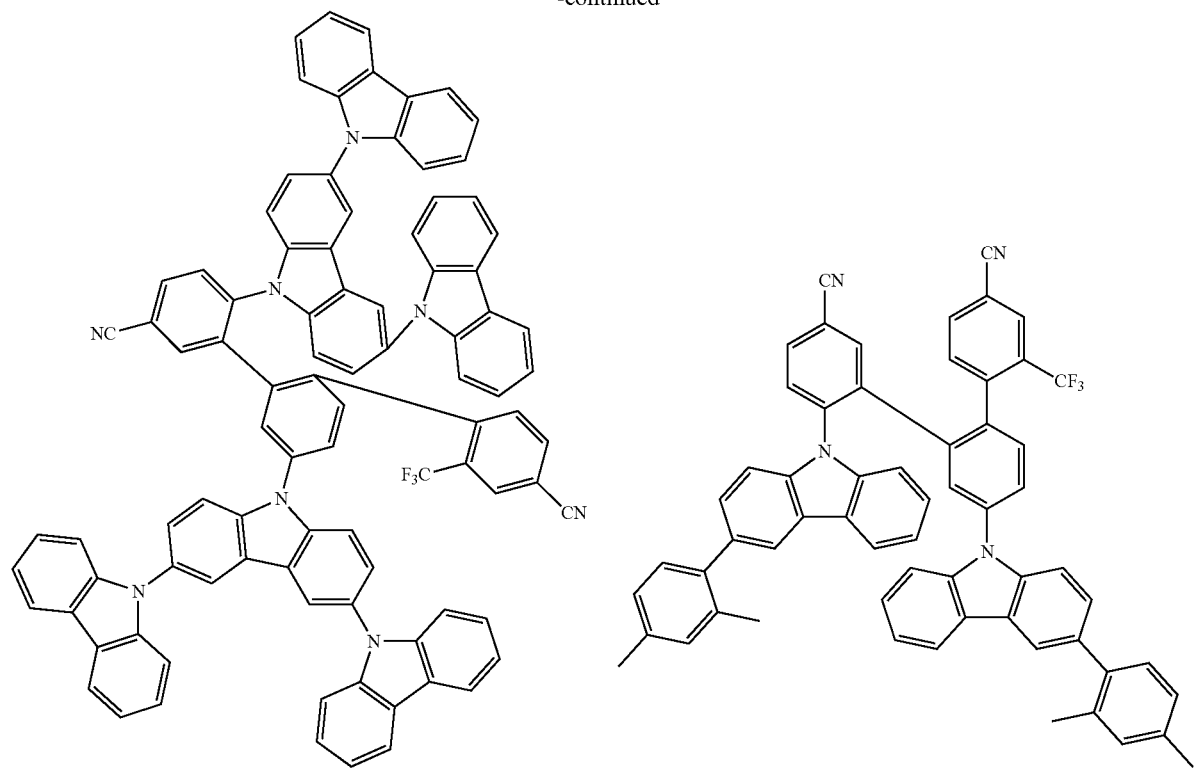
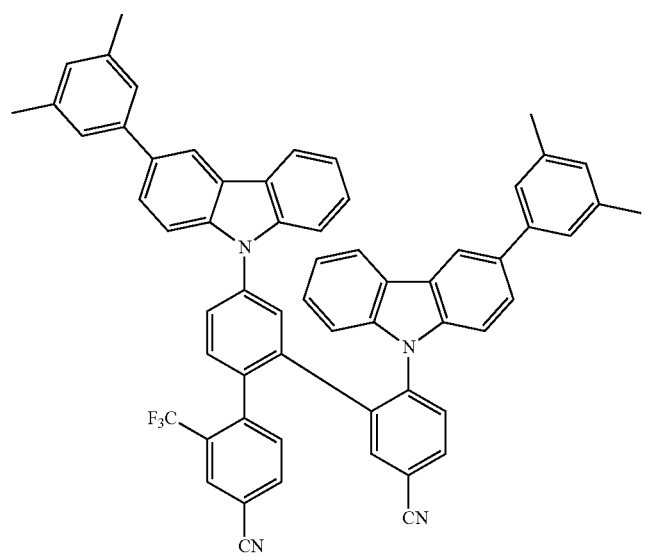

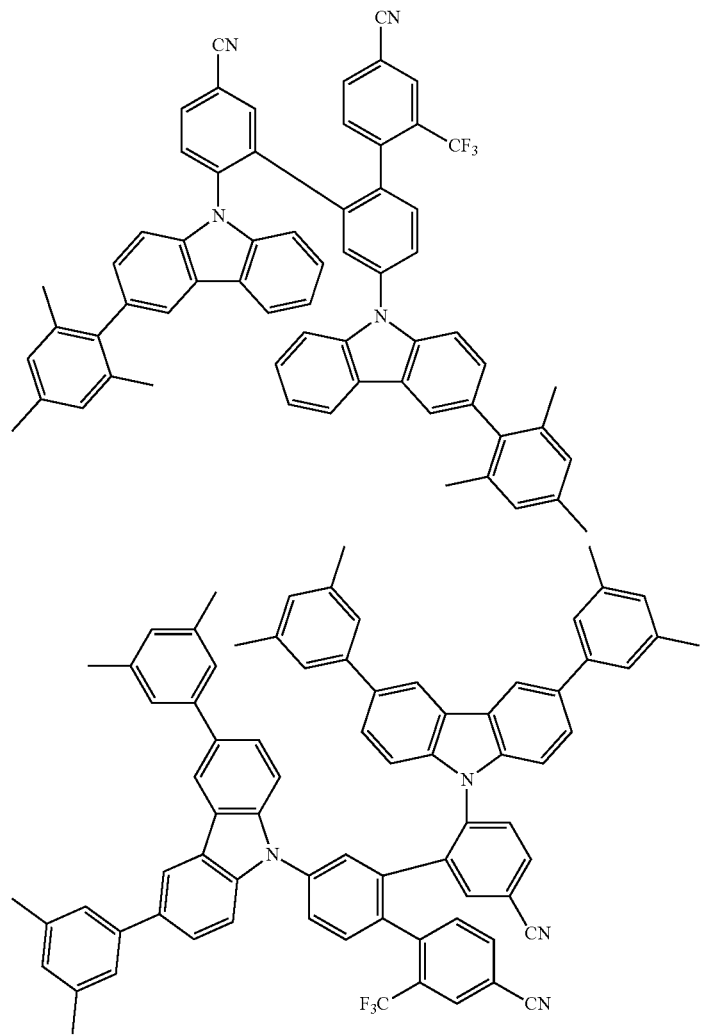
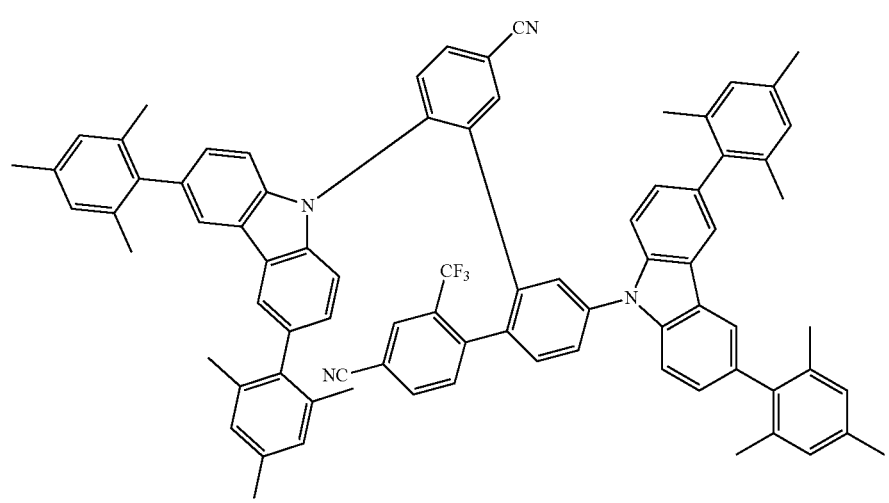

-continued
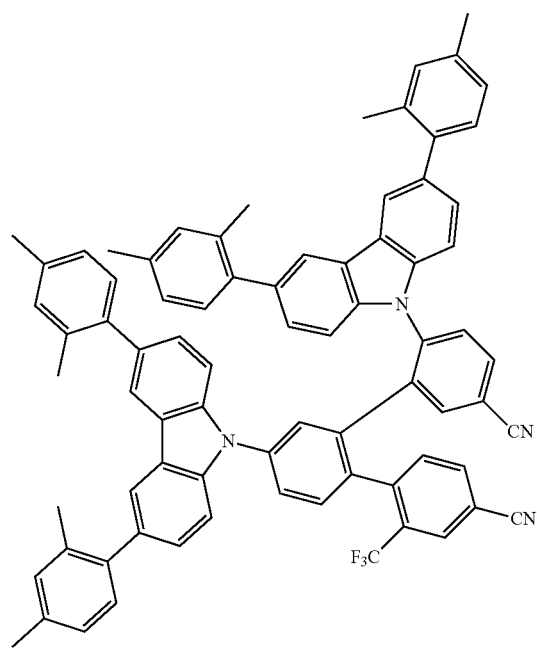
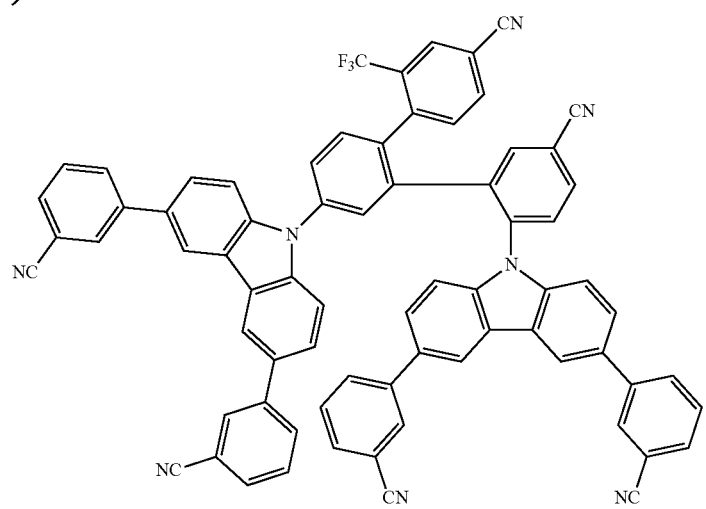
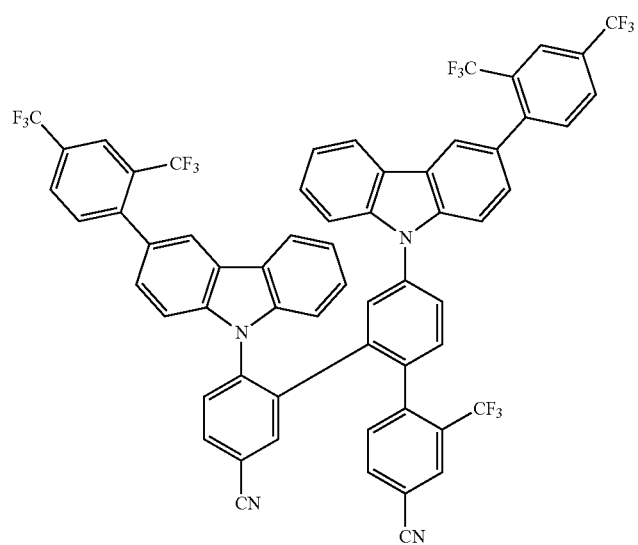

-continued
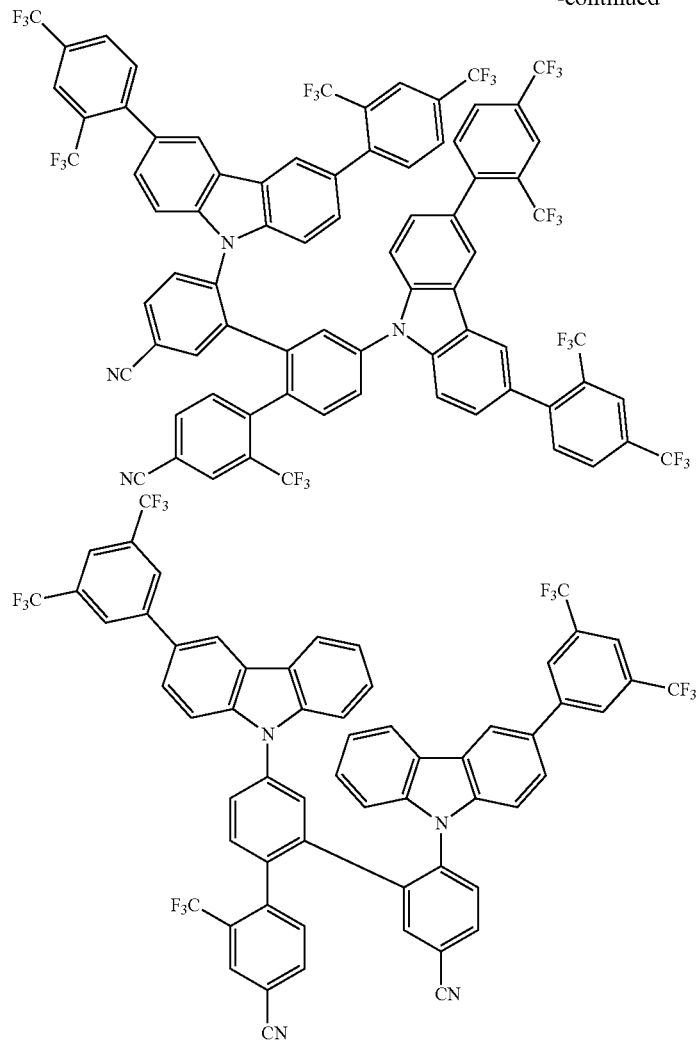
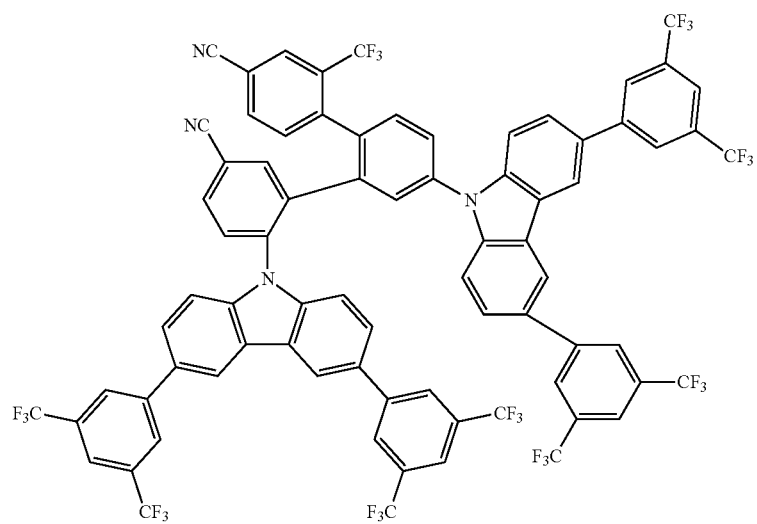

265                                    266
-continued
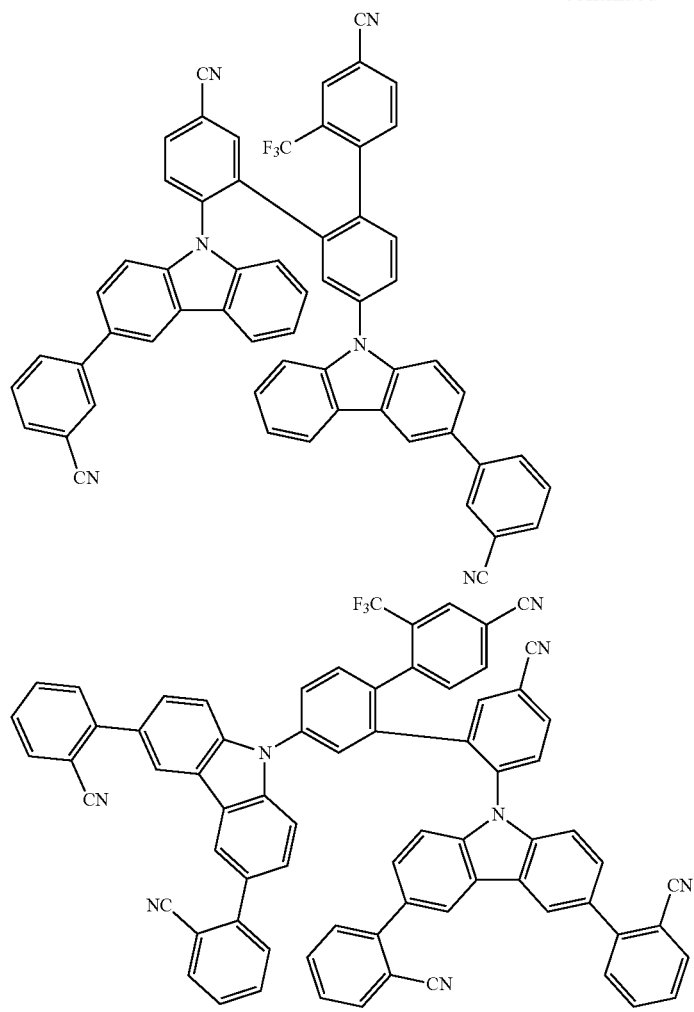
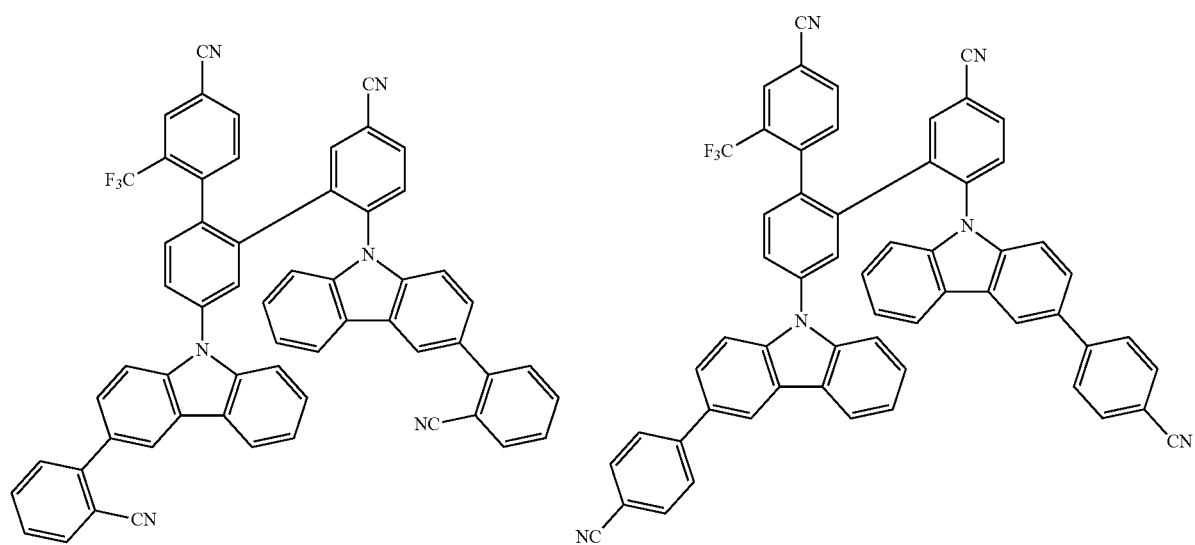

-continued
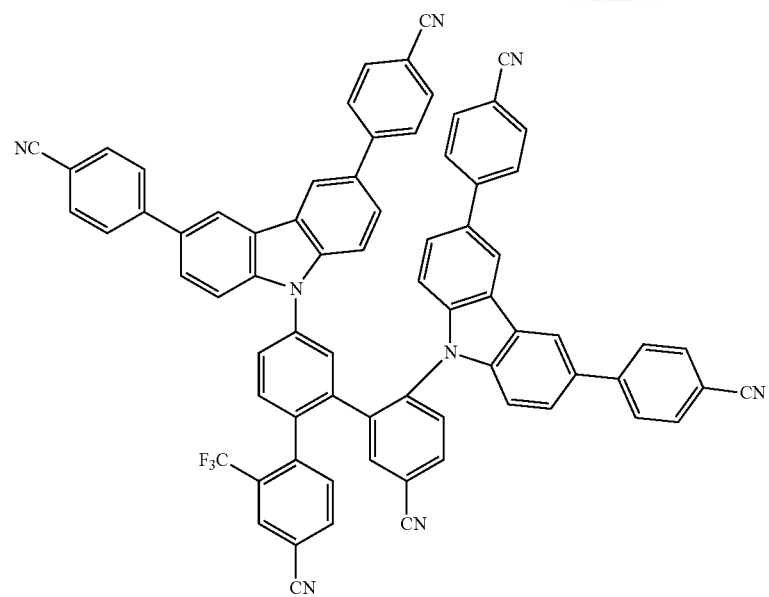
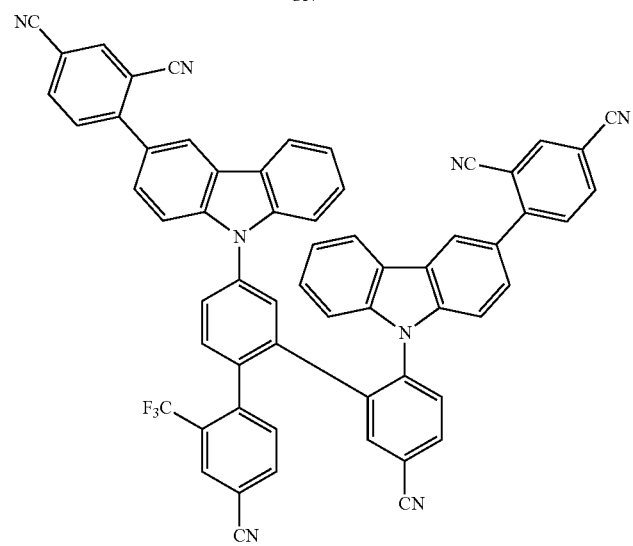
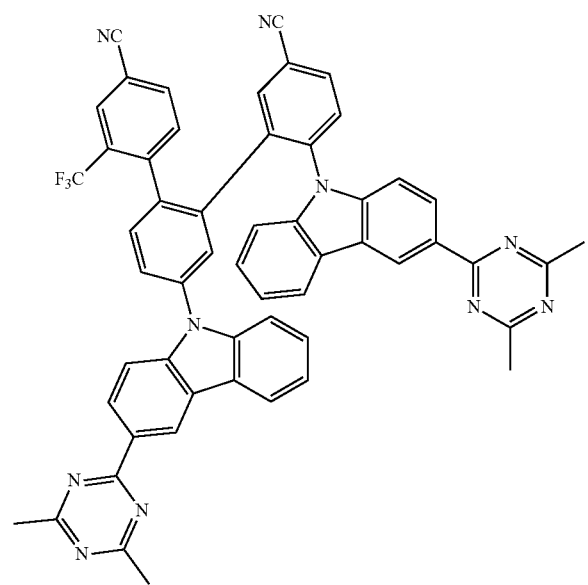

-continued
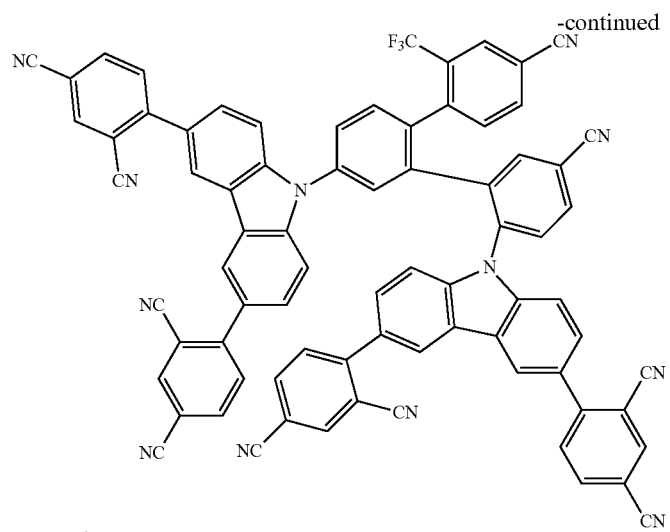
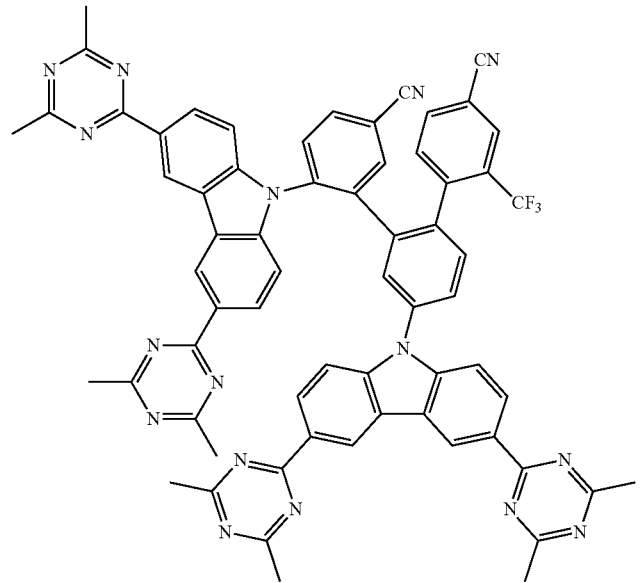
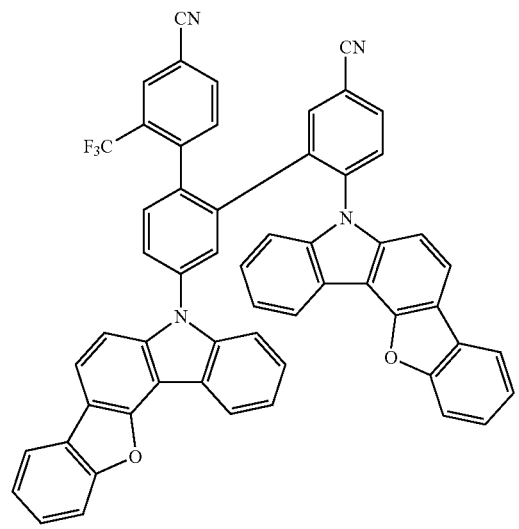
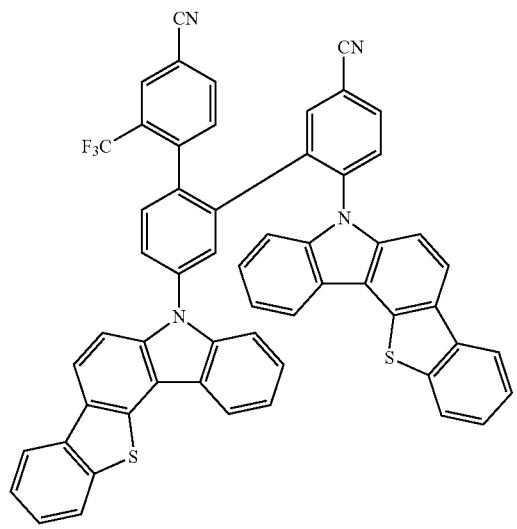

-continued
271
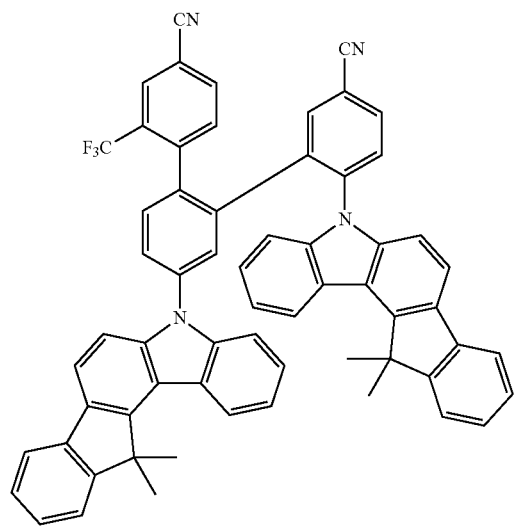
272
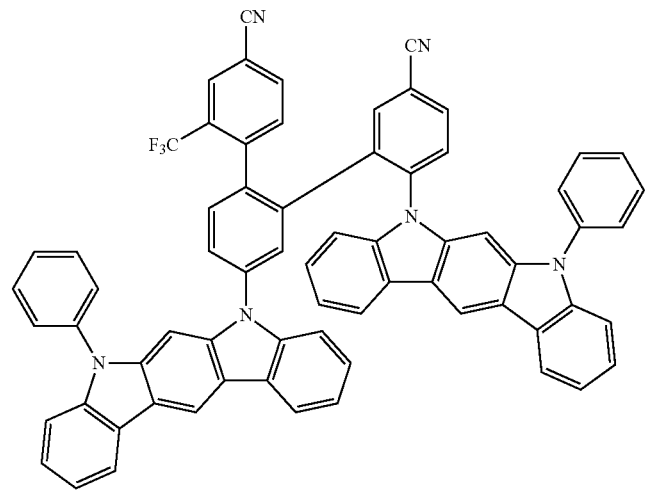
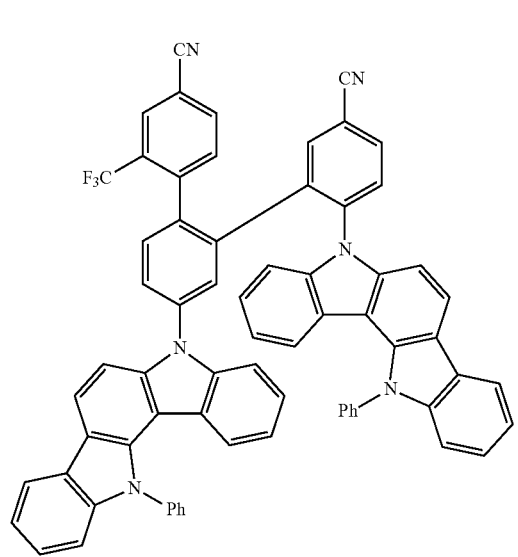
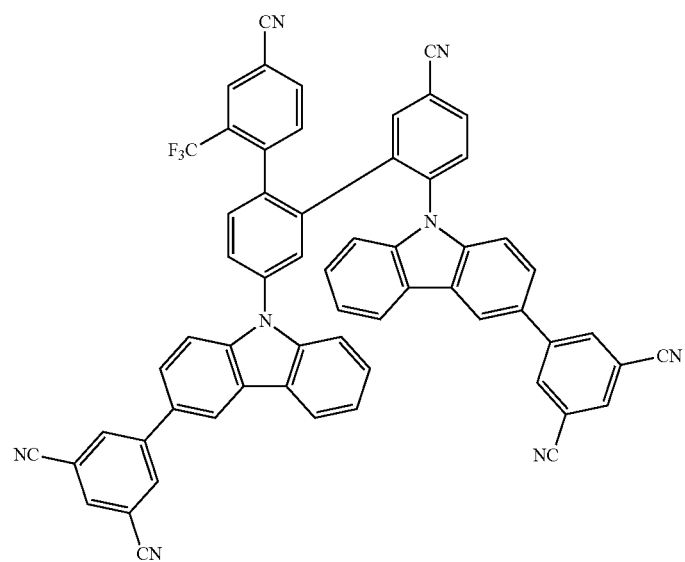

-continued
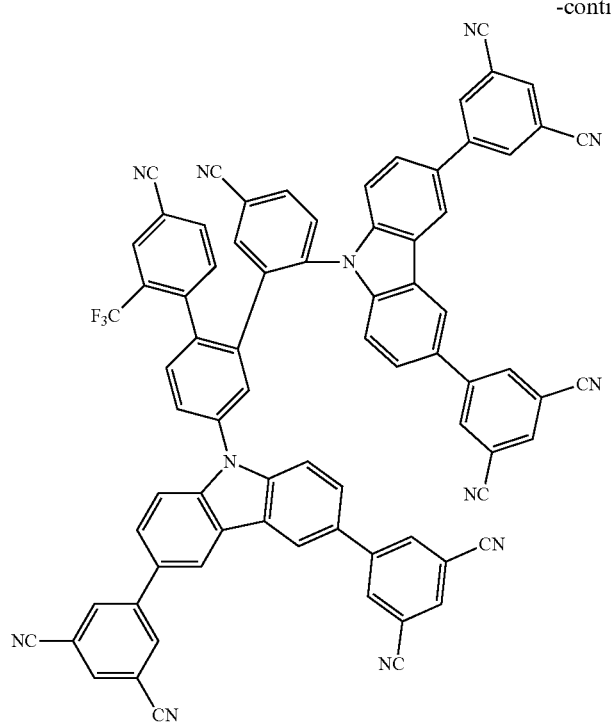
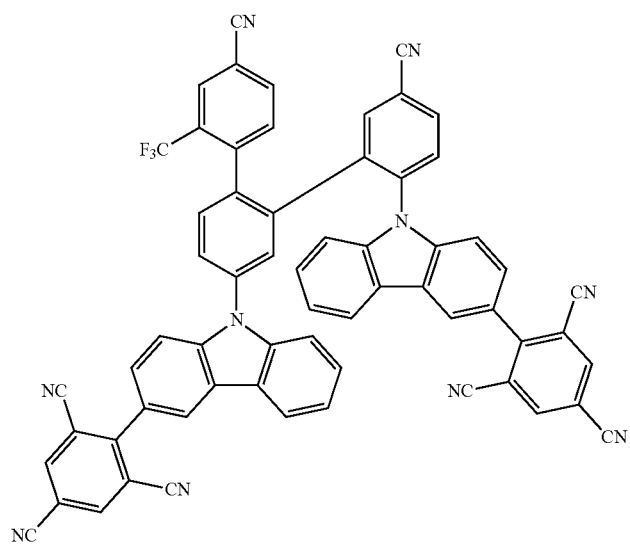

-continued
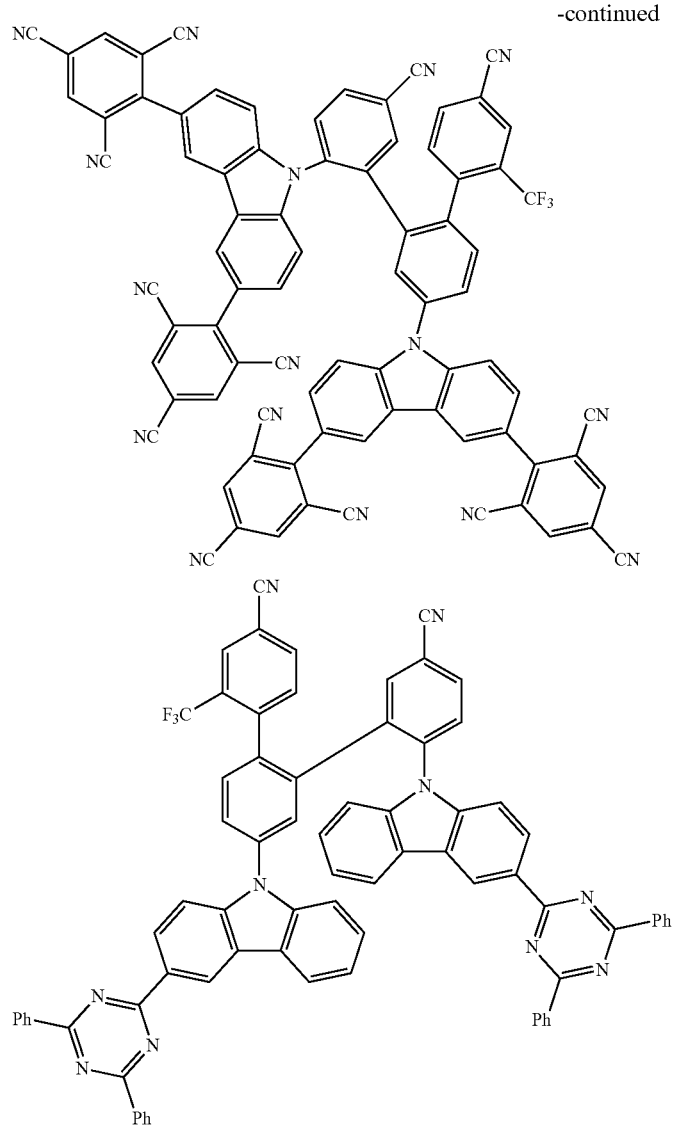
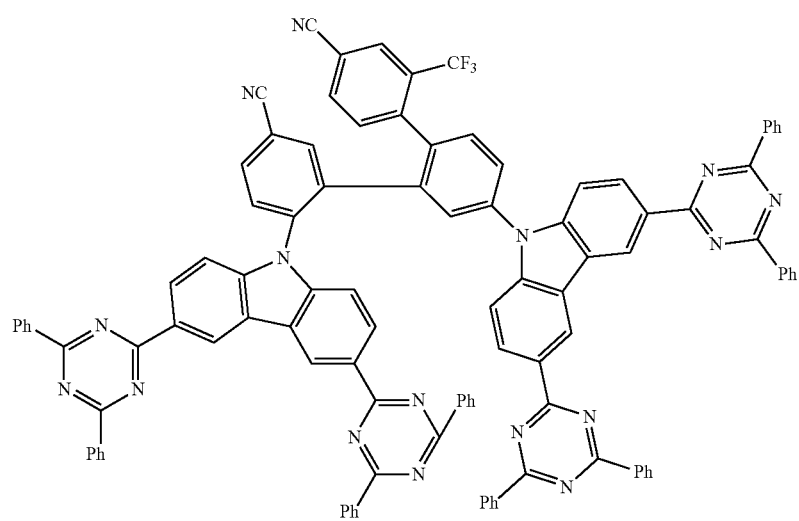

277                                                                 278
-continued
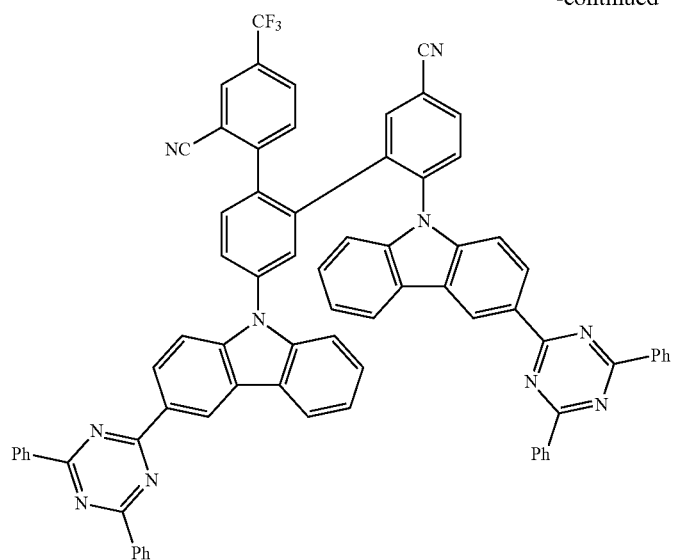
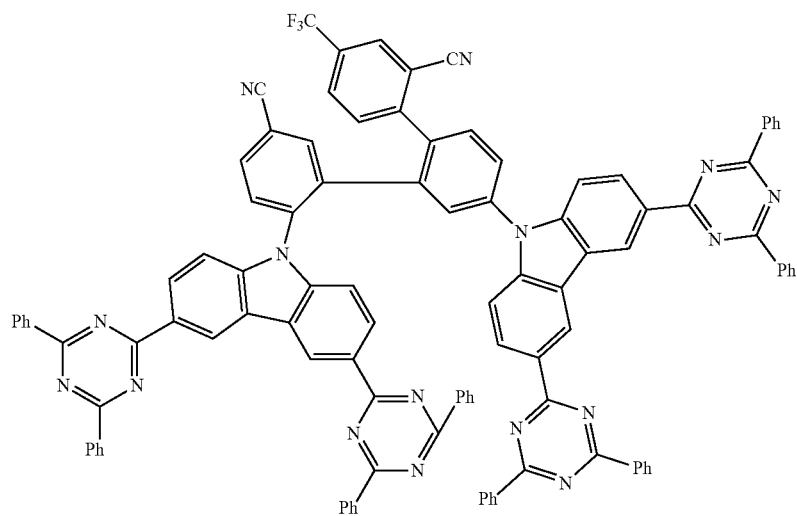
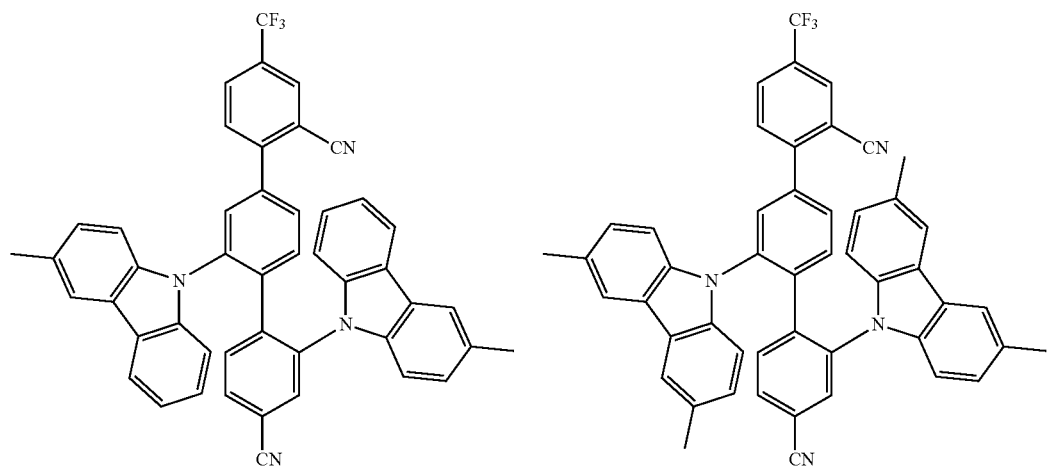

279 280
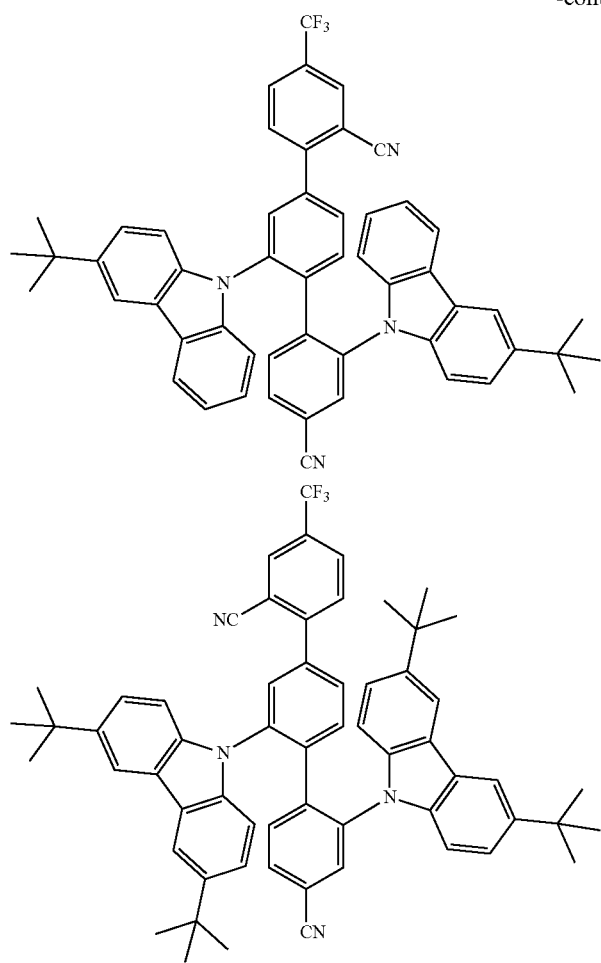
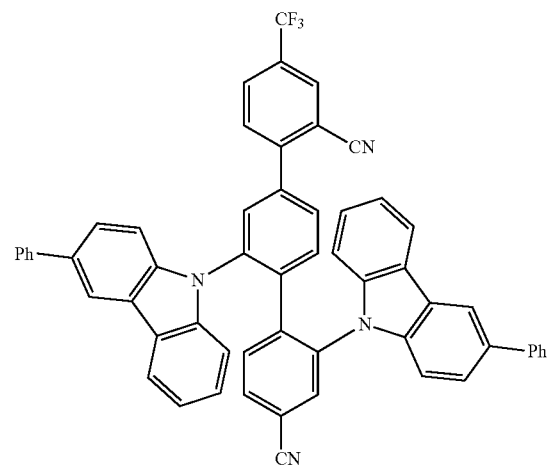
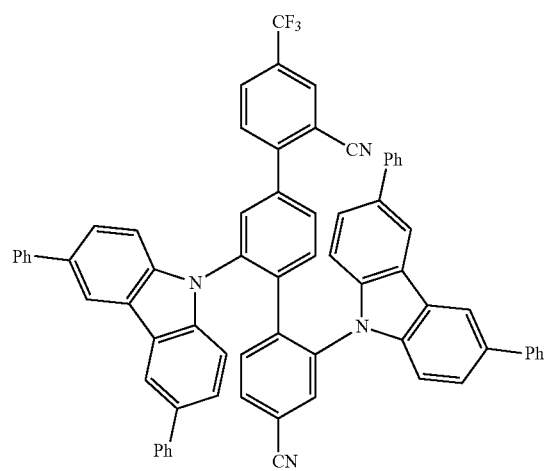

281
282
-continued
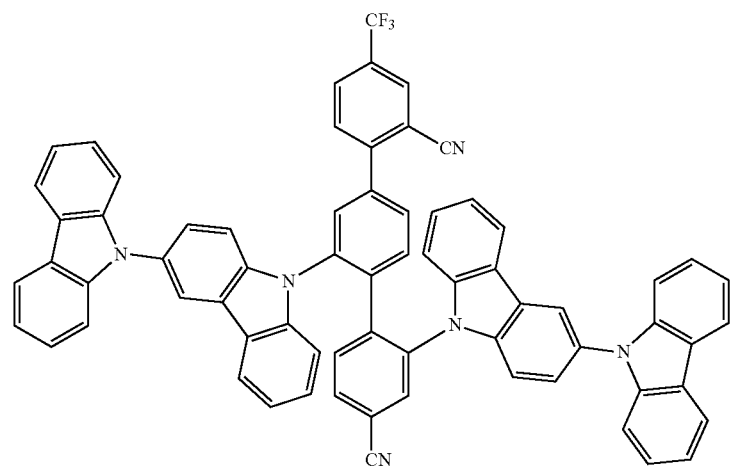
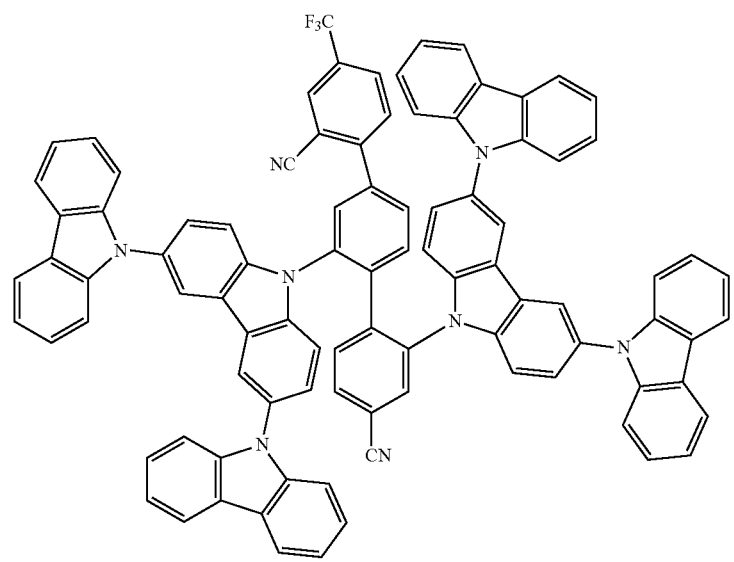
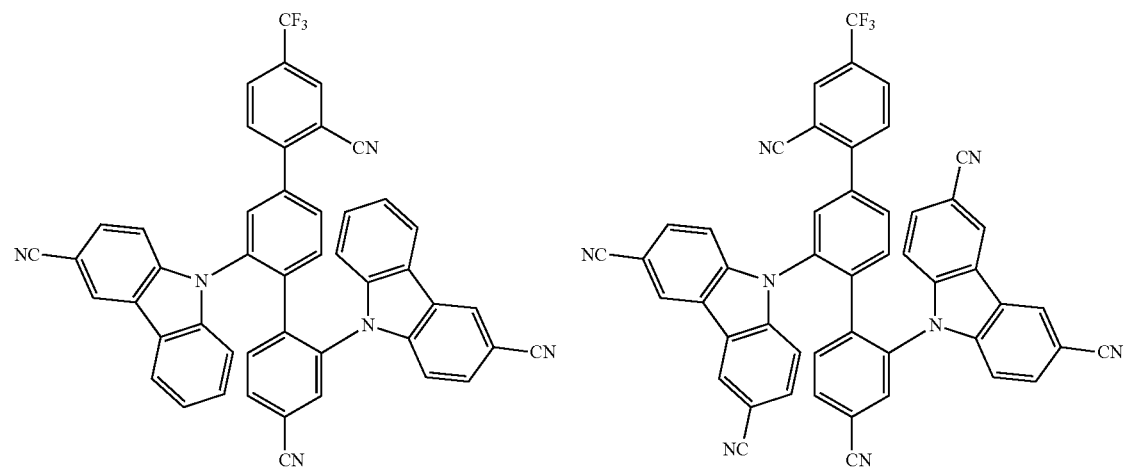

283 284
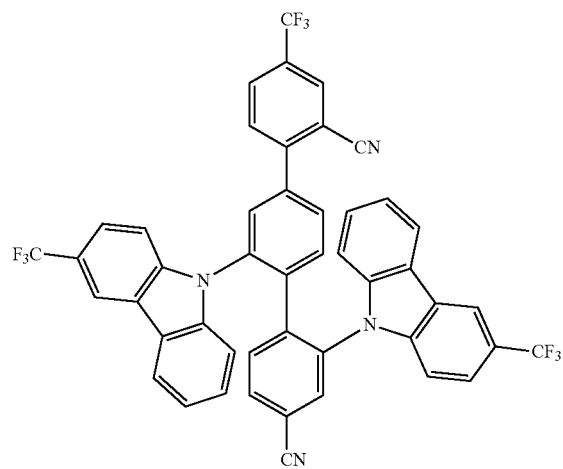 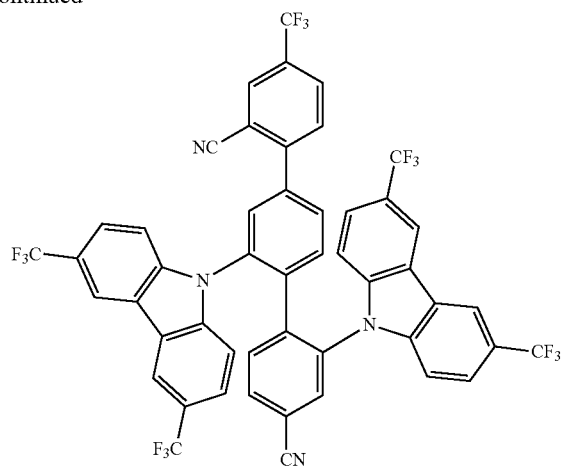
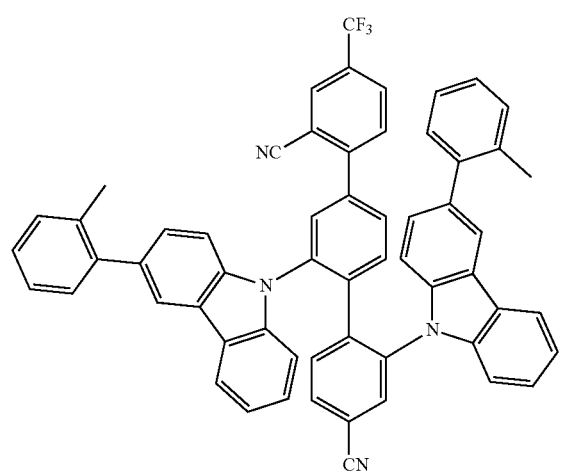 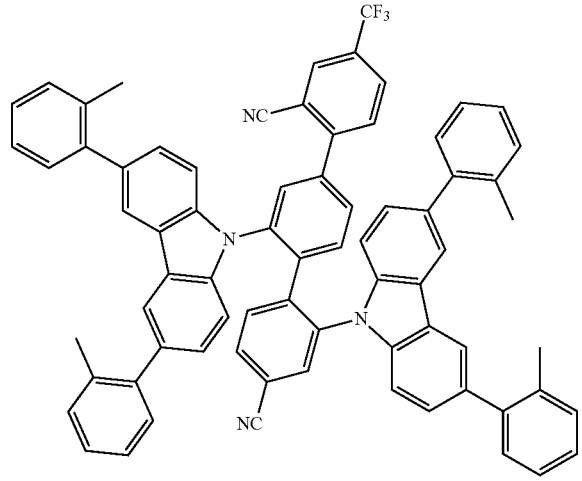
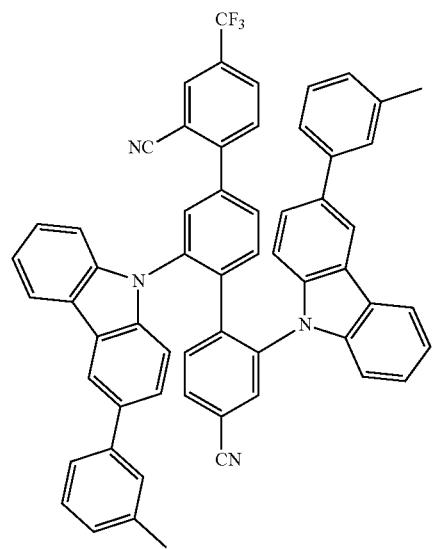 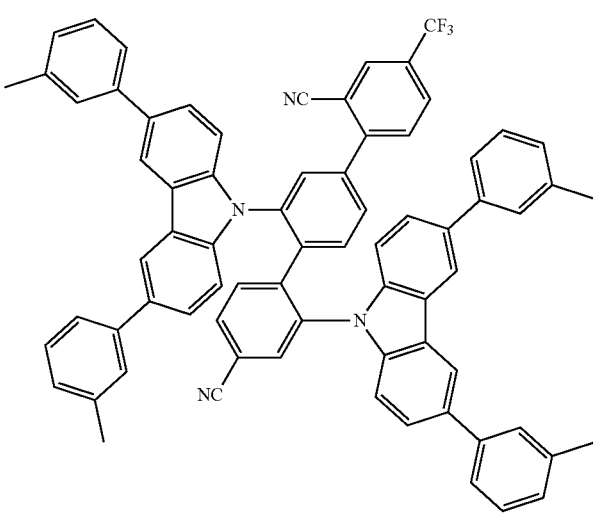

-continued
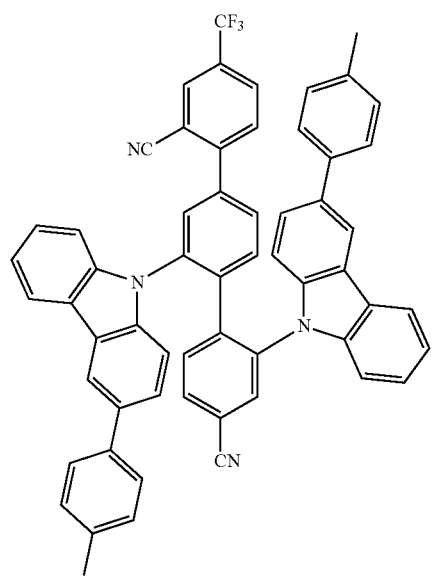
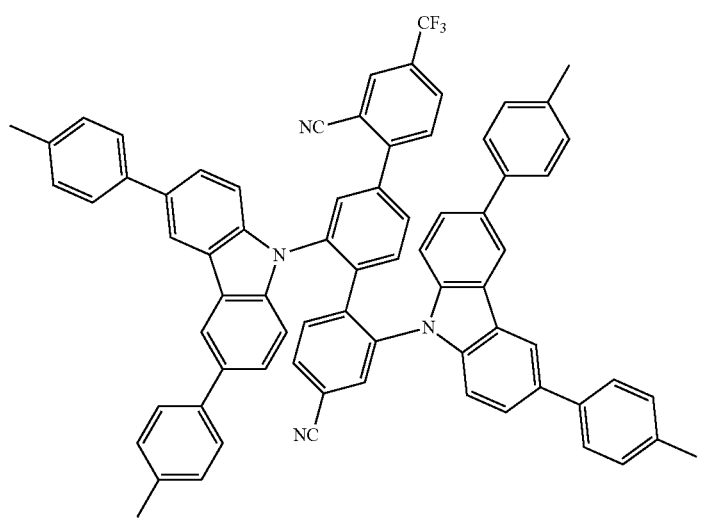
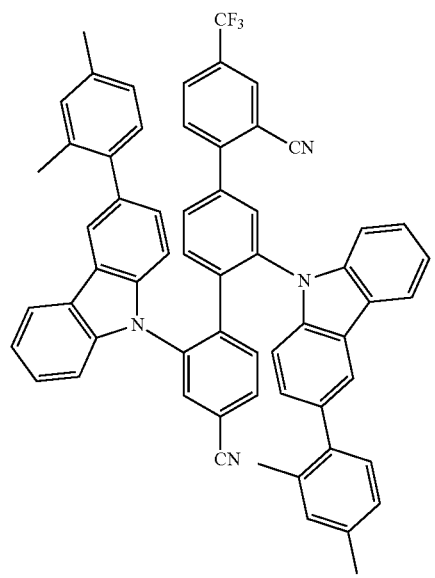
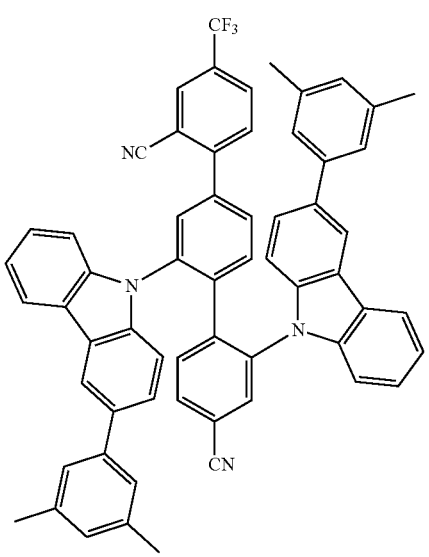
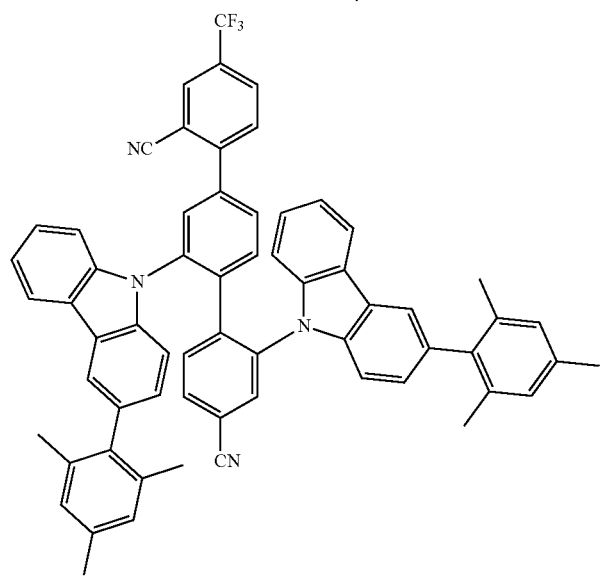

-continued
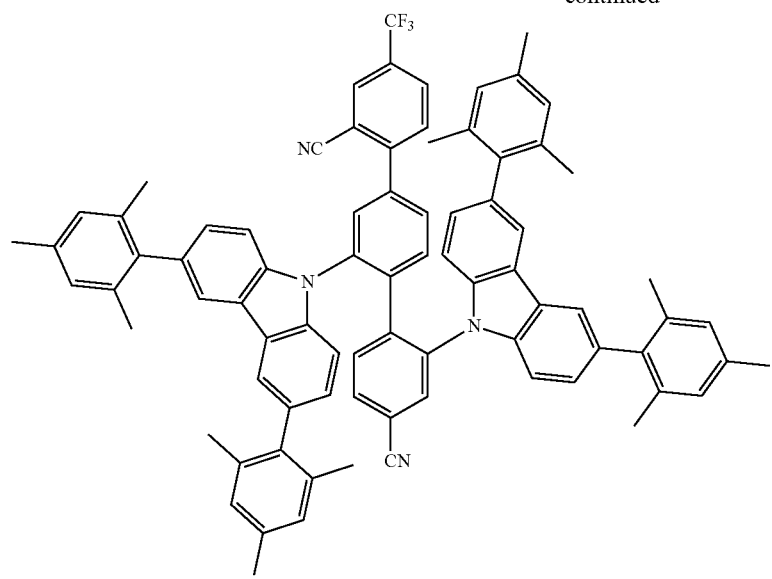
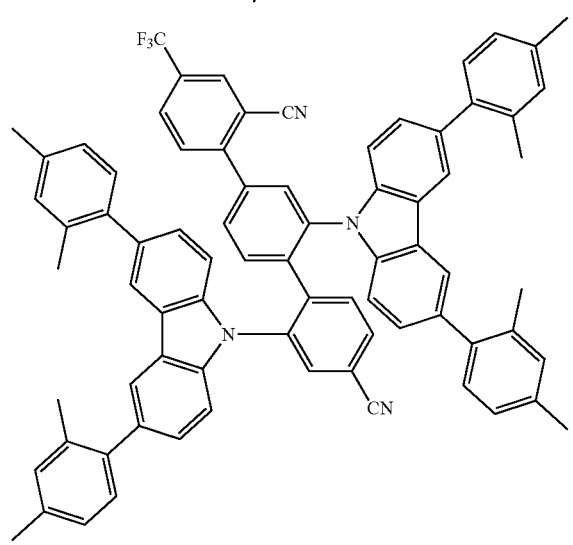
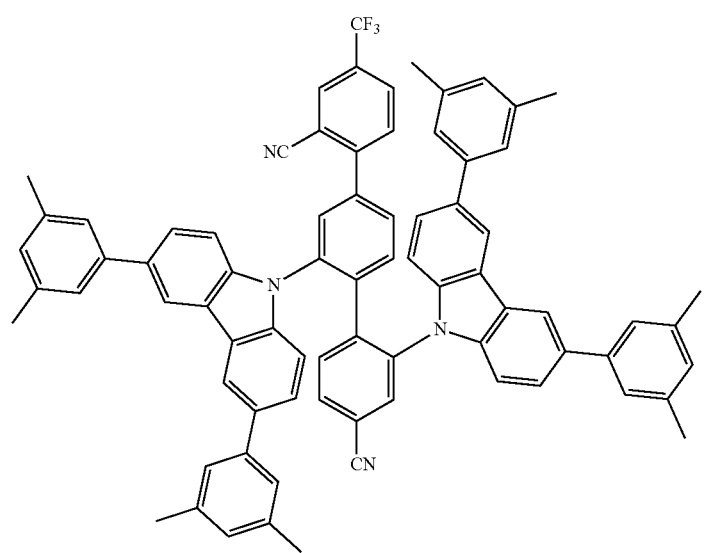

-continued
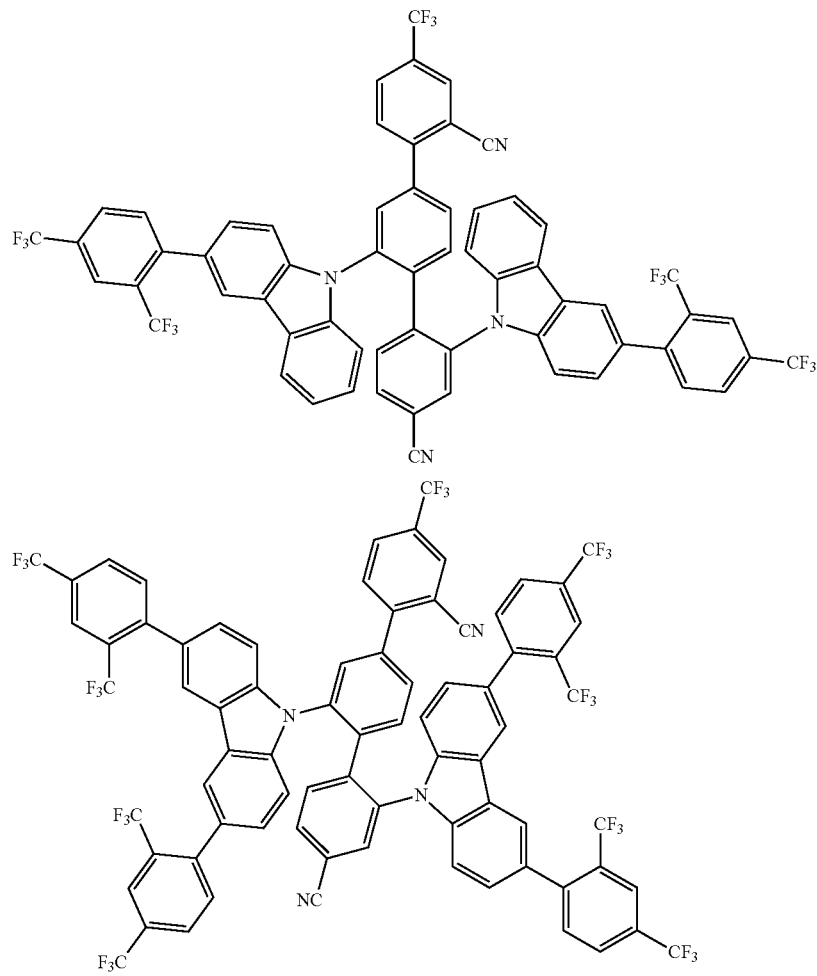
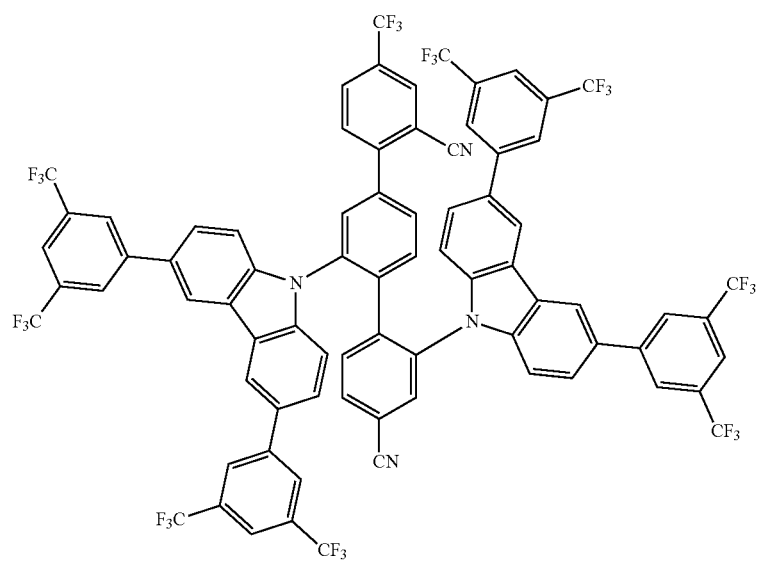

291 292
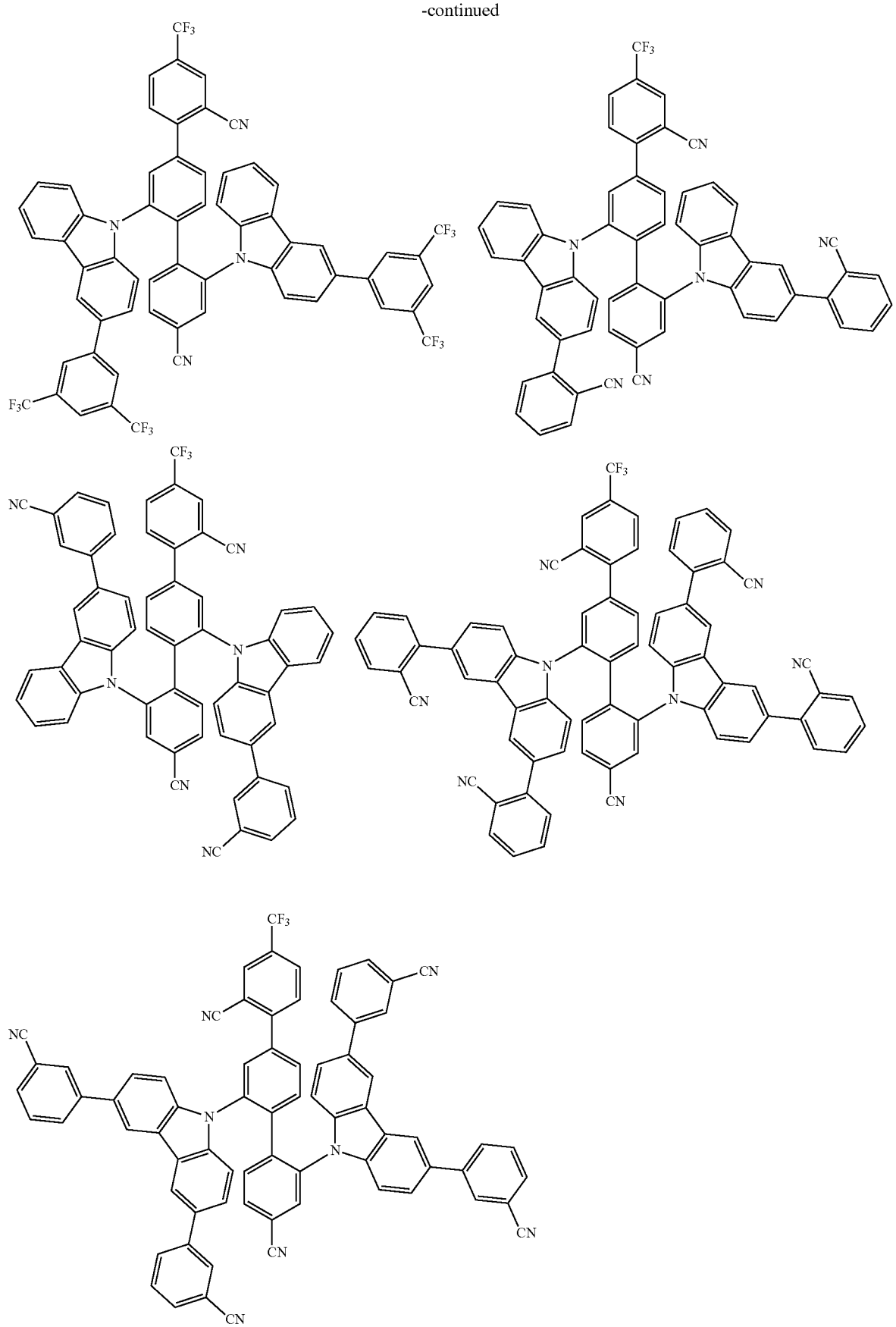
-continued 293
294
-continued
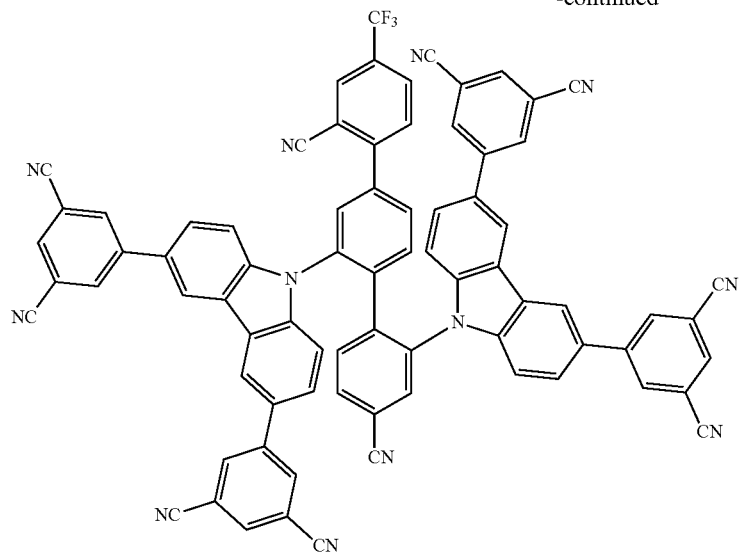
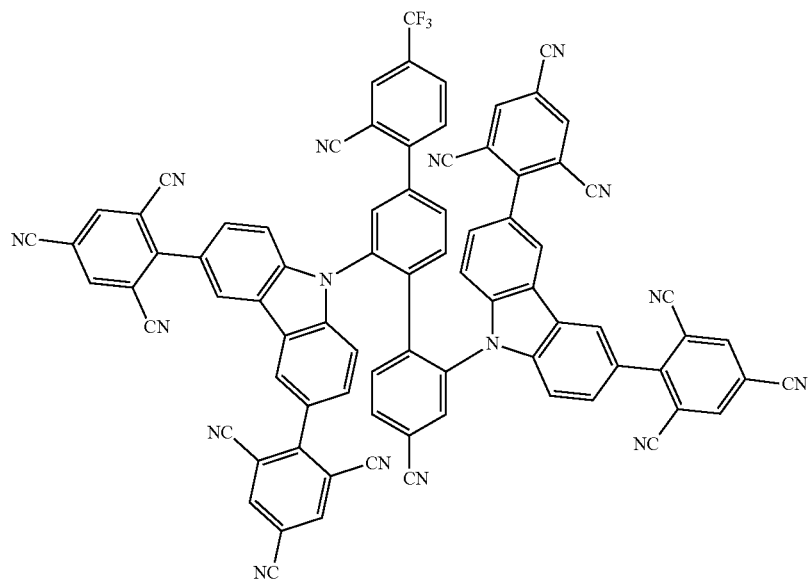
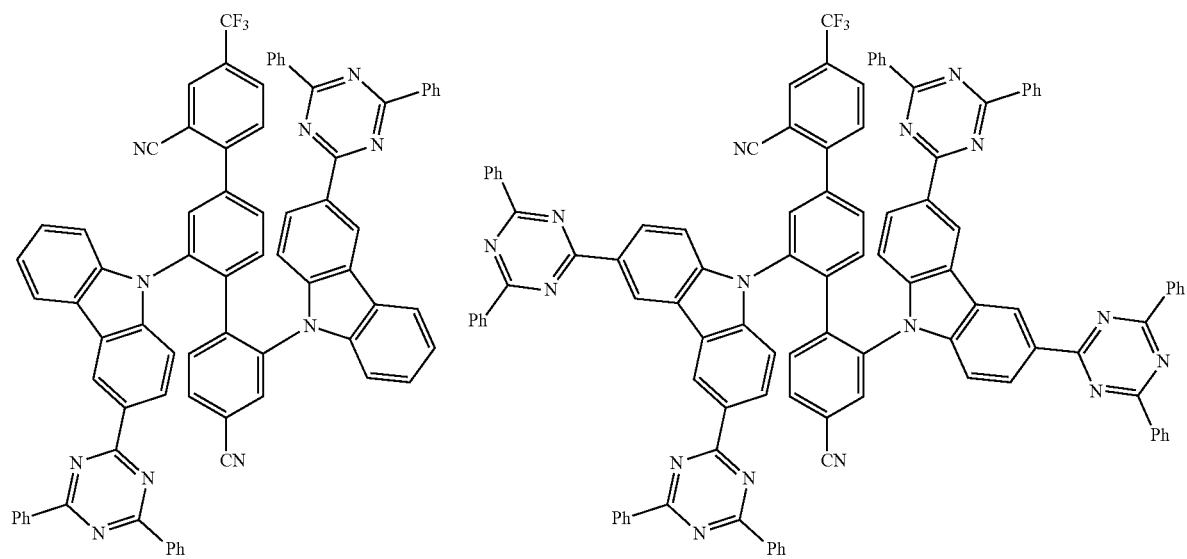

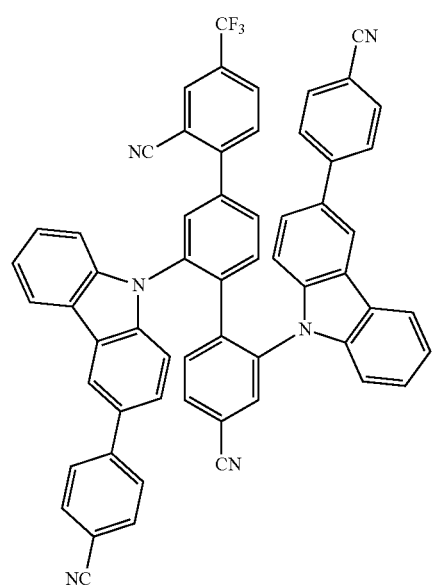
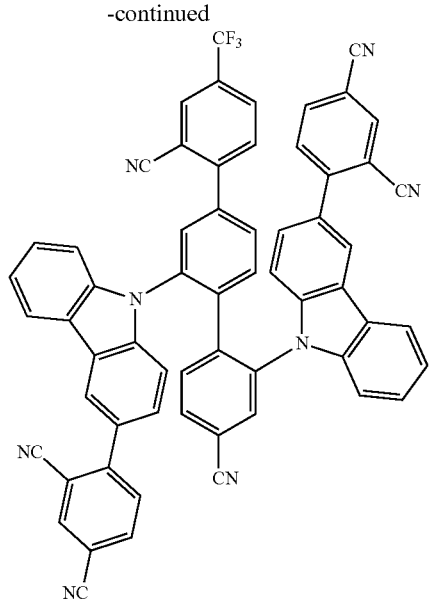
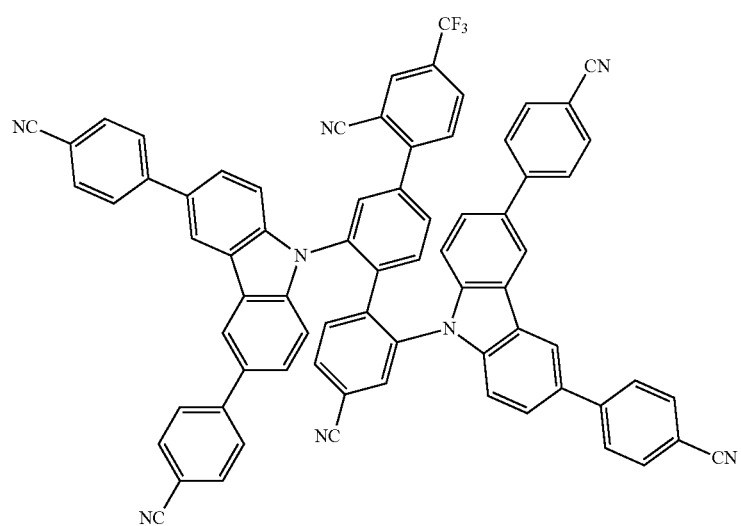
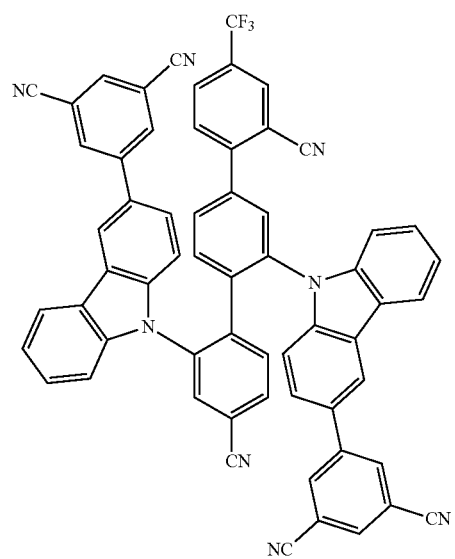

297
298
-continued
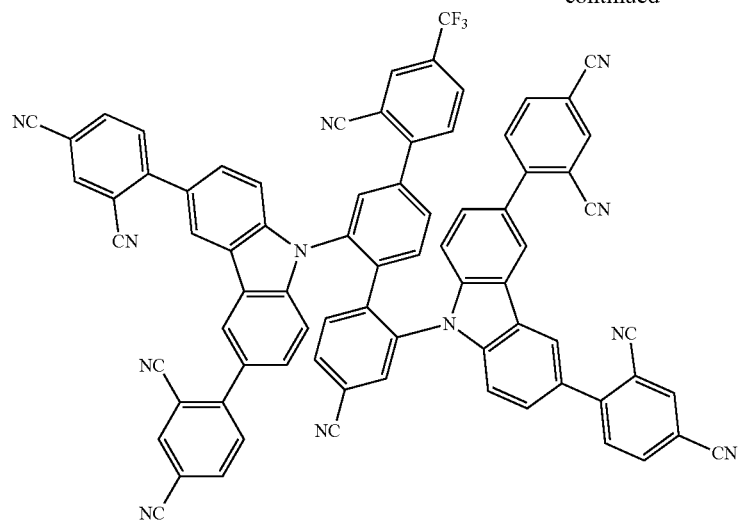
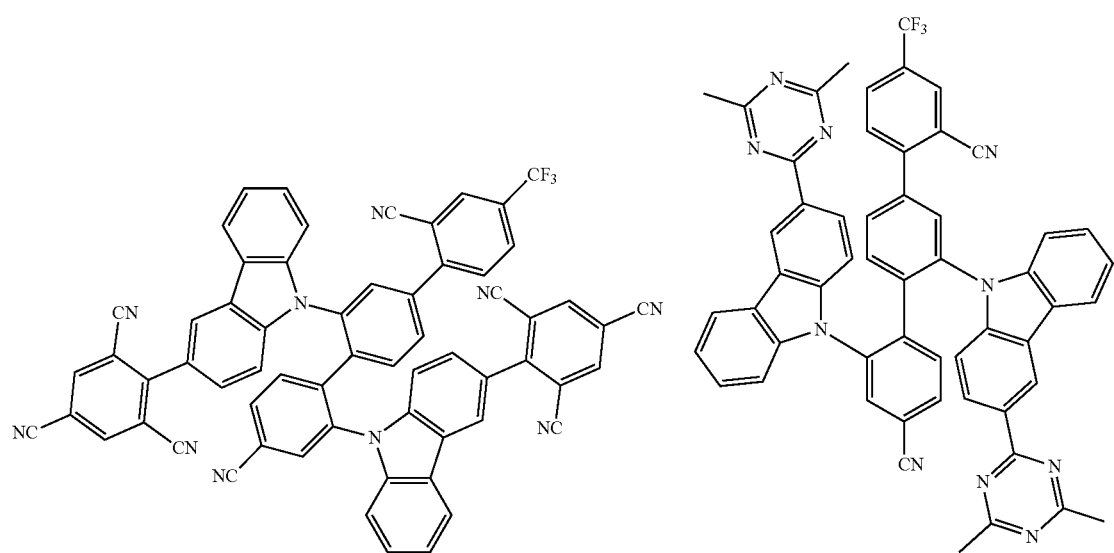
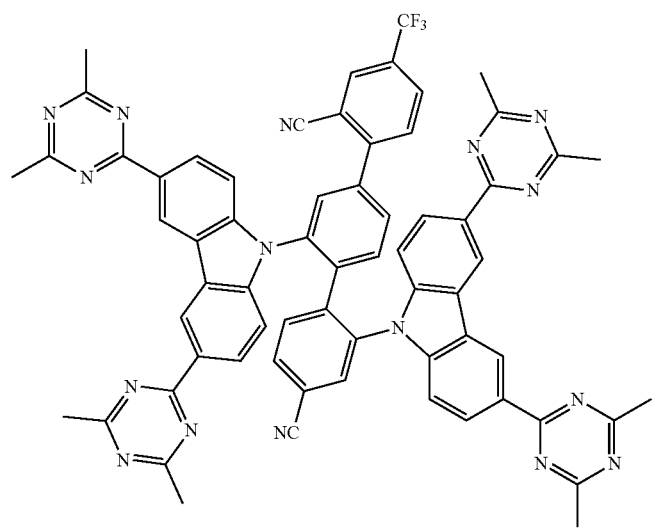
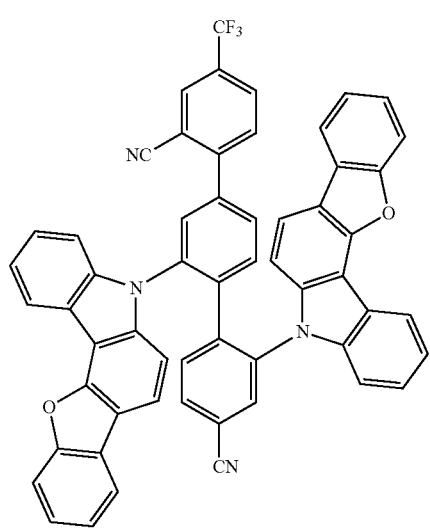

299
300
-continued
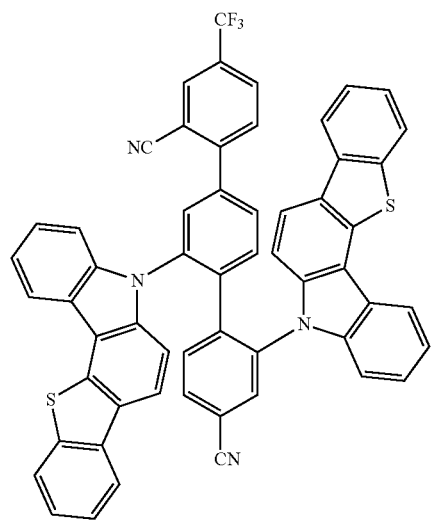
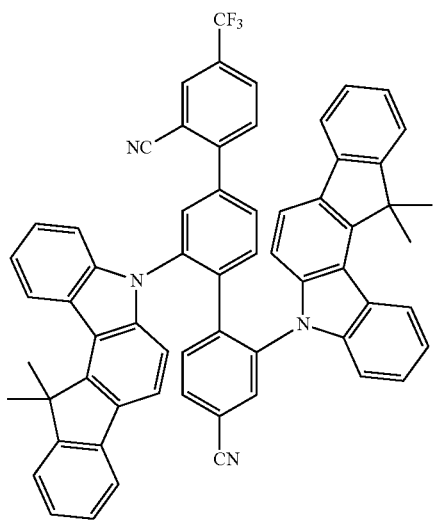
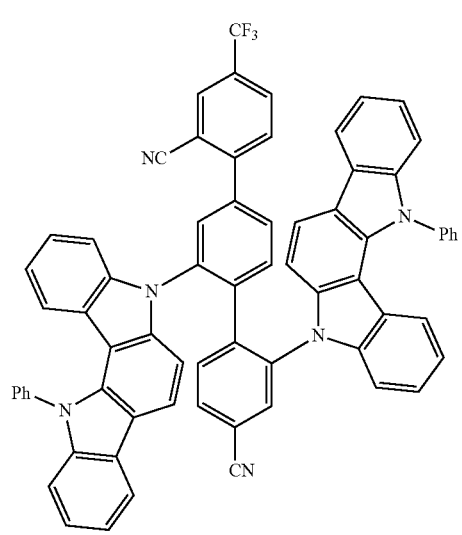
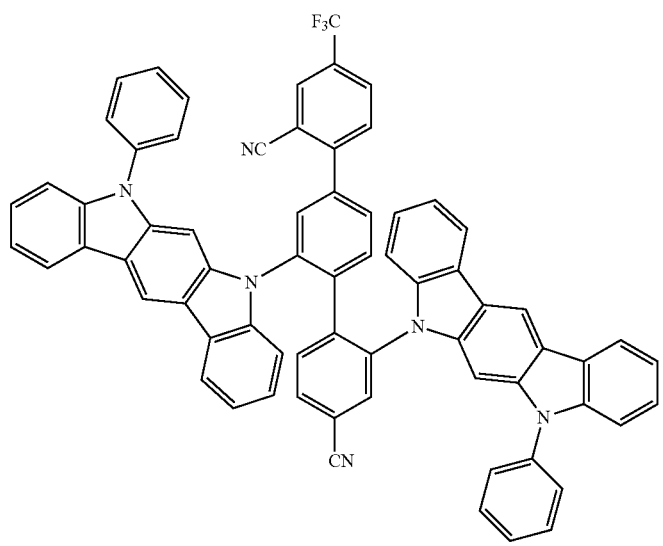
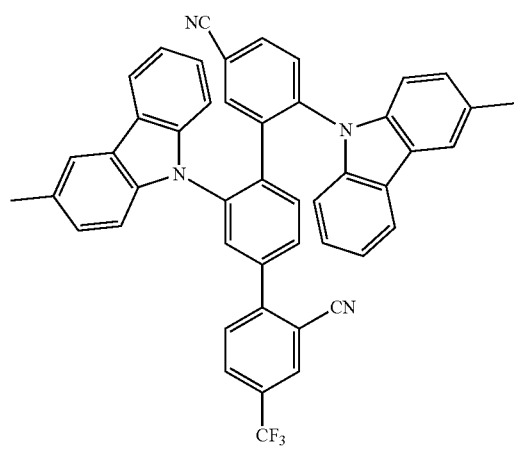
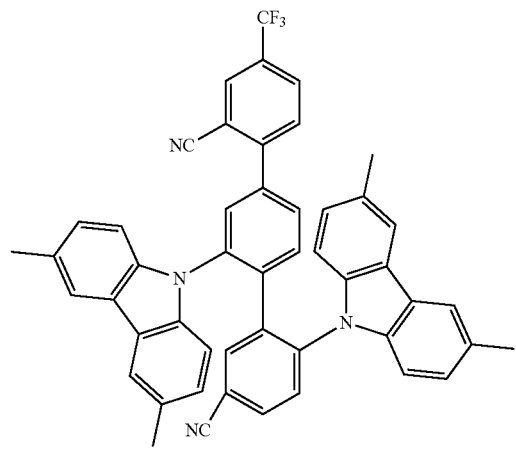

-continued
301
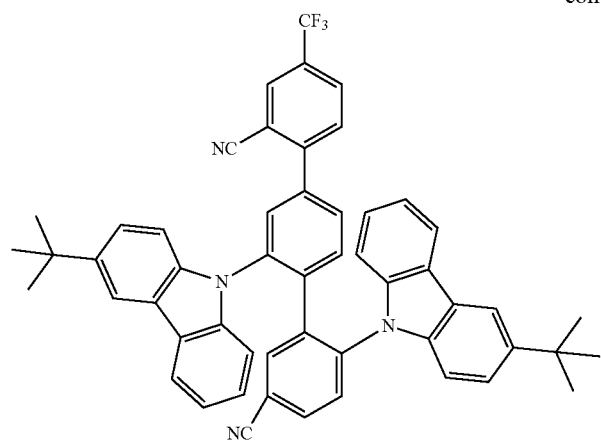
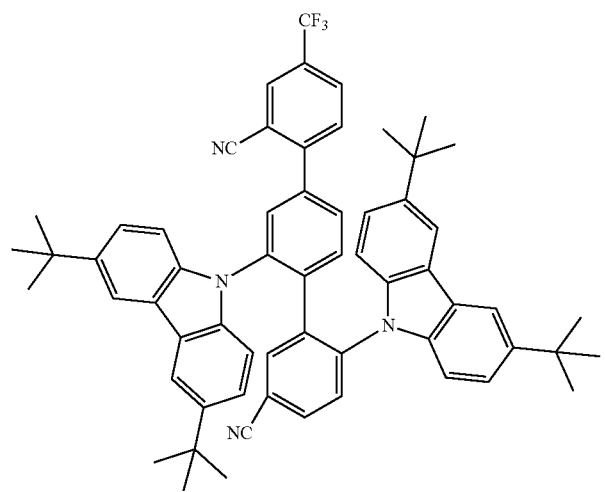
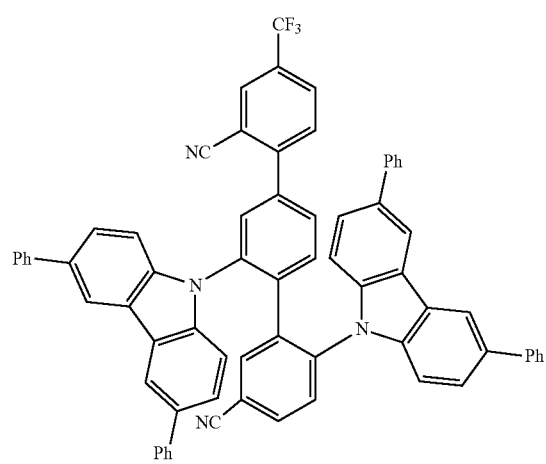
302
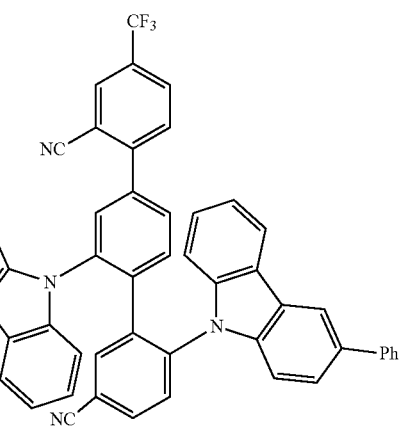
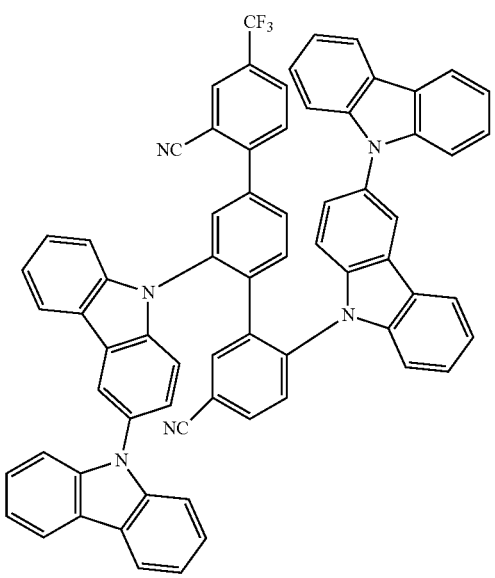

303
304
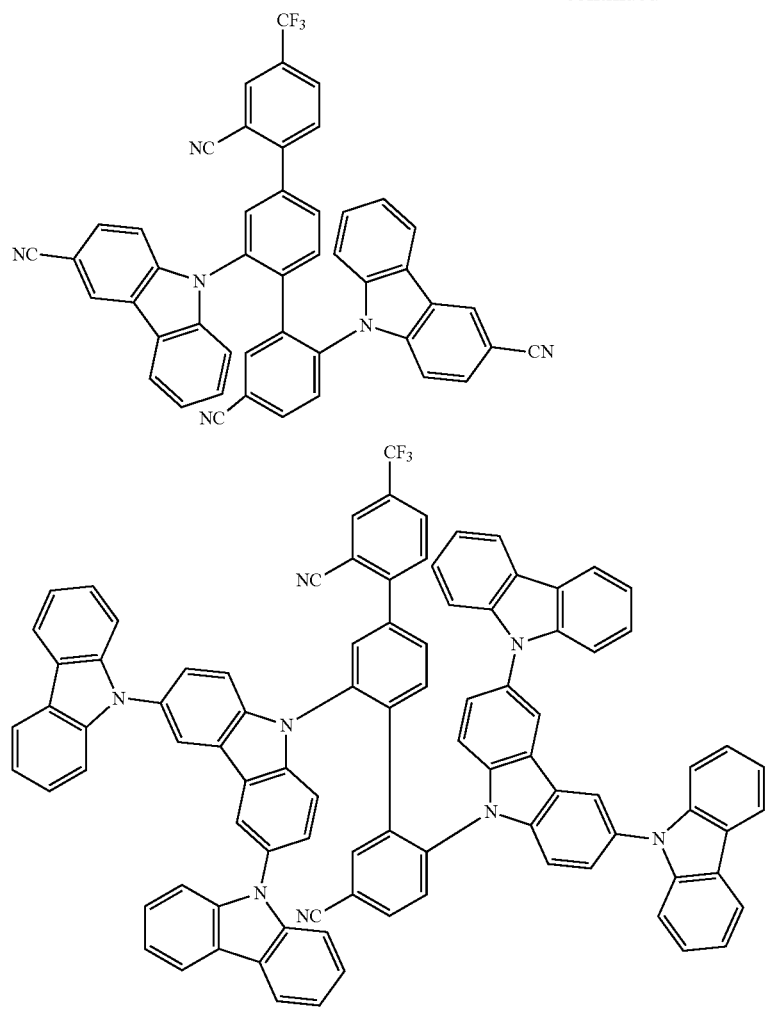
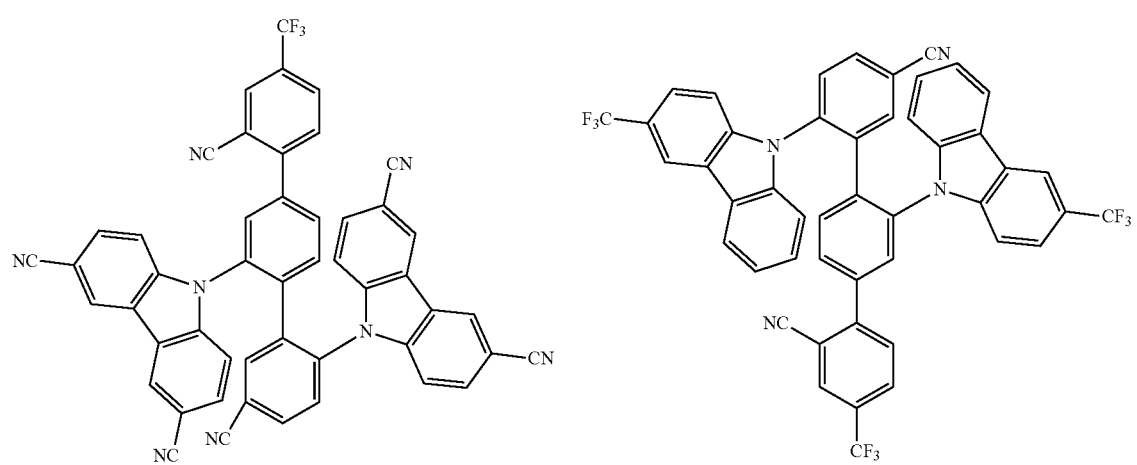

-continued
305
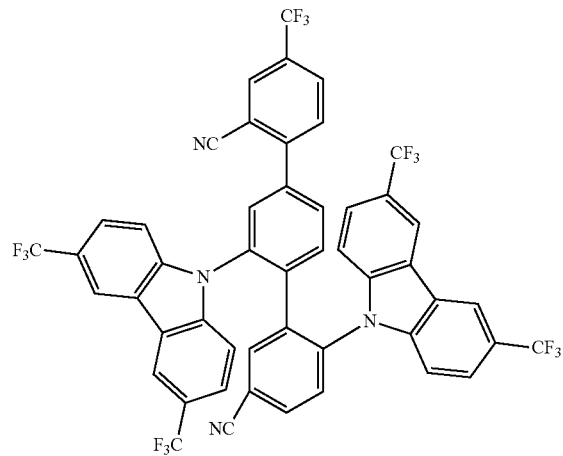
306
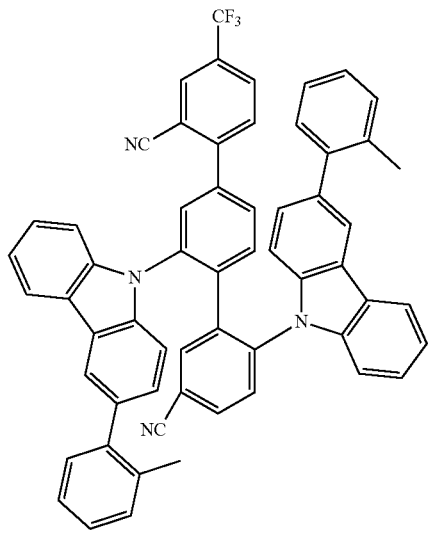
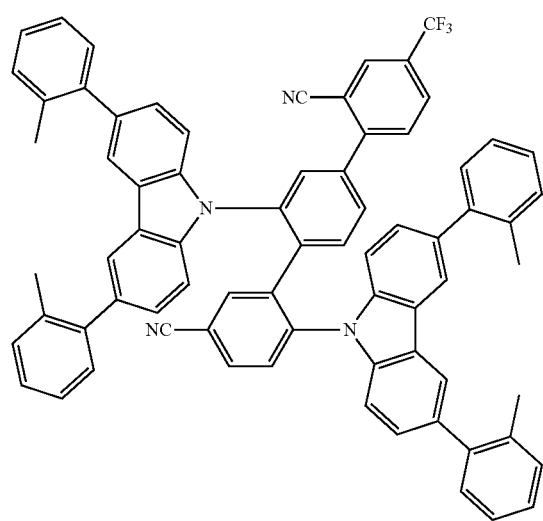
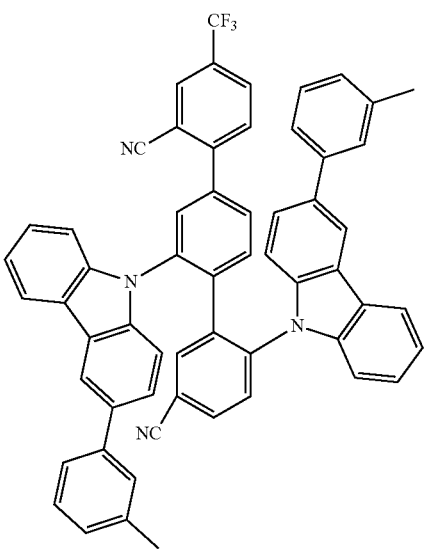
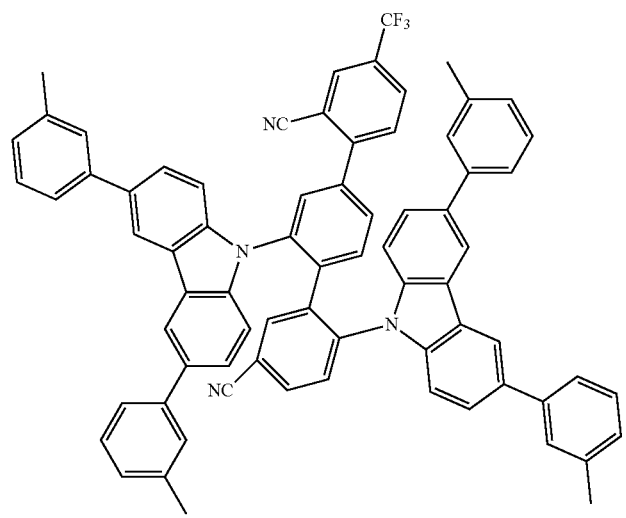
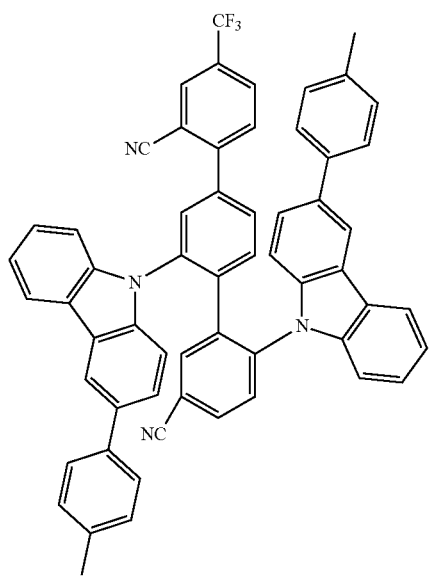

307 308
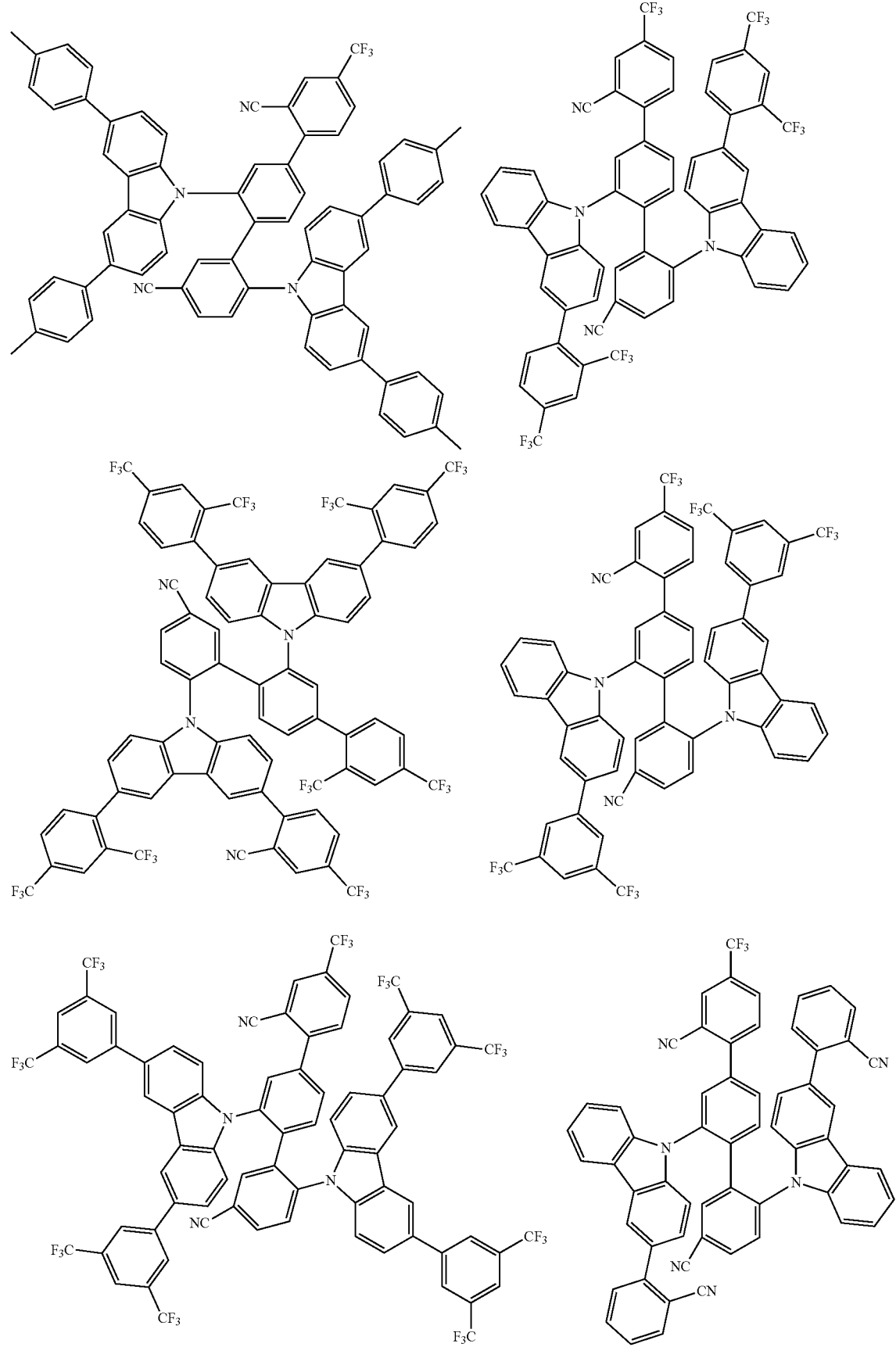
-continued 309 310
-continued
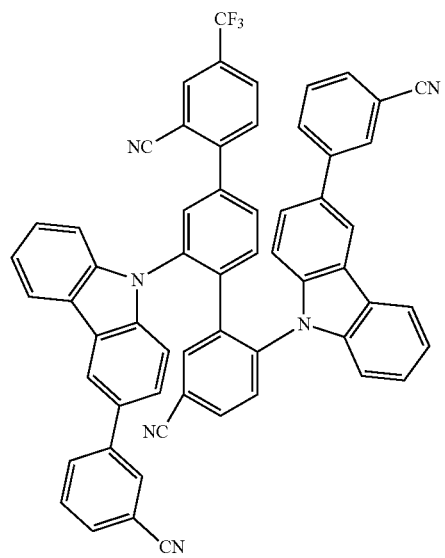
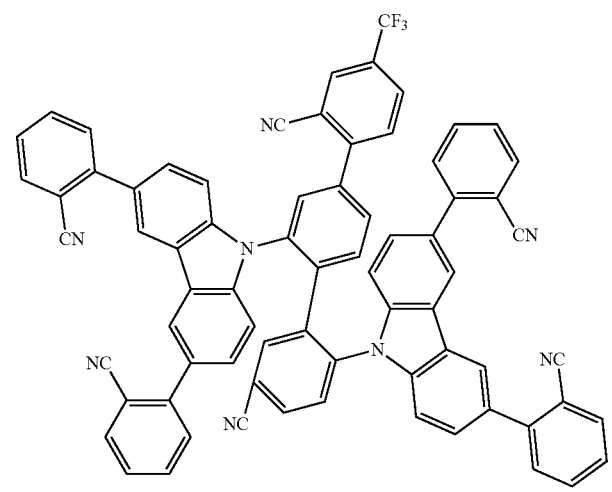
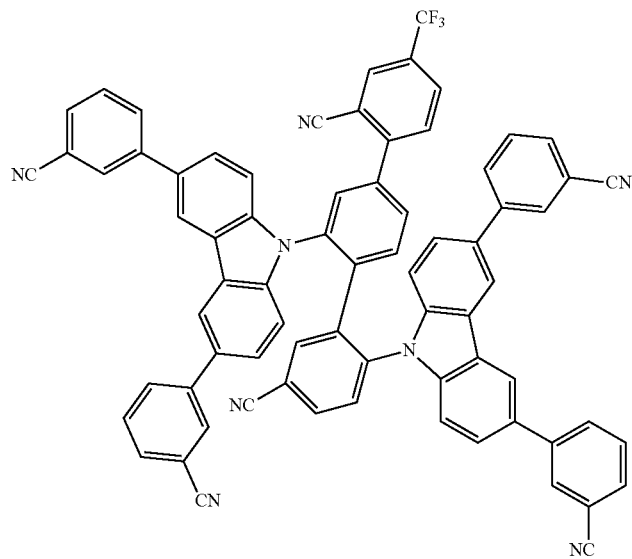
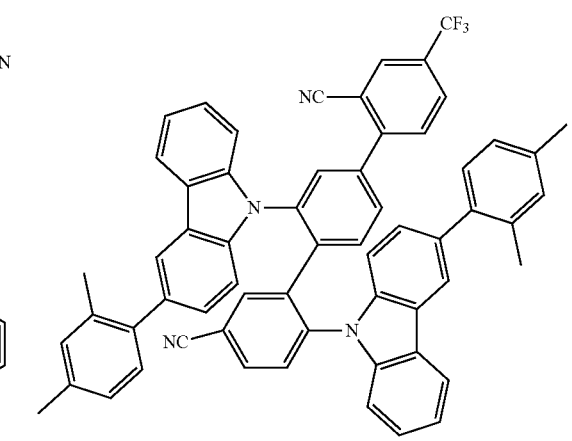
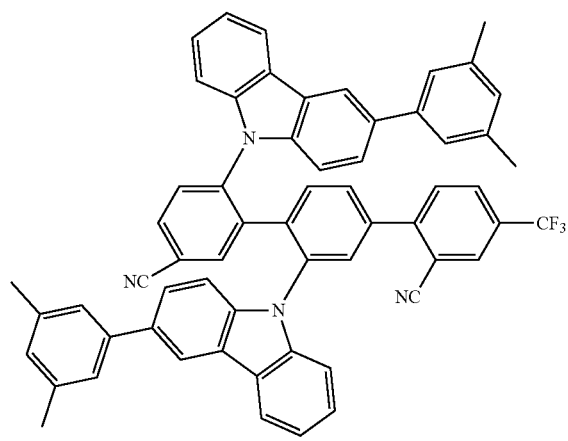
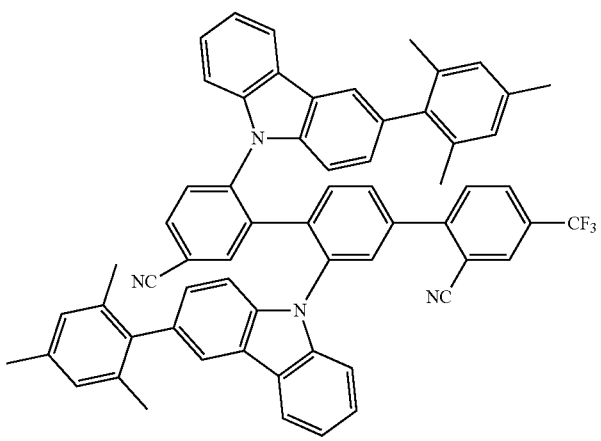

-continued
311
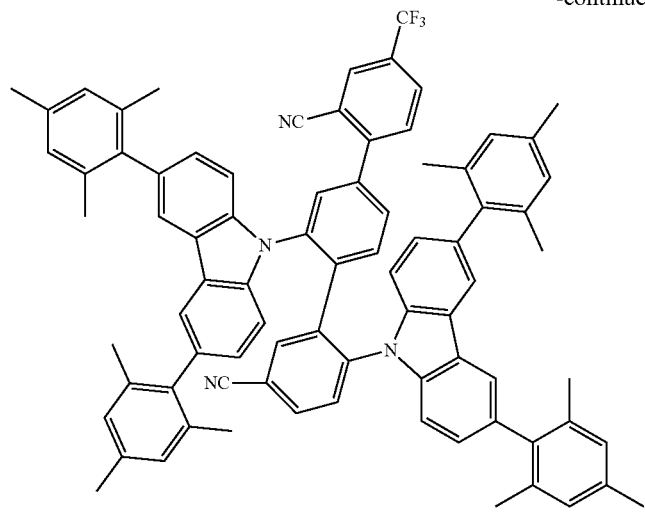
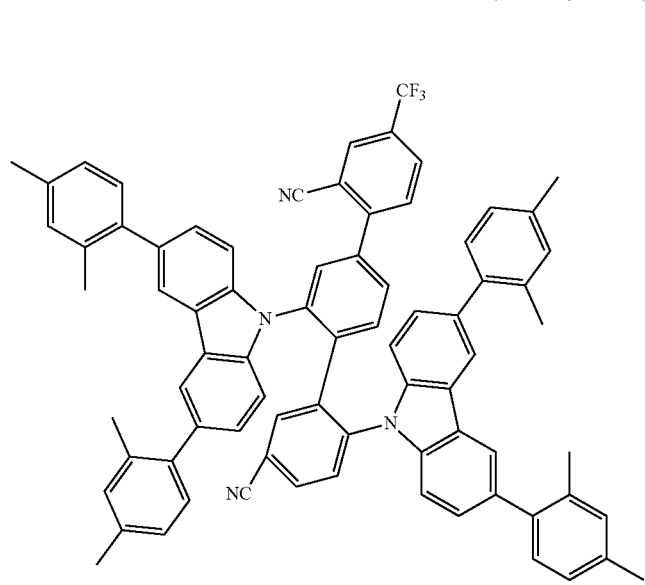
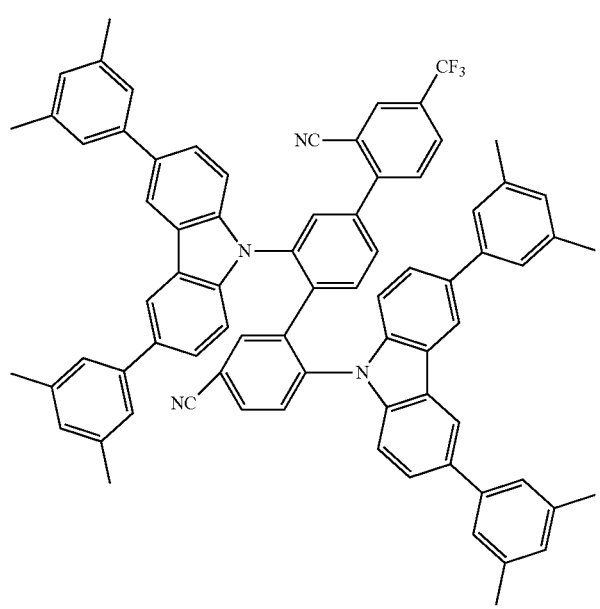
312
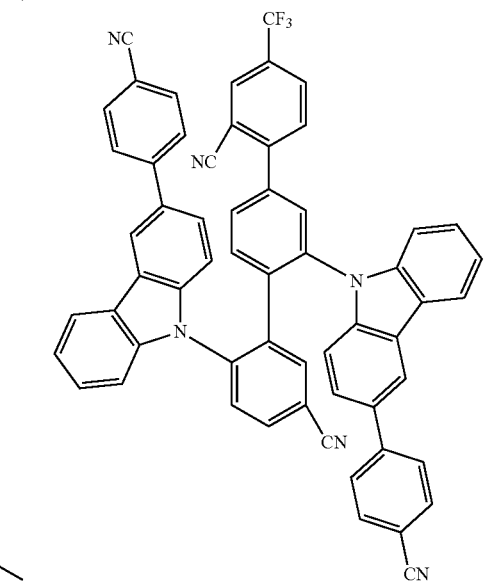
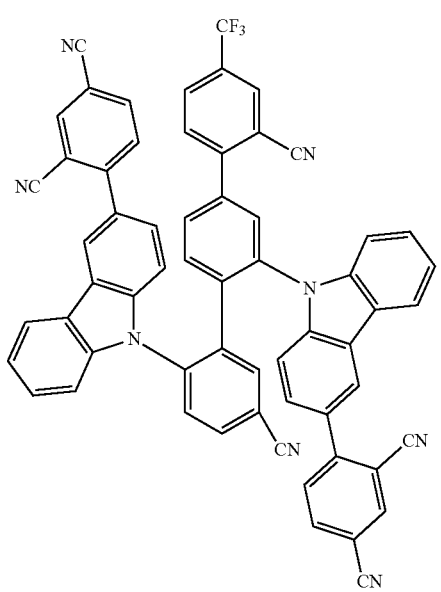

313 314
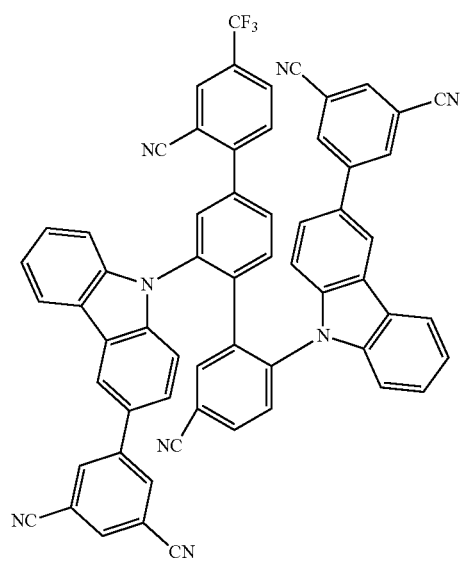 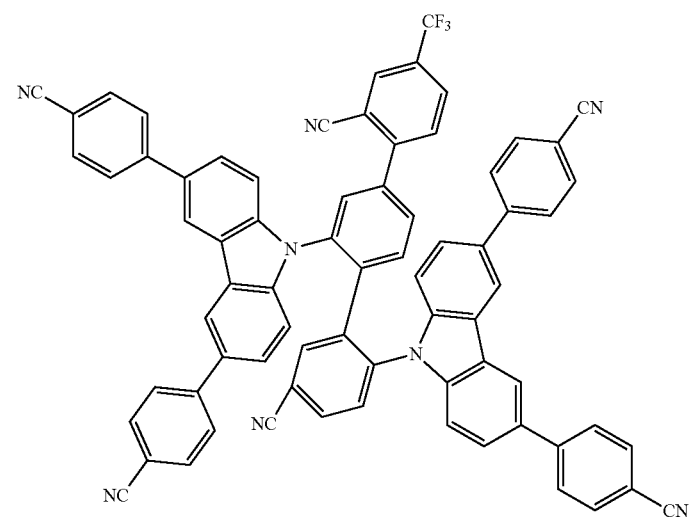
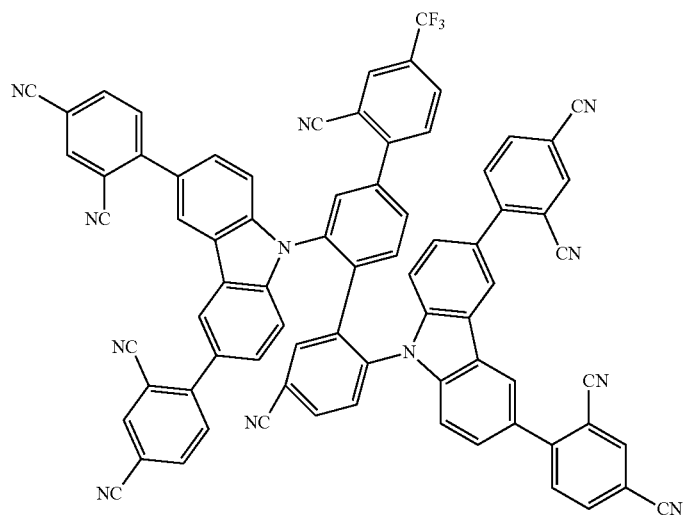
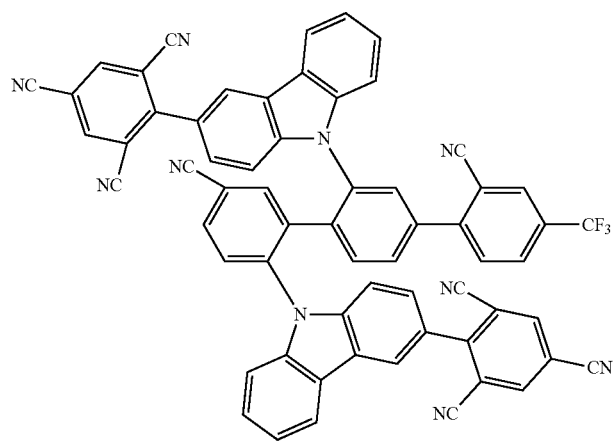

-continued
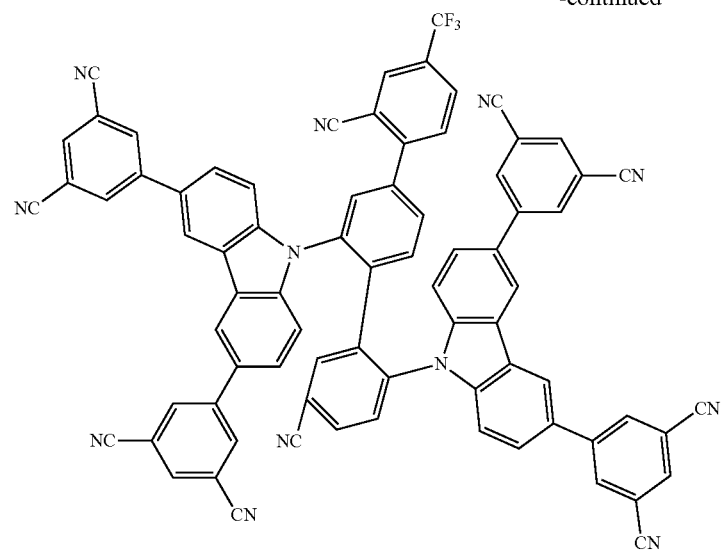
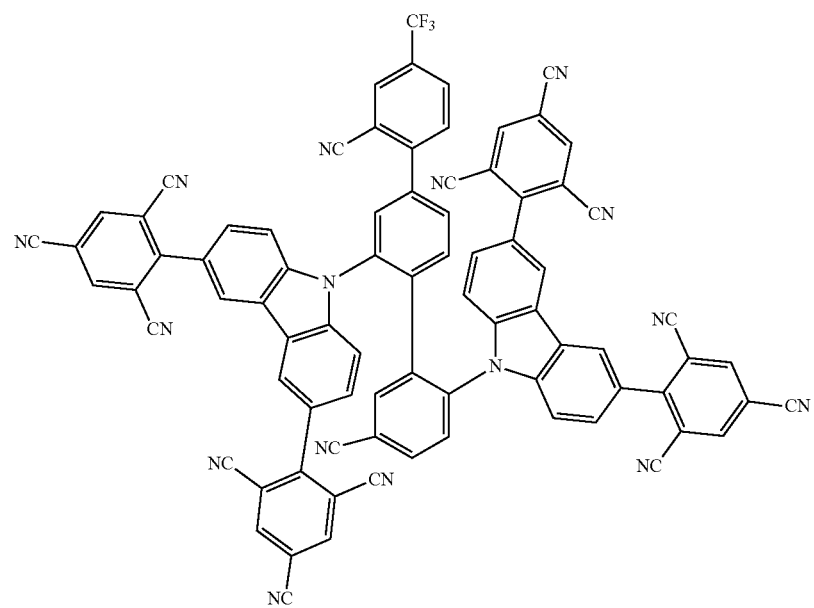
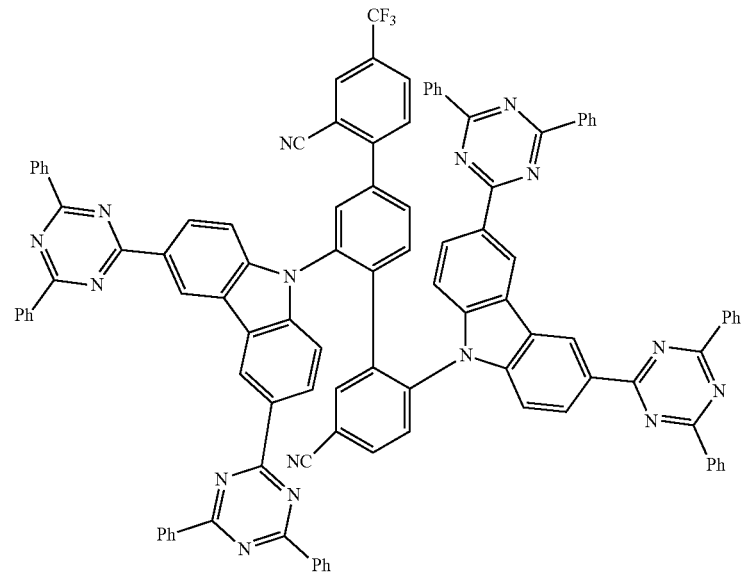

-continued
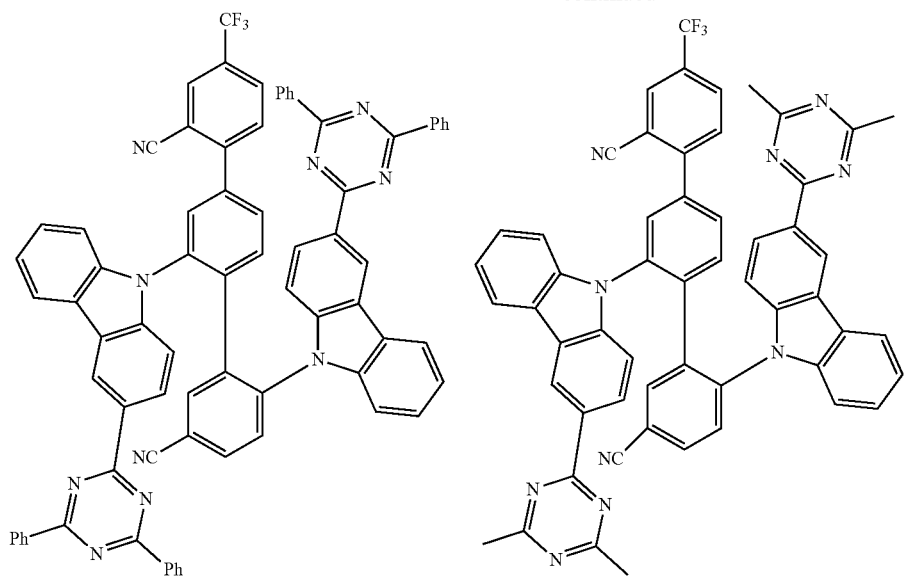
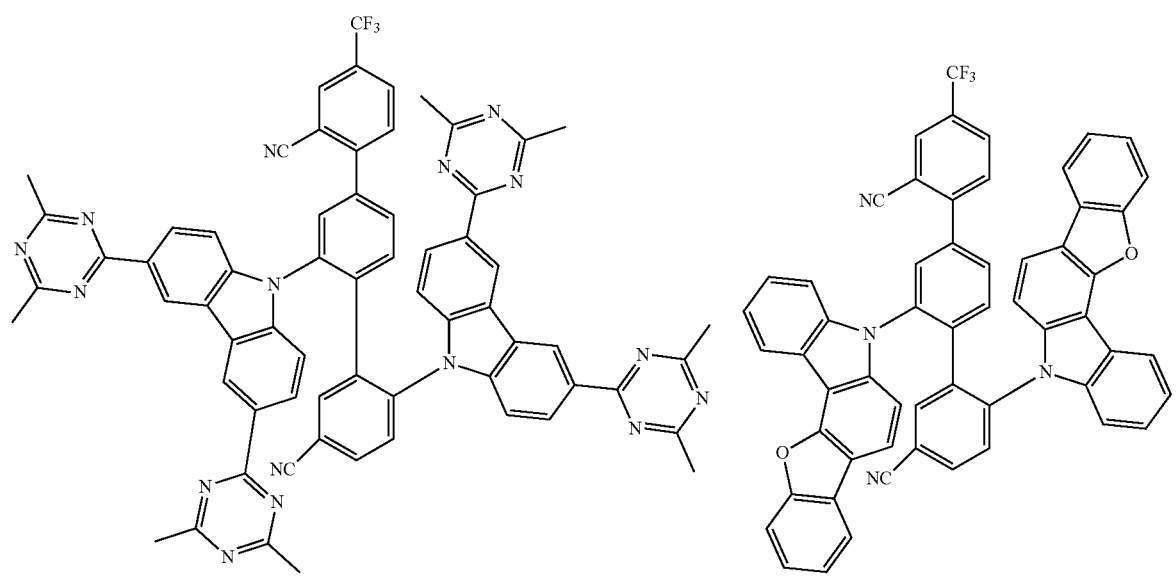
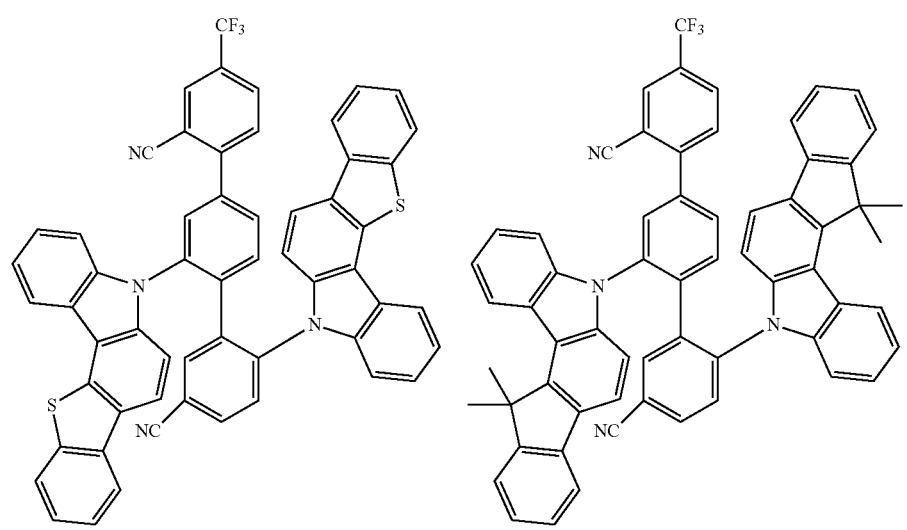

-continued
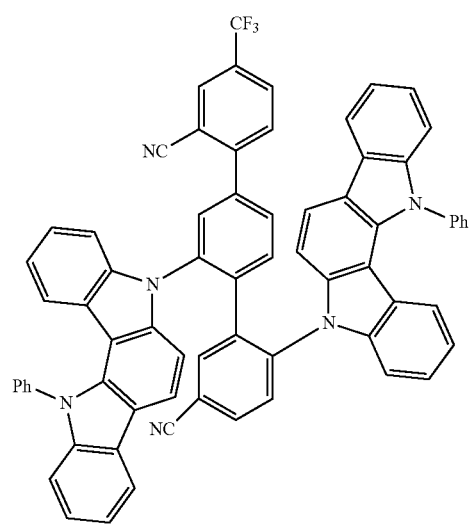
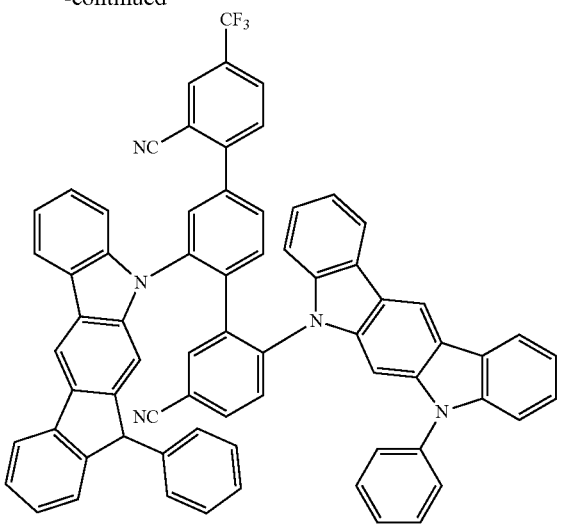
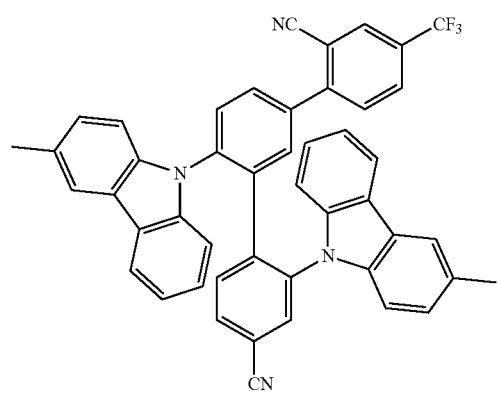
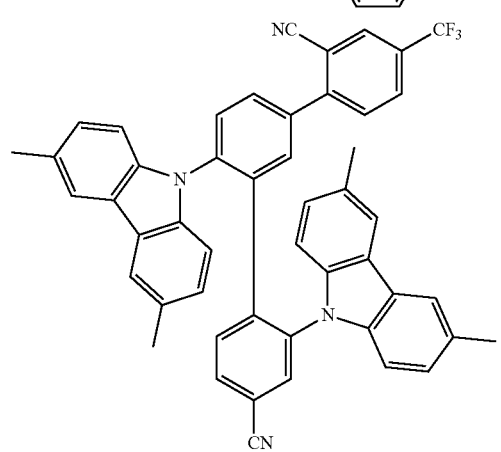
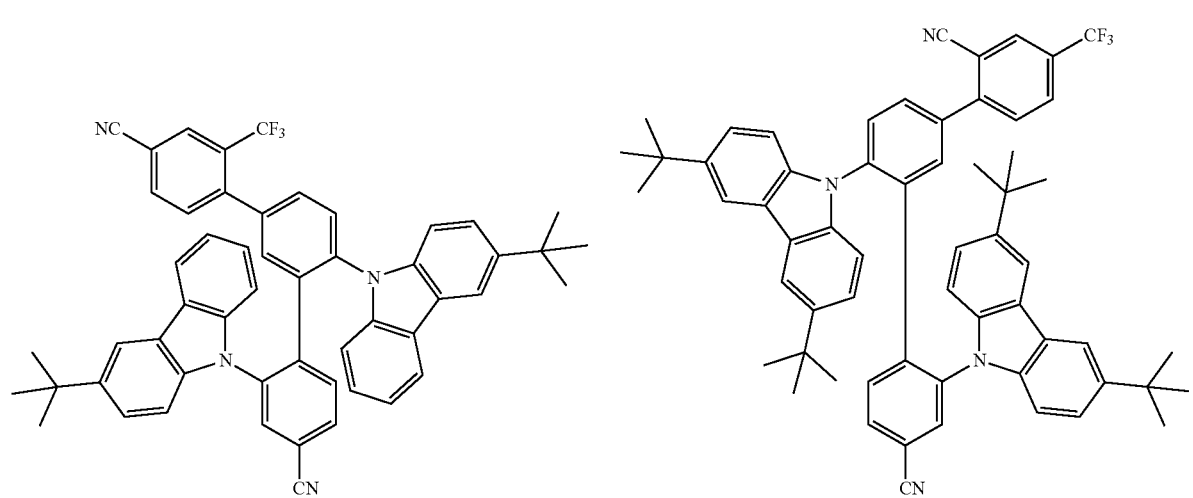
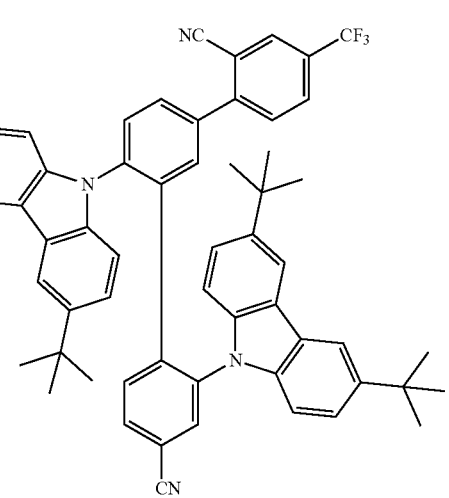

-continued
321
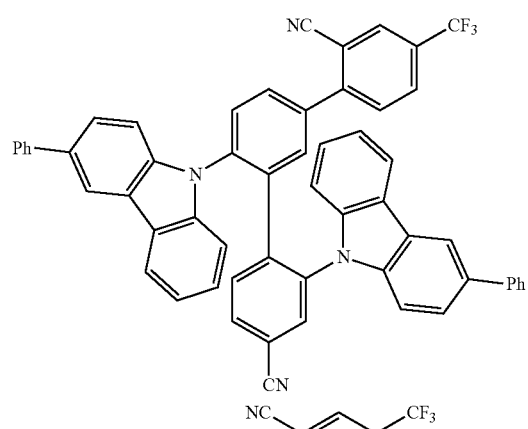
322
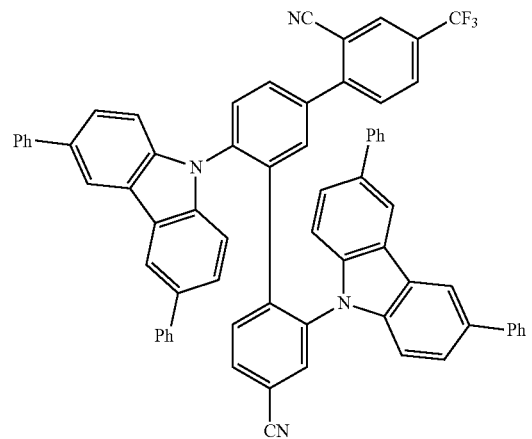
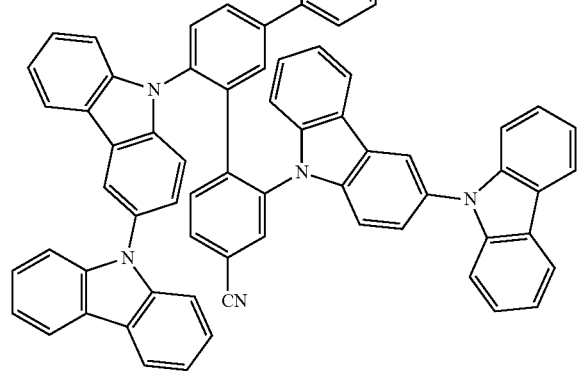
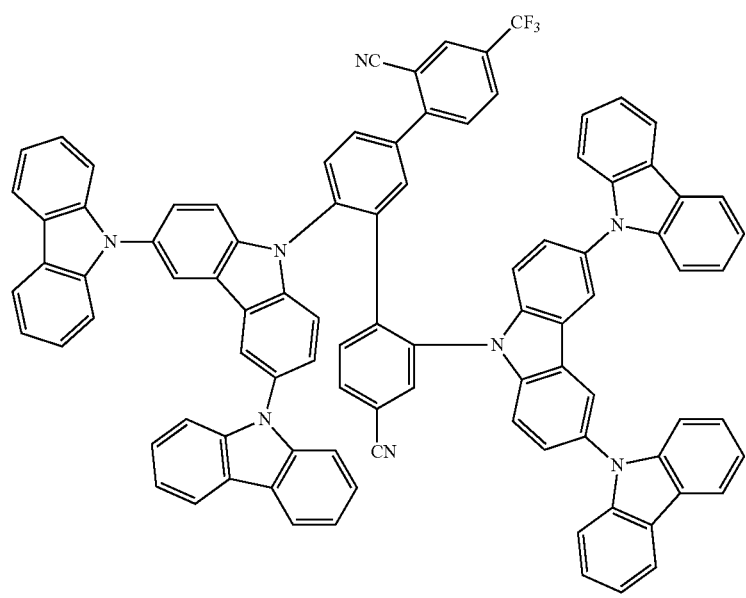

-continued
| 323 | 324 |
|---|---|
| 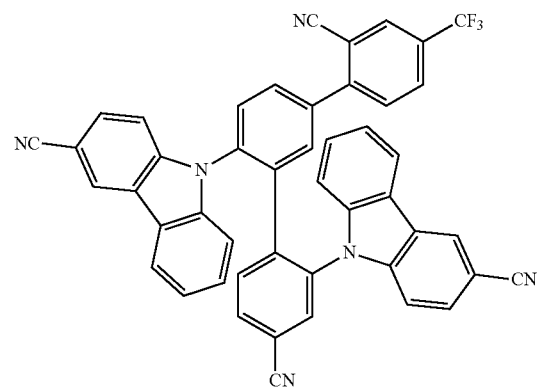 | 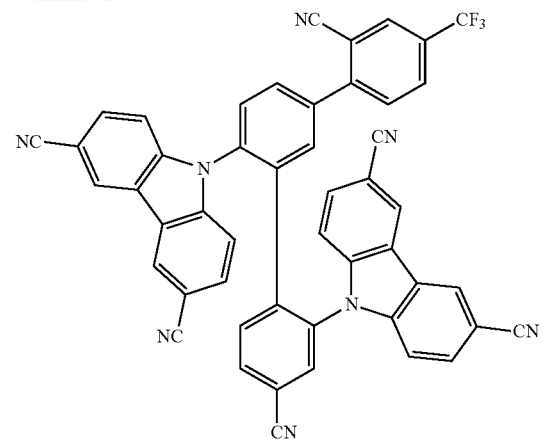 |
| 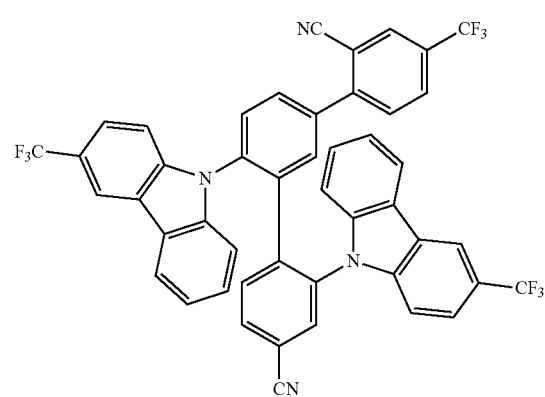 | 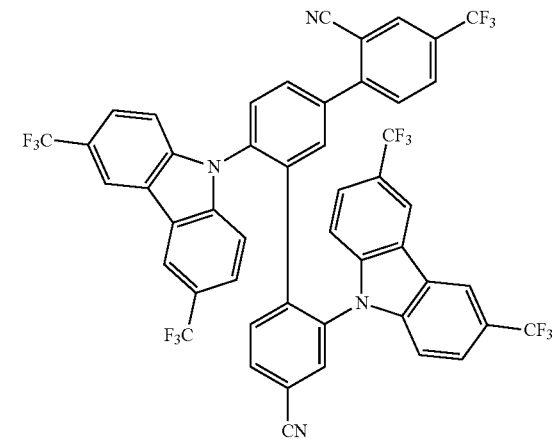 |
| 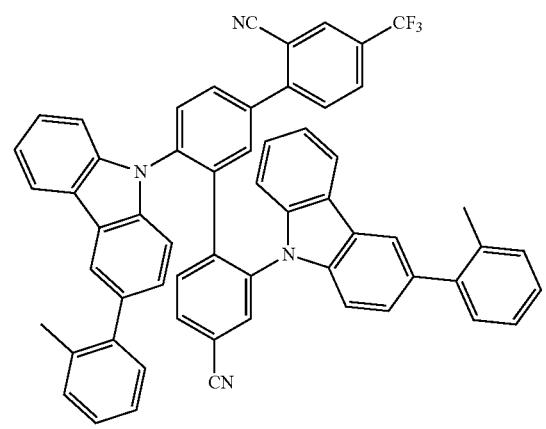 | |
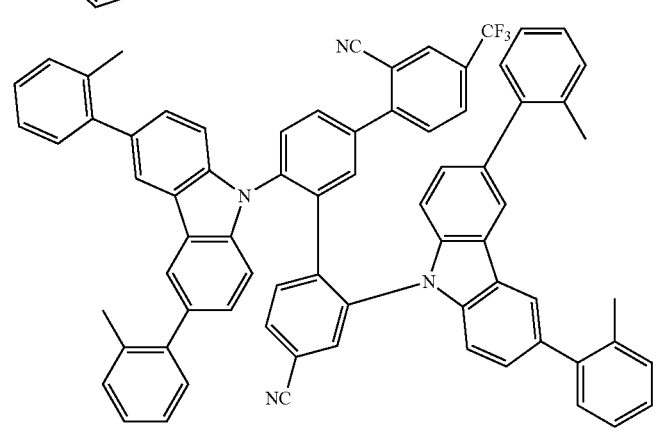

-continued
325
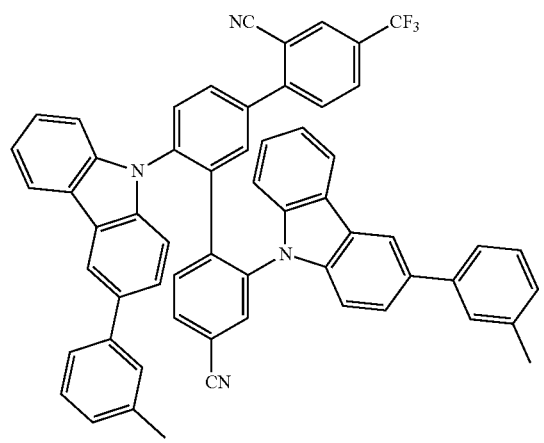
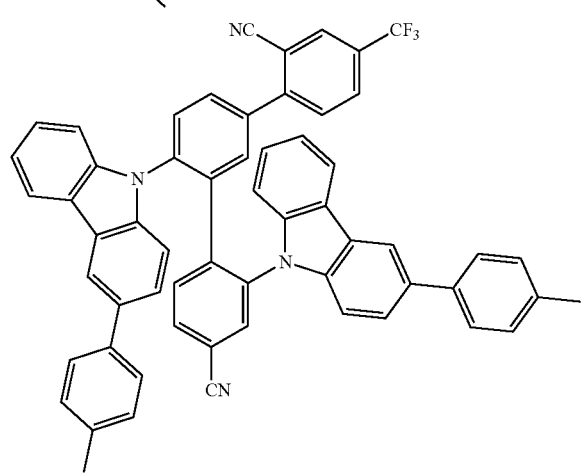
326
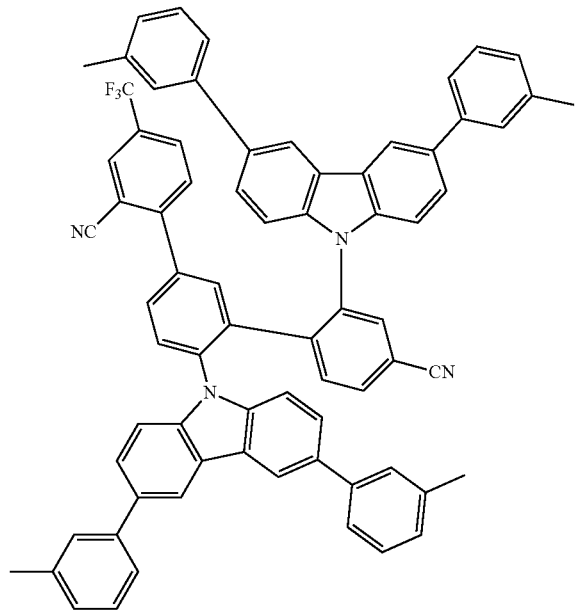
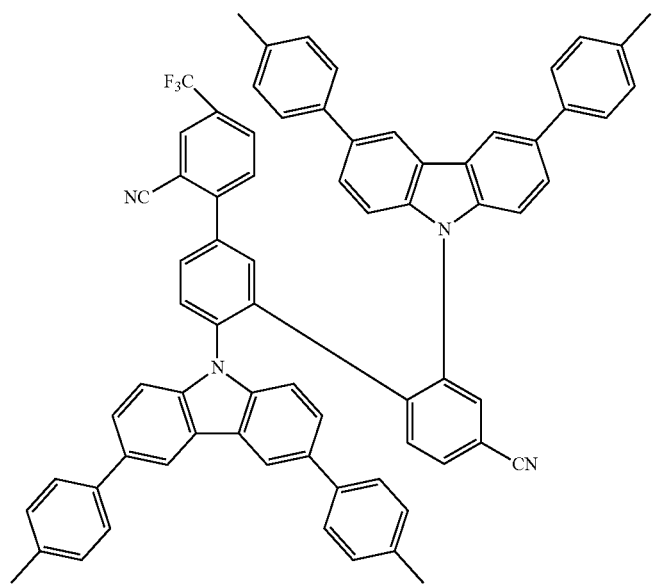

-continued
327
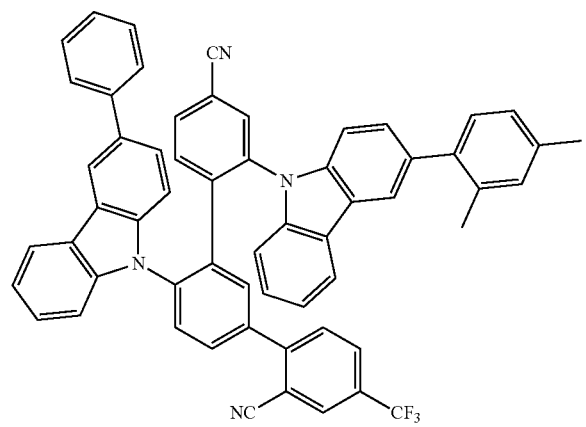
328
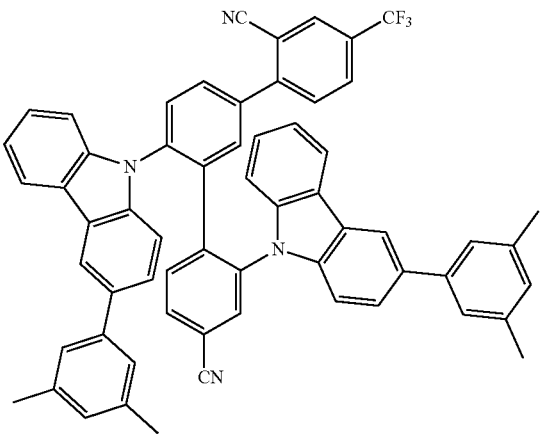
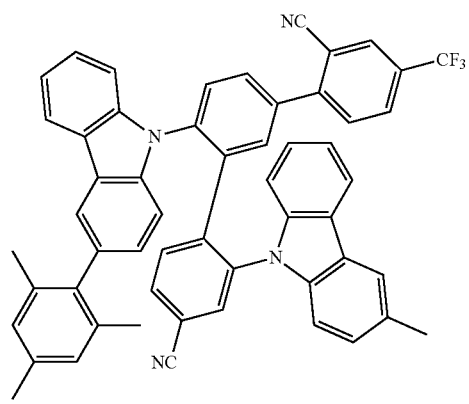
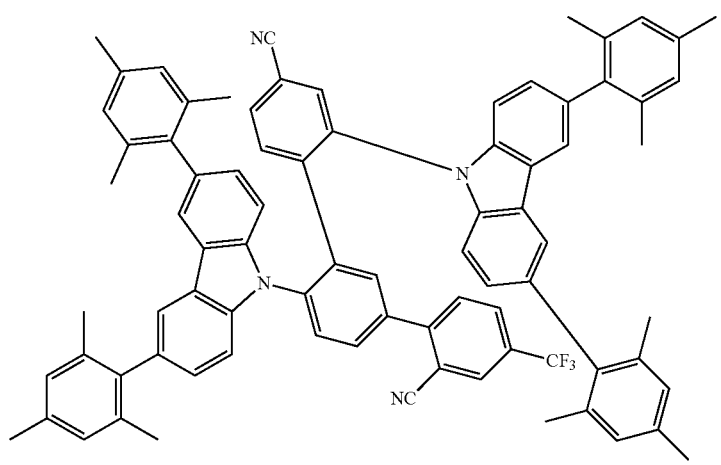
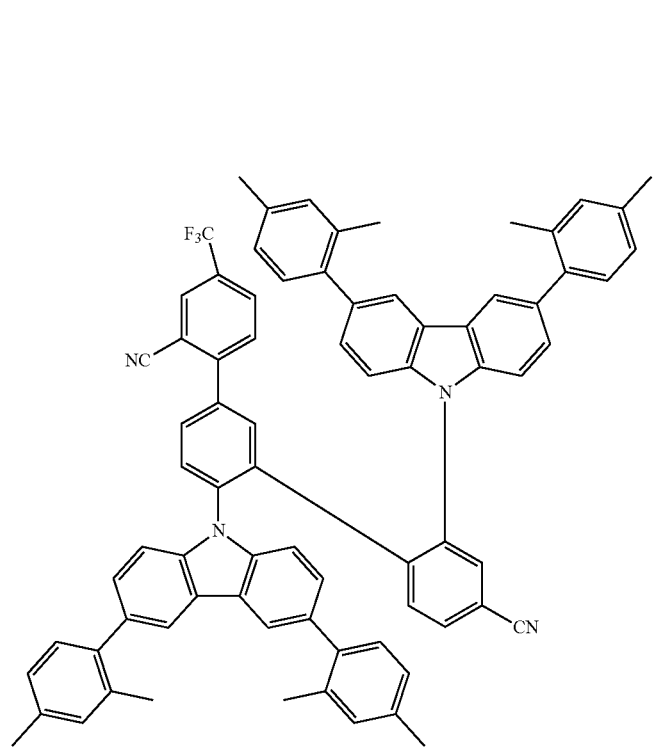
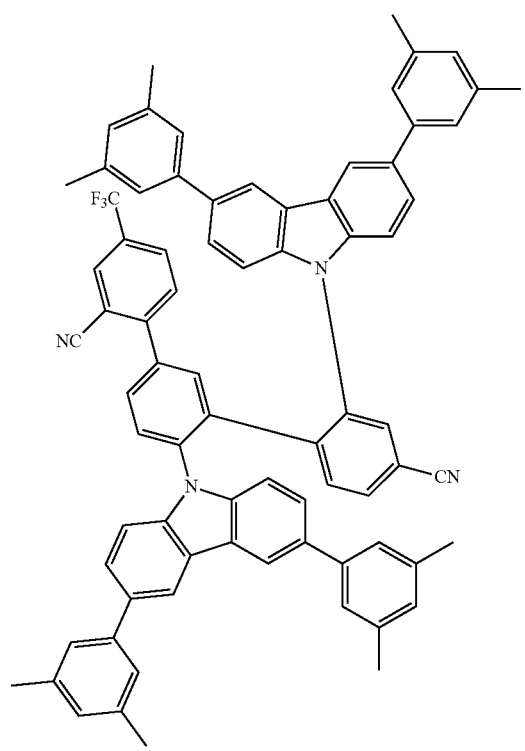

-continued
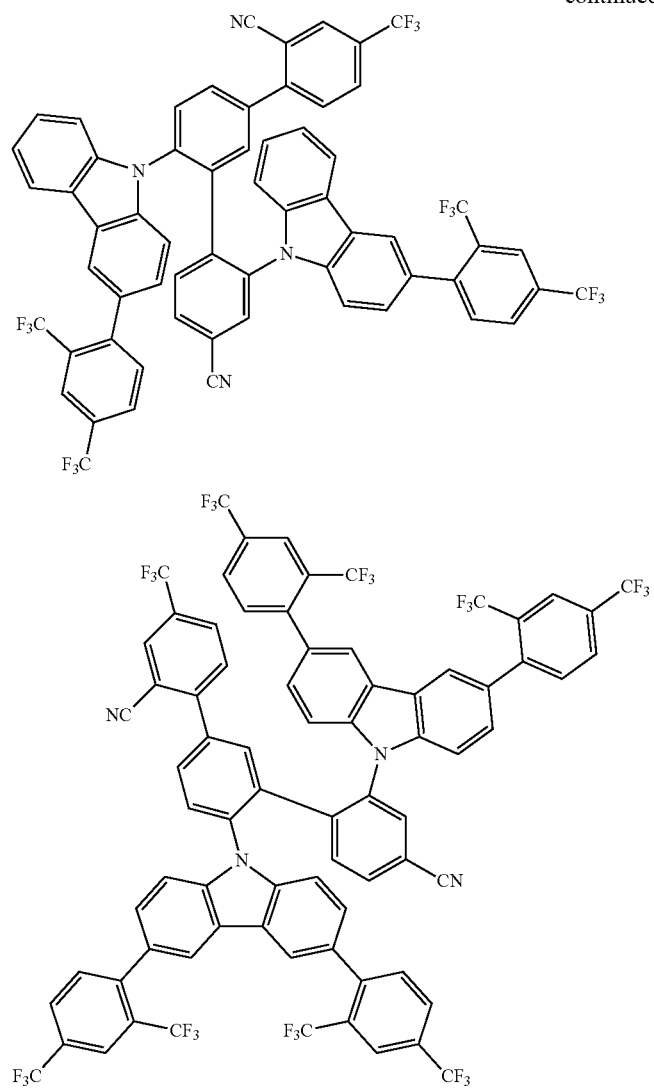
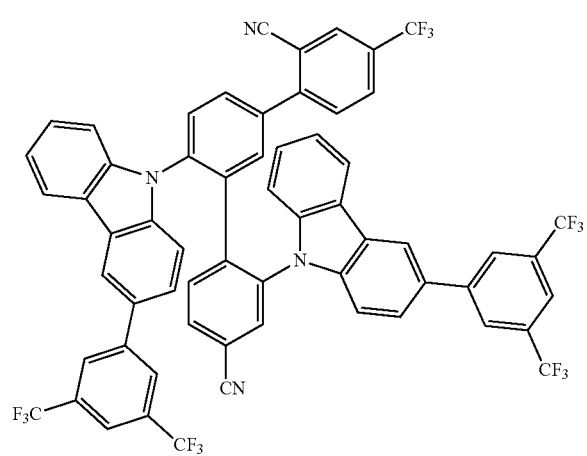

-continued
331
332
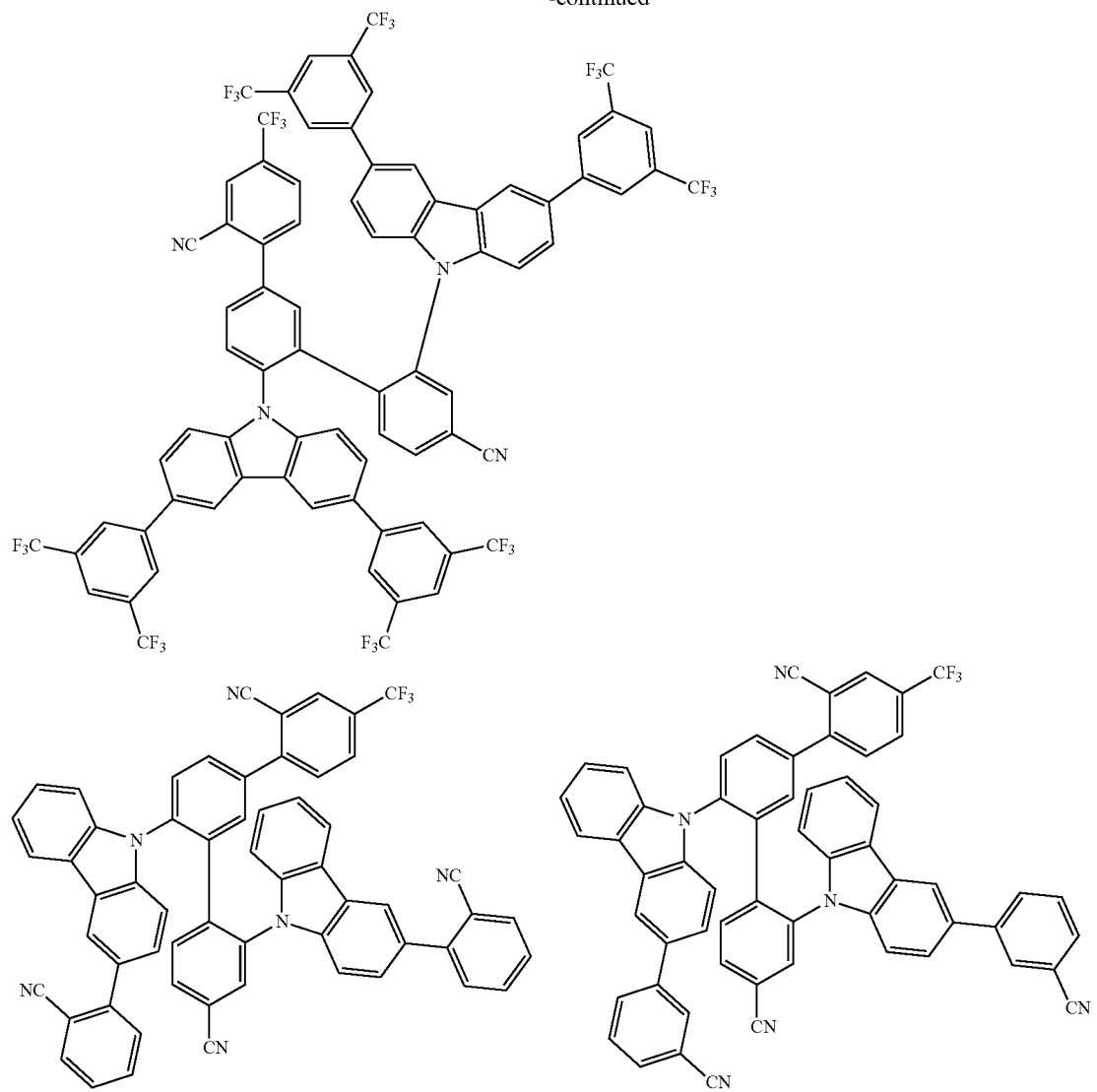
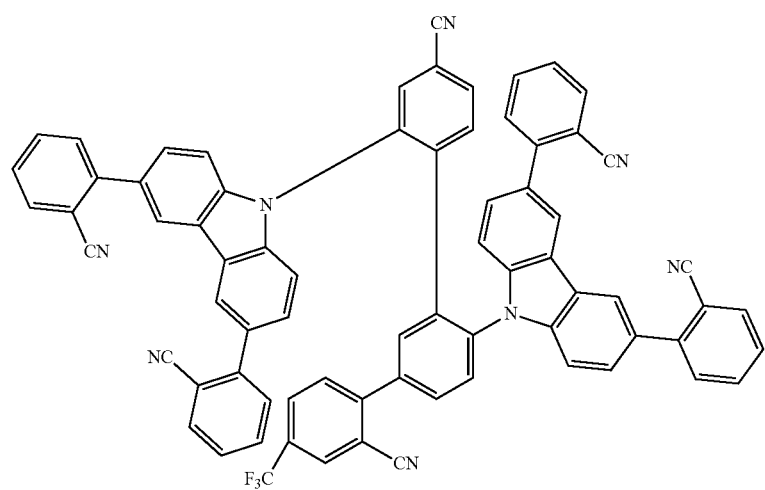

-continued
333
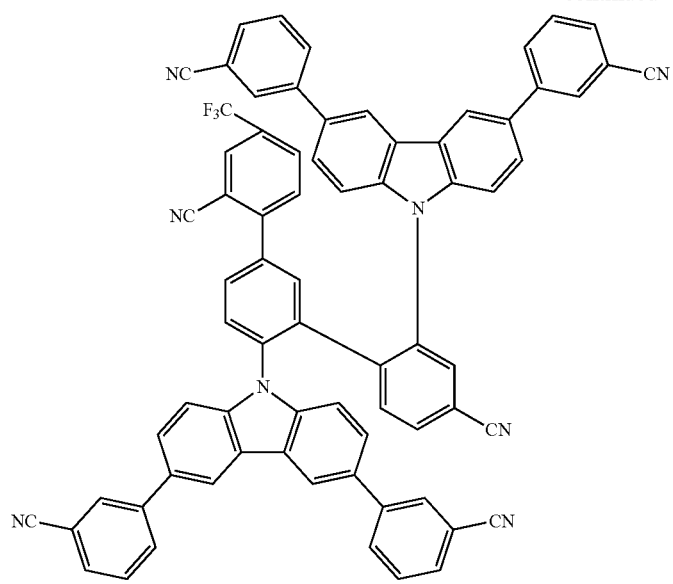
334
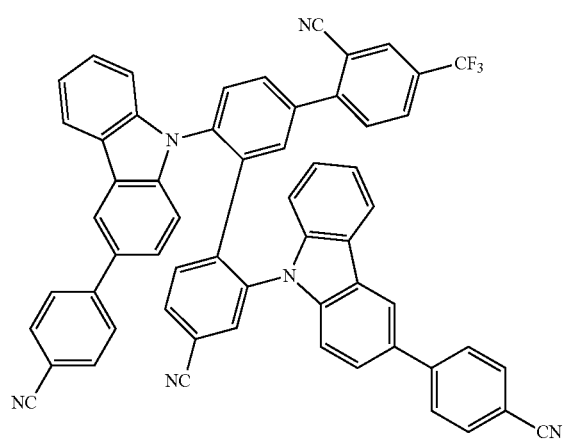 [SMILES: N#Cc1ccc(-c2ccc3c(c2)c2ccccc2n3-c2ccc(-c3ccc(C(F)(F)F)cc3C#N)cc2-c2ccc(C#N)cc2-n2c3ccccc3c3cc(-c4ccc(C#N)cc4)ccc32)cc1]

335
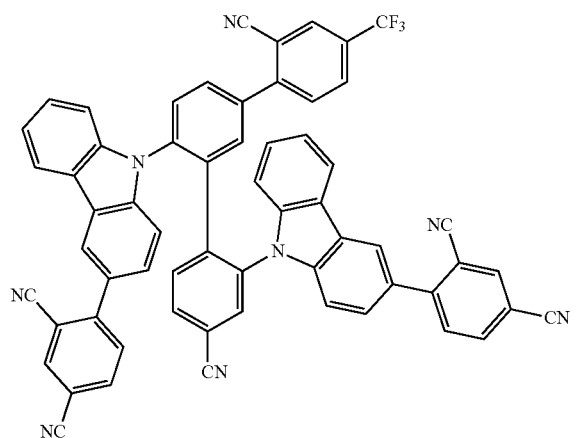
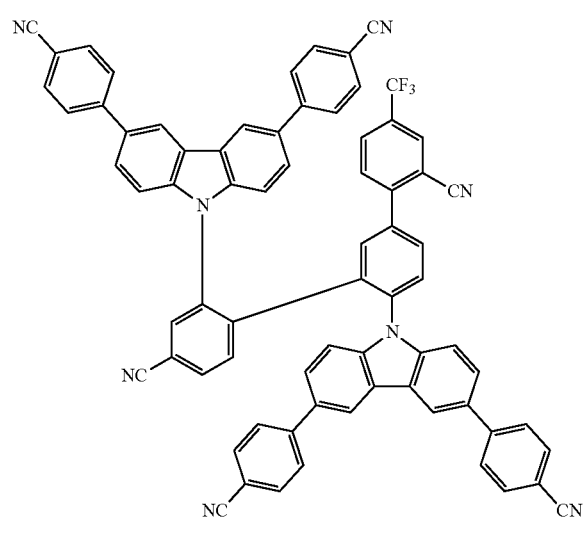
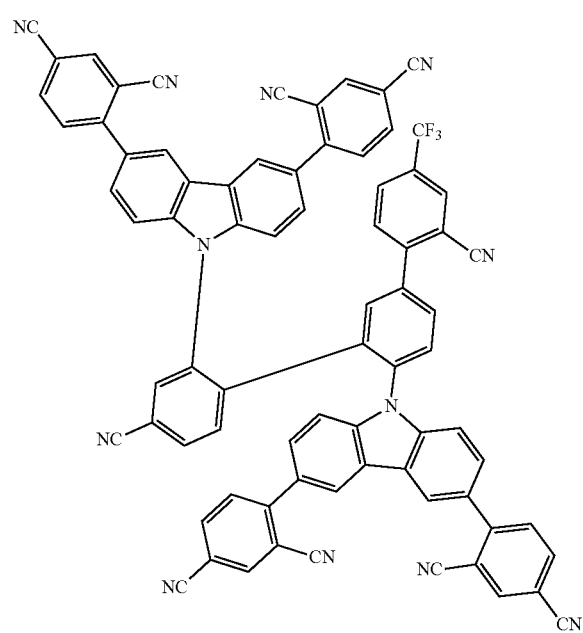
336
-continued
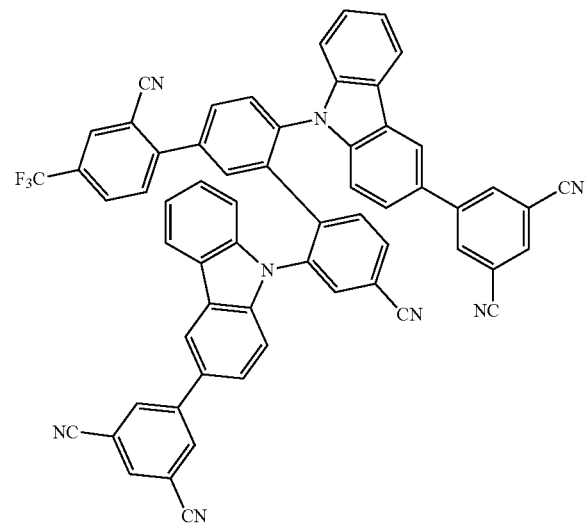
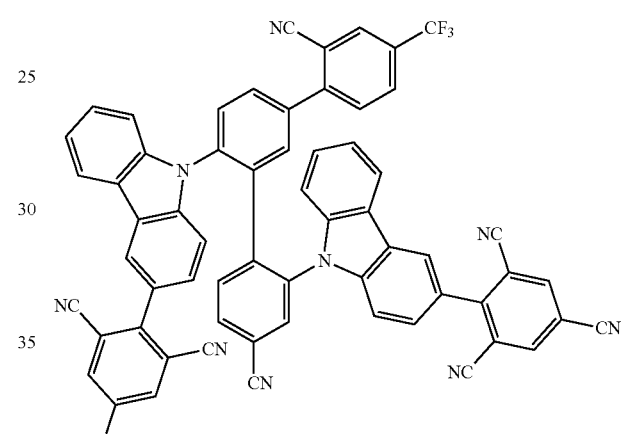
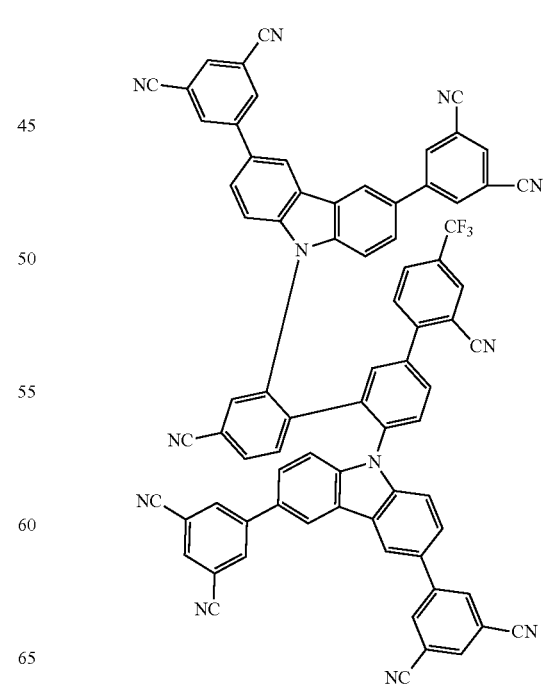

337
-continued
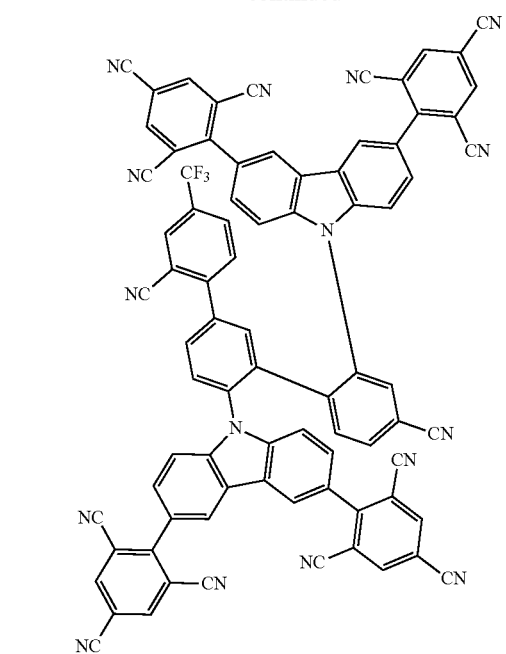
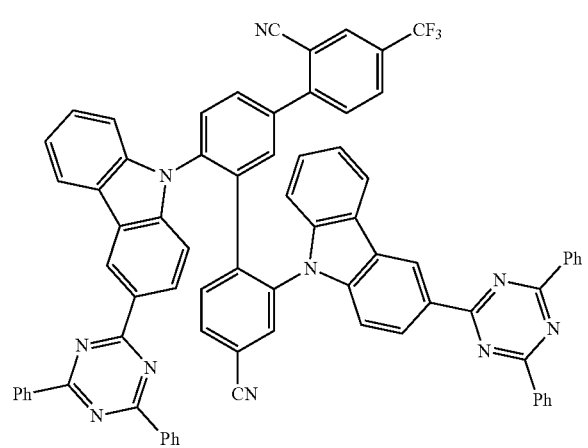
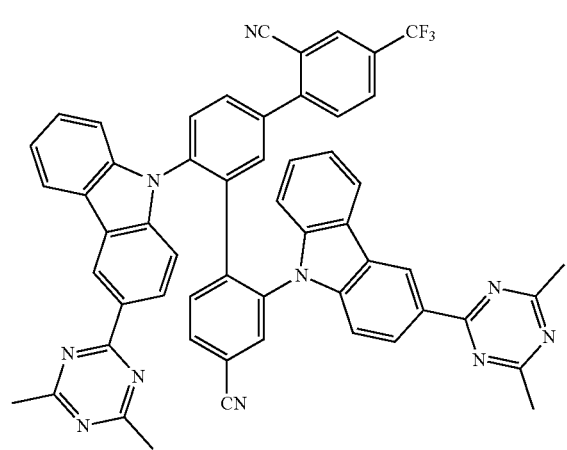
338
-continued
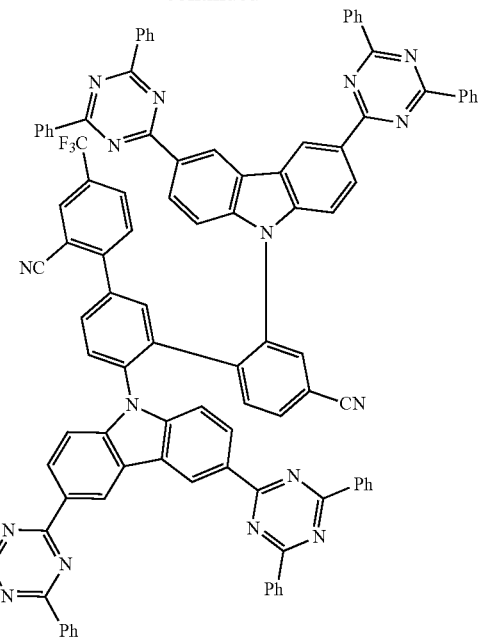
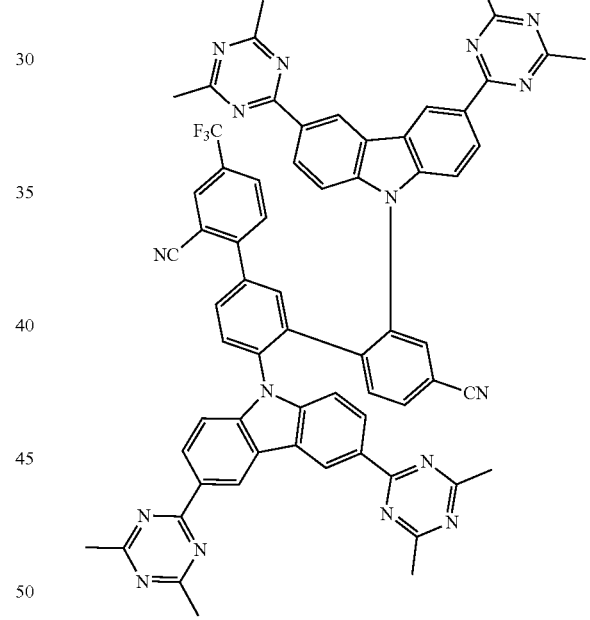
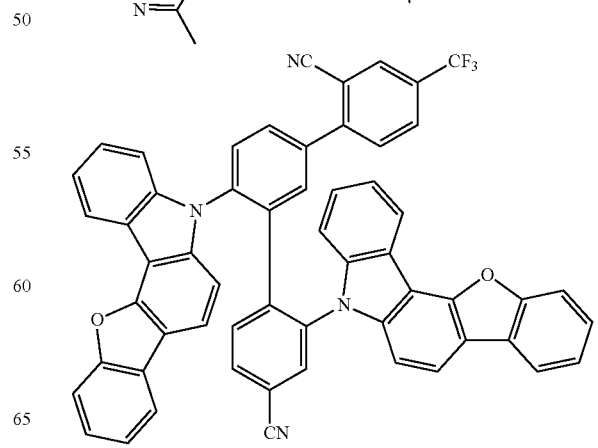

339
-continued
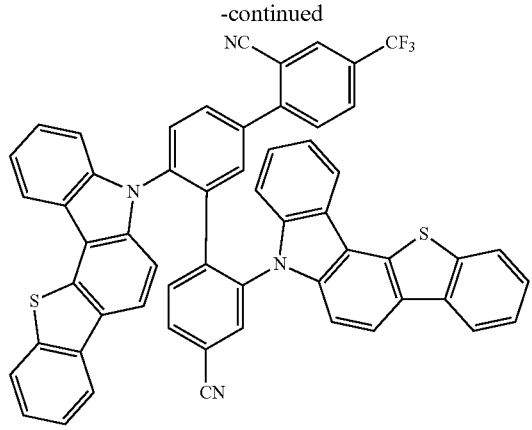
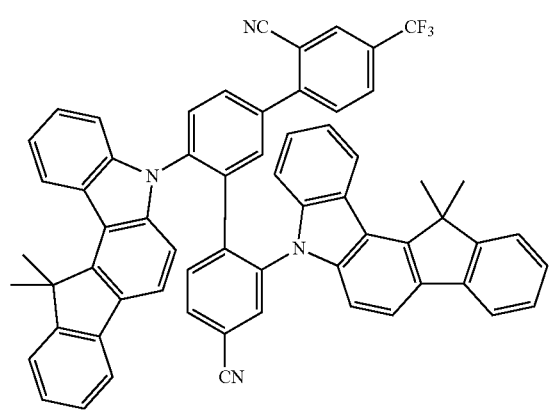
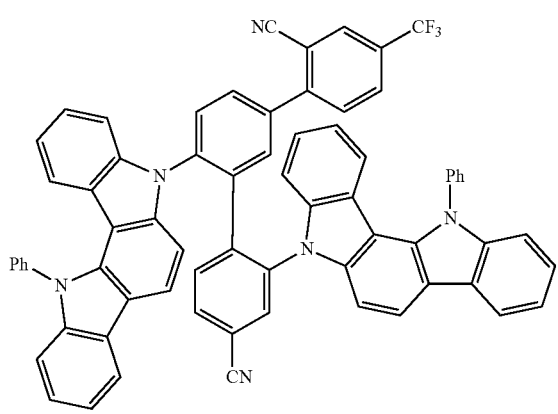
340
-continued
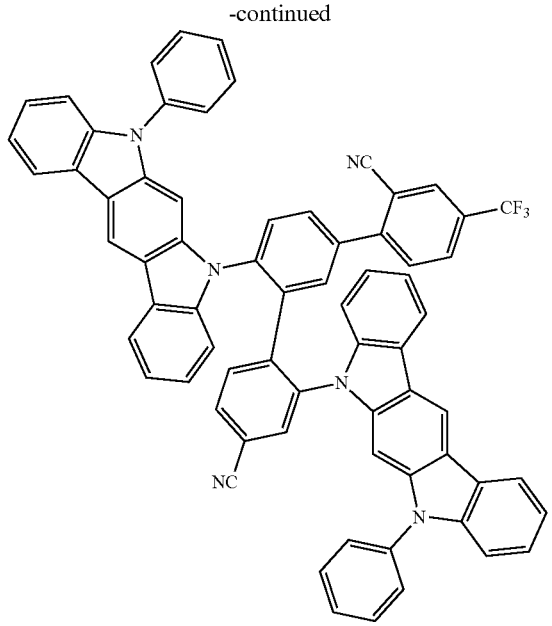
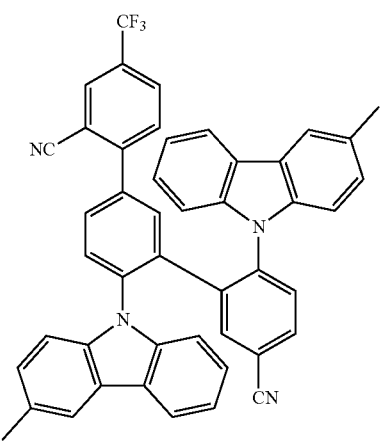
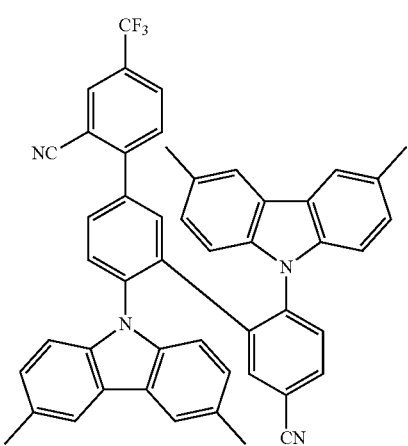

341
-continued
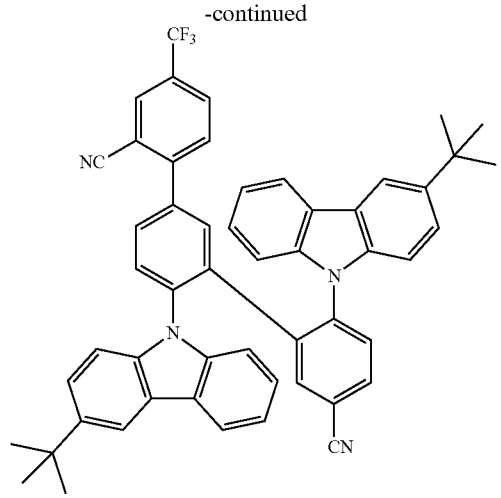
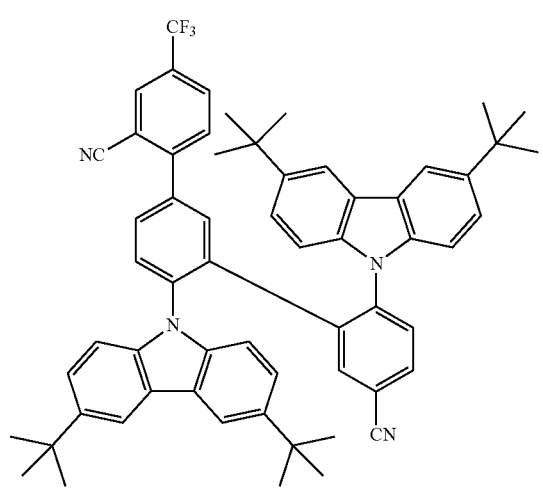
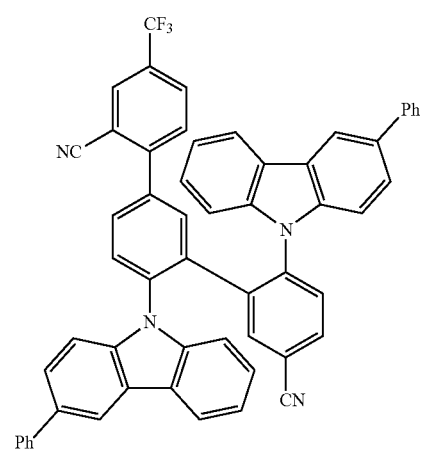
342
-continued
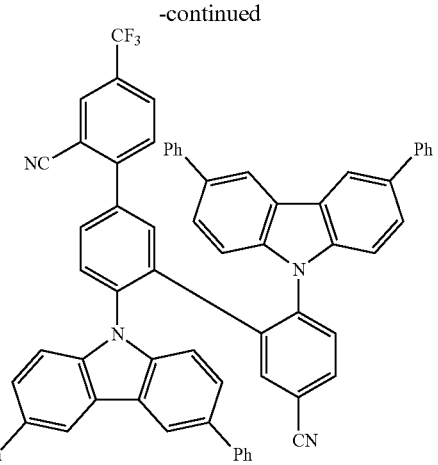
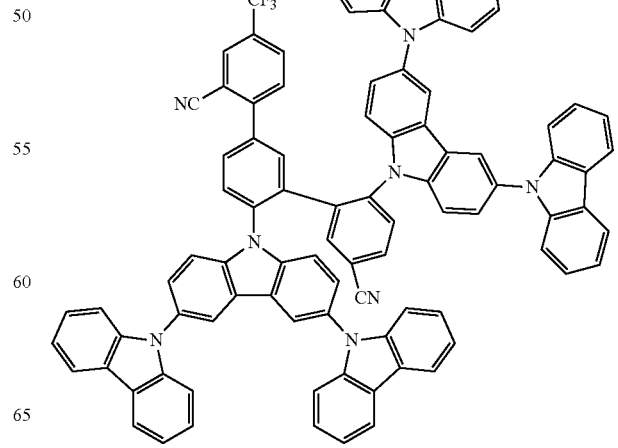

343
-continued
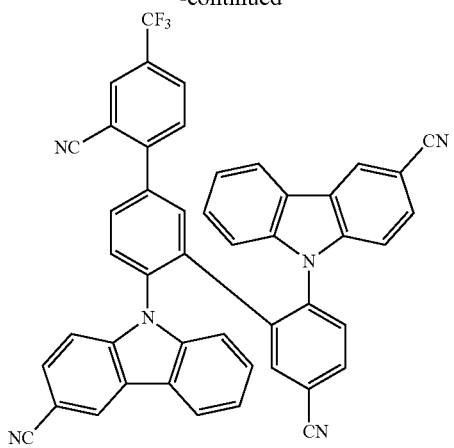
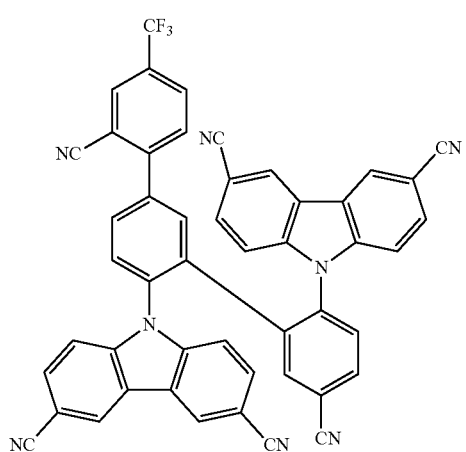
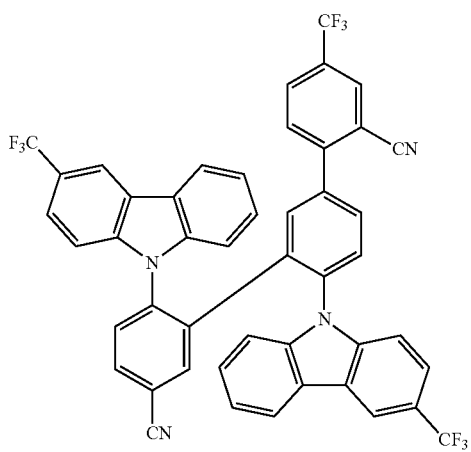
344
-continued
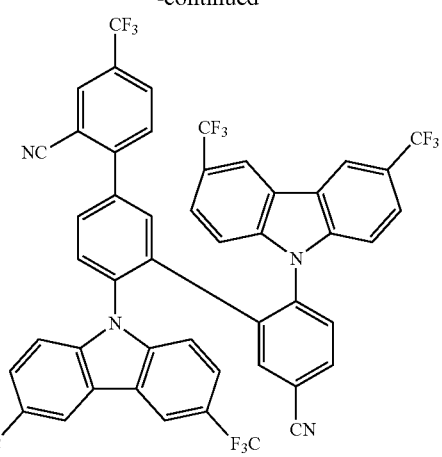
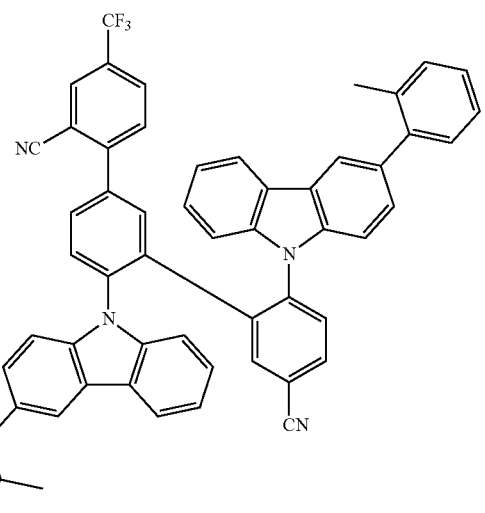
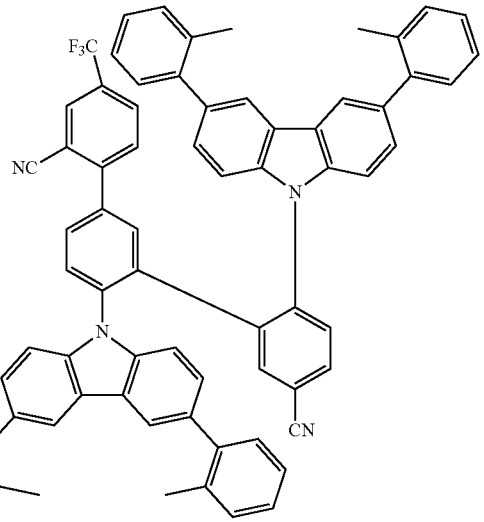

345
-continued
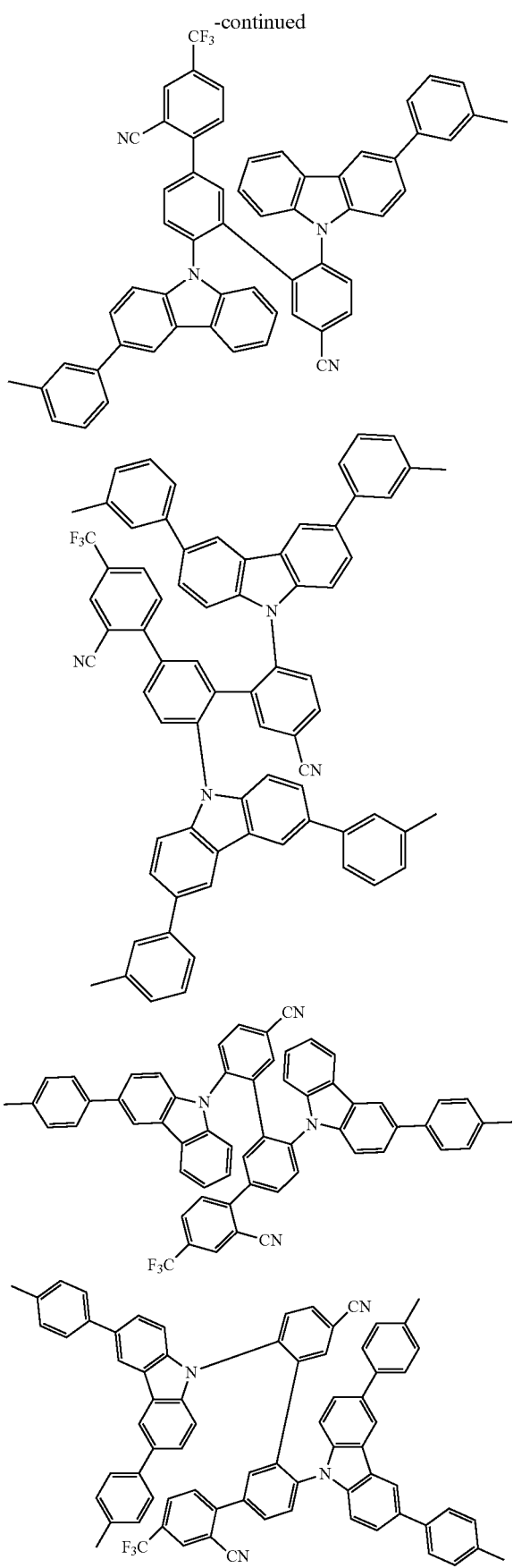
346
-continued
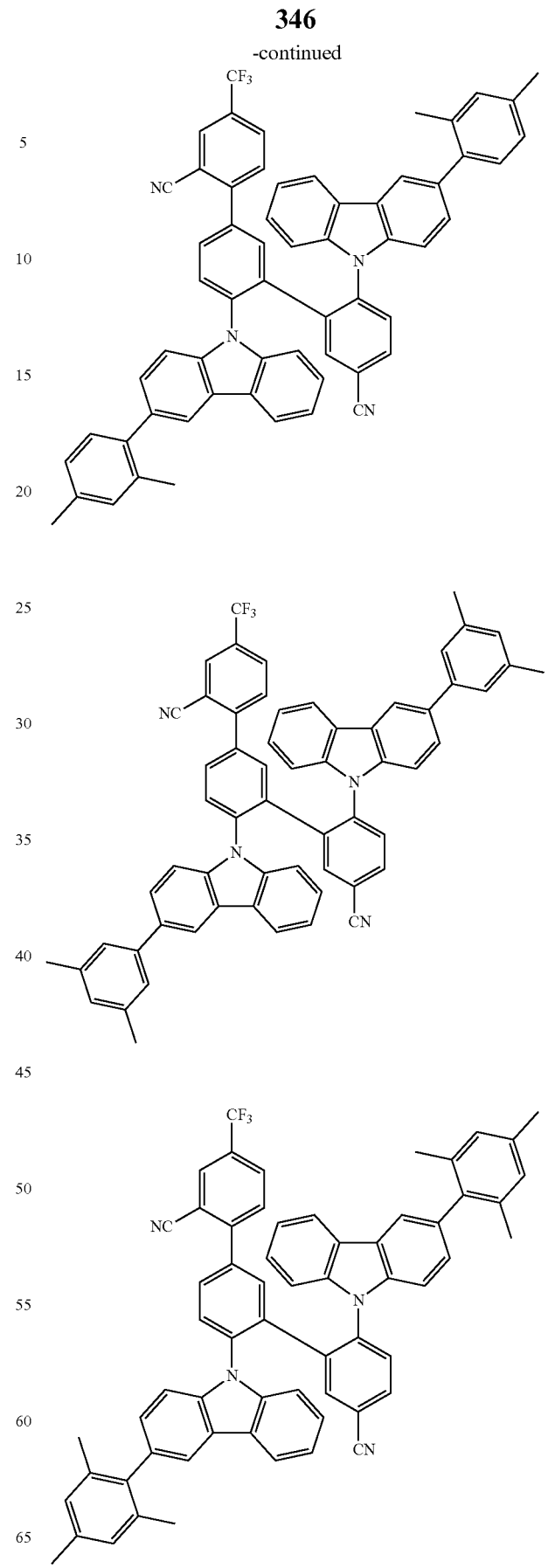

347
-continued
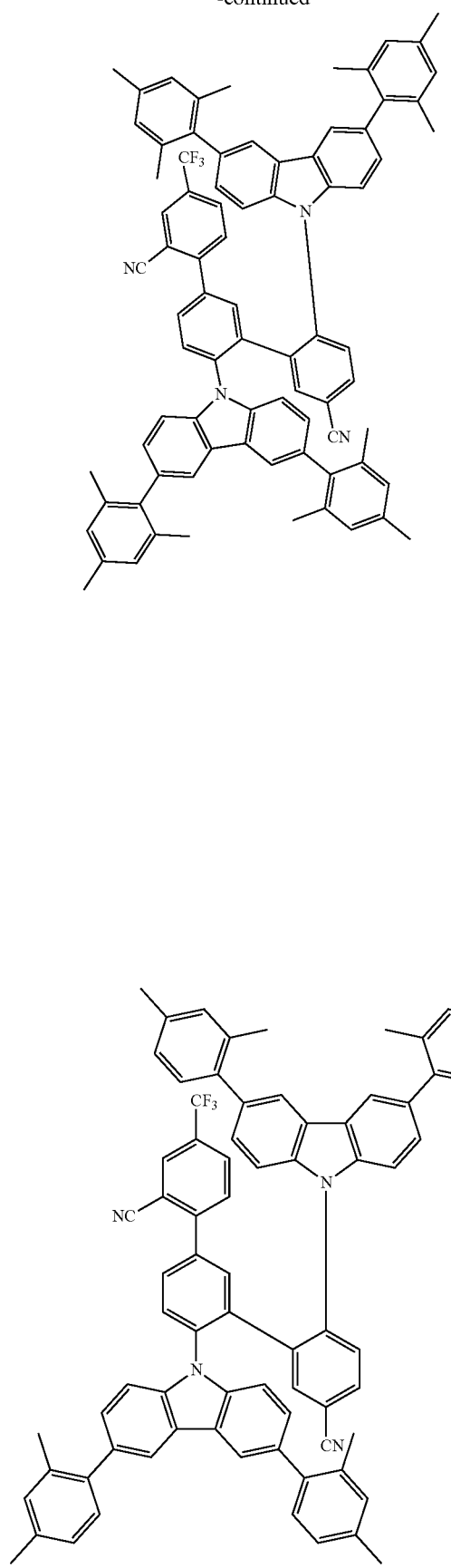
348
-continued
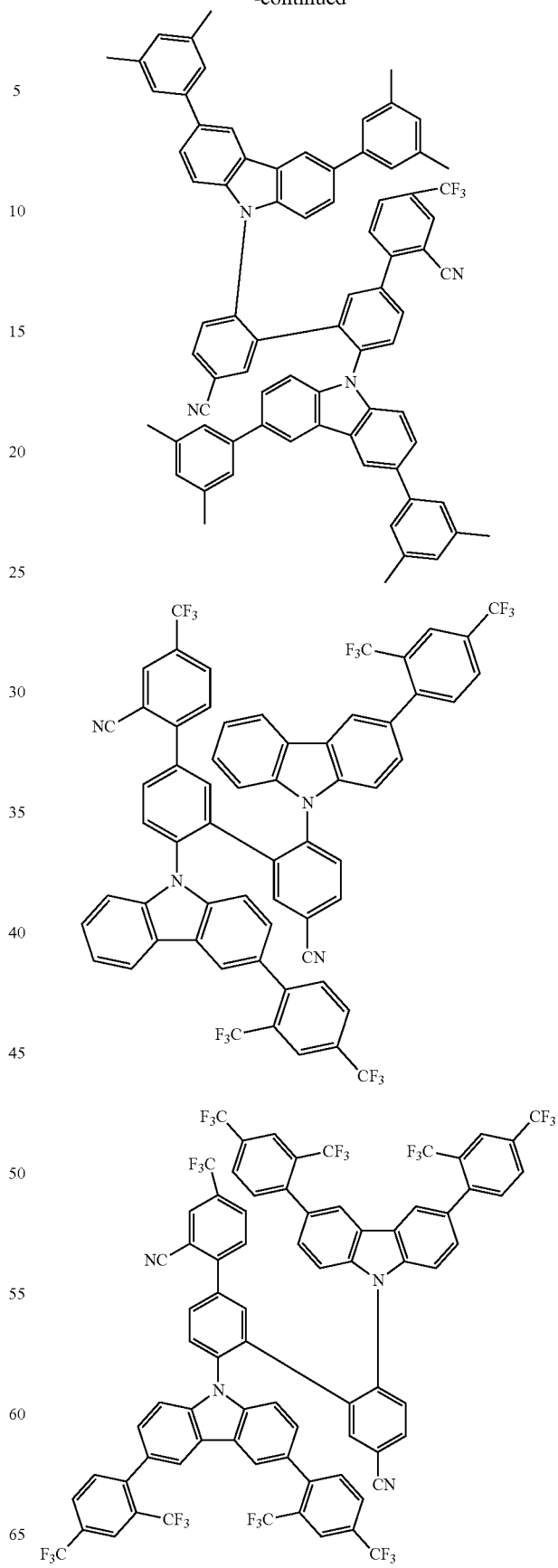

349
-continued
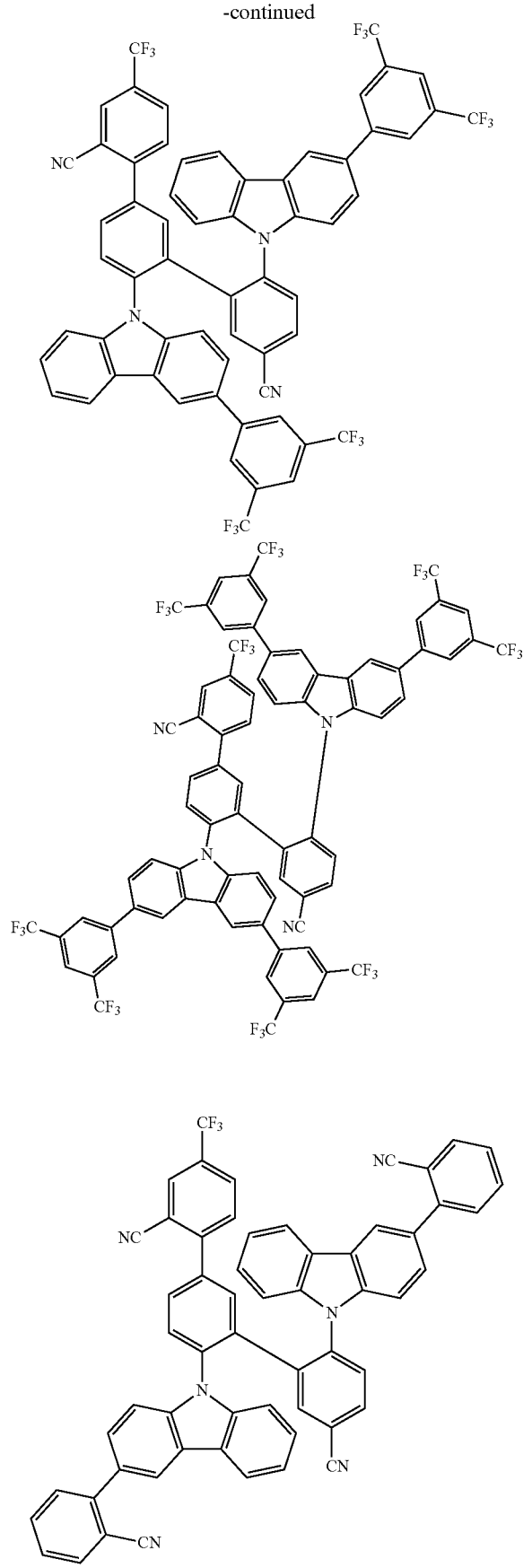
350
-continued
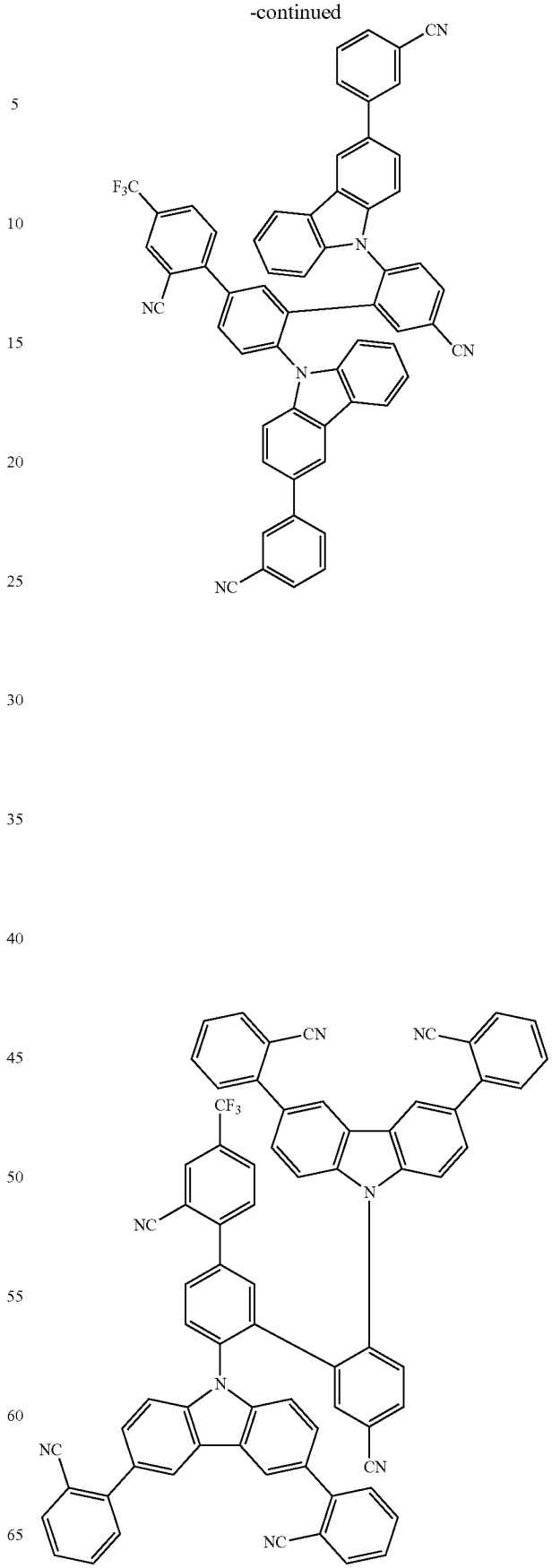

351
-continued
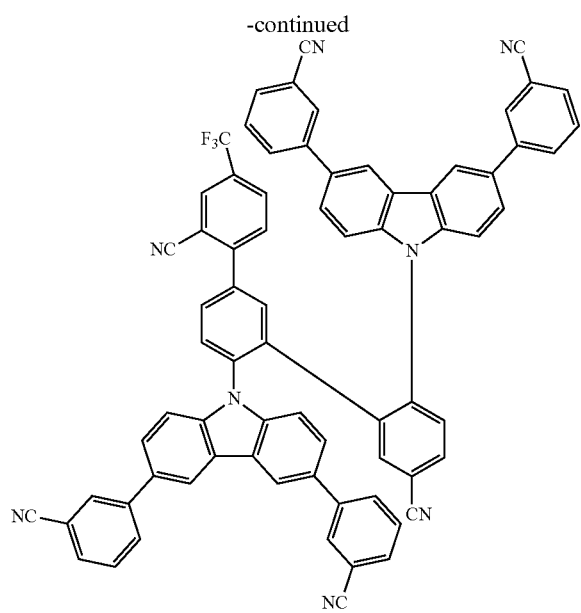
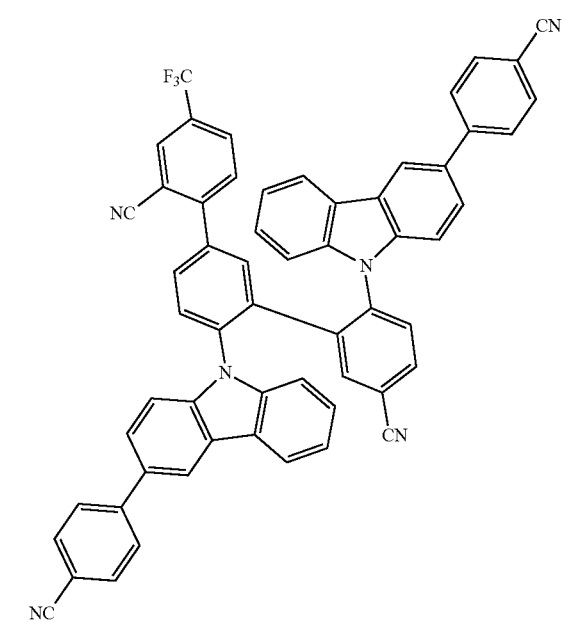
352
-continued
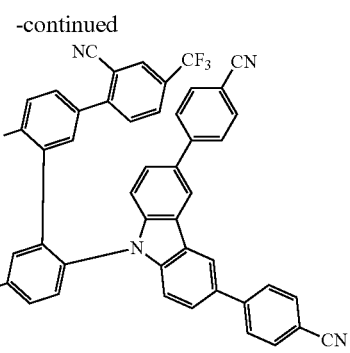
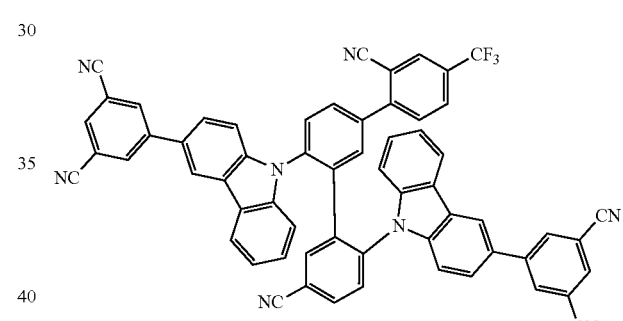
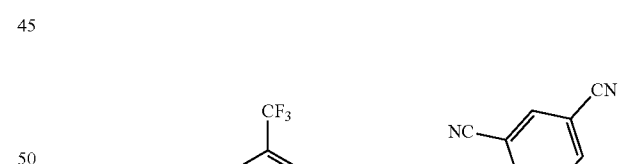
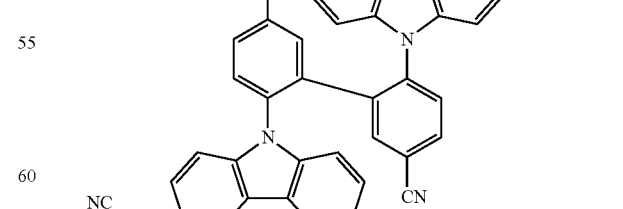
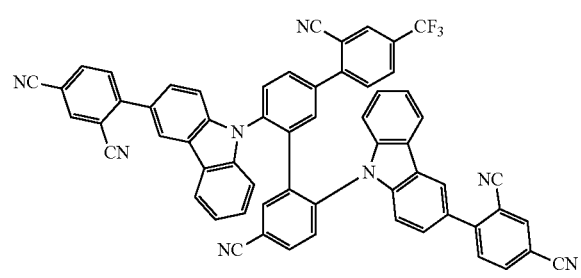
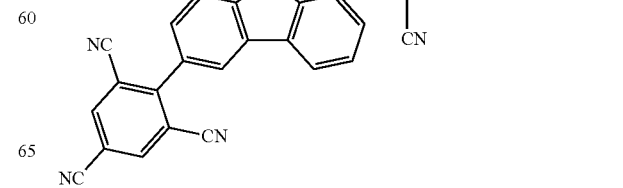

353
-continued
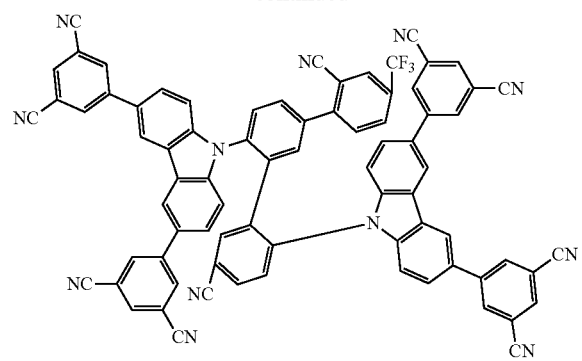
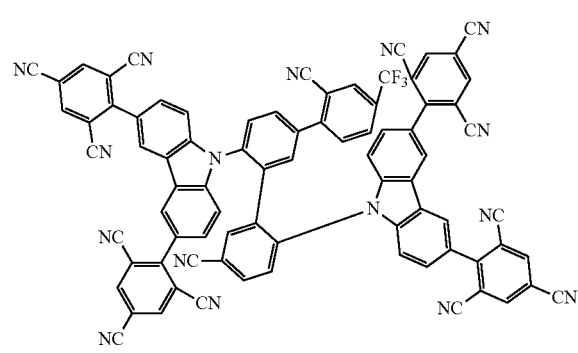
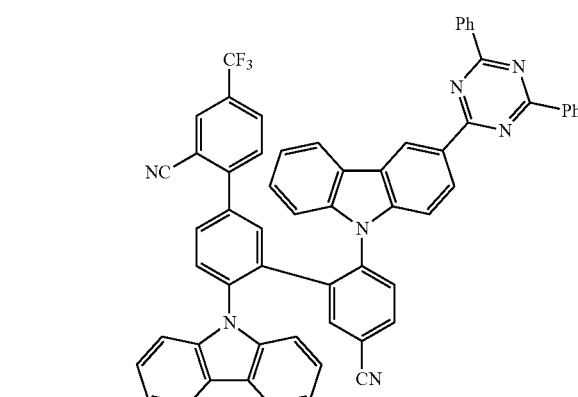
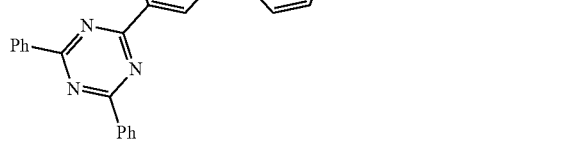
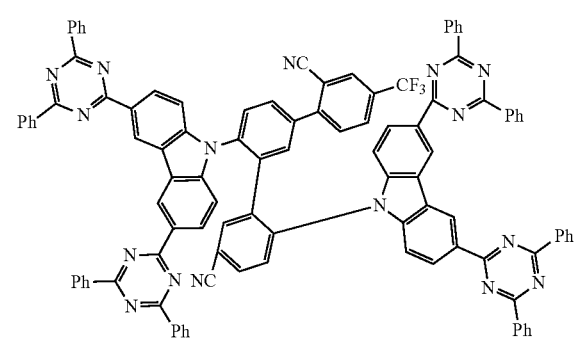
354
-continued
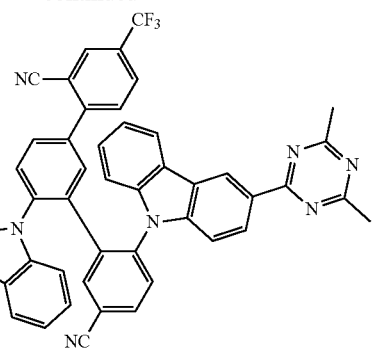
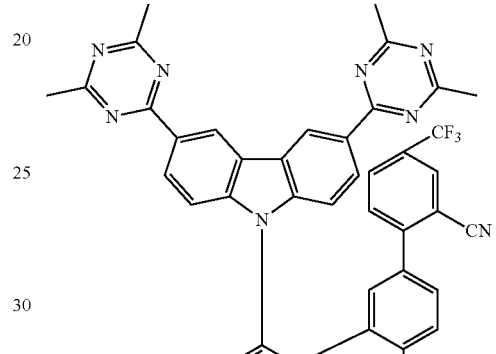
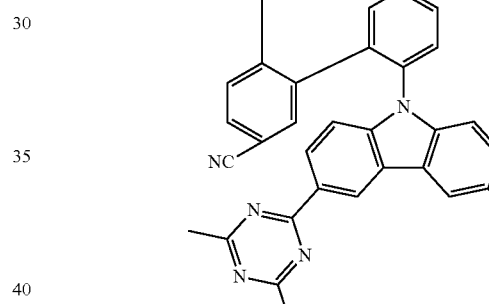
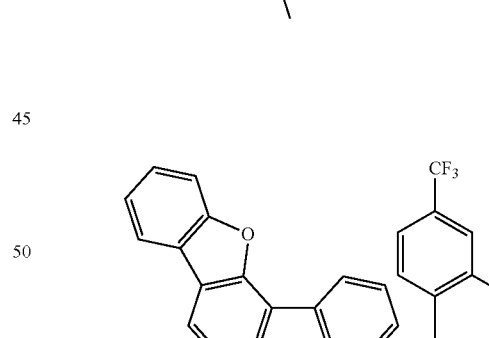
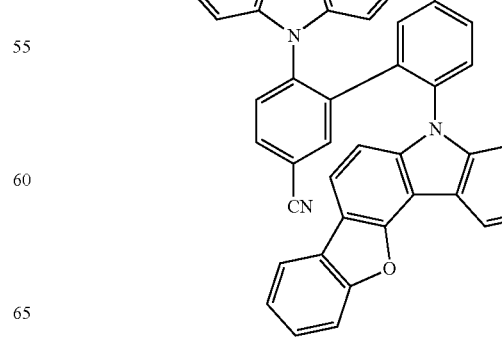

355
-continued
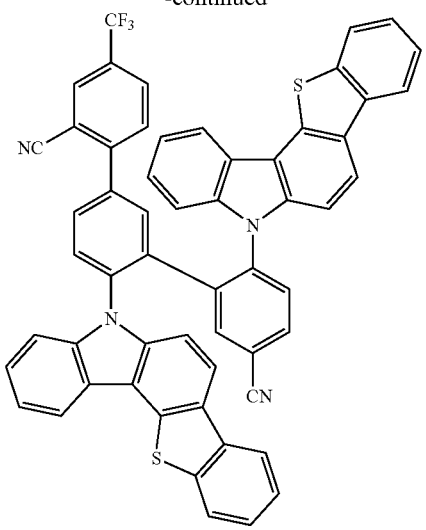
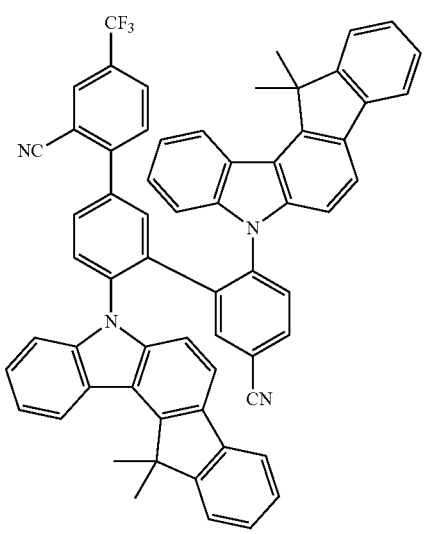
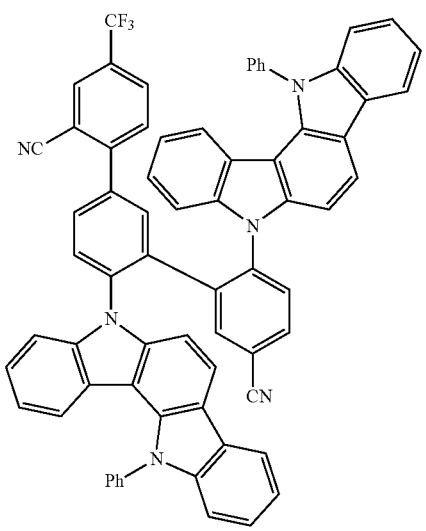
356
-continued
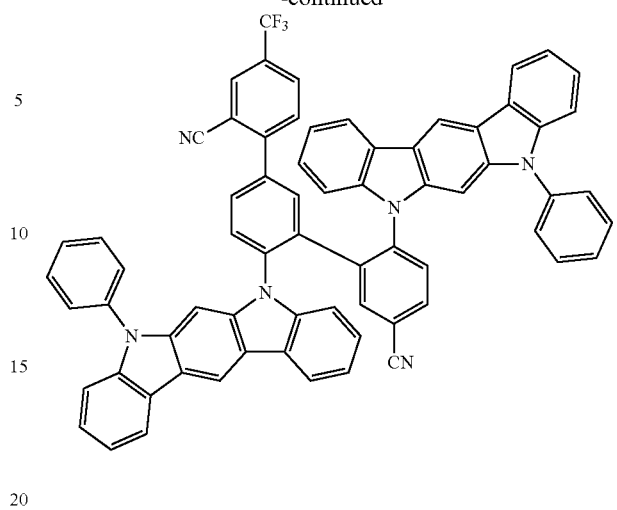
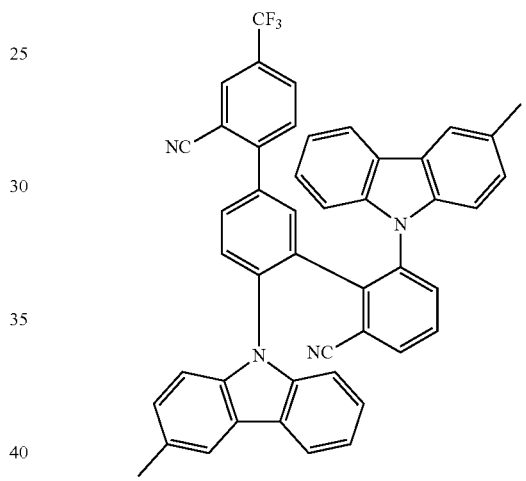
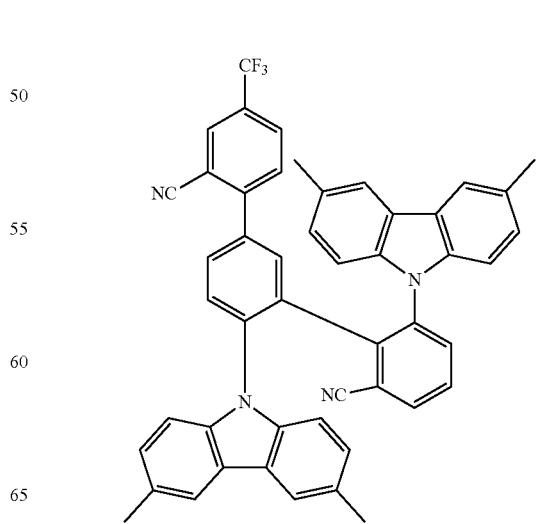

357
-continued
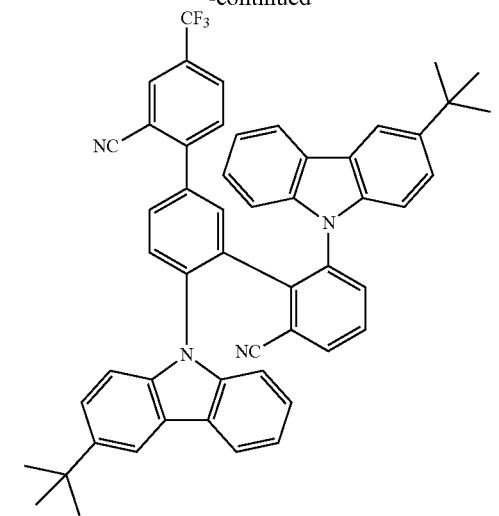
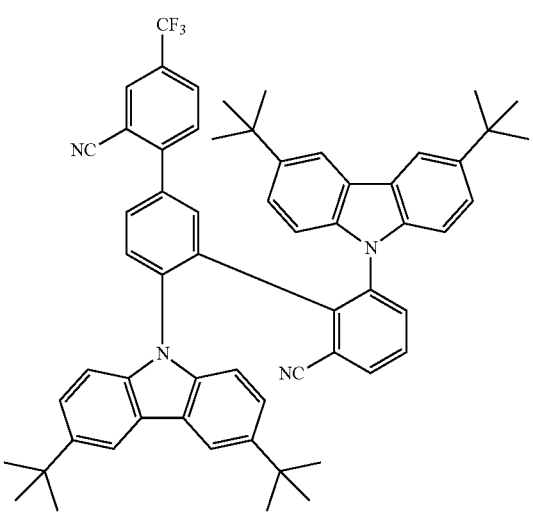
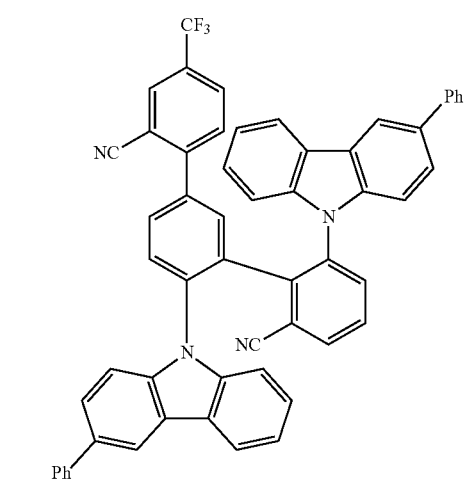
358
-continued
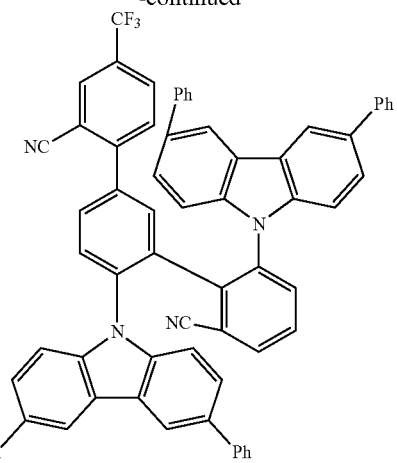
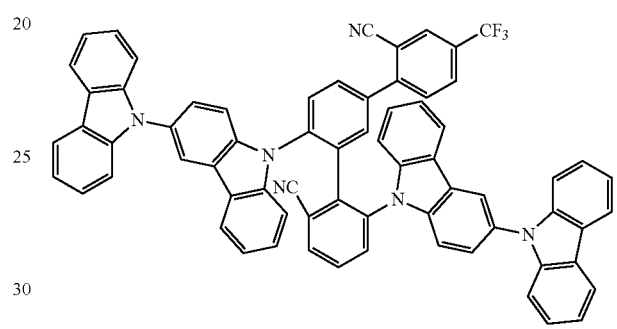
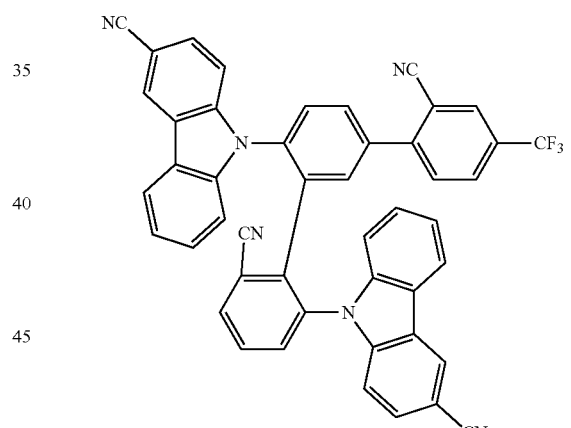
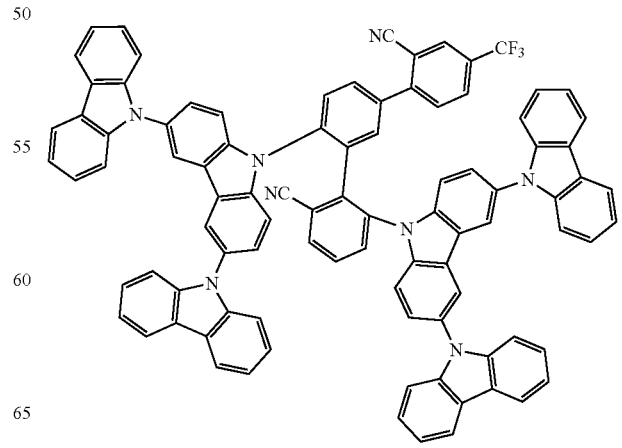

359
-continued
360
-continued
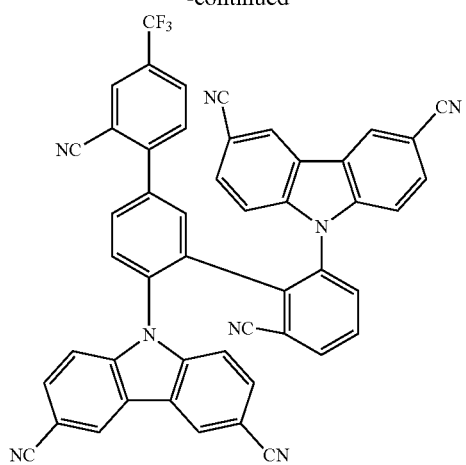
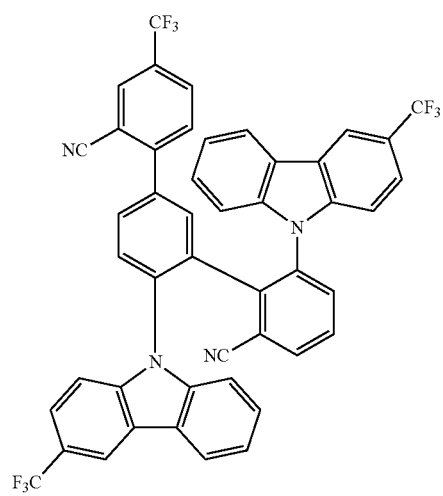
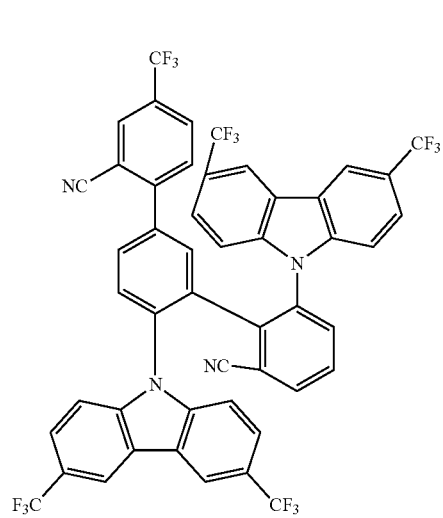
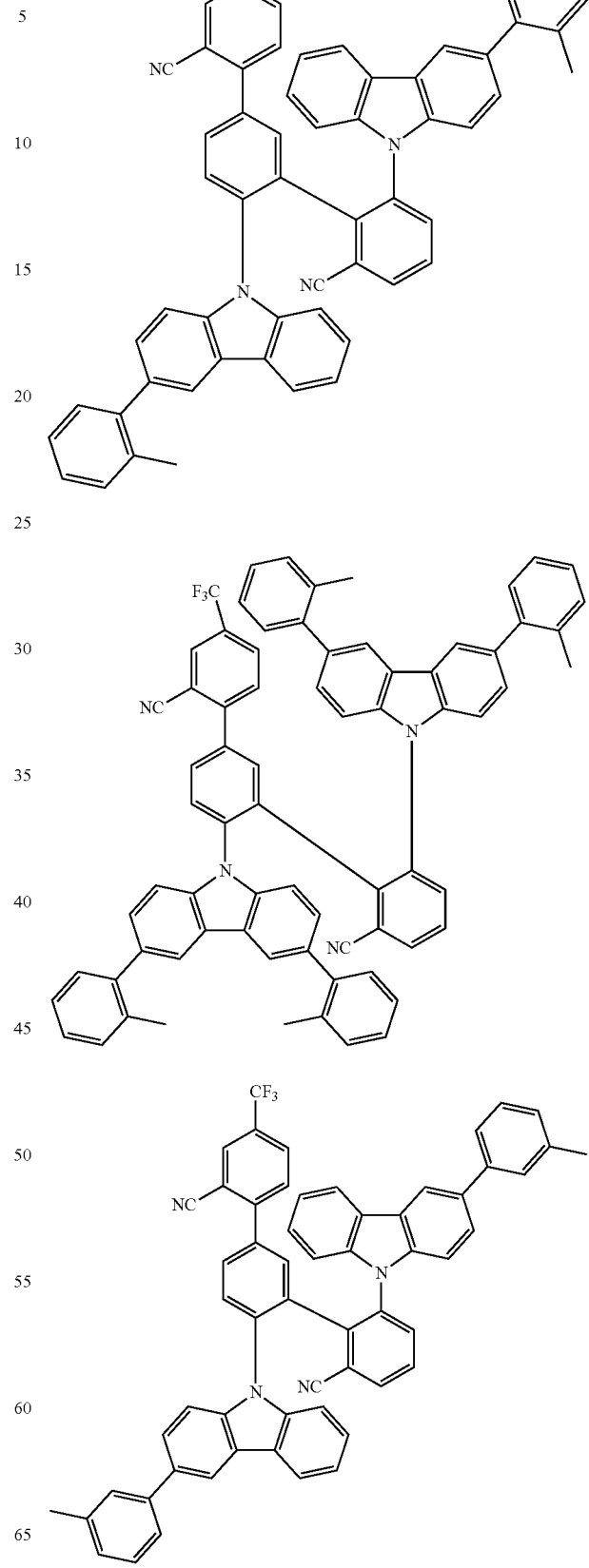

361
-continued
362
-continued
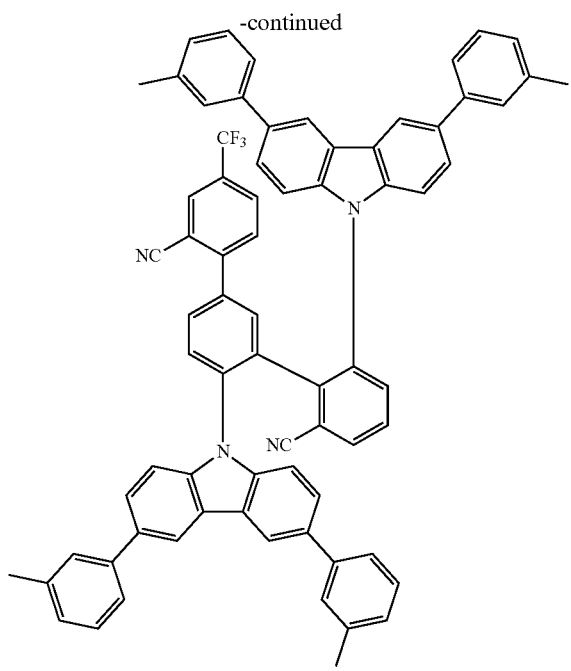
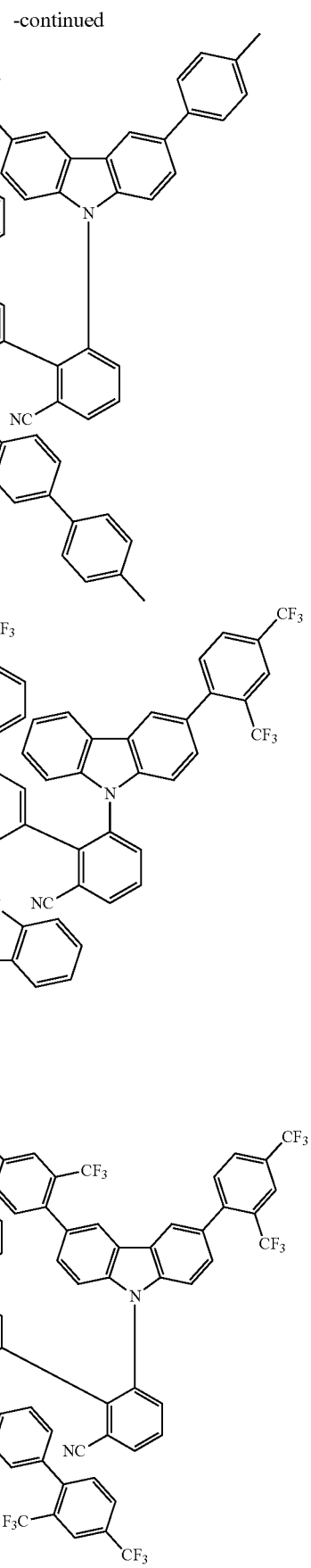
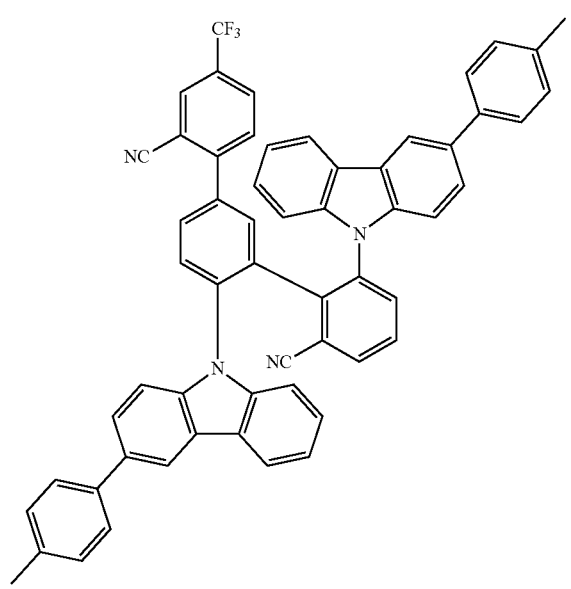

363
-continued
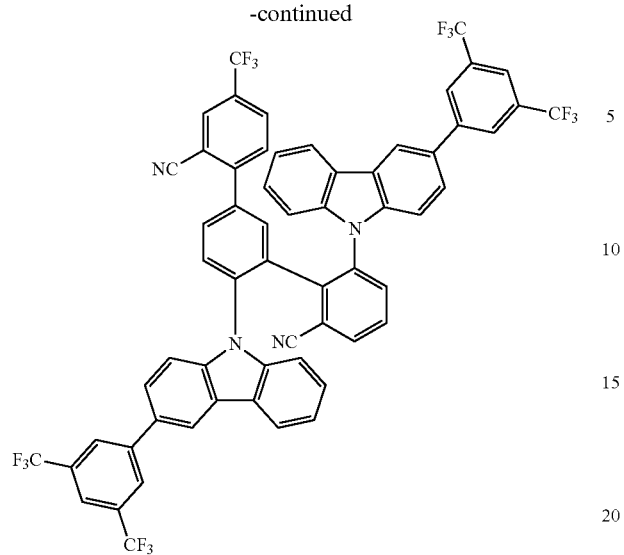
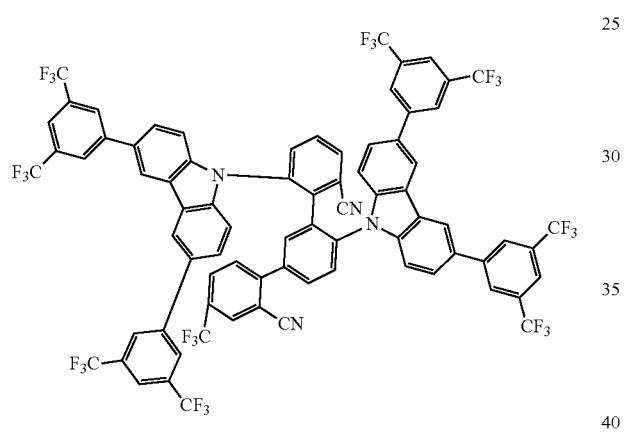
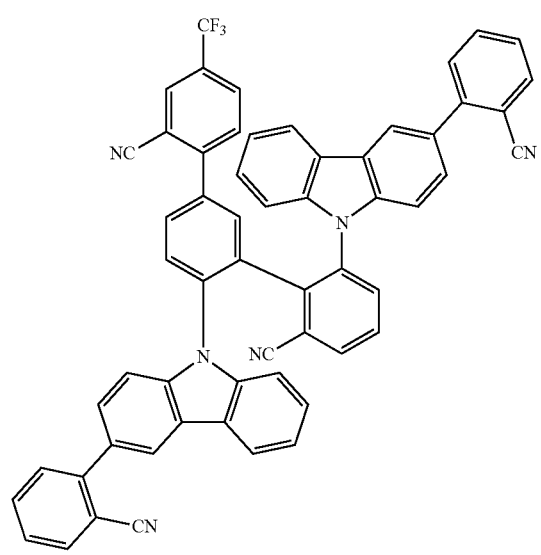
364
-continued
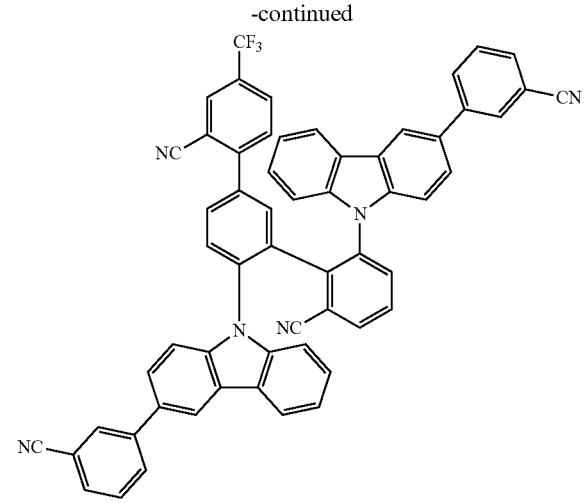
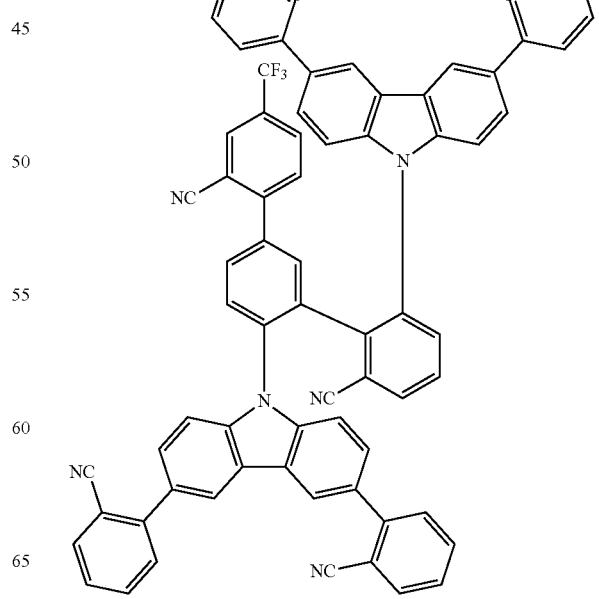

365
-continued
366
-continued
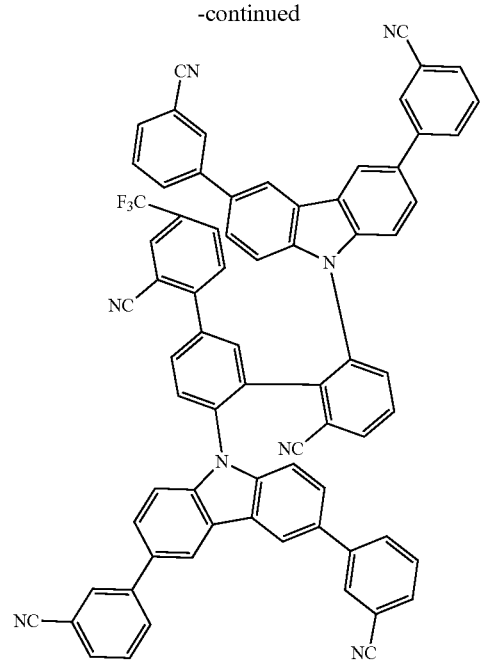
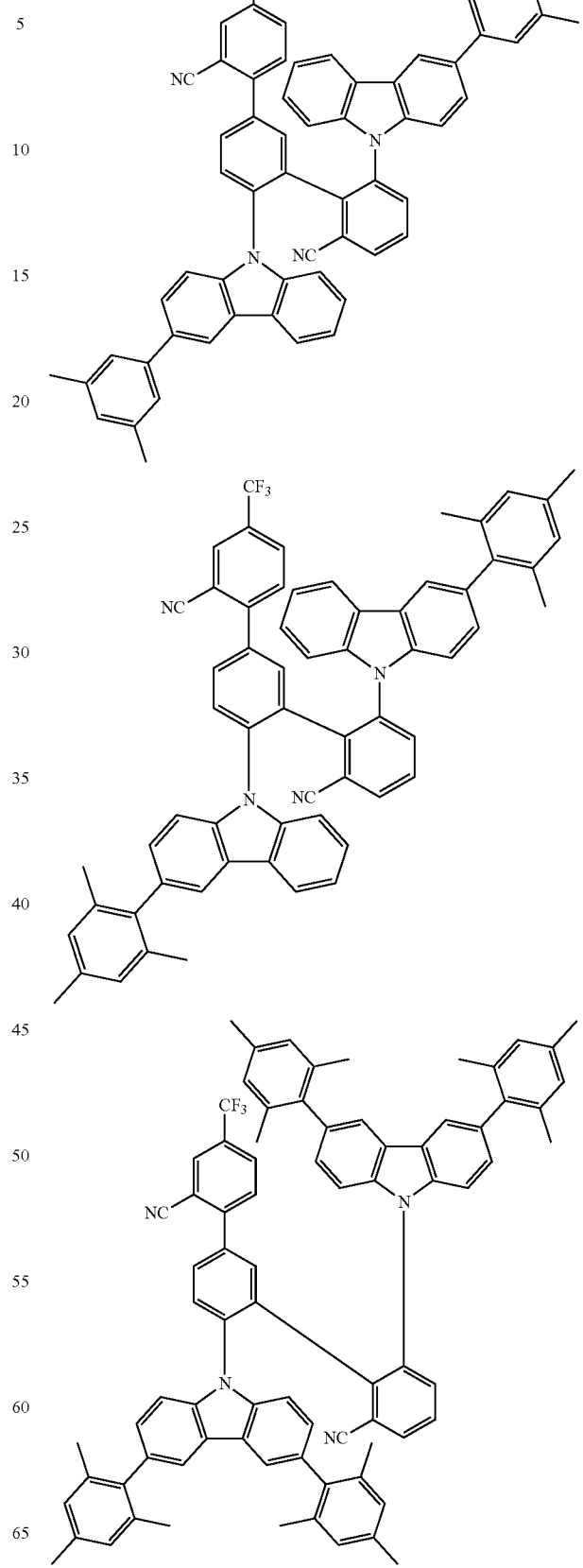

367
-continued
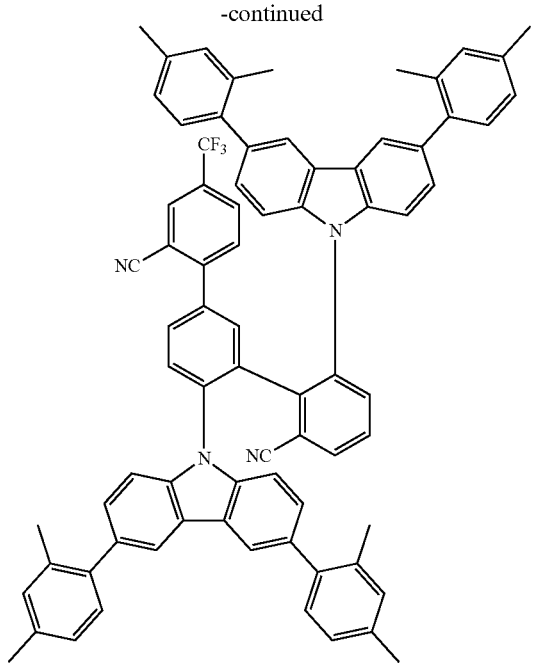
368
-continued
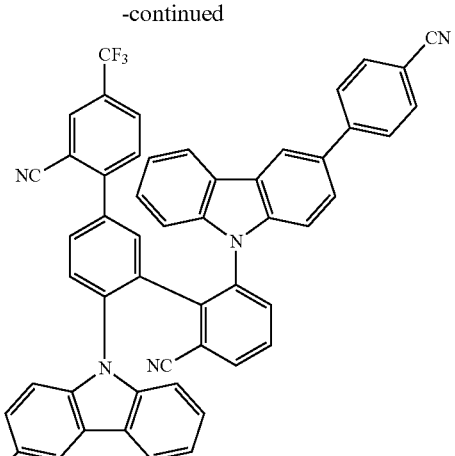
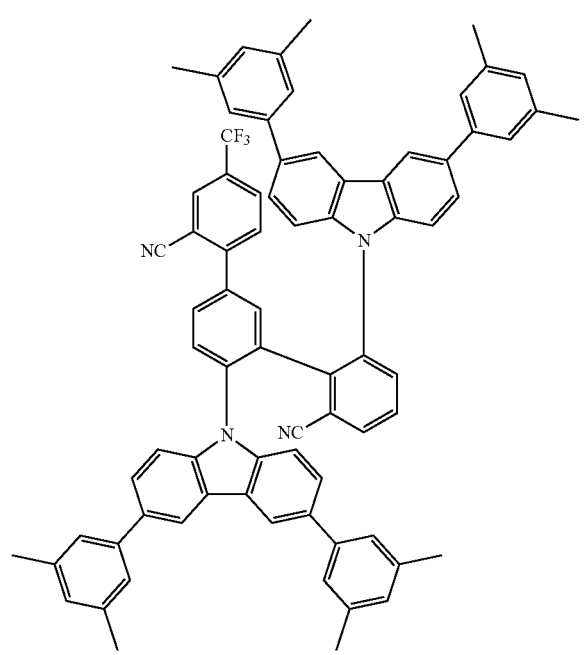
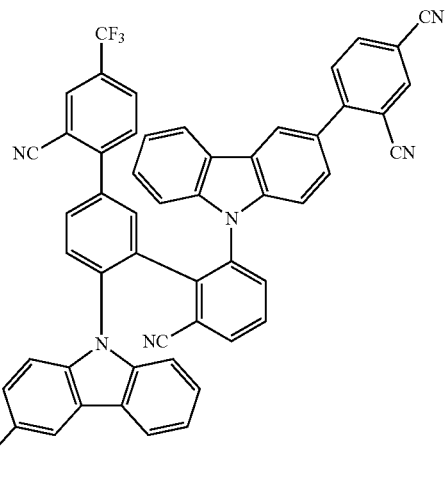

369
-continued
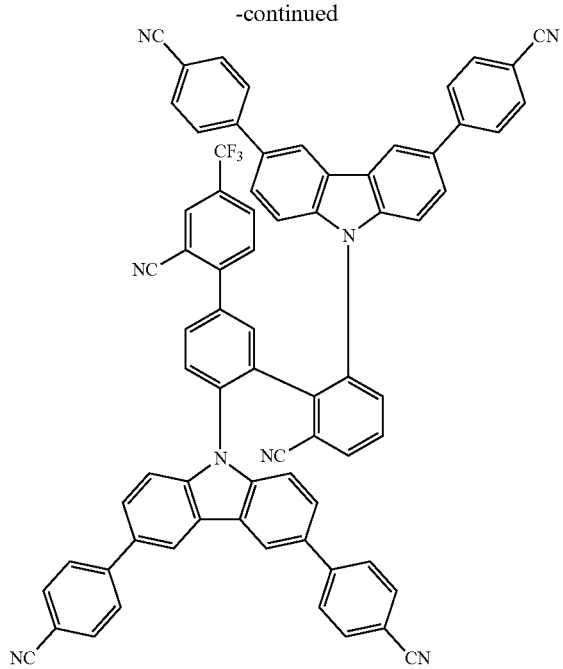
370
-continued
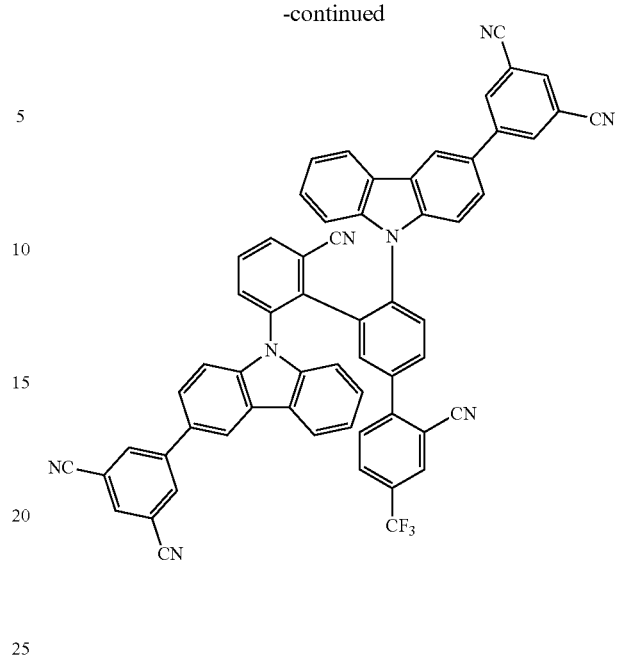
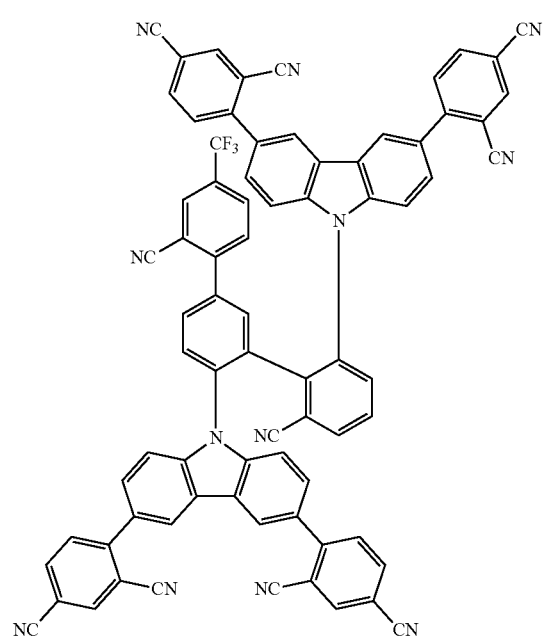
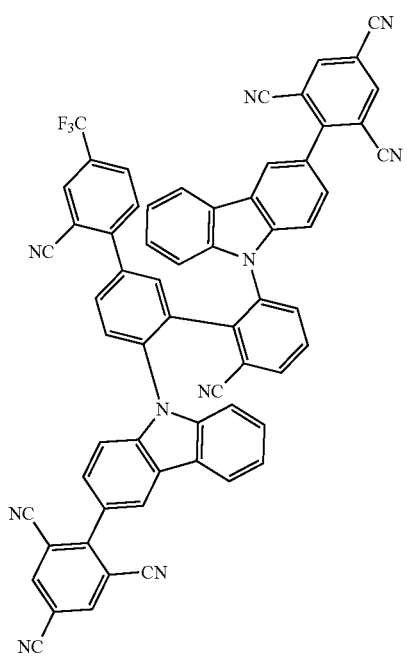

371
-continued
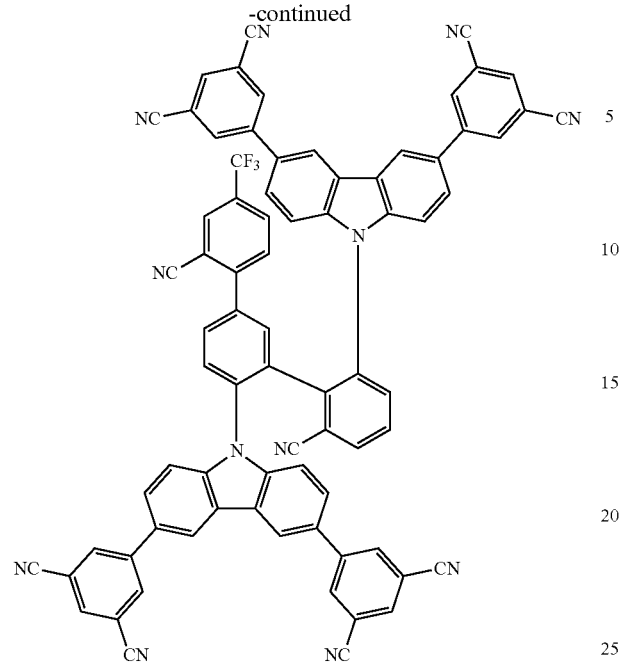
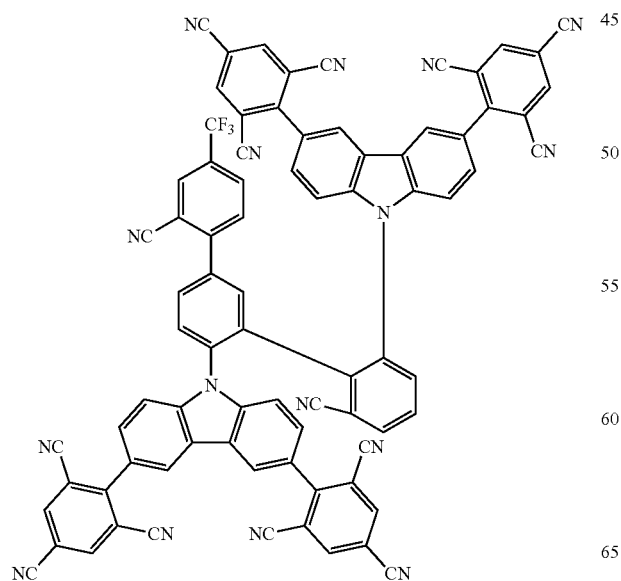
372
-continued
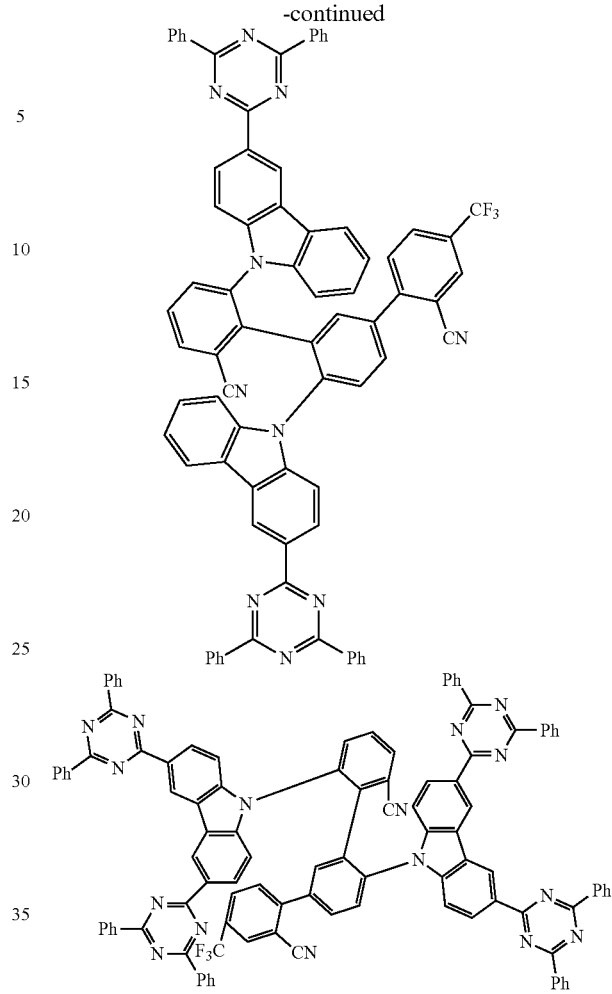
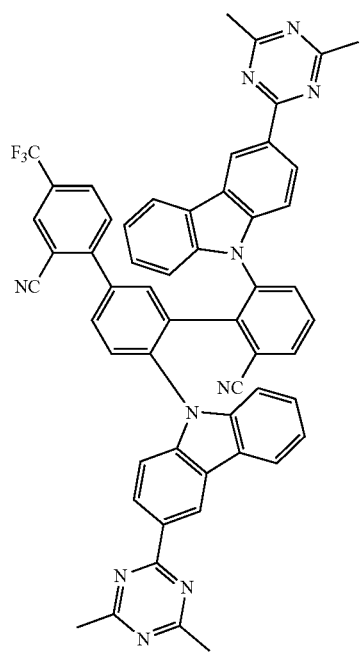

373
-continued
374
-continued
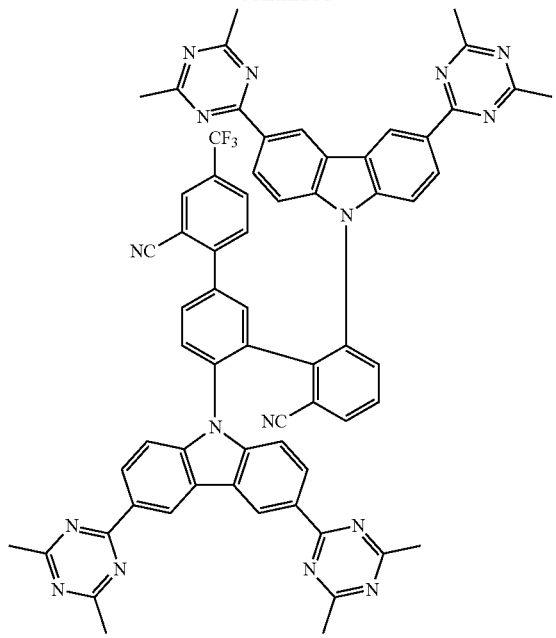
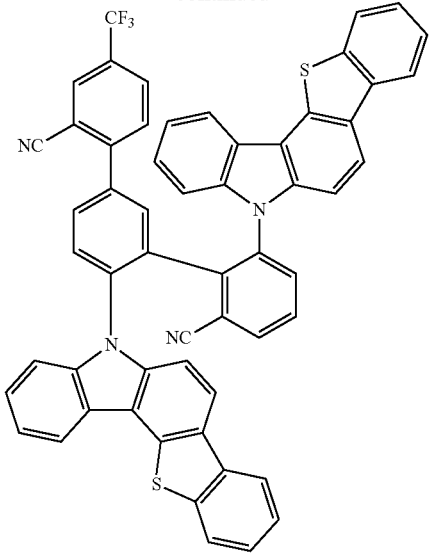
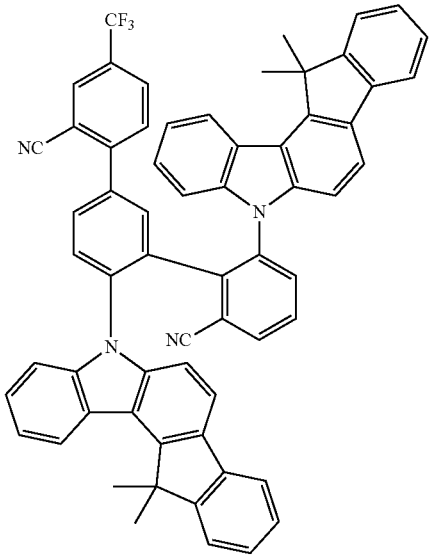
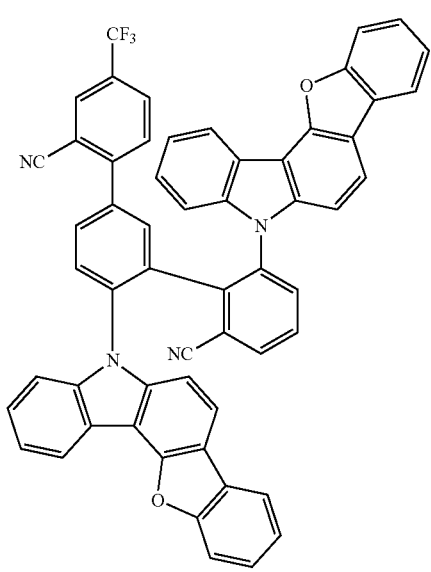
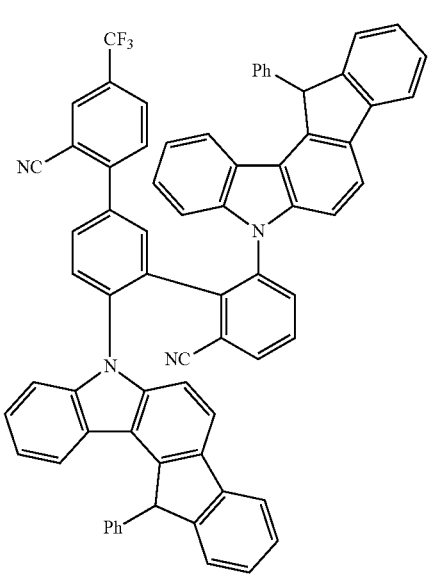

375
-continued
376
-continued
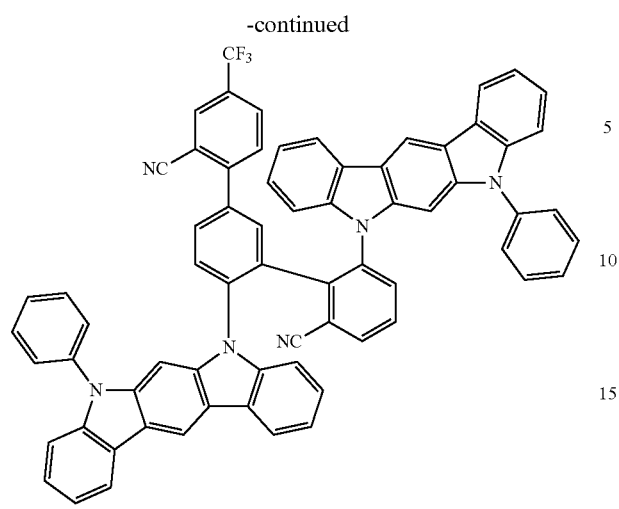
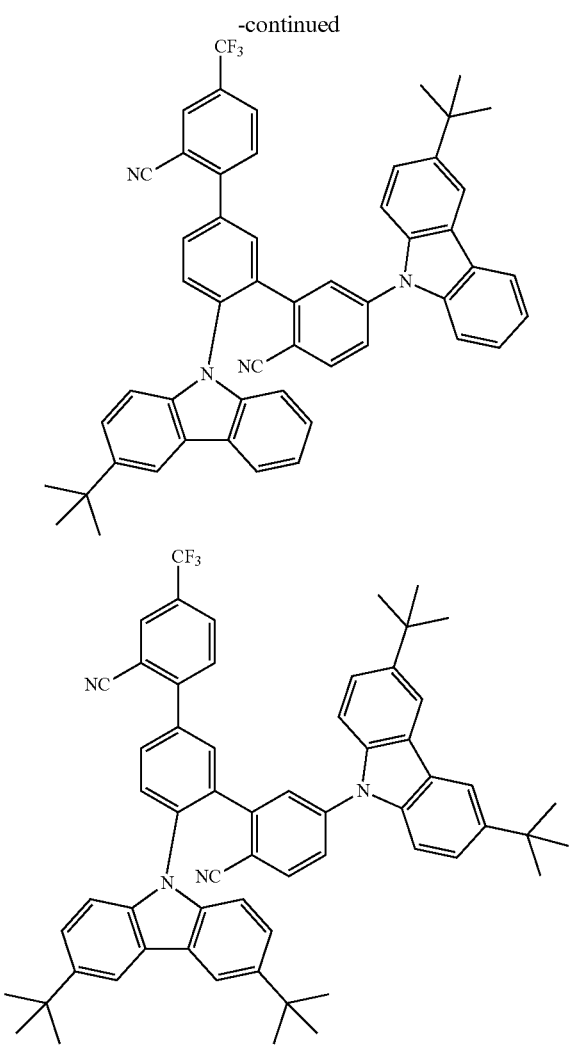
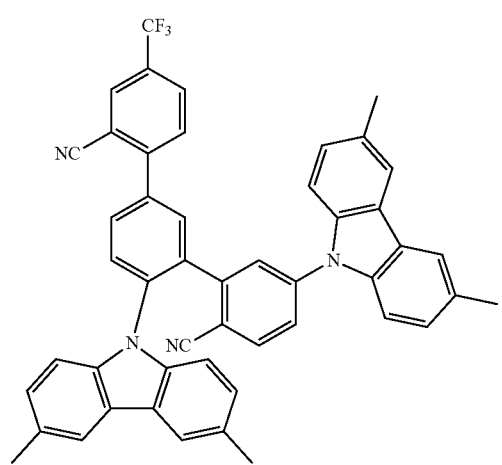
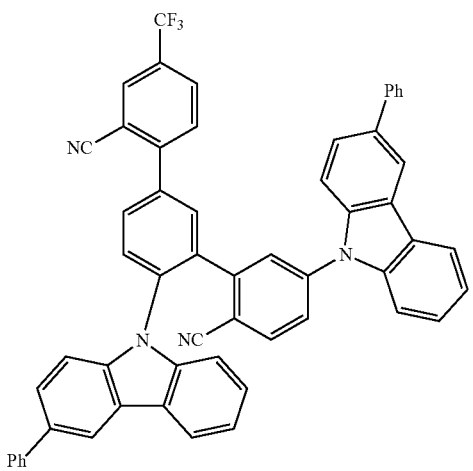

377
-continued
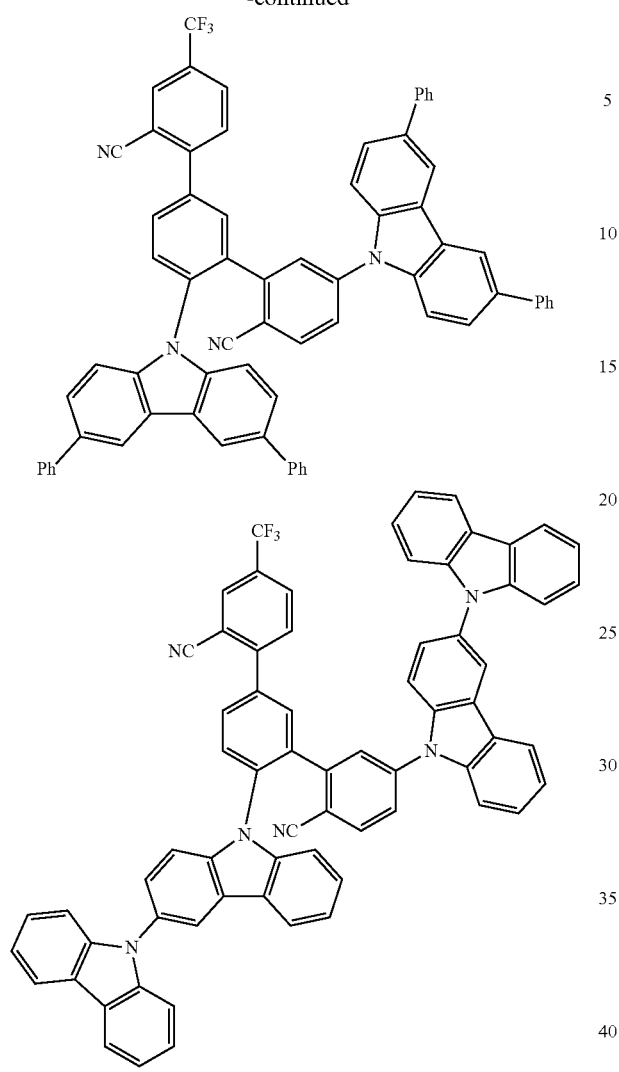
378
-continued
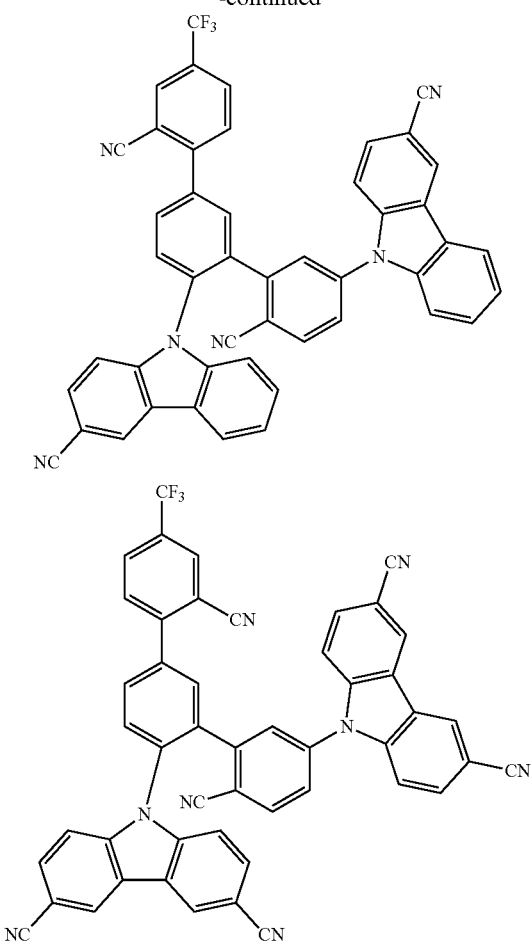
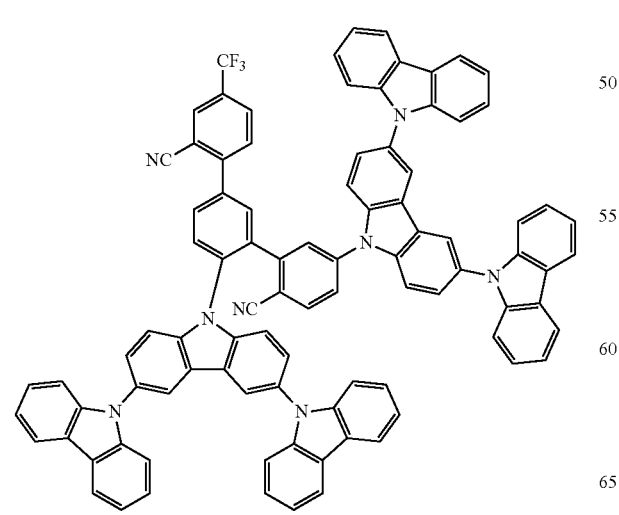
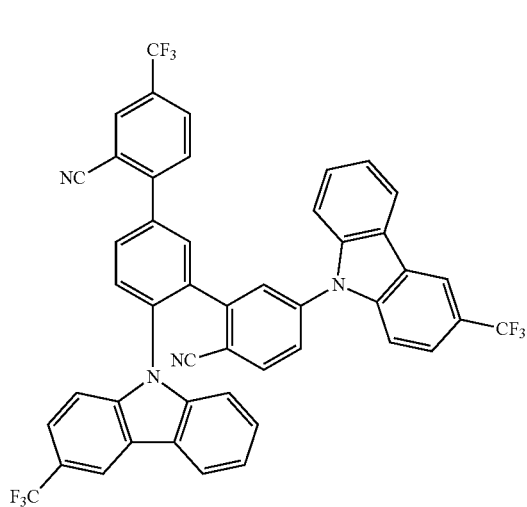

379
-continued
380
-continued
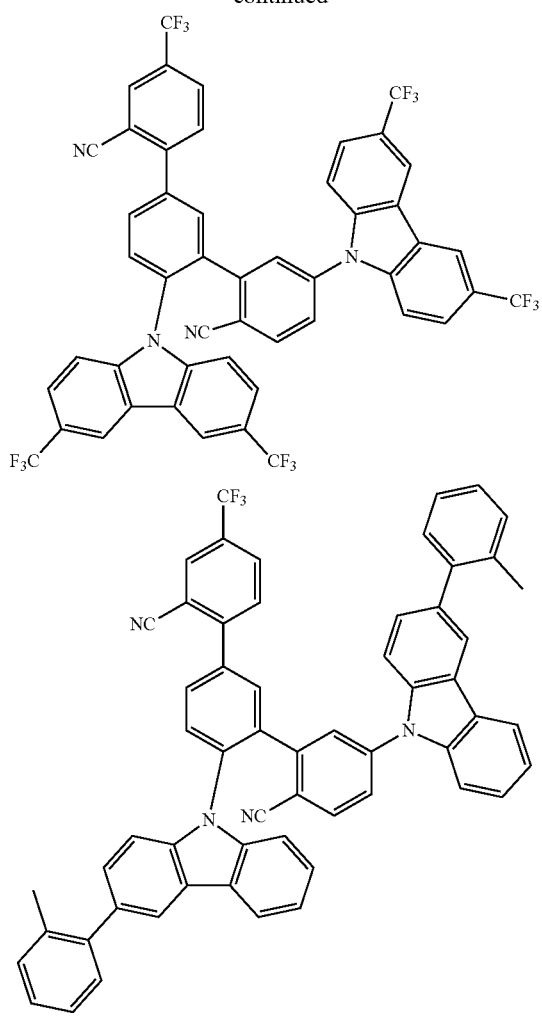
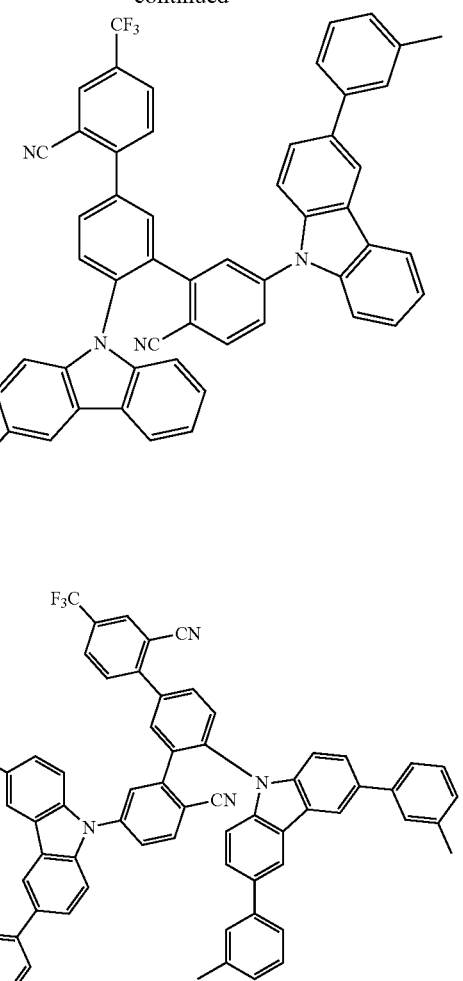
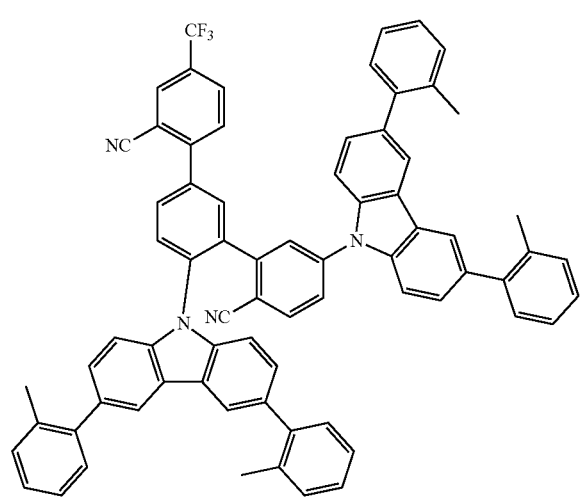

381
-continued
382
-continued
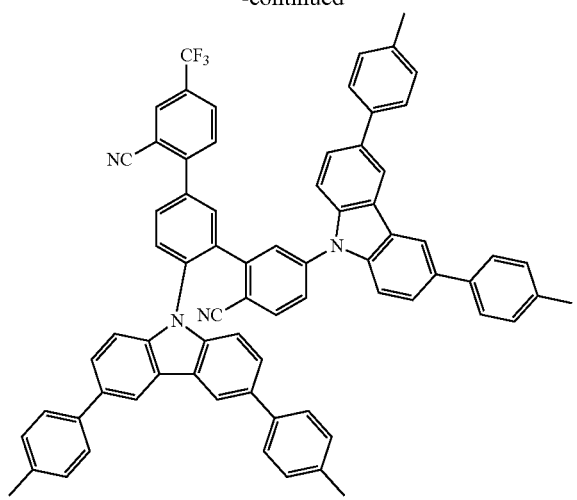
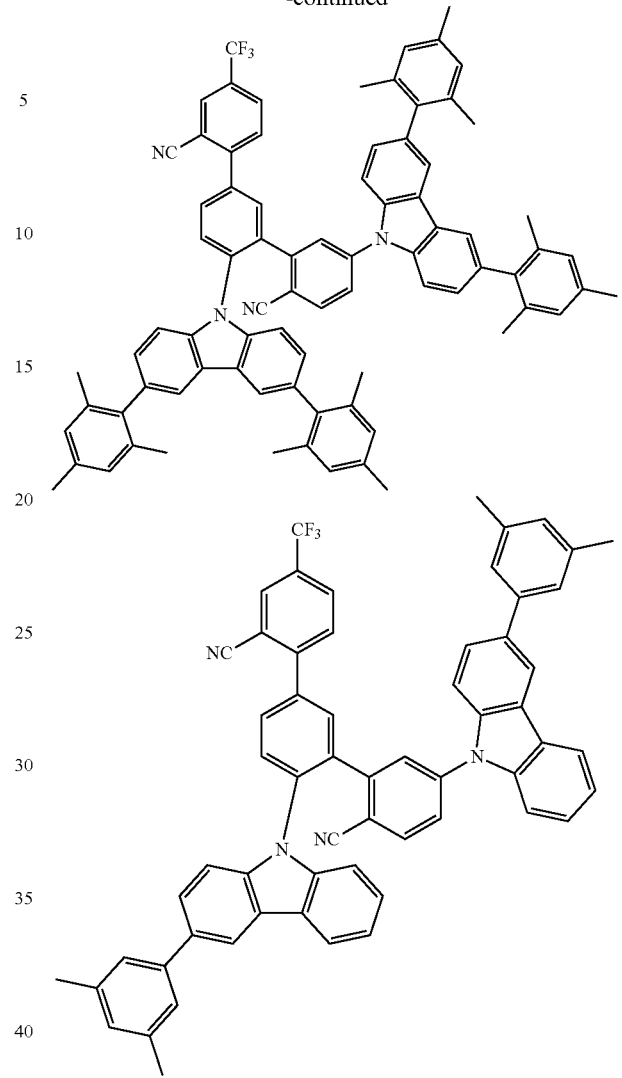
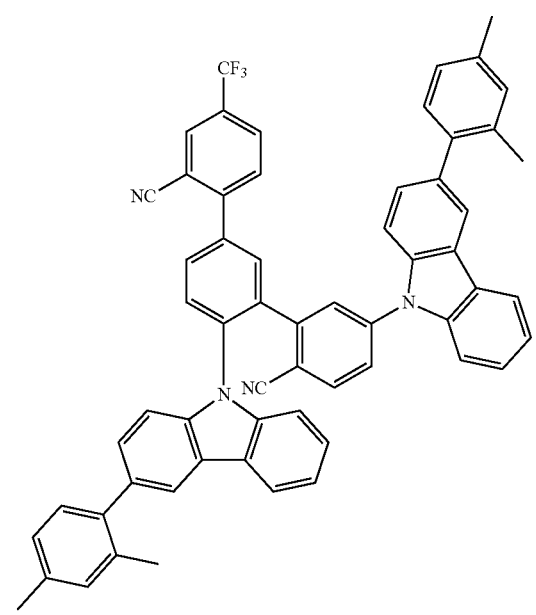

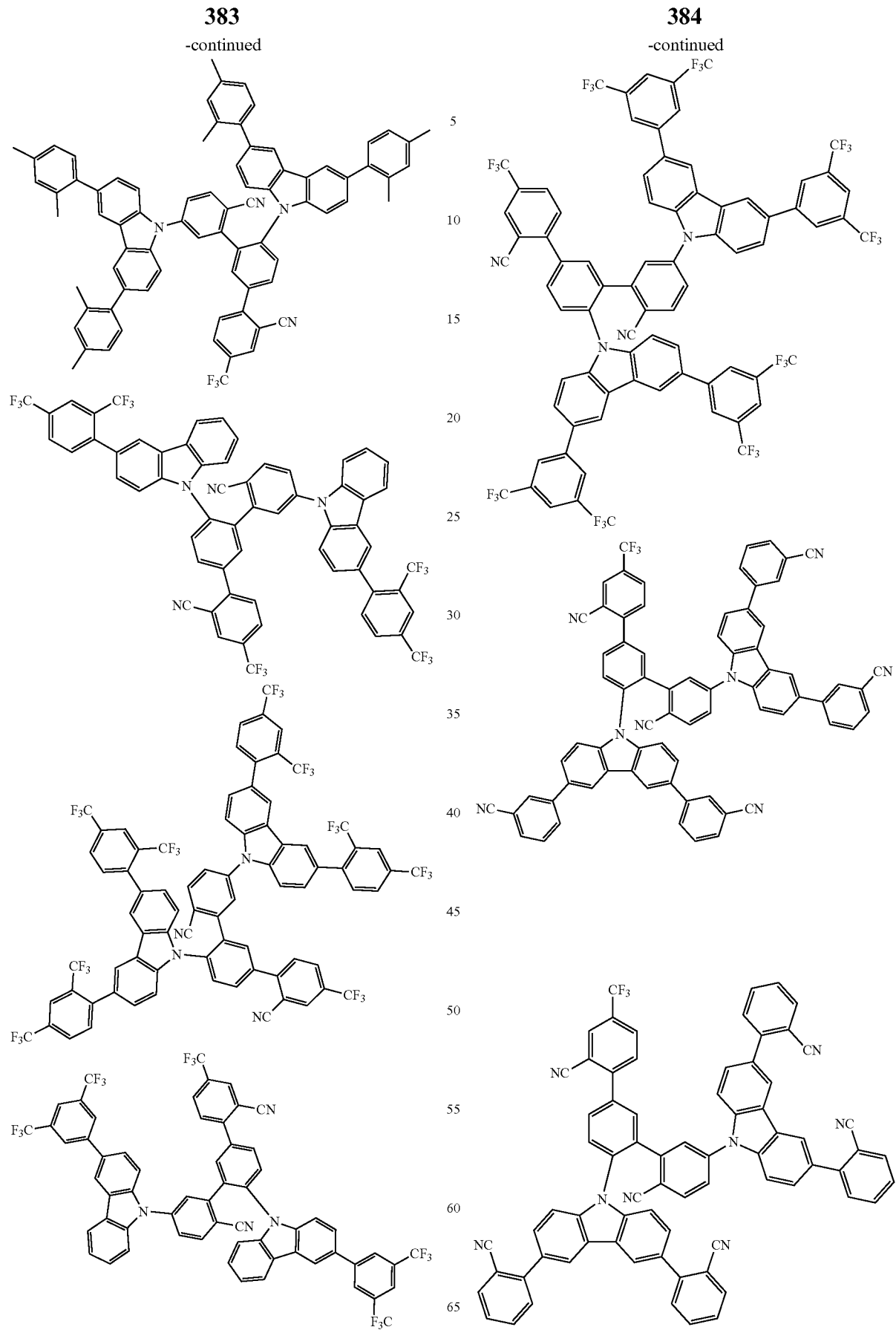

385
-continued
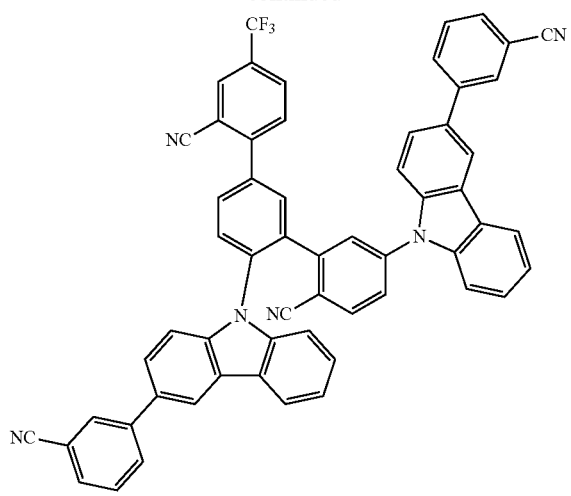
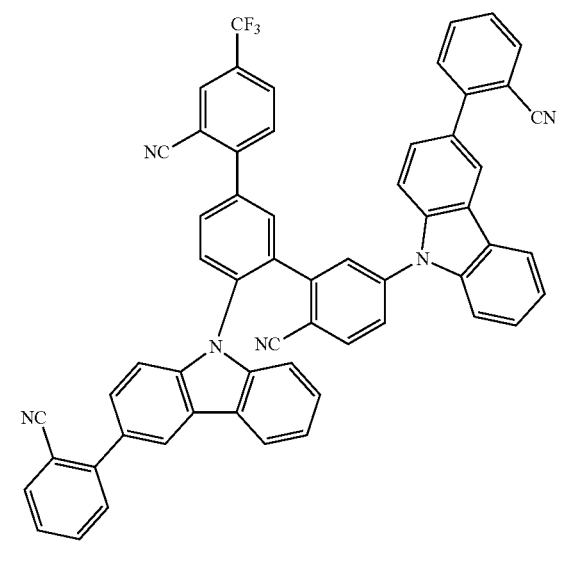
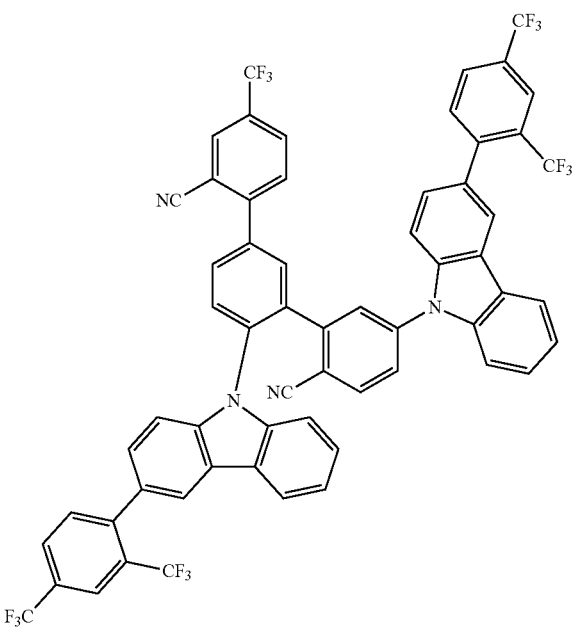
386
-continued
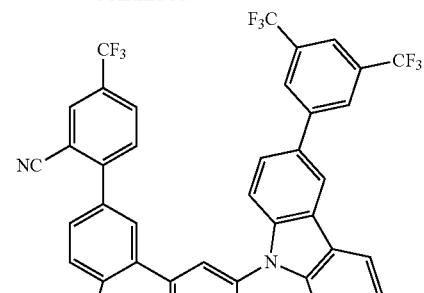
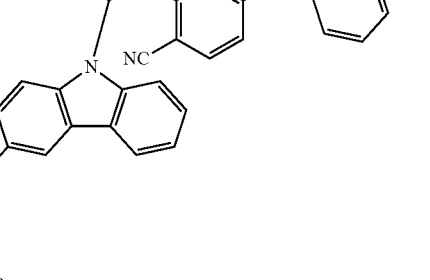
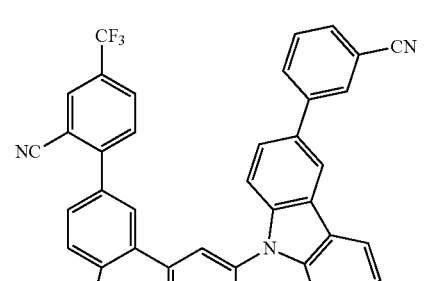
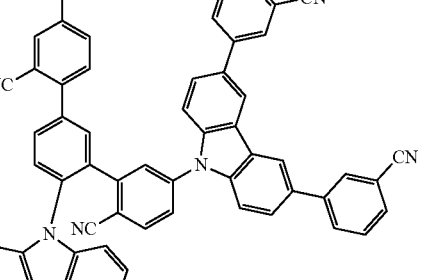

387
-continued
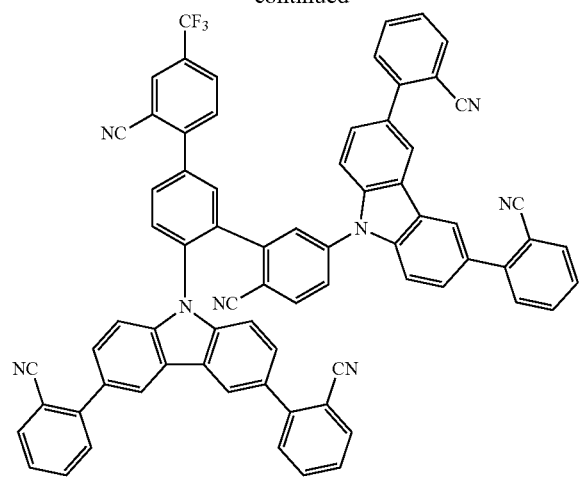
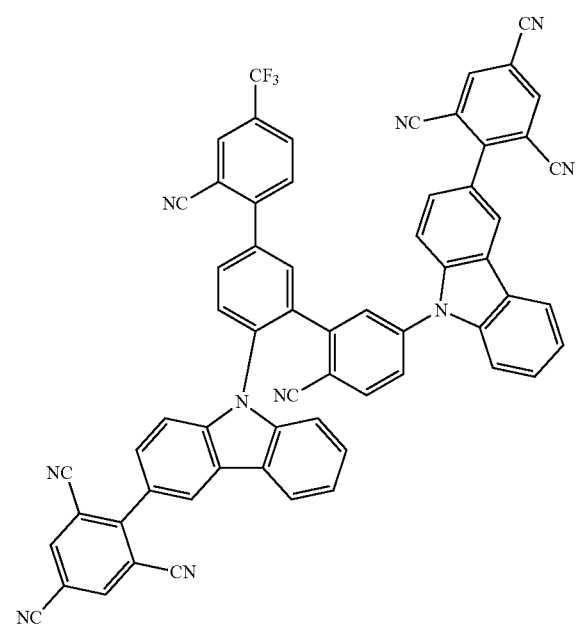
388
-continued
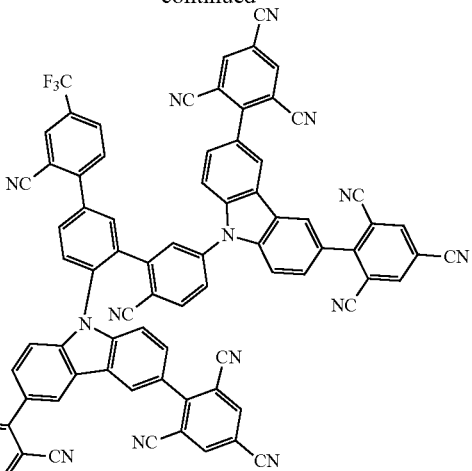
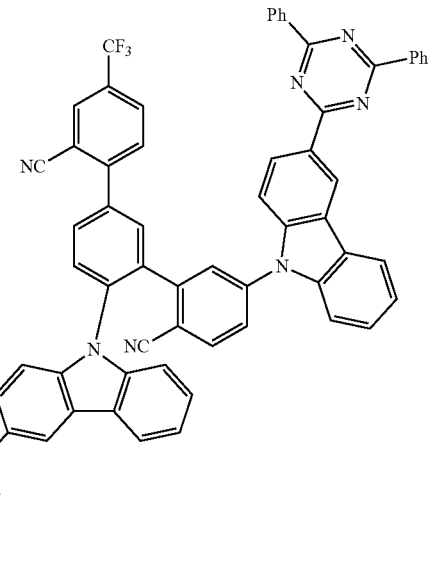
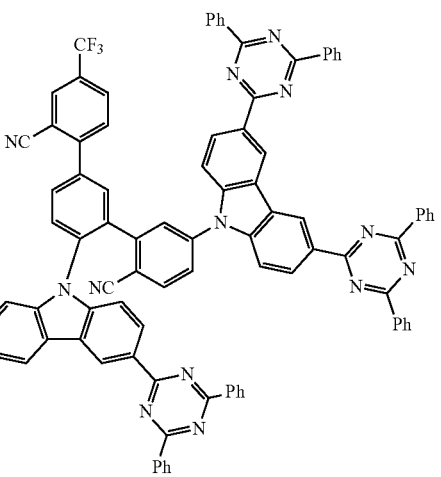

389
-continued
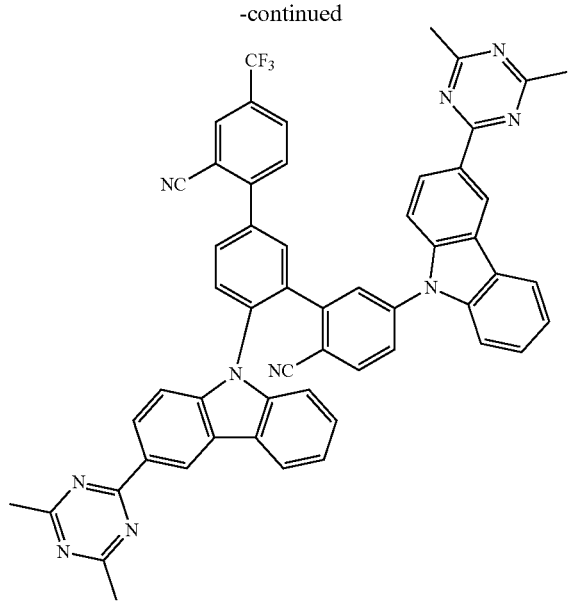
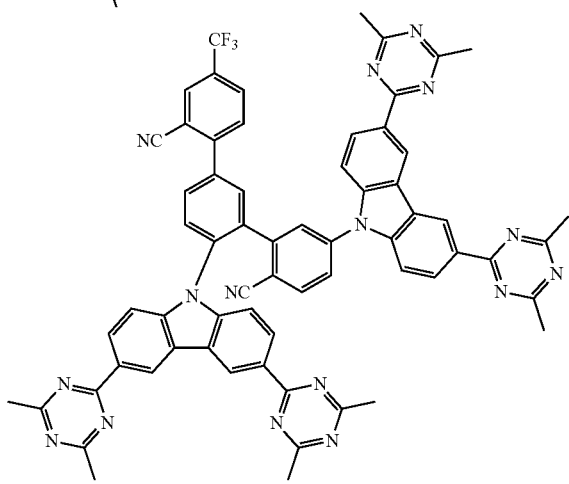
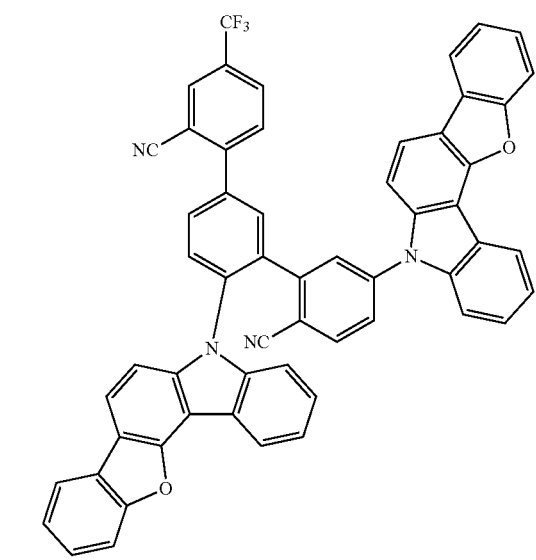
390
-continued
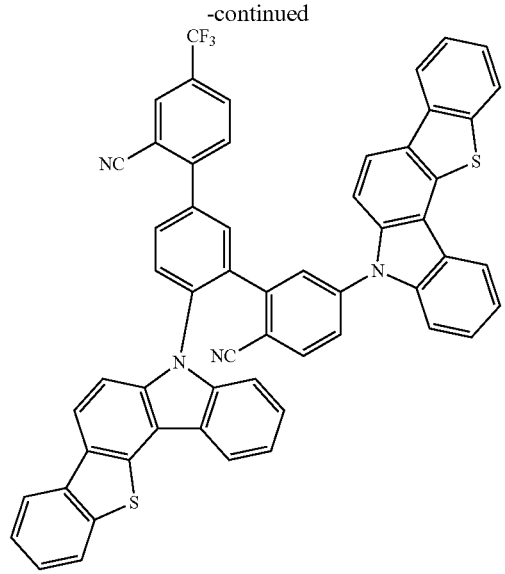
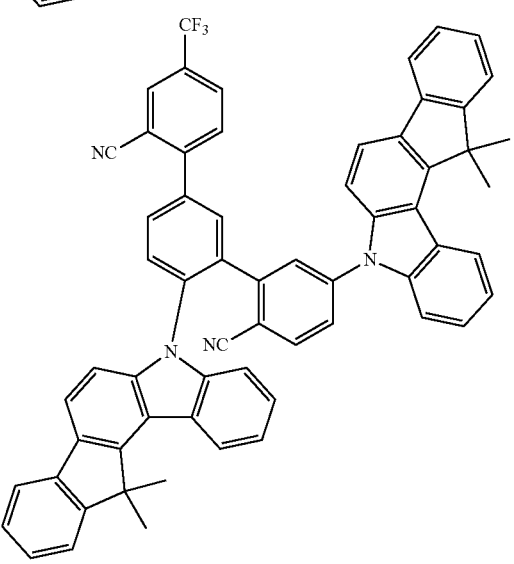
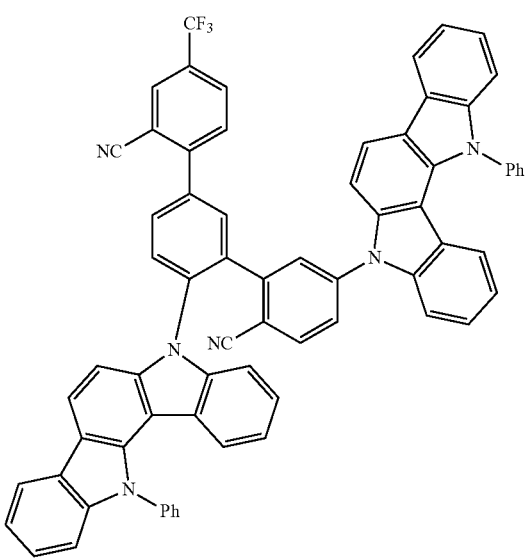

391
-continued
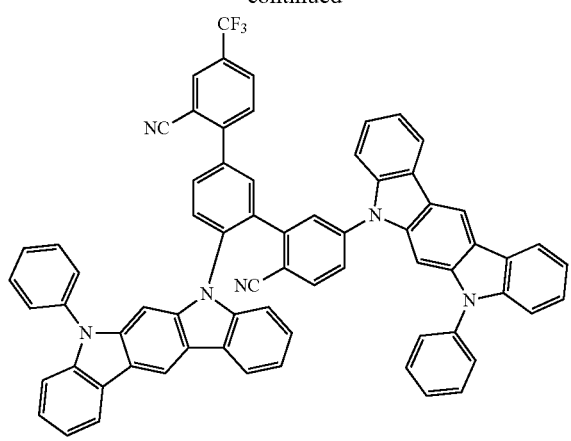
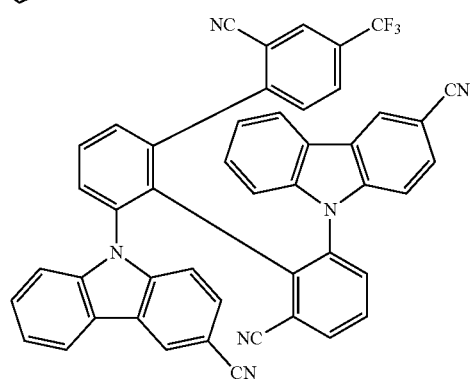
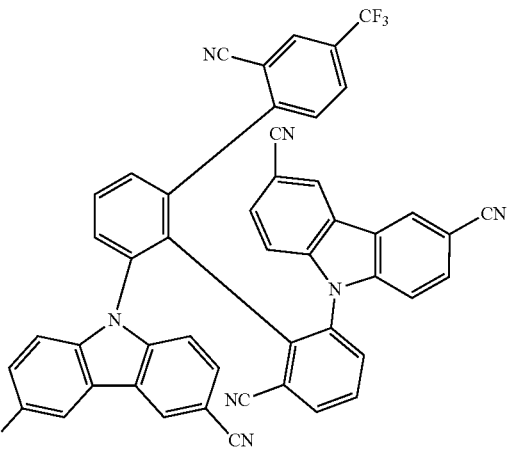
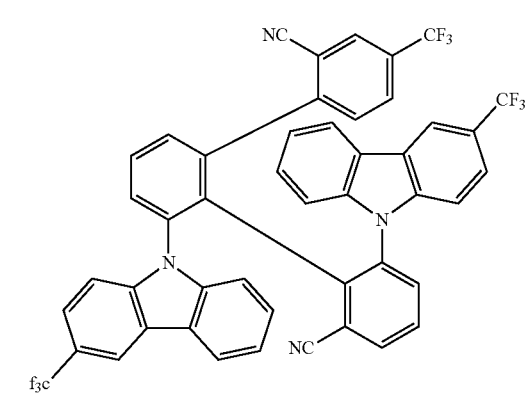
392
-continued
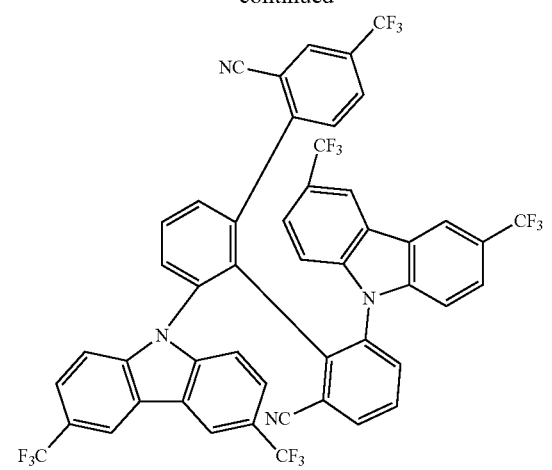
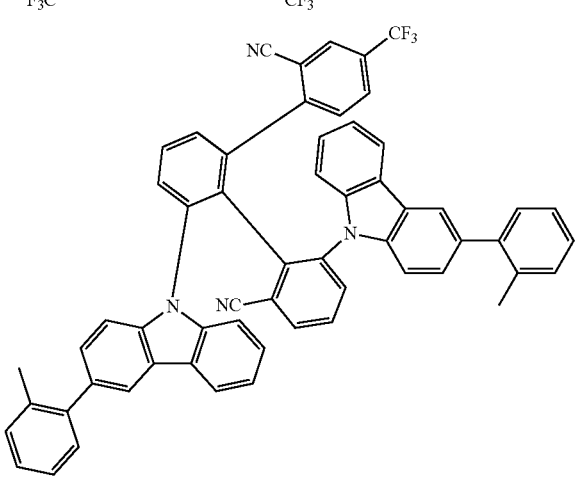
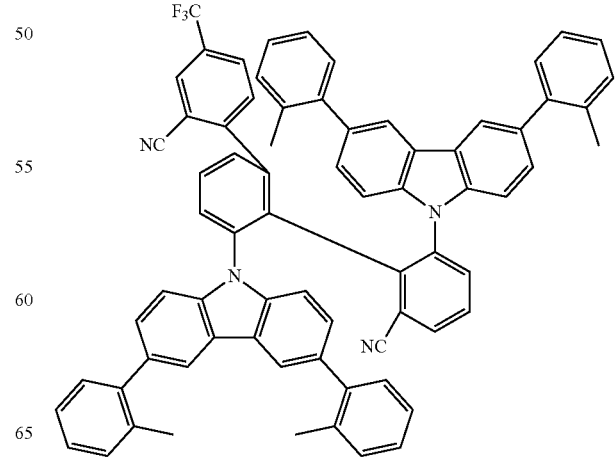

393
-continued
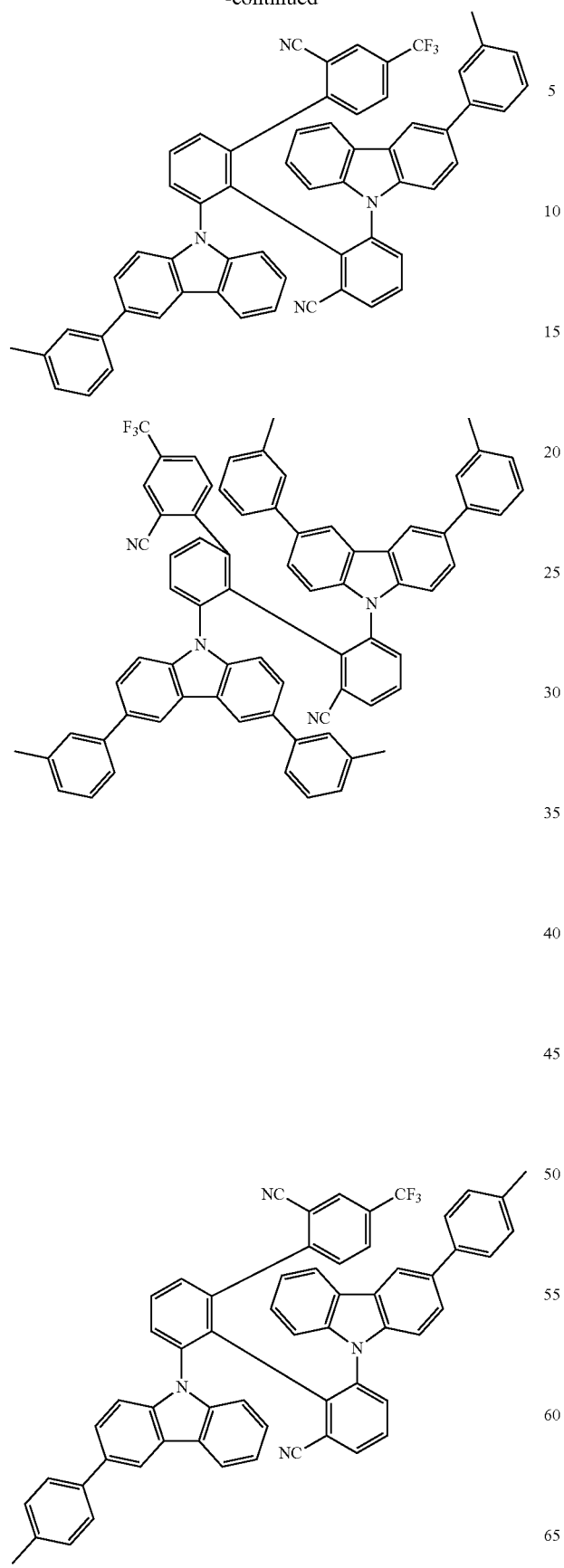
394
-continued
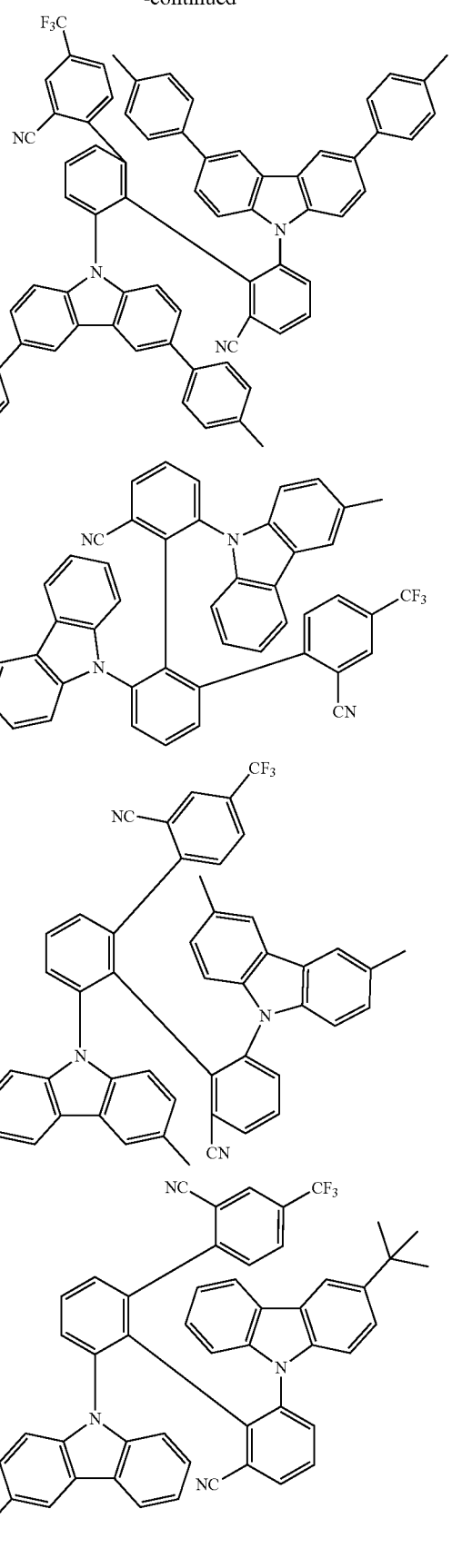

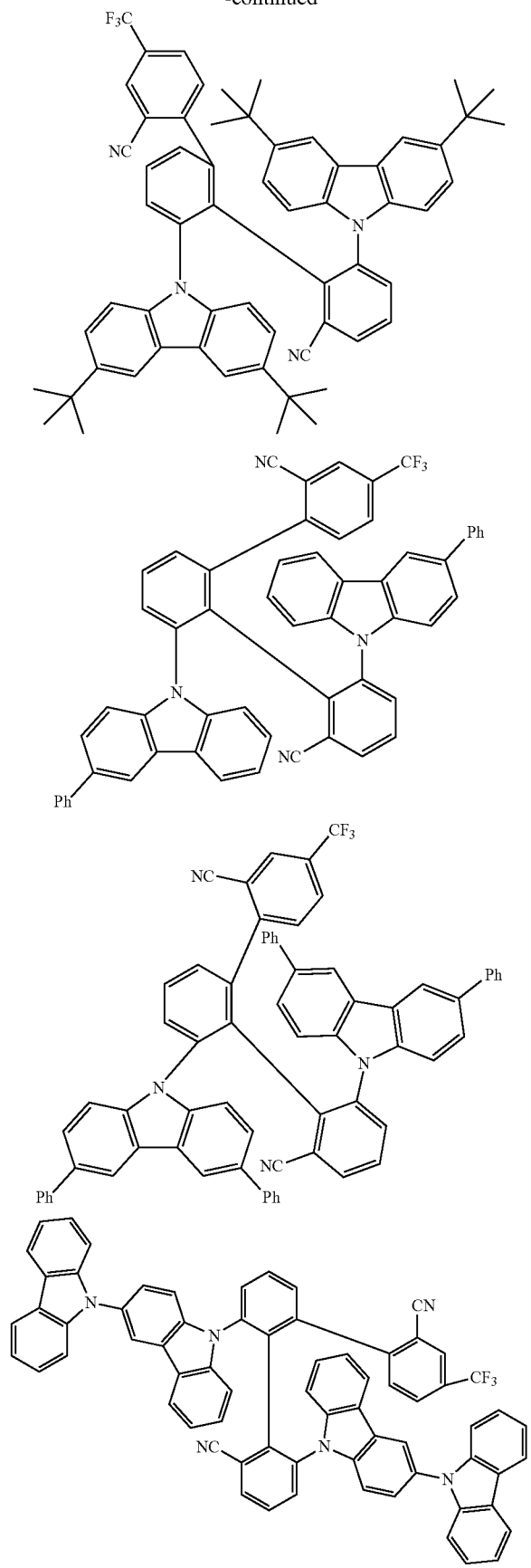
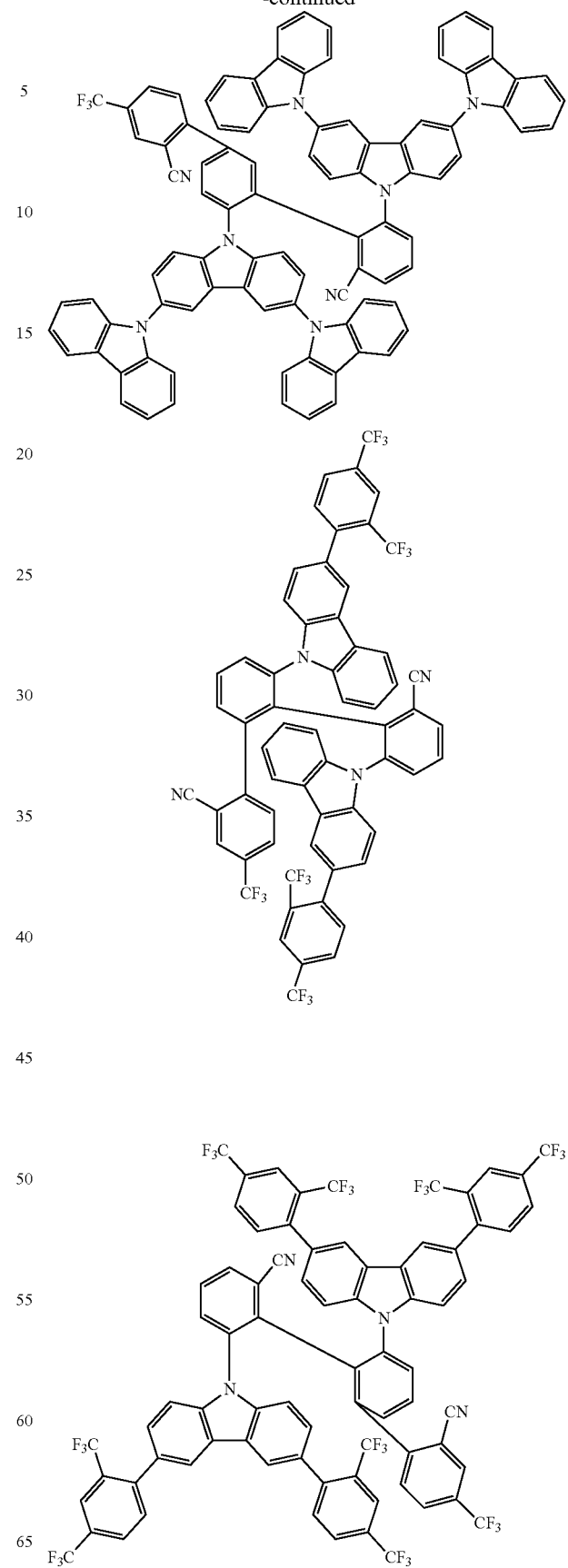

397
-continued
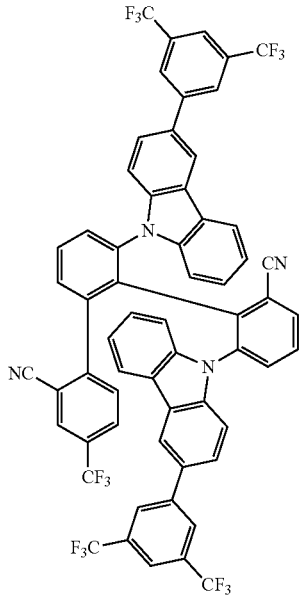
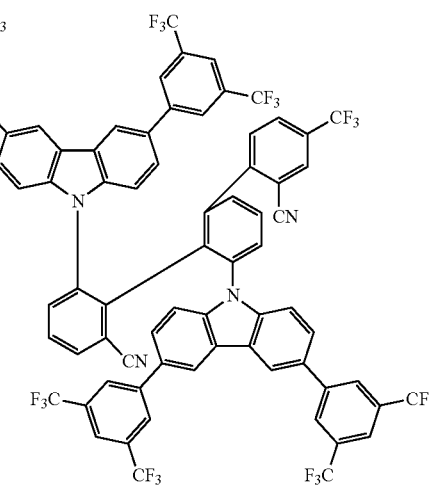
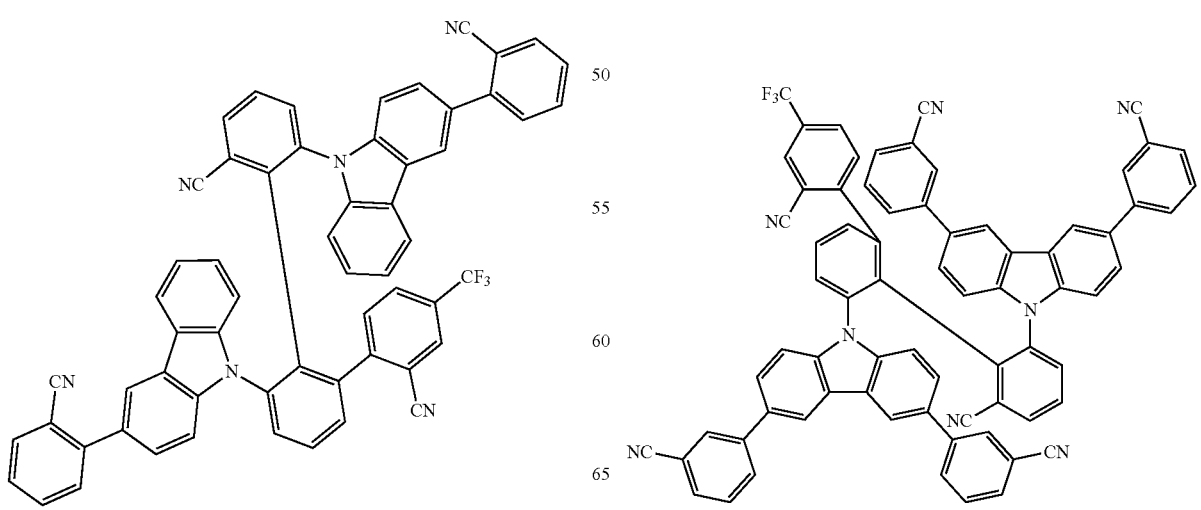
398
-continued
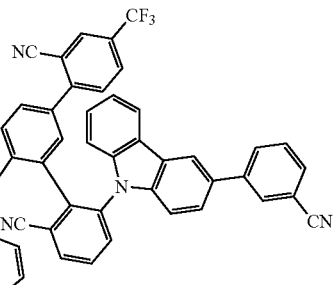
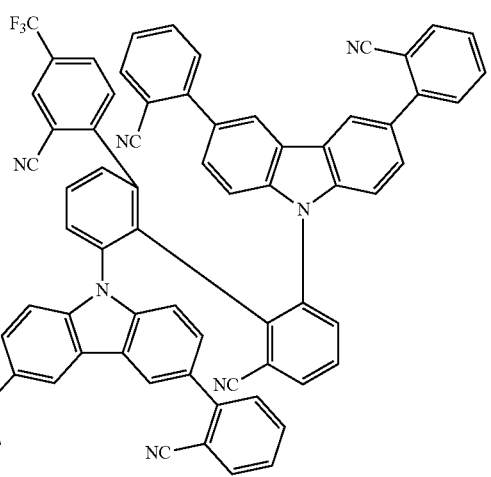

399
-continued
400
-continued
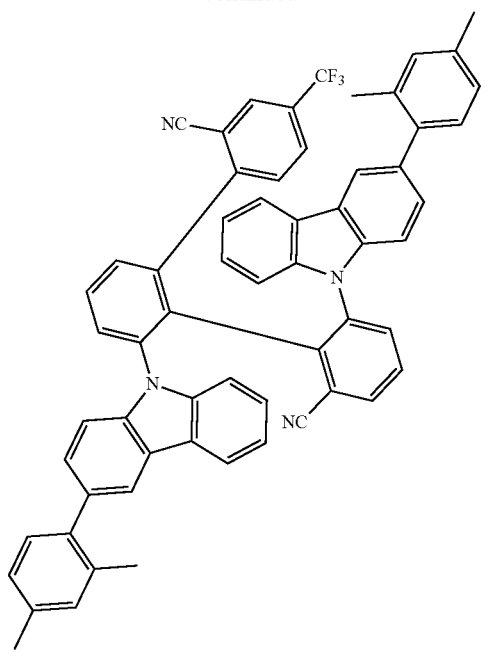
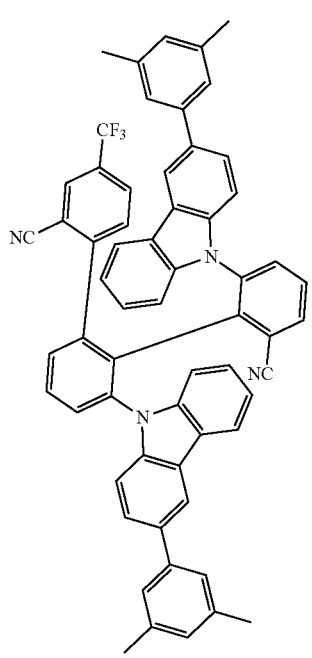
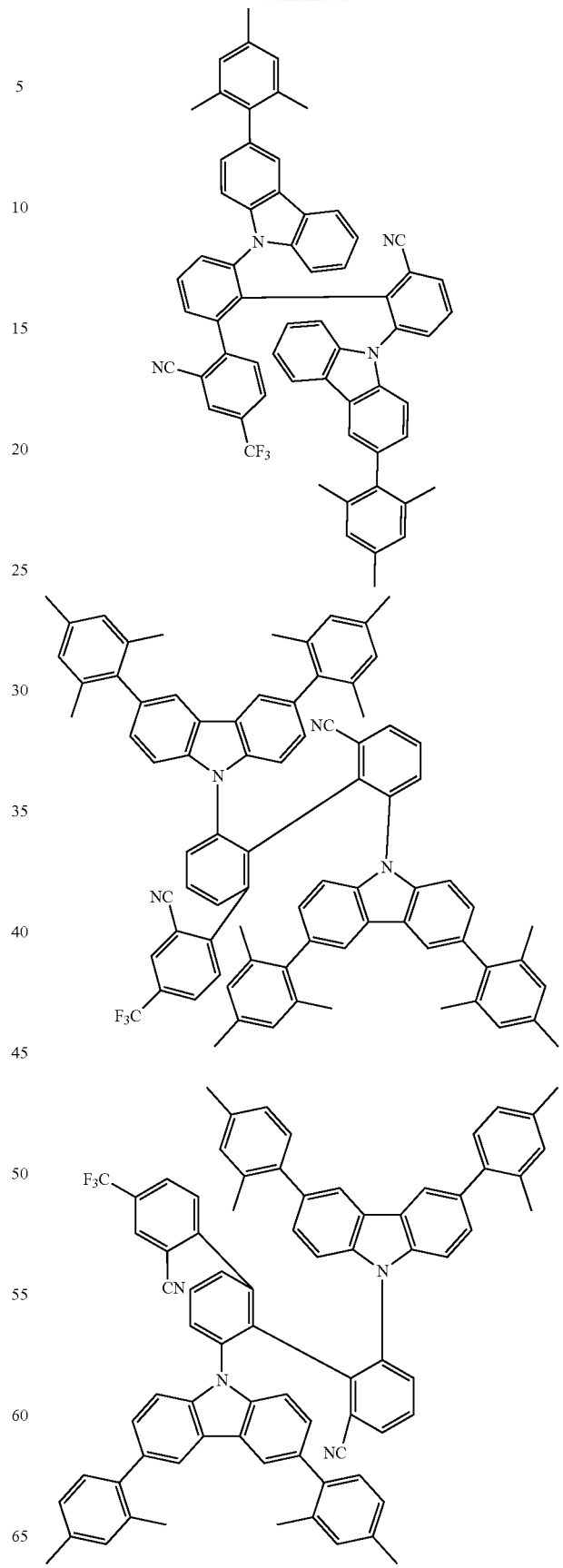

-continued
401
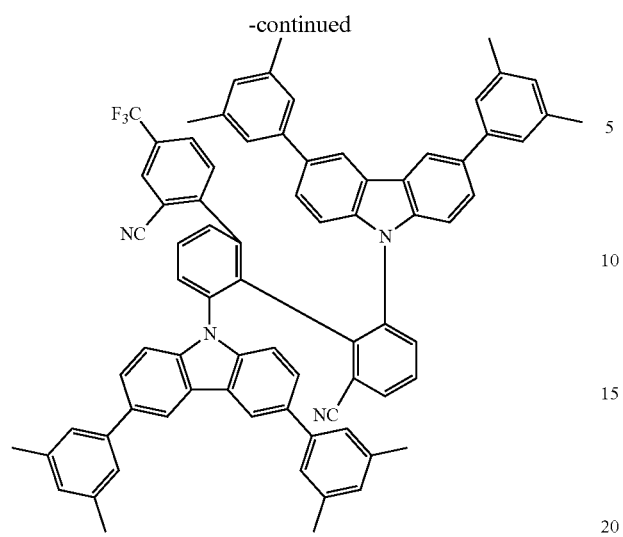
402
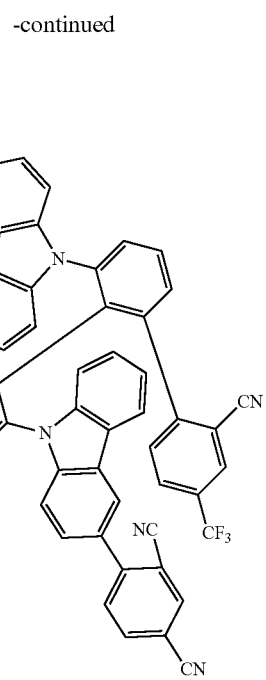
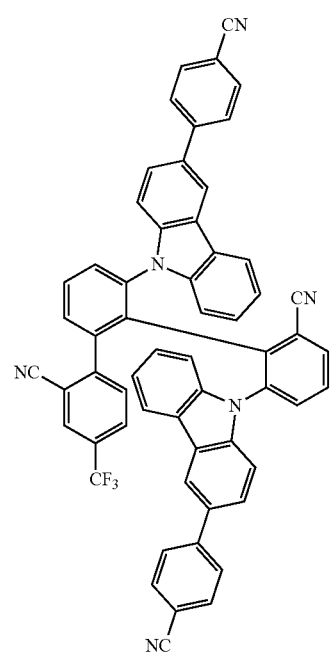
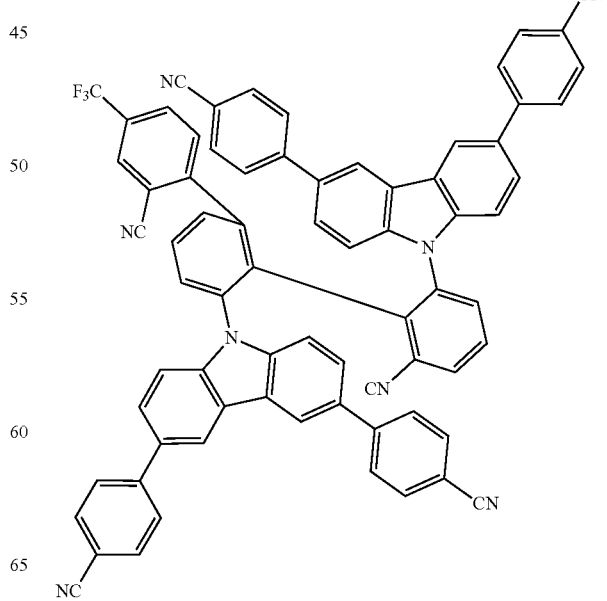

403
-continued
404
-continued
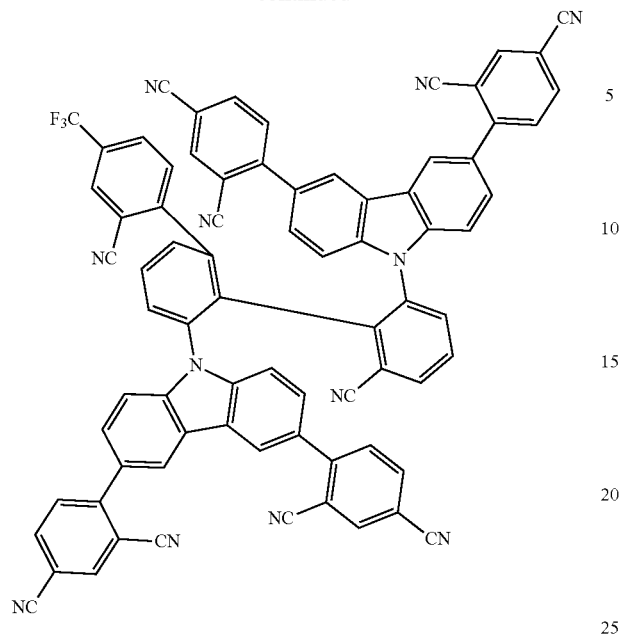
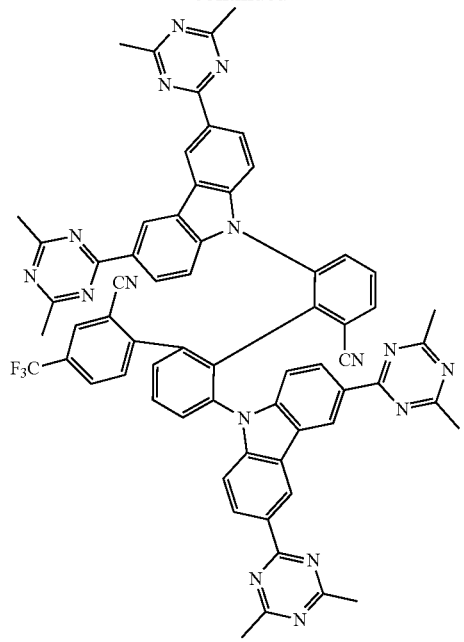
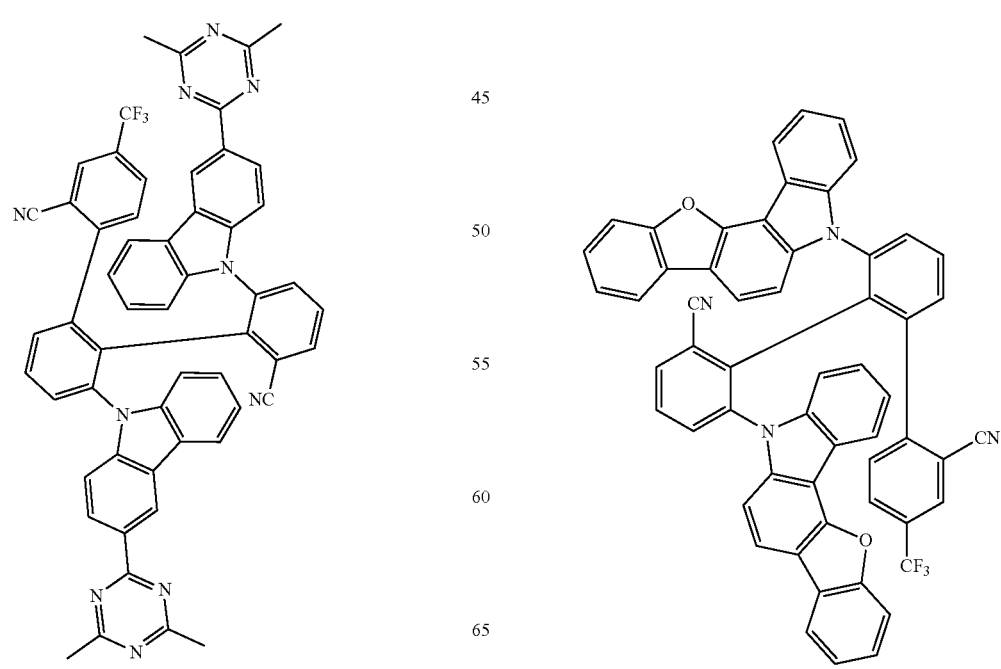

405
-continued
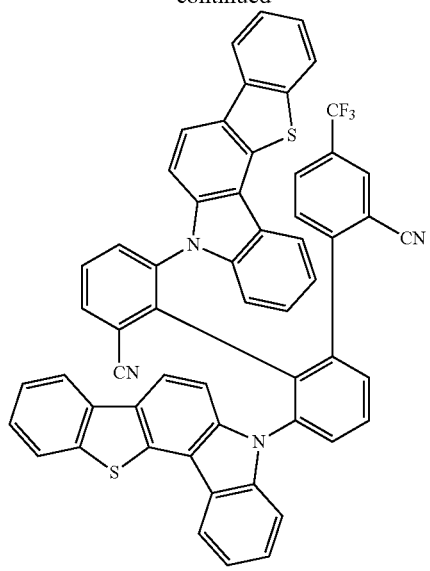
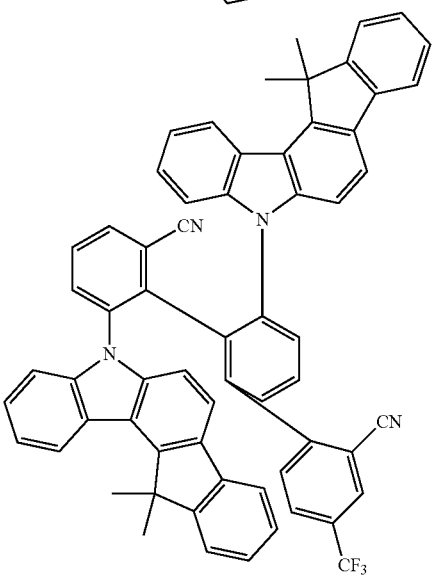
406
-continued
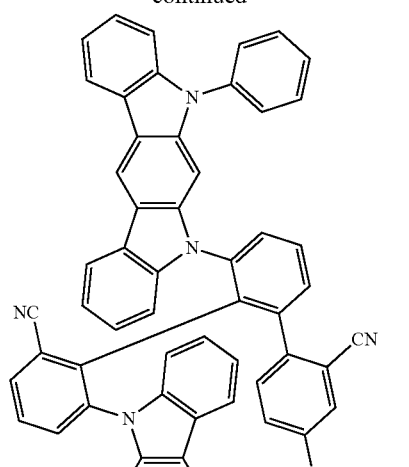
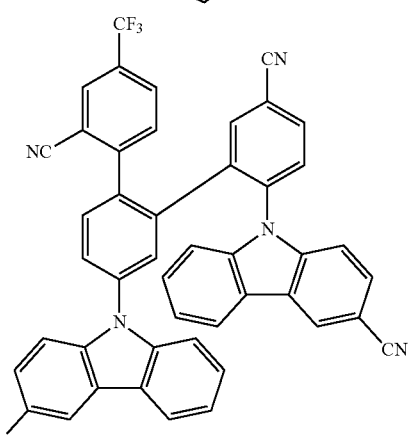
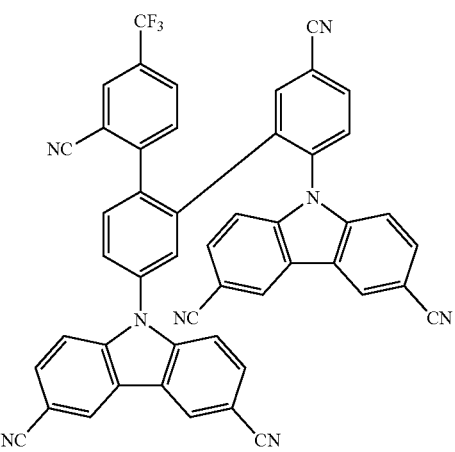

407
-continued
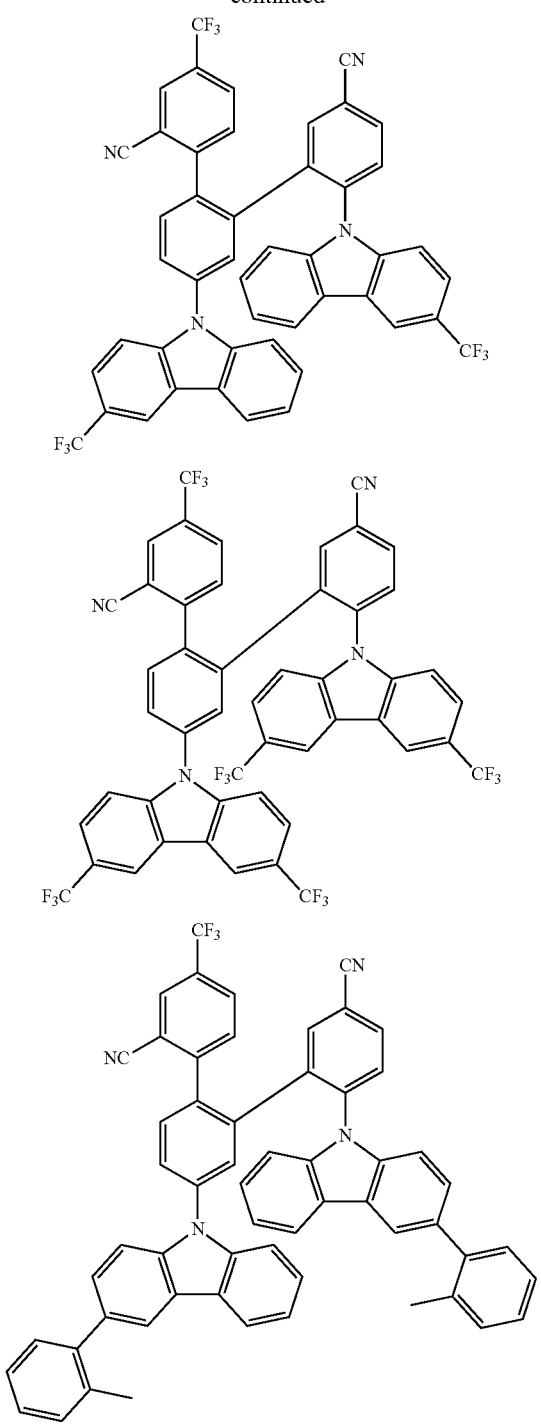
408
-continued
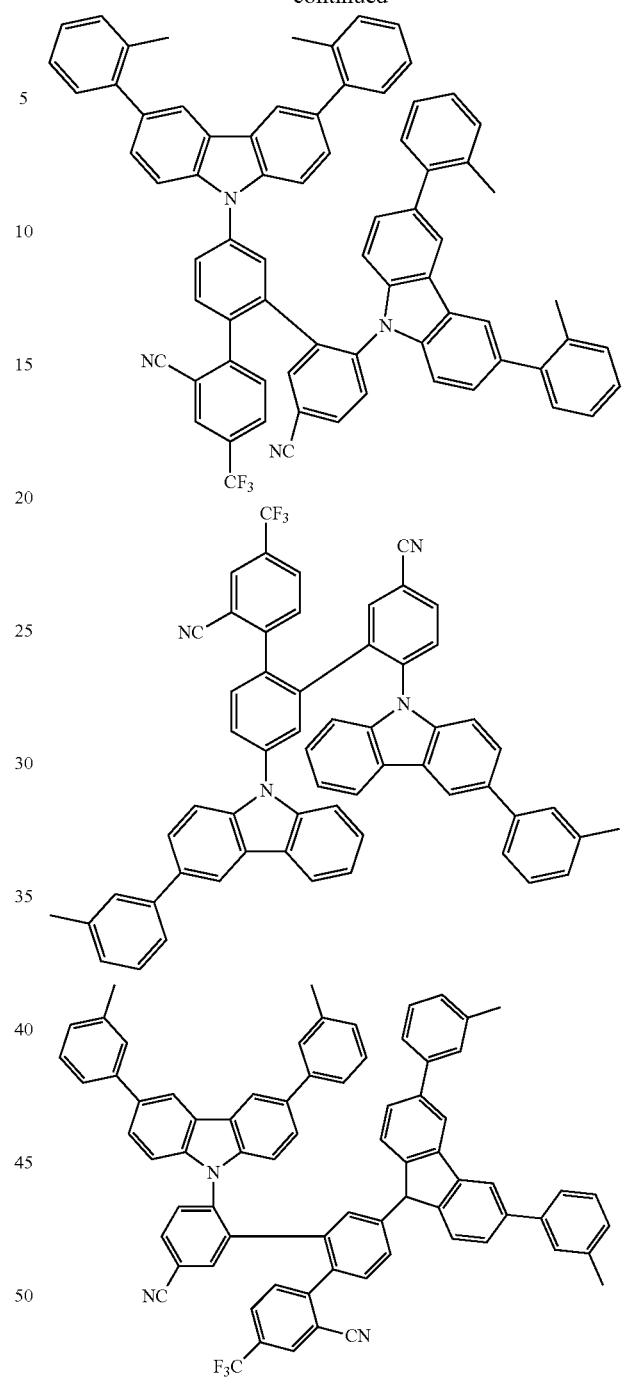

409
-continued
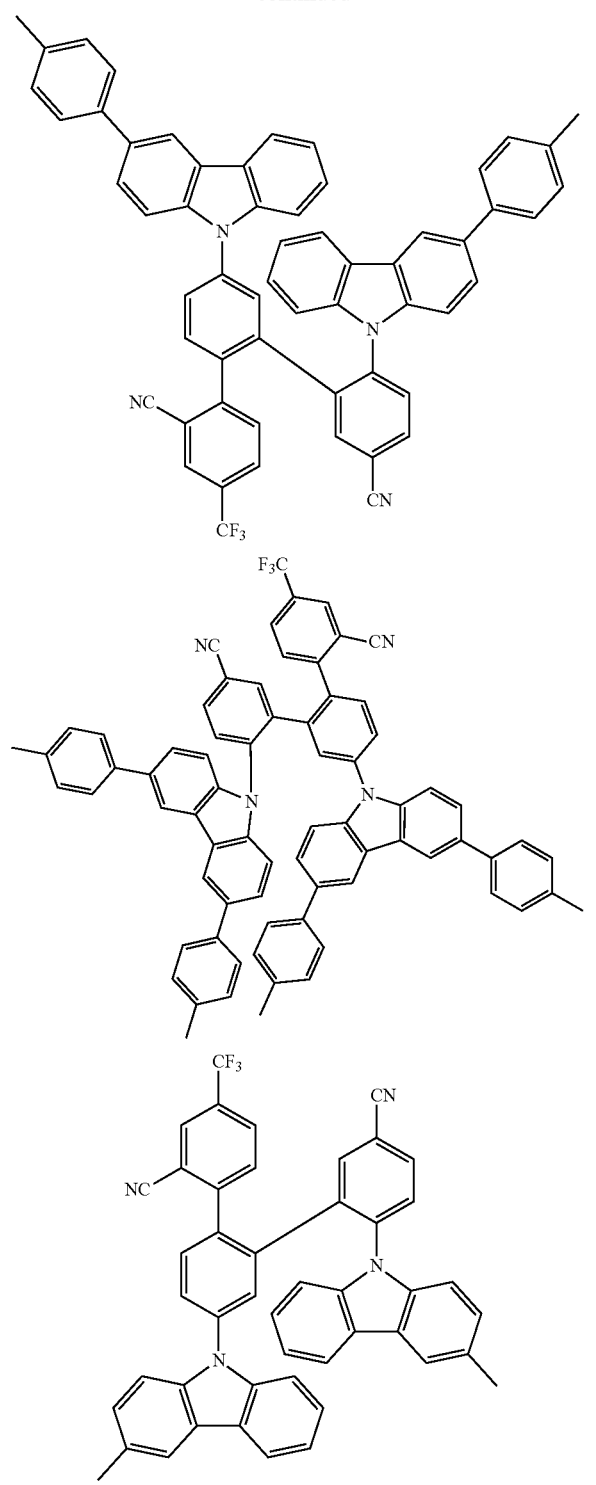
410
-continued
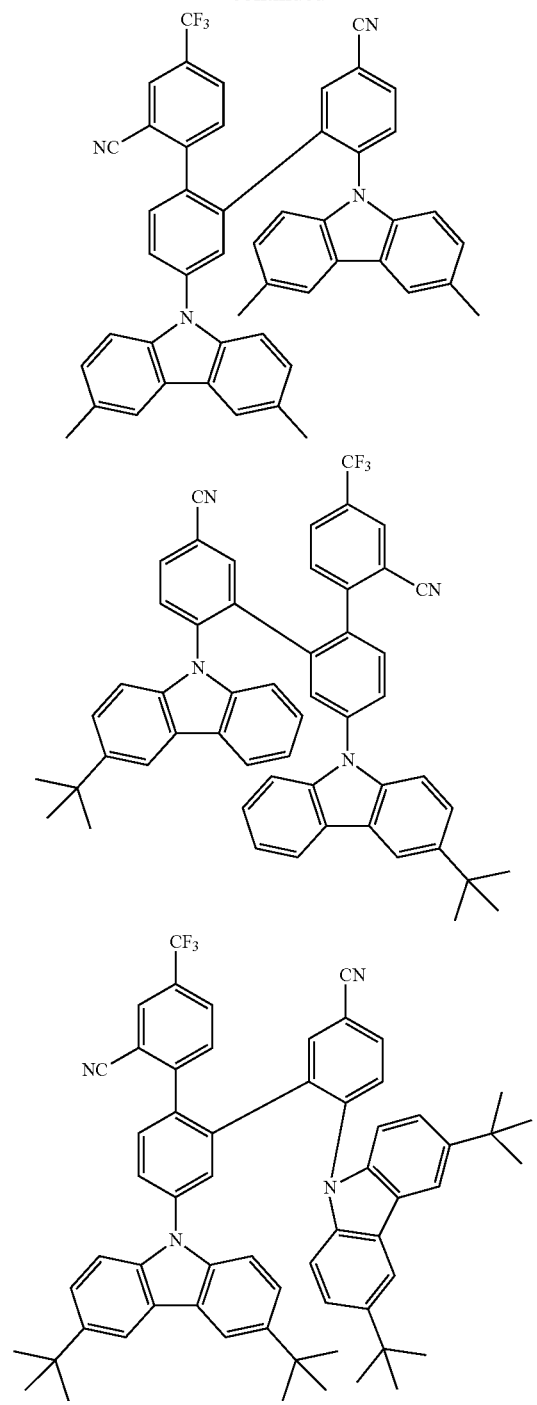

411
-continued
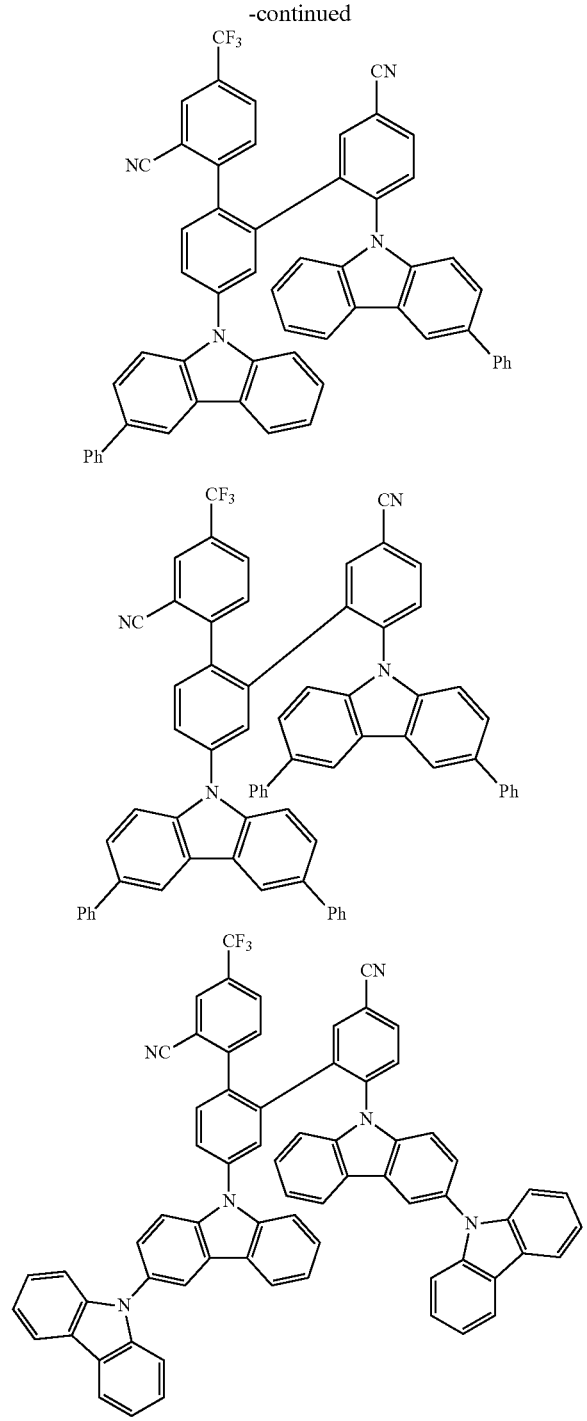
412
-continued
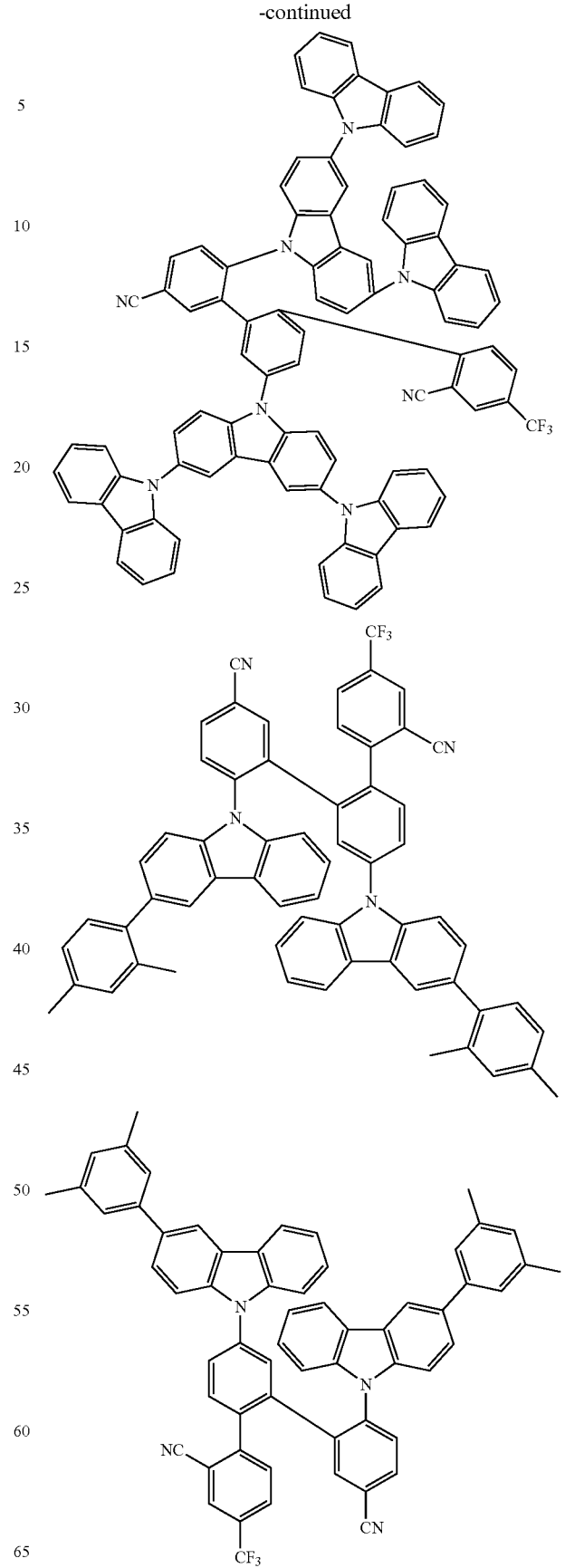

413
-continued
414
-continued
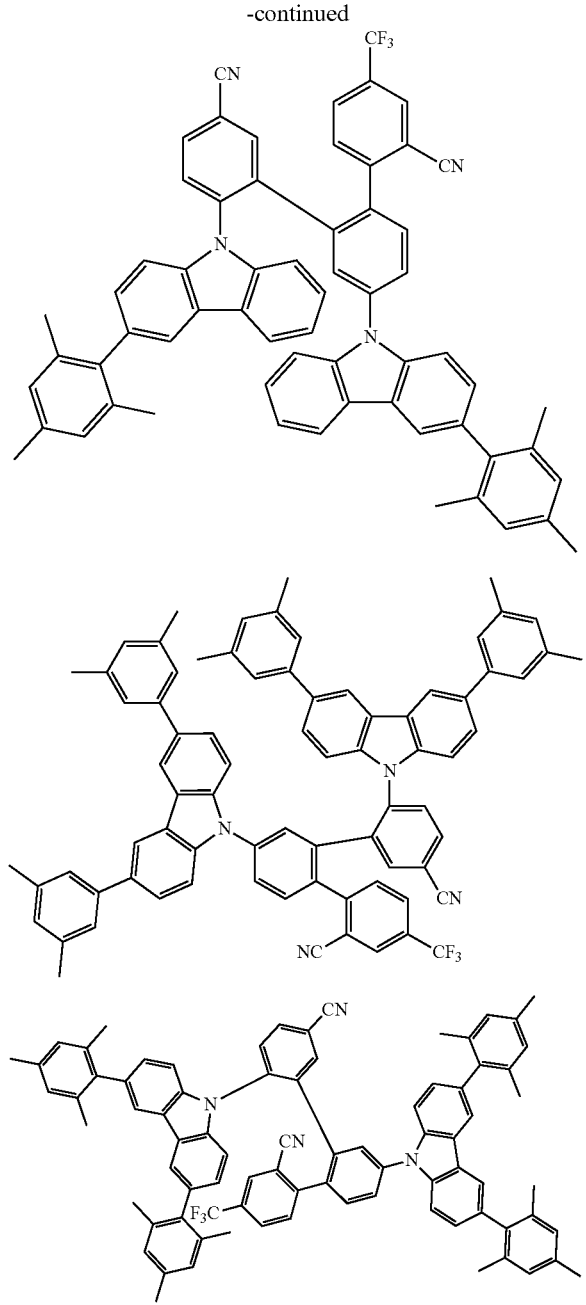
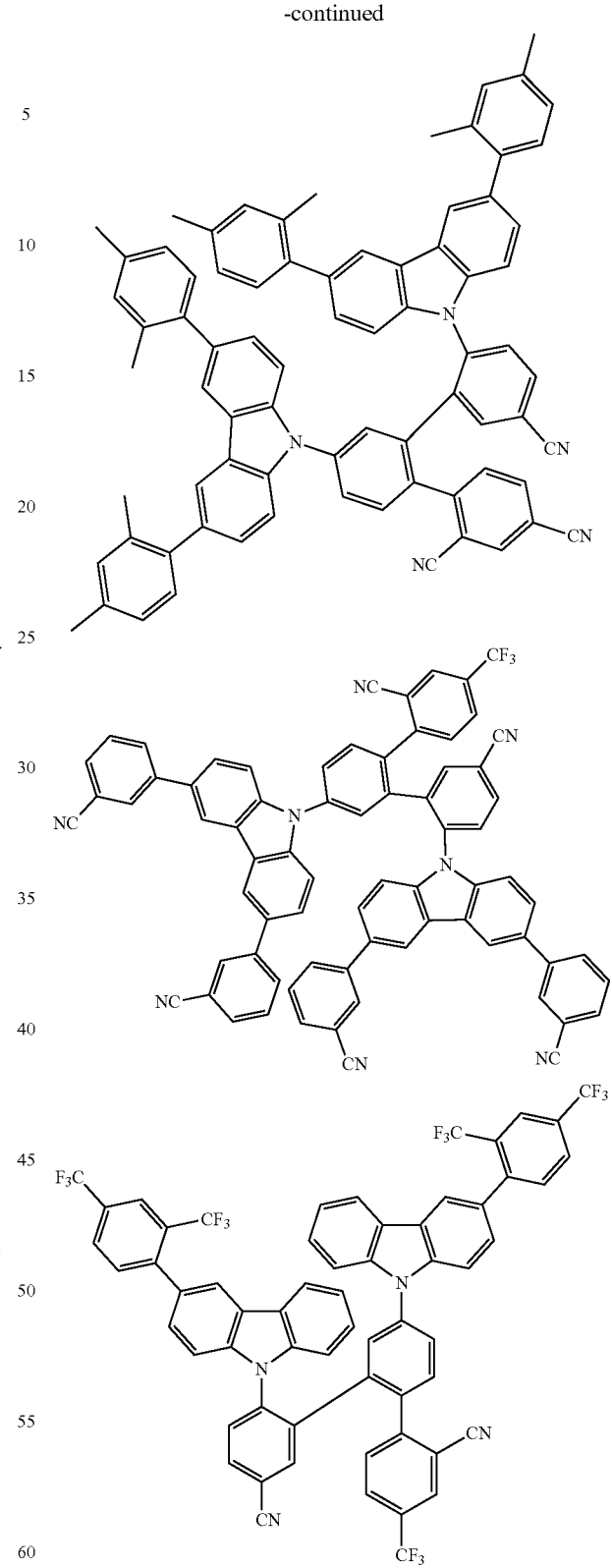

415
-continued
416
-continued
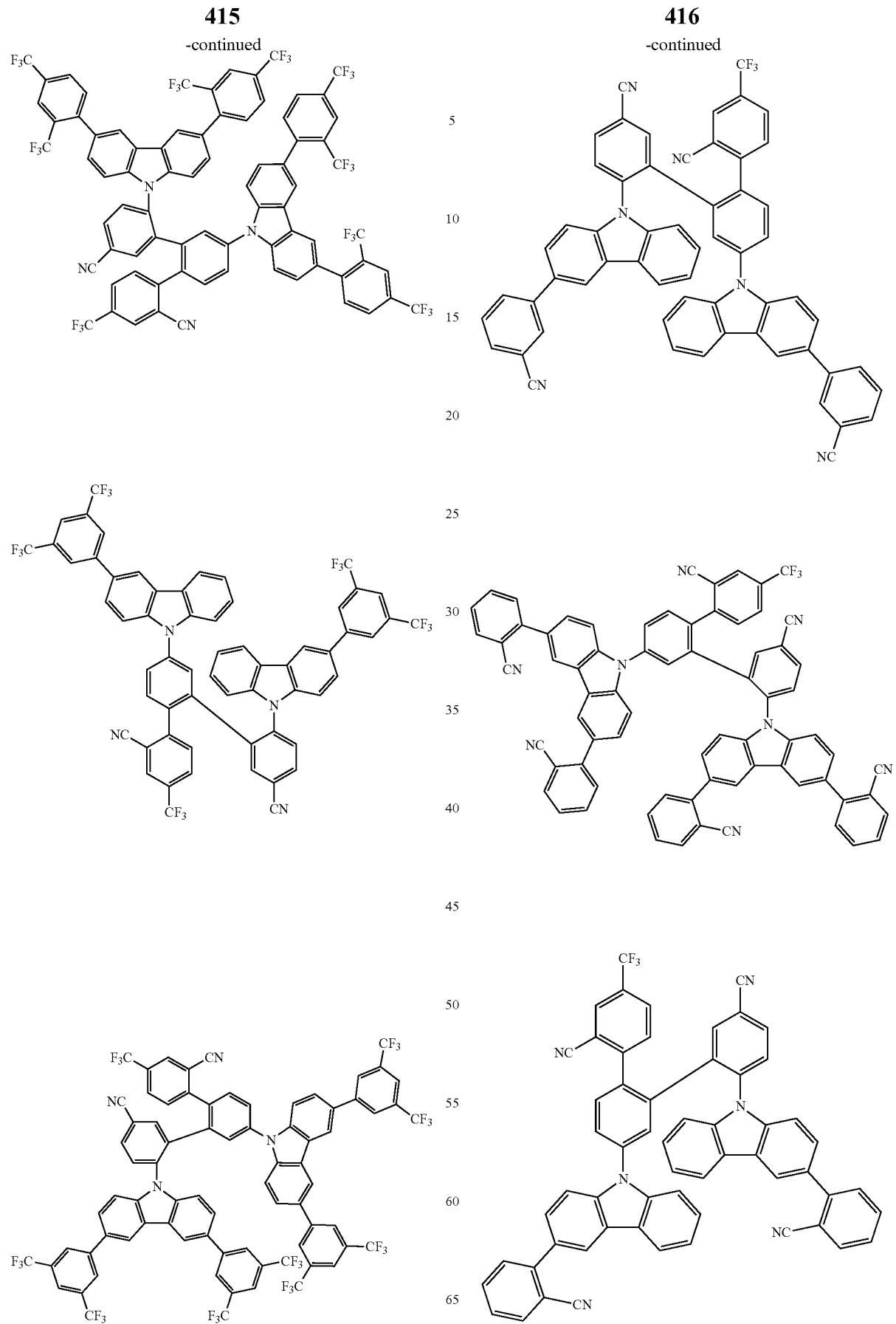

417
-continued
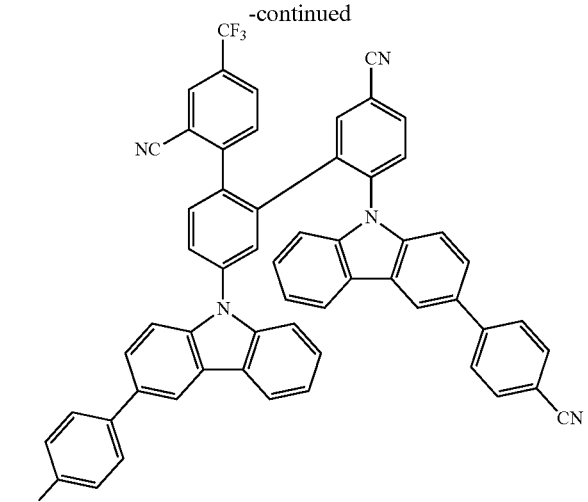
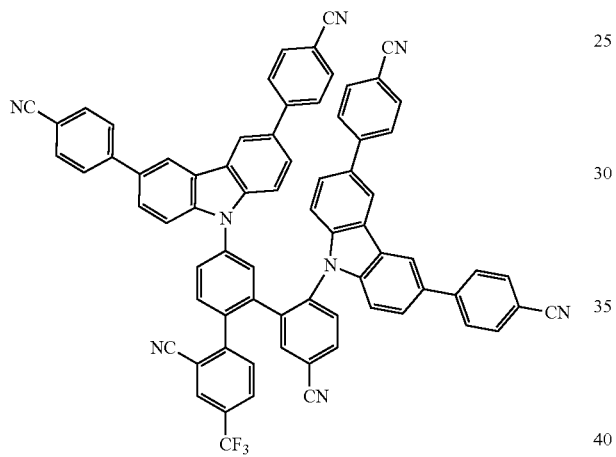
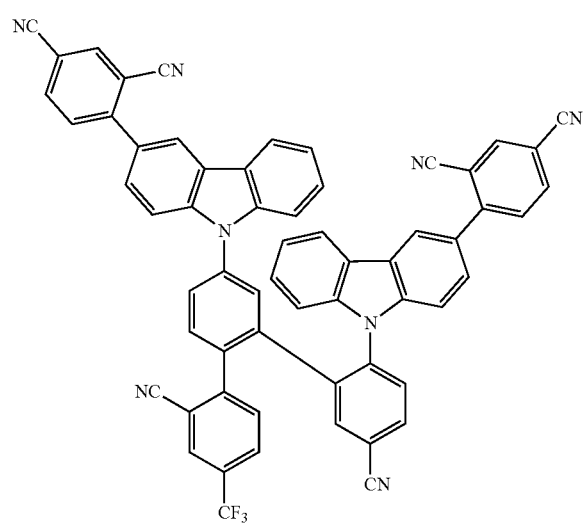
418
-continued
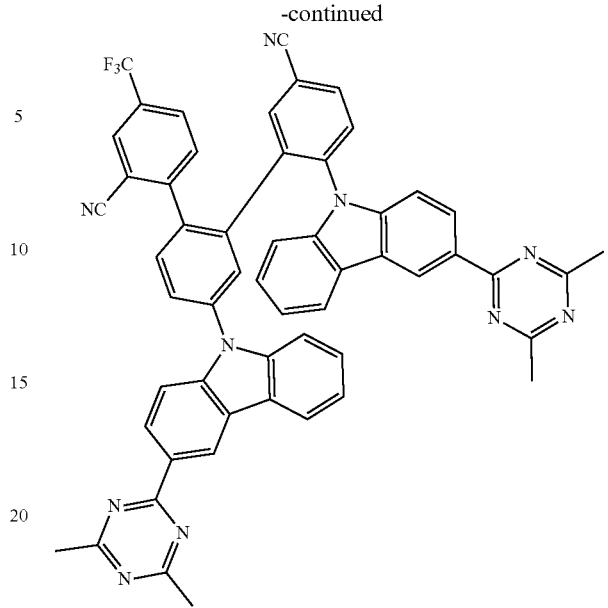
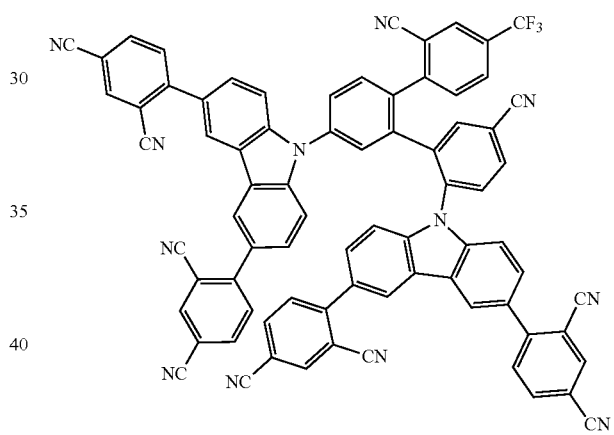
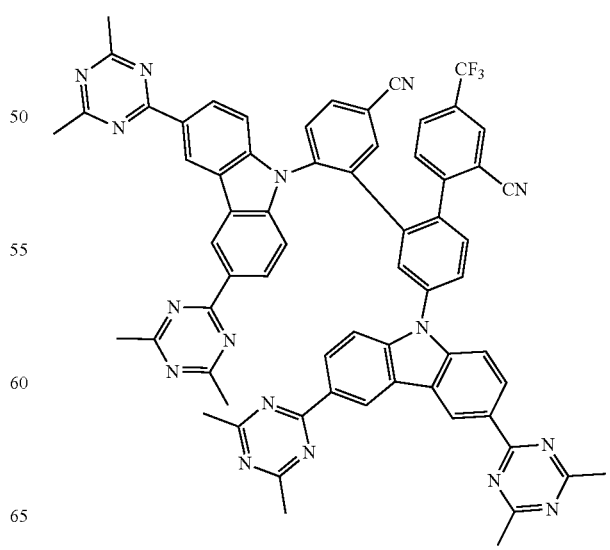

| 419 | 420 |
|---|---|
| -continued | -continued |
| 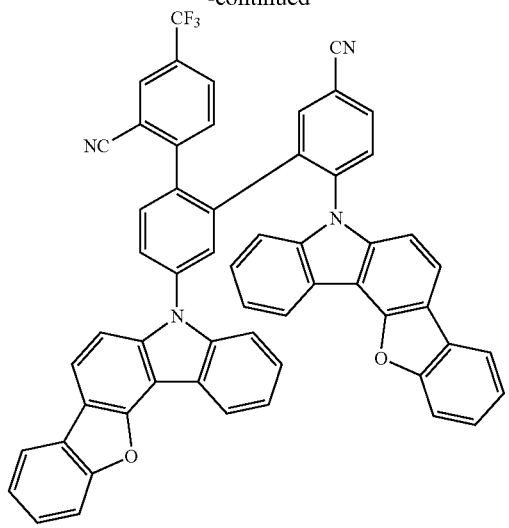 | 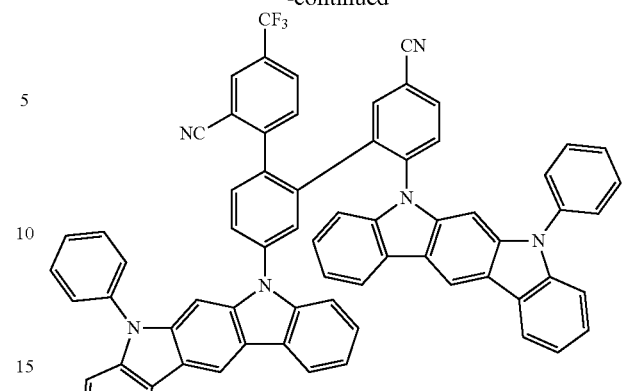 |
| 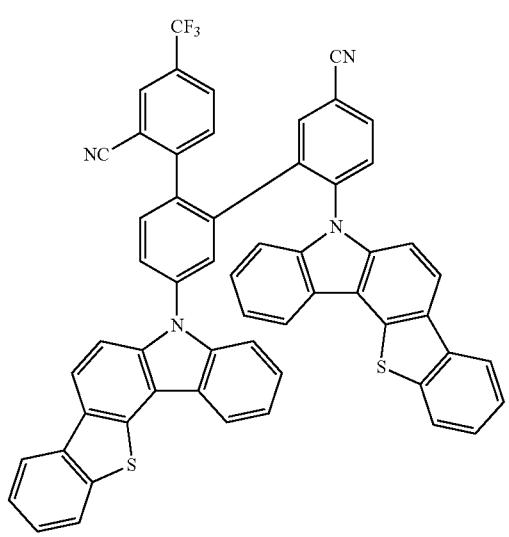 | 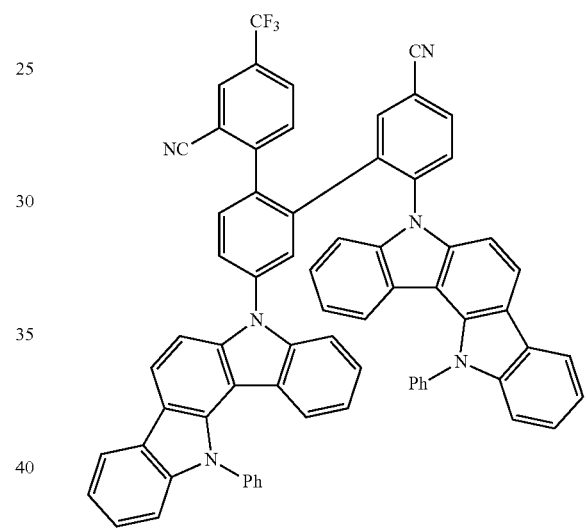 |
| 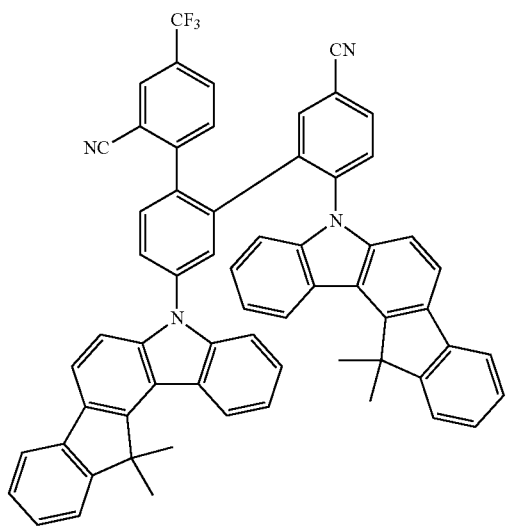 | 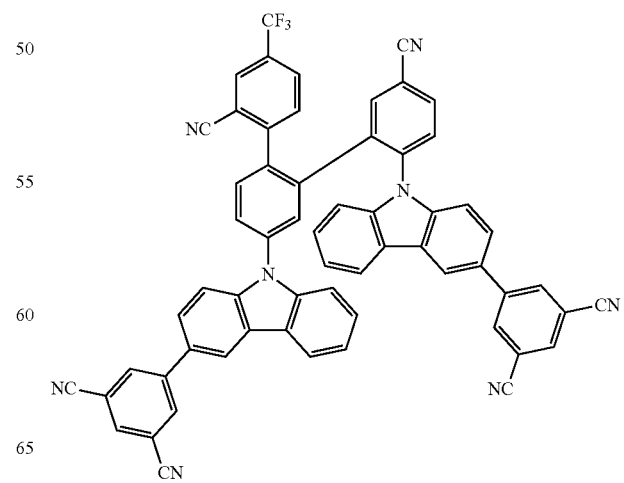 |

-continued

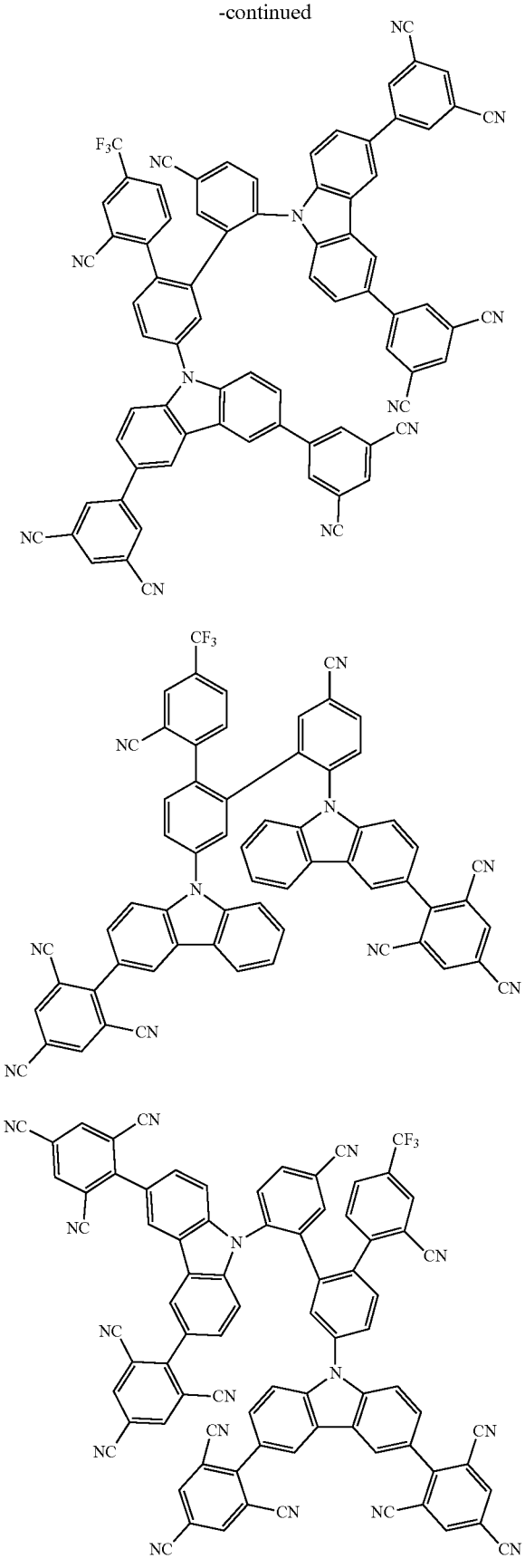

FIGURE LEGENDS

FIG. 1 Emission spectrum of example 1 (10% by weight) in PMMA.
FIG. 2 Emission spectrum of example 2 (10% by weight) in PMMA.
FIG. 3 Emission spectrum of example 3 (10% by weight) in PMMA.
FIG. 4 Emission spectrum of example 4 (10% by weight) in PMMA.
FIG. 5 Emission spectrum of example 5 (10% by weight) in PMMA.
FIG. 6 Emission spectrum of example 6 (10% by weight) in PMMA.
FIG. 7 Emission spectrum of example 7 (10% by weight) in PMMA.

SUMMARY

The invention relates to an organic compound, in particular for the application in organic optoelectronic devices. According to the invention, the organic compound has
a first chemical moiety with a structure of formula I,

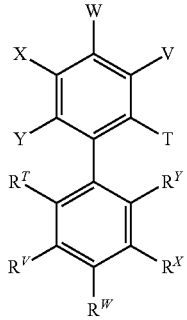

Formula I and
two second chemical moieties, each at each occurrence independently from another with a structure of formula II,

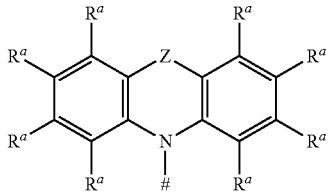

Formula II wherein the first chemical moiety is linked to each of the two second chemical moieties via a single bond;
wherein
T, V is selected from the group consisting of $R^A$ and $R^1$;
W is the binding site of a single bond linking the first chemical moiety to one of the two second chemical moieties or is selected from the group consisting of $R^A$ and $R^2$;
X is the binding site of a single bond linking the first chemical moiety to one of the two second chemical moieties or is $R^2$;
Y is the binding site of a single bond linking the first chemical moiety to one of the two second chemical moieties or is $R^2$;

$R^T$, $R^V$ is selected from the group consisting of CN and $R^1$;

$R^W$ is the binding site of a single bond linking the first chemical moiety to one of the two second chemical moieties or is selected from the group consisting of CN and $R^1$; $R^x$, $R^Y$ is the binding site of a single bond linking the first chemical moiety to one of the two second chemical moieties or is $R^I$.

The invention claimed is:

1. An organic molecule, comprising a structure of Formula I,

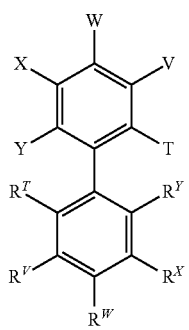

Formula I wherein
T=is selected from the group consisting of $R^A$ and $R^1$;
V=is selected from the group consisting of $R^A$ and $R^1$;
W=is the binding site of a single bond linking the first chemical moiety to one of the two second chemical moieties or is selected from the group consisting of $R^A$ and $R^2$;
X=is the binding site of a single bond linking the first chemical moiety to one of the two second chemical moieties or is $R^2$;
Y=is the binding site of a single bond linking the first chemical moiety to one of the two second chemical moieties or is $R^2$;
$R^T$=is selected from the group consisting of CN and $R^I$;
$R^V$=is selected from the group consisting of CN and $R^I$;
$R^W$=is the binding site of a single bond linking the first chemical moiety to one of the two second chemical moieties or is selected from the group consisting of CN and $R^I$;
$R^X$=is the binding site of a single bond linking the first chemical moiety to one of the two second chemical moieties or is $R^I$;
$R^Y$=is the binding site of a single bond linking the first chemical moiety to one of the two second chemical moieties or is $R^I$;
and
two second chemical moieties, each independently of one another comprising a structure of Formula II,

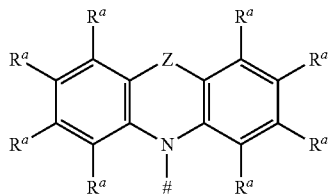

Formula II wherein
the first chemical moiety is linked to each of the two second chemical moieties via a single bond;
=represents the binding site of a single bond linking the second chemical moieties to the first chemical moiety;
Z=is at each occurrence independently from another selected from the group consisting of a direct bond, $CR^3R^4$, $C=CR^3R^4$, $C=O$, $C=NR^3$, $NR^3$, O, $SiR^3R^4$, S, S(O) and $S(O)_2$;
wherein
$R^A$ is selected from the group consisting of a structure of Formula A1 and a structure of Formula A2,

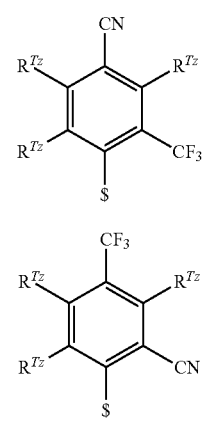

Formula A1

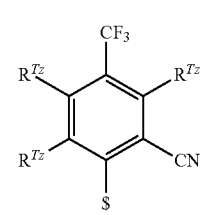

Formula A2 wherein $ represents the binding site of the single bond connecting $R^A$ and the first chemical moiety;

$R^1$, identically or differently at each occurrence, is selected from the group consisting of:
hydrogen, deuterium,
$C_1$-$C_5$-alkyl,
 wherein one or more hydrogen atoms are optionally substituted by deuterium;
$C_2$-$C_8$-alkenyl,
 wherein one or more hydrogen atoms are optionally substituted by deuterium;
$C_2$-$C_8$-alkynyl,
 wherein one or more hydrogen atoms are optionally substituted by deuterium; and
$C_6$-$C_{18}$-aryl,
 which is optionally substituted with one or more substituents $R^6$;

$R^2$, identically or differently at each occurrence, is selected from the group consisting of:
hydrogen, deuterium,
$C_1$-$C_5$-alkyl,
 wherein one or more hydrogen atoms are optionally substituted by deuterium;
$C_2$-$C_8$-alkenyl,
 wherein one or more hydrogen atoms are optionally substituted by deuterium;
$C_2$-$C_8$-alkynyl,
 wherein one or more hydrogen atoms are optionally substituted by deuterium; and
$C_6$-$C_{18}$-aryl,
 which is optionally substituted with one or more substituents $R^6$;

$R^I$, identically or differently at each occurrence, is selected from the group consisting of:
hydrogen, deuterium, $C_1$-$C_5$-alkyl,
  wherein one or more hydrogen atoms are optionally substituted by deuterium;
$C_2$-$C_8$-alkenyl,
  wherein one or more hydrogen atoms are optionally substituted by deuterium;
$C_2$-$C_8$-alkynyl,
  wherein one or more hydrogen atoms are optionally substituted by deuterium; and
$C_6$-$C_{18}$-aryl,
  which is optionally substituted with one or more substituents $R^6$;
$R^{Tz}$, identically or differently at each occurrence, is selected from the group consisting of
hydrogen,
deuterium,
$C_1$-$C_5$-alkyl,
  wherein one or more hydrogen atoms are optionally substituted by deuterium; and
$C_6$-$C_{18}$-aryl,
  which is optionally substituted with one or more substituents $R^6$;
$R^a$, $R^3$ and $R^4$, identically or differently at each occurrence, are selected from the group consisting of: hydrogen, deuterium, $N(R^5)_2$, $OR^5$, $Si(R^5)_3$, $B(OR^5)_2$, $OSO_2R^5$, $CF_3$, $CN$, $F$, $Br$, $I$,
$C_1$-$C_{40}$-alkyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;
$C_1$-$C_{40}$-alkoxy,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;
$C_1$-$C_{40}$-thioalkoxy,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;
$C_2$-$C_{40}$-alkenyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;
$C_2$-$C_{40}$-alkynyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;
$C_6$-$C_{60}$O-aryl,
  which is optionally substituted with one or more substituents $R^5$; and
$C_3$-$C_{57}$-heteroaryl,
  which is optionally substituted with one or more substituents $R^5$;

$R^5$, identically or differently at each occurrence, is selected from the group consisting of hydrogen, deuterium, $N(R^6)_2$, $OR^6$, $Si(R^6)_3$, $B(OR^6)_2$, $OSO_2R^6$, $CF_3$, $CN$, $F$, $Br$, $I$, $C_1$-$C_{40}$-alkyl,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;
$C_1$-$C_{40}$-alkoxy,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;
$C_1$-$C_{40}$-thioalkoxy,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;
$C_2$-$C_{40}$-alkenyl,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;
$C_2$-$C_{40}$-alkynyl,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;
$C_6$-$C_{60}$-aryl,
  which is optionally substituted with one or more substituents $R^6$; and
$C_3$-$C_{57}$-heteroaryl,
  which is optionally substituted with one or more substituents $R^6$;
$R^6$, identically or differently at each occurrence, is selected from the group consisting of:
hydrogen, deuterium, $OPh$, $CF_3$, $CN$, $F$,
$C_1$-$C_5$-alkyl,
  wherein one or more hydrogen atoms are optionally, independently from each other substituted by deuterium, $CN$, $CF_3$, or $F$;
$C_1$-$C_5$-alkoxy,
  wherein one or more hydrogen atoms are optionally, independently from each other substituted by deuterium, $CN$, $CF_3$, or $F$;
$C_1$-$C_5$-thioalkoxy,
  wherein one or more hydrogen atoms are optionally, independently from each other substituted by deuterium, $CN$, $CF_3$, or $F$;
$C_2$-$C_5$-alkenyl,
  wherein one or more hydrogen atoms are optionally, independently from each other substituted by deuterium, $CN$, $CF_3$, or $F$;
$C_2$-$C_5$-alkynyl,
  wherein one or more hydrogen atoms are optionally, independently from each other substituted by deuterium, $CN$, $CF_3$, or $F$;

$C_6$-$C_{18}$-aryl,
which is optionally substituted with one or more $C_1$-$C_5$-alkyl substituents;
$C_3$-$C_{17}$-heteroaryl,
which is optionally substituted with one or more $C_1$-$C_5$-alkyl substituents;
$N(C_6$-$C_{18}$-aryl$)_2$,
$N(C_3$-$C_{17}$-heteroaryl$)_2$, and
$N(C_3$-$C_{17}$-heteroaryl)($C_6$-$C_{18}$-aryl);
wherein the substituents $R^a$, $R^3$, $R^4$ or $R^5$ optionally form, independently from each other, a mono- or polycyclic, aliphatic, aromatic and/or benzo-fused ring system with one or more substituents $R^a$, $R^3$, $R^4$ or $R^5$;
wherein
exactly one substituent selected from the group consisting of T, V and W is $R^4$,
exactly one substituent selected from the group consisting of $R^T$, $R^V$ and $R^W$ is CN,
exactly one substituent selected from the group consisting of W, Y and X represents the binding site of a single bond linking the first chemical moiety and one of the two second chemical moieties and
exactly one substituent selected from the group consisting of $R^W$, $R^Y$ and $R^X$ represents the binding site of a single bond linking the first chemical moiety and one of the two second chemical moieties.

2. The organic molecule according to claim 1, wherein the first chemical moiety comprises a structure of Formula Ia-1:

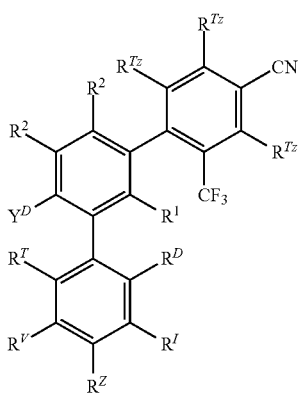

Formula Ia-1 wherein
$Y^D$=is the binding site of a single bond linking the first chemical moiety to one of the two second chemical moieties;
$R^D$=is the binding site of a single bond linking the first chemical moiety to one of the two second chemical moieties;
$R^Z$=is selected from the group consisting of $R^I$ and CN;
and wherein exactly one substituent selected from the group consisting of $R^V$, $R^T$ and $R^Z$ is CN;
and wherein apart from that the definitions in claim 1 apply.

3. The organic molecule according to claim 1, wherein $R^1$, $R^2$ and $R^I$, identically or differently at each occurrence, are selected from the group consisting of H, methyl, mesityl, tolyl and phenyl.

4. The organic molecule according to claim 1, wherein $R^{Tz}$ is independently from each other selected from the group of H, methyl and phenyl.

5. The organic molecule according to claim 1, wherein the two second chemical moieties, identically or differently at each occurrence, comprise a structure of Formula IIa:

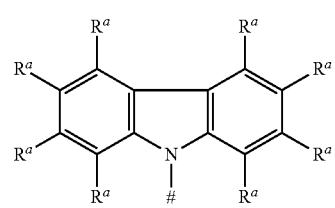

Formula IIa wherein # and $R^a$ are defined as in claim 1.

6. The organic molecule according to claim 1, wherein the two second chemical moieties, identically or differently at each occurrence, comprise a structure of Formula IIb:

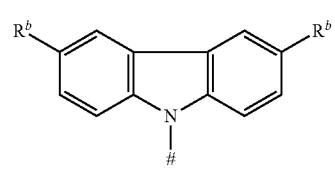

Formula IIb wherein
$R^b$=identically or differently at each occurrence, is selected from the group consisting of:
deuterium, $N(R^5)_2$, $OR^5$, $Si(R^5)_3$, $B(OR^5)_2$, $OSO_2R^5$, $CF_3$, CN, F, Br, I,
$C_1$-$C_{40}$-alkyl,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$;
$C_1$-$C_{40}$-alkoxy,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$;
$C_1$-$C_{40}$-thioalkoxy,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$;
$C_2$-$C_{40}$-alkenyl,
which is optionally substituted with one or more substituents $R^5$ and
wherein one or more non-adjacent $CH_2$-groups are optionally substituted by $R^5C=CR^5$, $C≡C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$;
$C_2$-$C_{40}$-alkynyl,
which is optionally substituted with one or more substituents $R^5$ and
wherein one or more non-adjacent $CH_2$-groups are optionally substituted by $R^5C=CR^5$, $C≡C$, $Si(R^5)_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_6$-C$_{60}$-aryl,
which is optionally substituted with one or more substituents R$^5$; and C$_3$-C$_{57}$-heteroaryl,
which is optionally substituted with one or more substituents R$^5$;

and wherein apart from that the definitions in claim 1 apply.

7. The organic molecule according to claim 1, wherein the two second chemical moieties, identically or differently at each occurrence, comprise a structure of Formula IIc:

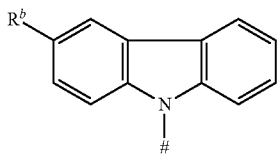

Formula IIc wherein

R$^b$=, identically or differently at each occurrence, is selected from the group consisting of deuterium, N(R$^5$)$_2$, OR$^5$, Si(R$^5$)$_3$, B(OR$^5$)$_2$, OSO$_2$R$^5$, CF$_3$, CN, F, Br, I, C$_1$-C$_{40}$-alkyl,
which is optionally substituted with one or more substituents R$^5$ and
wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_1$-C$_{40}$-alkoxy,
which is optionally substituted with one or more substituents R$^5$ and
wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_1$-C$_{40}$-thioalkoxy,
which is optionally substituted with one or more substituents R$^5$ and
wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_2$-C$_{40}$-alkenyl,
which is optionally substituted with one or more substituents R$^5$ and
wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_2$-C$_{40}$-alkynyl,
which is optionally substituted with one or more substituents R$^5$ and
wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_6$-C$_6$O-aryl,
which is optionally substituted with one or more substituents R$^5$; and C$_3$-C$_{57}$-heteroaryl,
which is optionally substituted with one or more substituents R$^5$;

and wherein apart from that the definitions in claim 1 apply.

8. The organic molecule according to claim 6, wherein Rb, identically or differently at each occurrence, is selected from the group consisting of Me, $^i$Pr, $^t$Bu, CN, CF$_3$, Ph, which is optionally substituted with one or more substituents independently from each other selected from the group consisting of Me, $^i$Pr, $^t$Bu, CN, CF$_3$ and Ph;

pyridinyl, which is optionally substituted with one or more substituents independently from each other selected from the group consisting of Me, $^i$Pr, $^t$Bu, CN, CF$_3$ and Ph;

pyrimidinyl, which is optionally substituted with one or more substituents independently from each other selected from the group consisting of Me, $^i$Pr, $^t$Bu, CN, CF$_3$ and Ph;

carbazolyl, which is optionally substituted with one or more substituents independently from each other selected from the group consisting of Me, $^i$Pr, $^t$Bu, CN, CF$_3$ and Ph;

triazinyl, which is optionally substituted with one or more substituents independently from each other selected from the group consisting of Me, $^i$Pr, $^t$Bu, CN, CF$_3$, and Ph; and N(Ph)$_2$.

9. A method for preparing an organic molecule according to claim 1, comprising providing a bromo-fluorobenzonitrile, substituted with either one R$^1$ and two R$^2$ or two R$^1$ and one R$^2$, as a reactant.

10. A composition, comprising:
(a) at least one organic molecule according to claim 1 in the form of an emitter and/or a host, and
(b) one or more emitter and/or host materials, which differ from the organic molecule of claim 1 and
(c) optionally, one or more dyes and/or one or more solvents.

11. An optoelectronic device, comprising one organic molecule according to claim 1 in form of a device selected from the group consisting of organic light-emitting diode (OLED), light-emitting electrochemical cell, OLED-sensor, organic diode, organic solar cell, organic transistor, organic field-effect transistor, organic laser and down-conversion element.

12. The optoelectronic device according to claim 11, comprising:
a substrate,
an anode, and
a cathode, wherein the anode or the cathode are disposed on the substrate, and
at least one light-emitting layer, which is arranged between anode and cathode and which comprises the organic molecule.

13. The optoelectronic device according to claim 11 comprising the organic molecule, in form of a device selected from the group consisting of organic light-emitting diode, (OLED), light-emitting electrochemical cell, OLED-sensor, organic diode, organic solar cell, organic transistor, organic field-effect transistor, organic laser and down-conversion element.

14. The optoelectronic device according to claim 11 comprising
- a substrate,
- an anode, and
- a cathode, wherein the anode or the cathode are disposed on the substrate, and
- at least one light-emitting layer, which is arranged between anode and cathode and which comprises the organic molecule.

15. A method for producing an optoelectronic device, wherein the organic molecule according to claim 1 is used, comprising the processing of the organic compound by vacuum evaporation method or from a solution.

16. The method for producing an optoelectronic device comprising the step of: processing by vacuum evaporation method or from a solution the at least one organic molecule according to claim 1 wherein the organic molecule is used in the form of an emitter and/or a host, in a composition with one or more emitter and/or host materials, which differ from the organic molecule of claim 1 and optionally, one or more dyes and/or one or more solvents.

* * * * *